(12) United States Patent
Govoni et al.

(10) Patent No.: US 9,115,354 B2
(45) Date of Patent: *Aug. 25, 2015

(54) DIFFOCINS AND METHODS OF USE THEREOF

(71) Applicant: AvidBiotics Corp.

(72) Inventors: Gregory R. Govoni, San Carlos, CA (US); Dana M. Gebhart, San Francisco, CA (US); Dean M. Scholl, Burlingame, CA (US)

(73) Assignee: AvidBiotics Corp., San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/829,725

(22) Filed: Mar. 14, 2013

(65) Prior Publication Data

US 2013/0203652 A1  Aug. 8, 2013

Related U.S. Application Data

(63) Continuation-in-part of application No. 13/117,467, filed on May 27, 2011, now Pat. No. 8,673,291.

(60) Provisional application No. 61/349,145, filed on May 27, 2010.

(51) Int. Cl.
| | |
|---|---|
| C12N 1/20 | (2006.01) |
| C07H 21/00 | (2006.01) |
| C12N 7/00 | (2006.01) |
| C07K 14/00 | (2006.01) |
| C12N 15/11 | (2006.01) |
| C07K 14/33 | (2006.01) |

(52) U.S. Cl.
CPC ............... *C12N 15/11* (2013.01); *C07K 14/33* (2013.01)

(58) Field of Classification Search
CPC ......... C07K 14/33; C12N 15/11; C12N 15/90
See application file for complete search history.

(56) References Cited

U.S. PATENT DOCUMENTS

| | | | |
|---|---|---|---|
| 7,585,957 B2 | 9/2009 | Miller et al. | |
| 7,700,729 B2 | 4/2010 | Scholl et al. | |
| 7,732,586 B2 | 6/2010 | Martin, Jr. et al. | |
| 8,206,971 B2 | 6/2012 | Scholl et al. | |
| 8,673,291 B2 * | 3/2014 | Scholl et al. | 424/93.21 |
| 2008/0171376 A1 | 7/2008 | Scholl et al. | |

FOREIGN PATENT DOCUMENTS

| | | |
|---|---|---|
| WO | WO01/01786 | 1/2001 |
| WO | WO02/077183 | 10/2002 |
| WO | WO2011/150342 A1 | 12/2011 |

OTHER PUBLICATIONS

Stabler et al., Comparative genome and phenotypic analysis of *Clostridium difficile* 027 strains provides insight into the evolution of a hypervirulent bacterium. Genome Biology 2009, 10:R102.1-102.15.*
Anastasio, KL, et al., 1971, "Boticinogeny and Actions of the Bacteriocin," J. of Bacteriology, vol. 107 143-149.
Blackwell, C.C. and J.A. Law, 1981, Typing of Non-Serogroupalbe *Neisseria* Meningitis by Means of Sensitivity to R-type pyocins of *Pseudomonas aeruginosa*. J. Infect. 3(4): 370-378.
Blackwell, C.C., F.P. Wistanley, and W.A. Telfer-Brunton, 1982. Sensitivity of thermophilic campylobacters to R-type pyocins of *Pseudomonas aeruginosa*. J. Med. Microbiol. 15:247-251.
Bradley, DE, Ultrastructure of Bacteriphage and Bacteriocins. Bacteriol. Rev. 21:230-314, 1967.
Campagnari, A.A.R. Karalus, M. Apicella, W. Melaugh, A.J. Lesse, and B.W. Gibson, 1994. Use of pyocin to select a *Haemophilus ducreyi* variant defective in lipooligosaccharide biosynthesis. Infect. Immun. 62:2379-2386.
Coetzee, H.L., H.C. De Klerk, J.N. Coetzee, and J.A. Smit. 1968. Bacteriophage-tail-like particles associated wiht intra-species killing of *Proteus vulgaris*. J. Gen. Virol. 2:29-36.
Database EMBL [Online] Oct. 1, 2009 (Oct. 10, 2009), "*Clostridium difficile* R20291 complete genome" XP00000268912, retrieved from EBI Accession No. EM_PRO: FN545816 p. 638-p. 641; sequence.
Database UniProt [Online] Nov. 4, 2009, "Subname: Full=Putative phage tail fiber protein;", XP000002658913, retrieved from EBI Accession No. UNIPROT: C9XPN8.
Database UniProt [Online] Nov. 24, 2009 "Subname: Full=Putative phage protien;", XP000002658914, retrieved from EBI Accession No. UNIPROT: C9YKW6.
Daw, MA, and FR Falkiner, 1996. Bacteriocins: nature, function, and structure. Review Article. Micron 27:467-479.
Ellison, JS and JA Kauttner, 1970. Purification and some properties of Two Boticins, J. of Bacteriology, 104: 19-26.
Filiatrault, M.J., R.S. Munson, Jr. and A.A. Campagnari, 2001. "Genetic Analysis of a Pyocin-Resistant Lipooligosaccharide (LOS) mutant of *Haemophilus ducreyi*: Restoration of Full-Length LOS Restores Pyocin Sensitivity," J. Inhibition Bacteriol. 183: 5756-5761.

(Continued)

*Primary Examiner* — Kevin Hill
*Assistant Examiner* — Arthur S Leonard
(74) *Attorney, Agent, or Firm* — Sughrue Mion, PLLC

(57) ABSTRACT

This disclosure relates to the discovery and isolation of the entire cluster of genes encoding R-type high molecular weight bacteriocins that specifically kill *Clostridium difficile* bacteria, dangerous pathogens. Also disclosed are methods of producing the R-type bacteriocins in innocuous aerobic producer cells. Disclosed also are small, non-ORF1374 receptor binding domains (RBDs), which are incorporated into diffocins to form engineered or variant diffocins having altered killing spectra. Variant diffocins provided herein may include a heterologous RBD and its cognate base plate attachment region (BPAR), or a fused BPAR. This invention offers a potent bactericidal agent with increased thermal and pH stability, and methods for producing it, in order to kill selectively *C. difficile* bacteria in the environment of the gastrointestinal tract where they can cause great harm and even death of the infected patient or farm animal.

29 Claims, 53 Drawing Sheets

(56) References Cited

OTHER PUBLICATIONS

Fortier, LC and S Moineau, 2007. "Morphological and Genetic Diversity of Temperate Phages in *Clostridium difficile*," Appl. Environ. Microbiol. 73:7358-7366.

Goh, S., PF Ong, KP Song, TV Riley and BJ Chang, 2007, "The Complete Genome Sequence of *Clostridium difficile* Phage and PhiC2 and Comparisons to phiCD119 and Inducible Prophages of CD630," Microbiology, 153:676-685.

Govind, R, JA Fralick, and RD Rolfe, 2006. "Genomic Organization and Molecular Characterizaton of *Clostridium difficile* Bacteriophage phiCD119," J. Bacteriol. 188:2568-2577.

Jabrane, A., A. Sabri, P. Comp re, P. Jacques, I. Vandenberghe, J. Van Beeumen, and P. Thenart. 2002. "Characterization of Serracin P, a Phagetail-like Bacteriocin, and its Activity Against *Erwinia amylovora*, the Fire Blight Pathogen," Appl. Environ. Microbiol. 68:5704-5710.

Kageyama, et al, Life Sciences 9:471-476, 1962.

Kageyama, M. 1975. Bacteriocins and Bacteriphages in *Pseudomonas aeruginosa*, 291-305, In T. Mitsuhashi and H. Hashimoto (ed.), Microbial Drug Resistance. University of Tokyo Press, Tokyo, Japan.

Kageyama, M. Ikeda, and F. Egami. 1964. "Studies of a Pyocin I. Physical and Chemical Properties." J. Biochem. 55:49-53.

Kageyama, M. K. Ikeda, and F. Egami, 1964. Studies of a Pyocin. III. Biological Properties of the Pyocin. J. Biochem. 55:59-64.

Kingsbury, D., 1966. "Bacteriocin Production by Strains of *Neisseria meningitidis*," J. Bacteriol. 91:1696-1699.

Krogh, S., M. O'Reilly, N. Nolan, and KM Devine, 1996. "The Phage-like Element PBSX and Part of the Skin Element, Which Are Resident At Different Locations on the *Bacillus subtilis* Chromosome, Are Highly Homologous." Microbiology. 142:2031-2040.

Liu, S., Endo K., Ara K, Ozaki K, Ogasawara N. 2008. "Introduction of Marker-Free Deletions in *Bacillus subtilis* Using the AraR Repressor and the ara Promoter." Microbiology, 154:2562-2570.

Long, J. et al, 2008. Differential Requirements of Two recA Mutants for Constitutive SOS Expression in *Escherichia coli* K-12. PLos ONE 3(12): e-4100. DOi: 10. 1371/journal.pone. 00041000.

Loo VG, Poirier L, Miller MA, Oughton M. Libman MD, Michaud S., et al. "A Predominantly Clonal Multi-Institutional Outbreak of *Clostridium difficile*-Associated Diarrhea With High Morbidity and Mortality." N. Engl. J. Med. 2005; 353:2442-24429.

Morse, S.A., B.V. Jones, and P.G. Lysko. 1980. "Pyocin of *Neisseria gonorrhoeae*: Mechanism of Action." Antimicrob. Agents Chemother. 18:416-423.

Nieves, BM, F. Gil and FJ Castillo, 1981. "Growth Inhibition Activity and Bacteriophge and Bacteriocinlike Particles Associated With Different Species of *Clostridium*." Can. J. Microbiol. 27:216-225.

Scholl, D., and DW Martin, Jr. 2008. "Antibacterial Efficacy of R-Type Pyocins Towards *Pseudomonas aeruginosa* in a Murine Peritonitis Model." Antimicrob. Agents Chemother. 52:1647-1652.

Scholl, D., M. Cooley, SR Williams, D. Gebhart, D. Martin, A. Bates, and R. Mandrell, 2009. "An Engineered R-Type Pyocin Is a Highly Specific and Senstive Bactericidal Agent for the Food-Borne Pathogen *Escherichia coli* 0157:H7." Antimicrob. Agents Chemother. 53:3074-3080.

Sell, et al. 1983. "Bacteriophage and Bacteriocin Typing Scheme for *Clostridium difficile*." J. Clin. Microb. 17(6): 1148-1152.

Strauch, E., H. Kaspar, C. Schaudinn, P. Dersch, K. Madela, C. Gewinner, S. Hertwig, J. Wecke, and B. Appel. 2001. "Characterization of Enterocoliticin, a Phage Tail-Like Bacteriocin and Its Effect on Pathogenic *Yersinia enterocolitica* Strains." Appl. Environ. Microbiol. 67:5634-5642.

Thompson, N. et al., Genetic Transformation in *Staphyloccous aureus*: Demonstration of a Competence-Conferring Factor of Bacteriophage Origin in Bacteriphage 80a Lysates. J. Bacteriology 148:294-300, 1981.

Williams, S., D.Gebhart, D.W. Martin, D. Scholl. 2008. "Re-Targeting R-Type Pyocins to Generate Novel Bactericidal Protein Complexes." Appl. Envrion. Microbiol. 74:3868-3876.

Wood, HE, MT Dawson, KM Devine, D.J. McConnell, 1990. Characterization of PBSX, a Defective Prophage of *Bacillus subtilis*. J. Bacteriology 172:2667-2674.

Zink, R., M.J. Loessner, and S. Schere. 1995. "Characterization of Cryptic Prophages (monocins) in *Listeria* and Sequence Analysis of a Holin/Endolysin Gene." Microbiology 141:2577-2584.

Gebhart, D. et al., "Novel high molecular weight, R-type bacteriocins from *Clostridium difficile*" J. Bacteriol., 194(22):6240-7, 2012.

Sebaihia, M. et al., "The multidrug-resistant human pathogen *Clostridium difficile* has a highly mobile, mosaic genome," Nature Genetics, 38(7):779-86, 2006.

Westers, L. et al., "*Bacillus subtilis* as cell factory for pharmaceutical proteins: a biotechnological approach to optimize the host organism." Biochim. Biophys. Acta. 1694(1-3):299-310, 2004.

Pulvirenti, J. et al., "Difference in the incidence of *Clostridium difficile* among patients infected with human immunodeficiency virus admitted to a public hospital and a private hospital." Infect. Control Hosp. Epidemiol. 23(11):641-7, 2002.

* cited by examiner

FIGURE 1. SEQ ID NO:1-80

SEQ ID NO:1          >Dif16 locus
GGCCGCAATACCCACTACACCTTCgTCATCTTTAAATTTAAGAGTTTTTACTATTGAATAATAA
AGGTATATTCCAGTAAAAATAATCTTTAAATACAAGAAAAATAAACTCTTTGGGTATATTAAAA
AGCTAAAAAGTGTAAATATAAAAGCAAGTAGAGTACTTATCCTGTAAAAGAAATCTATTTGTGT
AATGTCTTTATATTTTATCATAAACACCGAATATAAAATGATGAAAATAATTGCGACGATTGCA
TATATGGTAAATAACATATTTTCAAGAGTACCATTTGAAATTACTATCCACTTATACCACATAA
TTGGCCAAAATAATAGTGCTAAGAACTTAAAATAATTATCAAACAACTTTTCTTTATACATTCA
TCAAACAACCTTTCTTAACAAAAGCATATATTTGTTTTTAGAATTTTAAATAATATGATATCAT
TATTATATATTAATATTGAATTTATAGAAACCAAAATTTGTTAAAATAAATATATAGATTTTAC
TGTTAAGCCAGTTAAAATTACTACTATTTTTATTATGAAATTGGATCAAATATGTAGAAATACG
GCAAATTAGTTAATATTAAATATTTATTATTTCCAAGTTGTAAAGACTGTTTTTTAATGATAA
AAATTCTAATCTTTTTGAAAGAAAGTAATATCCACATTAAGTATGTCTGCCATTTCATAAACG
CAAGTGATGCCAGAATTAATTATGTTATTATATCTTCTTCAGTAATTAAGAACTCACAAGCCC
ATTTTAAGGCTTTATTTTCGCACTTATCTATAATAATTTTTGTATAATAATCGTTATAAGAGGA
TACATAGTATCCAAGGCTAGTGAAATGATGTCCAAGTTCTTCAGCTAAGATGGATGTCAATTTT
TTTGAGTTTTGTTTAAATTACTGAGTAATGATATAATTTTAATACCATGTTTGTTTATATATA
GCCCTTCTAAATCACCTGCAATATAAGTGGTATAATGAATTATTATCTCTTCTTGAGAAGCTAA
TTCAAAAAGCTTATCCAAATTATTCATAAAAATCCCCCTAAAATAGAATGTATGTTTGCCTTTA
AATTATATTAAAAGAGCAGAAAAATAGACTGCTCATCATATGGTTTATTTTTTTTATATTTAT
TTAGTAAAAATTCTATATAATCATTAAGTTGTTCTTGTGCTTCTTCAGGTAACTCTTCATGTGG
ATTTTTTCTATGTGCAGCTACTGTATCAATATTTTCCTTAACTAAGGTTCTTCCAAGAAGGTAA
TCAACTGATACATTAAATACATCAGCCAATTTGTTTAAAATGTGTTCATCAGGAAATCTGTTTT
CTGTTTCATAGTACCCTAAGACTCTTTGGGAAACGCCTACTTTTCTCCAAGTTCTCTTTGAGT
CAATCCAAATTCCTTTCTAAGTTCTCTTAATCTTTTGGCAAACATTATAACACCACCTTATGTA
TAGATTATAACAAATTGTTCTAAAAAATAAAACTAATAAAATATAAAAGAATATTTTTCTAAA
ATCTATTGATAAAGAACAAATGATTCTATATAATCTAAGTGTGGAAGAACAAAATATTCTTAAT
GGTAATGGAGGTATAAAACAATGTTTAAAAATAACTTGAAATATTATAGAAAATGCAAAGGTAT
GACACAAATTCAACTTGCCAGAAAGGCTGGAATTACAAATGACTATATATCTCAAATAGAAAGA
GGTATAAAAAATCCTGGTCTTCTTATGGCTAAGAAGATTTCTAGTATTTTAGAACAAAATATAG
AAGAAGTTTTTTTTATACAGTTATAGAACAATATGTTCTTGAAAGTTGTGAGATTAGTAAAAAA
CTGTGCACTAAAGAGATTATTGTAAATTTGAAGCTAATAATAAGTATATAAAAAAGGAGAAGTA
CTATGGAAAACAAAAAAGATATATTATTTAAAGAAACAGATGAAAGATTACATAATTATAAGTA
TTTGGATATAAAGATAAAGAATATTAATTTGGACATAAAAAGATGTGAGAATGAATACTCTGGA
TGTGGAGCAATGGTATATACAGAAAAGACTAGTAACACATATAACATAAGTTCTTCTGTGGAAA
ATGAGGTGTTAAAAAGAGAGGAAAGATTAAGAAAATTAAAAATGGAAAAAGAAGATATAGAAAT
AGAAAAAGAGAAGATAGAAAATGCTCTAACATGTCTAAATGATATAGAAATGGAATTTTTTAAT
CTTTTTTATAATAGTAAGACAAAAAACAATATGACATATATTTCTATGAAACTACACTTAGATA
GAACATCTTGCTACAATTTAAAGAAAAAATGATATTTAAATTGAGTGAGATATTATAAAAAAT
ATGACAACTTTACAACACTTTATATACACTATTGCAACACTAGGCAATAAAATATGTGAGATAA
TGTTATTGTGAAAGAAATCCATATTGAAGGAGGTGATAAATTGAAAAGAATAATATTACCTAAA
AATATAGAAGATATTTGACAGGAATAAATGAGATGTATATTTAAAAATGACTTATATCATTTAT
AGTAAGATTATCAGATTAAGCAAGAATATTTAGTGATAGTGTGGTGATTATTTGCTTAAATACA
AGGAAATATTAGAAACAATTATTGAGATTCTCAAAAAAACTTTACTGAAAGTATTTTTATTGA
TGATGAAAGTGTGCAAGGCTCTGAAGGGTCTTGTTTTTTGTAAGTATACTATCAGTTATTTGT
ACACCTATAATGTTAAATACGAATAATAAAGATATTGTTATCTCTATAAAATACTTACCAAAAC FIGURE 1 (Continued)

```
CACAGTCAAAGAGTATTAGAATGTATGAAATTTCAGATGAATTAAATAAGTTATTCAACAGAAA
TATAAAGGTAACAGACAGAAAATTAAATATAACAAAGCTAGAACAAAGTATTAAAAAAGAAGAG
TCAATTTATGTATTGAACTTTACAATTACACTAAATTATCTGGATAGTGTATATGAAGAAGATG
TAGTATATGAAAATATGGAAGAAATCAATTTAAATTTAGGAGAGTGATAGTATGGCTATAGGAT
TACCAAGTATCAACATATCATTTAAGGAGCTAGCTACAACTGTTAAAGAACGTTCAGCTAGAGG
AATAATTGCAATGGTGCTTAAAGATGCTAAGGCACTAGGTCTTAATGAAATACATGAAAAGAG
GATATACCAGTTGATTTATCTGCTGAAAATAAAGAGTATATAAATTTAGCTTTGATGGGAAATG
TTAACACTCCAAATAAATTATTAGTTTATGTAATAGAAGGAGAAGCAGATATTCAAACTGCATT
AGATTTTTAGAGACTAAGGAATTTAATTATCTATGTATGCCAAAAGCAGTAGAAGCTGATAAG
ACTGCTATAAAAATTGGATAATTAAACTTAGAGATATAGATAAGGTTAAGGTTAAAGCTGTAT
TAGGAAAAGTTGTAGGAAATCATGAAGGGATAATTAATTTTACTACAGAAGATGTGTTAGTTGG
AGAAAAGAAATACAGTGTTGATGAGTTTACAAGTAGGGTGGCTGGACTTATAGCAGGAACACCT
TTAAGTCAATCAGTAACTTATACTAAGCTTAGTGATGTAGTTGATATACCTAAGATGACGAAAG
TTGATGCAGAATCAAGGGTTAATAAAGGAGAGCTTATACTTATTAAGGAAGCAGGGGCTATAAG
AATTGCAAGAGGAGTAAATTCTTTAACTGAGTTAACAGAAGAAAAGGAGAAATGTTCCAGAAA
ATAAAAATAGTTGACACTTTAGATATTATACATAGTGACATAAGAAAGGTGATAATAGATGACT
ATATAGGAAAGGTTACTAACAGTTATGACAACAAATGTTTATTGATAGTAGCTATAAAAAGTTA
TTTAGAAGAATTAGAAAAGTCAGCACTTATAGAATCTGATTCTACTGTTGAAATAGATTTTGAA
GCACAAAAATCGTATTTAAAATCAAAAGGAGTAGATTTATCTTATATGACATTACAAGAAATAA
AAGAAGCTAACACAGGTTCTAAAGTATTTTTAAAAGCAAAAATAAAAGTACTTGATGCTATGGA
AGATATAGATTTATCAATAGAAATATAGGAGGATTATTAATATGGCAAATATGGAAGCTAGAAA
TGTAATGAGTGGTACTTGGGGAGAACTTTGGCTTGATGGAAACAAAGTAGCAGAAGTAAAGAAG
TTTCAAGCAAAGATGGAATTTACAAAAGAGGATATTATAATAGCAGGTCAAATGGGTACTGATA
CAAAGTATATGGGATATAAAGGAAAAGGTTCAATAACTCTATACCATGTTAGTTCAAGAATGCA
CAAGTTAATTGGAGAAAAGATAAAGAGAGGTTCTGAACCTAGATTTGTTGCTATATCTAAATTA
AATGACCCAGATTCTTATGGAGCAGAAAGAATAGCAGTAAAAAATATAGCATTTGATGATTTAA
CTTTAGCTGATTGGGAGGTTGGAGTAAAAGGAGAGATAGAAGCACCTTTCACATTTACTGAGTA
TGATTTCTTGATATAATTTAGTTTTATATTTGGTTTTATACTGATATTTAGTAGATATATACT
TAATAAATTTAGGTAGTTAATAAGTAAAAAGTTAGTTGATTGAATTTGATTGATAAAGGAGCA
AATAATAATGAATGAAAATGGATTATCAAAAATATAAACATAGTAGATTTACTTTTAAATGCA
GATACAGAAAACTTAGAAAGACCAAGTACTATAGTTGAACTTAAGAGATTATCAACTATATTTG
GGCAGGAATTTAAAGTAATGTGTAGAGCTTTAACAATAAGTAAAGATGAAGAGATACAAAATAC
TTGTCTTAAAATTGATGAAAATATGAAAACGGATATAGACTTACCGGAGATGCAGATGCTTACA
ATTATAGAAGGTGTTTGTGATTTGGATGGAAAGCTTTTATTTAAAAATAAGGAACTAATGGATA
AATTTAAGGCTCCAACACCAAAAGAATTGGCAAGAAAACTATTATTACCAGGTGAAATTACCAA
CCTATATAGAATACTTCAAGATGTTATGGGTTATGGTAAAAATGCAGTGATAGAAGAGGTAAAA
AACTAATAGGGACGGATACCAAGACTACAATAATGTACTATTATTGGAAGAAAAAGGTATAAG
ACCGTCCCTTTTTTATGCAATGGATAAAGGCGAATTAAAGCTTATTGAAGCTTTTTCGCCTTA
GAAATTGAGGAAGAAGTTGAAAAAATGAAACATGGATATGGAGTGTGTCCTTTGACAGGAGGTG
GTATGTAATGGGAAATGTGAGAGAAGAAGGTATAAATATGTATCTTACAGATAATTACACACCA
AAAATGAACCAAATTATATCAGTAACTGATAATTTTAGGAGAGCAACTGTGGCTGTTTCACTTT
CCACTAATGTAATGGCTAGTAGCATAAAAAATTCTATTGGAAGTGCAAGTAGTAGAGTAAACAG
TTTAAATTCCTCGTTAAGAAAAGTTCAAACTACTGCTAGTAGTGTAAGTTCAACTATGGCAAAA
TTAAGTTCTAGCATAAATGCTGTTTCAGGAGTTATTGGAAGTTTAAATGGAAGTATTATGAGAC
TAGCAATAACTATAGCTATGATTATTGATTATTTAATAAGTTGATTCAAAAGAAAATGAGTT
TAATTCAAATATTATGATTATATTAATATTTAAAGCTAAAAGTGATGAAGTAGAAAAAACTAAA
AATAAATTACTTGGAAATTTAAAAAAGATTGGTGGCAAGATTTGGAATATCGTAATAAAAGCAA
```

FIGURE 1 (Continued)

```
AAGATATGACTAAGAGAGTGATAAGTAGTATCTTGGGAAAATTAAAACGAGTAGAGAAACGTCC
TTATCAAGGAAGTATTAATCTTAAAGATATGGTAAGTAGTGCTATGGCTAGAATTTTGCCTAAG
TTAATGTTGTTTAAAAATACTTTTTGGAGTGGTGTAATAGCTATAAAAGATATGGCAAGTAGCA
TTATAAGTAAAGTATTTCCCAAATTGAGATTGTTTGCAGGTAAGGTATGGAGTGGTGCAATAGC
TGTAAAGGATATGGCAAGTGGAATACTTGGTTCGATAAAAGGGAAGATATCTGATTTGACAAAT
GGTGCTACTATAGGTGTCGCTGTGAAAAAGGGTGTTGACTTACTTGGTCAGGAACAAAATCAGA
AAGTTGTTCTAGAAAGTGTAATGAAAGAAATACTGGAAAAACTAGCCAAAAAGATGTTGATAA
GTATTATGACAGTTTAGTAAATATGGCAAATGATACGCCTTTTGACCCTGAAGATGTTGTTGCA
ATGGGAACTAAAGCTAAAATGATTAGTAATATTACTGGTGGCAAAAAGAAAAAGATATAACTC
AAGCTATGGTAGATGTTAGAGCTTTAAATATGAATACAAGTAGTGAACAAGATGTATCAGCAGC
TTTCTTAAGTGCAGCAAAAGGAAATATGGAATCTCTTAATACTCTGGTAGGAGAAAATTATAAA
ACTTTTGATGAAGCATTGGAAGGCATAAGTGTAAAGCAGATGGGGTAGCTAAAGAAATGAGTA
ATACAATACCAGGTATAATATCAGGAGCTCAAACAAGCATTAACAATGGTTTGAAGAGTATTGT
TAAACCTTTTGATGATATTTTAGGTCAAGGACTAAAGAAAATAAAAACTTTTATAGAAAGTGGA
TTAGGGAATTTAGCTGGCTTATCTGAAAAAATGGCTGGTAAAATAGGCAATGTAATGAATGGTA
AGATAATTATTGGCAACAAATATGACCAGATGCAATCTAGAAGTGTAAAAAATGGAAAAGAGTT
TTCTGATTCTACTCAATATCGAATTTCTAATGAGGCTGAAAAGCGTAAAATGATGGTTGAAAAT
AAGCAAGAACGTTTTGAAAATCATGCAGCAACAATGATAGGGAATGCACCAAAAGCAATTGTTA
ACGCAGGAAGTACACTATTACAAAATATTGATTTTACAGCATTAATAGATTCACTACTTCCAGT
AGTAAACTTAGTAAATAATTTACTAGATAGTATAAACAATAAATCACCAATTGCACAAGGATTA
ATAAGTATATTTGGTACAATAGTAACTACAGCATTCCAACTAATCGGACCTGTAGTTGAAGCTG
TTAGTCCTATTATCACAAGAATTTTTACTTTTTAGGTGAATATGCACCTCAAATAAACAATTT
TATAGAGACACTGGGTGTTATTTGGAAAACTGTATGGGAGACCTTAGGACCTCTGTTGGAAACT
GGATGGAAAATTATAGAGCCAATATTGGGAGCTTTTTTTAACATATTAGATAAAGTATGTAAAA
TAGTTAAAGATATATGCAAATGGTGGCAAACTATGATTAATAAGATAAAAATGGAAGCATCAC
AGGAACAGTTTTAAATCTAGTGGAAAAGAGTAAAAAAAATTACAAAGATAATCCATATGCTGGA
ACAAAGGCTGGTGATTCTGGTAAAGCTTATTCAAGTAAGAAAGGTAATAATGCATTTGGATTGA
ACTATGTTCCTTATAATGACTATCAAACCAGACTCCATGAAGGTGAAATGGTTTTAACTAAACA
AGAAGCAAATCAATATAGAAGCAGAAAAAATGGTGGAAATATAAACATAGCTAAGTTAGCTGAT
ACAATAGTGATTAGAGAAGAAGCTGATATAGAAAAGATAACATCAAAATTAGTTGCAAGTATCC
AATTGGCACAGTTAGGGGGTGTCTTATAATGGAAATGTGGCTTAGACAAGCAGAAGATAGATTT
AGATTTCCAGTATTTCCATCTTCCTTTAGTATTAATGGAAAAGCTGCTGTAAACTCTTCTAGTA
TACTCAAAATAGGTGAAGTAGCAACTTTTGGTGGTGTAGCTCTTAAAAGCATTTCAATATCAAG
TTTTTTTCCAAATAAAGACTACACTTTCTGTGACTATACAGGTTTTCCATCACCATATGATTGT
GTAAATAAGATAGAAAATGGATGAAGGAAGGTTTTATATTAAGATTTACAATTACGGAAACAA
ATATAAATATGGAAGTCATAATTGAAGGGTTTAGTTATGAAGAAAGAGATGGGAC
TCGAGATGTATATTTACATTAGATTTAAAAGAGTATAAAAGAATAAAGATACCAAAAGTAACT
CCAAAACAATAACTATTATAGATAATAAGTTGTAAGTAACTGCTGATAGAATTAAATGAAAAGG
CAGGTGATTTTTTATTATTAAGATTTGGGTACACATAAAAAACGGAAGTATATATGACATAACT
GACATAGTAGACAAGGTATCATGGTCAGGTGATTATAAATCTCCATCAAGGACACTAGAGTTTT
CAATAATACAATCATCATTTGATGTAAATTTCCAACAAATCGATATACCAATAGCTAGTACAGT
CTGTTTCTATGTAGATGAGAAAGAACTCTTTAGAGGAATGATAATTAATAGGTCTAAAGATTCA
AGCAGTAATGAAATTAGTTTTGTATCTAAAGATATGGGATTTTTACTTACACAAAGTGAAGTGT
CATACAATTTTAAAGATAAGTTAGTTGAAGACATAGCAAAGCAAGTATTTGCTGAAAATAGGCT
TTCAGTTGGAACAATAGCAAAGACCAATGTCAAGTATACAAAGATGTTTATAGGAGTAAATGGT
TATGACACAATAATGAGTGCATATACAGAGGCAAGTAAAAAGACAAAGAAAAAGTATATGATAG
AGGCTAATTTAGATAAGTTTAATGTTATTGAAAAAGGAACTGTTACATTAAGTGTTATGTTTGA
```

FIGURE 1 (Continued)

```
AGAGGGATTTAATATTATAAATACCACCTTTTCGGAGAGCATGGAAAATGTAAAAAATAAAGTA
ATAGTGGTAGACCAGTATGGAAGCAAGATTAGCGAAAAAATAGATAATGAAATTTTTAAGGAAG
TAAATGTAATAATGCAAAAAGTAATTCAGCAACAAGAAAATCAAGATGTAGATATTGATAGCGA
GTTTAATGGGATAGAAAAAAGCTGTTCTCTTAAaGGTTATGGAGATGTAAGTTGTATAACTGGT
AGAGGAGTAAAAGTTAAAGATTCTTATACAAAGCTTGTAGGACTATTTTATATAGATACAGACA
AACATACTTGGCAAAATGGAGAATATCAAATTGAGCTTGAACTTAATTTTCAAAATCTTATGGA
TGAAAAGTCAGCAGGACAGGATGAACCTAAGGAAGAAAGTAATTAGGGGGAGAAGATTATGCA
GGAGGAAAAGAGTTTACAGCAGAATTTACAGCTTACTGTCCTAGAAAAGAAGAAGGTGGAGATA
CAGATTGTAGAAAGAAAAAACTTGACCCATCTAAAAAACTTGCGCTGCTCCTATGGTTGGTAAA
TATGAGCAAACTTATTATACAAAAGAGTTTTTAAATAAACATCCTTTATTGAACTATGGAGATG
AAATACAGGTAATTACAGGAGTTTCTGGTCGTGATGGAGTCTATAAAGTAAATGACGTAGGACC
TGCAATAACTATAGAAAAAAATGGAACATACCATATAGATATTTATTTGGAAATGTTGAAGAA
GCTAGTAAATTTGGAAGAAGAAAAGGAAAAATTATTATTGGTGGTTATTCTGGTAATGTATCTG
ATAAAGCTAAAATAGTAATATCAGAGGCAAAAAAACATCTAGGTAAACCTTATAAATGGGGTGG
AAATGGACCAAGTAGTTTTGACTGTTCTGGTTTAATGGTCTACTGTTTAAAAAAGTTAATGTT
AGTTTGCCAAGAACGTCAAATCAACAATCTAAAAAAGGCAAGAAAGTAGAACAAAAAAATCTTC
AAGCAGGAGATTTAGTATTTTTTCATAATCCAGTCAGCCATGTTGGATTATATATAGGTAATGG
AGAATTTTTACATGCTCCACAAAAAGGTGATGTAGTTAAAATAAGTAAGTTAAGTAGTAGAAGA
GATTTTAATACAGCTAGGAGAGTATTATAAAAGGATGGTGATATAATGGCTAATCCAATAAATG
AATTTATAGGAATAATAAGAGAAGAAGGAAAGTATCATAATCAACCTTCTTTTTATTGGAAAA
TTAAAAGTAAATTACCAGATTTAAAAATAGAGACAAATAACATCATATTAGAAAAGAAGATAT
TTTGATAGATAGTTGGATGATTGATAGACAGCTAGAAACATTTGACACAGAAACAAATCAAGAA
CACCAGCATGAAGTAAAAAATCCTTTTATAGATAACTTTGAATCTGGGGATATGGTAATAATGT
TTAGAATAGGCGAAAAATTTGCTGTTGTAAGTAAGTTGGTGAGCTTATAATGAGTACAATATTT
CCTTTTATAGGTGTCCCAGAGGATTATATCTTACCTAAAACAGAAGAATTGCCAATCTTTCGTG
AAGTGGCATGGGATTTTGAAAAGATGAACCTATTTAGAAAAAGGTGACTTTAAAATAATTGA
AAAAAAAGAAGCCTTAAAAGTTTGGATATACAAGTGTATAAAGACAAATAGATATGAACATGA
GATATACTCTTTAGAATATGGGACAGAGCTTTCAGAACTAATAGGACAAAAATATACAAAAGGT
CTTACAGAAAGTGAAGCTAGTAGATTCATAAAAGAGGCCCTTCTAATAAATCCATATATATTAG
AAGTAAACGTAAAAAGTGCTAACTTTAACAGAGACGTATTGAGTGCAAATGTAAAAGTATCCAC
TATCTATGGGGAGGTGGAAATAAATGTATAGTGACCAGACATATGAAGTAATAAAAATAGAAC
TCTTGAAAATATTAATCTTGATATTTATAAAGGAGAAGGTTCTTTTCTAAACAACATGGTATCT
GGAAATAATCTAGAACTTTCGAAGATATATCTAGAACTTTCAAAGATACATAAAATGGCTTTTA
TACAAGACACATATAACCAGTTTCTTGATAAAAGAGTCAATGAATTTGGTGTATATAGAAAGTT
AGGTACAGAGTCAAATGGAGAAGTTGAATTATTGGAGAGAAAGGAACTGTAATAAATAATGGC
ACAATAATATCATATAGAGATTTACTATTTGTAGTAATAAAAGATGTAACTATTGGTAGTGAAG
AAGGTGACAATAGCCCAGTTCAAGCTCTGGAAGTTGGTAAGAAATATAATTTACCTACAAATTG
TGAATTTAAACTAGTTGATAATATATCTGGAGTAACAAAGATTACTAACACAAGAAGTTTTGAA
GGTGGTACAGATATAGAGACAGATGAAGAACTAAAAGAAAGATTTATAAAATCCAAAGAAATC
AAGCTACAAGTGGAAATAAAGCTCACTATGAAGAATGGGCTTTGGAAGTAGATGGAGTCTATAA
TGTTAAGGTTTATCCAAGATGGGATGGTCCAGGAACAGTTAAGGTCTTGATATTTGGGGAAAAT
AATCAAGCTGTTGATACAGAAACGATTGAAAGGTGTCAGCAACATATAGATGAAGAGAAGCCTA
TTGGACCAACTATAACAGTTGTGACACCATTACCAATAGAAATAAGTATAAGTGCAGTAATGAA
ACTAGAAGATGGATATACATTAGACAATGTAAAAGAATCTTTCCTAGAAAGTATAAATACATAC
TTTAGAGATATTAGAGGAGAGATAATCTATACAAAAGTCATGGGAATACTTATAAATACTACTG
GTGTACACGATTTAAGTAATCTACTTATAAATGGAAGTACAGATAATATAACTATTAATGAAGA
TAAAATACCTAGTGTAACAACTGTTAATTTTAGTGAGGTGGAAAATCAATGAAGCTAATTGATA
```

FIGURE 1 (Continued)

```
AACTACCATCATTTGATAGAAATTACATTGTAGAGGAGATACAAGGTGCATACGATACAGAATT
AAATATTCTTAAAGAAGATATTGATGATACCTTTAACCAATTATTTGTTGATACAGCGACATGG
GGATTAGATATGTGGGAAGACATACTCTGCATTGaAAAAAAAGAACTTGATTTTGACACAAGAC
GTAGCAATATAAAAGCTAAAATGAGAAGCAGAGGTACTAGTACTATTGAAGTTATAAAAAGTAT
ATGTGAGGCATATACAAAATCAGAAACAGATATAAAAGTTTATAGTGATGAATTTACATTCGTA
TTGAGTTTTATAGCAAATAACTGTGACTATAAAACTCTTTTAGATTGTAGCGAGATGATTGAAA
GAGTAAAACCTGCTCACTTATTACACTATTTAGAACCAATAATACTAGATAAAAGTATGGTCTA
TTGTGGTGGAGGTATGGTATGTAGTGAAGAGGTAAAAGTTCATCCATACTTTGAACCAATTATA
AAATGTAGTGCTGTTGTAAACTGTGGAGCTGGAATGTTAAGTAGAGAAGAAATAAAGGTTTATC
CTTTAAGCATTAAATGCATTGAAAATAATTGTAAGATTAATATAGCTATTGCAAATGATACAGG
CGTAGAAAATGTAGTAGTTTATCCTAAATCGGAGGTGGTATAATTGGAAGAAAAATTTTATATA
ATATTAACCAAAATTGGTAGAGAAAAAATAGCAAATGCAACTGCACTAGGAGAGCTTGTTGGAT
TAACCAAGTTTCAAGTTGGAGATAGTAATGGAGAATATTATGAGCCAACAGAGGAACAAACTGC
TTTAAAGAATGTAGTTTGGGAAGGAAATATAAATTCTCTAAGAATTGATGAAAAAAATCCTAAT
TGGATAGTTATAGAGACTATTTTACCAGGAACAGTTGGTGGATTTATGATAAGAGAAGCTGCTG
TTCTGGATAATGAGAATAATATAATAGCTATWGGTAAGTATCCAGAGACGTATAAGCCACGTGC
TGAAGATGGCAGTATTAAAGATTTGGTTGTAAAAATGATTTTACAATTGTCCAATACTTCAAAT
GTTACATTAGAAGTAGACCCGACGTTGGTTTTTGTAACTCAAAAGGATATTCAAGATTTAGATG
ATAAGTTTGATAAAAATATAAAAGAAATAAAAGTAAAAATTGGAGATACAGATATATTAACTAC
AGATTCTAAAGATTTATCAGGAGCTATAAATGAGGTAGTTAAAAAAATAGAAATATATCTTTT
GATGATGTTATAAGTGGTCAAATACAAACTGATATATCAGTATTAAAAAATAGCTATAACAAAT
TATCTGAAAAAGTGCTAGATATATTAATATACCTAGAATTAGAGTCAGAAGTAACTGTAGATGA
GGCTGGTTATTGGTATGATACATTAGCAAATGGAAATAACATAGTAGCTATAGAAGGGCTTAAG
TTAGATTTAAATAGAAAATGTATAACAGGTGAAATTGGTAATGTGATTTTAGAGATGTAGTAT
TACCATTTAGTGCAAATAGAGTTAGATATATACATGATATGGATAATAACTTTGTTGAGACAAA
ATCTAGTAACACTTATTTAAAAGAACAAAAGATATAACTCTAAGTAAATATTCATATGAAATA
AGATAAATAAAGGAGGTAGTACTAATAATGAAGCAAAATAAACTTTTACAGCGTGGTGCTTATT
TTAATGATAAGAACATATTGATTGATGATTTTGATAAAAGATATAATGATTATGATTTGTAGA
ATTTTTACTGGTATAAGTAATAGTACCTTTGGTTTAAAATCAGATGGTAATTTATATGCTTGT
GGCGATAATACAGGTTTTCAACTAGGACTTGGAAAAGATTCGTCAGAGAGAAGGATGTTTAGTA
AAGTAAAAATTGATAATGTAAAATATGTATCTTGTGGTTCAAAACACAGTGTAGCAGTAACTAA
AGATGGATTTGCATATGGAGCAGGAACAAGTAATGTAGGTCAATTAGGTGTAATTGAGTCTACA
GTATATTATGAATTTACTAAGCTACCAATAGATGATGTAAAAACTGTTGCATGTGGTTATGACT
TTACATTTGTGCTTAAAAATGATGGAACATTATATTCAGCAGGTTTAAACTCAAGTGGTCAACT
TGGACTAGGTGATACTAACAATAGAGCTACTTTTACTAAAGTAAATATAGATAGTGTGAAAGAT
GTAGTGACTTATAATCAATCTGTATTTATCATAAAAATGGATGGGACAGCACATGCATGTGGAT
TAAATTCAAATGGGCAGTTGGGAATTAATAGTACTTTAAATAAAAGTGTATTTAATAAAATAGA
AGGTATGGATAATGTAAAACAGATAGCGTGTGGTAGTAGTCATACAATTCTTATTAAGAATGAT
GGAACTATGTATACTACAGGCTATAATGGAGTTGGTCAGCTTGGTACAGGAAATAATAATAATT
CAATTGTATTTACTCTTTCTAGTATAAATAATGTTAAGTATGCTTCTTGTGGAAATAATCATAC
TATGATATTAAAATACGATAATACACTGTTTAGTACAGGACAAAACAATTATGGTCAACTAGCC
AATGCCAATAAAGATGTAGCATCAAGAAATACTTTGCTAAGGTTAATGTAGAAAATATAAAAG
ATATTAAATGTGGTTCTCAATTTAATTTTTtAATAAATGGTTCAAAAGAGATATTTGTATCTGG
CTGTAATTTAGCAGGTCAACTTGGTTCATTTTTCATACAACTTTTCTGTATGAGTTTTCAAAT
GTGCAATCTTCAAATTTAGATAATTATTCAGGTTTATTGGTTAATGATGATTATTTATATGTTA
CAAAGGACAATAGTGAATTTTTAAATGTAAAGTTAAGTGATAATTTTCAAGATTATAAGAAGAT
AGAGTTAACAGATAGCAATATGTTTATTGTTATGAATGATGGTACATTGTATGCTTGTGGTTTA
```

FIGURE 1 (Continued)

```
AATAATTATGGACAGTTAGGATTGGGAGATACTGTTAACAGGTCAGTTATGACTAAGGTGGATA
TAGATAATGTTTTGGATATAAAAGGAAACGGAAACTCAACTTTTGTGCTTAAGAATAATGGAAC
ATTATATTCATGTGGTTTAAATAGTAATGGACAATTGGGTTTAAGAGATGAAGTTAATAGAAAT
ATATTTACAAAAATAGAAATAGAGAATGTAAAGGATTTTGTGTAGGAAGCAATTATGTCATAG
CTTTAAATCACTCAAAAGAAGTATATGGATGGGGAAATAATCCTTATAATAATATAGAAAAAAC
TTCTAATTATCCATATAAGCAGGGAATAAGTAATATTGAAAAGATAGCAGCATATGATTATTCT
GTATATATGATAAACAGTGAAGGGAAACTATATGTTTCTGGATACAATTATAATTATCAATTAG
GTAAAGGAAATAATAGTAACCAAAGCAAAGCATTAGTATCTCAATGTAGAACAAATTCAACATC
TTCTACATCAAATGGACTTAGAACGTTACCTAAAATAACTAATGTTTTtCCTTTTTATGATGGT
TGTGCAATAATTGACGAAGGAGGTTATGTTTATTTAACAGGATATCATGGATATTTAAGAACAT
TAAATAGCAGTCCAAGTATATCTGATTATTCAAGATATGGAACTTTTATTGAGGCTACAAATTC
AAATCATAATACTTATTTTATACAAGAGACTGATTTTAGTGGAATTGAAAAAGTAATAGGGATG
TCAAATAATATATTATTTTTAAGAAAGGAAGTTCATATATTACTGGATATCCAAAAACATTTG
GCTCAACCATTACTGGACATAGAAGTTATACTAGTATTAATTCTGAGAGTTCTAATTTAGGAAG
TAATTTTATAATATATCATAGTAATTCCAAGTTATATGGAAAAGGGATTGCTAATAGTGGGCAA
TTTGGGAATTCAACAAATATAGATGGCACAAGTAACTATGATACAGGATTAAAAGACATAAAAG
ATATAATTGTAAAAGGAAATACTGTAGTAGTAGTAGATAAAAATAACAATATATATGTAACAGG
AATGAATCAGAATAACAAACTTGGGATAGGGAATATAACAACGAACCAGTAAAAAAATTCACA
AATATAACTGAACAATCAAACTCATTTATATTTATGGATGATATAAAAGAAATTACAACATCAA
GAAATACAATGTTTATAGTAAAAAATGATGGAACAGCCTATGCCACAGGAAATAATAGTTCTGG
ACAATTAGGATTAGGTGACACAATAAATAGAAATAAGTTCACTCAGATAAACCTTGATAATATA
AAGAAAATATCAACAAGTATAGATGGTAACACAACATTTGCAATTAGAAATGATGGAACACTAT
ACTCCACAGGATTAAATACCAAAGGACAACTGGGATTAGGTGATATAGTAAATAGAAATACATT
TACCAAAGTAAACATCCAAAATGTAAGAGATGTTGTTTAGGGACTACTCACTCGCATGCAATC
AAAGATGATAACACATTATATTCATGTGGAGaAAACACTCATGGGCAACTGGGCTTAGGAAGCG
AAAGCAACCATCCAGACGTATTGACATTTACTGTAAACAATATAACTAATGTAAGAGATGTGTA
CTGCTCAGATACAACAACATTTATTGTAAAGGACACAAACATTGCATATTGTTGTGGATACAAT
AATAATTCACAACTAGGTATGGGAAATACTACTGACCAGTATAGTTTTATAAAGTGTATGGAAA
ATGTAAAAGAAGTTATACCAAATGAAATAAATACCTATATAATAACAATCTATAATACTGCATA
TAGTACAGGTTTAAATACTGATTATTGCTTAGGTCTAAATAGTAATAGCAATCAAAGTTCATTT
TCTGAAATTCCAATTTCAAATGTAGTAAAAGTAGCTCCAAACAGAAATAATGCAGTACTTTTAC
TTACAAGTGAAGGGGATGTATATACTGCAGGCAAATGTAGTAATGGTTCAGGTACAGGAAGTGA
GACTCCAGAGAAGATTAAAAAAATAGCATCAAAGGCAAAGGATATTGGAATGAATTATAGATGT
GGACATTATGTAAGTGATAATGGAGACCTATATGGTACAGGTTTTAATAATAATGGACAATTAG
GTGTTGGTGATGTAACAAAAAGAGATACATTTATAAAAACCAATACAAGAGTAAAGAAAATACT
TCCTTTAGAATATGCAAATATAGCAATAAAAGATACTAATGATATATATATTTGTGGATTAAAT
AACTATGGACAATTAGGTGTTGGAAATAGATACGATAGTAGAAATAATGATAATAGAATATTTA
ATTATAAGCATATGAATTTTGTAATGGGTGATTTGACATCTATTAAAAACAGACATAACTTTAT
ACTTCTAAACAATAAGATAGTGATACCTACCACAAAAGACATAGATTATGGTTTAGTATTAGGA
AATTTATACAAAGGAGACCTTTATACTGAGCTTCCATATGAAGATATAAAAGAAGTATCTATTT
CTAAGACTCATATTATTATATTACTTAATGATGGAACAATGTATGGATGTGGTACAAACTACCA
TGGAGAATTATTGCAAGACTTGTCTATAAATCAAGTGGATGAATTTGTGCAGATTAATGTATCA
GATGTAAAGCATGTTTCATGTGGAGATAACTTTACTTATTTTATAAAATCTGATGATAGTCTTT
GGTCTATTGGTAAAAATTCCGAATATCAATTAGGTATAGGTCACAATAATCCAGTTACTGAATT
ACAAAGAATTACAACTATATCTAGCTGTAAAGAAGTACATTGTGGTAAAAACTATACATTAGTA
GTAACTACAGGTAATGAATTATTTGTACAAGGATATAATGATAAGGGAGCTTTAGGATTAGGAA
GCGATAGTGAAAATACTATAATTAAGTTCTTTACAAAAGCACTAACAGACATAAGAGAAATAAA
```

FIGURE 1 (Continued)

ATCTTATGGAAGTGACCATATATTAGTACTTAAAAATGATAATTCAGTATGGGTTACTGGAAAA
AATAGGGATGTATATAAAATTGAACAACCAGTAGAATTTTTAAAAGAATTTACTATAGTACCTA
TTTCTGAAGATGTAAATACAGTAAAGGATGTACTTGCAACAGACAATACATTATATATTATATC
AGAAGTAGGAACGACAAATGCTGCTATAGAAATTACTGAAAAATCAATTTCATCAATTAAGATA
AAAATACAAGACCCTAATAAAGATATAAGTAGAATAGAAATGCTTATAAATGGTGAAAGTGTAA
AATCTGTAAGTGATTTAACTACTGAAAAAATATCCTTTGAAGTACCACCAGATAAAATTAAAAT
AGGAGAGAATAAGATACTATTTAGAGCTTATTGTAAAGGTGATGATTTATATGCATCTTTATTT
ATTTTTAAAGAGAGTACTGGAAATTCTATAATTAAAGATTCTTATGTTATGATAGGTAATAGAA
TGTACAAGGTAGTTAATACAACATCTAATGAACAAGATATTACAATTACACTAGATAGAGGACT
TGAAGAAGATTTAAATCTTGGAGACCCTATATATCAATTAATAAATAAAACTAAAGTTCAAGTA
AAAATAAATAAATCTGACTTATTCAAAGACATGAAACTAGTTGAAATCAAAAAATCAGACTCAA
GTTATCAAGAAATCTATGAATTAGAAGAAGCCAACATAAAAAGTGCTCAGCCTAAAATCATAGT
AGAAAAAGGAGATAAATGGACAGCTATAAAACGTCCATCTATGATTTTTAGATATGATGCTGAA
AACAACGAGCCACAAGCTTAAAATGGAGGTGTAAAAATTGTTTAAATTCGATAAAAATAAAATA
GAACAAATCAAACAAGGTAGAAAAGTAGAAATGCAGTATAAAGACATTTCAGACATAAGTATAG
GTCAAGCAAAGCAAGATGATGATATAACAAATAATTTTATAGCAAATGCAGAAATATATGAGAT
GTTGTTAAGTCAAAGTTCTGTCAATGAAGCAAGTAATATAAGCACTTTTAGTGTAAGAAAATCT
GGAGGTGAGAGTGGAATGGTAGAAGTATATGTAGCTTTAATTTTAAGAGGCAGAAAAACAATAG
AAGAAGTACCAGCAGTAATTAGAGAGCAAGTTAGAATTAGATGTAAAGAATTAGAAATACCAGT
TGAATAGTAAATTTAGAATAACTATGTATTAGTTAtTTTTTTTATGTAAAGTACAAGGTCTTAA
CTTTAATAAGTAAGCCTTGTACTTATTTTTGTTATATTAGAAATTGTATATATATTTATTATT
TATTCAATCTATAAATTAAACCTACAATTTAAAGTACAGAAGATTAAATTGATAATCCTGAAAA
TATAATATTGCATGATGTAAGAATATAACAAAAATTAAAGCTATAAGTATAAAAAATTTAGACA
ATAGGAGGCTATAATGGATAAATTAATAACCGAATTGAGTAGTCTGGGGGCAATAGGTATACTA
TGTGCTCTATTATTTAAAAATACTATGCAGGAGAAAAAGAAGATAGAGACATGTATAAAAAAA
CTGTAGAAAATTTTATAGAATTATCTACACAACAACAAGAAATAAACAAAAATATACTTGTTCA
AATGGGAATAATGAAAACAGATGTAGAGGAAATTAAGGAAGATGTTACTGATATAAAAGGTATG
TTACAAAACGGTGTATAACATGAAAGTAGCAGTAGCACCAGATTATATATTATTAGGAAAAGAT
AAAGTAGTATTGTAGATAGTGCCCTATTTATTGAGAAGGATTTATATTTAAAATATTAATT
AAAAAAAGTAATAAAAATAATATATAAAAATAACATATAAAAATTCAAAAGGAGTTAAGCTTA
AATTTGATTAGAAAAAATCAATTTAAGACAACTCCTTTTTTTtATTAAATTATTGTCTATTAA
CCAAAATAGCTATTTTAGCATCTGGATTATAACTTATCTGAACCATTTGATTTTTCTTAACATG
TTCAAGGTCTTCACCACCATAAGCTATTTGTAACTTAACTGGTAACTTACCTTGTTTTATAATA
GCAACGTACTCTTTTTTACCTTTTTCTCTAAACTAATCAAATTGCCAACATAAGGTTTAAAGTT
CTGATACTTTTTACTAGAATTTCTTATGTAGAAGAAAGCACCAACAGCAATAACTAAATTTATG
CCAAGTGTAACCCAAGAATTGATTTAAGCATAGCTCCAGCGATTATTATCACGAACATTAAAA
CGATAGGTAATATAGCTTTCTTAAGAAGCAATTTACCCATTATTTCATTAGCCTTTTCTCAGG
GCCACTCATAGTTTTGATCTAGCAAATGATTGCGCGAATTTGTCTCTTAAGCCCATTTATCC
TCCTAATTTTAATAAATATTTAGTTATAATAACGAGATATTACTTGAAACTAAAAATTTACTAC
ATTTATATTATGTTTGACTTTTGTATAAATAATTACATTCAAGTAAAGCAAAATATACTAATTA
TTTTATCATAAAATTATAAAAAGAAAATAAATGAAATAAAAATATTAGAACAAAGAAATGATG
TAAAATCGTATCAAAAGCAACATAAAAATTATTTATCTATTTCTCATCTTTATTTTGTTATA
CTCAATTTTCCTAAATCCTTCTCTTTTCATATTCATGAAGTTTTAATTCAATCATACCTTCT
ATTTGGCTTTATCATAATCATTTAACTTTCTAAAGTTGTTTAAAAGCTTTATTTCATTAGAGT
TTATGCTATTAAGTGGATAGTTTGAGGAGGAATCGCAAATTAAATCTGATTTATGTGATAGATT
ATCTCCATTTAATAGCCAGTCTACTGAAACATTAAATATCTCAGCTATAGATTTAATATTTCA
TAATTTGGTTTTCTAATGTTTCTCTCAAATTTACTTAAGTTGTCACAGCCTAACATTTCTTCTA

FIGURE 1 (Continued)

GTTCATATTGTTTAAGGTTTTTTGCTTTTCTCAAATAAACAATTCTTTCTCCTAAAGTATCCAT
AAACACTCTCCATTCAATTAATGTCAAAAAGACTTTTTAAGATGTAAATAGTTTCAAATTAAAG
GTCAAAATGACATAAAAACCATTGACTTAAGGTCAAAATGACTTTATAATTAACTTAATGATAC
GAATTTACATCCTAATTTTAGCACAAAGTAATCAAAAAATCTTATTTAGTATTAAATAAATTTA
TATACTTAATATGTGTACATATTAAAAATATATACTAAATAGAGGGGGTGCGTAAGCTAAAGTA
ATATAAAAGTAAATATAAATCACTTAGAAAGGAAGTTGATAAATGGATGCTCGAAAAAAATGGA
TACCTTTTTTGGGAGTGCAAGTCAAGCAAAGACTTATTGAATTAAATATGACTCAAAGGGAATT
AGCGAAGAAAATAGGTGTTAATGAAAACTATTTGTCAGCTATTTTAAATGGAAGAAGAACAGGT
AAAAAATATAAATCATCAATTTATCAATTACTTAATATAGAATATTCAGAAGATGATTAATAAA
TAGTATATAAAGTAGGTGAATATTCTTGTGTGCAAATTGGATTCAGATGGGGTTATAGAGTGTT
GTAGAGCAATTGATGATTTTATTACAGCACTTAGTAATATAAAAAGCTTAAATATGGAAAGATT
AAATACTTTAACTAAATATTCTAGTACATGTTCAATCCTTCTTAAAGAGGGGAATTATGAAGGA
TGTACAATTGTGTATAGAAAGATGTTGGAAGAATTAAAAACATGAGTAATGCATTTCTTAGGAA
TATAAATTATACATAGAAATGTATTATATTTTTCAAAGTACTTAAACTAAAATATGGATAAGAT
AATCTAAATATTATAAATGTGCTTGAAATTAGACTATACTTGTTTTTAAATAATCCAATATCCA
TATTTTAGTAATATACTACAAAAAAAGAAGGTTAATAGATGATGTAAAATCGTATCAAATTATG
TATGTTTAAACCATTTTATCTTCATTATTATTAGAGGAATGCTTTTTAAGTCTTTATATTCAG
ATATCTTAAGTTCAAGTATTCCTTCTATTTTTATTTATCACGTTCGTTTAGTTGTCTGTATAG
ATTTAATATCATCATTTCATCATTAGTAACATGTAAGTAATCTTCTTTATCTTCTTTTACACTA
CTATTGACATTTACCTTCTCTTTACCATAGAGAAGCCAGTCAGTCGTAACATTAAAATAATCAG
CTATTGACATTAGTATATCACAATTAGGTTTTCTATCTCCTGTTTCATACTTGCCTAAGTTTTC
AAATTTTAAAATATCCATAAGTTTGCGCTGAGTAAGTTTTTGGAGTTTCTCAAATAAGCAATT
CTTTTTCCTAAAGTATCCACAAAATACACTCCTTTCTTTTTATGAGTAATGTCTAAATGACATT
TGAAATTAAAAATATATAAATTTATAATATAAAACTACTAAATTAAAGTCTAAATGACATTTTG
CTTAAATTAATATGCTCATAATATGATTTTAACATATTATAGTTGAAAATATATGGTTTATTTT
GATTTGTATATATAACAATAGATTTAATTGTTATAAAAATGTAAAGGGGTGTATGAATAGATTG
TATAAATTTATTTCGATAAACTAAGATTGCTTTTTGATTGTCTGTAAAAGAGAAAAAGATTAAG
ATAAAAATAGTATTATATTGTAATTTATATTAATCAATTACAAAGATTTTATGAATTTATTCTT
TAGGGTAAAATATTTAAGAATAAGATAAATTTACAATATAATACTATAACACTCTTTTATCTAG
TTTTATTTTCTTTATAGAACAATAATATTATAAATGCTAGTAGATTTACACAGAATACTGTTAT
ATACATCTGTTTGAATCCTGAGTTTAGAGTAGATTGTAGTGtGGATCCGG

SEQ ID NO:2          > orf 1360A (100% 630)
MFKNNLKYYRKCKGMTQIQLARKAGITNDYISQIERGIKNPGLLMAKKISSILEQNIEEVFFIQ
L SEQ ID NO:3          > orf 1361 (100% 630)
MENKKDILFKETDERLHNYKYLDIKIKNINLDIKRCENEYSGCGAMVYTEKTSNTYNISSSVEN
EVLKREERLRKLKMEKEDIEIEKEKIENALTCLNDIEMEFFNLFYNSKTKNNMTYISMKLHLDR
TSCYNLKKKMIFKLSEIL SEQ ID NO:4          > orf 1362
NFTESIFIDDESVQGSEGSCFFVSILSVICTPIMLNTNNKDIVISIKYLPKPQSKSIRMYEISD
ELNKLFNRNIKVTDRKLNITKLEQSIKKEESIYVLNFTITLNYLDSVYEEDVVYENMEEINLNL
GE FIGURE 1 (Continued)

SEQ ID NO:5          > orf 1363 (99+% 630)
MAIGLPSINISFKELATTVKERSARGIIAMVLKDAKALGLNEIHEKEDIPVDLSAENKEYINLA
LMGNVNTPNKLLVYVIEGEADIQTALDFLETKEFNYLCMPKAVEADKTAIKNWIIKLRDIDKVK
VKAVLGKVVGNHEGIINFTTEDVLVGEKKYSVDEFTSRVAGLIAGTPLSQSVTYTKLSDVVDIP
KMTKVDAESRVNKGELILIKEAGAIRIARGVNSLTELTEEKGEMFQKIKIVDTLDIIHSDIRKV
IIDDYIGKVTNSYDNKCLLIVAIKSYLEELEKSALIESDSTVEIDFEAQKSYLKSKGVDLSYMT
LQEIKEANTGSKVFLKAKIKVLDAMEDIDLSIEI SEQ ID NO:6          > orf 1364 (100% 630)
MANMEARNVMSGTWGELWLDGNKVAEVKKFQAKMEFTKEDIIIAGQMGTDTKYMGYKGKGSITL
YHVSSRMHKLIGEKIKRGSEPRFVAISKLNDPDSYGAERIAVKNIAFDDLTLADWEVGVKGEIE
APFTFTEYDFLDII SEQ ID NO:7          > orf 1365 (98+% 630)
MNENGLSKNINIVDLLLNADTENLERPSTIVELKRLSTIFGQEFKVMCRALTISKDEEIQNTCL
KIDENMKTDIDLPEMQMLTIIEGVCDLDGKLLFKNKELMDKFKAPTPKELARKLLLPGEITNLY
RILQDVMGYGKNAVIEEVKN SEQ ID NO:8          > orf 1365A (100% 630)
MYYYWKKKGIRPSLFYAMDKGELKLIEAFFALEIEEEVEKMKHGYGVCPLTGGGM SEQ ID NO:9          > orf 1366 (98% 630) Tape Measure
MGNVREEGINMYLTDNYTPKMNQIISVTDNFRRATVAVSLSTNVMASSIKNSIGSASSRVNSLN
SSLRKVQTTASSVSSTMAKLSSSINAVSGVIGSLNGSIMRLAITIAMIIDYFNKLIQKKNEFNS
NIMIILIFKAKSDEVEKTKNKLLGNLKKIGGKIWNIVIKAKDMTKRVISSILGKLKRVEKRPYQ
GSINLKDMVSSAMARILPKLMLFKNTFWSGVIAIKDMASSIISKVFPKLRLFAGKVWSGAIAVK
DMASGILGSIKGKISDLTNGATIGVAVKKGVDLLGQEQNQKVVLESVMKRNTGKTSQKDVDKYY
DSLVNMANDTPFDPEDVVAMGTKAKMISNITGGKKEKDITQAMVDVRALNMNTSSEQDVSAAFL
SAAKGNMESLNTLVGENYKTFDEALEGISVKQMGLAKEMSNTIPGIISGAQTSINNGLKSIVKP
FDDILGQGLKKIKTFIESGLGNLAGLSEKMAGKIGNVMNGKIIIGNKYDQMQSRSVKNGKEFSD
STQYRISNEAEKRKMMVENKQERFENHAATMIGNAPKAIVNAGSTLLQNIDFTALIDSLLPVVN
LVNNLLDSINNKSPIAQGLISIFGTIVTTAFQLIGPVVEAVSPIITRIFTFLGEYAPQINNFIE
TLGVIWKTVWETLGPLLETGWKIIEPILGAFFNILDKVCKIVKDICKWWQTMINKIKNGSITGT
VLNLVEKSKKNYKDNP
YAGTKAGDSGKAYSSKKGNNAFGLNYVPYNDYQTRLHEGEMVLTKQEANQYRSRKNGGNINIAK
LADTIVIREEADIEKITSKLVASIQLAQLGGVL SEQ ID NO:10         > orf 1367 (100% 630) Baseplate
MEMWLRQAEDRFRFPVFPSSFSINGKAAVNSSSILKIGEVATFGGVALKSISISSFFPNKDYTF
CDYTGFPSPYDCVNKIEKWMKEGFILRFTITETNINMEVIIEGFSYEERDGTRDVYFTLDLKEY
KRIKIPKVTPKQ

FIGURE 1 (Continued)

```
SEQ ID NO:11        > orf 1368 (100% 630) Baseplate
MIINRSKDSSSNEISFVSKDMGFLLTQSEVSYNFKDKLVEDIAKQVFAENRLSVGTIAKTNVKY
TKMFIGVNGYDTIMSAYTEASKKTKKKYMIEANLDKFNVIEKGTVTLSVMFEEGFNIINTTFSE
SMENVKNKVIVVDQYGSKISEKIDNEIFKEVNVIMQKVIQQQENQDVDIDSEFNGIEKSCSLKG
YGDVSCITGRGVKVKDSYTKLVGLFYIDTDKHTWQNGEYQIELELNFQNLMDEKSAGQDEPKEE
SNLGGEDYAGGKEFTAEFTAYCPRKEEGGDTDCRKKKLDPSKKTCAAPMVGKYEQTYYTKEFLN
KHPLLNYGDEIQVITGVSGRDGVYKVNDVGPAITIEKNGTYHIDILFGNVEEASKFGRRKGKII
IGGYSGNVSDKAKIVISEAKKHLGKPYKWGGNGPSSFDCSGLMVYCFKKVNVSLPRTSNQQSKK
GKKVEQKNLQAGDLVFFHNPVSHVGLYIGNGEFLHAPQKGDVVKISKLSSRRDFNTARRVL SEQ ID NO:12        > orf 1369 (100% 630)
MANPINEFIGIIREEGKYHNQPSFFIGKIKSKLPDLKIETNNIILEKEDILIDSWMIDRQLETF
DTETNQEHQHEVKNPFIDNFESGDMVIMFRIGEKFAVVSKLVSL SEQ ID NO:13        > orf 1370 (99+% 630)
MSTIFPFIGVPEDYILPKTEELPIFREVAWDFEKDEPILEKGDFKIIEKKEALKVWIYKCIKTN
RYEHEIYSLEYGTELSELIGQKYTKGLTESEASRFIKEALLINPYILEVNVKSANFNRDVLSAN
VKVSTIYGEVEINV SEQ ID NO:14        > orf 1371 (100% 630) Tail
MYSDQTYEVIKNRTLENINLDIYKGEGSFLNNMVSGNNLELSKIYLELSKIHKMAFIQDTYNQF
LDKRVNEFGVYRKLGTESNGEVEFIGEKGTVINNGTIISYRDLLFVVIKDVTIGSEEGDNSPVQ
ALEVGKKYNLPTNCEFKLVDNISGVTKITNTRSFEGGTDIETDEELKERFYKIQRNQATSGNKA
HYEEWALEVDGVYNVKVYPRWDGPGTVKVLIFGENNQAVDTETIERCQQHIDEEKPIGPTITVV
TPLPIEISISAVMKLEDGYTLDNVKESFLESINTYFRDIRGEIIYTKVMGILINTTGVHDLSNL
LINGSTDNITINEDKIPSVTTVNFSEVENQ SEQ ID NO:15        > orf 1372 (100% 630)
MKLIDKLPSFDRNYIVEEIQGAYDTELNILKEDIDDTFNQLFVDTATWGLDMWEDILCIEKKEL
DFDTRRSNIKAKMRSRGTSTIEVIKSICEAYTKSETDIKVYSDEFTFVLSFIANNCDYKTLLDC
SEMIERVKPAHLLHYLEPIILDKSMVYCGGGMVCSEEVKVHPYFEPIIKCSAVVNCGAGMLSRE
EIKVYPLSIKCIENNCKINIAIANDTGVENVVVYPKSEVV SEQ ID NO:16        > orf 1373 (99% 630) Tail fiber
MEEKFYIILTKIGREKIANATALGELVGLTKFQVGDSNGEYYEPTEEQTALKNVVWEGNINSLR
IDEKNPNWIVIETILPGTVGGFMIREAAVLDNENNIIAIGKYPETYKPRAEDGSIKDLVVKMIL
QLSNTSNVTLEVDPTLVFVTQKDIQDLDDKFDKNIKEIKVKIGDTDILTTDSKDLSGAINEVVK
KIENISFDDVISGQIQTDISVLKNSYNKLSEKVLDILIYLELESEVTVDEAGYWYDTLANGNNI
VAIEGLKLDLNRKCITGEIGNVIFRDVVLPFSANRVRYIHDMDNNFVETKSSNTYLKEQKDITL
SKYSYEIR SEQ ID NO:17        > orf 1374 of #16 receptor binding-variable
MKQNKLLQRGAYFNDKNILIDDFDKRYNDYDFVEFFTGISNSTFGLKSDGNLYACGDNTGFQLG
LGKDSSERRMFSKVKIDNVKYVSCGSKHSVAVTKDGFAYGAGTSNVGQLGVIESTVYYEFTKLP
IDDVKTVACGYDFTFVLKNDGTLYSAGLNSSGQLGLGDTNNRATFTKVNIDSVKDVVTYNQSVF
IIKMDGTAHACGLNSNGQLGINSTLNKSVFNKIEGMDNVKQIACGSSHTILIKNDGTMYTTGYN
GVGQLGTGNNNSIVFTLSSINNVKYASCGNNHTMILKYDNTLFSTGQNNYGQLANANKDVASR
```

FIGURE 1 (Continued)

NTFAKVNVENIKDIKCGSQFNFLINGSKEIFVSGCNLAGQLGSFFHTTFLYEFSNVQSSNLDNY
SGLLVNDDYLYVTKDNSEFLNVKLSDNFQDYKKIELTDSNMFIVMNDGTLYACGLNNYGQLGLG
DTVNRSVMTKVDIDNVLDIKGNGNSTFVLKNNGTLYSCGLNSNGQLGLRDEVNRNIFTKIEIEN
VKDFCVGSNYVIALNHSKEVYGWGNNPYNNIEKTSNYPYKQGISNIEKIAAYDYSVYMINSEGK
LYVSGYNYNYQLGKGNNSNQSKALVSQCRTNSTSSTSNGLRTLPKITNVFPFYDGCAIIDEGGY
VYLTGYHGYLRTLNSSPSISDYSRYGTFIEATNSNHNTYFIQETDFSGIEKVIGMSNNILFFKK
GSSYITGYPKTFGSTITGHRSYTSINSESSNLGSNFIIYHSNSKLYGKGIANSGQFGNSTNIDG
TSNYDTGLKDIKDIIVKGNTVVVVDKNNNIYVTGMNQNNKLGIGEYNNEPVKKFTNITEQSNSF
IFMDDIKEITTSRNTMFIVKNDGTAYATGNNSSGQLGLGDTINRNKFTQINLDNIKKISTSIDG
NTTFAIRNDGTLYSTGLNTKGQLGLGDIVNRNTFTKVNIQNVRDVVLGTTHSHAIKDDNTLYSC
GENTHGQLGLGSESNHPDVLTFTVNNITNVRDVYCSDTTTFIVKDTNIAYCCGYNNNSQLGMGN
TTDQYSFIKCMENVKEVIPNEINTYIITIYNTAYSTGLNTDYCLGLNSNSNQSSFSEIPISNVV
KVAPNRNNAVLLLTSEGDVYTAGKCSNGSGTGSETPEKIKKIASKAKDIGMNYRCGHYVSDNGD
LYGTGFNNNGQLGVGDVTKRDTFIKTNTRVKKILPLEYANIAIKDTNDIYICGLNNYGQLGVGN
RYDSRNNDNRIFNYKHMNFVMGDLTSIKNRHNFILLNNKIVIPTTKDIDYGLVLGNLYKGDLYT
ELPYEDIKEVSISKTHIIILLNDGTMYGCGTNYHGELLQDLSINQVDEFVQINVSDVKHVSCGD
NFTYFIKSDDSLWSIGKNSEYQLGIGHNNPVTELQRITTISSCKEVHCGKNYTLVVTTGNELFV
QGYNDKGALGLGSDSENTIIKFFTKALTDIREIKSYGSDHILVLKNDNSVWVTGKNRDVYKIEQ
PVEFLKEFTIVPISEDVNTVKDVLATDNTLYIISEVGTTNAAIEITEKSISSIKIKIQDPNKDI
SRIEMLINGESVKSVSDLTTEKISFEVPPDKIKIGENKILFRAYCKGDDLYASLFIFKESTGNS
IIKDSYVMIGNRMYKVVNTTSNEQDITITLDRGLEEDLNLGDPIYQLINKTKVQVKINKSDLFK
DMKLVEIKKSDSSYQEIYELEEANIKSAQPKIIVEKGDKWTAIKRPSMIFRYDAENNEPQA

SEQ ID NO:18        >orf1375
MQYKDISDISIGQAKQDDDITNNFIANAEIYEMLLSQSSVNEASNISTFSVRKSGGESGMVEVY
VALILRGRKTIEEVPAVIREQVRIRCKELEIPVE SEQ ID NO:19        >orf 1376 (100% 630)
MDKLITELSSLGAIGILCALLFKNTMQEKKEDRDMYKKTVENFIELSTQQQEINKNILVQMGIM
KTDVEEIKEDVTDIKGMLQNGV SEQ ID NO:20        >1377 (100% 630)
MGLRDKFAQSFARSKTMSGPEKKANEIMGKLLLKKAILPIVLMFVIIAGAMLKINSWVTLGIN
LVIAVGAFFYIRNSSKKYQNFKPYVGNLISLEKKGKKEYVAIIKQGKLPVKLQIAYGGEDLEHV
KKNQMVQISYNPDAKIAILVNRQ SEQ ID NO:21        >AV1378 (100% 630)
MDTLGERIVYLRKAKNLKQYELEEMLGCDNLSKFERNIRKPNYEILKSIAEIFNVSVDWLLNGD
NLSHKSDLICDSSSNYPLNSINSNEIKLLNNFRKLNDYDKAKIEGMIELKLHEYEKEKDLGKIE
YNKNKDEKIDK SEQ ID NO:22        >1378A (100% 630) regulatory
MDARKKWIPFLGVQVKQRLIELNMTQRELAKKIGVNENYLSAILNGRRTGKKYKSSIYQLLNIE
YSEDD FIGURE 1 (Continued)

SEQ ID NO:23          >AV1379
VDTLGKRIAYLRNSKKLTQRKLMDILKFENLGKYETGDRKPNCDILMSIADYFNVTTDWLLYGK
EKVNVNSSVKEDKEDYLHVTNDEMMILNLYRQLNERDKIKIEGILELKISEYKDLKKHSSNNNE
DKMV

SEQ ID NO:24          >AV1419
tttcttGAAGACcAtcgaAgcaccaccaccaccactg

SEQ ID NO:25          >AV1420
tttttttGAAGACAAtcgaAgggcttcgccctgtcgctcgac

SEQ ID NO:26          >AV1416
ttccttGAAGACCTaattTggggcaatcccgcaaggag

SEQ ID NO:27          >AV1245
cccctttGAAGACCCaattTcgtatggcaatgaaagacgg

SEQ ID NO:28          >AV1372
aattGCGGCCGCagctcGCTAGCggtacCTCGAGgatatcttcgaaGAAGACACATCCg SEQ ID NO:29          >AV1373
aattccgggatGCATGCctctaGGATCCGGCGCGCC SEQ ID NO:30          >AV1374
agctGGCGCGCCGGATCCtagagGCATGCatcccggaattcGGATGTGTCTTCtt SEQ ID NO:31          >AV1375
cgaagatatcCTCGAGgtaccGCTAGCgagctGCGGCCGC SEQ ID NO:32          5' fragment
GGCCGCAATACCCACTACACCTTCgTCATCTTTAAATTTAAGAGTTTTTACTATTGAATAATAA
AGGTATATTCCAGTAAAAATAATCTTTAAATACAAGAAAAATAAACTCTTTGGGTATATTAAAA
AGCTAAAAAGTGTAAATATAAAAGCAAGTAGAGTACTTATCCTGTAAAAGAAATCTATTTGTGT
AATGTCTTTATATTTTATCATAAACACCGAATATAAAATGATGAAAATAATTGCGACGATTGCA
TATATGGTAAATAACATATTTTCAAGAGTACCATTTGAAATTACTATCCACTTATACCACATAA
TTGGCCAAAATAATAGTGCTAAGAACTTAAAATAATTATCAAACAACTTTTCTTTATACATTCA
TCAAACAACCTTTCTTAACAAAAGCATATATTTGTTTTAGAATTTTAAATAATATGATATCAT
TATTATATATTAATATTGAATTTATAGAAACCAAAATTTGTTAAAATAAATATATAGATTTTAC
TGTTAAGCCAGTTAAAATTACTACTATTTTATTATGAAATTGGATCAAATATGTAGAAATACG
GCAAATTAGTTAATATTAAATATTTATTATTTCCAAGTTGTAAAGACTGTTTTTTTAATGATAA
AAATTCTAATCTTTTTTGAAAGAAAGTAATATCCACATTAAGTATGTCTGCCATTTCATAAACG
CAAGTGATGCCAGAATTAATTATGTTTATTATATCTTCTTCAGTAATTAAGAACTCACAAGCCC
ATTTTAAGGCTTTATTTTCGCACTTATCTATAATAATTTTGTATAATAATCGTTATAAGAGGA
TACATAGTATCCAAGGCTAGTGAAATGATGTCCAAGTTCTTCAGCTAAGATGGATGTCAATTTT
TTTGAGTTTTGTTTTAAATTACTGAGTAATGATATAATTTTAATACCATGTTTGTTTATATATA
GCCCTTCTAAATCACCTGCAATATAAGTGGTATAATGAATTATTATCTCTTCTTGAGAAGCTAA
TTCAAAAAGCTTATCCAAATTATTCATAAAAATCCCCCTAAAATAGAATGTATGTTTGCCTTTA FIGURE 1 (Continued)

```
AATTATATTAAAAGAGCAGAAAAATAGACTGCTCATCATATGGTTTATTTTTTTTATATTTAT
TTAGTAAAAATTCTATATAATCATTAAGTTGTTCTTGTGCTTCTTCAGGTAACTCTTCATGTGG
ATTTTTTCTATGTGCAGCTACTGTATCAATATTTTCCTTAACTAAGGTTCTTCCAAGAAGGTAA
TCAACTGATACATTAAATACATCAGCCAATTTGTTTAAAATGTGTTCATCAGGAAATCTGTTTT
CTGTTTCATAGTACCCTAAGACTCTTTGGGAAACGCCTACTTTTTCTCCAAGTTCTCTTTGAGT
CAATCCAAATTCCTTTCTAAGTTCTCTTAATCTTTTGGCAAACATTATAACACCACCTTATGTA
TAGATTATAACAAATTGTTCTAAAAAATAAAACTAATAAAATATAAAAGAATATTTTTCTAAA
ATCTATTGATAAAGAACAAATGATTCTATATAATCTAAGTGTGGAAGAACAAAATATTCTTAAT
GGTAATGGAGGTATAAAACAATGTTTAAAAATAACTTGAAATATTATAGAAAATGCAAAGGTAT
GACACAAATTCAACTTGCCAGAAAGGCTGGAATTACAAATGACTATATATCTCAAATAGAAAGA
GGTATAAAAAATCCTGGTCTTCTTATGGCTAAGAAGATTTCTAGTATTTTAGAACAAAATATAG
AAGAAGTTTTTTTTATACAGTTATAGAACAATATGTTCTTGAAAGTTGTGAGATTAGTAAAAAA
CTGTGCACTAAAGAGATTATTGTAAATTTGAAGCTAATAATAAGTATATAAAAAGGAGAAGTA
CTATGGAAAACAAAAAGATATATTATTTAAAGAAACAGATGAAAGATTACATAATTATAAGTA
TTTGGATATAAAGATAAAGAATATTAATTTGGACATAAAAAGATGTGAGAATGAATACTCTGGA
TGTGGAGCAATGGTATATACAGAAAAGACTAGTAACACATATAACATAAGTTCTTCTGTGGAAA
ATGAGGTGTTAAAAAGAGAGGAAAGATTAAGAAAATTAAAAATGGAAAAAGAAGATATAGAAAT
AGAAAAAGAGAAGATAGAAAATGCTCTAACATGTCTAAATGATATAGAAATGGAATTTTTAAT
CTTTTTTATAATAGTAAGACAAAAAACAATATGACATATATTTCTATGAAACTACACTTAGATA
GAACATCTTGCTACAATTTAAAGAAAAAATGATATTTAAATTGAGTGAGATATTATAAAAAAT
ATGACAACTTTACAACACTTTATATACACTATTGCAACACTAGGCAATAAAATATGTGAGATAA
TGTTATTGTGAAAGAAATCCATATTGAAGGAGGTGATAAATTGAAAAGAATAATATTACCTAAA
AATATAGAAGATATTTGACAGGAATAAATGAGATGTATATTTAAAAATGACTTATATCATTTAT
AGTAAGATTATCAGATTAAGCAAGAATATTTAGTGATAGTGTGGTGATTATTTGCTTAAATACA
AGGAAATATTAGAAACAATTATTGAGATTCTCAAAAAAAACTTTACTGAAAGTATTTTTATTGA
TGATGAAAGTGTGCAAGGCTCTGAAGGGTCTTGTTTTTTGTAAGTATACTATCAGTTATTTGT
ACACCTATAATGTTAAATACGAATAATAAAGATATTGTTATCTCTATAAAATACTTACCAAAAC
CACAGTCAAAGAGTATTAGAATGTATGAAATTTCAGATGAATTAAATAAGTTATTCAACAGAAA
TATAAAGGTAACAGACAGAAAATTAAATATAACAAAGCTAGAACAAAGTATTAAAAAAGAAGAG
TCAATTTATGTATTGAACTTTACAATTACACTAAATTATCTGGATAGTGTATATGAAGAAGATG
TAGTATATGAAAATATGGAAGAAATCAATTTAAATTTAGGAGAGTGATAGTATGGCTATAGGAT
TACCAAGTATCAACATATCATTTAAGGAGCTAGCTACAACTGTTAAAGAACGTTCAGCTAGAGG
AATAATTGCAATGGTGCTTAAAGATGCTAAGGCACTAGGTCTTAATGAAATACATGAAAAGAG
GATATACCAGTTGATTTATCTGCTGAAAATAAAGAGTATATAAATTTAGCTTTGATGGGAAATG
TTAACACTCCAAATAAATTATTAGTTTATGTAATAGAAGGAGAAGCAGATATTCAAACTGCATT
AGATTTTTAGAGACTAAGGAATTTAATTATCTATGTATGCCAAAAGCAGTAGAAGCTGATAAG
ACTGCTATAAAAAATTGGATAATTAAACTTAGAGATATAGATAAGGTTAAGGTTAAAGCTGTAT
TAGGAAAAGTTGTAGGAAATCATGAAGGGATAATTAATTTTACTACAGAAGATGTGTTAGTTGG
AGAAAAGAAATACAGTGTTGATGAGTTTACAAGTAGGGTGGCTGGACTTATAGCAGGAACACCT
TTAAGTCAATCAGTAACTTATACTAAGCTTAGTGATGTAGTTGATATACCTAAGATGACGAAAG
TTGATGCAGAATCAAGGGTTAATAAAGGAGAGCTTATACTTATTAAGGAAGCAGGGGCTATAAG
AATTGCAAGAGGAGTAAATTCTTTAACTGAGTTAACAGAAGAAAAGGAGAAATGTTCCAGAAA
ATAAAAATAGTTGACACTTTAGATATTATACATAGTGACATAAGAAAGGTGATAATAGATGACT
ATATAGGAAAGGTTACTAACAGTTATGACAACAAATGTTTATTGATAGTAGCTATAAAAAGTTA
TTTAGAAGAATTAGAAAAGTCAGCACTTATAGAATCTGATTCTACTGTTGAAATAGATTTTGAA
GCACAAAAATCGTATTTAAAATCAAAAGGAGTAGATTTATCTTATATGACATTACAAGAAATAA
AAGAAGCTAACACAGGTTCTAAAGTATTTTTAAAAGCAAAAATAAAAGTACTTGATGCTATGGA
```

FIGURE 1 (Continued)

```
AGATATAGATTTATCAATAGAAATATAGGAGGATTATTAATATGGCAAATATGGAAGCTAGAAA
TGTAATGAGTGGTACTTGGGGAGAACTTTGGCTTGATGGAAACAAAGTAGCAGAAGTAAAGAAG
TTTCAAGCAAAGATGGAATTTACAAAAGAGGATATTATAATAGCAGGTCAAATGGGTACTGATA
CAAAGTATATGGGATATAAAGGAAAAGGTTCAATAACTCTATACCATGTTAGTTCAAGAATGCA
CAAGTTAATTGGAGAAAAGATAAAGAGAGGTTCTGAACCTAGATTTGTTGCTATATCTAAATTA
AATGACCCAGATTCTTATGGAGCAGAAAGAATAGCAGTAAAAAATATAGCATTTGATGATTTAA
CTTTAGCTGATTGGGAGGTTGGAGTAAAAGGAGAGATAGAAGCACCTTTCACATTTACTGAGTA
TGATTTTCTTGATATAATTTAGTTTTATATTTGGTTTTATACTGATATTTAGTAGATATATACT
TAATAAATTTAGGTAGTTAATAAGTAAAAAGTTAGTTGATTGAATTTGATTGATAAAGGAGCA
AATAATAATGAATGAAAATGGATTATCAAAAAATATAAACATAGTAGATTTACTTTTAAATGCA
GATACAGAAAACTTAGAAAGACCAAGTACTATAGTTGAACTTAAGAGATTATCAACTATATTTG
GGCAGGAATTTAAAGTAATGTGTAGAGCTTTAACAATAAGTAAAGATGAAGAGATACAAAATAC
TTGTCTTAAAATTGATGAAAATATGAAAACGGATATAGACTTACCGGAGATGCAGATGCTTACA
ATTATAGAAGGTGTTTGTGATTTGGATGGAAAGCTTTTATTTAAAAATAAGGAACTAATGGATA
AATTTAAGGCTCCAACACCAAAAGAATTGGCAAGAAAACTATTATTACCAGGTGAAATTACCAA
CCTATATAGAATACTTCAAGATGTTATGGGTTATGGTAAAAATGCAGTGATAGAAGAGGTAAAA
AACTAATAGGGACGGATACCAAGACTACAATAATGTACTATTATTGGAAGAAAAAAGGTATAAG
ACCGTCCCTTTTTTATGCAATGGATAAAGGCGAATTAAAGCTTATTGAAGCTTTTTCGCCTTA
GAAATTGAGGAAGAAGTTGAAAAAATGAAACATGGATATGGAGTGTGTCCTTTGACAGGAGGTG
GTATGTAATGGGAAATGTGAGAGAAGAAGGTATAAATATGTATCTTACAGATAATTACACACCA
AAAATGAACCAAATTATATCAGTAACTGATAATTTTAGGAGAGCAACTGTGGCTGTTTCACTTT
CCACTAATGTAATGGCTAGTAGCATAAAAAATTCTATTGGAAGTGCAAGTAGTAGAGTAAACAG
TTTAAATTCCTCGTTAAGAAAAGTTCAAACTACTGCTAGTAGTGTAAGTTCAACTATGGCAAAA
TTAAGTTCTAGCATAAATGCTGTTTCAGGAGTTATTGGAAGTTTAAATGGAAGTATTATGAGAC
TAGCAATAACTATAGCTATGATTATTGATTATTTAATAAGTTGATTCAAAAGAAAAATGAGTT
TAATTCAAATATTATGATTATATTAATATTTAAAGCTAAAAGTGATGAAGTAGAAAAAACTAAA
AATAAATTACTTGGAAATTTAAAAAAGATTGGTGGCAAGATTTGGAATATCGTAATAAAAGCAA
AAGATATGACTAAGAGAGTGATAAGTAGTATCTTGGGAAAATTAAAACGAGTAGAGAAACGTCC
TTATCAAGGAAGTATTAATCTTAAAGATATGGTAAGTAGTGCTATGGCTAGAATTTTGCCTAAG
TTAATGTTGTTTAAAAATACTTTTTGGAGTGGTGTAATAGCTATAAAAGATATGGCAAGTAGCA
TTATAAGTAAAGTATTTCCCAAATTGAGATTGTTTGCAGGTAAGGTATGGAGTGGTGCAATAGC
TGTAAAGGATATGGCAAGTGGAATACTTGGTTCGATAAAAGGGAAGATATCTGATTTGACAAAT
GGTGCTACTATAGGTGTCGCTGTGAAAAAGGGTGTTGACTTACTTGGTCAGGAACAAAATCAGA
AAGTTGTTCTAGAAAGTGTAATGAAAAGAAATACTGGAAAAACTAGCCAAAAAGATGTTGATAA
GTATTATGACAGTTTAGTAAATATGGCAAATGATACGCCTTTTGACCCTGAAGATGTTGTTGCA
ATGGGAACTAAAGCTAAAATGATTAGTAATATTACTGGTGGCAAAAAAGAAAAGATATAACTC
AAGCTATGGTAGATGTTAGAGCTTTAAATATGAATACAAGTAGTGAACAAGATGTATCAGCAGC
TTTCTTAAGTGCAGCAAAAGGAAATATGGAATCTCTTAATACTCTGGTAGGAGAAAATTATAAA
ACTTTTGATGAAGCATTGGAAGGCATAAGTGTAAAGCAGATGGGGTTAGCTAAAGAAATGAGTA
ATACAATACCAGGTATAATATCAGGAGCTCAAACAAGCATTAACAATGGTTTGAAGAGTATTGT
TAAACCTTTTGATGATATTTTAGGTCAAGGACTAAAGAAAATAAAAACTTTTATAGAAAGTGGA
TTAGGGAATTTAGCTGGCTTATCTGAAAAAATGGCTGGTAAAATAGGCAATGTAATGAATGGTA
AGATAATTATTGGCAACAAATATGACCAGATGCAATCTAGAAGTGTAAAAAATGGAAAGAGTT
TTCTGATTCTACTCAATATCGAATTTCTAATGAGGCTGAAAAGCGTAAAATGATGGTTGAAAAT
AAGCAAGAACGTTTTGAAAATCATGCAGCAACAATGATAGGGAATGCACCAAAAGCAATTGTTA
ACGCAGGAAGTACACTATTACAAAATATTGATTTTACAGCATTAATAGATTCACTACTTCCAGT
AGTAAACTTAGTAAATAATTTACTAGATAGTATAAACAATAAATCACCAATTGCACAAGGATTA
```

FIGURE 1 (Continued)

ATAAGTATATTTGGTACAATAGTAACTACAGCATTCCAACTAATCGGACCTGTAGTTGAAGCTG
TTAGTCCTATTATCACAAGAATTTTTACTTTTTTAGGTGAATATGCACCTCAAATAAACAATTT
TATAGAGACACTGGGTGTTATTTGGAAAACTGTATGGGAGACCTTAGGACCTCTGTTGGAAACT
GGATGGAAAATTATAGAGCCAATATTGGGAGCTTTTTTTAACATATTAGATAAAGTATGTAAAA
TAGTTAAAGATATATGCAAATGGTGGCAAACTATGATTAATAAGATAAAAAATGGAAGCATCAC
AGGAACAGTTTTAAATCTAGTGGAAAAGAGTAAAAAAAATTACAAAGATAATCCATATGCTGGA
ACAAAGGCTGGTGATTCTGGTAAAGCTTATTCAAGTAAGAAAGGTAATAATGCATTTGGATTGA
ACTATGTTCCTTATAATGACTATCAAACCAGACTCCATGAAGGTGAAATGGTTTTAACTAAACA
AGAAGCAAATCAATATAGAAGCAGAAAAAATGGTGGAAATATAAACATAGCTAAGTTAGCTGAT
ACAATAGTGATTAGAGAAGAAGCTGATATAGAAAAGATAACATCAAAATTAGTTGCAAGTATCC
AATTGGCACAGTTAGGGGGTGTCTTATAATGGAAATGTGGCTTAGACAAGCAGAAGATAGATTT
AGATTTCCAGTATTTCCATCTTCCTTTAGTATTAATGGAAAAGCTGCTGTAAACTCTTCTAGTA
TACTCAAAATAGGTGAAGTAGCAACTTTTGGTGGTGTAGCTCTTAAAAGCATTTCAATATCAAG
TTTTTTTCCAAATAAAGACTACACTTTCTGTGACTATACAGGTTTTCCATCACCATATGATTGT
GTAAATAAGATAGAAAAATGGATGAAGGAAGGTTTTATATTAAGATTTACAATTACGGAAACAA
ATATAAATATGGAAGTCATAATTGAAGGTTTAGTTATGAAGAAAGAGATGGGAC

SEQ ID NO:33         Middle fragment
TCGAGATGTATATTTTACATTAGATTTAAAAGAGTATAAAAGAATAAAGATACCAAAAGTAACT
CCAAAACAATAACTATTATAGATAATAAGTTGTAAGTAACTGCTGATAGAATTAAATGAAAAGG
CAGGTGATTTTTTATTATTAAGATTTGGGTACACATAAAAAACGGAAGTATATATGACATAACT
GACATAGTAGACAAGGTATCATGGTCAGGTGATTATAAATCTCCATCAAGGACACTAGAGTTTT
CAATAATACAATCATCATTTGATGTAAATTTCCAACAAATCGATATACCAATAGCTAGTACAGT
CTGTTTCTATGTAGATGAGAAAGAACTCTTTAGAGGAATGATAATTAATAGGTCTAAAGATTCA
AGCAGTAATGAAATTAGTTTTGTATCTAAAGATATGGGATTTTTACTTACACAAAGTGAAGTGT
CATACAATTTTAAAGATAAGTTAGTTGAAGACATAGCAAAGCAAGTATTTGCTGAAAATAGGCT
TTCAGTTGGAACAATAGCAAAGACCAATGTCAAGTATACAAAGATGTTTATAGGAGTAAATGGT
TATGACACAATAATGAGTGCATATACAGAGGCAAGTAAAAAGACAAAGAAAAGTATATGATAG
AGGCTAATTTAGATAAGTTTAATGTTATTGAAAAGGAACTGTTACATTAAGTGTTATGTTTGA
AGAGGGATTTAATATTATAAATACCACCTTTTCGGAGAGCATGGAAAATGTAAAAAATAAAGTA
ATAGTGGTAGACCAGTATGGAAGCAAGATTAGCGAAAAAATAGATAATGAAATTTTTAAGGAAG
TAAATGTAATAATGCAAAAAGTAATTCAGCAACAAGAAAATCAAGATGTAGATATTGATAGCGA
GTTTAATGGGATAGAAAAAAGCTGTTCTCTTAAaGGTTATGGAGATGTAAGTTGTATAACTGGT
AGAGGAGTAAAAGTTAAAGATTCTTATACAAAGCTTGTAGGACTATTTTATATAGATACAGACA
AACATACTTGGCAAAATGGAGAATATCAAATTGAGCTTGAACTTAATTTTCAAAATCTTATGGA
TGAAAAGTCAGCAGGACAGGATGAACCTAAGGAAGAAAGTAATTTAGGGGGAGAAGATTATGCA
GGAGGAAAAGAGTTTACAGCAGAATTTACAGCTTACTGTCCTAGAAAAGAAGAAGGTGGAGATA
CAGATTGTAGAAAGAAAAAACTTGACCCATCTAAAAAACTTGCGCTGCTCCTATGGTTGGTAAA
TATGAGCAAACTTATTATACAAAAGAGTTTTTAAATAAACATCCTTTATTGAACTATGGAGATG
AAATACAGGTAATTACAGGAGTTTCTGGTCGTGATGGAGTCTATAAAGTAAATGACGTAGGACC
TGCAATAACTATAGAAAAAATGGAACATACCATATAGATATTTATTTGGAAATGTTGAAGAA
GCTAGTAAATTTGGAAGAAGAAAAGGAAAATTATTATTGGTGGTTATTCTGGTAATGTATCTG
ATAAAGCTAAAATAGTAATATCAGAGGCAAAAAAACATCTAGGTAAACCTTATAAATGGGGTGG
AAATGGACCAAGTAGTTTTGACTGTTCTGGTTTAATGGTCTACTGTTTAAAAAAGTTAATGTT
AGTTTGCCAAGAACGTCAAATCAACAATCTAAAAAAGGCAAGAAAGTAGAACAAAAAAATCTTC
AAGCAGGAGATTTAGTATTTTTTCATAATCCAGTCAGCCATGTTGGATTATATATAGGTAATGG
AGAATTTTTACATGCTCCACAAAAAGGTGATGTAGTTAAAATAAGTAAGTTAAGTAGTAGAAGA FIGURE 1 (Continued)

```
GATTTTAATACAGCTAGGAGAGTATTATAAAAGGATGGTGATATAATGGCTAATCCAATAAATG
AATTTATAGGAATAATAAGAGAAGAAGGAAAGTATCATAATCAACCTTCTTTTTTATTGGAAAA
TTAAAAGTAAATTACCAGATTTAAAAATAGAGACAAATAACATCATATTAGAAAAAGAAGATAT
TTTGATAGATAGTTGGATGATTGATAGACAGCTAGAAACATTTGACACAGAAACAAATCAAGAA
CACCAGCATGAAGTAAAAAATCCTTTTATAGATAACTTTGAATCTGGGGATATGGTAATAATGT
TTAGAATAGGCGAAAAATTTGCTGTTGTAAGTAAGTTGGTGAGCTTATAATGAGTACAATATTT
CCTTTTATAGGTGTCCCAGAGGATTATATCTTACCTAAAACAGAAGAATTGCCAATCTTTCGTG
AAGTGGCATGGGATTTTGAAAAAGATGAACCTATTTAGAAAAAGGTGACTTTAAAATAATTGA
AAAAAAAAGAAGCCTTAAAAGTTTGGATATACAAGTGTATAAAGACAAATAGATATGAACATGA
GATATACTCTTTAGAATATGGGACAGAGCTTTCAGAACTAATAGGACAAAAATATACAAAAGGT
CTTACAGAAAGTGAAGCTAGTAGATTCATAAAAGAGGCCCTTCTAATAAATCCATATATATTAG
AAGTAAACGTAAAAAGTGCTAACTTTAACAGAGACGTATTGAGTGCAAATGTAAAAGTATCCAC
TATCTATGGGGAGGTGGAAATAAATGTATAGTGACCAGACATATGAAGTAATAAAAAATAGAAC
TCTTGAAAATATTAATCTTGATATTTATAAAGGAGAAGGTTCTTTTCTAAACAACATGGTATCT
GGAAATAATCTAGAACTTTCGAAGATATATCTAGAACTTTCAAAGATACATAAAATGGCTTTTA
TACAAGACACATATAACCAGTTTCTTGATAAAAGAGTCAATGAATTTGGTGTATATAGAAAGTT
AGGTACAGAGTCAAATGGAGAAGTTGAATTTATTGGAGAGAAAGGAACTGTAATAAATAATGGC
ACAATAATATCATATAGAGATTTACTATTTGTAGTAATAAAAGATGTAACTATTGGTAGTGAAG
AAGGTGACAATAGCCCAGTTCAAGCTCTGGAAGTTGGTAAGAAATATAATTTACCTACAAATTG
TGAATTTAAACTAGTTGATAATATATCTGGAGTAACAAAGATTACTAACACAAGAAGTTTTGAA
GGTGGTACAGATATAGAGACAGATGAAGAACTAAAAGAAAGATTTTATAAAATCCAAAGAAATC
AAGCTACAAGTGGAAATAAAGCTCACTATGAAGAATGGGCTTTGGAAGTAGATGGAGTCTATAA
TGTTAAGGTTTATCCAAGATGGGATGGTCCAGGAACAGTTAAGGTCTTGATATTTGGGGAAAAT
AATCAAGCTGTTGATACAGAAACGATTGAAAGGTGTCAGCAACATATAGATGAAGAGAAGCCTA
TTGGACCAACTATAACAGTTGTGACACCATTACCAATAGAAATAAGTATAAGTGCAGTAATGAA
ACTAGAAGATGGATATACATTAGACAATGTAAAAGAATCTTTCCTAGAAAGTATAAATACATAC
TTTAGAGATATTAGAGGAGAGATAATCTATACAAAAGTCATGGGAATACTTATAAATACTACTG
GTGTACACGATTTAAGTAATCTACTTATAAATGGAAGTACAGATAATATAACTATTAATGAAGA
TAAAATACCTAGTGTAACAACTGTTAATTTTAGTGAGGTGGAAAATCAATGAAGCTAATTGATA
AACTACCATCATTTGATAGAAATTACATTGTAGAGGAGATACAAGGTGCATACGATACAGAATT
AAATATTCTTAAAGAAGATATTGATGATACCTTTAACCAATTATTTGTTGATACAGCGACATGG
GGATTAGATATGTGGGAAGACATACTCTGCATTGaAAAAAAAGAACTTGATTTTGACACAAGAC
GTAGCAATATAAAAGCTAAAATGAGAAGCAGAGGTACTAGTACTATTGAAGTTATAAAAAGTAT
ATGTGAGGCATATACAAAATCAGAAACAGATATAAAAGTTTATAGTGATGAATTTACATTCGTA
TTGAGTTTTATAGCAAATAACTGTGACTATAAAACTCTTTTAGATTGTAGCGAGATGATTGAAA
GAGTAAAACCTGCTCACTTATTACACTATTTAGAACCAATAATACTAGATAAAAGTATGGTCTA
TTGTGGTGGAGGTATGGTATGTAGTGAAGAGGTAAAAGTTCATCCATACTTTGAACCAATTATA
AAATGTAGTGCTGTTGTAAACTGTGGAGCTGGAATGTTAAGTAGAGAAGAAATAAAGGTTTATC
CTTTAAGCATTAAATGCATTGAAAATAATTGTAAGATTAATATAGCTATTGCAAATGATACAGG
CGTAGAAAATGTAGTAGTTTATCCTAAATCGGAGGTGGTATAATTGGAAGAAAATTTTATATA
ATATTAACCAAAATTGGTAGAGAAAAAATAGCAAATGCAACTGCACTAGGAGAGCTTGTTGGAT
TAACCAAGTTTCAAGTTGGAGATAGTAATGGAGAATATTATGAGCCAACAGAGGAACAAACTGC
TTTAAAGAATGTAGTTTGGGAAGGAAATATAAATTCTCTAAGAATTGATGAAAAAAATCCTAAT
TGGATAGTTATAGAGACTATTTTACCAGGAACAGTTGGTGGATTTATGATAAGAGAAGCTGCTG
TTCTGGATAATGAGAATAATATAATAGCTATWGGTAAGTATCCAGAGACGTATAAGCCACGTGC
TGAAGATGGCAGTATTAAAGATTTGGTTGTAAAAATGATTTTACAATTGTCCAATACTTCAAAT
GTTACATTAGAAGTAGACCCGACGTTGGTTTTTGTAACTCAAAAGGATATTCAAGATTTAGATG
```

FIGURE 1 (Continued)

```
ATAAGTTTGATAAAAATATAAAAGAAATAAAAGTAAAAATTGGAGATACAGATATATTAACTAC
AGATTCTAAAGATTTATCAGGAGCTATAAATGAGGTAGTTAAAAAAATAGAAAATATATCTTTT
GATGATGTTATAAGTGGTCAAATACAAACTGATATATCAGTATTAAAAAATAGCTATAACAAAT
TATCTGAAAAAGTGCTAGATATATTAATATACCTAGAATTAGAGTCAGAAGTAACTGTAGATGA
GGCTGGTTATTGGTATGATACATTAGCAAATGGAAATAACATAGTAGCTATAGAAGGGCTTAAG
TTAGATTTAAATAGAAATGTATAACAGGTGAAATTGGTAATGTGATTTTTAGAGATGTAGTAT
TACCATTTAGTGCAAATAGAGTTAGATATATACATGATATGGATAATAACTTTGTTGAGACAAA
ATCTAGTAACACTTATTTAAAAGAACAAAAGATATAACTCTAAGTAAATATTCATATGAAATA
AGATAAATAAAGGAGGTAGTACTAATAATGAAGCAAAATAAACTTTTACAGCGTGGTGCTTATT
TTAATGATAAGAACATATTGATTGATGATTTTGATAAAAGATATAATGATTATGATTTGTAGA
ATTTTTTACTGGTATAAGTAATAGTACCTTTGGTTTAAAATCAGATGGTAATTTATATGCTTGT
GGCGATAATACAGGTTTTCAACTAGGACTTGGAAAAGATTCGTCAGAGAGAAGGATGTTTAGTA
AAGTAAAAATTGATAATGTAAAATATGTATCTTGTGGTTCAAAACACAGTGTAGCAGTAACTAA
AGATGGATTTGCATATGGAGCAGGAACAAGTAATGTAGGTCAATTAGGTGTAATTGAGTCTACA
GTATATTATGAATTACTAAGCTACCAATAGATGATGTAAAAACTGTTGCATGTGGTTATGACT
TTACATTTGTGCTTAAAAATGATGGAACATTATATTCAGCAGGTTTAAACTCAAGTGGTCAACT
TGGACTAGGTGATACTAACAATAGAGCTACTTTTACTAAAGTAAATATAGATAGTGTGAAAGAT
GTAGTGACTTATAATCAATCTGTATTTATCATAAAAATGGATGGGACAGCACATGCATGTGGAT
TAAATTCAAATGGGCAGTTGGGAATTAATAGTACTTTAAATAAAAGTGTATTTAATAAAATAGA
AGGTATGGATAATGTAAAACAGATAGCGTGTGGTAGTAGTCATACAATTCTTATTAAGAATGAT
GGAACTATGTATACTACAGGCTATAATGGAGTTGGTCAGCTTGGTACAGGAAATAATAATAATT
CAATTGTATTTACTCTTTCTAGTATAAATAATGTTAAGTATGCTTCTTGTGGAAATAATCATAC
TATGATATTAAAATACGATAATACACTGTTTAGTACAGGACAAAACAATTATGGTCAACTAGCC
AATGCCAATAAAGATGTAGCATCAAGAAATACTTTTGCTAAGGTTAATGTAGAAAATATAAAAG
ATATTAAATGTGGTTCTCAATTTAATTTTTtAATAAATGGTTCAAAAGAGATATTTGTATCTGG
CTGTAATTTAGCAGGTCAACTTGGTTCATTTTTTCATACAACTTTTCTGTATGAGTTTTCAAAT
GTGCAATCTTCAAATTTAGATAATTATTCAGGTTTATTGGTTAATGATGATTATTTATATGTTA
CAAAGGACAATAGTGAATTTTTAAATGTAAAGTTAAGTGATAATTTTCAAGATTATAAGAAGAT
AGAGTTAACAGATAGCAATATGTTTATTGTTATGAATGATGGTACATTGTATGCTTGTGGTTTA
AATAATTATGGACAGTTAGGATTGGGAGATACTGTTAACAGGTCAGTTATGACTAAGGTGGATA
TAGATAATGTTTTGGATATAAAAGGAAACGGAAACTCAACTTTTGTGCTTAAGAATAATGGAAC
ATTATATTCATGTGGTTTAAATAGTAATGGACAATTGGGTTTAAGAGATGAAGTTAATAGAAAT
ATATTTACAAAAATAGAAATAGAGAATGTAAAGGATTTTTGTGTAGGAAGCAATTATGTCATAG
CTTTAAATCACTCAAAAGAAGTATATGGATGGGGAAATAATCCTTATAATAATATAGAAAAAAC
TTCTAATTATCCATATAAGCAGGGAATAAGTAATATTGAAAAGATAGCAGCATATGATTATTCT
GTATATATGATAAACAGTGAAGGGAAACTATATGTTTCTGGATACAATTATAATTATCAATTAG
GTAAAGGAAATAATAGTAACCAAAGCAAAGCATTAGTATCTCAATGTAGAACAAATTCAACATC
TTCTACATCAAATGGACTTAGAACGTTACCTAAAATAACTAATGTTTTtCCTTTTTATGATGGT
TGTGCAATAATTGACGAAGGAGGTTATGTTTATTTAACAGGATATCATGGATATTTAAGAACAT
TAAATAGCAGTCCAAGTATATCTGATTATTCAAGATATGGAACTTTTATTGAGGCTACAAATTC
AAATCATAATACTTATTTTATACAAGAGACTGATTTAGTGGAATTGAAAAAGTAATAGGGATG
TCAAATAATATATTATTTTTTAAGAAAGGAAGTTCATATATTACTGGATATCCAAAAACATTTG
GCTCAACCATTACTGGACATAGAAGTTATACTAGTATTAATTCTGAGAGTTCTAATTTAGGAAG
TAATTTTATAATATATCATAGTAATTCCAAGTTATATGGAAAAGGGATTGCTAATAGTGGGCAA
TTTGGG
```

FIGURE 1 (Continued)

SEQ ID NO:34        3' fragment
AATTCAACAAATATAGATGGCACAAGTAACTATGATACAGGATTAAAAGACATAAAAGATATAA
TTGTAAAAGGAAATACTGTAGTAGTAGTAGATAAAAATAACAATATATATGTAACAGGAATGAA
TCAGAATAACAAACTTGGGATAGGGGAATATAACAACGAACCAGTAAAAAAATTCACAAATATA
ACTGAACAATCAAACTCATTTATATTTATGGATGATATAAAAGAAATTACAACATCAAGAAATA
CAATGTTTATAGTAAAAAATGATGGAACAGCCTATGCCACAGGAAATAATAGTTCTGGACAATT
AGGATTAGGTGACACAATAAATAGAAATAAGTTCACTCAGATAAACCTTGATAATATAAAGAAA
ATATCAACAAGTATAGATGGTAACACAACATTTGCAATTAGAAATGATGGAACACTATACTCCA
CAGGATTAAATACCAAAGGACAACTGGGATTAGGTGATATAGTAAATAGAAATACATTTACCAA
AGTAAACATCCAAAATGTAAGAGATGTTGTTTTAGGGACTACTCACTCGCATGCAATCAAAGAT
GATAACACATTATATTCATGTGGAGaAAACACTCATGGGCAACTGGGCTTAGGAAGCGAAAGCA
ACCATCCAGACGTATTGACATTTACTGTAAACAATATAACTAATGTAAGAGATGTGTACTGCTC
AGATACAACAACATTTATTGTAAAGGACACAAACATTGCATATTGTTGTGGATACAATAATAAT
TCACAACTAGGTATGGGAAATACTACTGACCAGTATAGTTTTATAAAGTGTATGGAAAATGTAA
AAGAAGTTATACCAAATGAAATAAATACCTATATAATAACAATCTATAATACTGCATATAGTAC
AGGTTTAAATACTGATTATTGCTTAGGTCTAAATAGTAATAGCAATCAAAGTTCATTTTCTGAA
ATTCCAATTTCAAATGTAGTAAAAGTAGCTCCAAACAGAAATAATGCAGTACTTTTACTTACAA
GTGAAGGGGATGTATATACTGCAGGCAAATGTAGTAATGGTTCAGGTACAGGAAGTGAGACTCC
AGAGAAGATTAAAAAAATAGCATCAAAGGCAAAGGATATTGGAATGAATTATAGATGTGGACAT
TATGTAAGTGATAATGGAGACCTATATGGTACAGGTTTTAATAATAATGGACAATTAGGTGTTG
GTGATGTAACAAAAGAGATACATTTATAAAAACCAATACAAGAGTAAAGAAAATACTTCCTTT
AGAATATGCAAATATAGCAATAAAAGATACTAATGATATATATATTTGTGGATTAAATAACTAT
GGACAATTAGGTGTTGGAAATAGATACGATAGTAGAAATAATGATAATAGAATATTTAATTATA
AGCATATGAATTTTGTAATGGGTGATTTGACATCTATTAAAAACAGACATAACTTTATACTTCT
AAACAATAAGATAGTGATACCTACCACAAAAGACATAGATTATGGTTTAGTATTAGGAAATTTA
TACAAAGGAGACCTTTATACTGAGCTTCCATATGAAGATATAAAAGAAGTATCTATTTCTAAGA
CTCATATTATTATATTACTTAATGATGGAACAATGTATGGATGTGGTACAAACTACCATGGAGA
ATTATTGCAAGACTTGTCTATAAATCAAGTGGATGAATTTGTGCAGATTAATGTATCAGATGTA
AAGCATGTTTCATGTGGAGATAACTTTACTTATTTTATAAAATCTGATGATAGTCTTTGGTCTA
TTGGTAAAAATTCCGAATATCAATTAGGTATAGGTCACAATAATCCAGTTACTGAATTACAAAG
AATTACAACTATATCTAGCTGTAAAGAAGTACATTGTGGTAAAAACTATACATTAGTAGTAACT
ACAGGTAATGAATTATTTGTACAAGGATATAATGATAAGGGAGCTTTAGGATTAGGAAGCGATA
GTGAAAATACTATAATTAAGTTCTTTACAAAAGCACTAACAGACATAAGAGAAATAAAATCTTA
TGGAAGTGACCATATATTAGTACTTAAAAATGATAATTCAGTATGGGTTACTGGAAAAAATAGG
GATGTATATAAAATTGAACAACCAGTAGAATTTTAAAAGAATTTACTATAGTACCTATTTCTG
AAGATGTAAATACAGTAAAGGATGTACTTGCAACAGACAATACATTATATATTATATCAGAAGT
AGGAACGACAAATGCTGCTATAGAAATTACTGAAAAATCAATTTCATCAATTAAGATAAAAATA
CAAGACCCTAATAAAGATATAAGTAGAATAGAAATGCTTATAAATGGTGAAAGTGTAAAATCTG
TAAGTGATTTAACTACTGAAAAATATCCTTTGAAGTACCACCAGATAAAATTAAAATAGGAGA
GAATAAGATACTATTTAGAGCTTATTGTAAAGGTGATGATTTATATGCATCTTTATTTATTTTT
AAAGAGAGTACTGGAAATTCTATAATTAAAGATTCTTATGTTATGATAGGTAATAGAATGTACA
AGGTAGTTAATACAACATCTAATGAACAAGATATTACAATTACACTAGATAGAGGACTTGAAGA
AGATTTAAATCTTGGAGACCCTATATATCAATTAATAAATAAACTAAAGTTCAAGTAAAAATA
AATAAATCTGACTTATTCAAAGACATGAAACTAGTTGAAATCAAAAAATCAGACTCAAGTTATC
AAGAAATCTATGAATTAGAAGAAGCCAACATAAAAAGTGCTCAGCCTAAAATCATAGTAGAAAA
AGGAGATAAATGGACAGCTATAAAACGTCCATCTATGATTTTAGATATGATGCTGAAAACAAC
GAGCCACAAGCTTAAAATGGAGGTGTAAAAATTGTTTAAATTCGATAAAAATAAAATAGAACAA FIGURE 1 (Continued)

ATCAAACAAGGTAGAAAAGTAGAAATGCAGTATAAAGACATTTCAGACATAAGTATAGGTCAAG
CAAAGCAAGATGATGATATAACAAATAATTTTATAGCAAATGCAGAAATATATGAGATGTTGTT
AAGTCAAAGTTCTGTCAATGAAGCAAGTAATATAAGCACTTTTAGTGTAAGAAAATCTGGAGGT
GAGAGTGGAATGGTAGAAGTATATGTAGCTTTAATTTTAAGAGGCAGAAAAACAATAGAAGAAG
TACCAGCAGTAATTAGAGAGCAAGTTAGAATTAGATGTAAAGAATTAGAAATACCAGTTGAATA
GTAAATTTAGAATAACTATGTATTAGTTAtTTTTTTTATGTAAAGTACAAGGTCTTAACTTTAA
TAAGTAAGCCTTGTACTTATTTTTGTTATATTAGAAATTGTATATATATTTATTATTTATTCA
ATCTATAAATTAAACCTACAATTTAAAGTACAGAAGATTAAATTGATAATCCTGAAAATATAAT
ATTGCATGATGTAAGAATATAACAAAAATTAAAGCTATAAGTATAAAAAATTTAGACAATAGGA
GGCTATAATGGATAAATTAATAACCGAATTGAGTAGTCTGGGGGCAATAGGTATACTATGTGCT
CTATTATTTAAAAATACTATGCAGGAGAAAAAGAAGATAGAGACATGTATAAAAAACTGTAG
AAAATTTTATAGAATTATCTACACAACAACAAGAAATAAACAAAAATATACTTGTTCAAATGGG
AATAATGAAAACAGATGTAGAGGAAATTAAGGAAGATGTTACTGATATAAAAGGTATGTTACAA
AACGGTGTATAACATGAAAGTAGCAGTAGCACCAGATTATATATTATTAGGAAAAGATAAAGTA
GTATTGTAGATAGTGCCCTATTTTATTGAGAAGGATTTTATATTTTAAAATATTAATTAAAAAA
AGTAATAAAAATAATATATAAAAATAACATATAAAAATTCAAAAAGGAGTTAAGCTTAAATTTG
ATTAGAAAAAATCAATTTTAAGACAACTCCTTTTTTTtATTAAATTATTGTCTATTAACCAAAA
TAGCTATTTTAGCATCTGGATTATAACTTATCTGAACCATTTGATTTTCTTAACATGTTCAAG
GTCTTCACCACCATAAGCTATTTGTAACTTAACTGGTAACTTACCTTGTTTATAATAGCAACG
TACTCTTTTTTACCTTTTTCTCTAAACTAATCAAATTGCCAACATAAGGTTTAAAGTTCTGATA
CTTTTTACTAGAATTTCTTATGTAGAAGAAAGCACCAACAGCAATAACTAAATTTATGCCAAGT
GTAACCCAAGAATTGATTTAAGCATAGCTCCAGCGATTATTATCACGAACATTAAAACGATAG
GTAATATAGCTTTCTTAAGAAGCAATTTACCCATTATTTCATTAGCCTTTTTCTCAGGGCCACT
CATAGTTTTTGATCTAGCAAATGATTGCGCGAATTTGTCTCTTAAGCCCATTTTATCCTCCTAA
TTTTAATAAATATTTAGTTATAATAACGAGATATTACTTGAAACTAAAAATTTACTACATTTAT
ATTATGTTTGACTTTTGTATAAATAATTACATTCAAGTAAAGCAAAATATACTAATTATTTTAT
CATAAAATTATAAAAAGAAAATAAATGAAATAAAAATATTAGAACAAAGAAATGATGTAAAAT
CGTATCAAAAGCAACATAAAAATTATTTATCTATTTTCTCATCTTTATTTTTGTTATACTCAAT
TTTTCCTAAATCCTTCTCTTTTTCATATTCATGAAGTTTTAATTCAATCATACCTTCTATTTTG
GCTTTATCATAATCATTTAACTTTCTAAAGTTGTTAAAAGCTTTATTTCATTAGAGTTTATGC
TATTAAGTGGATAGTTTGAGGAGGAATCGCAAATTAAATCTGATTTATGTGATAGATTATCTCC
ATTTAATAGCCAGTCTACTGAAACATTAAATATCTCAGCTATAGATTTAATATTTCATAATTT
GGTTTTCTAATGTTTCTCTCAAATTTACTTAAGTTGTCACAGCCTAACATTTCTTCTAGTTCAT
ATTGTTTAAGGTTTTTTGCTTTTCTCAAATAAACAATTCTTTCTCCTAAAGTATCCATAAACAC
TCTCCATTCAATTAATGTCAAAAGACTTTTTAAGATGTAAATAGTTTCAAATTAAAGGTCAAA
ATGACATAAAAACCATTGACTTAAGGTCAAAATGACTTTATAATTAACTTAATGATACGAATTT
ACATCCTAATTTTAGCACAAAGTAATCAAAAAATCTTATTTAGTATTAAATAAATTTATATACT
TAATATGTGTACATATTAAAAATATATACTAAATAGAGGGGGTGCGTAAGCTAAAGTAATATAA
AAGTAAATATAAATCACTTAGAAAGGAAGTTGATAAATGGATGCTCGAAAAAATGGATACCTT
TTTTGGGAGTGCAAGTCAAGCAAAGACTTATTGAATTAAATATGACTCAAAGGGAATTAGCGAA
GAAAATAGGTGTTAATGAAAACTATTTGTCAGCTATTTAAATGGAAGAAGAACAGGTAAAAAA
TATAAATCATCAATTTATCAATTACTTAATATAGAATATTCAGAAGATGATTAATAAATAGTAT
ATAAAGTAGGTGAATATTCTTGTGTGCAAATTGGATTCAGATGGGGTTATAGAGTGTTGTAGAG
CAATTGATGATTTTATTACAGCACTTAGTAATATAAAAGCTTAAATATGGAAAGATTAAATAC
TTTAACTAAATATTCTAGTACATGTTCAATCCTTCTTAAAGAGGGGAATTATGAAGGATGTACA
ATTGTGTATAGAAGATGTTGGAAGAATTAAAAACATGAGTAATGCATTTCTTAGGAATATAAA
TTATACATAGAAATGTATTATATTTTTCAAAGTACTTAAACTAAAATATGGATAAGATAATCTA

FIGURE 1 (Continued)

```
AATATTATAAATGTGCTTGAAATTAGACTATACTTGTTTTTAAATAATCCAATATCCATATTTT
AGTAATATACTACAAAAAAAGAAGGTTAATAGATGATGTAAAATCGTATCAAATTATGTATGTT
TAAACCATTTTATCTTCATTATTATTAGAGGAATGCTTTTTAAGTCTTTATATTCAGATATCT
TAAGTTCAAGTATTCCTTCTATTTTATTTTATCACGTTCGTTAGTTGTCTGTATAGATTTAA
TATCATCATTTCATCATTAGTAACATGAAGTAATCTTCTTTATCTTCTTTTACACTACTATTG
ACATTTACCTTCTCTTTACCATAGAGAAGCCAGTCAGTCGTAACATTAAAATAATCAGCTATTG
ACATTAGTATATCACAATTAGGTTTTCTATCTCCTGTTTCATACTTGCCTAAGTTTTCAAATTT
TAAAATATCCATAAGTTTGCGCTGAGTAAGTTTTTGGAGTTTCTCAAATAAGCAATTCTTTTT
CCTAAAGTATCCACAAAATACACTCCTTTCTTTTATGAGTAATGTCTAAATGACATTTGAAAT
TAAAAATATATAAATTTATAATATAAAACTACTAAATTAAAGTCTAAATGACATTTTGCTTAAA
TTAATATGCTCATAATATGATTTTAACATATTATAGTTGAAAATATATGGTTTATTTTGATTTG
TATATATAACAATAGATTTAATTGTTATAAAAATGTAAAGGGGTGTATGAATAGATTGTATAAA
TTTATTTCGATAAACTAAGATTGCTTTTTGATTGTCTGTAAAAGAGAAAAAGATTAAGATAAAA
ATAGTATTATATTGTAATTTATATTAATCAATTACAAAGATTTTATGAATTTATTCTTTAGGGT
AAAATATTTAAGAATAAGATAAATTTACAATATAATACTATAACACTCTTTTATCTAGTTTTAT
TTTCTTTATAGAACAATAATATTTATAAATGCTAGTAGATTTACACAGAATACTGTTATATACAT
CTGTTTGAATCCTGAGTTTAGAGTAGATTGTAGTGtGGATCCGG

SEQ ID NO:35        >AV1368
tttttttGCGGCCGCaatacccactacaccttcgtc

SEQ ID NO:36        >AV1289
Tatacatctcgagtcccatctctttc

SEQ ID NO:37        >AV1288
gaagaaagagatgggactcgagatg

SEQ ID NO:38        >AV1366
CTTGTGCCATCTATATTTGTTG

SEQ ID NO:39        >AV1367
GGAAAAGGGATTGCTAATAGTG

SEQ ID NO:40        >AV1300
tcccccGGATCCacactacaatctactctaaactcagg

SEQ ID NO:41        >DG1
GGCGCGCCACTAGTACCGGTGCCATGGCGGCCGC

SEQ ID NO:42        >DG2
AGCTGCGGCCGCCATGGCACCGGTACTAGTGGCGCGCCCATG

SEQ ID NO:43        >DG9
ttccttggtctcAcgcgAACAAAATTCTCCAGTCTTC

SEQ ID NO:44        >DG10
ttccttggtctcAggccGTCGCGACTAAGAAAATGCC
```

FIGURE 1 (Continued)

SEQ ID NO:45          >DG13
gtgagcggataacaattccc

SEQ ID NO:46          >DG14
AGATTGTAGTGtGGATCCGG

SEQ ID NO:47          >DG15
tccttcggcgcgccTCAAATTTAAGCTTAACTCC

SEQ ID NO:48          >DG16
TTTAGGGACTACTCACTCGC

SEQ ID NO:49          >CD4  Orf1374
MKRTKLLQRGNFFGDKNMVVDEFDEGYDNYDFINFFTGCCNYTFGLKNNNILYGCGDNSNFQLG
LGEDNTTRKLFTKIPNISTNIKKVACGESHAVILTSDGELLVAGINTDGQMGLGLEKVGKTVST
FEKVPEIKGVKDIACGLQSTYLLYNDGTLYVAGNNLYGQLGLGTNGASANVNTFTKVDVDNVKA
VFSYNKSAFIIKNDNKCYSTGFNNQGQLGLGDKNNRDLFSLVSINDVKTIACGSEHTVLMTYNN
DIYGCGKEKCFGNALQSSLFTKIEEVNIKTIACGHGNTMLIDNKGTLKVAGNNDIYQLGIANYS
ENIDNSFIDLKNIVAKNIFIGLSHSILIDSNNDSYCTGDNTYGQLGSFFDDMHIVEFKKMDSEK
YSYSNYINLIKSEDKLTLLKEEMEIKDIELPLDIHSVRDVVFSPYCTLVILGNGDVYGLGNNRY
KGMGSDLPSQLNELTKLSISNVKSIVASKNISGGIFYIKNDDTCYYSGPNSNSIAGVLPSNSDV
FKKISIDNVKKVVINTDLSNWFSLIVTNNKQIYTSGKSSSYVNGLSNALISQYTEISLSNVTDA
YSSYNATFIVVDEKKVYATGINTNYLLGFSTSDGSNVNLGLLSDWYYINISGSSYSRVSCTNNI
TKINNIIIYEYVTVFCTNIGSFLTGYHGTSWTKPTDSSYRVQYQGISYAGYLDSYIYNYYPTRC
TQSSSSTTFAYLYNGESSSNLKNVNPDNLLISGGSSYIHQYGRNYLNNQSSNNIAASNINSGPI
TSDKAIFLYKALLYLSSNTLYGFGNISESAKELDVSDTQDGYNATNYKKVMKNIKNIFIPPYDL
SRDKTRFAILTDKSLFICGYNSKGTHGISVNSSLNLNNKINYNKKNSSSEISSNIQEIYSHSKS
TYLLTNNNMLYSVGLNDVGQLGVGDEINRKVFTKINIDNIKSINVNRFTDNSKHAFAIKNDNTC
YAVGLNNSGQLGIGDNVNRNIFTKINVENVKYVAVYGNTSLLLTNDGLLYGAGNNGKGQLGLGD
TTSRNIFTRIPINGVRDVYLCNDVSIIVKNDNTCYVCGLVNGYFGFTEGSISTFTKINIENVKS
VVTAGSEATFFITNDNMIYTTGKKERVFFSTETNDIKGIRVINNIINAKKIVVNGYTSAILTND
NKLFVGGLSGYGSIANNNNTNSVEDVKDVFVTANNTLYIDNNNNLISSGRDTYGISDESYRDMS
VPYYKVSIKKDVDTVFSSYNTIFIKDIYGKFYSSTRDNRYNHLGIHHRYDNDKNEALEGSLHSY
FKTDNTSDKIVFNKKNEKLVMFNDKYIKTNNKYINYKNIFKDNFKYTSIILPFEVSDIDISKTH
SLAVAKDGKLYGIGSNSYKEINQTLEDIELLTLTEVNISDVKKVACGDNYSYIIKTDNTLWSYG
KNTEYQLGVHNNDVRELQKVTGLPSVKDISIYNSMTLVLTNEGELYAQGYNTNGLFGLGESEK
DKIIRTFTKVLTNVKEIKSHNDDHILVIKNDNSLWITGKNKSMYKISISITDLYEFTKIPIPEH
LNDILDIELSDDTIYMITKVDTSKASIEIVEKSISQVRVVVQDPNNVIEKLEMFINDELISTKT
NLEINSIIFEIPQNKIVLGENKILIKASSPTGDLYSSMFIFKSETGLKVKKDSILMINNKVYSI
INITENNTDLIVTLNEGLKDDMMENNPIYQLINKTKVQVKINKSDLFKDMKLVEIKKSDSSYQE
IYELEEANIKSAQPKIIVEKGDKWTAIKRPSMIFRYDAENNEPQA

FIGURE 1 (Continued)

SEQ ID NO:50          >CD108    Orf1374
MKQNKLLQRGAYFNDKNILIDDFDKRYNDYDFVEFFTGISNSTFGLKSDGNLYACGDNTGFQLG
LGKDSSERRMFSKVKIDNVKYVSCGSKHSVAVTKDGFAYGAGTSNVGQLGVIESTVYYEFTKLP
IDDVKTVACGYDFTFVLKNDGTLYSAGLNSSGQLGLGDTNNRVTFTKVNIDSVKDVVTYNQSVF
IIKMDGTAHACGLNSNGQLGINSTLNKSVFNKIEGMDNVKQIACGSSHTILIKNDGTMYTTGSN
GYGQLGTGNNNNSIVFTLSSINNVKYASCGNNHTMILKYDNTLFSTGQNNYGQLANANKDVASR
NTFVKVNVENIKDIKCGSQFNFLINGSKEIFVSGCNLAGQLGSFFHTTFLYEFSKVQSSNLDNY
SGLLVNDDYLYVTKDNSEFLNVKLSDNFQDYKKIELTDNNMFIVMNDGTLYACGLNNYGQLGLG
DTVNRSVMTKVDIDNVLDIKGNGNSTFVLKNNGTLYSCGYNSSGILGLKDNTNRNIFTKIEIEN
IKEFCVESNYIVALNHSKELYGWGNQSYIVYGDNRNYPYKDTRVSNVEKIATWSDTLYILDSTG
ATKTIGYSYNGSGGYPAPSSSSTYREGGYINKNTSYRTLEFYNTSKTKLVNLFAFYNGCVFVDE
NGLAYCIGENNINFRGGSTTNENNSLRFINNSGVYYTNTDGTDYTCYQWTYKLIRCSIFDSPQN
IIGNSKNILYLSKNNSTFKCTGNCITYGINSQNWYSYFSDSSNGAIALGNEFILKNYSGECLLK
GYGKATNGEFGNSTNISSISNYDTGLKDIKDIIVKNNTVVVVDKNNNIYVTGANQFNKLGIGEY
NNQPIRKFTNITEQSNSFIFMDDIKEITTSRNTMFIVKNDGTAYATGNNSSGQLGLGDTINRNK
FTQINLDNIKKISTSIDGNTTFAIRNDGTLYSTGLNTKGQLGLGDIVNRNTFTKVNIQNVRDVV
LGTTHSHAIKDDNTLYSCGENTHGQLGLGSESNHPDVLTFTVNNITNVRDVYCSDTTTFIVKDT
NIAYCCGYNNNSQLGMGNTTDQYSFIKCMENVKEVIPNEINTYIITIYNTAYSTGLNTDYCLGL
NSNSNQSSFSEIPISNVVKVAPNRNNAVLLLTSEGDVYTAGKCSNGSGTGSETPEKIKKIASKA
KDIGMNYRCGHYVSDNGDLYGTGFNDCGQLGVGNVTKRDTFIKTNTRVKKILPLEYANIAIKDT
NDIYICGLNNYGQLGVGNRYDSRNNDNRIFNYKHMNFVMGDLTSIKNRHNFILLNNKIVIPTTK
DIDYGLVLGNLYKGDLYTELPYEDIKEVSISKTHIIILLNDGTMYGCGTNYHGELLQDLSINQV
DEFVQINVSDVKHVSCGDNFTYFIKSDDSLWSIGKNSEYQLGIGHNNPVTELQRITTISSCKEV
HCGKNYTLVVTTSNELFVQGYNDKGALGLGSDSENTIIKFFTKALTDIREIKSYGSDHILVLKN
DNSVWVTGKNRDVYKIEQPVEFLKEFTIVPISEDVNTVKDVLATDNTLYIISEVGTTNAAIEIT
EKSISSIKIKIQDPNKDISRIEMLINGESVKSVSDLITEKISFEVPPDKIKIGENKILFRAYCK
GDDLYASLFIFKESTGNSIIKDSYVMIGNRMYKVVNTTSNEQDITITLDRGLEEDLNLGDPIYQ
LINKTKVQVKINKSDLFKDMKLVEIKKSDSSYQEIYELEEANIKSAQPKIIVEKGDKWTAIKRP
SMIFRYDAENNEPQA

SEQ ID NO:51          >CD123    Orf1374
MKRTKLLQRGNFFGDKNMVVDEFDEGYDNYDFINFFTGCCNYTFGLKNNNILYGCGDNSNFQLG
LGEDNTTRKLFTKIPNISTNIKKVACGESHAVILTSDGELLVAGINTDGQMGLGLEKVGKTVST
FEKVPEIKGVKDIACGLQSTYLLYNDGTLYVAGNNLYGQLGLGTNGASANVNTFTKVDVDNVKA
VFSYNKSAFIIKNDNKCYSTGFNNQGQLGLGDKNNRDLFSLVSINDVKTIACGSEHTVLMTYNN
DIYGCGKEKCFGNALQSSLFTKIEEVNIKTIACGHGNTMLIDNKGTLKVAGNNDIYQLGIANYS
ENIDNSFIDLKNIVAKNIFIGLSHSILIDSNNDSYCTGDNTYGQLGSFFDDMHIVEFKKMDSEK
YSYSNYINLIKSEDKLTLLKEEMEIKDIELPLDIHSVRDVVFSPYCTLVILGNGDVYGLGNNRY
KGMGSDLPSQLNELTKLSISNVKSIVASKNISGGIFYIKNDDTCYYSGPNSNSIAGVLPSNSDV
FKKISIDNVKKVVINTDLSNWFSLIVTNNKQIYTSGKSSSYVNGLSNALISQYTEISLSNVTDA
YSSYNATFIVVDEKKVYATGINTNYLLGFSTSDGSNVNLGLLSDWYYINISGSSYSRVSCTNNI
TKINNIIIYEYVTVFCTNIGSFLTGYHGTSWTKPTDSSYRVQYQGISYAGYLDSYIYNYYPTRC
TQSSSSTTFAYLYNGESSSNLKNVNPDNLLISGGSSYIHQYGRNYLNNQSSNNIAASNINSGPI
TSDKAIFLYKALLYLSSNTLYGFGNISESAKELDVSDTQDGYNATNYKKVMKNIKNIFIPPYDL
SRDKTRFAILTDKSLFICGYNSKGTHGISVNSSLNLNNKINYHKKNSSSEISSNIQEIYSHSKS
TYLLTNNNMLYSVGLNDVGQLGVGDEINRKVFTKINIDNIKSINVNRFTDNSKHAFAIKNDNTC
YAVGLNNSGQLGIGDNVNRNIFTKINVENVKYVAVYGNTSLLLTNDGLLYGAGNNGKGQLGLGD

FIGURE 1 (Continued)

```
TTSRNIFTRIPINGVRDVYLCNDVSIIVKNDNTCYVCGLVNGYFGFTEGSISTFTKINIENVKS
VVTAGSEATFFITNDNMIYTTGKKERVFFSTETNDIKGIRVINNIINAKKIVVNGYTSAILTND
NKLFVGGLSGYGSIANNNNTNSVEDVKDVFVTANNTLYIDNNNNLISSGRDTYGISDESYRDMS
VPYYKVSIKKDVDTVFSSYNTIFIKDIYGKFYSSTRDNRYNHLGIHHRYDNDKNEALEGSLHSY
FKTDNTSDKIVFNKKNEKLVMFNDKYIKTNNKYINYKNIFKDNFKYTSIILPFEVSDIDISKTH
SLAVAKDGKLYGIGSNSYKEINQTLEDIELLTLTEVNISDVKKVACGDNYSYIIKTDNTLWSYG
KNTEYQLGVGHNNDVRELQKVTGLPSVKDISIYNSMTLVLTNEGELYAQGYNTNGLFGLGESEK
DKIIRTFTKVLTNVKEIKSHNDDHILVIKNDNSLWITGKNKSMYKISISITDLYEFTKIPIPEH
LNDILDIELSDDTIYMITKVDTSKASIEIVEKSISQVRVVVQDPNNVIEKLEMFINDELISTKT
NLEINSIIFEIPQNKIVLGENKILIKASSPTGDLYSSMFIFKSETGLKVKKDSILMINNKVYSI
INITENNTDLIVTLNEGLKDDMMENNPIYQLINKTKVQVKINKSDLFKDMKLVEIKKSDSSYQE
IYELEEANIKSAQPKIIVEKGDKWTAIKRPSMIFRYDAENNEPQA

SEQ ID NO:52         >CD126 Orf1374
MKQNKLLQRGAYFNDKNILIDDFDKRYNDYDFVEFFTGISNSTFGLKSDGNLYACGDNTGFPLG
LGKDSSERRMFSKVKIDNVKYVSCGSKHSVAVTKDGFAYGAGTSNVGQLGVIESTVYYEFTKLP
IDDVKTVACGYDFTFVLKNDGTLYSAGLNSSGQLGLGDTNNRATFTKVNIDSVKDVVTYNQSVF
IIKMDGTAHACGLNSNGQLGINSTLNKSVFNKIEGMDNVKQIACGSSHTILIKNDGTMYTTGYN
GVGQLGTGNNNSIVFTLSSINNVKYASCGNNHTMILKYDNTLFSTGQNNYGQLANANKDVASR
NTFAKVNVENIKDIKCGSQFNFLINGSKEIFVSGCNLAGQLGSFFHTTFLYEFSNVQSSNLDNY
SGLLVNDDYLYVTKDNSEFLNVKLSDNFQDYKKIELTDSNMFIVMNDGTLYACGLNNYGQLGLG
DTVNRSVMTKVDIDNVLDIKGNGNSTFVLKNNGTLYSCGLNSNGQLGLRDEVNRNIFTKIEIEN
VKDFCVGSNYVIALNHSKEVYGWGNNPYNNIEKTSNYPYKQGISNIEKIAAYDYSVYMINSEGK
LYVSGYNYNYQLGKGNNSNQSKALVSQCRTNSTSSTSNGLRTLPKITNVFPFYDGCAIIDEGGY
VYLTGYHGYLRTLNSSPSISDYSRYGTFIEATNSNHNTYFIQETDFSGIEKVIGMSNNILFFKK
GSSYITGYPKTFGSTITGHRSYTSINSESSNLGSNFIIYHSNSKLYGKGIANSGQFGNSTNIDG
TSNYDTGLKDIKDIIVKGNTVVVVDKNNNIYVTGMNQNNKLGIGEYNNEPVKKFTNITEQSNSF
IFMDDIKEITTSRNTMFIVKNDGTAYATGNNSSGQLGLGDTINRNKFTQINLDNIKKISTSIDG
NTTFAIRNDGTLYSTGLNTKGQLGLGDIVNRNTFTKVNIQNVRDVVLGTTHSHAIKDDNTLYSC
GENTHGQLGLGSESNHPDVLTFTVNNITNVRDVYCSDTTTFIVKDTNIAYCCGYNNNSQLGMGN
TTDQYSFIKCMENVKEVIPNEINTYIITIYNTAYSTGLNTDYCLGLNSNSNQSSFSEIPISNVV
KVAPNRNNAVLLLTSEGDVYTAGKCSNGSGTGSETPEKIKKIASKAKDIGMNYRCGHYVSDNGD
LYGTGFNNNGQLGVGDVTKRDTFIKTNTRVKKILPLEYANIAIKDTNDIYICGLNNYGQLGVGN
RYDSRNNDNRIFNYKHMNFVMGDLTSIKNRHNFILLNNKIVIPTTKDIDYGLVLGNLYKGDLYT
ELPYEDIKEVSISKTHIIILLNDGTMYGCGTNYHGELLQDLSINQVDEFVQINVSDVKHVSCGD
NFTYFIKSDDSLWSIGKNSEYQLGIGHNNPVTELQRITTISSCKEVHCGKNYTLVVTTGNELFV
QGYNDKGALGLGSDSENTIIKFFTKALTDIREIKSYGSDHILVLKNDNSVWVTGKNRDVYKIEQ
PVEFLKEFTIVPISEDVNTVKDVLATDNTLYIISEVGTTNAAIEITEKSISSIKIKIQDPNKDI
SRIEMLINGESVKSVSDLTTEKISFEVPPDKIKIGENKILFRAYCKGDDLYASLFIFKESTGNS
IIKDSYVMIGNRMYKVVNTTSNEQDITITLDRGLEEDLNLGDPIYQLINKTKVQVKINKSDLFK
DMKLVEIKKSDSSYQEIYELEEANIKSAQPKIIVEKGDKWTAIKRPSMIFRYDAENNEPQA

SEQ ID NO:53         >43593 Orf1374
MKQNKLLQRGAYFNDKNILIDDFDKRYNDYDFVEFFTGISNSTFGLKSDGNLYACGNNTGFPLG
LGKDSSERRMFSKVKIDNVKYVSCGSKHSVAVTKDGFAYGAGTSNVGQLGVIESTVYYEFTKLP
IDDVKTVACGYDFTFVLKNDGTLYSAGLNSSGQLGLGDTNNRATFTKVNIDSVKDVVTYNQSVF
IIKMDGTAHACGLNSNGQLGINSTLNKSVFNKIEGMDNVKQIACGSSHTILIKNDGTMYTTGYN
```

FIGURE 1 (Continued)

```
GVGQLGTGNNNNSIVFTLSSINNVKYASCGNNHTMILKYDNTLFSTGQNTYGQLANANKDVASR
NTFAKVNVENIKDIKCGSQFNFLINGSKEIFVSGCNLAGQLGSFFHTTFLYEFSKVQSSNLDNY
SGLLVNDDYLYVTKDNSEFLNVKLSDNFQDYKKIELTDNNMFIVMNDGTLYACGLNNYGQLGLG
DTVNRSVMTKVDIDNVLDIKGNGNSTFVLKNNGTLYSCGYNSSGILGLKDNTNRNIFTKIEIEN
VKAFCVESNYIVVLNHSKELYGWGNESYIVYGNSRNYPYKDTRVSNVEKIATWSDTLYILDSTG
ATKTIGYSYNGSGGYPAPSSSSTYRDGGYINKNTSYRTLEFYNTSKTKLVNLFAFYNGCVFVDE
NGLAYCIGENNINFRGNSTTNENNSLRFINNSGVYYTNTDGTDYTCYQWTYKLIRCSIFDSPQN
IIGNSKNILYLSKNNSTFKCTGNCITYGINSQNWYSYFSDSSNGAIALGNEFILKNYSGECLLK
GYGKATNGEFGNSTNISSISNYDTGLKDIKDIIVKNNTVVVVDKNNNIYVTGANQFNKLGIGEY
NNQPIKKFTNITEQSNSFIFMDDIKEITTSRNTMFIVKNDGTAYATGNNSSGQLGLGDTINRNK
FTQINLDNIKKISTSIDGNTTFAIRNDGTLYSTGLNTKGQLGLGDIVNRNTFTKVNIQNVRDVV
LGTTHSHAIKDDNTLYSCGENTHGQLGLGSESNHPDVLTFTVNNITNVRDVYCSDTTTFIVKDT
NIAYCCGYNNNSQLGMGNTTDQYSFIKCMENVKEVIPNEINTYIITIYNTAYSTGLNTDYCLGL
NSNSNQSSFSEIPISNVVKVAPNRNNAVLLLTSEGDVYTAGKCSNGSGTGSETPEKIKKIASKA
KDIGMNYRCGHYVSDNGDLYGTGFNDCGQLGVGDVTKRDTFIKTNTRVKKILPLEYANIAIKDT
NDIYICGLNNYGQLGVGNRYDSRNNDNRIFNYKHMNFVMGDLTSIKNRHNFILLNNKIVIPTTK
DIDYGLVLGNLYKGDLYTELPYEDIKEVSISKTHIIILLNDGTMYGCGTNYHGELLQDLSINQV
DEFVQINVSDVKHVSCGDNFTYFIKSDDSLWSIGKNSEYQLGIGHNNPVTELQRITTISSCKEV
HCGKNYTLVVTTGNELFVQGYNDKGALGLGSDSENTIIKFFTKALTDIREIKSYGSDHILVLKN
DNSVWVTGKNRDVYKIEQPVEFLKEFTIIPISEDVNTVKDVLATDNTLYIISEVGTTNAAIEIT
EKSISSIKIKIQDPNKDISRIEMLINGESVKSVSDLITEKISFEVPPDKIKIGENKILFRAYCK
GDDLYASLFIFKESTGNSIIKDSYVMIGNRMYKVVNTTSNEQDITITLDRGLEEDLNLGDPIYQ
LINKTKVQVKINKSDLFKDMKLVEIKKSDSSYQEIYELEEANIKSAQPKIIVEKGDKWTAIKRP
SMIFRYDAENNEPQA

SEQ ID NO:54       >ΦC2    Orf1373
MAIDKSYYTIITDVGKAKIANASVTGNKVGFVKIQLGDGGGSEYTPTESQTALKNVVWEGNIGN
TTTDETAPNCIILESLIPSSVGGFMIREIGYLDDENNLIAISKYKECYKPSIEQGAVVDMKVKT
VLIVSNVNNIELKIDPTIIFATLKDIQDLETKIGTVNTKIDTTKTELTSNIETTKTELNTRIDT
ENEKQNIKIDQLIAGGSNVASTQIITIDDWVEDAENGFKATVTHSLLTQRIVVNIIDATTKENV
VTNFKIIDDNSIEIRSEVKVELNVYVINGNAETHFINATVDDNRVSEMTTYSSKKIEDRLVNIE
EKVNGGLSNIATSVNELITYC

SEQ ID NO:55       >ΦCD119  Orf1373
MAEQQYFTLVTDIGKAAIANASVTGEKVDFAKIKVGDGGGSSYTPNESQTALKNVVWESTLEHA
QVDKDNPNWVVIQKFIPGDVGGFEIREVGLFDSKDQLLAVSSYPTTYKPESRFGDCKRTINKSN
ISCI

SEQ ID NO:56       >ΦCD27   Orf1373
MPNELNFNNEIEEYLITTPAHANEFNNRQQKLLDNDKYLNNKIDTTKTELNTRIDTENEKQNIK
IDQLIAGGSNVAYTQRVAIDDWVEDAENGFKATVTHSLLTQRIVVNIIDATTKENVVTNFKIID
DNSIEIRSETRSELNVYVINGNAETHFINATVDDNRVSEMTTYSSKKIEDRLVNIEEKVNGGLS
NIATSVNELITYC

SEQ ID NO:57       >DG211
ggccgcctcgaggg
```

FIGURE 1 (Continued)

```
SEQ ID NO:58        >DG212
cgcgccctcgaggc

SEQ ID NO:59        >DG210
TGAAGTACCATGGTATCCAG

SEQ ID NO:60        >DG209
ACTGGATACCATGGTACTTC

SEQ ID NO:61        >Dif4 Locus without orf1377-1379
GCAATACCCACTACACCTTCGTCATCTTTAAATTTAAGAGTTTTTACTATTGAATAATAAAGGT
ATATTCCAGTAAAAATAATCTTTAAATACAAGAAAAATAAACTCTTTGGGTATATTAAAAAGCT
AAAAAGTGTAAATATAAAAGCAAGTAGAGTACTTATCCTGTAAAAGAAATCTATTTGTGTAATG
TCTTTATATTTTATCATAAACACCGAATATAAAATGATGAAAACAATTGCGACGATTGCATATA
TGGTAAATAACATATTTTCAAGAGTACCATTTGAAATTACTATCCACTTATACCACATAATTGG
CCAAAATAATAGTGCTAAGAACTTAAAATAATTATCAAACAACTTTTCTTTATACATTCATCAA
ACAACCTTTCTTAACAAAAGCATATATTTGTTTTTAGAATTTTAAATAATATGATATCATTATT
ATATATTAATATTGAATTTATAGAAACCAAAATTTGTTAAAATAAATATATAGATTTTACTGTT
AAGCCAGTTAAAATTACTACTATTTTTATTATGAAATTGGATCAAATATGTAGAAATACGGCAA
ATTAGTTAATATTAAATATTTATTATTTCCAAGTTGTAAAGACTGTTTTTTAATGATAGAAAT
TCTAATCTTTTTTGAAAGAAAGTAATATCCACATTAAGTATGTCTGCCATTTCATAAACGCAAG
TGATGCCAGAGTTAATTATGTTTATTATATCTTCTTCAGTAATTAAGAACTCACAAGCCCATTT
TAAGGCTTTATTTTCGCACTTATCTATAATAATTTTGTATAATAATCGTTATAAGAGGATACA
TAGTATCCAAGGCTAGTGAAATGATGTCCAAGTTCTTCAGCTAAGATGGATGTCAATTTTTTTG
AGTTTTGTTTTAAATTACTGAGTAATGATATAATTTAATACCATGTTTGTTTATATATAGTCC
TTCTAAATCACCTGCAATATAAGTGGTATAATGAATTATTATCTCTTCTTGAGAAGCTAATTCA
AAAAGCTTATCCAAATTATTCATAAAAATCCCCTAAAATAGAATGTATGTTTGCCTTTAAATT
ATATTAAAAGAGCAGAAAAATAGACTGCTCATCATATGGTTTATTTTTTTTATATTTATTTAG
TAAAAATTCTATATAATCATTAAGTTGTTCTTGTGCTTCTTCAGGTAACTCTTCATGTGGATTT
TTTCTATGTGCAGCTACTGTATCAATATTTTCCTTAACTAAGGTTCTTCCAAGAAGGTAATCAA
CTGATACATTAAATACATCAGCCAATTTATTTAAAATGTGTTCATCAGGAAATCTGTTTTCTGT
TTCATAGTACCCTAAGACTCTTTGGGAAACGCCTACTTTTTCTCCAAGTTCTCTTTGAGTCAAT
CCAAATTCCTTTCTAAGTTCTCTTAATCTTTTGGCAAACATTATAACACCACCTTATGTATAGA
TTATAACAAATTGTTCTAAAAAATAAAACTAATAAAATATAAAGAATATTTTTTTCTAAAATC
TATTGATAAAGAACAAATAATTCTATATAATCTAAGTGAGGAAGAACAAAATATTCTTAATAGT
AATGGAGGTATAAAACAATGTTTAAAAATAACTTGAAATATTATAGAAAATGCAAAGGTATGAC
ACAAATTCAACTTGCCAGAAAGGCTGGAATTACAAATGATTATATATCTCAAATAGAAAGAGGT
ATAAAAAATCCTGGACTTCTTATGGCTAAGAAGATTTCTAGTATTTAGAACAAAATATAGAAG
AAGTTTTTTTATACAGTTATAGAACAATATGTTCTTGAAAGTTGTGAGATTAGTAAAAAACTG
TGCACTAAAGAGATTATTGTAAATTTGAAGCTAATAATAAGTATATAAAAAAGGGGAAGTACTA
TGGAAAACAAAAAGATATATTATTTAAAGAAACAGATAAAGATTACATAATTATAAGTATTT
GGATATAAAGATAAAGAATATTAACTTGGACATAAAAAGATGTGAGAATGAATACTCTGGATGT
GGAGCAATGGTATATACAGAAAAGACTAGTAACACATATAACATAAGCTCTTCTGTGGAAAATG
AGGTGTTAAAAGAGAGGAAAGATTAAGAAAATTAAAAATGGAAAAGAAGATATAGAAATAGA
AAAAGAGAAGATAGAAAATGCTCTAACGTGTCTAAATGATATAGAAATGGAATTTTTAATCTT
TTTTATAATAGTAAGACAAAAAACAATATGACATATATTTCTATGAAACTACACTTAGATAGAA
```

FIGURE 1 (Continued)

```
CATCTTGCTACAATTTAAAGAAAAAGATGATATTTAAATTGAGTGAGATATTATAAAAAATAGG
ACAATTTTACAACACTTTATATACACCATTGCAACAATAGGCAATAAAATATGTGAGATAATGT
TATTGTGAAAGAAATCCATATTGAAGGAGGTGATAGATTGAAAAGAATAATATTACCTAAAAAT
ATAGAAGATACTTGACAGGAATAAATGAGATATATATTTAAAAATGACTTATATCATTTATAGT
AAGATTATCAGATTAAGCAAGAATATTTAGTGATAGTGTGGTGATTATTTGCTTAAATACAAGG
AAATATTAGAAACAATTATTGAGATTCTCAAAAAAAACTTTACTGAAAGTATTTTATTGATGA
TGAAAGTGTGCAAGGCTCTGAAGGGTCTTGTTTTTTGTAAGTATACTATCAGTTATTTGTACA
CCTGTAATGTTAAATACGAATAACAAAGATATTGTTATCTCTATAAAATACTTACCAAAACCAC
AGTCAAAGAGTATTAGAATGTATGAAATTTCAGATGAATTAAATAAGCTATTTAACAGAAATAT
AAAGGTAACAGACAGAAAATTAAATATAACAAAGCTAGAACAAAGTATTAAAAAAGAAGAGTCA
ATTTATGTATTGAACTTTACATTTACACTAAACTATCTGGATAGTGTATATGAAGAAGATGTAG
TATATGAAAATATGAAAGAAATCAATTTAAATTTAGGAGAGTGATAGTATGGCTATAGGATTAC
CAAGTATCAACATATCATTTAAGGAGCTAGCTACAACTGTTAAAGAACGTTCAGCTAGAGGAAT
AATTGCAATGGTACTTAAAGATGCTAAGGCACTAGGTCTTAATGAAATACATGAAAAGAGGAT
ATACCAGTTGATTTATCTGCTGAAAATAAAGAATATATAAATTTAGCTTTGATGGGAAATGTTA
ACACTCCAAATAAATTATTAGTTTATGTAATAGAAGGAGAAGCAGATATTCAAACTGCATTAGA
TTTTTTAGAGACTAAGGAATTTAATTATCTATGTATGCCAAAAGCAGTAGAAGCTGATAAGACT
GCTATAAAAAATTGGATAATTAAACTTAGAGATATAGATAAGGTTAAGGTTAAAGCTGTATTAG
GAAAAGTTGTAGGAAATCATGAAGGGATAATTAATTTTACTACAGAAGATGTGTTAGTTGGAGA
AAAGAAATACAGTGTTGATGAGTTTACAAGCAGGGTGGCTGGACTTATAGCAGGTACACCTTTA
AGTCAATCAGTAACTTATACTAAACTTAGTGATGTAGTCGATATACCTAAGATGACGAAAGTTG
ATGCAGAATCAAGGGTTAATAAAGGAGAGCTTATACTTATTAAAGAAGCAGGAGCTATAAGAAT
TGCTAGAGGAGTAAATTCTTTAACTGAATTAACAGCAGAAAAAGGAGAAATGTTCCAGAAAATA
AAAATAGTTGACACTTTAGATATTATACATAGTGACATAAGAAAGGTGATAATAGATGACTATA
TAGGAAAGGTTACTAACAGTTATGACAACAAATGTTTATTGATAGTAGCTATAAAAAGTTATTT
AGAAGAATTAGAAAAATCAGCACTTATAGAATCTGATTCTACTGTTGAAATAGATTTTGAAGCA
CAAAAATCGTATTTAAAATCAAAAGGAGTAGATTTATCTTATATGACATTACAAGAAATAAAAG
AAGCTAACACAGGTTCTAAAGTATTTTAAAAGCAAAAATAAAAGTACTTGATGCTATGGAAGA
TATAGATTTATCAATAGAAATATAGGAGGATTATTAATATGGCAAATATGGAAGCTAGAAATGT
AATGAGTGGTACTTGGGGAGAACTTTGGCTTGATGGAAACAAAGTAGCAGAAGTAAAGAAATTT
CAAGCAAAGATGGAATTTACAAAAGAAGATATTATAATAGCAGGTCAAATGGGTACTGATACAA
AGTATATGGGATATAAAGGAAAAGGCTCAATAACTCTATACCACGTTAGTTCAAGAATGCACAA
GTTAATTGGAGAAAAGATAAAGAGAGGTTCTGAACCTAGATTTGTTGCTATATCAAAATTAAAT
GACCCAGATTCTTATGGAGCAGAAAGAATAGCAGTAAAAAATATAGCATTTGATGATTTAACTT
TAGCTGATTGGGAGGTTGGAGTAAAAGGAGAGATAGAAGCTCCTTTCACATTTACTGAGTATGA
TTTTCTTGATATAATTTAGTTTTATATTTAGTTTTATACTGATATTTAGTAAGTATATACTTAA
TAAATTCAGATAGTTAATAAGTAAAAAGTTAGTTGATTGAATTTGATTGATAAAGGAGCAAAT
AATAATGAGTGAAAATGGATTATCAAAAATATAAACATAGTAGATTTACTTTTAAATTCAGAT
ACAGAAAACTTAGAAAGACCAAGTACTATAGTTGAACTTAAGAGATTATCAACTATATTTGGGC
AGGAATTTAAAGTAATGTGTAGAGCTTTAACAATAAGTAAAGATGAAGAAATACAAAATACTTG
TCTTAAAATTGATGAAAATATGAAAACGGATATAGACTTACCGGAGATGCAGATGCTTACAATT
ATAGAAGGTGTTTGTGATTTGGATGGAAAGCTTTTATTTAAAAATAAGGAGCTAATGGATAAAT
TTAAGGCTCCAACACCAAAAGAATTAGCAAGAAAATTATTATTACCAGGTGAAATTACCAACTT
ATATAGAATACTTCAAGATGTTATGGGTTATGGTAAAAATGCAGTGATAGAAGAGGTAAAAAAC
TAATAGGGACGGATACCAGGACTACAATAATGTACTATTATTGGAAGAAAAAGGTATAAGACC
GTCCCTTTTTTATGCAATGGATAAAGGCGAATTAAAGCTTATTGAAGCTTTTTTCGCCTTAGAA
ATTGAGGAAGAAGTTGAAAAAATGAAACATGGATATGGAGTGTGTCCTTTGACAGGAGGTGGTA
```

FIGURE 1 (Continued)

```
TGTAATGGGAAATGTGAGAGAAGAAGGTATAAATATGTACCTTACAGATAATTACACACCAAAA
ATGAATCAAATTATATCAGTAACTGATAATTTTAGGAGAGCAACTGTGGCTGTTTCACTTTCCA
CTAATGTAATGGCTAGTAGCATAAAAAATTCTATTGGAAGTGCAAGTAATAGAGTAAACAGTTT
AAATTCCTCGTTAAGAAAAGTTCAAACTACTGCTAGTAGTGTAAGTTCAACTATGACAAAATTA
AGTTCTAGCATAAATGCTGTTTCAGGAGTTATTGGAAGTTTAAATGGAAGTATTATGAGACTAG
CAATAACTATAGCTATGATTATTGATTATTTAATAAGTTGATTCAAAAGAAAAATGAGTTTAA
TTCAAATATTATGATTATATTAATATTTAAAGCTAAAAGTGATGAAGTAGAAAAAACTAAAAAT
AAATTACTTGGAAATTTAAAAAAGATTGGTGGCAAGATTTGGAATATCGTAATAAAAGCAAAAG
ATATGACTAAGAGAGTGATAAGTAGTATCTTGGGAAAATTAAAACAAGTAGAGAAACGTCCTTA
TCAAGGAAGTATTAATCTTAAAGATATGGTGAGTAGTGCTATGGGTAGAATTTTGCCTAAGTTA
ATGTTGTTTAAAAATACTTTTTGGAGTGGTGTAATAGCTATAAAAGATATGGCAAGTGGCATTA
TAAGTAAAGTATTTCCCAAATTGAGATTATTTGCAGGTAAGGTATGGAGTGGTGCAATAGCTGT
AAAGGATATGGCAAGTGGAATACTTGGTTCGATAAAAGGGAAGATATCTGATTTGACAAATGGT
GCTACTATAGGTGTCGCTGTGAAAAAGGGTGTTGATTTACTTGGTCAGGAACAAAATCAGAAAG
TTGTTCTAGAAAGTGTAATGAAAAGAAATACTGGAAAAGTTAATCAAATAGATGTTGATGATTA
TTATGGCAGTTTAGTAAGAATGGCAAATGATACGCCTTTTGACCCTGAAGATGTTGTTGCAATG
GGAACTAAAGCTAAAATGATTAGTAATATTACTGGTGGCAAAAAAGAAAAAGATATAACTCAAG
CTATGGTAGATGTTAGAGCTTTAAATATGAATACAAGTAGTGAACAAGATGTATCAGCAGCTTT
CTTAAGTGCAGCAAAAGGAAACATGGAATCTCTTAATACTCTGGTAGGAGAAAATTATAAAACT
TTTGATGAAGCATTGGAAGGCATAAGTGTAAAGCAGATGGGGTTAGCTAAAGAAATGAGTAATA
CAATACCAGGTATAATATCAGGAGCTCAAACAAGCATTAACAATGGCTTGAAGAGTATTGTTAA
ACCTTTTGATGATATTTTAGGTCAAGGACTAAAGAAAATAAAAACTTTTATAGAAAGTGGATTA
GGCAATTTAGCTGGCTTATCTGAAAAAATGGCTGGTAAAATAGGCAATGTAATGAATGGTAAGA
TAATTATTGGCAACAAATATGACCAGATGCAATCTAGAAGTGTAAAAAATGGAAAAGAGTTTTC
TGATTCTACTCAATATCGAATTTCTAATGAGGCTGAAAAGCGTAAAATGATGGTTGAAAATAAG
CAAGAACGTTTTGAAAATCATGCAGCAACAATGATAGGGAATGCACCAAAAGCAATTGTTAACG
CAGGAAGTACACTATTACAAAATATCGATTTTACAGCATTAATAGATTCATTACTTCCAGTAGT
AAACTTAGTAAATAATTTACTAGATAGTATAAACAATAAATCACCAATTGCACAAGGATTAATA
AGTATATTTGGTACAATAGTAACTACAGCATTCCAACTAATCGGACCTGTAGTTGAAGCTGTTA
GTCCTATTATCACAAGAATTTTTACTTTTTTAGGTGAATATGCACCTCAAATAAACAATTTTAT
AGAGACACTGGGTGTTATTTGGAAAACTGTATGGGAGACCTTAGGACCTCTGTTGGAAACTGGA
TGGAAAATTATAGAGCCAATATTGGGAGCTTTTTTTAACATATTAGATAAAGTATGTAAAATAG
TTAAAGATATATGTAAATGGTGGCAAACTATGATTAATAAGATAAAAAATGGAAGCATCACAGG
AACAGTTTTAAATCTAGTGGAAAAGAGTAAAAAAAATTACAAAGATAATCCATATGCTGGAACA
AAGGCTGGTGATTCTGGTAAAGCTTATTCAGGTAAGAAAGGTAATAATGCATTTGGATTGAACT
ATGTTCCTTATAATGACTATCAAACCAGACTCCATGAAGGTGAAATGGTTTTAACTAAACAAGA
AGCAAATCAATATAGAAGCAGAAAAAATGGTGGAAATATAAACATAGCTAAGTTAGCTGATACA
ATAGTGATTAGAGAAGAAGCTGATATAGAAAGATAACATCAAAATTAGTTGCAAGTATCCAAT
TGGCACAGTTAGGGGGTGTCTTATAATGGAAATGTGGCTTAGACAAGCTGAAGATAGATTTAGA
TTTCCAGTATTTCCATCTTCCTTTAGTATTAATGGAAAAGCTGCTGTAAACTCTTCTAGTATAC
TCAAAATAGGTGAAATAGCAACTTTTGGTGGTGTAGCTCTTAAAAGCATTTCAATATCAAGTTT
TTTTCCAAATAAAGACTATACTTTCTGTGACTATACAGGTTTTCCATCACCATATGATTGTGTA
AATAAGATAGAAAATGGATGAAGGAAGGTTTTATATTAAGATTTACAATTACGGAAACAAATA
TAAATATGGAAGTCATAATTGAAGGGTTTAGTTATGAAGAAGAGATGGGACTCGAGATGTATA
TTTTACATTAGATTTAAAAGAGTATAAAAGAATAAAGATACCAAAAGTAACTCCAAAACAATAA
CTATTATAGATAATAAGTTATAAATAACTGCTGATAGAATTAAATGAAAGGCAGGTGATTTTT
TATTATTAAGATTTGGGTACACATAAAAAACGGAAGTATATATGACATAACTGACATAGTAGAC
```

FIGURE 1 (Continued)

```
AAGGTATCATGGTCAGGTGATTATAAATCTCCATCAAGGACACTAGAGTTTTCAATAATACAAT
CATCATTTGATGTAAATTTCCAACAAATCGATATACCAATAGCTAGTACAGTCTGTTTCTATGT
AGATGAGAAAGAACTCTTTAGAGGAATGATAATTAATAGGTCTAAAGATTCAAGCAGTAATGAA
ATTAGTTTTGTATCTAAAGATATGGGATTTTTACTTACACAAAGTGAAGTGTCATACAATTTTA
AAGATAAGTTAGTTGAAGACATAGCAAAGCAAGTATTTGCTGAAAATAGGCTTTCAGTTGGAAT
AATAGCAAAGACCAATGTCAAGTATACAAAGATGTTTATAGGAGTAAATGGTTATGACACAATA
ATGAGTGCATATACAGAAGCAAGTAAAAAGACAAAGAAAAGTATATGATAGAGGCCAATTTAG
ATAAGTTTAATGTTATTGAAAAGGAACTGTTACATTAAGTGTTATGTTTGAAGAGGGATTTAA
TATTATAAATACCACCTTTTCGGAGAGCATGGAAAATGTAAAAAATAAAGTAATAGTGGTAGAC
CAGTATGGAAGCAAGATTAGCGAAAAATAGATAATGAAATTTTTAAGGAAGTAAATGTAATAA
TGCAAAAAGTAATTCAGCAACAAGAAAATCAAGATGTAGATATTGATAGCGAGTTTAATGGGAT
AGAAAAAAGCTGTTCTCTTAAAGGTTATGGAGATGTAAGTTGTATAACTGGTAGAGGAGTAAAA
GTTAAAGATTCTTATACAAAGCTTGTAGGACTATTTTATATAGATACAGACAAACATACTTGGC
AAAATGGAGAATATCAAATTGAGCTTGAACTTAATTTTCAAAATCTTATGGATGAAAAGTCAGC
AGGACAGGATGAACCTAAGGAAGAAAGTAATTTAGGGGGAGAAGATTATGCAGGAGGAAAAGAG
TTTACAGCAGAATTTACAGCTTACTGTCCTAGAAAAGAAGAAGGTGGAGATACAGATTGTAGAA
AGAAAAAACTTGACCCATCTAAAAAAACTTGCGCTGCTCCTATGGTTGGTAAATATGAGCAAAC
TTATTATACAAAAGAGTTTTTAAATAAACATCCTTTATTAAACTATGGAGATGAAATACAGGTA
ATTACAGGAGTTTCTGGTCGTGATGGAGTCTATAAAGTAAATGACGTAGGACCTGCAATAACTA
TAGAAAAGAATGGAACATACCATATAGATATTTTATTTGGAAATGTTGAAGAAGCTAGTAAATT
TGGAAGAAGAAAAGGAAAAATTATTATTGGTGGTTATTCTGGTAATGTATCTGATAAAGCTAAA
ATAGTAATATCAGAAGCAAAAAAACATCTAGGTAAACCTTATAAATGGGGTGGAAATGGACCAA
GTAGTTTTGACTGTTCTGGTTTAATGGTCTATTGTTTAAAAAAGTTAATGTTAGTTTGCCAAG
AACGTCAAATCAACAATCTAAAAAAGGCAAGAAAGTAGAACAAAAAAATCTTCAAGCAGGAGAT
TTAGTATTTTTTCATAATCCAGTCAGCCATGTTGGATTATATATAGGTAATGGAGAATTTTTAC
ATGCTCCACAAAAAGGTGATGTAGTTAAAATAAGTAAGTTAAGTAGTAGAAGAGATTTTAACAC
AGCTAGGAGAGTATTATAAAAGGATGGTGATATAATGGCTAATCCAATAAATGAATTTATAGGA
ATAATAAGAGAAGAAGGAAAGTATCATAATCAACCTTCTTTTTTATTGGAAAAATTAAAAGTA
AATTACCAGATTTAAAAATAGAGACAAATAACATCATATTAGAAAAGAAGATATTTGATAGA
TAGTTGGATGATTGATAGACAGCTAGAAACATTTGACACAGAAACAAATCAAGAACACCAGCAT
GAAGTAAAAAATCCTTTTATAGATAACTTTGAATCTGGGGATATGGTAATAATGTTTAGAATAG
GCGAAAAATTTGCTGTTGTAAGTAAGTTGGTGAGCTTATAATGAGTACAATATTTCCTTTTATA
GGTGTCCCAGAGGATTATATCTTACCTAAAACAGAAGAATTGCCAATCTTTCGTGAAGTGGCAT
GGGATTTTGAAAAGATGAACCTATTTTAGAAAAAGGTGACTTTAAAATAATTGAAAAAAAAGA
AGCCTTAAAAGTTTGGATATACAAGTGTATAAAGACAAATAGATATGAACATGAGATATACTCT
TTAGAATATGGGACAGAGCTTTCAGAACTAATAGGACAAAAATATACAAAAGGTCTTACAGAAA
GTGAAGCTAGTAGATTCATAAAAGAGGCCCTTCTAATAAATCCATATATATTAGAAGTAAACGT
AAAAAGTGCTAACTTTAACAGAGACATATTGAGTGCAAATGTAAAAGTATCCACTATCTATGGG
GAGGTGGAAATAAATGTATAGTGACCAGACATATGAAGTAATAAAAAATAGAACTCTTGAAAAT
ATTAATCTTGATATTTATAAAGGAGAAGGTTCTTTCTAAACAACATGGTATCTGGAAATAATC
TAGAACTTTCGAAGATATATCTAGAACTTTCAAAGATGCATAAAATGGCTTTATACAAGACAC
ATATAACCAGTTTCTTGATAAAAGAGTCAATGAATTTGGTGTATATAGAAAGTTAGGTACAGAG
TCAAATGGAGAAGTTGAATTATTGGAGAGAAAGGTACTGTAATAAATAATGGCACAATAATAT
CATATAGAGATTTACTATTTGTAGTAATAAAAGATGTAACTATTGGTAGTGAAGAAGGTGACAA
TAGCCCAGTTCAAGCTCTGGAAGTTGGTAAGAAATATAATTTACCTACAAATTGTGAATTTAAA
CTAGTTGATAATATATCTGGAGTAACAAAGATTACTAACACAAGAAGTTTTGAAGGTGGTACAG
ATATAGAGACAGATGAAGAACTAAAAGAAAGATTTTATAAAATCCAAAGAAATCAAGCTACAAG
```

FIGURE 1 (Continued)

```
TGGAAATAAAGCTCACTATGAAGAATGGGCTTTGGAAGTAGATGGAGTCTATAATGTTAAGGTT
TATCCAAGATGGGATGGTCCGGGAACAGTTAAGGTCTTGATATTTGGGAAAAATAATCAAGCTG
TTGATACAGAAACAATTGAAAGGTGTCAGCAACATATAGATGAAGAGAAGCCTATTGGACCAAC
TATAACAGTTGTGACACCATTACCAATAGAAATAAGTATAAGTGCAGTAATGAAACTAGAAGAT
GGATATACATTAGACAATGTAAAAGAATCTTTCCTAGAAAGTATAAATACATACTTTAGAGATA
TTAGAGGAGAGATAATCTATACAAAAGTAATGGGAATACTTATAAATACTACTGGTGTACACGA
TTTAAGTAACCTACTTATAAATGGAAGTACAGATAATATAACTATTAATGAAGATAAAATACCT
AGTGTAACAACTGTTAATTTTAGTGAGGTGGAAAATCAATGAAGCTAATTGATAAACTACCATC
ATTTGATAGAAATTACATTGTAGAGGAGATACAAGGTGCATACGATACAGAATTAAATATTCTT
AAAGAAGATATTGATGATACCTTTAACCAATTATTTGTTGACACTGCAACATGGGGATTAGATA
TGTGGGAAGACATACTCTGCATTGAAAAAAAGAACTTGATTTTGACACAAGACGTAGCAATAT
AAAAGCTAAAATGAGAAGCAGAGGTACTAGTACTATTGAAGTTATAAAAGTATATGTGAGGCA
TATACAAATCAGAAACAGATATAAAAGTTTATAGTGATGAATTTACATTCGTATTGAGTTTTA
TAGCAAATAACTGTGACTATAAAACTCTTTTAGATTGTAGCGATATGATTGAAAGAGTAAAACC
TGCTCACTTATTACACTATTTAGAACCAATAATACTAGATAAAAGTATGGTCTATTGTGGTGGA
GGTATGGTATGTAGTGAAGAGGTAAAAGTTCATCCATACTTTGAACCAATTATAAAATGTAGTG
CTGTTGTAAACTGTGGAGCTGGAATGATAAGTAGAGAAGAAATAAAGGTTTATCCTTTAAGCAT
TAAATGCATTGAAAATAATTGTAAGATTAATATAGCTATTGCAAATGATACAGGTGTAGAAAAT
GTAGTAGTTTATCCTAAATCGGAGGTGGTATAATTGGAAGAAAAATTTTATATAATATTAACCA
AAATTGGTAGAGAAAAAATAGCAAATGCAACTGCACTAGGAGAGCTTGTTGGATTAACCAAGTT
TCAAGTTGGAGATAGTAATGGAGAATATTATGAGCCAACAGAGGAACAAACTGCTTTAAAGAAT
GTAGTTTGGGAAGGAAATATAAATTCTCTAAGAATTGATGAAAAAAATCCTAATTGGATAGTTA
TAGAGACTATTTTACCAGGAACAGTTGGTGGATTTATGATAAGAGAAGCTGCTGTTCTGGATAA
TGAGAATAATATAATAGCTATAGGTAAGTATCCAGAGACGTATAAGCCACGTGCTGAAGATGGC
AGTATTAAAGATTTGGTTGTAAAAATGATTTTACAATTGTCCAATACTTCAAATGTTACATTAG
AAGTAGACCCGACGTTGGTTTTTGTAACTCAAAAGGATATTCAAGATTTAGATGATAAGTTTGA
TAAAAATATAAAAGAAATAAAAGTAAAAATTGGCGAAGAACTCTTATCTACAGAAGCTAAAAAC
TTATCAGGAGCTATAAATGAGGTAGTAGAAAAAATTAAAAATATATCTATTGATGATGTAATAG
GAGGTCAAATACAAACTGAACTATCTGTATTAAAAAATAGTTACAATAAATTATCTGAAAAAGT
ATTAGATATCTTAATATACTTAGAATTAGAGTCAGAAATAGATGTAGATGAAGCTGGATATTGG
TATGATACCTTAACTAATGCTAAAAACATAATAGCTATAGAAGGCCTTAAGTTAGATTTAAATA
GAAAGTGTATAACTGGAGAACTTGGTAGTGTTACATTTAAGAATGTGGTGCTACCATTTAATGC
AAATAGAGTTAGATATATACATGAAATGGATAATAACTTTGTTGAAACAAAATCTAATAGGGCA
TATTCAATTGGTCAGACAGATATAACTTTAAATAAATATTCGTATGAAATAAGATAATTAGGAG
GTTTTTATAATGAAAAGAACTAAACTACTTCAAAGAGGTAATTTCTTTGGCGATAAAAATATGG
TAGTTGATGAATTTGATGAAGGGTATGATAATTATGACTTTATTAATTTTTTACTGGATGTTG
TAACTATACATTTGGTCTAAAAAATAATAATATCTTGTATGGATGTGGAGATAATAGTAACTTT
CAACTTGGATTGGGAGAAGACAATACAACAAGAAAATTATTTACGAAAATACCAATATATCTA
CCAATATTAAAAAGTTGCATGTGGAGAATCTCATGCAGTTATACTTACTTCAGATGGAGAATT
ACTTGTCGCAGGTATAAATACAGATGGTCAAATGGGATTGGGATTAGAAAAAGTAGGGAAAACA
GTTTCTACATTTGAGAAGGTTCCAGAAATAAAAGGCGTAAAGGATATTGCATGTGGACTTCAAT
CAACATATCTTTTATACAATGATGGAACTTTATATGTTGCTGGAAATAATTTGTATGGTCAATT
AGGTCTAGGAACTAATGGAGCATCTGCAAATGTAAATACATTTACAAAAGTAGATGTTGACAAT
GTAAAGGCTGTATTTTCATATAATAAATCAGCTTTTATAATAAAGAATGACAATAAATGCTATT
CTACTGGTTTTAATAATCAAGGTCAACTAGGTTTAGGAGATAAGAATAATAGAGATTTATTTAG
TTTAGTTTCTATTAATGATGTTAAGACTATAGCTTGTGGTTCTGAACACACTGTGTTAATGACG
TATAATAATGATATATATGGTTGTGGAAAGGAAAAATGTTTTGGAAATGCACTTCAATCATCAC
```

FIGURE 1 (Continued)

```
TATTTACTAAGATAGAAGAAGTAAATATAAAAACTATTGCATGTGGTCATGGTAACACTATGCT
TATAGATAACAAAGGTACTTTAAAGGTTGCTGGAAATAATGATATATATCAGTTAGGTATAGCA
AATTACTCTGAGAATATAGATAATTCATTTATAGATTTAAAAAATATTGTAGCTAAGAATATTT
TCATTGGTTTATCACATAGCATACTAATTGATTCAAATAATGATTCATATTGTACAGGAGATAA
TACTTATGGACAATTAGGTTCGTTTTTGATGATATGCACATTGTAGAATTTAAGAAAATGGAT
AGTGAAAAATATAGTTATAGTAATTATATAAATTTAATTAAATCTGAGGATAAATTAACTTTAT
TAAAAGAAGAAATGGAAATAAAGGATATTGAACTTCCACTAGATATACATTCTGTAAGAGATGT
CGTTTTTAGTCCTTATTGTACTCTGGTTATTTAGGGAATGGAGATGTATATGGTCTAGGAAAT
AATAGATACAAAGGAATGGGTTCTGACTTACCAAGTCAATTAAATGAGTTGACAAAATTAAGTA
TCTCTAATGTAAAGTCTATAGTAGCATCAAAAAATATTTCTGGAGGAATATTCTACATTAAAAA
TGATGATACTTGTTATTATTCTGGACCAAATAGTAACTCAATAGCAGGTGTTCTTCCTTCTAAT
TCAGATGTATTTAAGAAAATATCTATAGATAATGTAAAAAAGTTGTTATAAATACTGATTTAT
CAAACTGGTTTTCATTAATTGTAACTAATAATAAGCAAATATACACTTCTGGAAAGAGTTCAAG
TTATGTTAATGGACTTAGTAATGCATTAATAAGTCAATATACTGAGATTAGCCTTAGTAATGTA
ACTGATGCTTATAGTTCATATAATGCAACATTTATTGTAGTTGATGAAAAAAGGTATATGCAA
CTGGTATAAATACAAATTACCTGTTAGGTTTTAGTACTTCTGATGGATCTAATGTAAATCTAGG
TTTATTAAGTGATTGGTATTATATAAATATATCAGGGTCAAGTTATAGTAGAGTTTCATGCACG
AATAATATTACTAAAATTAATAATATTATCATATATGAGTATGTAACTGTATTTGTACAAACA
TTGGATCTTTTCTAACTGGATACCATGGTACTTCATGGACAAAACCAACTGATTCAAGCTATAG
AGTTCAATATCAGGGAATTTCATATGCAGGATATCTTGATTCTTATATATATAATTATTATCCT
ACAAGATGTACACAATCATCATCTTCTACAACTTTTGCTTATTTATATAATGGGGAATCGTCAA
GTAATTTAAAAAATGTCAATCCAGATAATTTACTTATTTCTGGAGGTTCATCTTATATACATCA
ATATGGAAGGAATTATCTTAACAATCAATCATCTAATAATATTGCAGCATCTAATATAAATTCA
GGTCCTATTACCTCTGATAAAGCCATATTTTTATATAAAGCTCTATTGTATTTATCTTCTAACA
CGCTATATGGTTTTGGGAATATATCTGAAAGTGCAAAAGAACTAGATGTTTCAGATACACAAGA
TGGATATAATGCCACTAATTATAAAAGGTAATGAAAAATATAAAAAATATATTTATACCTCCT
TATGATTTAAGTAGAGATAAAACTAGATTTGCAATATTAACTGATAAGAGCTTATTTATATGTG
GATATAACTCTAAGGGTACGCATGGTATATCAGTTAATAGTAGTTTAAATTTAAATAATAAGAT
AAATTACAATAAAAAGAATAGCAGTAGTGAAATATCTTCTAATATACAAGAAATATATAGCCAT
TCAAAGTCTACATATTTATTAACTAATAATAATATGCTTTACAGTGTTGGTTTAAATGATGTAG
GTCAATTAGGAGTGGGAGATGAGATAAATAGAAAGGTATTTACTAAAATAAATATTGATAATAT
AAAATCTATAAATGTAAATAGATTTACTGACAATAGTAAACATGCATTTGCGATAAAAAATGAT
AATACCTGTTATGCTGTTGGTTTAAATAATTCTGGTCAGTTAGGAATAGGAGATAATGTAAATA
GAAATATATTTACTAAAATAAATGTTGAAAATGTAAAATATGTAGCTGTATATGGAAACACATC
TCTATTATTAACTAATGATGGTCTTTTATATGGAGCAGGTAATAATGGAAAAGGACAGTTAGGA
TTGGGTGATACTACAAGTAGGAATATATTTACACGTATACCTATAAATGGTGTTAGAGATGTAT
ATCTATGTAATGATGTATCAATCATTGTTAAAAATGATAATACATGCTATGTATGTGGACTTGT
AAATGGCTATTTTGGGTTTACTGAAGGAAGTATAAGTACATTTACAAAAATAAATATTGAGAAT
GTAAAATCTGTTGTGACAGCAGGAAGTGAAGCTACATTTTTTATAACAAATGACAATATGATTT
ATACTACAGGGAAAAAGAGAGGGTATTCTTTTCAACAGAGACTAATGATATAAAGGGGATACG
AGTAATTAATAATATTATAAATGCAAAAAAATAGTAGTTAATGGATATACTTCAGCCATTTTA
ACAAATGACAATAAACTATTTGTTGGAGGTCTTAGTGGATATGGAAGTATAGCAAATAATAATA
ATACAAATAGTGTGGAAGATGTTAAAGATGTTTTGTAACAGCTAATAATACACTTTATATAGA
TAATAATAACAATTTGATATCATCAGGTAGAGATACTTATGGTATATCTGATGAATCTTATAGG
GATATGTCAGTTCCATATTATAAAGTATCTATAAAGAAAGATGTTGATACTGTATTTTCTAGTT
ACAATACTATATTTATTAAAGATATATATGGAAAATTTTATTCTTCAACAAGAGATAATAGATA
TAATCATTTAGGTATTCACCATAGATATGATAATGATAAAAATGAAGCTCTTGAAGGTTCCCTA
```

FIGURE 1 (Continued)

```
CATTCATATTTTAAAACAGATAACACATCAGATAAAATAGTTTTTAATAAGAAAAATGAAAAGC
TAGTAATGTTTAATGATAAGTATATAAAAACAAATAATAAGTATATAAATTATAAAAACATATT
TAAAGATAATTTTAAGTATACTTCAATAATATTGCCATTTGAGGTATCTGATATTGATATATCA
AAAACACATTCATTGGCTGTTGCTAAGGATGGCAAGTTATATGGAATAGGAAGTAATTCATATA
AAGAAATTAATCAAACCCTTGAAGATATAGAATTATTAACTCTTACTGAAGTAAATATATCAGA
TGTCAAAAAAGTTGCTTGTGGAGATAACTACTCCTATATTATTAAGACAGATAATACTCTATGG
TCATATGGAAAGAATACTGAGTACCAATTGGGAGTTGGCCACAATAATGATGTAAGAGAGTTAC
AAAAGGTTACTGGATTACCTTCTGTTAAAGATATAAGTATATATAACTCAATGACACTTGTTTT
AACTAATGAGGGAGAGTTGTACGCTCAAGGGTACAATACAAATGGATTATTTGGACTAGGAGAA
AGTGAAAAGATAAGATAATAAGAACTTTTACTAAAGTATTAACTAATGTTAAAGAAATTAAGT
CACATAATGATGACCACATACTAGTAATTAAAAATGATAATAGTCTATGGATAACTGGTAAAAA
TAAATCTATGTATAAAATATCTATATCAATTACTGATTTATATGAATTTACTAAAATACCAATT
CCTGAACATCTAAATGATATTTTAGATATAGAGCTTTCAGATGATACAATATACATGATAACAA
AAGTAGATACAAGTAAAGCATCTATAGAAATAGTTGAAAAATCAATATCTCAAGTGAGAGTTGT
AGTACAAGACCCTAATAATGTTATAGAAAAACTTGAAATGTTTATAAATGATGAATTAATATCT
ACTAAGACTAATTTGGAAATAAATAGCATTATATTTGAGATACCACAAAATAAAATAGTATTAG
GAGAAAATAAGATACTGATTAAAGCCAGTAGTCCTACAGGCGATTTATATTCAAGTATGTTTAT
ATTTAAATCAGAAACAGGGCTTAAAGTAAAAAAGGATTCTATTTTAATGATAAACAATAAAGTA
TATTCAATCATAAACATTACTGAAAATAACACTGACTTAATAGTAACATTAAATGAGGGATTAA
AGGATGATATGATGGAAAACAATCCTATATATCAATTAATAAATAAAACTAAAGTTCAAGTAAA
AATAAATAAATCTGACTTATTCAAAGACATGAAACTAGTTGAAATCAAAAAATCAGACTCAAGT
TACCAAGAAATCTATGAATTAGAAGAAGCCAACATAAAAAGTGCTCAGCCTAAAATCATAGTAG
AAAAAGGAGATAAATGGACAGCTATAAAACGTCCATCTATGATTTTTAGATATGATGCTGAAAA
CAACGAGCCACAAGCTTAAAATGGAGGTGTGAAAATTGTTTAAATTCGATAAAAATAAAATAGA
ACAAATCAAACAAGGTAGAAAAGTAGAAATGCAGTATAAAGACATTTCAGACATAAGTATAGGT
CAAGTAAAGCAAGATGATGATATAACAAATAATTTTATAGCAAATGTAGAAATATATGAGATGT
TGTTAAATCAAAGTTCTGTCAATGAAGCAAGTAATATAAGCACTTTTAGTGTAAGAAAATCTGG
AGGTGAGAGTGGAATGGTAGAAGTATATGTAGCTTTAATTTTAAGAGGCAAAAAAACAATAGAA
GAAGTACCAGCAGTAATTAGAGAGCAAGTTAGAATTAGATGTAAAGAATTAGAAATACCAGTTG
AATAGTAAATTTAGAATAACTATGTATTAGTTATTTTTTTATGTAAAGTACAAGGTCTTAACT
TTAATAAGTAAGCCTTGTACTTATTTTTGTTACATTAGAACTTGTATATATATTTATTATTTA
TTCAATCTATAAATTACACCTACAATTTAAAGTACAGAAGATTAAATTGATAATCCTGAAAATA
TAATATTGCATGATGTAAGAATACAACAAAAATTAAAGCTATAAGTATAAAAAATTTAGACAAT
AGGAGGCTATAATGGATAAATTAATAACCGAATTGAGTAGTCTAGGGGCAATAGGTATACTATG
TGCTCTATTATTTAAAAATACTATGCAGGAGAAAAAAGAAGATAGAGACATGTATAAAAAAACT
GTAGAAAATTTTATAGAATTATCTACACAACAACAAGAAATAAACAAAAATATACTTGTTCAAA
TGGGTATAATGAAAACAGATGTAGAGGAAATTAAGGAAGATGTTACTGATATAAAAGGTATGTT
ACAAAATGGTGTATAACATGAAAGAGTAGCACCAGATTATATATTGTTAGGAAAAGATAAAGTA
GTATTGTAGATAGTTCACTATTTTATTGAGAAGGATTTAATATTTAAAATATTAATTAAAAAAA
GTAATAAAAATAACATATAAAAATTAAAAAAGGAGTTAAGCTTAAATTTGAGGCGCG

SEQ ID NO:62        >CD4-1359
MNNLDKLFELASQEEIIIHYTTYIAGDLEGLYINKHGIKIISLLSNLKQNSKKLTSILAEELGH
HFTSLGYYVSSYNDYYTKIIIDKCENKALKWACEFLITEEDIINIINSGITCVYEMADILNVDI
TFFQKRLEFLSLKKQSLQLGNNKYLILTNLPYFYIFDPIS
```

FIGURE 1 (Continued)

```
SEQ ID NO:63          >CD4-1360
MFAKRLRELRKEFGLTQRELGEKVGVSQRVLGYYETENRFPDEHILNKLADVFNVSVDYLLGRT
LVKENIDTVAAHRKNPHEELPEEAQEQLNDYIEFLLNKYKKK

SEQ ID NO:64          >CD4-1360A
MFKNNLKYYRKCKGMTQIQLARKAGITNDYISQIERGIKNPGLLMAKKISSILEQNIEEVFFIQ
L

SEQ ID NO:65          >CD4-1361
MENKKDILFKETDKRLHNYKYLDIKIKNINLDIKRCENEYSGCGAMVYTEKTSNTYNISSSVEN
EVLKREERLRKLKMEKEDIEIEKEKIENALTCLNDIEMEFFNLFYNSKTKNNMTYISMKLHLDR
TSCYNLKKKMIFKLSEIL

SEQ ID NO:66          >CD4-1362
LLKYKEILETIIEILKKNFTESIFIDDESVQGSEGSCFFVSILSVICTPVMLNTNNKDIVISIK
YLPKPQSKSIRMYEISDELNKLFNRNIKVTDRKLNITKLEQSIKKEESIYVLNFTFTLNYLDSV
YEEDVVYENMKEINLNLGE

SEQ ID NO:67          >CD4-1363
MAIGLPSINISFKELATTVKERSARGIIAMVLKDAKALGLNEIHEKEDIPVDLSAENKEYINLA
LMGNVNTPNKLLVYVIEGEADIQTALDFLETKEFNYLCMPKAVEADKTAIKNWIIKLRDIDKVK
VKAVLGKVVGNHEGIINFTTEDVLVGEKKYSVDEFTSRVAGLIAGTPLSQSVTYTKLSDVVDIP
KMTKVDAESRVNKGELILIKEAGAIRIARGVNSLTELTAEKGEMFQKIKIVDTLDIIHSDIRKV
IIDDYIGKVTNSYDNKCLLIVAIKSYLEELEKSALIESDSTVEIDFEAQKSYLKSKGVDLSYMT
LQEIKEANTGSKVFLKAKIKVLDAMEDIDLSIEI

SEQ ID NO:68          >CD4-1364
MANMEARNVMSGTWGELWLDGNKVAEVKKFQAKMEFTKEDIIIAGQMGTDTKYMGYKGKGSITL
YHVSSRMHKLIGEKIKRGSEPRFVAISKLNDPDSYGAERIAVKNIAFDDLTLADWEVGVKGEIE
APFTFTEYDFLDII

SEQ ID NO:69          >CD4-1365
MSENGLSKNINIVDLLLNSDTENLERPSTIVELKRLSTIFGQEFKVMCRALTISKDEEIQNTCL
KIDENMKTDIDLPEMQMLTIIEGVCDLDGKLLFKNKELMDKFKAPTPKELARKLLLPGEITNLY
RILQDVMGYGKNAVIEEVKN

SEQ ID NO:70          >CD4-1365A
MYYYWKKKGIRPSLFYAMDKGELKLIEAFFALEIEEEVEKMKHGYGVCPLTGGGM

SEQ ID NO:71          >CD4-1366
MGNVREEGINMYLTDNYTPKMNQIISVTDNFRRATVAVSLSTNVMASSIKNSIGSASNRVNSLN
SSLRKVQTTASSVSSTMTKLSSSINAVSGVIGSLNGSIMRLAITIAMIIDYFNKLIQKKNEFNS
NIMIILIFKAKSDEVEKTKNKLLGNLKKIGGKIWNIVIKAKDMTKRVISSILGKLKQVEKRPYQ
GSINLKDMVSSAMGRILPKLMLFKNTFWSGVIAIKDMASGIISKVFPKLRLFAGKVWSGAIAVK
DMASGILGSIKGKISDLTNGATIGVAVKKGVDLLGQEQNQKVVLESVMKRNTGKVNQIDVDDYY
GSLVRMANDTPFDPEDVVAMGTKAKMISNITGGKKEKDITQAMVDVRALNMNTSSEQDVSAAFL
SAAKGNMESLNTLVGENYKTFDEALEGISVKQMGLAKEMSNTIPGIISGAQTSINNGLKSIVKP
```

FIGURE 1 (Continued)

```
FDDILGQGLKKIKTFIESGLGNLAGLSEKMAGKIGNVMNGKIIIGNKYDQMQSRSVKNGKEFSD
STQYRISNEAEKRKMMVENKQERFENHAATMIGNAPKAIVNAGSTLLQNIDFTALIDSLLPVVN
LVNNLLDSINNKSPIAQGLISIFGTIVTTAFQLIGPVVEAVSPIITRIFTFLGEYAPQINNFIE
TLGVIWKTVWETLGPLLETGWKIIEPILGAFFNILDKVCKIVKDICKWWQTMINKIKNGSITGT
VLNLVEKSKKNYKDNPYAGTKAGDSGKAYSGKKGNNAFGLNYVPYNDYQTRLHEGEMVLTKQEA
NQYRSRKNGGNINIAKLADTIVIREEADIEKITSKLVASIQLAQLGGVL

SEQ ID NO:72         >CD4-1367
MEMWLRQAEDRFRFPVFPSSFSINGKAAVNSSSILKIGEIATFGGVALKSISISSFFPNKDYTF
CDYTGFPSPYDCVNKIEKWMKEGFILRFTITETNINMEVIIEGFSYEERDGTRDVYFTLDLKEY
KRIKIPKVTPKQ

SEQ ID NO:73         >CD4-1368
MIINRSKDSSSNEISFVSKDMGFLLTQSEVSYNFKDKLVEDIAKQVFAENRLSVGIIAKTNVKY
TKMFIGVNGYDTIMSAYTEASKKTKKKYMIEANLDKFNVIEKGTVTLSVMFEEGFNIINTTFSE
SMENVKNKVIVVDQYGSKISEKIDNEIFKEVNVIMQKVIQQQENQDVDIDSEFNGIEKSCSLKG
YGDVSCITGRGVKVKDSYTKLVGLFYIDTDKHTWQNGEYQIELELNFQNLMDEKSAGQDEPKEE
SNLGGEDYAGGKEFTAEFTAYCPRKEEGGDTDCRKKKLDPSKKTCAAPMVGKYEQTYYTKEFLN
KHPLLNYGDEIQVITGVSGRDGVYKVNDVGPAITIEKNGTYHIDILFGNVEEASKFGRRKGKII
IGGYSGNVSDKAKIVISEAKKHLGKPYKWGGNGPSSFDCSGLMVYCFKKVNVSLPRTSNQQSKK
GKKVEQKNLQAGDLVFFHNPVSHVGLYIGNGEFLHAPQKGDVVKISKLSSRRDFNTARRVL

SEQ ID NO:74         >CD4-1369
MANPINEFIGIIREEGKYHNQPSFFIGKIKSKLPDLKIETNNIILEKEDILIDSWMIDRQLETF
DTETNQEHQHEVKNPFIDNFESGDMVIMFRIGEKFAVVSKLVSL

SEQ ID NO:75         >CD4-1370
MSTIFPFIGVPEDYILPKTEELPIFREVAWDFEKDEPILEKGDFKIIEKKEALKVWIYKCIKTN
RYEHEIYSLEYGTELSELIGQKYTKGLTESEASRFIKEALLINPYILEVNVKSANFNRDILSAN
VKVSTIYGEVEINV

SEQ ID NO:76         >CD4-1371
MYSDQTYEVIKNRTLENINLDIYKGEGSFLNNMVSGNNLELSKIYLELSKMHKMAFIQDTYNQF
LDKRVNEFGVYRKLGTESNGEVEFIGEKGTVINNGTIISYRDLLFVVIKDVTIGSEEGDNSPVQ
ALEVGKKYNLPTNCEFKLVDNISGVTKITNTRSFEGGTDIETDEELKERFYKIQRNQATSGNKA
HYEEWALEVDGVYNVKVYPRWDGPGTVKVLIFGKNNQAVDTETIERCQQHIDEEKPIGPTITVV
TPLPIEISISAVMKLEDGYTLDNVKESFLESINTYFRDIRGEIIYTKVMGILINTTGVHDLSNL
LINGSTDNITINEDKIPSVTTVNFSEVENQ

SEQ ID NO:77         >CD4-1372
MKLIDKLPSFDRNYIVEEIQGAYDTELNILKEDIDDTFNQLFVDTATWGLDMWEDILCIEKKEL
DFDTRRSNIKAKMRSRGTSTIEVIKSICEAYTKSETDIKVYSDEFTFVLSFIANNCDYKTLLDC
SDMIERVKPAHLLHYLEPIILDKSMVYCGGGMVCSEEVKVHPYFEPIIKCSAVVNCGAGMISRE
EIKVYPLSIKCIENNCKINIAIANDTGVENVVVYPKSEVV
```

FIGURE 1 (Continued)

```
SEQ ID NO:78        >CD4-1373
LEEKFYIILTKIGREKIANATALGELVGLTKFQVGDSNGEYYEPTEEQTALKNVVWEGNINSLR
IDEKNPNWIVIETILPGTVGGFMIREAAVLDNENNIIAIGKYPETYKPRAEDGSIKDLVVKMIL
QLSNTSNVTLEVDPTLVFVTQKDIQDLDDKFDKNIKEIKVKIGEELLSTEAKNLSGAINEVVEK
IKNISIDDVIGGQIQTELSVLKNSYNKLSEKVLDILIYLELESEIDVDEAGYWYDTLTNAKNII
AIEGLKLDLNRKCITGELGSVTFKNVVLPFNANRVRYIHEMDNNFVETKSNRAYSIGQTDITLN
KYSYEIR

SEQ ID NO:79        >CD4-1375
MQYKDISDISIGQVKQDDDITNNFIANVEIYEMLLNQSSVNEASNISTFSVRKSGGESGMVEVY
VALILRGKKTIEEVPAVIREQVRIRCKELEIPVE

SEQ ID NO:80        >CD4-1376
MDKLITELSSLGAIGILCALLFKNTMQEKKEDRDMYKKTVENFIELSTQQQEINKNILVQMGIM
KTDVEEIKEDVTDIKGMLQNGV
```

Diffocin 16

← 1/10 dilutions

FIGURE 8.

```
CD108    MKQNKLLQRGAYFNDKNILIDDFDKRYNDYDFVEFFTGISNSTFGLKSDGNLYACGDNTG 60
43593    MKQNKLLQRGAYFNDKNILIDDFDKRYNDYDFVEFFTGISNSTFGLKSDGNLYACGNNTG 60
CD16     MKQNKLLQRGAYFNDKNILIDDFDKRYNDYDFVEFFTGISNSTFGLKSDGNLYACGDNTG 60
CD126    MKQNKLLQRGAYFNDKNILIDDFDKRYNDYDFVEFFTGISNSTFGLKSDGNLYACGDNTG 60
CD4      MKRTKLLQRGNFFGDKNMVVDEFDEGYDNYDFINFFTGCCNYTFGLKNNNILYGCGDNSN 60
CD123    MKRTKLLQRGNFFGDKNMVVDEFDEGYDNYDFINFFTGCCNYTFGLKNNNILYGCGDNSN 60
         **:.****** :*.***:::*:**: *::***::**** .* *****.:. **.**:*:.

CD108    FQLGLGKDSSERRMFSKVK--IDNVKYVSCGSKHSVAVTKDGFAYGAGTSNVGQLGVIES 118
43593    FPLGLGKDSSERRMFSKVK--IDNVKYVSCGSKHSVAVTKDGFAYGAGTSNVGQLGVIES 118
CD16     FQLGLGKDSSERRMFSKVK--IDNVKYVSCGSKHSVAVTKDGFAYGAGTSNVGQLGVIES 118
CD126    FPLGLGKDSSERRMFSKVK--IDNVKYVSCGSKHSVAVTKDGFAYGAGTSNVGQLGVIES 118
CD4      FQLGLGEDNTTRKLFTKIPNISTNIKKVACGESHAVILTSDGELLVAGINTDGQMGLGLE 120
CD123    FQLGLGEDNTTRKLFTKIPNISTNIKKVACGESHAVILTSDGELLVAGINTDGQMGLGLE 120
         * ****:*.: *::*:*:    *:* *:**..*:* :*.**    ** .. **:*:  .

CD108    TV---YYEFTKLP-IDDVKTVACGYDFTFVLKNDGTLYSAGLNSSGQLGLG---DTNNRV 171
43593    TV---YYEFTKLP-IDDVKTVACGYDFTFVLKNDGTLYSAGLNSSGQLGLG---DTNNRA 171
CD16     TV---YYEFTKLP-IDDVKTVACGYDFTFVLKNDGTLYSAGLNSSGQLGLG---DTNNRA 171
CD126    TV---YYEFTKLP-IDDVKTVACGYDFTFVLKNDGTLYSAGLNSSGQLGLG---DTNNRA 171
CD4      KVGKTVSTFEKVPEIKGVKDIACGLQSTYLLYNDGTLYVAGNNLYGQLGLGTNGASANVN 180
CD123    KVGKTVSTFEKVPEIKGVKDIACGLQSTYLLYNDGTLYVAGNNLYGQLGLGTNGASANVN 180
         .*     * *:* *..** :***  : *::* ****** ** *  ******    : *

CD108    TFTKVNIDSVKDVVTYNQSVFIIKMDGTAHACGLNSNGQLGINSTLNKSVFNKIEGMDNV 231
43593    TFTKVNIDSVKDVVTYNQSVFIIKMDGTAHACGLNSNGQLGINSTLNKSVFNKIEGMDNV 231
CD16     TFTKVNIDSVKDVVTYNQSVFIIKMDGTAHACGLNSNGQLGINSTLNKSVFNKIEGMDNV 231
CD126    TFTKVNIDSVKDVVTYNQSVFIIKMDGTAHACGLNSNGQLGINSTLNKSVFNKIEGMDNV 231
CD4      TFTKVDVDNVKAVFSYNKSAFIIKNDNKCYSTGFNNQGQLGLGDKNNRDLFSLVS-INDV 239
CD123    TFTKVDVDNVKAVFSYNKSAFIIKNDNKCYSTGFNNQGQLGLGDKNNRDLFSLVS-INDV 239
         *****::*.** *.:**:*.**** *...:: *:*.:****:... *:..*. :. ::*

CD108    KQIACGSSHTILIKNDGTMYTTGSNGYGQLGTGNNNNSIVFTLSSINNVKYASCGNNHTM 291
43593    KQIACGSSHTILIKNDGTMYTTGYNGVGQLGTGNNNNSIVFTLSSINNVKYASCGNNHTM 291
CD16     KQIACGSSHTILIKNDGTMYTTGYNGVGQLGTGNNNNSIVFTLSSINNVKYASCGNNHTM 291
CD126    KQIACGSSHTILIKNDGTMYTTGYNGVGQLGTGNNNNSIVFTLSSINNVKYASCGNNHTM 291
CD4      KTIACGSEHTVLMTYNNDIYGCGK----EKCFGNALQSSLFTKIEEVNIKTIACGHGNTM 295
CD123    KTIACGSEHTVLMTYNNDIYGCGK----EKCFGNALQSSLFTKIEEVNIKTIACGHGNTM 295
         * *****.**:*:. :. :*   *        :   ** :* :**   . *:*  :**:.:**

CD108    ILKYDNTLFSTGQNNYGQLANANKDVASRNTFVKVNVENIKDIKCGSQFNFLINGSKEIF 351
43593    ILKYDNTLFSTGQNTYGQLANANKDVASRNTFAKVNVENIKDIKCGSQFNFLINGSKEIF 351
CD16     ILKYDNTLFSTGQNNYGQLANANKDVASRNTFAKVNVENIKDIKCGSQFNFLINGSKEIF 351
CD126    ILKYDNTLFSTGQNNYGQLANANKDVASRNTFAKVNVENIKDIKCGSQFNFLINGSKEIF 351
CD4      LIDNKGTLKVAGNNDIYQLGIANYSENIDNSFIDLKNIVAKNIFIGLSHSILIDSNNDSY 355
CD123    LIDNKGTLKVAGNNDIYQLGIANYSENIDNSFIDLKNIVAKNIFIGLSHSILIDSNNDSY 355
         ::. ..** :*:*  **. ** .    *:*  .::    *:* *  ...:**:..:: :

CD108    VSGCNLAGQLGSFFHTTFLYEFSKVQSS--NLDNYSGLLVNDDYLYVTKDNSEFLNVKLS 409
43593    VSGCNLAGQLGSFFHTTFLYEFSKVQSS--NLDNYSGLLVNDDYLYVTKDNSEFLNVKLS 409
CD16     VSGCNLAGQLGSFFHTTFLYEFSNVQSS--NLDNYSGLLVNDDYLYVTKDNSEFLNVKLS 409
CD126    VSGCNLAGQLGSFFHTTFLYEFSNVQSS--NLDNYSGLLVNDDYLYVTKDNSEFLNVKLS 409
CD4      CTGDNTYGQLGSFFDDMHIVEFKKMDSEKYSYSNYINLIKSEDKLTLLKEEMEIKDIELP 415
CD123    CTGDNTYGQLGSFFDDMHIVEFKKMDSEKYSYSNYINLIKSEDKLTLLKEEMEIKDIELP 415
         :* *  *******.  .: **.:::*.  . .** .*: .:* * : *:: *: :::*.
```

FIGURE 8 (Continued)

```
CD108       DNFQDYKKIELTDNNMFIVMNDGTLYACGLNNYGQLGLGDTVNRSVMTKVDIDNVLDIKG 469
43593       DNFQDYKKIELTDNNMFIVMNDGTLYACGLNNYGQLGLGDTVNRSVMTKVDIDNVLDIKG 469
CD16        DNFQDYKKIELTDSNMFIVMNDGTLYACGLNNYGQLGLGDTVNRSVMTKVDIDNVLDIKG 469
CD126       DNFQDYKKIELTDSNMFIVMNDGTLYACGLNNYGQLGLGDTVNRSVMTKVDIDNVLDIKG 469
CD4         LDIHSVRDVVFSPYCTLVILGNGDVYGLGNNRYKGMGSDLPSQLNELTKLSISNVKSIVA 475
CD123       LDIHSVRDVVFSPYCTLVILGNGDVYGLGNNRYKGMGSDLPSQLNELTKLSISNVKSIVA 475
            ::::. :.: ::      :::::.:* :*. * *.*   :*   . : . :**:.*.** .* .

CD108       NGNST---FVLKNNGTLYSCGYNSSGILGLKDNTNRNIFTKIEIENIKEFCVESN----Y 522
43593       NGNST---FVLKNNGTLYSCGYNSSGILGLKDNTNRNIFTKIEIENVKAFCVESN----Y 522
CD16        NGNST---FVLKNNGTLYSCGLNSNGQLGLRDEVNRNIFTKIEIENVKDFCVGSN----Y 522
CD126       NGNST---FVLKNNGTLYSCGLNSNGQLGLRDEVNRNIFTKIEIENVKDFCVGSN----Y 522
CD4         SKNISGGIFYIKNDDTCYYSGPNSNSIAGVLP-SNSDVFKKISIDNVKKVVINTDLSNWF 534
CD123       SKNISGGIFYIKNDDTCYYSGPNSNSIAGVLP-SNSDVFKKISIDNVKKVVINTDLSNWF 534
            . * :   * :**:.* * .* **..  *:    *  ::*.**.*:*:* . : ::    :

CD108       IVALNHSKELYGWGNQS--YIVYGDNRNYPYKDTRVSNVEKIATWSDTLYILDSTGATKT 580
43593       IVVLNHSKELYGWGNES--YIVYGNSRNYPYKDTRVSNVEKIATWSDTLYILDSTGATKT 580
CD16        VIALNHSKEVYGWGNNP--YNNIEKTSNYPYKQG-ISNIEKIAAYDYSVYMINSEGKLYV 579
CD126       VIALNHSKEVYGWGNNP--YNNIEKTSNYPYKQG-ISNIEKIAAYDYSVYMINSEGKLYV 579
CD4         SLIVTNNKQIYTSGKSSSYVNGLSNALISQYTEISLSNVTDAYSSYNATFIVVDEKKVYA 594
CD123       SLIVTNNKQIYTSGKSSSYVNGLSNALISQYTEISLSNVTDAYSSYNATFIVVDEKKVYA 594
            : :.:.*::*  *:..        .         *.:  :**: .  :   : :::  .      .

CD108       IGYSYNGSGGYPAPSSSSTYR----EGGYINKNTSYRTLEFYNTSKTKLVNLFAFYNGCV 636
43593       IGYSYNGSGGYPAPSSSSTYR----DGGYINKNTSYRTLEFYNTSKTKLVNLFAFYNGCV 636
CD16        SGYNYNYQLGKGNNSNQSKAL----VSQCRTNSTSSTSNGLR--TLPKITNVFPFYDGCA 633
CD126       SGYNYNYQLGKGNNSNQSKAL----VSQCRTNSTSSTSNGLR--TLPKITNVFPFYDGCA 633
CD4         TGINTNYLLGFSTSDGSNVNLGLLSDWYYINISGSSYSRVSCTNNITKINNIIIYEYVTV 654
CD123       TGINTNYLLGFSTSDGSNVNLGLLSDWYYINISGSSYSRVSCTNNITKINNIIIYEYVTV 654
             * . *    *    ....           . . *   :       . .*: *:: :    .

CD108       FVDENGLAYCIGENNINFRGGSTTNENNSLRFINNSGVYYT--------NTDGTDYTCYQ 688
43593       FVDENGLAYCIGENNINFRGNSTTNENNSLRFINNSGVYYT--------NTDGTDYTCYQ 688
CD16        IIDEGGYVYLTG-----YHGYLRT--LNSSPSISDYSRYGT--------FIEATNSNHNT 678
CD126       IIDEGGYVYLTG-----YHGYLRT--LNSSPSISDYSRYGT--------FIEATNSNHNT 678
CD4         FCTNIG-SFLTG-----YHGTSWTKPTDSSYRVQYQGISYAGYLDSYIYNYYPTRCTQSS 708
CD123       FCTNIG-SFLTG-----YHGTSWTKPTDSSYRVQYQGISYAGYLDSYIYNYYPTRCTQSS 708
            : : *   *       ::*  *  :*  :. . :               *   .

CD108       WTYKLIRCSIFDSPQNIIGNSKNILYLSKNNSTFKCTGNCITYGINSQNWYSYFS----- 743
43593       WTYKLIRCSIFDSPQNIIGNSKNILYLSKNNSTFKCTGNCITYGINSQNWYSYFS----- 743
CD16        Y---FIQETDFSGIEKVIGMSNNILFFKKGSS--YITGYPKTFGSTITGHRSYTS----- 728
CD126       Y---FIQETDFSGIEKVIGMSNNILFFKKGSS--YITGYPKTFGSTITGHRSYTS----- 728
CD4         SSTTFAYLYNGESSSNLKNVNPDNLLISGGSS--YIHQYGRNYLNNQSSNNIAASNINSG 766
CD123       SSTTFAYLYNGESSSNLKNVNPDNLLISGGSS--YIHQYGRNYLNNQSSNNIAASNINSG 766
                :        .. .::  . . :  *  :. ...*          .:  . .      *

CD108       -DSSNGAIALGNEFILKNYSGECLLKGYG----KATNGEFGNSTNISSISNYDTGLKDIK 798
43593       -DSSNGAIALGNEFILKNYSGECLLKGYG----KATNGEFGNSTNISSISNYDTGLKDIK 798
CD16        -INSE-SSNLGSNFIIYHSN--SKLYGKG----IANSGQFGNSTNIDGTSNYDTGLKDIK 780
CD126       -INSE-SSNLGSNFIIYHSN--SKLYGKG----IANSGQFGNSTNIDGTSNYDTGLKDIK 780
CD4         PITSDKAIFLYKALLYLSSN---TLYGFGNISESAKELDVSDTQDGYNATNYKKVMKNIK 823
CD123       PITSDKAIFLYKALLYLSSN---TLYGFGNISESAKELDVSDTQDGYNATNYKKVMKNIK 823
             .*: :  *  . ::   .      * * *      *.. :..:: :   . :**.. :*:**
```

FIGURE 8 (Continued)

```
CD108    DIIV------KNNTVVVVDKNNNIYVTGANQFNKLGIGEYNNQPIRKFTNITEQSNSFIF 852
43593    DIIV------KNNTVVVVDKNNNIYVTGANQFNKLGIGEYNNQPIKKFTNITEQSNSFIF 852
CD16     DIIV------KGNTVVVVDKNNNIYVTGMNQNNKLGIGEYNNEPVKKFTNITEQSNSFIF 834
CD126    DIIV------KGNTVVVVDKNNNIYVTGMNQNNKLGIGEYNNEPVKKFTNITEQSNSFIF 834
CD4      NIFIPPYDLSRDKTRFAILTDKSLFICGYNSKGTHGISVNSSLNLNNKINYNKKNSSSEI 883
CD123    NIFIPPYDLSRDKTRFAILTDKSLFICGYNSKGTHGISVNSSLNLNNKINYHKKNSSSEI 883
         :*::      :..:  ..: .::.:::  * *. .. **.  ..  :.:  *  ::..*  :

CD108    MDDIKEITTSRNTMFIVKNDGTAYATGNNSSGQLGLGDTINRNKFTQINLDNIKKIST-- 910
43593    MDDIKEITTSRNTMFIVKNDGTAYATGNNSSGQLGLGDTINRNKFTQINLDNIKKIST-- 910
CD16     MDDIKEITTSRNTMFIVKNDGTAYATGNNSSGQLGLGDTINRNKFTQINLDNIKKIST-- 892
CD126    MDDIKEITTSRNTMFIVKNDGTAYATGNNSSGQLGLGDTINRNKFTQINLDNIKKIST-- 892
CD4      SSNIQEIYSHSKSTYLLTNNNMLYSVGLNDVGQLGVGDEINRKVFTKINIDNIKSINVNR 943
CD123    SSNIQEIYSHSKSTYLLTNNNMLYSVGLNDVGQLGVGDEINRKVFTKINIDNIKSINVNR 943
         .:*:**  :  ::  :::.*:.  *:.* *. ****:** ***: **:**:****.*..

CD108    -SIDGNTTFAIRNDGTLYSTGLNTKGQLGLGDIVNRNTFTKVNIQNVRDVVLGTTHSHAI 969
43593    -SIDGNTTFAIRNDGTLYSTGLNTKGQLGLGDIVNRNTFTKVNIQNVRDVVLGTTHSHAI 969
CD16     -SIDGNTTFAIRNDGTLYSTGLNTKGQLGLGDIVNRNTFTKVNIQNVRDVVLGTTHSHAI 951
CD126    -SIDGNTTFAIRNDGTLYSTGLNTKGQLGLGDIVNRNTFTKVNIQNVRDVVLGTTHSHAI 951
CD4      FTDNSKHAFAIKNDNTCYAVGLNNSGQLGIGDNVNRNIFTKINVENVKYVAVYGNTSLLL 1003
CD123    FTDNSKHAFAIKNDNTCYAVGLNNSGQLGIGDNVNRNIFTKINVENVKYVAVYGNTSLLL 1003
          : :.: :***:**.* *:.***..****:** **** ***:*::**: *.:  . *  :

CD108    KDDNTLYSCGENTHGQLGLGSESNHPDVLTFTVNNITNVRDVYCSDTTTFIVKDTNIAYC 1029
43593    KDDNTLYSCGENTHGQLGLGSESNHPDVLTFTVNNITNVRDVYCSDTTTFIVKDTNIAYC 1029
CD16     KDDNTLYSCGENTHGQLGLGSESNHPDVLTFTVNNITNVRDVYCSDTTTFIVKDTNIAYC 1011
CD126    KDDNTLYSCGENTHGQLGLGSESNHPDVLTFTVNNITNVRDVYCSDTTTFIVKDTNIAYC 1011
CD4      TNDGLLYGAGNNGKGQLGLGDTTSRN---IFTRIPINGVRDVYLCNDVSIIVKNDNTCYV 1060
CD123    TNDGLLYGAGNNGKGQLGLGDTTSRN---IFTRIPINGVRDVYLCNDVSIIVKNDNTCYV 1060
         .:*. **..*:* :******. :.:      **  *..***** .: .::***: * .*

CD108    CGYNNNSQLGMGNTTDQYSFIKCMENVKEVIPN-EINTYIITIYNTAYSTGLNTDYCLGL 1088
43593    CGYNNNSQLGMGNTTDQYSFIKCMENVKEVIPN-EINTYIITIYNTAYSTGLNTDYCLGL 1088
CD16     CGYNNNSQLGMGNTTDQYSFIKCMENVKEVIPN-EINTYIITIYNTAYSTGLNTDYCLGL 1070
CD126    CGYNNNSQLGMGNTTDQYSFIKCMENVKEVIPN-EINTYIITIYNTAYSTGLNTDYCLGL 1070
CD4      CGLVNGYFGFTEGSISTFTKIN-IENVKSVVTAGSEATFFITNDNMIYTTGKKERVFFST 1119
CD123    CGLVNGYFGFTEGSISTFTKIN-IENVKSVVTAGSEATFFITNDNMIYTTGKKERVFFST 1119
         ** *. .: . :: *: :****.*:. . *::** * *:**  : :  :.

CD108    NSNSNQSSFSEIPISNVVKVAPNRNNAVLLLTSEGDVYTAGKCSNGSGTGSETPEKIKKI 1148
43593    NSNSNQSSFSEIPISNVVKVAPNRNNAVLLLTSEGDVYTAGKCSNGSGTGSETPEKIKKI 1148
CD16     NSNSNQSSFSEIPISNVVKVAPNRNNAVLLLTSEGDVYTAGKCSNGSGTGSETPEKIKKI 1130
CD126    NSNSNQSSFSEIPISNVVKVAPNRNNAVLLLTSEGDVYTAGKCSNGSGTGSETPEKIKKI 1130
CD4      ETNDIKGIRVINNIINAKKIVVN-GYTSAILTNDNKLFVGG----LSGYGSIANNNNTNS 1174
CD123    ETNDIKGIRVINNIINAKKIVVN-GYTSAILTNDNKLFVGG----LSGYGSIANNNNTNS 1174
         ::*. :.      * *. *:. *  . :  :**.::..:..*     ** **  : ::  .:

CD108    ASKAKDIGMNYRCGHYVSDNGDLYGTGFNDCGQLGVGNVTKRDTFIKTNTR-VKKILPLE 1207
43593    ASKAKDIGMNYRCGHYVSDNGDLYGTGFNDCGQLGVGDVTKRDTFIKTNTR-VKKILPLE 1207
CD16     ASKAKDIGMNYRCGHYVSDNGDLYGTGFNNGQLGVGDVTKRDTFIKTNTR-VKKILPLE 1189
CD126    ASKAKDIGMNYRCGHYVSDNGDLYGTGFNNNGQLGVGDVTKRDTFIKTNTR-VKKILPLE 1189
CD4      VEDVKDVFVTANNTLYIDNNNNLISSGRDTYGISDESYRDMSVPYYKVSIKKDVDTVFSS 1234
CD123    VEDVKDVFVTANNTLYIDNNNNLISSGRDTYGISDESYRDMSVPYYKVSIKKDVDTVFSS 1234
         ....**: :. .   *:.:*.:* .:*  :  *   .  .:  *.. :.     .  :  .
```

FIGURE 8 (Continued)

```
CD108   YANIAIKDTN-DIYICGLNN-YGQLGVGNRYDSRNN---DNRIFNYKHMNFVMGDLTSIK 1262
43593   YANIAIKDTN-DIYICGLNN-YGQLGVGNRYDSRNN---DNRIFNYKHMNFVMGDLTSIK 1262
CD16    YANIAIKDTN-DIYICGLNN-YGQLGVGNRYDSRNN---DNRIFNYKHMNFVMGDLTSIK 1244
CD126   YANIAIKDTN-DIYICGLNN-YGQLGVGNRYDSRNN---DNRIFNYKHMNFVMGDLTSIK 1244
CD4     YNTIFIKDIYGKFYSSTRDNRYNHLGIHHRYDNDKNEALEGSLHSYFKTDNTSDKIVFNK 1294
CD123   YNTIFIKDIYGKFYSSTRDNRYNHLGIHHRYDNDKNEALEGSLHSYFKTDNTSDKIVFNK 1294
        * .* ***      .:*   :* *.:**: :***. :*   :. :..* : : ...:. *

CD108   NRHNFILLNNKIVIPTTKDIDYGLVLGNLYKGDLYTELPYEDIKEVSISKTHIIILLNDG 1322
43593   NRHNFILLNNKIVIPTTKDIDYGLVLGNLYKGDLYTELPYEDIKEVSISKTHIIILLNDG 1322
CD16    NRHNFILLNNKIVIPTTKDIDYGLVLGNLYKGDLYTELPYEDIKEVSISKTHIIILLNDG 1304
CD126   NRHNFILLNNKIVIPTTKDIDYGLVLGNLYKGDLYTELPYEDIKEVSISKTHIIILLNDG 1304
CD4     KNEKLVMFNDKYIKTNNKYINYKNIFKDNFK--YTSIILPFEVSDIDISKTHSLAVAKDG 1352
CD123   KNEKLVMFNDKYIKTNNKYINYKNIFKDNFK--YTSIILPFEVSDIDISKTHSLAVAKDG 1352
        :...::::::*:*  : ...* *:*   ::  : :*     : :   ::.::.***** : : :**

CD108   TMYGCGTNYHGELLQDLSINQVDEFVQINVSDVKHVSCGDNFTYFIKSDDSLWSIGKNSE 1382
43593   TMYGCGTNYHGELLQDLSINQVDEFVQINVSDVKHVSCGDNFTYFIKSDDSLWSIGKNSE 1382
CD16    TMYGCGTNYHGELLQDLSINQVDEFVQINVSDVKHVSCGDNFTYFIKSDDSLWSIGKNSE 1364
CD126   TMYGCGTNYHGELLQDLSINQVDEFVQINVSDVKHVSCGDNFTYFIKSDDSLWSIGKNSE 1364
CD4     KLYGIGSNSYKEINQTLEDIELLTLTEVNISDVKKVACGDNYSYIIKTDNTLWSYGKNTE 1412
CD123   KLYGIGSNSYKEINQTLEDIELLTLTEVNISDVKKVACGDNYSYIIKTDNTLWSYGKNTE 1412
        .:** *:* : *:  * *.  ::   :.::*:****:*:****:*:**:*:*** ***:*

CD108   YQLGIGHNNPVTELQRITTISSCKEVHCGKNYTLVVTTSNELFVQGYNDKGALGLGSDSE 1442
43593   YQLGIGHNNPVTELQRITTISSCKEVHCGKNYTLVVTTSNELFVQGYNDKGALGLGSDSE 1442
CD16    YQLGIGHNNPVTELQRITTISSCKEVHCGKNYTLVVTTGNELFVQGYNDKGALGLGSDSE 1424
CD126   YQLGIGHNNPVTELQRITTISSCKEVHCGKNYTLVVTTGNELFVQGYNDKGALGLGSDSE 1424
CD4     YQLGVGHNNDVRELQKVTGLPSVKDISIYNSMTLVLTNEGELYAQGYNTNGLFGLGESEK 1472
CD123   YQLGVGHNNDVRELQKVTGLPSVKDISIYNSMTLVLTNEGELYAQGYNTNGLFGLGESEK 1472
        ****:**** * ***::* :.* *::    :.  ***:*. .**:.**** :* :***...:

CD108   NTIIKFFTKALTDIREIKSYGSDHILVLKNDNSVWVTGKNRDVYKIEQPVEFLKEFTIVP 1502
43593   NTIIKFFTKALTDIREIKSYGSDHILVLKNDNSVWVTGKNRDVYKIEQPVEFLKEFTIIP 1502
CD16    NTIIKFFTKALTDIREIKSYGSDHILVLKNDNSVWVTGKNRDVYKIEQPVEFLKEFTIVP 1484
CD126   NTIIKFFTKALTDIREIKSYGSDHILVLKNDNSVWVTGKNRDVYKIEQPVEFLKEFTIVP 1484
CD4     DKIIRTFTKVLTNVKEIKSHNDDHILVIKNDNSLWITGKNKSMYKISISITDLYEFTKIP 1532
CD123   DKIIRTFTKVLTNVKEIKSHNDDHILVIKNDNSLWITGKNKSMYKISISITDLYEFTKIP 1532
        :.**: ***.**::;:****:..*****:*****:*:****:.:***. .:  * *** :*

CD108   ISEDVNTVKDVLATDNTLYIISEVGTTNAAIEITEKSISSIKIKIQDPNKDISRIEMLIN 1562
43593   ISEDVNTVKDVLATDNTLYIISEVGTTNAAIEITEKSISSIKIKIQDPNKDISRIEMLIN 1562
CD16    ISEDVNTVKDVLATDNTLYIISEVGTTNAAIEITEKSISSIKIKIQDPNKDISRIEMLIN 1544
CD126   ISEDVNTVKDVLATDNTLYIISEVGTTNAAIEITEKSISSIKIKIQDPNKDISRIEMLIN 1544
CD4     IPEHLNDILDIELSDDTIYMITKVDTSKASIEIVEKSISQVRVVVQDPNNVIEKLEMFIN 1592
CD123   IPEHLNDILDIELSDDTIYMITKVDTSKASIEIVEKSISQVRVVVQDPNNVIEKLEMFIN 1592
        *.*.:*  : *:   :*:*:*:*::*.*.:::*:***.*****.::: :****: *.::**:**

CD108   GESVKSVSDLITEKISFEVPPDKIKIGENKILFRAYCKGDDLYASLFIFKESTGNSIIKD 1622
43593   GESVKSVSDLITEKISFEVPPDKIKIGENKILFRAYCKGDDLYASLFIFKESTGNSIIKD 1622
CD16    GESVKSVSDLTTEKISFEVPPDKIKIGENKILFRAYCKGDDLYASLFIFKESTGNSIIKD 1604
CD126   GESVKSVSDLTTEKISFEVPPDKIKIGENKILFRAYCKGDDLYASLFIFKESTGNSIIKD 1604
CD4     DELISTKTNLEINSIIFEIPQNKIVLGENKILIKASSPTGDLYSSMFIFKSETGLKVKKD 1652
CD123   DELISTKTNLEINSIIFEIPQNKIVLGENKILIKASSPTGDLYSSMFIFKSETGLKVKKD 1652
        .* ::.: ::*  :.* **:* :** :*****::* .  .***:*;****..** .: **
```

FIGURE 8 (Continued)

```
CD108      SYVMIGNRMYKVVNTTSNEQDITITLDRGLEEDLNLGDPIYQLINKTKVQVKINKSDLFK 1682
43593      SYVMIGNRMYKVVNTTSNEQDITITLDRGLEEDLNLGDPIYQLINKTKVQVKINKSDLFK 1682
CD16       SYVMIGNRMYKVVNTTSNEQDITITLDRGLEEDLNLGDPIYQLINKTKVQVKINKSDLFK 1664
CD126      SYVMIGNRMYKVVNTTSNEQDITITLDRGLEEDLNLGDPIYQLINKTKVQVKINKSDLFK 1664
CD4        SILMINNKVYSIINITENNTDLIVTLNEGLKDDMMENNPIYQLINKTKVQVKINKSDLFK 1712
CD123      SILMINNKVYSIINITENNTDLIVTLNEGLKDDMMENNPIYQLINKTKVQVKINKSDLFK 1712
           *  :**.*::*.::*  *.*:  *:  :**:.**::*:   .:************************

CD108      DMKLVEIKKSDSSYQEIYELEEANIKSAQPKIIVEKGDKWTAIKRPSMIFRYDAENNEPQ 1742
43593      DMKLVEIKKSDSSYQEIYELEEANIKSAQPKIIVEKGDKWTAIKRPSMIFRYDAENNEPQ 1742
CD16       DMKLVEIKKSDSSYQEIYELEEANIKSAQPKIIVEKGDKWTAIKRPSMIFRYDAENNEPQ 1724
CD126      DMKLVEIKKSDSSYQEIYELEEANIKSAQPKIIVEKGDKWTAIKRPSMIFRYDAENNEPQ 1724
CD4        DMKLVEIKKSDSSYQEIYELEEANIKSAQPKIIVEKGDKWTAIKRPSMIFRYDAENNEPQ 1772
CD123      DMKLVEIKKSDSSYQEIYELEEANIKSAQPKIIVEKGDKWTAIKRPSMIFRYDAENNEPQ 1772
           ************************************************************
```

FIGURE 11. SEQ ID NOs:87-163

SEQ ID NO:87    >M68_1374

MKQNKLLQRGAYFNDKNILIDDFDKRYNDYDFVEFFTGISNSTFGLKSDGNLYACGDNTGFQLGLGKDSS
ERRMFSKVKIDNVKYVSCGSKHSVAVTKDGFAYGAGTSNVGQLGVIESTVYYEFTKLPIDDVKTVACGYD
FTFVLKNDGTLYSAGLNSSGQLGLGDTNNRATFTKVNIDSVKDVVTYNQSVFIIKMDGTAHACGLNSNGQ
LGINSTLNKSVFNKIEGMDNVKQIACGSSHTILIKNDGTMYTTGYNGVGQLGTGNNNNSIVFTLSSINNV
KYASCGNNHTMILKYDNTLFSTGQNNYGQLANANKDVASRNTFAKVNVENIKDIKCGSQFNFLINGSKEI
FVSGCNLAGQLGSFFHTTFLYEFSKVQSSNLDNYSGLLVNDDYLYVTKDNSEFLNVKLSDNFQDYKKIEL
TDNNMFIVMNDGSLYACGLNNAGQLGLGDTVNRSVMTKVDIDNVLDIKGNGSSTFVLKNNGTLYSCGLNS
SGILGLKDNTNRNIFTKIEIENIKEFCVESNYIVALNHSKELYGWGNQSYIVYGDNRNYPYKDTRVSNVE
KIATWSDTLYILDSTGAAKTIGYSYNGSGGYPAPSTSSSYQSKGYNAWNTSYRTLEFYNTAQTKLINLFA
FYRGCMFFDESDRAYCIGENNMKFTSSSQITPESELRFSSNSGIYHTNSDGGVYTCYQWTYKLIRCSVFD
SSKSVVGNSKNILSLLKNNSTFRCTGSCLTYGQTNQNWSSYLSDNCNGAVSLGNEFILKNYSGESVLKGY
GKSNNGEFGSSTSISNASNYDTGLKDIKDIIVKNNTVVVVDKNNNIYVTGTNQFNKLGIGEYNNQPIKKF
TNITEQSNSFIFMDDIKEITTSRNTMFIVKNDGTAYATGNNSSGQLGLGDTINRNKFTQINIDNIKKIST
SIDGNTTFAIRNDGTLYSTGLNTKGQLGLGDIVNRNTFTKVNIQNVRDVVLGTTHSHAIKDDNTLYSCGE
NTHGQLGLGSESNHPDVLTFTVNNITNVRDVYCSDTTTFIVKDTNIAYCCGYNNNSQLGMGNTTDQYSFI
KCMENVKEVIPNEINTYIITIYNTAYSTGLNTDYCLGLNSNSNQSSFSEIPISNVVKVAPNRNNAVLLLT
SEGDVYTAGKCSNGSGTGSETPEKIKKIASKAKDIGMNYRCGHYVSDNGDLYGTGFNNNGQLGVGDVTKR
DTFIKTNTRVKKILPLEYANIAIKDTNDIYICGLNNYGQLGVGNRYDSRNNDNRIFNYKHMNFVMGDLTS
IKNRHNFILLNNKIVIPTTKDIDYGLVLGNLYKGDLYTELPYEDIKEVSISKTHIIILLNDGTMYGCGTN
YHGELLQDLSINQVDEFVQINVSDVKHVSCGDNFTYFIKSDDSLWSIGKNSEYQLGIGHNNPVTELQRIT
TISSCKEVHCGKNYTLVVTTGNELFVQGYNDKGALGLGSDSENTIIKFFTKALTDIREIKSYGSDHILVL
KNDNSVWVTGKNRDVYKIEQPVEFLKEFTIIPISEDVNTVKDVLATDNTLYIISEVGTTNAAIEITEKSI
SSIKIKIQDPNKDISRIEMLINGESVKSVSDLITEKISFEVPPDKIKIGENKILFRAYCKGDDLYASLFI
FKESTGNSIIKDSYVMIGNRMYKVVNTTSNEQDITITLDRGLEEDLNLGDPIYQLINKTKVQVKINKSDL
FKDMKLVEIKKSDSSYQEIYELEEANIKSAQPKIIVEKGDKWTAIKRPSMIFRYDAENNEPQA

SEQ ID NO:88    >fused_M68-1373_BPAR

LEEKFYIILTKIGREKIANATALGELVGLTKFQVGDSNGEYYEPTEEQTALKNVVWEGNINSLRIDEKNP
NWIVIETILPGTVGGFMIREAAVLDNENNIIAIGKYPETYKPRAEDGSIKDLVVKMILQLSNTSNVTLEV
DPTLVFVTQKDIQDLDDKFDKNIKEIKVNIGDVNILTTYSKDLSGAINEVVKKIENISFDDVISGQIQTD
ISVLKNSYNKLSEKVLDILIYLELESEVTVDEAGYWYDTLANGNNIVAIEGLKLDLNRKCITGEIGNVIF
RDVVLPFSANRVRYIHDMDNNFVETKSSNTYLKEQKDITLNKYSYEI

SEQ ID NO: 89    >ATCC43593 CD1375

LFKFDKNKIEQIKQGRKVEMQYKDISDISIGQVKQDDDITNNFIANAEIYEMLLSQSSVNEASNISTFSV
RKSGGESGMVEVYVALILRGKKTIEEVPAVIREQVRIRCKELEIPVE

SEQ ID NO: 90    >ATCC 43593 CD1376

FIGURE 11 (Continued)

MDKLITELSSLGAIGILCALLFKNTMQEKKEDRDMYKKTVENFIELSTQQQEINKNILVQMGIMKTDVEE
IKEDVTDIKGMLQNGV

SEQ ID NO:91    >fused_MR68RBD1_BPAR_

LEEKFYIILTKIGREKIANATALGELVGLTKFQVGDSNGEYYEPTEEQTALKNVVWEGNINSLRIDEKNP
NWIVIETILPGTVGGFMIREAAVLDNENNIIAIGKYPETYKPRAEDGSIKDLVVKMILQLSNTSNVTLEV
DPTLVFVTQKDIQDLETKIGTVNTKIDTTKTELTSNIETAKTELNTKIDQLIAGGSNVAYTQRVAIDDWV
EDAESGFKATVTHSLLTHRIVVNIIDATTKENIVPNFKIVDDNSIEIRSEVKVELNVYVINGNAETHFIN
ATVDDNRVSEMTTYSSKKIEDRLVNIEEKVNGGLSNIATSVNELITY

SEQ ID NO:92    >M68-RBD1

MQTEWNFNYANYVQNVSLPPGRYKLECWGACGGAVDTSDWTDCAKGGYSKGEIVFKKRTNLQICVGQSGY
EKVSEGSSLTRSGFNGAGAAGKVTTGSFAYSKYGGGATDIRLYHPSATWGNTESLLSRILVAGGGGGMKN
NFASARSIGHGGGYVGVNGVGRDRDFCGGGSQYQGGTSYDTEEYHGSLGKGGYGNIGIGGGGGWYGGAGS
YSNECGGGGSGYALNKDSYKAPGYIPTPEYYLENIVMTTGGNTTKADGYAKITLLQALPFLTVSSYNSTQ
ATFKADHTDPALLTKIEWFIDDVLKETITTNLTEEKTINYTLEDNALHTLKIVVTDSNNATAEKVLSISK
NIMPLPENVNLNDISTKLVEVNAGFKVGKTSIINTLALKNIEASLNNTLVELSEKIKTSFDSSDTSVQDL
QNQVTQKNNTITQLETELSKRKRFITGTYTFTKTDAENFNLSIYDKEGTSKTLTIPVNMGFSPSLIVLSG
VTFSTTSKSYVYFDNVCNSNFYNFGYNSDSTHSNPKAVGILNVSNVGYSSLVLTLYKLSMSEAVGIWAKE
GATLTYKIYI

SEQ ID NO:93    >fused_M68-RBD2_BPAR

LEEKFYIILTKIGREKIANATALGELVGLTKFQVGDSNGEYYEPTEEQTALKNVVWEGNINSLRIDEKNP
NWIVIETILPGTVGGFMIREAAVLDNENNIIAIGKYPETYKPRAEDGSIKDLVVKMILQLSNTSNVTLEV
DPTLVFVTQKDIQDLETKIGTVNIKIDTTKTELTSNIETTKTELIGKIGDTTQLTTTDKTNIVSALNEVK
TSVDSIETTADKTSIKDTDNLFESDNVEGALKEVMQEVKGNRSSIISSINSNLIPM

SEQ ID NO:94    >M68-RBD2

MATYDVDRGVKLREGEHTDEEIFLRACSYQTGGRTYYGTFEVGNEIKVFELETRLYTATTTNVRYYSTSG
SEVMVRDVVMRQNVTAMFVAKPTINIKDNLGIISDACEIEYTISDGFPELRYNIVYKLNNDIIGQIVNTV
DSKYKISLTDEYLSKLSHNSTNHIVIEFNDFNNRNMLTKTVIFTKGNTKPKLNITSYNSTTTIFTAIDTD
NNLSKIEWFIDDVLKETITTDLYLEKIINYELTDNAVHTLKIVATDAENATVEKVLSISKEIMPFQSDAS
LSDISTKLAEIGEGFKNGKTSIINTLALKNIEASLNNTLVELSEKIKTSFDSSDASVQDLMNQLTQANNT
ISQLDSKYKYASGTANARENSSLIACIYDPNTSHTVEETSPYWLDLNGIGFIPDIFFAECEYEPNSDAFY
KYFVFAIKNTFSISNNTGFVVNITFNKEYGDRSFKLRGDLYTLGKRHVSMDNTGVRVPALNTLNNLRAYK
WHAAKFK

SEQ ID NO:95    >fused_M68-RBD4_BPAR

LEEKFYIILTKIGREKIANATALGELVGLTKFQVGDSNGEYYEPTEEQTALKNVVWEGNINSLRIDEKNP
NWIVIETILPGTVGGFMIREAAVLDNENNIIAIGKYPETYKPRAEDGSIKDLVVKMILQLSNTSNVTLEV
DPTLVFVTQKDIQELDTKIDTTKTELTSNIETAKTELNTRIDTENEKQNIKIDQLVAGGVNVSHTHIIEV
ADWILNNETNMYEVTINHPLLTKRILIALYDEIGEALTPNARAIDDNSILVRNEENIKMYVYLINGNAET
HFINATVDDNRVSEMTTYSSKKIEDRLVNIEEKLSGNLSDIATSVNELITYC

FIGURE 11 (Continued)

SEQ ID NO:96    >M68-RBD4

VATEWNFDFKAEAQPITLKAGKYKLECWGAHGKVWGGDSQSSGGYSYGELTLKKETTLYVYTGATGSSNK
YEKFTFNGGGLGVNNGGGGATDIRLVNGDWNNEQGLLSRIIVAGGGGGAFSKTPAGKGGGFKGGNSTNDD
NSSMLIVPGGTQYDGGRGYCDEWDGVFGCGGGSILGLERGKYPYNSGGGGWFGGAGARNTSSGGGGSGYV
LTKDSYKPVGYIPTSEYWLENVGSITGGNTAKVNGYAKITLLQALPILTISSYNSTQATFKADHTDPTLL
TKIEVFIDDTLKETITTDLTLEKTINYTLEDNALHTLKIVVTDSNNATAEKVLSISKNIMPLPENVNLQD
ISTKLTEVNAGFKSGKTSIINTLALKNIEASLNNTLIELSEKIKISFDSSDASVQDLMNQLTQANNTISQ
LNTKYKVASGRTSTLTDTTSTAYLYVNSQSNPNYPINPGGWVNIKGLNFIPNIFFAECECTTNSPTQFYK
YLIFATYLIPSLSDKDFVITTALRKTNSDTKFTADSQVYINNRGNTYINNQGVYVPAYRPSVSYTLYNWY
AIKFV

SEQ ID NO:97    >fused_M68-RBD5_BPAR

LEEKFYIILTKIGREKIANATALGELVGLTKFQVGDSNGEYYEPTEEQTALKNVVWEGNINSLRIDEKNP
NWIVIETILPGTVGGFMIREAAVLDNENNIIAIGKYPETYKPRAEDGSIKDLVVKMILQLSNTSNVTLEV
DPTLVFVTQKDIQDLDSKIDTTKTELTSNIETAKTELNTRIDTENEKQNIKIDQLIAGGSNVASTQTITI
DDWVEDAENGFKATVTHSLLTQRIVVNIIDATTKENVVTNFKIIDDNSIEIRSETRSELNVYVINGNAET
RFINATVDDNRVSEMTTYSSKKIEDRLVNIEEKVNGNLSNIATSVNELITYC

SEQ ID NO:98    >M68-RBD5

VATEWNFDFKAEAQPITLKAGKYKLECWGAHGRVWTGDSPSNGGYSYGELTLKKETTLYVYTGAAGSSNK
YEEFTFNGGGLGVNSGGGGATDIRLVNGDWNNEQGLLSRIIVAGGGGGAFSKTPAGKGGGFKGGNSTNDD
NSSMLIVPGGTQYDGGRGYYDEWDGVFGCGGGSILGLERGKYPYNSGGGGWFGGAGARNTSSGGGGSGYV
LTKDSYKPVGYIPTSEYWLENVGSITGGNTAKVNGYAKITLLQALPILTISSYNSTQATFKADHTDPTLL
TKIEYFIDDVLKETITTDLTLEKTINYTLEDNALHTLKIVVTDSNNATAEKVLSISKNIMPLPENVNLQD
ISSKLIEINTGFKTGKTSIINTLALKNIEASLNNTLVELSEKIKTSFDSSDASVQELQNRITELTNQLSQ
RIKYATGTYTIPDGTSSLVVPTNLTFVPKTIIVKIFSVKDGSNPSKTLSAYPCMTGVNQNLRYDNGSYTR
VIGNASIRDVTADSFKIELGKSDFNAGVEFPFTFYSKTFRWYALDIEFLNN

SEQ ID NO:99    >fused_R20291-RBD1_BPAR

LEEKFYIILTKIGREKIANATALGELVGLTKFQVGDSNGEYYEPTEEQTALKNVVWEGNINSLRIDEKNP
NWIVIETILPGTVGGFMIREAAVLDNENNIIAIGKYPETYKPRAEDGSIKDLVVKMILQLSNTSNVTLEV
DPTLVFVTQKDIQDLDAKISNVNTKIDTTKTELTSNIETAKTELNTRIDTENEKQNIKIDQLIAGGSNVA
STQTITIDDWIDNQEGGFKATVTHGLLTQRITVSIIDATTKDNVVPDFTIIDDNSIEVRSGVKVELNVYV
INGNAETHFINATVDDNRVSEMTTYSSKKIHEEIGKVAEQLTGINSNIISTVNNDILPI

SEQ ID NO:100    >R20291-RBD1

MALSMSYFNLPDKRKYTKNLAFNPFAGGRQNFEWTGGDHGLNGEFKETCLSCTYNGSTLNWGSGNVWVLG
EYGQYTFTYNCESMHVDTQQKFPYTSNRIITIKGRPVISGSDTSLGNKRKGFSVDFTVSDDTPNVNLIVR
AYLDDKLIQNITPVVQNSTLTATVTDSQLNSLSVDGNHKLKIQLNDGYDNFDRIFTFKKIEKGIDISTSL
VTDSQAKFTVTKIYSELTKIECYLDETLKETFTTDLYSEKTINYELIDNAIHTLKIVVTDAENVVEEKVI
SISKNIMPLQPDATLQDISTKLTEIGQGVRNGKTSIINTLALKNIDASLNNTLVELSEKIKGGFDSGDAS
LQDLMNQLTQANNTISQLNTKYKVASGTVTSFADSTKIAYPYLTDNVTKPGSWIKVSNLGFKPNIFFADF

FIGURE 11 (Continued)

DYYDAEYKNNYKLFLFACNGVATQRGVDFSSVTSFIRKSGDEYFHANGWLYSNSEGDVYFNNTGVQIPAY
NFDSTQKHTYKWYAIKFI

SEQ ID NO:101    >fused_BI9-RBD2_BPAR

LEEKFYIILTKIGREKIANATALGELVGLTKFQVGDSNGEYYEPTEEQTALKNVVWEGNINSLRIDEKNP
NWIVIETILPGTVGGFMIREAAVLDNENNIIAIGKYPETYKPRAEDGSIKDLVVKMILQLSNTSNVTLEV
DPTLVFVTQKDIQDLETKIGTVNTKIDTTKTELNSKVGDTTLLTTTDKTNIVNALNEVKKTSVDSIETTA
EKTSYNNATSKLNATNVQGAIDEIVAEVRGNRSSIISSINDNLIPM

SEQ ID NO:102    >BI9-RBD2

MPPAETFICNRIVKKRRGYYSERDVFLSPCPYVYGEGGMYESTYYGEFDLSNSKYITVPTSTKYEKTATR
VYFISGGNMITSSSGMKQAITLELIPDPNIIINDDLGVISDSCNINYRIPDSNTSVKFDVTEKLNGVVIS
KKNYALDGNYTLNLTDEHLSTLSFNSTNNITIELSTYQGGKFLEKTVTFTKGNTKPKLNITSYNSTTAIF
TAIDIDNNLSKIEWFIDDVLKETITTDLYLEKTINYELTDNAIHTLKIVATDAENATVEKVLSISKEIMP
LQEDASLSDISTKLAEIGEEFRNGKTSIINTLALKNIEASLNNTLVELSEKIKTSFDSSDASVQDLQNRI
TELNNQLSQRKKWATGRYTFTDLDISNFTLNSESIVQTKSIITDLSFTPSIIIIDSIQMKSGTDRVYFRS
ITNLDITIGAKYTNSSLPVGGSGYIYIQKPTPSNNFLLILTRLDGQGREISFSPIVGETLTWYAFE

SEQ ID NO:103    >fused_TL174-RBD_BPAR

LEEKFYIILTKIGREKIANATALGELVGLTKFQVGDSNGEYYEPTEEQTALKNVVWEGNINSLRIDEKNP
NWIVIETILPGTVGGFMIREAAVLDNENNIIAIGKYPETYKPRAEDGSIKDLVVKMILQLSNTSNVTLEV
DPTLVFVTQKDIQDLDTKIDTTKAELTSNIETAKTELNNKIGDTTLLTTTDKTNIVSAINEVKTSVDSIE
TTAEKTSYNNATSNLNATNVQGAIDEVVRKIENFNEININIQNDMLPI

SEQ ID NO:104 >TL174-RBD

MQTVWNFDYANYVRSISLLPGRYKLECWGACGGGKGASSFNECAKGGYAKGEIILKKRTNLIVCVGQSGY
EKLAKDSNITRTGFNGGGRAGSTNIGDYIYAGYGGGATDIRLYYSSTTWDSSEGLLSRILVAGGAGAISG
FSYPHPSIGHGGGEKGSDGVSANTNRFSGGGSQYQGGSNQETIEYHGSFGKGGIGYYSVGGGGGWYGGGG
TNAGNVAGGGSGYALTKDSYKPPGYIPTSEYWLENVVMTTGGNTTRADGYAKITLLQALPFLNISSYNST
QVTFKADHTDPTLLTKIEVFIDDTLKETITTDLTTEKTINYTLEDNALHTLKIVVTDSNNATAEKVLSIS
KGIAPLPAGSTTDEVTNKWIEIKDTFRSGKTSIINTLALKNIEASLNNTLVELSEKIKVGFDSKDASLQD
LIKQLTQANNTISQLNTKYKVASGTTTALEAEGRGSLFEVTYSGGKSYAYNRWVKVTGLNFTPNIFITFE
NHKTSYPYFYCNFTFACQGVFDKDFAVVTFYSFRGQPGETTYDATGNVIHIDKGAPYMNENGVYLPVYTQ
EGYLTRNWYAIKFK

SEQ ID NO:105 >fused_CD305-RBD1_BPAR

LEEKFYIILTKIGREKIANATALGELVGLTKFQVGDSNGEYYEPTEEQTALKNVVWEGNINSLRIDEKNP
NWIVIETILPGTVGGFMIREAAVLDNENNIIAIGKYPETYKPRAEDGSIKDLVVKMILQLSNTSNVTLEV
DPTLVFVTQKDIQDLETKIGTVNTKIDTTKTELTSNIETAKTELNNKIGDTTQLTTIDKTNIVSALNEVK
ASVDSIETTAEKTSYNNATSNLIATNVQGAIDEVVRKIENFNEVNISIQNDMLPI

FIGURE 11 (Continued)

SEQ ID NO:106    >CD305-RBD1

MAIVYEFNYTGAEQSVVLPPGKYKFECFGACGGNYYDFVQCAKGGYTAGSLILKENTTLHVYVGQSGYCK
GVNGIETCRSGFNGAGGITTYKSTSDGYYSLAGGGATDIRLIGGNWDNLQSLLSRIIVAGGGGGGSGNSH
DSIGHGGGTKGKDGISIANKYFAGGGSQFQGGLTFNSLYNGSFGVSGAGDGISGVGGGGGWYCGAGSFYA
EFGGGGSGYILTKDSYKPANYSPSSKYYFSDINSVVGGNTTKQDGYAKITLLQALPFLTISSYNSTTATF
KADHTDPTLLTKIEYFIDDVLKETITTDLTLEKTINYTLEDNALHTLKIVVTDSANATAEKVVSISKGIA
PLPAGSTTDEVTSKWIEIKDAFKSGKTSIINTLALKNIEASLNNTLVELSEKIKTSFDSSDASVQDLMNQ
LTQANNTISQLNTKYKVASGRTSALTDTISTAYLYVNSQSNPNYPINPGGWINIEGLNFIPNIFFAECEC
TANSPTQFYKYLVFATYSIPSLSDKDFVITTALRKTNSDTKFTADSQVYINNRGNTYINNQGVYVPAYRP
SVSYTLYNWYAIKFI

SEQ ID NO:107    >fused_BI9-RBD5_BPAR

LEEKFYIILTKIGREKIANATALGELVGLTKFQVGDSNGEYYEPTEEQTALKNVVWEGNINSLRIDEKNP
NWIVIETILPGTVGGFMIREAAVLDNENNIIAIGKYPETYKPRAEDGSIKDLVVKMILQLSNTSNVTLEV
DPTLVFVTQKDIQDLDAKIDTTKTELTSNIETTKTELNTKIGDTTQLTTTDKTNIVSALNEVKSSVDSIE
TTAEKTSIKDTDNLFSSDNVEGALKEVMQEVKGNRSSIISTVNNNLIPM

SEQ ID NO:108    >BI9-RBD5

MSTTVLERTVKRRRGYYRMTDIHASRLTYNDGSPYYTDFVAYYTLDQYERVSISATKKFVAYSTRACQII
NGREVDISRNFTQETTVQFVPDPTIFISNDLGVIGNACSINYRISDSDSSVRFKIIEKINGVKIAEKNNV
VDGNYELIITDELLSELAFNSVNNITIELDNGYGGIFLDKTVTFTKGNTKPKLNITSYNSTSATFTAIDT
DNNLSKIEWFIDDVLKETITTDLTTEKTINYELADNAIHTLKIVATDSENATAEKVLSISKEIMPLQSDA
SLSDISTKLIEIGEGFRNGKTSIINTLALKNIEASLNNTLVELSEKIKQSFDSGDASLQDLMNQLTQANN
TISQLNSKYKVASGTVTSFADSAKIAYPYLTDRTFKPGTWVKISNLDFKPNIFFADFDYYDTEYKNNYKL
FLFACRGVATQRGVDFSSVTAFIRKNSDENFHANGWLYNNSEGDVYFNNTGVQIPAYNFDSTQRHIYKWY
AIKFI

SEQ ID NO:109    >fused_phi027B-RBD_BPAR

LEEKFYIILTKIGREKIANATALGELVGLTKFQVGDSNGEYYEPTEEQTALKNVVWEGNINSLRIDEKNP
NWIVIETILPGTVGGFMIREAAVLDNENNIIAIGKYPETYKPRAEDGSIKDLVVKMILQLSNTSNVTLEV
DPTLVFVTQKDIQDLDAKIDTTKTELTSNIETTKTELNTKIGDTTQLTTTDKTNIVSALNEVKSSVDSIE
TTAEKTSIKDTDNLFSSGNVEGALKEVMQEVKGNRSSIISTVNNNLIPM

SEQ ID NO:110    >phi027B-RBD

MSTTVLERTVKRRRGYYRMTDIHASRLTYNDGSPYYTDFVAYYTLDQYERVSISATKKFVAYSTRACQII
NGREVDISRNFTQETTVQFVPDPTIFISNDLGVIGNACSINYRISDSDSSVRFKIIEKINGVKIAEKNNV
VDGNYELIITDELLSELAFNSVNNITIELDNGYGGIFLDKTVTFTKGNTKPKLNITSYNSTSATFTAIDT
DNNLSKIEWFIDDVLKETITTDLTTEKTINYELADNAIHTLKIVATDSENATAEKVLSISKEIMPLQSDA
SLSDISTKLIEIGEGFRNGKTSIINTLALKNIEASLNNTLVELSEKIKQSFDSGDASLQDLMNQLTQANN
TISQLNSKYKVASGTVTSFADSAKIAYPYLTDRTFKPGTWVKISNLDFKPNIFFADFDYYDTEYKNNYKL
FLFACRGVATQRGVDFSSVTAFIKKNSDENFHANGWLYNNSEGDVYFNNTGVQIPAYNFDSTQRHIYKWY
AIKFI

FIGURE 11 (Continued)

SEQ ID NO:111    >fused_CD630-RBD1_BPAR

LEEKFYIILTKIGREKIANATALGELVGLTKFQVGDSNGEYYEPTEEQTALKNVVWEGNINSLRIDEKNP
NWIVIETILPGTVGGFMIREAAVLDNENNIIAIGKYPETYKPRAEDGSIKDLVVKMILQLSNTSNVTLEV
DPTLVFVTQKDIQELETKIGTINTKIDTTKTELTSNIETAKTELSNKIGDTTQLNTTDKTNIVSALNEVK
TSVDSIETTAEKTSYNNATSKLTATTVQGAIDEVVAKIENFNEVNISIQNDMLPI

SEQ ID NO:112    >CD630-RBD1

MTTEWNFNYIGTGKKVILKPGKYKLECWGASGGGRFDEWTECAKGGYSKGELTLKKETILYVYAGESGYK
KFSNISDWAGFNGGGRGPNEGVDPKFTTCGGGATDIRLIGGVWNDEQGLLSRIIVAGGGGSIGTSSFSSI
GLGGGFAGGMGVGAGTTCTGGTQYEGGVTVNSNGNGSFGKGGIGNVCAGGGGWYGGAGASSSGVGGGGSG
YVLTKDSYKPKGYIPTSEYWLENVNSIAGDNTSNAHGYAKITLLQALPFLNISSYNSSTATFKADHTDPT
LLTKIEYFIDDVLKETITTDLTLEKTINYTLEDNALHTLKIVVTDSANATVEKVVSVSRGIAPLPSGSTT
DEVTNKWIEIKDAFKTGKTSIINTLALKNIEANLNNTLVELSEKIKTSFDSSDASVQDLMNQLTEKNNII
SQLNAKYKIAHGTTSIIQNSLWSAYLYDSNHNNNYERQPKTWIGVEGLNFVPNLFFAECEYKDSSSVYYK
HFVFGTSGIPSISGETDFVVTSKFRKPYGNQNYSAFGQAYKSNKGSIWIENNTYVPAIIPEIDGVLYNWY
AIKFI

SEQ ID NO:113    >R20291-RBD1_1375_cognate

MNVPNRIIYDQTGRTIFETGESCGDVLPHYTITELHYIDIEYGSIDYTRNRVIGINIETKEPILEEIPVY
ITDEEKRIQELENQLLIAENEKVGGLL

SEQ ID NO:114    >R20291-RBD1_1376_cognate

MNINNVVVRILAERILSKGLNPLKNREFQLDDVTNTEYRKAVEDYIIKNSGVVEGAEPTI

SEQ ID NO:115    >fused_phi147-RBD_BPAR

LEEKFYIILTKIGREKIANATALGELVGLTKFQVGDSNGEYYEPTEEQTALKNVVWEGNINSLRIDEKNP
NWIVIETILPGTVGGFMIREAAVLDNENNIIAIGKYPETYKPRAEDGSIKDLVVKMILQLSNTSNVTLEV
DPTLVFVTQKDIQDLETKIGTVNTKIDTTKTELTSNIETAKTEIDEKIGDTTQLTTTDKTNIVGALNEVK
TSVDSIETTAEKTSYNNATSNLAATNVQGAIDEVVRKIEKFNEVNISIQNDMLPI

SEQ ID NO:116    >phi147-RBD

MQSEWNFDYTGAEQNVTLKPGKYKLECWGACGGGWFSEWTKGAKGGYSKAELTLKKETILYVYAGETGCQ
KFENSINNWTGFNGGGRGTNAGADPKFILCGGGATDIRLIRGSWSNEQGLLSRILVAGGAGAISSSDYGV
GNGGGMEGSKGFDGSNAFVTGGTQYQGGIGLEDKYNGSFGRASSTGTGQGGGGGWFGGAGGLNYNAAGGS
GYALTKDSYKPPGYIPTSKYYLDNVVMTTGGNTTKADGYAKITLLQALPFLTVSSYNSTTATFKADHTDP
TLLTKIEWFIDEKLKETITSKLTIEKTINYTLEDNALHTIKIVVTDSSNATAERIFTVSKGIAPLPTGSS
SEEVTNKWREIKDSFKTGKTSIINTLALKNIESNLNNTLVELSEKIKQSFDSSDASVQELENQILLNENE
KVGGIL

FIGURE 11 (Continued)

SEQ ID NO:117    >phi147-RBD_1376_cognate

MNINNVVRILAERILNGGLNPLKNREFQLDDVTNIGYRKAVEDYIIEHSGVVEGAEPTK

SEQ ID NO:118    >DG494

TTCTAAACAACATGGTATCTGG

SEQ ID NO:119    >DG578

AACAGTACCTATTTTAGTTTCTAAGTCTTGAATATCCTTTTGAGTTACAA

SEQ ID NO:120    >DG579

GGTTTTTGTAACTCAAAAGGATATTCAAGACTTAGAAACTAAAATAGGTACTGTT

SEQ ID NO:121    >DG492

CGAATTTAAACAATTTTCACACCTCCATTTTAAATATATATTTTGTAAGTTAATGTAGC

SEQ ID NO:122    >DG493

GCTACATTAACTTACAAAATATATATTTAAAATGGAGGTGTGAAAATTGT

SEQ ID NO:123    >DG495

ATTTCCTTACGCGAAATACG

SEQ ID NO:124    >DG540

AACAGTACCTATTTTAGTTTCTAAGTCTTGAATATCCTTTTGAGTTACAA

SEQ ID NO:125    >DG541

CGTTGGTTTTTGTAACTCAAAAGGATATTCAAGACTTAGAAACTAAAATAGGTACTGTTA

SEQ ID NO:126    >DG544

TCGAATTTAAACAATTTTCACACCTCCATTTTATTTAAATTTTGCCGCAT

SEQ ID NO:127    >DG545

TATAAATGGCATGCGGCAAAATTTAAATAAAATGGAGGTGTGAAAATTGT

SEQ ID NO:128    >DG15

TCCTTCGGCGCGCCTCAAATTTAAGCTTAACTCC

SEQ ID NO:129    >DG546

AGTTGTATCAATTTTAGTGTCTAATTCTTGAATATCCTTTTGAGTTACAA

FIGURE 11 (Continued)

```
SEQ ID NO:130    >DG547
TGGTTTTTGTAACTCAAAAGGATATTCAAGAATTAGACACTAAAATTGATACAAC

SEQ ID NO:131    >DG548
TTTAAACAATTTTCACACCTCCATTTTATACAAATTTTATAGCATACCAA

SEQ ID NO:132    >DG549
TACAATTGGTATGCTATAAAATTTGTATAAAATGGAGGTGTGAAAATTGT

SEQ ID NO:133    >DG550
AGTTGTATCAATTTTAGAGTCTAGGTCTTGAATATCCTTTTGAGTTACAA

SEQ ID NO:134    >DG551
TTTTGTAACTCAAAAGGATATTCAAGACCTAGACTCTAAAATTGATACAA

SEQ ID NO:135    >DG552
ATCGAATTTAAACAATTTTCACACCTCCATTTTAATTATTTAAAAATTCTATATCTAACG

SEQ ID NO:136    >DG553
GCGTTAGATATAGAATTTTTAAATAATTAAAATGGAGGTGTGAAAATTGT

SEQ ID NO:137    >DG591
TCTGGAAATAATCTAGAACTTTCGAAGATATATCTAGAACTTTCAAAGATG

SEQ ID NO:138    >DG602
GCTTATTTTAGCATCTAAATCTTGAATATCCTTTTGAGTTACA

SEQ ID NO:139    >DG603
TAACTCAAAAGGATATTCAAGATTAGATGCTAAAATAAGCA

SEQ ID NO:140    >DG604
AATTTTCACACCTCCATTTTAAATAAATTTAATAGCATACCATT

SEQ ID NO:141    >DG605
GGTATGCTATTAAATTTATTTAAAATGGAGGTGTGAAAATTGT

SEQ ID NO:142    >DG590
GGCGCTCAGGATCCGGCGCGCCTCAAATTTAAGCTT
```

FIGURE 11 (Continued)

```
SEQ ID NO:143      >DG606
GTACCTATTTTAGTTTCTAAGTCTTGAATATCCTTTTGAGTTACA

SEQ ID NO:144      >DG607
AACTCAAAAGGATATTCAAGACTTAGAAACTAAAATAGGTACTG

SEQ ID NO:145      >DG608
AATTTTCACACCTCCATTTTATTCAAATGCATACCATG

SEQ ID NO:146      >DG609
TGGTATGCATTTGAATAAAATGGAGGTGTGAAAATTGT

SEQ ID NO:147      >DG651
TCAATTTTAGTGTCTAGGTCTTGAATATCCTTTTGAGTTACA

SEQ ID NO:148      >DG652
TAACTCAAAAGGATATTCAAGACCTAGACACTAAAATTGATACA

SEQ ID NO:149      >DG653
AATTTTCACACCTCCATTTTATTTAAATTTTATAGCATACCAG

SEQ ID NO:150      >DG654
GGTATGCTATAAAATTTAAATAAAATGGAGGTGTGAAAATTGT

SEQ ID NO:151      >DG655
ACCTATTTTAGTTTCTAAGTCTTGAATATCCTTTTGAGTTACA

SEQ ID NO:152      >DG656
ATTTTCACACCTCCATTTTATATGAATTTTATAGCATACCAA

SEQ ID NO:153      >DG657
GGTATGCTATAAAATTCATATAAAATGGAGGTGTGAAAATTGT

SEQ ID NO:154      >DG664
TATCAATTTTAGCGTCTAAATCTTGAATATCCTTTTGAGTTACA

SEQ ID NO:155      >DG665
ACTCAAAAGGATATTCAAGATTTAGACGCTAAAATTGATAC
```

FIGURE 11 (Continued)

```
SEQ ID NO:156    >DG666
ATTTTCACACCTCCATTTTAAATAAATTTAATAGCATACCAT
SEQ ID NO:157    >DG667
GGTATGCTATTAAATTTATTTAAAATGGAGGTGTGAAAATTGT
SEQ ID NO:158    >DG700
CCTATTTTAGTTTCCAATTCTTGAATATCCTTTTGAGTTACA
SEQ ID NO:159    >DG701
ACTCAAAAGGATATTCAAGAATTGGAAACTAAAATAGGTAC
SEQ ID NO:160    >DG702
ATTTTCACACCTCCATTTTAAATAAATTTTATAGCATACCAAT
SEQ ID NO:161    >DG703
GGTATGCTATAAAATTTATTTAAAATGGAGGTGTGAAAATTGT
SEQ ID NO:162    >DG785
GGCGCTCAGGATCCGGCGCGCCCTATATAGTTGGTTCTGCTCC
SEQ ID NO:163    >DG808
GGCGCTCAGGATCCGGCGCGCCTCCTTTTACTACTCCACTATGC
```

DIFFOCINS AND METHODS OF USE THEREOF

RELATED APPLICATIONS

This application is a continuation-in-part application of U.S. application Ser. No. 13/117,467, filed May 27, 2011, which claims benefit of priority under 35 U.S.C. §119(e) from U.S. Provisional Application Ser. No. 61/349,145, filed May 27, 2010, the entire content of which is incorporated by reference as if fully set forth.

GRANT INFORMATION

This invention was made with government support under Grant No. R43AI098186-01 awarded by the National Institute of Allergy and Infectious Diseases, National Institutes of Health. The United States government has certain rights in the invention.

SEQUENCE LISTING

The instant application contains a Sequence Listing which has been submitted in ASCII format via EFS-Web and is hereby incorporated by reference in its entirety. Said ASCII copy, created on Aug. 20, 2013, is named CA2367_SL.txt and is 475,155 bytes in size.

FIELD OF THE INVENTION

This application relates generally to the identification and isolation of a cluster of genes sufficient to produce a bacteriocin, and more specifically, an R-type high molecular weight bacteriocin that specifically kills *Clostridium difficile*, and methods to alter its bactericidal specificity, produce and use the same.

BACKGROUND OF THE INVENTION

*Clostridium difficile* is an obligate anaerobic, spore-forming, gram positive bacterium that is a notorious pathogen for humans and other mammals (Bartlett et al., 1977; Bartlett et al., 1979; Keel et al., 2007; Sunenshine & McDonald, 2006). At low densities *C. difficile* can reside innocuously in the mammalian gastrointestinal (GI) tract, but upon expansion, frequently as the result of administered antibiotics reducing the commensal bacteria, *C. difficile* bacteria produce sufficient exotoxins to cause a range of diseases from a mild diarrheal disease to a characteristic pseudo-membranous colitis, which is life-threatening, particularly to older humans and others with significant co-morbidities (Bartlett, 2002).

Because spores formed by this pathogen disseminate widely and are difficult to eradicate or inactivate in hospitals and chronic care facilities, the probability of patients being colonized by *C. difficile* increases sharply upon their entering such a facility (Bartlett, 2007). In fact, a relatively new strain of *C. difficile* that is a hypervirulent toxigenic bacterial strain of *C. difficile*, BI/NAP1/027, which causes severe disease in massive outbreak settings, has recently been well documented (Spigaglia et al., 2002; Pépin et al., 2004; McDonald et al., 2005; Muto et al., 2005; Loo et al., 2005; Belmares et al., 2009). The incidence of *C. difficile* associated disease (CDAD) in children, previously at low risk, has also increased substantially (Benson et al., 2007; Zilberberg et al., 2010).

Eliminating the pathogen prophylactically in asymptomatic carrier or colonized subjects by administering antibiotics is strongly contraindicated because of the high risk of inducing *C. difficile* associated disease.

R-type bacteriocins made by gram negative bacteria have been described and have been deployed by such bacteria to kill other competitive gram negative strains, even in some circumstances other species or genera of gram negative bacteria (Kageyama et al., 1964; Kageyama et al., 1964a; Kingsbury, D, 1966; Blackwell and Law, 1981; Blackwell et al., 1982; Campagnari et al., 1994; Strauch et al., 2001; Jabrane et al., 2002). The fusion of base plate attachment regions (BPAR) of R-type pyocins to heterologous receptor binding domains (RBD), resulting in the creation of novel R-type pyocins with novel bactericidal specificities for gram negative bacteria has been described (Williams et al., 2008; Scholl et al., 2009).

Other high-molecular-weight bacteriocins or R-type bacteriocins have been described in gram-positive bacteria (Coetzee et al., 1968; Thompson and Pattee, 1981; Zink et al., 1995). However, much less is known about R-type high molecular weight bacteriocin structures produced by gram positive bacteria. But while such have been described, none has been characterized at a genetic level or manipulated in a manner supportive or necessary for developing a useful agent. High molecular weight bacteriocins have been described for 2 *Clostridium* species, *botulinum* and *perfringens* (Ellison and Kautter, 1970; Anastasio et al., 1971; Nieves et al., 1981). None has been described that is produced by *C. difficile* or kills *C. difficile*.

SUMMARY OF THE INVENTION

This invention is based on the isolation of the entire genetic locus or gene cluster encoding the *C. difficile*-specific R-type bacteriocins (herein termed "diffocins") that are bactericidal against other strains of *C. difficile*; the expression of the diffocin gene cluster and production of diffocins in aerobic bacteria; and the discovery that the open reading frame (ORF) 1374 of the diffocin gene cluster determines the bactericidal spectrum of that diffocin against *C. difficile* strains. This invention provides a practical means of altering the specificity of diffocins by genetic engineering to produce novel diffocins and of manufacturing and administering directly or indirectly diffocins to eliminate *C. difficile* from the gastrointestinal (GI) tract of colonized animals, including humans. The administration of diffocins can treat or prevent the development of *C. difficile* infection and associated disease without harming, as do traditional antibiotics, the commensal GI bacteria so necessary for good health.

In accordance with the present invention, there are provided isolated nucleic acid molecules encoding R-type high molecular weight (hmw) bacteriocins. In one embodiment there are provided, isolated nucleic acid molecules encoding R-type high molecular weight (hmw) bacteriocins, wherein the nucleic acid molecule is from a genome of a strain of *Clostridium difficile*, and wherein the R-type hmw bacteriocin comprises a polypeptide that is at least 80% identical to a polypeptide selected from the group consisting of SEQ ID NOs: 4-16, 18, 19, and 66-80, and the R-type hmw bacteriocin has a receptor binding domain (RBD) that binds a receptor of at least one other strain of *C. difficile* and therefore has bactericidal activity against the other strain or strains of *C. difficile*. In particular embodiments, the nucleic acid molecule is from a genome of a strain of *Clostridium difficile* selected from the group consisting of Cd4, Cd16, Cd19108, Cd19123, Cd19126, Cd19145, and ATCC Accession No. 43593. In some embodiments, the strain is Cd16 and the nucleic acid molecule includes SEQ ID NO:1 or the strain is Cd4 and the nucleic acid molecule includes SEQ ID NO:61.

In another embodiment there are provided isolated nucleic acid molecules encoding an R-type high molecular weight (hmw) bacteriocin, wherein the nucleic acid molecule is from a genome of a first strain of *Clostridium difficile* and comprises a first polynucleotide sequence that is at least 80% identical to a polynucleotide encoding SEQ ID NOs: 66-77, wherein the nucleic acid molecule further comprises a heterologous sequence encoding a receptor binding domain (RBD) of a prophage or prophage remnant from the genome of a second strain of *C. difficile* or an RBD of a bacteriophage that infects *C. difficile*, and wherein the R-type hmw bacteriocin comprises at least 50 contiguous amino acids of the amino terminal portion of a first base plate attachment region (BPAR) polypeptide that is at least 80% identical to a polypeptide of SEQ ID NO: 78, and wherein the R-type hmw bacteriocin has bactericidal activity against at least one strain of *C. difficile*.

In another embodiment of the invention, there are provided isolated R-type bacteriocins encoded by a nucleic acid molecule of the invention. In one aspect, the R-type bacteriocins are expressed in an aerobic producer bacterium. In some embodiments, the R-type bacteriocins can be administered orally to animals and be excreted in feces in a form still exhibiting bactericidal activity. In particular embodiments, the R-type bacteriocin retains some bactericidal activity after incubation at a pH between about 2.5 and 10.6 for 30 minutes at 25° C. In one aspect, the R-type bacteriocin retains some bactericidal activity after incubation at a pH between about 3.4 and 9 for 30 minutes at 25° C. In other embodiments, the R-type bacteriocin retains some bactericidal activity after incubation for 60 minutes at 45° C.

In another embodiment of the invention, there are provided isolated R-type high molecular weight (hmw) bacteriocins having bactericidal activity, wherein the R-type hmw bacteriocin includes a base plate attachment region (BPAR) of a first strain of a first species of bacteria of genus *Clostridium*, and a receptor binding domain (RBD) from a second strain of the first species, or from a second species of the genus *Clostridium* or of a bacteriophage that infects a *Clostridium* species, or a modified form of an RBD, wherein the bacteriocin has bactericidal activity against at least one strain of *Clostridium difficile*. In particular embodiments, the BPAR is from a first strain of *Clostridium difficile* and the RBD is from a second strain of *Clostridium difficile* or from a bacteriophage that infects *Clostridium difficile*. In some embodiments, the BPAR is at least 80% identical to the corresponding segment of one or more of SEQ ID NOs: 16, 54-56 and 78. In certain embodiments, the BPAR is at least 80% identical to a polypeptide containing 50 or more contiguous amino acids of SEQ ID NO:16 or 78 or containing 50 or more contiguous amino acids of SEQ ID NOs: 54-56. In some embodiments, the BPAR is a fusion of the amino-terminal portion of a first BPAR that is at least 80% identical to SEQ ID NO:78 and the C-terminal portion of a second BPAR that is cognate to the heterologous RBD.

In some embodiments, the RBD is at least 80% identical to the corresponding segment of one or more of SEQ ID NOs: 17, and 49-56. In other embodiments, the encoded RBD is at least 80% identical to an RBD selected from the group consisting of SEQ ID NOs: 92, 94, 96, 98, 100, 102, 104, 106, 108, 110, 112, and 116.

In another embodiment of the invention, there are provided expression cassettes containing a nucleic acid molecule of the invention. Expression cassettes may be contained within an expression vector, such as a plasmid, or may be contained within the chromosome of a producer cell. In some embodiments, the expression cassette contains a heterologous promoter operably linked to the nucleic acid molecule encoding the R-type bacteriocin. The promoter may be inducible, repressible, or constitutively active. In one aspect, the promoter is inducible; in another aspect the promoter is repressible. In some embodiments, the promoter is induced by adding or removing a small molecule inducer, repressor, or de-repressor. In one aspect, the promoter is induced by a small molecule inducer or de-repressor. In some embodiments, the small molecule inducer or de-repressor is a reactive oxygen species (ROS) or a generator of an ROS. In one aspect, the ROS is a peroxide that is non-toxic to humans or other animals. In one example, the peroxide is hydrogen peroxide. In a particular aspect, the expression of the cassette is regulated by an operably linked recA gene encoding a constitutively active RecA protein and under the control of a heterologous promoter responsive to a small molecule inducer or de-repressor.

In still another embodiment of the invention, there are provided producer cells containing the expression cassettes of the invention. The expression cassette may be contained in an episomal expression vector within the producer cell. Alternatively, the producer cells may contain within their chromosome a nucleic acid molecule or expression cassette of the invention. In certain embodiments, the producer cell is a non-pathogenic and not obligate anaerobic bacterium. In some embodiments, the non-pathogenic and not obligate anaerobic bacterium is a species from a genus of bacteria selected from the group consisting of *Bacillus, Lactobacillus*, and *Listeria*. In certain embodiments, the non-pathogenic and not obligate anaerobic bacterium is from the genus *Bacillus*. In some aspects, the bacterium is *Bacillus subtilis*. In a particular aspect, the *B. subtilis* lacks the PBSX gene cluster. In another embodiment the producer cell is an obligate anaerobic but non-pathogenic bacterium.

In yet another embodiment of the invention, there are provided methods of producing an R-type hmw bacteriocin of the invention. The method includes exposing a producer cell containing a nucleic acid sequence of the invention operably linked to an inducible or derepressible promoter sensitive to an inducing or repressing agent, to the agent in a concentration effective to induce expression of the R-type bacteriocin, and purifying the expressed R-type bacteriocin. In some embodiments, the nucleic acid molecule encoding the R-type bacteriocin is heterologous to the genome of the producer cell. In particular aspects, the nucleic acid molecule is contained within the producer cell's chromosome or is contained in an extrachromosomal expression vector within the producer cell. In certain embodiments, the producer cell is a non-pathogenic and not obligate anaerobic bacterium. In some embodiments, the non-pathogenic and not obligate anaerobic bacterium is a species from a genus of bacteria selected from the group consisting of *Bacillus, Lactobacillus*, and *Listeria*. In certain embodiments, the non-pathogenic and not obligate anaerobic bacterium is from the genus *Bacillus*. In some aspects, the bacterium is *Bacillus subtilis*. In a particular aspect, the *B. subtilis* does not lyse when induced to produce the R-type bacteriocin. In a further aspect, the *B. subtilis* lacks the PBSX gene cluster.

In a further embodiment of the invention, there are provided methods of killing a pathogenic bacterium. The method includes contacting the pathogenic bacterium with an R-type bacteriocin of the invention, whereby the R-type bacteriocin binds and kills the pathogenic bacterium. In one aspect, the pathogenic bacterium is *Clostridium difficile*. In one aspect, the *Clostridium difficile* is in an animal and a bactericidal amount of the R-type bacteriocin is administered to the animal.

In another embodiment of the invention there are provided methods of treating or preventing a disease-causing infection of *Clostridium difficile* in an animal. The method includes administering a bactericidal amount of an R-type bacteriocin of the invention directly to an animal in need thereof, administering the agent indirectly by administering producer cells, or administering spores of *C. difficile* bacteria which produce natural diffocins but have been genetically modified to not produce toxins. In particular embodiments, an infection of *Clostridium difficile* in an animal is treated by administering to an animal in need thereof an amount of a producer cell of the invention to produce a bactericidal amount of the bacteriocin, thereby treating the infection. In one aspect, the nucleic acid encoding the bacteriocin is under the control of a lac promoter and the animal is administered lactose. In some embodiments, the animal is a mammal. In one aspect, the mammal is a human.

BRIEF DESCRIPTION OF THE DRAWINGS

FIG. 1 provides the nucleic acid or amino acid sequences of SEQ ID NOs:1-80.

FIG. 8 provides the results of a ClustalW analysis of partial amino acid sequences (SEQ ID NOs:81-86, respectively, in order of appearance) encoded by the ORF 1374 gene from each of 5 strains of *C. difficile* that produced active diffocins. Under each row of aligned sequences the "*" represents amino acid identities at that position encoded by all 5 genes, the ":" represents highly similar amino acids at that position encoded by all 5 genes, and the "." represents somewhat similar amino acids at that position encoded by all 5 genes; and the blank at a given position in the sequence alignment represents no amino acid similarity encoded by all 5 genes.

FIG. 11 provides the nucleic acid or amino acid sequences of SEQ ID NOs:87-163.

DETAILED DESCRIPTION OF THE INVENTION

Definitions

Figure 2:
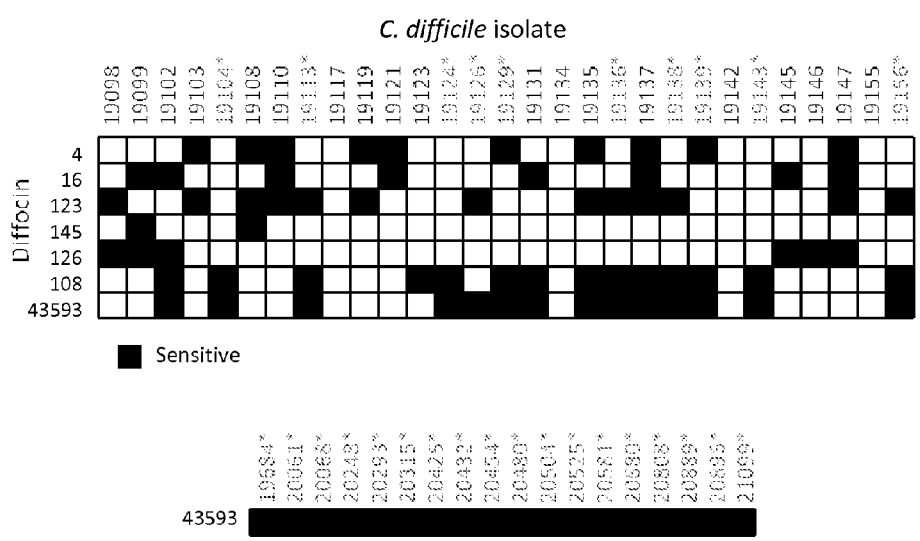
FIG. 2. Bactericidal activity of diffocins on clinical *C. difficile* isolates. The indicator strain numbers are shown along the top of the matrices; the asterisk-marked strains are NAP1/027/BI strains. The identities of the *C. difficile* sources of the diffocins tested are shown along the left borders. Strains were acquired from LC Fortier (4 and 16), ATCC (43593), or RM Alden Research Lab, Culver City, Calif.

As used herein, an "R-type high molecular weight (hmw) bacteriocin" is also known as simply an "R-type bacteriocin" and includes R-type pyocins, diffocins, monocins, enterocolitucins, meningocins, or other high molecular weight (hmw) bacteriocins related structurally or genetically to the myoviridae family of bacteriophages. An R-type bacteriocin includes modified versions of R-type pyocins, diffocins, enterocoliticins, monocins, and meningocins (Williams et al. 2008; Strauch et al., 2001; Kingsbury, 1966; Zink et al. 1995).

The term "diffocin," as used herein refers to an R-type high molecular weight bacteriocin isolated from or derived from *Clostridium difficile* and includes native particles obtained from *C. difficile* as well as particles obtained through expression of the diffocin gene cluster in a non-natural producer cell. A diffocin may also be an engineered particle comprised of polypeptides encoded by genes derived from one or more strains of *C. difficile*, and 80% or more identical to one or more polypeptides of SEQ ID NOs: 2-23, 49 and 62-80.

An R-type bacteriocin of the invention may be thermolabile, mild acid resistant, trypsin resistant, sedimentable by centrifugation at about 65,000×g, and resolvable by electron microscopy (Kageyama et al., 1962; Bradley, 1967; Daw et al., 1996; Jabrane et al., 2002; Fortier et al., 2007). In many cases, an engineered R-type bacteriocin disclosed herein has one or more, in any combination, of these properties. An additional property common to the R-type bacteriocins disclosed herein is that they do not contain nucleic acid and thus are replication deficient such that they cannot reproduce themselves after or during the killing of a target bacterium, as can many bacteriophages. They are purely proteins, not organisms.

R-type bacteriocins disclosed herein are complex molecules comprising multiple protein, or polypeptide, subunits and resemble the tail structures of bacteriophages of the myoviridae family. In naturally occurring R-type bacteriocins, the subunit structures are encoded by the bacterial genome such as that of *C. difficile* or *P. aeruginosa* and form R-type bacteriocins to serve as natural defenses against other bacteria (Kageyama, 1975). A sensitive, target bacterium can typically be killed by a single R-type bacteriocin molecule (Kageyama et al., 1964; Kageyama et al., 1964a; Morse et al., 1980; Strauch et al., 2001).

A "target bacterium" or "target bacteria" refers to a bacterium or bacteria that are bound by an R-type bacteriocin of the disclosure and/or whose growth, survival, or replication is inhibited thereby. In some embodiments, the target bacterium is from the genus *Clostridum*. In particular embodiments, the bacterium is *Clostridium difficile*. In one aspect, more than one strain of *C. difficile* is targeted. Exemplary strains of *C. difficile* include but are not limited to NAP1/BI/ribotype 027, as well as those listed in FIG. 2.

The term "growth inhibition" or variations thereof refers to the slowing or stopping of the rate of a bacterial cell's division or cessation of bacterial cell division, or to death of the bacterium or bacteria.

As used herein, a "nucleic acid" or a "nucleic acid molecule" typically refers to deoxyribonucleotide or ribonucleotides polymers (pure or mixed) in single- or double-stranded form. The term may encompass nucleic acids containing nucleotide analogs or modified backbone residues or linkages, which are synthetic, naturally occurring, and non-naturally occurring, which have similar binding, structural, or functional properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-0-methyl ribonucleotides, and peptide-nucleic acids (PNAs). The term nucleic acid may, in some contexts, be used interchangeably with gene, cDNA, mRNA, oligonucleotide, and polynucleotide.

A particular nucleic acid sequence also encompasses conservatively modified variants thereof (such as degenerate codon substitutions) and complementary sequences, as well as the sequence explicitly indicated. Specifically, degenerate codon substitutions may be achieved by generating sequences in which the third ("wobble") position of one or more selected (or all) codons is substituted with mixed-base and/or deoxyinosine residues. Thus, a nucleic acid sequence encoding a protein sequence disclosed herein also encompasses modified variants thereof as described herein.

The term "segment" as used herein in reference to an amino acid sequence refers to a contiguous sequence of amino acids that may be 10, 12, 15, 20, 25, 50, or 100 amino acid residues in length.

As used herein, the term "heterologous," when used with reference to portions of a protein or nucleic acid sequence, indicates that the sequence comprises two or more subsequences that are not usually found in the same relationship to each other in nature. In one example, the heterologous sequences are from different species of bacteria. In another example, heterologous sequences are from different strains of the same species of bacteria. In one aspect, the heterologous sequences are from different strains of *C. difficile*. In another aspect the heterologous sequences are from a bacterium and a bacteriophage or prophage, or from a bacterium and a synthetic, non-natural sequence of DNA.

The terms "polypeptide", "peptide", and "protein" are typically used interchangeably herein to refer to a polymer of amino acid residues. Amino acids may be referred to herein by either their commonly known three letter symbols or by the one-letter symbols recommended by the IUPAC-IUB Biochemical Nomenclature Commission.

Virulence factors are those molecules that contribute to the pathogenicity of an organism but not necessarily its general viability. Upon the loss of a virulence factor the organism is less pathogenic but not necessarily less viable. Virulence factors may have any one of numerous functions, for example, regulating gene expression, providing adhesion or mobility, providing a toxin, injecting a toxin, pumping out antibiotic agents, or forming protective coatings including biofilms.

Fitness factors are those molecules that contribute to the organism's general viability, growth rate or competitiveness in its environment. Upon the loss of a fitness factor, the organism is less viable or competitive and because of this compromise, indirectly less pathogenic. Fitness factors may also possess any one of numerous functions, for example, acquiring nutrients, ions or water, forming components or protectants of cell membranes or cell walls, replicating, repairing or mutagenizing nucleic acids, providing defense from or offense towards environmental or competitive insults.

The term "producer cell" as used herein refers to a cell that is capable of producing or expressing a diffocin-encoding nucleic acid molecule and which does not naturally contain such a nucleic acid molecule. The producer cell may be capable of surviving and growing in the presence of oxygen and is transformed with a vector containing a nucleic acid molecule encoding the diffocin, which may be integrated into the chromosome of the producer cell or may be episomal. The producer cell may be a gram positive bacterium. In certain embodiments, the producer cell may be a bacterium from the genus *Bacillus, Lactobacillus, Lactococcus, Clostridium*, or *Listeria*. In preferred embodiments, the producer cell is a bacterium from the genus *Bacillus, Lactobacillus, Lactococcus*, or *Listeria*. In some embodiments, the bacterium is a species from the genus *Bacillus* selected from the group consisting of *subtilis, amyloliquefaciens*, and *megaterium*. In one aspect, the bacterium is *Bacillus subtilis*. In a particular aspect, the producer cell is a *B. subtilis* strain that lacks the PBSX gene cluster. In other embodiments, the bacterium is a species from the genus *Lactobacillus* selected from the group consisting of *acidophilus, casei*, and *bulgaricus*. In still other embodiments, the bacterium is *Listeria innocua*. In another embodiment, the non-pathogenic producer cell may be *Escherichia coli* or of the genus *Clostridium*.

DETAILED DESCRIPTION OF MODES OF PRACTICING THE DISCLOSURE

R-Type Bacteriocins Isolated from *C. Difficile* have Bactericidal Activity.

Figure 3:
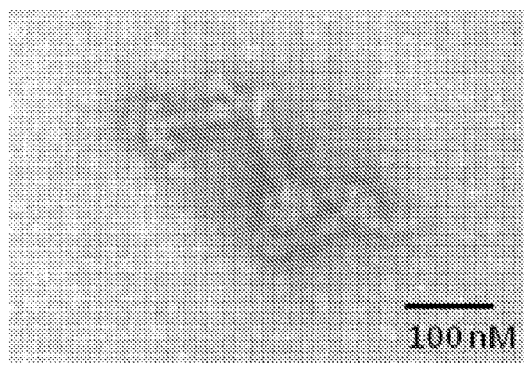
FIG. 3 shows a scanning electron micrograph of dif16. Note the flower-like tail fiber appendages.
Figure 4:
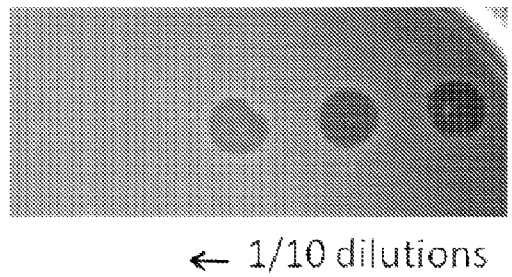
FIG. 4 shows a photograph of the results of a spot test of dif4 on the target strain Cd19135. Purified diffocin was serially diluted 10-fold, and 5 µl aliquots of the dilutions were spotted on a lawn of target *C. difficile* bacteria. After anaerobic incubation at 37° C. overnight, diffocin killing was indicated by the clearing of growth on the lawn.

To test for bactericidal activity, lysates of two *C. difficile* strains, Cd4 and Cd16 (from LC Fortier), were made by growing the cells to mid-log phase under strict anaerobic conditions throughout and then exposing the culture to 3 μg/ml of mitomycin C. After the bacterial cells lysed, particles in the lysates were concentrated and purified by high speed centrifugation (see Example 1). These preparations were shown by electron microscopy to contain concentrated headless phage-like particles (FIG. 3). After concentration and purification, the preparations were assessed for bactericidal activity by a spot plate method whereby samples were applied to an overlay lawn of target *C. difficile* bacteria, again under strict anaerobic conditions. Since most phage tail-like bacteriocins typically target strains different from the producing bacteria, target strains consisting initially of a panel of 29 *C. difficile* clinical isolates were tested. After overnight incubation, the plates were examined for the presence of killing activity as indicated by a clearing in the lawn of *C. difficile* bacteria where the purified materials were spotted. FIG. 4 shows a typical spot assay of diffocin from Cd4 (dif 4) spotted onto *C. difficile* strain, Cd19135.

Dif4 (diffocin from Cd4) and dif16 (diffocin from Cd16) demonstrated different bactericidal spectra based on spot assays (FIG. 2). Dif4 showed bactericidal activity on 10 of 29

C. difficile clinical isolate strains, whereas dif16 had activity against 8 of 29 strains. There was some overlap of strains susceptible to both diffocins, but the two diffocins had distinct bactericidal spectra. Diffocins from Cd108 and Cd 43593 had very similar killing spectra and killed at least 9 of the 10 NAP1/027/BI hypervirulent strains in the panel of 29 C. difficile clinical isolates. When tested further, dif43593 killed all 18 additional, independent NAP1/027/BI isolates. Thus, dif43593 kills all 28 tested strains of NAP1/027/BI C. difficile, FIG. 2.

Identification of the Diffocin Locus.

Figure 5:
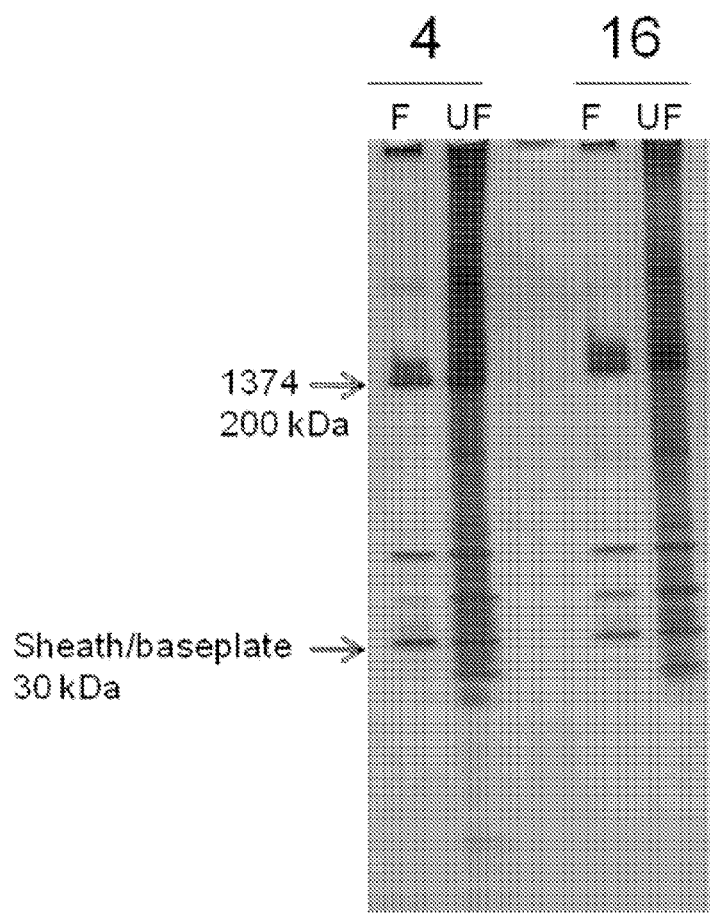
FIG. 5 shows a photograph of a silver stained SDS-PAGE of both filtered ("F") and unfiltered ("UF") preparations of dif4 ("4") and dif16 ("16"). The arrows indicate bands that were excised and identified by mass spectrometry.

Diffocin particles, isolated and purified from strain Cd4, were denatured, and the protein components were separated by sodium dodecyl sulfate polyacrylamide gel electrophoresis (SDS PAGE) and detected by silver stain (FIG. 5). Two individual bands, ~200 kD and ~40 kD, were excised and analyzed by mass spectrometry. Peptides from the 40 kD band were found to match the predicted products from two C. difficile open reading frames (ORF) encoded in several of the C. difficile strains for which the complete genomes have been sequenced, including the reference strain Cd630 (GenBank Acc. No. NC_009089.1). The first of these was ORF 1363 (SEQ ID NO:5), a 39,192 Dalton phage-like protein. The second predominant polypeptide in this band corresponded to ORF 1371 (SEQ ID NO:14), a 39,565 Dalton phage-like baseplate protein. Since these proteins were coincidentally very close in molecular weight, they migrated in the same SDS PAGE band. The 200 kD band yielded a dominant polypeptide that corresponded to a portion of the C-terminus of ORF 1374 (SEQ ID NO:17), just downstream of the two other phage-like ORFs.

Figure 6:
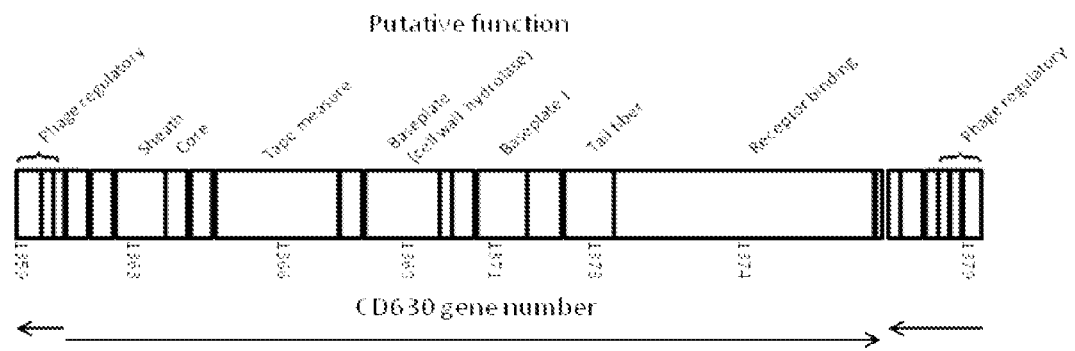
FIG. 6 shows a schematic of the diffocin gene cluster from Cd630 and Cd16. The locus consisted of the ORFs that encode structural proteins and structural assembly proteins typical of a Myoviridae phage tail apparatus, ORF1362 to ORF1375, indicated below the map. Flanking these genes were genes that encode putative phage-like regulatory proteins. The bottom arrows indicate the direction in which the ORFs are transcribed and the putative functions of the ORFs are indicated above the map.

Since these ORFs mapped in very close proximity within the Cd630 genome, the surrounding region was analyzed. A prophage-like element was found between bases 1574593 and 1596384, which includes ORFs 1360A-1379 (FIG. 6 and SEQ ID NO:1-23). Of particular note was that the structural genes encoded in this region corresponded only to the components of the tail structure of a typical Myoviridae phage; no genes for capsid, capsid assembly protein, or portal proteins were found. Also absent were any ORFs which encoded putative DNA replication or DNA packaging machinery. Thus, this locus was consistent with that of an R-type (Myoviridae phage tail-like) bacteriocin. Flanking the structural genes were several ORFs that encode putative phage-like regulatory proteins. Since several ORFs from this locus encoded polypeptides found in diffocin particles and the fact that the gene cluster resembled that of an R-type bacteriocin, we assigned the diffocin locus to this region.

The structural genes were all encoded on one strand and transcribed in the same direction. The organization of the genes resembled that of the genes of R-type pyocins and many Myoviridae phages. Several of the structural proteins displayed sequence similarity to known C. difficile bacteriophages including phages ΦI19, and ΦC2 (Goh et al., 2007; Govind et al., 2006). C. difficile strain Cd630 was also known to encode two intact prophages, both of which were known to be inducible (Goh et al., 2007). Several of the diffocin ORFs had sequence similarity to prophage 1 and 2 of C. difficile strain Cd630, suggesting that these C. difficile Myoviridae phages and the diffocins share common ancestry.

Of particular note was ORF 1374 (SEQ ID NO:17) of the diffocin. This gene encoded a large polypeptide that is located just downstream of ORF 1373, SEQ ID NO:16, a location in the cluster that indicated that ORF 1374 was part of the R-type bacteriocin tail fiber, that is, a receptor binding domain (RBD). Since electron micrographs of what have been designated as diffocins revealed a large flower like structure in the tail fiber region, it was apparent that this structure comprised a large protein. ORF 1373 (SEQ ID NO:16) encoded the base plate attachment region, BPAR, of the diffocin tail fiber and appeared to be a truncated form of a the analogous ORF 1373 in phages of C. difficile which encoded the RBD as well as the BPAR, given that such phages lack an ORF 1374. Thus, the tail fibers of naturally occurring diffocins are comprised of two proteins, ORF1373 and ORF1374, which form a jointed tail fiber, whereas bacteriophages of C. difficile have a tail fiber comprised of a single protein, a somewhat longer ORF1373 which provides the BPAR and the RBD functions. With this knowledge the nucleic acids encoding either ORF1373 (SEQ ID NO:16) or ORF1374 (SEQ ID NO:17) were deployed herein as substrates from which to engineer new RBD specificity functions.

Diffocins are Wide-Spread Among *C. Difficile* Isolates.

A series of independent clinical isolates of *C. difficile* were tested for the ability to produce diffocin particles that might have different bactericidal spectra. Clinical isolates Cd19123, Cd19145, Cd19126, Cd19108 (from RM Alden Research Laboratory, Culver City, Calif.), and ATCC Cd43593 were induced with mitomycin C under strict anaerobic conditions, followed by purification and concentration of particles that were produced. The purified materials were then spotted separately on lawns of other *C. difficile* strains in the clinical collection to detect bactericidal activity. The results showed that each of these isolates produced particles (diffocins termed dif123, dif145, dif126, dif108, and dif43593 from clinical isolates Cd19123, Cd19145, Cd19126, Cd19108, and ATCC Cd43593, respectively) with differing bactericidal spectra (FIG. 2.). Dif108 and dif43593 had very similar and broad spectra, whereas strain Cd19145 produced particles with a narrow bactericidal spectrum. Some isolates that were tested for induction, including Cd19113 and Cd19150, lysed after exposure to mitomycin but did not produce detectable diffocin particles.

It was recognized herein that the genome sequenced laboratory strain Cd630 encoded a diffocin locus; and, in fact, this genome was used herein to identify the diffocin genes. However, while strain Cd630 lysed after induction with mitomycin C, no detectable diffocin particles were produced. Instead, small amounts of prophage 1 and prophage 2 were produced.

Identification and Cloning of a Diffocin Cluster.

Cd630 did not produce detectable diffocin particles upon induction of lysis by mitomycin C. Accordingly, the diffocin gene cluster from Cd16 was cloned, instead. A draft genome sequence of Cd16 was first obtained. A diffocin locus, analogous to that of Cd630, was identified and annotated. The entire diffocin gene cluster from producer strain Cd16 was cloned (SEQ ID NO:1) into a BAC and subsequently demonstrated to include all the genes necessary to produce an active diffocin in a non-pathogenic microorganism and one that is not an obligate anaerobe. *C. difficile* is both pathogenic and an obligate anaerobic bacterium, making it an impractical production cell for natural diffocins or diffocins modified by recombinant DNA engineering. The isolated diffocin cluster can also be engineered by recombinant DNA technology to have its expression regulated by a heterologous promoter responding to a non-toxic small molecule inducer or de-repressor added to the culture or induction medium of the producer microorganism. Such small molecules include but are not limited to tetracycline, anhydrotetracycline, lactose, arabinose, xylose and their non-metabolized analogs, such as IPTG to replace lactose.

Diffocins

Diffocins are R-type hmw bacteriocins isolated from *Clostridium difficile*, which are bactericidal against other strains of *C. difficile*. Diffocins may be isolated from *C. difficile* strains grown under anaerobic conditions in the presence of mitomycin C. In some embodiments, the diffocin is from *C. difficile* clinical isolate Cd4, Cd16, Cd19123, Cd19145, Cd19126, Cd19108, or ATCC Cd43593 (termed dif 4, dif 16, dif123, dif145, dif126, dif108, and dif43593, respectively). In one aspect, the diffocin is from Cd4; in another aspect the diffocin is from Cd16.

In another embodiment of the invention, there are provided isolated nucleic acid molecules encoding diffocins derived from the genome of the genus *Clostridium* bacteria. In one aspect, the nucleic acid molecule contains the gene cluster of SEQ ID NO:1. In another aspect, the nucleic acid molecule contains the gene cluster of SEQ ID NO:61. In other embodiments, the nucleic acid molecule encodes a diffocin that includes one or more polypeptides selected from the group consisting of SEQ ID NOs: 2-23; 49, 62-80. In still other embodiments, the nucleic acid molecule encodes a diffocin that includes one or more polypeptides selected from the group consisting of SEQ ID NOs: 4-16, 18, 19, and 66-80. In one aspect, the nucleic acid molecule encodes the polypeptides of SEQ ID NOs: 2-23. In another aspect, the nucleic acid molecule encodes the polypeptides of SEQ ID NOs: 49 and 62-80.

Also provided are variant diffocins. Variant diffocins include those diffocins having an amino acid sequence that are at least 80% identical to a polypeptide selected from the group consisting of SEQ ID NOs: 4-16, 18, 19, and 66-80. In other embodiments, the variant diffocin has an amino acid sequence that is at least 85%, 88%, 89%, 90%, 95%, 96%, 97%, 98%, or even 99% identical to a polypeptide selected from the group consisting of SEQ ID NOs: 4-16, 18, 19, and 66-80.

In some embodiments, the variant diffocin may include a heterologous base plate attachment region (BPAR), wherein the BPAR is at least 80% identical to the corresponding segment of one or more of SEQ ID NOs: 16, 54-56, and 78. In another embodiment, the BPAR is at least 85% identical to the corresponding segment of one or more of SEQ ID NOs: 16, 54-56, and 78. In another embodiment, the BPAR is at least 89% identical to the corresponding segment of one or more of SEQ ID NOs: 16, 54-56, and 78. In another embodiment, the BPAR is at least 90% identical to the corresponding segment of one or more of SEQ ID NOs: 16, 54-56, and 78. In still another embodiment, the BPAR is at least 95% identical to the corresponding segment of one or more of SEQ ID NOs: 16, 54-56, and 78. In yet another embodiment, the BPAR is at least 98% identical to the corresponding segment of one or more of SEQ ID NOs: 16, 54-56, and 78. In a further embodiment, the BPAR is at least 99% identical to the corresponding segment of one or more of SEQ ID NOs: 16, 54-56, and 78.

In some embodiments, the variant diffocin includes at least 50 contiguous amino acids of the amino terminal portion of the native BPAR polypeptide. In further embodiments, the variant diffocin includes at least 100 contiguous amino acids of the amino terminal portion of the native BPAR polypeptide. In particular embodiments, the at least 50 contiguous amino acids are from an amino terminal portion of a BPAR that is at least 80% identical to a polypeptide of SEQ ID NO: 78. In certain aspects, the at least 50 contiguous amino acids are from an amino terminal portion of a BPAR that is at least 85%, 90%, 95%, or 98% identical to a polypeptide of SEQ ID NO: 78. In other aspects, the at least 100 contiguous amino acids are from an amino terminal portion of a BPAR that is at least 85%, 88%, 89%, 90%, 95%, 96%, 97%, 98%, or even 99% identical to a polypeptide of SEQ ID NO: 78.

In other embodiments, the variant diffocin contains a BPAR that is cognate to the RBD. As used herein, a "BPAR that is cognate to an RBD" or a "cognate BPAR" refers to a BPAR and RBD pair that occur together in a natural diffocin, *C. difficile* genome, bacteriophage, or prophage. In particular embodiments, the RBD and its cognate BPAR are heterologous to the rest of the diffocin molecule. In one aspect the cognate BPAR is fused to the amino terminal portion of the native BPAR of the diffocin, to form a "fused BPAR." Thus, in some embodiments, the variant diffocin comprises a fused BPAR. In certain embodiments, the variant diffocin contains a heterologous RBD and its cognate BPAR. In some embodiments, the fused BPAR is at least 80% identical to a sequence selected from the group consisting of SEQ ID NOs: 88, 91, 93, 95, 97, 99, 101, 103, 105, 107, 109, 111, and 115. In other embodiments, the fused BPAR is at least 85%, 88%, 89%, 90%, 95%, 96%, 97%, 98%, or even 99% identical to a sequence selected from the group consisting of SEQ ID NOs: 88, 91, 93, 95, 97, 99, 101, 103, 105, 107, 109, 111, and 115.

In further embodiments, the variant diffocin may include a heterologous receptor binding domain (RBD), wherein the RBD is at least 80% identical to the corresponding segment of one or more of SEQ ID NO:17 and 49-53, or at least 80% identical to a polypeptide containing the receptor binding domain (RBD) region of a polypeptide selected from the group consisting of SEQ ID NOs:54-56. In another embodiment, the RBD is at least 85% identical to the corresponding segment of one or more of SEQ ID NO:17 and 49-53, or at least 85% identical to a polypeptide containing the receptor binding domain (RBD) region of a polypeptide selected from the group consisting of SEQ ID NOs:54-56. In another embodiment, the RBD is at least 89% identical to the corresponding segment of one or more of SEQ ID NO:17 and 49-53, or at least 89% identical to a polypeptide containing the receptor binding domain (RBD) region of a polypeptide selected from the group consisting of SEQ ID NOs:54-56. In another embodiment, the RBD is at least 90% identical to the corresponding segment of one or more of SEQ ID NO:17 and 49-53, or at least 90% identical to a polypeptide containing the receptor binding domain (RBD) region of a polypeptide selected from the group consisting of SEQ ID NOs:54-56. In another embodiment, the RBD is at least 95% identical to the corresponding segment of one or more of SEQ ID NO:17 and 49-53, or at least 95% identical to a polypeptide containing the receptor binding domain (RBD) region of a polypeptide selected from the group consisting of SEQ ID NOs:54-56. In another embodiment, the RBD is at least 98% identical to the corresponding segment of one or more of SEQ ID NO:17 and 49-53, or at least 98% identical to a polypeptide containing the receptor binding domain (RBD) region of a polypeptide selected from the group consisting of SEQ ID NOs:54-56. In another embodiment, the RBD is at least 99% identical to the corresponding segment of one or more of SEQ ID NO:17 and 49-53, or at least 99% identical to a polypeptide containing the receptor binding domain (RBD) region of a polypeptide selected from the group consisting of SEQ ID NOs:54-56. In some embodiments, the receptor binding domain (RBD) region comprises amino acid residue 51 to the carboxy-terminal residue of SEQ ID NOs:54, 55, or 56.

In still other embodiments, the RBD is from a *C. difficile* genome, a bacteriophage, a prophage insertion or a prophage remnant that is contained within a *C. difficile* genome. A "prophage remnant" or prophage element or portion, refers to a sequence that encodes only a portion of a phage or discrete phage protein(s), rather than a full phage molecule. Thus, in some embodiments, a prophage remnant may include, for example, sequence encoding an RBD and its cognate BPAR, and a baseplate gene. In some embodiments the RBD is at least 80% identical to an RBD selected from the group consisting of SEQ ID NOs: 92, 94, 96, 98, 100, 102, 104, 106, 108, 110, 112, and 116. In other embodiments the RBD is at least 85%, 88%, 89%, 90%, 95%, 96%, 97%, 98%, or even 99% identical to an RBD selected from the group consisting of SEQ ID NOs: 92, 94, 96, 98, 100, 102, 104, 106, 108, 110, 112, and 116.

In another embodiment, diffocins can be engineered to have altered bactericidal spectra by fusing phage tail RBD to the product of diffocin ORF 1373. While ORF 1374 encodes the primary spectra determinant or RBD of natural diffocins, this very large protein is complexed with the ORF 1373 protein, and ORF 1373 protein provides the BPAR, i.e., it attaches the RBD of ORF 1374 protein to the diffocin baseplate structure. ORF 1373 is analogous to, and shares amino acid sequence identity with, the tail fiber genes of myoviridae bacteriophages such as ΦCD2 (SEQ ID NO:54), ΦCD119 (SEQ ID NO:55), and ΦCD27 (SEQ ID NO:56) as well as with the tail fibers of R-type pyocins. The ORF 1373 (e.g., SEQ ID NOs:16 or 78) of diffocins shares significant sequence identity, particularly in the first 160 amino acids at the N-terminal portion or BPAR, with the tail fibers of the *C. difficile* myoviridae phage, ΦCD2 (SEQ ID NO:54). The phage tail fibers are, however, longer than diffocin ORF 1373 protein and contain a C-terminal RBD for recognizing their bacterial targets. Diffocins' ORF 1373 proteins do not contain this latter domain, the RBD function of which has been replaced by a separate polypeptide, encoded by ORF1374. Thus, ORF 1374 can be deleted altogether from the diffocin cluster and an RBD of a phage tail fiber, such as that of ΦCD2, can be fused to the diffocin BPAR, encoded by ORF 1373, thereby generating a diffocin that has a phage tail fiber-like protein and accordingly, a bactericidal spectrum related to the host range of the donor phage. Importantly, because the regions of amino acid sequence homology between the *C. difficile* phage tail fibers and the ORF 1373 protein enable successful functional fusions between the two, one can select host-range variants from mutagenized or non-mutagenized *C. difficile* phages that can then be sources of novel RBD's for creating modified diffocins with novel bactericidal spectra.

In one embodiment of an engineered diffocin, there is provided a diffocin in which the RBD has been replaced with an RBD from another strain of *C. difficile* or with an RBD from a bacteriophage that infects *C. difficile*. In one example, the nucleic acid molecule comprises a sequence encoding SEQ ID NO:16 or 78 but does not contain the corresponding native RBD (i.e., the sequence encoding SEQ ID NO:17 or 49, respectively); instead, the native RBD is replaced with a heterologous sequence encoding an RBD. In particular embodiments, the nucleic acid molecule contains a heterologous sequence encoding a receptor binding domain (RBD) of an R-type bacteriocin of a different strain of *C. difficile*. In one aspect, the nucleic acid molecule contains a sequence encoding SEQ ID NO:16 or 78 and a sequence encoding a polypeptide selected from the group consisting of SEQ ID NOs: 49-53 or the receptor binding region of a polypeptide selected from the group consisting of SEQ ID NOs: 54-56. In another aspect, the nucleic acid molecule is comprised of a sequence encoding SEQ ID NOs:2-16 and 18-23 or SEQ ID NOs: 62-80, and a heterologous sequence encoding an RBD from a polypeptide selected from the group consisting of SEQ ID NOs: 17 and 49-56.

In other embodiments of an engineered diffocin, the RBD of the diffocin may be replaced with a modified form of a native RBD. A "native RBD" refers to a RBD having an amino acid sequence that is identical to a RBD isolated or cloned from a strain of *C. difficile* or from a bacteriophage that infects *C. difficile*. Exemplary native RBDs from a number of *C. difficile* strains include SEQ ID NOs: 17 and 49-53. Exemplary native RBDs from bacteriophages that infect *C. difficile* include SEQ ID NOs: 54-56 (e.g., amino acid residue 51 to the carboxy terminal residue). In some embodiments, a modified RBD includes a change in the amino acid sequence of the RBD relative to a native RBD. Non-limiting examples of a change in amino acid sequence include substitution, insertion (or addition), or deletion of one or more amino acids. In further embodiments, a diffocin includes a substitution with, or insertion of, an RBD derived from an organism that diversifies the structure by deploying a Diversity Generating Retroelement (DGR), as described in published Patent Application US 2006-0121450, published Jun. 8, 2006 (incorporated herein by reference as if fully set forth).

In some embodiments, the modified form has a bactericidal spectrum that is different from the corresponding unmodified or native RBD. In particular embodiments, the modified form is at least 80% identical the native RBD. In other embodiments, the RBD has an amino acid sequence that is at least 85%, 88%, 89%, 90%, 95%, 96%, 97%, 98%, or even 99% identical to a polypeptide selected from the group consisting of SEQ ID NOs: 17 and 49-53 or the receptor binding region of a polypeptide selected from the group consisting of SEQ ID NOs: 54-56 and the modified RBD has a bactericidal spectrum that is different from the corresponding unmodified or native RBD.

In some embodiments, the nucleic acid molecule further comprises a polynucleotide encoding a cognate chaperone protein of the RBD. In one aspect, the cognate chaperone is selected from the group consisting of SEQ ID NOs: 89, 90, 113, 114, and 117.

Target Bacteria

*Clostridium difficile* strains isolated from patients vary widely by pulse gel electrophoresis and in their pathogenicity. The BI/NAP1 or ribotype 027 strains that hyperproduce toxins are particularly virulent as a result of their having lost the function of gene tcdC that negatively regulates the expression level of toxin A and toxin B (McDonald et al., 2005).

In fact, *C. difficile* strains harboring a specific mutant allele of the tcdC gene have been shown to spread epidemically within and among healthcare facilities. These epidemic and highly virulent strains are especially important target bacteria that could be eliminated prophylactically from the GI tract of carrier patients by oral application of diffocins prior to or shortly after the commencement of traditional antibiotic therapy. *C. difficile* bacteria that produce wild-type levels of toxins A and B are important target pathogens as well since they are also potentially lethal, particularly to patients older than 50 years or with co-morbidities (Bartlett J G, 2002).

Targeting surface accessible virulence or fitness factors such as S-layer proteins, prevalent on *C. difficile* strains, whether hyperproducers or not, offer an attractive means of forcing such pathogens to compromise their virulence or fitness if they emerge as resistant to the targeted R-type bacteriocin. Because of the high specificity of the RBD of diffocins, organisms other than *C. difficile* are not targets, a distinct and powerful advantage of diffocins since they will not cause collateral damage to commensal bacteria of the GI tract—bacteria necessary for normal GI function and good health.

An "infection" refers to growth of bacteria, such as in a subject or tissue or non-bacterial cell, wherein the bacteria actually or potentially could cause disease or a symptom in the subject, tissue or non-bacterial cell. Treatment of an infection may include prophylactic treatment with substances, materials, producer cells, or the spores of detoxified *C. difficile* bacteria capable of producing diffocins such as dif43593. Non-limiting examples of treated objects include donated organs, tissues, and cells; medical equipment, like a respirator or dialysis machine; or wounds, such as those during or after surgery. Other uses include the removal of target bacteria which may cause problems upon further growth. In additional embodiments, an hmw bacteriocin is used to treat food, plants or harvested parts of plants with bacterial infections or contaminations, or to treat environmental occurrences of the target bacteria, such as in a hospital or commercial setting.

As described herein, an anti-bacterial R-type bacteriocin may be used to inhibit growth, survival, or replication of a particular bacterium. The bacterium may be a pathogenic or environmentally deleterious strain, or may be treated in a prophylactic manner. A pathogenic microorganism generally causes disease, sometimes only in particular circumstances.

Preparation and Use of Diffocins

Diffocins are particles of approximately 10 million daltons and thus can be isolated and purified by differential centrifugation, differential filtration, aqueous two-phase separations, polyethylene glycol (PEG) precipitation and/or ion exchange chromatography to create biopharmaceutical grade oral antibacterial agents. R-type bacteriocins have been found to be stable to freezing-thawing and can be spray dried to create stable formulations.

In some embodiments of the invention, there are provided methods of producing an R-type hmw bacteriocin. The method includes exposing a producer cell to a nucleic acid sequence encoding an R-type hmw bacteriocin operably linked to an inducible promoter sensitive to an inducing agent in a concentration that brings about expression of the R-type bacteriocin, and purifying the expressed R-type bacteriocin. In one aspect, the R-type high molecular weight (hmw) bacteriocin contains one or more polypeptides selected from the group consisting of SEQ ID NOs:2-23 or SEQ ID NOs:49 and 62-80. The nucleic acid molecule is heterologous to the natural nucleic acid of the producer cell and may be contained in the producer cell's chromosome or may be contained in an episomal expression vector.

As targeted, potent antibacterial agents, diffocins will be used to remove, or decolonize, *C. difficile* from the lower GI tract of humans and other animals so as to prevent CDAD. Animals and humans treated with broad spectrum antibiotics are at high risk to develop potentially lethal CDAD if they have been colonized by *C. difficile*. Decolonization is a particularly attractive utility of diffocins because of their sparing of the healthy GI microbiota. In addition, diffocins can be administered directly or indirectly via administered producer cells or spores of detoxified *C. difficile* bacteria capable of producing diffocins to reduce the pathogen load in acute CDAD and/or to reduce the high incidence or recurrence or relapse of CDAD after successful treatment by other modalities.

Modes of Administration

R-type bacteriocins are inactivated by pH 4.0 or lower, the acidity of a normally functioning, fed stomach and upper duodenum. However, diffocins must transit the upper GI tract to reach the targeted bacterial pathogen colonizing predominately the lower GI tract. Thus, diffocins can be formulated by one or several known methods that protect a vulnerable agent from the acid and proteases of the upper GI tract and deliver such agent in an active state to the distal upper GI tract or lower GI tract. In addition, animals can be treated with antihistamines such as cimetidine or proton pump inhibitors to prevent stomach acidification before oral administration of R-type bacteriocins. Thus, oral administration of properly formulated diffocins, producer cells capable of producing diffocins, or spores of diffocin-producing detoxified *C. difficile* bacteria to humans or animals with normal stomachs or to those in whom the acidification has been pharmaceutically prevented will enable delivery to the colonized portion of the intestine and thereby enable efficacy. Based on bowel transit time, the frequency of per oral administration directly or indirectly of diffocins to decolonize asymptomatic persons or animals may be every 6, every 12, every 18, every 24 hours, weekly, or monthly. Diffocins may also be administered to patients with CDAD, or recently "cured" of CDAD, at frequencies the same or greater. Particularly for management of active CDAD, diffocins may be formulated for and administered directly or indirectly per rectum by suppository, enema or colonic perfusion.

An engineered diffocin of the disclosure may be administered to any subject afflicted with, diagnosed as afflicted with, or suspected of being afflicted with, an infection or contamination by bacteria susceptible to the diffocin. Non-limiting examples of such a subject include animal (mammalian, reptilian, amphibian, avian, and fish) species as well as insects, plants and fungi. Representative, and non-limiting, examples of mammalian species include humans; non-human primates; agriculturally relevant species such as cattle, pigs, goats, and sheep; rodents, such as mice and rats; mammals for companionship, display, or show, such as dogs, cats, guinea pigs, rabbits, and horses; and mammals for work, such as dogs and horses. Representative, and non-limiting, examples of avian species include chickens, ducks, geese, and birds for companionship or show, such as parrots and parakeets. An animal subject treated with an engineered diffocin of the disclosure may also be a quadruped, a biped, an aquatic animal, a vertebrate, or an invertebrate, including insects.

In some embodiments, the subject to be treated is a human child or other young animal which has yet to reach maturity. Thus the disclosure includes the treatment of pediatric conditions comprising infection with bacteria or other microorganism susceptible to a diffocin of the disclosure.

The disclosure also provides for the treatment or prevention of an opportunistic infection, such as that resulting from an undesirable growth of bacteria that are present in the microbial flora of a human subject or a non-human animal. An opportunistic infection may be the result of an immunosuppressed condition in a subject or the result of antibiotic treatment that alter the commensal flora of the genitourinary (GU) or gastrointestinal (GI) tract. Thus the disclosure also provides for the treatment or prophylaxis of immunosuppressed subjects and subjects exposed to other pharmaceutical agents. A diffocin with its anti-bacterial activity may be used in combination with another anti-bacterial or anti-microbial agent, such as an antibiotic or anti-fungal agent as non-limiting examples. An "anti-microbial agent" is an agent or compound that can be used to inhibit the growth of, or to kill, single celled organisms. Anti-microbial agents include antibiotics, chemotherapeutic agents, antibodies (with or without complement), chemical inhibitors of DNA, RNA, protein, lipid, or cell wall synthesis or functions.

In some embodiments, diffocins, producer cells, or spores of detoxified *C. difficile* bacteria capable of producing diffocins are formulated with a "pharmaceutically acceptable" excipient, enteric coating or carrier. Such a component is one that is suitable for use with humans, animals, and/or plants without undue adverse side effects. Non-limiting examples of adverse side effects include toxicity, irritation, and/or allergic response. The excipient or carrier is typically one that is commensurate with a reasonable benefit/risk ratio. Non-limiting pharmaceutically suitable carriers include sterile aqueous or non-aqueous solutions, suspensions, and emulsions. Examples include, but are not limited to, standard pharmaceutical excipients such as a phosphate buffered saline solution, water, emulsions such as oil/water emulsion, and various types of wetting agents. Examples of non-aqueous solvents are propylene glycol, polyethylene glycol, vegetable oils such as olive oil, and injectable organic esters such as ethyloleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers (such as those based on Ringer's dextrose), and the like.

Additional formulations and pharmaceutical compositions disclosed herein comprise an isolated diffocin specific for a bacterial pathogen; a mixture of two, three, five, ten, or twenty or more different diffocins, producer cells or spores of detoxified *C. difficile* bacteria capable of producing diffocins that target the same bacterial pathogen; and a mixture of two, three, five, ten, or twenty or more that target different bacterial pathogens or different strains of the same bacterial pathogen.

Optionally, a composition comprising a diffocin or producer cells of the disclosure may also be spray dried or lyophilized using means well known in the art. Subsequent reconstitution and use may be practiced as known in the field.

A diffocin is typically used in an amount or concentration that is "safe and effective", which refers to a quantity that is sufficient to produce a desired therapeutic response without undue adverse side effects like those described above. A diffocin may also be used in an amount or concentration that is "therapeutically effective", which refers to an amount effective to yield a desired therapeutic response, such as, but not limited to, an amount effective to slow the rate of bacterial cell division, or to cause cessation of bacterial cell division, or to cause death or decrease rate of population growth of the bacteria. The safe and effective amount or therapeutically or prophylactically effective amount will vary with various factors but may be readily determined by the skilled practitioner without undue experimentation. Non-limiting examples of factors include the particular condition being treated, the physical condition of the subject, the type of subject being treated, the duration of the treatment, the nature of concurrent therapy (if any), and the specific formulations employed.

Having now generally described the inventive subject matter, the same will be more readily understood through reference to the following examples which are provided by way of illustration, and are not intended to be limiting of the disclosure, unless specified.

EXAMPLES

1. Determination of the Bactericidal Activity of Diffocins

*C. difficile* cultures were grown under strict anaerobic conditions in a Form a Scientific environmental chamber with an atmosphere of 10% $CO_2$, 10% $H_2$, 80% $N_2$. All media, buffers, and plates were reduced in this atmosphere for at least 24 hours prior to use. Cultures were streaked on *C. difficile* selective agar plates (BD Diagnostics, BBL Cat. 222228), and incubated at 37° C. for two days. These plates as stocks were then stored anaerobically at ambient temperature.

To induce diffocins, *C. difficile* bacteria were grown in liquid cultures using *Brucella* medium (Difco) at 37° C. with no shaking. At an $OD_{600}$ of approximately 0.2, mitomycin C was added to a final concentration of 3 µg/ml. Cultures were then incubated for 3-16 hours. Bacterial lysis was detected by a visual clearing of the culture.

Cultures were removed from the anaerobic chamber, and cellular debris was removed by centrifugation at 5,000×g. The supernatants were then passed through a 0.2 µm cellulose acetate syringe filter. The filtrate was centrifuged at 90,000×g for 2 hours to pellet the diffocin particles. The pellets were resuspended in 10 mM Tris pH 7.5, 50 mM NaCl, 3% mannitol in 1/50 original culture volume.

Target strains were grown in *Brucella* broth overnight at 37° C. Culture volumes of 100 µl were added to 5 ml of tempered, reduced, *Brucella* overlay agar (0.5% agar), poured onto a *Brucella* agar plate (1.5% agar) and allowed to set. Samples of 5 µl of the diffocin preparations were spotted onto the plates and allowed to air dry (about 30 min). The plates were then incubated anaerobically at 37° C. overnight. Bactericidal activity was determined by a clearing, or lack of bacterial growth, at the position or spot where a sample was applied to the lawn.

2. Cloning of the Cd16 Diffocin Locus

A draft genome sequence of *C. difficile* strain Cd16 was obtained by 454 instrument sequence analysis of genomic DNA. The entire dif16 locus or cluster (SEQ ID NO:1) was identified by comparison to strain Cd630 (see above).

Preparing a Backbone BAC Vector.

The starting vector was pETcoco1 (Novagen). This was modified to remove the two XhoI sites with primers AV1419 (SEQ ID NO:24) and AV1420 (SEQ ID NO:25), which have BbsI ends. To do so, a specific region was amplified from pETcoco1 DNA with these primers, and subsequently the PCR product was cut with BbsI and ligated back into the larger pETcoco1 vector fragment that was previously cut with XhoI. This ligation destroyed the two XhoI sites of pETcoco1. This latter plasmid was then further modified by a similar strategy to destroy the EcoRI sites using primers AV1416 (SEQ ID NO:26) and AV1245 (SEQ ID NO:27). The resulting vector was termed SW251.

Preparing a pUC19 Vector to Accept Fragments of the Diffocin Cluster.

The polylinker of pUC19 (New England BioLabs) was modified by digesting with EcoRI and HindIII and ligating in oligos AV1372 (SEQ ID NO:28), AV1373 (SEQ ID NO:29), AV1374 (SEQ ID NO:30), and AV1375 (SEQ ID NO:31). This changed the polylinker to NotI-NheI-KpnI-XhoI-EcoRV-BstBI-BbsI-EcoRI-NsiI-SphI-BamHI-AscI. This was termed SW232.

Cloning the Diffocin Cluster into SW232.

Three fragments of the diffocin cluster, SEQ ID NO 1, were individually amplified by PCR from Cd16 DNA. The 5' fragment (SEQ ID NO: 32) was amplified with primers 1368 (SEQ ID NO:35) and 1289 (SEQ ID NO:36), which had NotI and XhoI ends, respectively. The middle fragment (SEQ ID NO:33) was amplified with primers AV1288 (SEQ ID NO:37) and AV1366 (SEQ ID NO:38), which had XhoI and EcoR1 ends, respectively. The 3' fragment, SEQ ID NO:34, was amplified with primers AV1367 (SEQ ID NO:39) and AV1300 (SEQ ID NO:40), which had EcoR1 and BamH1 ends, respectively. These three PCR fragments were separately cloned into SW232, and termed SW241, SW242, and SW243 for the 5', middle, and 3' portions, respectively.

Cloning the Diffocin Cluster into the BAC SW251.

The three fragments of the diffocin cluster (in SW241, SW242, and SW243), each having been expanded by cloning in *E. coli* and purified, were excised from the SW241, SW242, and SW243 vectors. SW241 was digested with NotI and XhoI, SW242 was digested with XhoI and EcoRI, and SW243 was digested with EcoRI and AscI. (Note that this AscI sites was part of the modified SW232 polylinker described above.)

These three fragments were assembled into SW251 that was first digested with NotI and AscI. The resulting plasmid was termed DG461 and contained the entire dif16 cluster. It was amplified in *E. coli*.

Making a Diffocin Integration Vector for Expression in *B. subtilis*.

The *B. subtilis* integration vector, pDR111, which included portions of the amyE gene flanking a cloning/promoter region and a spectinomycin-resistance gene, was used.

The pDR111 polylinker was modified by digesting the vector with HindIII and SphI and ligating in oligos DG1 (SEQ ID NO:41) and DG2 (SEQ ID NO:42). This added NotI and AscI sites to pDR111. The region containing the entire amyE front and back region with the modified polylinker was then amplified using primers DG9 (SEQ ID NO:43) and DG10 (SEQ ID NO:44), which both have BsaI ends. This fragment was ligated into the NotI and AscI sites of SW251 (resulting in destruction of the two sites) and created DG487. Note that there were new NotI and AscI sites introduced into DG487 by the modified poly linker of the pDR111-derived insert.

After expansion of DG487 in *E. coli* the NotI/AscI fragment containing the diffocin cluster from DG461 was then excised and cloned into the NotI/AscI site of DG487. This new construct was named DG488 and was the vector used to introduce the entire diffocin gene cluster into *B. subtilis* (below).

3. Expression of a Diffocin Gene Cluster in *Bacillus subtilis*

The natural diffocin producer is *C. difficile*, an obligate anaerobe. If exposed to even traces of oxygen, *C. difficile* bacteria sporulate and die promptly. The ability to generate even trace amounts of diffocins from cultured *C. difficile* is difficult and taxing, and certainly the production of quantities of diffocins useful for prophylactic or therapeutic applications is not practical under the required strict anaerobic conditions. Accordingly, the entire diffocin gene cluster from *C. difficile* was first identified and then isolated by molecular cloning and introduced the cluster into an aerobic gram positive bacterium, *Bacillus subtilis*, for further engineering and production.

The *Bacillus subtilis* integration vector, DG488, was made as described in Example 2 and contained the entire 22,827 base diffocin locus (SEQ ID NO:1). This vector was used to recombine the diffocin locus into the *Bacillus subtilis* genome.

The recipient *Bacillus subtilis* strain was BDR123, which had a chloramphenicol resistance marker inserted within the amyE gene. When this strain was transformed with DG488, recombination occurred between the front and back amyE sequences within the vector and the genomic amyE sequences. This resulted in insertion, into the BDR123 genome, of all of the sequences between the front and back amyE regions of DG488 including the diffocin locus and the spectinomycin resistance gene. Successful recombinants were spectinomycin resistant but had become chloramphenicol-sensitive due to loss of that genomic marker as a result of the recombination event. This *B. subtilis* strain was termed BDR123-488.

Figure 7:
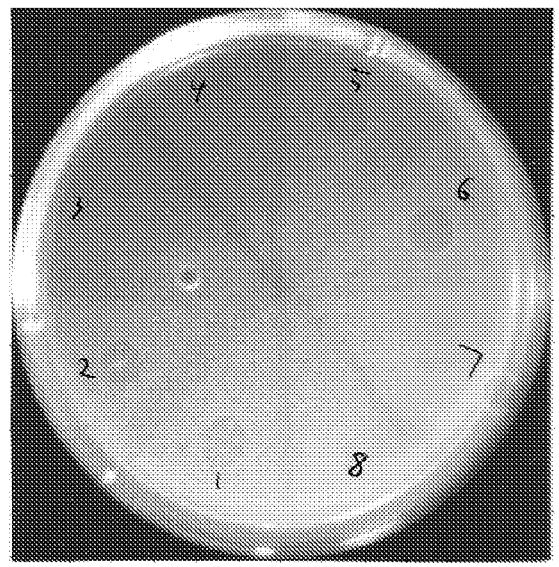
FIG. 7 is an image of spot tests of dif16 produced by *Bacillus subtilis* BDR123-488 (sector 1) and BDR123-491 (sector 2) tested on a lawn of *C. difficile* strain 19099.

Since the entire diffocin locus was inserted into the DG488 vector (Example 2), it therefore was also inserted in its entirety into BDR123-488. This inserted diffocin locus included all of the regulatory genes that were required for normal expression in *Clostridium*, and the structural diffocin particle genes were under control of these genes and/or regulatory elements. Because *Bacillus* and *Clostridium* are related bacteria, it was predicted that these diffocin regulatory elements would function in the *Bacillus* background and, as in their natural state, would be induced by DNA damage through a RecA-mediated mechanism. This in fact was the case, and diffocin particle production was induced in BDR123-488 by contact with the DNA damaging agent mitomycin C and killed strain Cd19099, FIG. 7.

Diffocin regulatory genes (ORFs 1359, 1360, 1361) were located in the 5' region of the locus in relation to the structural genes. There were also regulatory genes (ORFs 1377 (SEQ ID NO:20), 1378 (SEQ ID NO:21), and 1379 (SEQ ID NO:23)) located downstream, 3' in relation to the structural genes. To eliminate these latter regulatory genes DG491 was generated from DG488 in a single three way ligation. One PCR fragment was made from DG488 by PCR amplification with primers DG13 (SEQ ID NO:45) and DG14 (SEQ ID NO:46), and the other was made by PCR amplification with primers DG15 (SEQ ID NO:47) and DG16 (SEQ ID NO:48). Both PCR fragments were digested with AscI and SphI. DG488 was then digested with SphI, and the two digested PCR fragments were ligated into the large vector fragment from SphI-digested DG488 to produce DG491. DG491 was transformed into BDR123 (BDR123-491) to generate recombinant *B. subtilis* that contained the diffocin gene cluster lacking ORFs1377 (SEQ ID NO:20), 1378 (SEQ ID NO:21), and 1379 (SEQ ID NO:23). The modified diffocin cluster lacking these ORFs expressed active diffocins upon exposure to mitomycin C (FIG. 7), as did the wild type diffocin cluster in BDR123-488.

4. Characterization of Bactericidal Spectrum-Determining Sequences from Multiple Diffocins A comparison of the Cd16 diffocin locus (SEQ ID NO:1) with that of Cd630 as well as other Cd strains that have been sequenced (QCD-66c26; QCD-23 m63; QCD-32g58; QCD-63q42) and Cd4 (SEQ ID NO:61) showed that, with one exception, all of the open reading frames (SEQ ID NOs:1 and 61) shared 89-100% amino acid sequence identity. The exception was ORF 1374. This exceptional sequence was variable among all the sequenced diffocins and although similar in size, shared as little as 30% sequence identity. The position of ORF1374 within the diffocin cluster was consistent with that of a receptor binding domain. The sequences of the ORF1374s of the active diffocins that were isolated were determined and it was found that they too were highly variable in sequence (SEQ ID NO:17, 49-53). A comparison of these sequences is shown in FIG. 8. Furthermore, the spectra of the isolated diffocins (FIG. 2) reflected the similarities or dissimilarities of the ORF1374 amino acid sequences, FIG. 8. For example, the sequences of ORF1374 of dif16 (SEQ ID NO:17) and dif126 (SEQ ID NO:52) differed by only 1 amino acid and their bactericidal spectra were nearly identical. Whereas the sequences of ORF1374 of dif16 (SEQ ID NO:17) and dif108 (SEQ ID NO:50) differed by 188 amino acids, and their bactericidal spectra were very dissimilar with little overlap. For this reason and because ORF1374 was the only variable protein in the gene cluster, it was concluded that ORF1374 was the target recognition determinant and responsible for the unique spectrum of each particular diffocin.

5. Cloning and Expression of Dif4 in *B. Subtilis*

The diffocin 4 locus was cloned from Cd4 by methods similar to those for diffocin 16. However, some modifications were required due to the absence of an EcoR1 site within the dif4 gene cluster, SEQ ID NO:61. Plasmid SW251 (see Example 2 above) was modified to have an XhoI site in the polylinker using oligos DG211, SEQ ID NO:57 and DG212, SEQ ID NO:58, to introduce NotI and AscI sites, respectively. This created vector DG577.

The diffocin cluster from Cd4 DNA was amplified in three fragments. The first used primers DG210 (SEQ ID NO:59) and AV1288 (SEQ ID NO:37) to introduce XhoI and NcoI sites. The second used primers DG209 (SEQ ID NO:60) and DG15 (SEQ ID NO:47) to introduce NcoI and AscI sites. These two were cloned into DG577, previously cut with XhoI/AscI to create DG578. The third fragment was amplified using AV1368 (SEQ ID NO:35) and AV1289 (SEQ ID NO:36) to introduce XhoI and NotI sites and cloned into DG578, previously cut with XhoI and NotI to create DG579. This latter construct containing the dif4 cluster (SEQ ID NO:61) was the equivalent of DG491 for dif16, i.e. it lacked ORF1377, ORF1378 and ORF1379, the unnecessary presumed regulatory sequences downstream of the structural genes for diffocin. The integration vector for introducing the dif4 cluster into *B. subtilis* was made by taking the NotI AscI fragment from DG579 and cloning it into DG487 (see Example 2 above). This constructed plasmid was DG580.

To express dif4 in *B. subtilis*, DG580, which contained the dif4 locus without ORF1377-1379 (SEQ ID NO:61), was recombined into the *Bacillus subtilis* genome. The recipient *Bacillus subtilis* strain was BDR123, which had a chloramphenicol resistance marker inserted within the amyE gene. When this strain was transformed with DG580, recombination occurred between the front and back amyE sequences within the vector and the genomic amyE sequences. This resulted in insertion, into the BDR123 genome, of all of the sequences between the front and back amyE regions of DG580 including the diffocin locus and the spectinomycin resistance gene. Successful recombinants were spectinomycin resistant but had become chloramphenicol-sensitive due to loss of that genomic marker as a result of the recombination event. This *B. subtilis* strain was termed BDR123-580.

Figure 9:
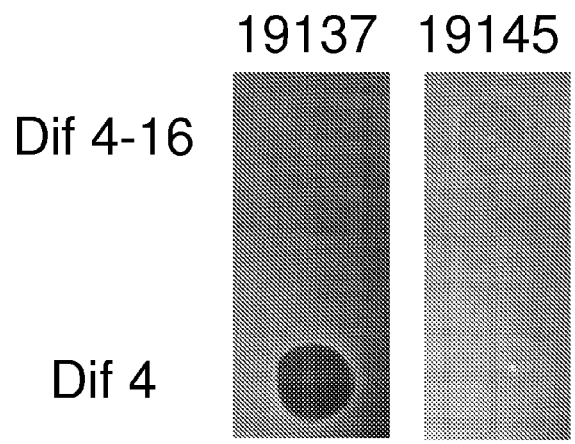
FIG. 9 is an image of spot tests of "Dif4" produced by BDR123-580 and "Dif 4-16". The latter was produced by *Bacillus subtilis* BDR123-587 in which the ORF1374 of dif4 (SEQ ID NO:49) was switched to ORF1374 of dif16 (SEQ ID NO:17). These two diffocins produced by *B. subtilis* were both tested on lawns of strains 19137 and 19145, as indicated. The specificity of killing by "Dif 4-16" has been switched from that of dif4 to that of dif16.

This integrated dif4 locus included all of the regulatory genes required for normal diffocin expression in *C. difficile*, and as expected and shown previously for dif16 in *B. subtilis*, dif4 particle production was induced in BDR123-580 by contact with mitomycin C, FIG. 9. Thus, the present examples provide the cloning of the genetic loci for both dif4 and dif16 and the expression of each in *B. subtilis*, an example of a non-pathogenic aerobic production bacterium.

6. ORF1374 Determines the Bactericidal Spectra of Diffocins

ORF 1374 encodes a large predicted polypeptide (~200 kDa) that was shown by mass spectrometry to be part of the purified diffocin structure. When comparing the gene clusters of diffocins 16 and diffocin 4, most of the gene products, particularly those that are predicted to be structural components, are nearly identical at the amino acid level. The major amino acid sequence difference between the two clusters is ORF1374. For this reason and other reasons discussed below, it was speculated that this gene product confers the target specificity of the diffocins. To test this, ORF 1374 of dif 4 (i.e., the sequence encoding SEQ ID NO:49) was replaced in DG580 with ORF 1374 from Cd16 (i.e., the sequence encoding SEQ ID NO:17) to create DG587. DG587 was integrated into the genome of *B. subtilis* BDR123 to make a BDR123-587 recombinant, as provided above for dif16 and dif4. The resulting BDR123-587 was exposed to mitomycin and the lysate treated so as to prepare diffocins. The resulting diffocin particles had bactericidal activity against *C. difficile* strain 19145, which was sensitive to diffocin 16, and had lost the ability to kill strain 19137, which was sensitive to dif4 (FIG. 9). This experiment was further refined. Construction of DG587 resulted in ORF1373 being a chimera of Cd4 and Cd16. A construct was made such that ORF 1373 of DG587 was restored to be 100% identical to the original Cd4 1373, SEQ ID NO:78, thus creating a construct that was a clean replacement of only ORF 1374, SEQ ID NO:17. This construct was termed DG603. This construct was integrated into the *B. subtilis* BDR123 genome and induced with mitomycin C as described above. The resulting diffocin particles had bactericidal activity against strains 19099 and 19145 and lost the ability to kill 19137. Thus, the bactericidal sprectra of diffocins was determined by the protein encoded by ORF1374, and changing ORF1374 changed the bactericidal spectrum of diffocin, as demonstrated herein.

7. Producer Cell without PBSX that does not Lyse when RecA is Activated

The PBSX prophage is ubiquitous in wild type *Bacillus subtilis*. The prophage when induced is defective in that it possesses a stunted head structure and contains only small, random fragments of DNA. It is under the control of RecA, thus it is induced by DNA damaging agents, e.g. mitomycin C, and other forms of severe stress to the bacterium. When induced it causes lysis of the bacterium and releases PBSX particles. In order to avoid contamination of culture medium with PBSX particles and to eliminate lysis of the *Bacillus subtilis* producer bacteria when the expression of diffocins is regulated by modifying recA or dinR/lexA activity, the PBSX gene cluster was eliminated from *Bacillus subtilis* BDR11 bacteria.

The PBSX knockout was constructed by following the procedure outlined in Liu et al. Briefly, using the primers and overlapped extension PCR techniques used in the Liu paper, the araR gene of parental strain BDR11 was deleted and replaced with the neomycin/kanamycin-resistance gene under the *Bacillus* arabinose promoter, $P_{araA}$-neo$^R$, to make strain BDG2. This deletion of the araR gene was confirmed by PCR and by the conferral of resistance to kanamycin.

Next, a DNA construct was made to delete the PBSX locus itself. To make this construct, the following five PCR products were spliced by overlapped extension PCR into one large product: 1 kb of sequence 5' of the xylB gene, amplified from BDR11; 1 kb of sequence 3' of the xylA gene, amplified from BDR11; a chloramphenicol resistance gene, cat, amplified from plasmid pJW034; araR, amplified from BDR11; and finally, 1 kb of sequence containing the xylB gene, amplified from BDR11. The overlapped extension PCR product was cloned into the XmaI and SpeI sites of pUC19. This construct was then linearized with SacII and transformed into strain BDG2 bacteria, which were plated onto LB agar plates supplemented with 5 µg chloramphenicol/ml. Colonies were picked from this plate and patched onto LB agar plates supplemented with either 5 μg chloramphenicol/ml or 20 μg kanamycin/ml. Strains that were chloramphenicol resistant and kanamycin sensitive were grown for 4 hours in LB broth with no antibiotic selection and then plated onto LB agar plates supplemented with 20 μg kanamycin/ml. The colonies that grew on these plates were tested by colony PCR for the presence of PBSX genes. The deletion of the PBSX gene cluster was confirmed in strain BDG 9 by sequencing PCR products that spanned the site of PBSX genes in wt strain BD123. Further analysis showed that unlike *Bacillus subtilis* strains BD123 or BDG2, BDG9 did not lyse or produce PBSX particles in the presence of 3 μg mitomycin C/ml.

The PBSX deletion strain, BDG9, was transformed with plasmid DG580, to create BDG27. Integration of the Cd4 diffocin cluster was confirmed by spectinomycin resistance. BDG27 was grown and induced with mitomycin C as described above. After 16 hours cells were harvested and lysed with BugBuster (Novagen) to break open the cells since, without PBSX, we expected the diffocins to accumulate intracellularly. After lysing the cells with BugBuster, debris was removed by centrifugation, and the supernatant was tested for bactericidal activity against strain 19137. The diffocin produced by BDG27 showed activity against Cd19137 but not Cd19099, thus demonstrating that diffocin 4 was produced in this non-lytic, PBSX deleted strain.

8. The Small Molecule Inducer, Hydrogen Peroxide, Induced Diffocin Expression in *B. subtilis*

In Example 3, mitomycin C was used to induce production of Diffocins in *B. subtilis* strain BDR123. Since mitomycin C is a DNA damaging agent and carcinogen, an alternative small molecule inducer was sought. Hydrogen peroxide ($H_2O_2$) has been shown to cause an SOS response in a manner similar to mitomycin C (Imlay and Linn, 1987)); however, $H_2O_2$ is generally regarded as safe (GRAS) by the U.S. FDA. Also, $H_2O_2$ has been shown to cause prophage induction in several aerobic bacterial species, including *E. coli* and *B. subtilis* (Imlay and Linn, 1987; Bol and Yasbin, 1990). The effect of $H_2O_2$ on prophage and/or Diffocin production in *C. difficile* was not known, as *C. difficile* is an obligate anaerobic and resides in a niche in the gastrointestinal tract that does not normally contain $H_2O_2$.

To determine whether $H_2O_2$ can induce Diffocin production in *B. subtilis*, a study comparing the ability of $H_2O_2$ and mitomycin C to induce Diffocin in *B. subtilis* strain BDG45 was initiated. BDG45 contains in its genome the Diffocin4 gene cluster (SEQ ID NO: 61) linked to a chloramphenicol resistance gene integrated into the amyE sequence. BDG45 cultures were grown overnight, back-diluted, and grown until reaching an OD600 of about 1.0. At that time, cultures were left untreated, or treated with 0.5 ug/mL mitomycin C, 0.2 mM $H_2O_2$, or 1 mM $H_2O_2$ and incubated at 28° C. Samples were taken 21 hours post-induction, and Diffocin preparations were made as in Example 1, except the Diffocin pellets were resuspended in 10 mM Hepes pH 7.4, 50 mM NaCl (HN50). Bactericidal activities of the preparations were determined as in Example 1 with samples serially (5-fold) diluted in HN50 before being spotted on a bacterial lawn containing an isolate (19137) sensitive to Diffocin4. The results of the bactericidal assay are shown in Table I. Twenty-one hours post-induction, both the mitomycin C and the 1 mM $H_2O_2$ treatments produced Diffocin bactericidal activity easily detectable after 625-fold and 3,125-fold dilutions, respectively. The 0.2 mM $H_2O_2$ modestly induced Diffocin production. Subsequent studies demonstrated that Diffocin production was induced with $H_2O_2$ concentrations from 0.2 mM to 20 mM.

TABLE I

Spot assay results for serial 5-fold dilutions of Diffocins induced in *B. subtilis* with either mitomycin C (Mito-C) or hydrogen peroxide ($H_2O_2$).

| | 21 Hr Post-Induction | | | |
|---|---|---|---|---|
| | No treat | Mito-C | 0.2 mM $H_2O_2$ | 1 mM $H_2O_2$ |
| No. of spots | 1 | 4-5 | 1-2 | 5-6 |

9. Nucleic Acids Isolated from *C. Difficile* Genomes, Phages and Prophages Encode Functional RBD Proteins for Heterologous Diffocins Diffocin preparations made from the M68 *C. difficile* isolate had a broad bactericidal spectrum (Table II). When the Diffocin4 ORF1374 (SEQ ID NO: 49) was replaced with the heterologous ORF1374 (SEQ ID NO: 87) from strain M68 and the 3' portion of Diffocin4 BPAR (SEQ ID NO: 78) was replaced with the 3' end of the cognate BPAR (SEQ ID NO: 88) from strain M68 along with the chaperones from ATCC43593 (SEQ ID NOs: 89 and 90) and expressed in *B. subtilis* as described in Example 6, the resulting Diffocin, Diff4_M68-1374, had a bactericidal spectrum more narrow than Diffocin preparations isolated directly from the mitomycin C-induced M68 strain. While no other Diffocin gene cluster was found in the M68 genome sequence, several putative prophage gene insertions with homology to known myoviridae phages were found. Since some genes in the Diffocin cluster share homology with genes in the contractile tails of *C. difficile* myoviridae phages, it was hypothesized that genes from *C. difficile* phages and *C. difficile* genomes, including but not limited to prophage sequences, might serve as sources of heterologous RBDs to redirect targeting for Diffocins. However, there was no prior identification of the spectrum determinant or RBD gene for any *C. difficile* phage, prophage or other ORF in its genome sequence.

TABLE II

Sensitivities of *C. difficile* strains to preparations of heterologous Diffocins and the natural M68 Diffocin.

| Diffocin | Source of RBD | Sensitive Strains | | | | | | | |
|---|---|---|---|---|---|---|---|---|---|
| natural M68 | M68 | 19098 | 19099 | 19102 | 19103 | 19123 | 19126 | 19131 | 19135 |
| | | 19137 | 19139 | 19145 | 19146 | 20068 | ATCC43255 | BI-9 | CD4 |
| | | CD62 | CD242 | CHI | LIV22 | LIV24 | M120 | R20291 | TL174 |
| | | TL176 | TL178 | | | | | | |

TABLE II-continued

Sensitivities of *C. difficile* strains to preparations of heterologous Diffocins and the natural M68 Diffocin.

| Diffocin | Source of RBD | Sensitive Strains | | | | | | | |
|---|---|---|---|---|---|---|---|---|---|
| Diff4_M68-1374 | M68 | 19102 | 19126 | 13135 | 19137 | 20068 | BI-9 | CD4 | CD62 |
| | | CD242 | CHI | LIV22 | LIV24 | M120 | R20291 | TL176 | |
| Diff4_M68-RBD1 | M68 | 19099 | 19123 | 19131 | CD4 | M120 | TL174 | TL178 | |
| Diff4_M68-RBD2 | M68 | 19123 | 19126 | 19135 | 19137 | 20068 | ATCC43255 | BI-9 | CD4 |
| | | LIV24 | R20291 | | | | | | |
| Diff4_M68-RBD4 | M68 | 19117 | 19121 | 19134 | CD630 | CF5 | CHI | M68 | |
| Diff4_M68-RBD5 | M68 | 19117 | 19121 | 19134 | CD630 | CF5 | CHI | M68 | |
| Diff4_027B-RBD | phi027B | 19135 | 19137 | 20315 | ATCC43255 | R20291 | | | |
| Diff4_phi147-RBD | phi147 | 19108 | 19147 | | | | | | |
| Diff4_BI9-RBD2 | BI-9 | CF5 | CHI | M68 | | | | | |
| Diff4_BI9-RBD5 | BI-9 | 19135 | 19137 | 20315 | ATCC43255 | R20291 | | | |
| Diff4_CD305-RBD1 | CD305 | 19155 | CD305 | | | | | | |
| Diff4_TL174-RBD | TL174 | 19123 | | | | | | | |
| Diff4_CD630-RBD1 | CD630 | 19098 | 19108 | | | | | | |
| Diff4_R20291-RBD1 | R20291 | 19135 | 19137 | 20315 | ATCC43255 | R20291 | | | |
| Diff4_R20291-RBD1+ | R20291 | 19135 | 19137 | 20315 | ATCC43255 | R20291 | | | |

A comparison of the ORFs from the Diffocin gene cluster to the ORFs from the putative prophage insertions in M68 showed many similar genes and similar gene cluster architecture. However, downstream of the ORFs with homology to the predicted Baseplate J assembly protein and the BPAR, at a location where the ORF encoding the ~1700 amino acid residues for the typical Diffocin RBD (for examples: SEQ ID NOS 17, 49-53) typically resides, much shorter ORFs encoding proteins of 400-560 amino acid residues (Table III and SEQ ID NOs: 92, 94, 96, 98) that did not share homology with the typical Diffocin RBD were found.

TABLE III

SEQ ID NOs. for heterologous RBDs, BPAR fusions, and chaperones of heterologous Diffocins constructed by strategies I, II, or III.

| Strategy | Fused BPAR | RBD | Chaperone(s) | Diffocin | RBD template | Construct |
|---|---|---|---|---|---|---|
| | SEQ ID NO: 88 | SEQ ID NO: 87 | SEQ ID NOs: 89, 90 | M68-1374 | M68 gDNA | |
| I | SEQ ID NO: 91 | SEQ ID NO: 92 | n/a | M68-RBD1 | M68 gDNA | DG711 |
| I | SEQ ID NO: 93 | SEQ ID NO: 94 | n/a | M68-RBD2 | M68 gDNA | DG702 |
| I | SEQ ID NO: 95 | SEQ ID NO: 96 | n/a | M68-RBD4 | M68 gDNA | DG703 |
| I | SEQ ID NO: 97 | SEQ ID NO: 98 | n/a | M68-RBD5 | M68 gDNA | DG704 |
| II | SEQ ID NO: 99 | SEQ ID NO: 100 | n/a | R20291-RBD1 | R20291 gDNA | DG721 |
| II | SEQ ID NO: 101 | SEQ ID NO: 102 | n/a | BI9-RBD2 | BI-9 gDNA | DG723 |
| II | SEQ ID NO: 103 | SEQ ID NO: 104 | n/a | TL174-RBD | TL174 gDNA | DG738 |
| II | SEQ ID NO: 105 | SEQ ID NO: 106 | n/a | CD305-RBD1 | CD305 gDNA | DG739 |
| II | SEQ ID NO: 107 | SEQ ID NO: 108 | n/a | BI9-RBD5 | BI-9 gDNA | DG742 |
| II | SEQ ID NO: 109 | SEQ ID NO: 110 | n/a | 027B-RBD | phi027B gDNA | DG746 |
| II | SEQ ID NO: 111 | SEQ ID NO: 112 | n/a | 630-RBD1 | CD630 gDNA | DG761 |
| III | SEQ ID NO: 99 | SEQ ID NO: 100 | SEQ ID NOs: 113, 114 | R20291-RBD1+ | R20291 gDNA | DG779 |
| III | SEQ ID NO: 115 | SEQ ID NO: 116 | SEQ ID NOs: 117 | phi147-RBD | phi147 gDNA | DG785 |

Sequence analyses of these ORFs downstream to the putative prophage BPARs revealed that they shared homology to each other in at least one of three domains (N-terminal, mid-section, and C-terminal) and to an ORF (SEQ ID NO: 92) downstream of the annotated BPAR in the phiC2 phage, SEQ ID NO. 54. Interestingly, the DNA sequence encoding SEQ ID NO:92 in phiC2 was not annotated as a predicted protein in the phiC2 phage. Because the ORFs immediately downstream of the BPAR in phage and prophage sequences share homology in a domain-like way and were all found downstream of BPAR homologues, as are the genes encoding ORF1374, it was prophesized that these ORFs encode potential RBDs. As presented herein, many more DNA sequences encoding potential RBDs downstream of putative BPARs in genomes of other *C. difficile* isolates or in phages that infect *C. difficile* were identified since that original observation from *C. difficile* M68. The SEQ ID NOs. for RBDs used to make functional heterologous Diffocins are listed in (Table III).

To determine whether these newly identified ORFs with previously unknown functions could direct Diffocin killing to new *C. difficile* target strains, novel heterologous Diffocins were engineered by replacing the Diffocin4 ORF 1374 (SEQ ID NO: 49) with the ORFs encoding putative RBDs. The nucleic acid sequences encoding putative RBDs and the adjacent 3' portion of the ORF encoding its cognate BPAR were cloned into the vector (described in Example 2) containing the Diff4 gene cluster (SEQ ID NO: 61), replacing the entire Diffocin4 ORF 1374 (SEQ ID NO: 49) and the C-terminal portion of the Diffocin4 BPAR (SEQ ID NO: 78). The SEQ ID NOs. for amino acid residues of fused BPARs are provided in Table III. We had observed that a given putative RBD incorporated into a heterologous Diffocin4 without the inclusion of at least the C-terminal half of its cognate BPAR generated minimal or no bactericidal activity. Since the inserts did not have compatible cloning sites within the vector backbone, 3 cloning strategies were devised to overcome this obstacle.

For constructs made with Strategy I, 3 double-stranded DNA segments (termed upstream segment, mid-segment, and downstream segment) containing overlapping ends were generated by PCR (Table IV; Panels A, B and C). The upstream segment (Table IV, Panel A) consisted of the unique BstBI site in SEQ ID NO:61 through the 5' end of the BPAR gene encoding SEQ ID NO: 78. The mid-segment (Table IV, Panel B) consisted of the entire ORF of the putative RBD and the 3' one-half of its upstream cognate BPAR. The downstream segment (Table IV, Panel C) consisted of the region immediately downstream of SEQ ID NO: 49 and encoding SEQ ID NOs: 79 and 80 extending to the unique Asc I restriction site in the vector polylinker described in Example 2 above. All 3 segments were made using oligonucleotides complementary to the template and containing overhangs complementary to adjacent fragments to enable proper assembly. Coding strand and non-coding strand oligonucleotides used to amplify each construct are listed by SEQ ID NO in Table IV. The DNA templates for each PCR reaction are also listed in Table IV. Next, the 3 segments for each construction were combined and amplified into a single fragment by PCR using oligonucleotides complementary to the coding strand in the upstream segment and the non-coding strand in the downstream segment (see SEQ ID NOs. in Table IV). The resulting, combined single PCR fragments were then cleaved with BstBI and AscI and ligated to the Diff4 vector backbone pre-digested with BstBI and AscI to make the constructs listed. Each construct was then transformed into *B. subtilis* and expressed as previously described in Example 3 except that 0.5 mM $H_2O_2$ was used as the small molecule inducer.

For constructs made with Strategy II, overlapping PCR products complementary to the upstream segment, the mid-segment containing the RBD region, and the downstream segment were made as described for Strategy I with oligonucleotides and templates for each construct listed in Table IV. Next, the overlapping PCR products were mixed with the vector backbone (described in Example 4) containing SEQ ID NO: 61 pre-digested with BstBI and AscI and assembled into a single construct by the Gibson method (Gibson et al. 2009). Each resulting construct was then individually transformed into *B. subtilis* and expressed as previously described in Example 3 except that 0.5 mM $H_2O_2$ was used as the small molecule inducer.

Strategy III constructs were made in a manner identical to Strategy II except that the downstream segments were not created. Instead, the mid-segments containing the RBD regions were extended to include the ORFs immediately downstream of the putative RBD (SEQ ID NOs listed for each construct in Table IV) and to overlap with the vector backbone AscI site. As a result, DNA encoding SEQ ID NOs 79-80, putative chaperones for Diffocin4 tail structure assembly, were replaced with DNA sequences encoding ORF's found immediately downstream of the cognate putative RBDs and which it was conceived could be chaperones for assembly of the putative, cognate RBDs. Each resulting construct was then transformed into *B. subtilis* and expressed as previously described in Example 3 except that 0.5 mM $H_2O_2$ was used as the small molecule inducer.

TABLE IV

Oligonucleotides and their SEQ ID NOs., templates, and strategies used to construct heterologous Diffocins. (Panel A) For upstream segment. (Panel B) For mid-segment. (Panel C) For downstream segment.

Panel A

| | | | upstream segment | | |
|---|---|---|---|---|---|
| Strategy | Construct | Diffocin | upstream template | coding strand oligo | non-coding strand oligo |
| I | DG711 | Diff4_M68-RBD1 | pDG579 | SEQ ID NO: 118 | SEQ ID NO: 119 |
| I | DG702 | Diff4_M68-RBD2 | pDG579 | SEQ ID NO: 118 | SEQ ID NO: 124 |
| I | DG703 | Diff4_M68-RBD4 | pDG579 | SEQ ID NO: 118 | SEQ ID NO: 129 |
| I | DG704 | Diff4_M68-RBD5 | pDG579 | SEQ ID NO: 118 | SEQ ID NO: 133 |
| II | DG721 | Diff4-R20291-RBD1 | pDG579 | SEQ ID NO: 137 | SEQ ID NO: 138 |
| II | DG723 | Diff4_BI9-RBD2 | pDG579 | SEQ ID NO: 137 | SEQ ID NO: 143 |
| II | DG738 | Diff4_TL174-RBD | pDG579 | SEQ ID NO: 137 | SEQ ID NO: 147 |
| II | DG739 | Diff4_CD305-RBD1 | pDG579 | SEQ ID NO: 137 | SEQ ID NO: 151 |
| II | DG742 | Diff4_BI9-RBD5 | pDG579 | SEQ ID NO: 137 | SEQ ID NO: 154 |
| II | DG746 | Diff4_027B-RBD | pDG579 | SEQ ID NO: 137 | SEQ ID NO: 154 |
| II | DG761 | Diff4_CD630-RBD1 | pDG579 | SEQ ID NO: 137 | SEQ ID NO: 158 |
| III | DG779 | Diff4_R20291-RBD1 + | pDG579 | SEQ ID NO: 137 | SEQ ID NO: 138 |
| III | DG785 | Diff4_phi147-RBD | pDG579 | SEQ ID NO: 137 | SEQ ID NO: 124 |

Panel B

| | | | mid-segment | | |
|---|---|---|---|---|---|
| Strategy | Construct | Diffocin | mid-segment template | coding strand oligo | non-coding strand oligo |
| I | DG711 | Diff4_M68-RBD1 | M68 gDNA | SEQ ID NO: 120 | SEQ ID NO: 121 |
| I | DG702 | Diff4_M68-RBD2 | M68 gDNA | SEQ ID NO: 125 | SEQ ID NO: 126 |
| I | DG703 | Diff4_M68-RBD4 | M68 gDNA | SEQ ID NO: 130 | SEQ ID NO: 131 |
| I | DG704 | Diff4_M68-RBD5 | M68 gDNA | SEQ ID NO: 134 | SEQ ID NO: 135 |
| II | DG721 | Diff4-R20291-RBD1 | R20291 gDNA | SEQ ID NO: 139 | SEQ ID NO: 140 |
| II | DG723 | Diff4_BI9-RBD2 | BI-9 gDNA | SEQ ID NO: 144 | SEQ ID NO: 145 |
| II | DG738 | Diff4_TL174-RBD | TL174 gDNA | SEQ ID NO: 148 | SEQ ID NO: 149 |

TABLE IV-continued Oligonucleotides and their SEQ ID NOs., templates, and strategies used to construct heterologous Diffocins. (Panel A) For upstream segment. (Panel B) For mid-segment. (Panel C) For downstream segment.

| II | DG739 | Diff4_CD305-RBD1 | CD305 gDNA | SEQ ID NO: 125 | SEQ ID NO: 152 |
| II | DG742 | Diff4_BI9-RBD5 | BI-9 gDNA | SEQ ID NO: 155 | SEQ ID NO: 156 |
| II | DG746 | Diff4_027B-RBD | phi027B gDNA | SEQ ID NO: 155 | SEQ ID NO: 156 |
| II | DG761 | Diff4_CD630-RBD1 | CD630 gDNA | SEQ ID NO: 159 | SEQ ID NO: 160 |
| III | DG779 | Diff4_R20291-RBD1+ | R20291 gDNA | SEQ ID NO: 139 | SEQ ID NO: 162 |
| III | DG785 | Diff4_phi147-RBD | phi147 gDNA | SEQ ID NO: 125 | SEQ ID NO: 163 |

Panel C

| Strategy | Construct | Diffocin | Down-stream template | coding strand oligo | non-coding strand oligo |
|---|---|---|---|---|---|
| I | DG711 | Diff4_M68-RBD1 | pDG579 | SEQ ID NO: 122 | SEQ ID NO: 123 |
| I | DG702 | Diff4_M68-RBD2 | pDG579 | SEQ ID NO: 127 | SEQ ID NO: 128 |
| I | DG703 | Diff4_M68-RBD4 | pDG579 | SEQ ID NO: 132 | SEQ ID NO: 128 |
| I | DG704 | Diff4_M68-RBD5 | pDG579 | SEQ ID NO: 136 | SEQ ID NO: 128 |
| II | DG721 | Diff4-R20291-RBD1 | pDG579 | SEQ ID NO: 141 | SEQ ID NO: 142 |
| II | DG723 | Diff4_BI9-RBD2 | pDG579 | SEQ ID NO: 146 | SEQ ID NO: 142 |
| II | DG738 | Diff4_TL174-RBD | pDG579 | SEQ ID NO: 150 | SEQ ID NO: 142 |
| II | DG739 | Diff4_CD305-RBD1 | pDG579 | SEQ ID NO: 153 | SEQ ID NO: 142 |
| II | DG742 | Diff4_BI9-RBD5 | pDG579 | SEQ ID NO: 157 | SEQ ID NO: 142 |
| II | DG746 | Diff4_027B-RBD | pDG579 | SEQ ID NO: 157 | SEQ ID NO: 142 |
| II | DG761 | Diff4_CD630-RBD1 | pDG579 | SEQ ID NO: 161 | SEQ ID NO: 142 |
| III | DG779 | Diff4_R20291-RBD1+ | | | |
| III | DG785 | Diff4_phi147-RBD | | | |

Diffocin preparations from each expressed heterologous Diffocin DNA construction from Strategies I-III were made and assayed for bactericidal activity against a panel of *C. difficile* isolates. Isolates sensitive to the bactericidal activity of each heterologous Diffocin constructions are listed in Table II. More robust killing activity was observed for the Diff4_R20291-RBD1+ construct containing the cognate chaperones (SEQ ID NOs:113, 114) for the R20291-RBD1 as compared to the Diff4_R20291-RBD1 construction, which contained the natural Diffocin4 chaperones (SEQ ID NO: 79-80).

10. Increased Stability of Heterologous Diffocins Containing Novel, Non-1374-Based RBDs Diffocins need to remain active in many different physical environments in order to be effectively manufactured and delivered to an animal in need. With that in mind, the physical properties of naturally-occurring and heterologous Diffocins were investigated. Diffocins were made as described in Example 9, except centrifugal pellets of the prepared Diffocins were resuspended in a buffer appropriate for each study.

For the temperature stability study (Table V), the Diffocins were resuspended in HN50 (pH 7.4) and incubated at the temperatures and times indicated.

TABLE V

Thermal sensitivities of natural Diffocin4 and heterologous Diffocins as determined by spot assays. Shown are the number of serial 5-fold dilutions at which bactericidal activity was observed at each thermal condition.

| Indicator strain | Diffocin | 4° C. 60 min | 37° C. 15 min | 37° C. 60 min | 45° C. 15 min | 45° C. 30 min | 45° C. 60 min |
|---|---|---|---|---|---|---|---|
| 19137 | Diffocin4 | 3 | n.d. | n.d. | n.d. | 2-3 | 2 |
| TL176 | Diff4_43593-1374 | 2 | n.d. | n.d. | n.d. | 0 | 0 |
| CD4 | Diff4_M68-RBD1 | n.d. | 3-4 | 4 | 4-5 | n.d. | 5-6 |
| M68 | Diff4_M68-RBD1 | n.d. | 5-6 | 5-6 | 5-6 | n.d. | 5-6 |
| M68 | Diff4_M68-RBD1 | n.d. | 5-6 | 5-6 | 5-6 | n.d. | 5-6 |

For the pH sensitivity study (Table VI), the Diffocins were either resuspended in a 5 mM sodium citrate solution acidified with citric acid to the specified acidic pH, or in a 12.5 mM sodium bicarbonate/HN50 (or in TN50 for Diffocin4 solution alkalinized with NaOH to the specified alkaline pH). At the specified pH, the samples were incubated at room temperature for 30 minutes.

in vivo where they are likely to encounter acidic environments such as the stomach. These results indicated that the heterologous Diffocins containing an RBD from the novel class of non-1374, smaller RBDs were more robust as compared to natural Diffocins or those Diffocins with large, heterologous 1374-based RBDs, and thus possessed advantages for efficient production and therapeutic applications.

TABLE VI

Sensitivities of natural Diffocin4 and heterologous Diffocins to acid (Panel A) and alkaline solutions (Panel B) as determined by spot assays. Shown are the number of serial 5-fold dilutions at which bactericidal activity was observed under each pH condition.

Panel A

| Indicator strain | Diffocin | 5 mM Na-Citrate Buffer | | | | | | | | | | | | | |
|---|---|---|---|---|---|---|---|---|---|---|---|---|---|---|---|
| | | pH 2 | pH 2.5 | pH 3 | pH 3.4 | pH 3.5 | pH 4 | pH 4.5 | pH 5 | pH 5.4 | pH 5.5 | pH 6 | pH 7 | pH 7.5 | pH 7.7 |
| M68 | Diff4_M68-RBD4 | 1 | 2-3 | 2-3 | 4-5 | | 5 | | 5 | 5 | | 5 | 4-5 | | 4-5 |
| 19137 | Diffocin4 | | | 0 | | | 0 | 0 | 1-2 | | 3 | 3 | | 3 | |

Panel B

| Indicator strain | Diffocin | TN50 or Na-Bicarbonate in HN50 Buffer | | | | | | |
|---|---|---|---|---|---|---|---|---|
| | | pH 7 | pH 7.5 | pH 8 | pH 8.2 | pH 9 | pH 10 | pH 10.6 |
| M68 | Diff4_M68-RBD4 | 4-5 | | | 4-5 | 4-5 | | 2 |
| 19137 | Diffocin4 | | 6-7 | 6-7 | | 6-7 | 6-7 | |

For both studies, the samples were then serially (5-fold) diluted in HN50 and assayed for bactericidal activity by spot assays on sensitive *C. difficile* isolates. (The sensitive strain used to assay bactericidal activity for each Diffocin is indicated in Tables V and VI). Studied Diffocins included: natural Diffocin4 (encoded by SEQ ID NO: 61) heterologous Diff4_43593-1374 (RBD encoded by SEQ ID NO:53), heterologous Diff4_M68-RBD1 (BPAR and RBD encoded by SEQ ID NOs:91 and 92), heterologous Diff4_M68-RBD4 (BPAR and RBD encoded by SEQ ID NOs:95 and 96), heterologous Diff4_M68-RBD5 (BPAR and RBD encoded by SEQ ID NOs:97 and 98).

Heterologous Diffocins containing phage RBDs were stable longer at higher temperature than natural Diffocins or heterologous Diffocins containing ORF1374 proteins as RBDs (Table V). Preparations of heterologous Diffocins containing novel RBDs M68-RBD1 (SEQ ID NOs:91, 92), M68-RBD4 (SEQ ID NOs:95, 96) and M68-RBD5 (SEQ ID NOs: 97, 98) maintained or increased activity when incubated at 45° C. for 1 hr as compared to incubation at 37° C. for 15 minutes (Table V). Interestingly, Diffocins containing CD1374 RBDs, such as natural Diffocin4 RBD (SEQ ID NO:49) and the RBD (SEQ ID NO:53) of heterologous Diff4_43593-1374, did not retain activities comparable to those retained by the heterologous Diffocins with the novel, smaller, non-1374-based RBDs under the same thermal conditions (Table V). When these two former Diffocins with 1374-based RBDs were heated to 45° C. for 1 hr, they lost 80% and greater than 95% bactericidal activity, respectively.

In addition to exhibiting increased thermal stability, a heterologous Diffocin containing RBD M68-RBD4 (SEQ ID NO:96) was stable over a larger pH range than natural Diffocin 4 containing an ORF1374 (Table VI). Results for the bactericidal spot assay showed that Diff4_M68-RBD4 retained activity from pH 3.4 to pH 9 and even retained some residual activity detectable down to pH 2.5 and up to pH 10.6. Diffocin4 remained active only from pH 5.5 to pH 10. Diffocins with an expanded pH range are better suited to function 11. Bactericidal Activity of Heterologous Diffocins Containing Novel RBDs Survived the Murine GI Tract The ability of orally administered Diffocins to survive in vivo was evaluated in mice. A cocktail consisting of natural Diffocin4 (encoded by SEQ ID NO: 61), heterologous Diff4_M68-RBD4, and an unrelated engineered R-type bacteriocin, AvR2-V10, as a positive control (Scholl et al., 2009), was formulated in 12.5 mM sodium bicarbonate and administered via oral gavage to normal, healthy mice (n=3). Two hours prior to the gavage, mice were injected with the $H_2$ receptor antagonist, Ranitidine (100 mg/kg), to prevent or minimize acidification of the stomach. Feces were collected hourly for 8 hours, homogenized in HN50 containing protease inhibitors, and centrifuged to remove debris. The supernatants were filtered through a 0.45 micron filter, serially diluted 5-fold in HN50 and then assayed for bactericidal activity via spot assay on lawns of susceptible *C. difficile* isolates. Since *C. difficile* strain 19137 was uniquely sensitive to killing by Diffocin4, *C. difficile* strain CF5 was uniquely sensitive to killing by Diffocin4_M68-RBD4, and *Escherichia coli* EDL933 was uniquely sensitive to killing by AvR2-V 10, relative recovery could be observed specifically for each unique bactericidal component in the administered cocktail. Bactericidal assay results on each susceptible strain were shown side-by-side for feces from each mouse tested. An aliquot of the administered cocktail was saved and spotted in parallel as a positive control on each bacterial lawn.

In the fecal samples bactericidal activities were recovered for the heterologous Diff4_M68-RBD4, but not for natural Diffocin 4 (Table VII).

TABLE VII

Recovery of bactericidal activity of natural Diffocin 4 and of heterologous Diff4_M68-RBD4 in feces of mice after oral administration. Shown are the number of serial 5-fold dilutions at which bactericidal activity was observed by spot assay at each indicated time point.

| Indicator strain | Diffocin | | Time after Diffocin | | | | | | | Pre-Admin Cocktail |
|---|---|---|---|---|---|---|---|---|---|---|
| | | | 2 hr | 3 hr | 4 hr | 5 hr | 6 hr | 7 hr | 8 hr | |
| CF5 | Diff4_M68-RBD4 | mouse #1 | 2-3 | 3-4 | 2-3 | 2-3 | 1-2 | 1 | 0-1 | 4+ |
| | | mouse #2 | 1-2 | 2 | 2-3 | 2 | 1-2 | 1-2 | 0-1 | |
| | | mouse #3 | 2 | 2-3 | 2-3 | 1-2 | 1 | 0 | 1 | |
| 19137 | Diffocin 4 | mouse #1 | 0 | 0 | 0 | 0 | 0 | 0 | 0 | 4+ |
| | | mouse #2 | 0 | 0 | 0 | 0 | 0 | 0 | 0 | |
| | | mouse #3 | 0 | 0 | 0 | 0 | 0 | 0 | 0 | |

Comparing activity between mice, Diff4_M68-RBD4 activity was observed as early as 2 hours and as late as 8 hours after gavage. The peak recovery of activity was observed 3 to 4 hours after gavage with bactericidal activity observed after a 25-fold dilution. No activity of natural Diffocin 4 was recovered in the feces at any time point. Activity of a reserved aliquot of the cocktail solution on strain 19137 confirmed that natural Diffocin4 in the administered cocktail was active at the time of administration. These results and those in Example 10 showed that the heterologous Diffocins containing novel, non-1374-based RBDs, compared to natural Diffocins, were stable at higher temperatures and in more acidic environments. Furthermore and likely related, when administered orally, their bactericidal activity survived exposure to an animal GI tract, the site of *C. difficile* proliferation and pathogenesis.

12. A Heterologous Diffocin Reduced CDI In Vivo

Figure 10:
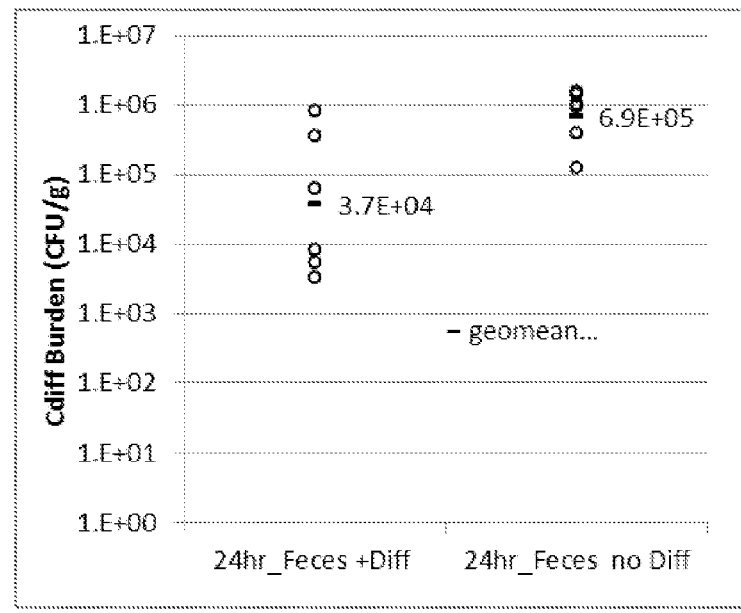
FIG. 10 shows a plot comparing the *C. difficile* burden in mice treated with heterologous Diffocins to that in untreated mice. Diffocins with novel, non-1374-based RBD functioned in vivo to reduce CDI. As compared to untreated mice challenged with *C. difficile* spores ("no Diff"), mice challenged with *C. difficile* spores and orally administered Diffocins ("+Diff") with a novel, non-1374-based RBD exhibited statistically significant ($p<0.05$ by Student t-test) reduction of *C. difficile* shedding in feces.

The effect of Diffocin on *C. difficile* infection was investigated using mice challenged with *C. difficile* spores. Two groups of mice (6 per group) were pre-treated for 5 days with drinking water containing sufficient cefoperazone (0.5 mg/mL), to disrupt the gastrointestinal microbiota and make the mice susceptible to *C. difficile* infection from challenge with orally administered spores. Both groups were then allowed to recover for 36 hrs before receiving Ranitidine in the drinking water (dose: 100 mg/kg/day). Twelve hours after the start of Ranitidine administration, the treatment group received heterologous Diffocin4_M68-RBD4 via oral gavage in a 12.5 mM sodium bicarbonate solution (dose: $10^{11}$ Killing Units—with killing units being described and defined in Gebhart et al., 2012; Ritchie et al., 2011; Scholl et al., 2009). Two hours later both groups of mice were challenged with $2\times10^5$ CFU of *C. difficile* spores prepared from strain CD630. The treatment group continued to receive the Diffocin by gavage starting 4 hrs after spore challenge and then every 6 hrs. Twenty-four hours after spore challenge, feces from mice in both groups were collected, weighed, homogenized and plated in serial 10-fold dilutions on *C. difficile* selective agent plates containing 0.05% sodium taurocholate to promote germination. Total CFUs per sample were counted and converted to CFU/g feces (FIG. 10). The geometric mean CFU/g feces was calculated for each group and compared by Student t-test.

Analysis of the data showed that the heterologous Diffocin, Diff4_M68-RBD4 was active in vivo, reducing shedding and thus colonization of *C. difficile* strain CD630. Mice that did not receive Diffocin were shedding *C. difficile* at $6.9\times10^5$ CFU/g feces (geometric mean), while mice that received the heterologous Diffocin prior to and during *C. difficile* challenge were shedding *C. difficile* at $3.7\times10^4$ CFU/g feces (geometric mean). This represented an 18.6-fold reduction in *C. difficile* shedding. Comparison of shedding results by Student t-test gave a null hypothesis p-value<0.05, and indicated the difference in shedding caused by Diffocin was statistically significant. This experiment demonstrated that heterologous Diffocins with novel, non-1374-based RBDs were active in vivo and reduced *C. difficile* shedding and colonization.

The term "comprising", which is used interchangeably with "including," "containing," or "characterized by," is inclusive or open-ended language and does not exclude additional, unrecited elements or method steps. The phrase "consisting of" excludes any element, step, or ingredient not specified in the claim. The phrase "consisting essentially of" limits the scope of a claim to the specified materials or steps and those that do not materially affect the basic and novel characteristics of the claimed invention. The present disclosure contemplates embodiments of the invention compositions and methods corresponding to the scope of each of these phrases. Thus, a composition or method comprising recited elements or steps contemplates particular embodiments in which the composition or method consists essentially of or consists of those elements or steps.

All references cited herein, including patents, patent applications, and publications, are hereby incorporated by reference in their entireties, whether previously specifically incorporated or not.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the invention following, in general, the principles of the invention and including such departures from the present disclosure as come within known or customary practice within the art to which the invention pertains and as may be applied to the essential features hereinbefore set forth.

Although the invention has been described with reference to the above examples, it will be understood that modifications and variations are encompassed within the spirit and scope of the invention. Accordingly, the invention is limited only by the following claims.

REFERENCES

Anastasio, K L, J A Soucheck, and H Sugiyama, 1971. Boticinogeny and Actions of the Bacteriocin. J. of Bacteriology 107: 143-149.

Bartlett J G, Onderdonk A B, Cisneros R L, Kasper D L. 1977. Clindamycin-associated colitis due to a toxin-producing species of *Clostridium* in hamsters. J Infect Dis. 136:701-705.

Bartlett J G, Chang T, Taylor N S, Onderdonk A B. 1979. Colitis induced by *Clostridium difficile*. Rev Infect Dis 1:370-8.

Bartlett J G. 2002. Antibiotic-associated Diarrhea. N Engl J Med 346: 334-9.

Bartlett J G, 2007. *Clostridium difficile*: Old and New Observations. J Clin Gastroenterol. 41 Suppl 1:S24-9.

Benson L, Song X, Campos J, Singh N. Changing epidemiology of *Clostridium difficile*-associated disease in children. Infect Control Hosp Epidemiol. 2007; 28:1233-5.

Blackwell, C. C. and J. A. Law. 1981. Typing of non-serogroupable *Neisseria meningitidis* by means of sensitivity to R-type pyocins of *Pseudomonas aeruginosa*;

Blackwell, C. C., F. P. Winstanley, and W. A. Telfer-Brunton. 1982. Sensitivity of thermophilic campylobacters to R-type pyocines of *Pseudomonas aeruginosa*. J. Med. Microbiol. 15:247-251.

Bradley. Bacteriocins. Bacteriol. Rev. 31:230-314, 1967.

Bol D K, Yasbin R E. Characterization of an inducible oxidative stress system in *Bacillus subtilis*. J. Bacteriol. 1990 June; 172(6):3503-6.

Campagnari, A. A., R. Karalus, M. Apicella, W. Melaugh, A. J. Lesse, and B. W. Gibson. 1994. Use of pyocin to select a *Haemophilus ducreyi* variant defective in lipooligosaccharide biosynthesis. Infect. Immun. 62:2379-2386.

Coetzee, H. L., H. C. De Klerk, J. N. Coetzee, and J. A. Smit. 1968. Bacteriophage—tail-like particles associated with intra-species killing of *Proteus vulgaris*. J. Gen. Virol. 2:29-36.

Daw, M A, and F R Falkiner, 1996. Bacteriocins: nature, function and structure Review Article. Micron 27:467-479.

DeMarini D M, Lawrence B K. Prophage induction by DNA topoisomerase II poisons and reactive-oxygen species: role of DNA breaks. Mutat Res. 1992 May; 267(1):1-17.

Ellison, J S and J A Kautter, 1970. Purification and Some Properties of Two Boticins. J. of Bacteriology, 104: 19-26.

Filiatrault, M. J., R. S. Munson, Jr., and A. A. Campagnari. 2001. Genetic analysis of a pyocin-resistant lipooligosaccharide (LOS) mutant of *Haemophilus ducreyi*: restoration of full-length LOS restores pyocin sensitivity. J. inhibition Bacteriol. 183:5756-5761.

Fortier, L C and S Moineau, 2007. Morphological and genetic diversity of temperate phages in *Clostridium difficile*. Appl Environ Microbiol. 73:7358-7366.

Goh, S, P F Ong, K P Song, T V Riley and B J Chang, 2007. The complete genome sequence of *Clostridium difficile* phage phiC2 and comparisons to phiCD119 and inducible prophages of CD630. *Microbiology*, 153: 676-685.

Gebhart D, Williams S R, Bishop-Lilly K A, Govoni G R, Willner K M, Butani A, Sozhamannan S, Martin D, Fortier L C, Scholl D. Novel high-molecular-weight, R-type bacteriocins of *Clostridium difficile*. J. Bacteriol. 2012 November; 194(22):6240-7.

Gibson D G, Young L, Chuang R Y, Venter J C, Hutchison C A 3rd, Smith H O. Enzymatic assembly of DNA molecules up to several hundred kilobases. Nat. Methods. 2009 May; 6(5):343-5.

Govind, R, J A Fralick, and R D Rolfe, 2006. Genomic organization and molecular characterization of *Clostridium difficile* bacteriophage phiCD119. *J. Bacteriol*. 188:2568-2577.

Imlay J A, Linn S. Mutagenesis and stress responses induced in *Escherichia coli* by hydrogen peroxide. J. Bacteriol. 1987 July; 169(7):2967-76.

Jabrane, A., A. Sabri, P. Compere, P. Jacques, I. Vandenberghe, J. Van Beeumen, and P. Thenart. 2002. Characterization of serracin P, a phagetail-like bacteriocin, and its activity against *Erwinia amylovora*, the fire blight pathogen. Appl. Environ. Microbiol. 68:5704-5710.

Kageyama et al. Life Sciences 9:471-476, 1962.

Kageyama, M., K. Ikeda, and F. Egami. 1964. Studies of a pyocin. III. Biological properties of the pyocin. J. Biochem. 55:59-64.

Kageyama, M., K. Ikeda, and F. Egami. 1964a. Studies of a pyocin. I. Physical and chemical properties. J. Biochem. 55:49-53.

Kageyama, M. 1975. Bacteriocins and bacteriophages in *Pseudomonas aeruginosa*, p. 291-305. In T. Mitsuhashi and H. Hashimoto (ed.), Microbial drug resistance. University of Tokyo Press, Tokyo, Japan.

Keel, K, J S Brazier, K W Post, S Weese and J G Songer, 2007. Prevalence of PCR Ribotypes Among *Clostridium Difficile* Isolates from Pigs, Calves, and Other Species J. Clinical Microbiology, 45: 1963-1964.

Kingsbury, D, 1966. Bacteriocin production by strains of *Neisseria meningitidis*." J. Bacteriol. 91:1696-9.

Krogh, S, M O'Reilly, N Nolan and K M Devine, 1996. The phage-like element PBSX and part of the skin element, which are resident at different locations on the *Bacillus subtilis* chromosome, are highly homologous. Microbiology 142: 2031-2040

Liu S, Endo K, Ara K, Ozaki K, Ogasawara N. 2008. Introduction of marker-free deletions in *Bacillus subtilis* using the AraR repressor and the ara promoter. Microbiology. 154: 2562-70.

Loo V G, Poirier L, Miller M A, Oughton M, Libman M D, Michaud S, et al. A predominantly clonal multi-institutional outbreak of *Clostridium difficile*-associated diarrhea with high morbidity and mortality. N Engl J. Med. 2005; 353:2442-9.

McDonald L C, Killgore G E, Thompson A, Owens R C Jr. Kazakova S V, Samobl S P, et al. An epidemic, toxin gene-variant strain of *Clostridium difficile*. N Engl J. Med. 2005; 353:2433-41.

Morse, S. A., B. V. Jones, and P. G. Lysko. 1980. Pyocin of *Neisseria gonorrhoeae*: mechanism of action. Antimicrob. Agents Chemother. 18:416-423.

Muto C A Pokrywa M, Shutt K, Mendelsohn M B, Nouri K, Posey K, et al. A large outbreak of *Clostridium difficile*-associated disease with an unexpected proportion of deaths and colectomies at a teaching hospital following increased fluoroquinolone use. Infect Control Hosp Epidemiol. 2005; 26:273-80.

Nieves, B M, F Gil and F J Castillo, 1981. Growth inhibition activity and bacteriophage and bacteriocin like particles associated with different species of *Clostridium*. Can. J. Microbiol. 27: 216-225.

Pépin J, Valiquette L, Alary M E, Villemure P, Pelletier A, Forget K, et al. *Clostridium difficile*-associated diarrhea in a region of Quebec from 1991 to 2003: a changing pattern of disease severity. CMAJ. 2004; 171:466-72.

Ritchie J M, Greenwich J L, Davis B M, Bronson R T, Gebhart D, Williams S R, Martin D, Scholl D, Waldor M K. An *Escherichia coli* O157-specific engineered pyocin prevents and ameliorates infection by *E. coli* O157:H7 in an animal model of diarrheal disease. Antimicrob Agents Chemother. 2011 December; 55(12):5469-74.

Scholl, D, and D W Martin, Jr., 2008. Antibacterial efficacy of R-type pyocins towards *Pseudomonas aeruginosa* in a murine peritonitis model. Antimicrob. Agents Chemother. 52:1647-1652.

Scholl, D, M Cooley, S R Williams, D Gebhart, D Martin, A Bates, and R Mandrell, 2009. An Engineered R-Type Pyocin Is a Highly Specific and Sensitive Bactericidal Agent for the Food-Borne Pathogen *Escherichia coli* O157:H7. Antimicrob. Agents Chemother. 53: 3074-3080.

Strauch, E., H. Kaspar, C. Schaudinn, P. Dersch, K. Madela, C. Gewinner, S. Hertwig, J. Wecke, and B. Appel. 2001. Characterization of enterocoliticin, a phage tail-like bacteriocin, and its effect on pathogenic *Yersinia enterocolitica* strains. Appl. Environ. Microbiol. 67:5634-5642.

Sunenshine, R H & L C McDonald, 2006. *Clostridium difficile*-associated disease: New challenges from an established pathogen, Cleveland Clinic J. of Medicine, 73: 187.

Williams, S., D. Gebhart, D. W. Martin, and D. Scholl. 2008. Re-targeting R-type pyocins to generate novel bactericidal protein complexes. Appl. Environ. Microbiol. 74:3868-3876.

Wood, H E, M T Dawson, K M Devine, D J McConell, 1990. Characterization of PBSX, a Defective Prophage of *Bacillus subtilis*. J Bacteriology 172: 2667-2674.

Zilberberg, M D, Tillotson, G S and McDonald, L C., 2010 *Clostridium difficile* Infections Among Hospitalized Children, United States, 1997-2006. Emerging Infect Dis 16: 604-609.

Zink, R., M. J. Loessner, and S. Schere. 1995. Characterization of cryptic prophages (monocins) in *Listeria* and sequence analysis of a holin/endolysin gene. Microbiology 141:2577-2584.

What is claimed is:

1. A nucleic acid molecule encoding an R-type hmw bacteriocin, wherein the nucleic acid molecule is from a genome of a first strain of *Clostridium difficile* and comprises a polynucleotide sequence that encodes polypeptides that are at least 80% identical to SEQ ID NOs: 66-77, wherein the nucleic acid molecule further comprises a heterologous sequence encoding a receptor binding domain (RDB) of a prophage, or an RBD of a prophage remnant from the genome of a second strain of *C. difficile*, or an RBD of a bacteriophage, wherein the R-type hmw bacteriocin comprises a base plate attachment region (BPAR) comprised of a portion of the amino terminus of a first BPAR polypeptide that is at least 80% identical to the amino terminus of SEQ ID NO:78, and comprising a second polynucleotide encoding a portion of the carboxy terminus of a BPAR that is cognate to the RBD, and wherein the R-type hmw bacteriocin has bactericidal activity against a strain of *C. difficile*.

2. The nucleic acid molecule of claim 1, wherein the RBD is at least 80% identical to an RBD selected from the group consisting of SEQ ID NOs: 92, 94, 96, 98, 100, 102, 104, 106, 108, 110, 112, and 116.

3. The nucleic acid molecule of claim 1, wherein the second polynucleotide encoding a portion of the cognate BPAR of the RBD is joined to the nucleic acid molecule so that the encoded carboxy-terminal portion of the cognate BPAR of the RBD is fused to the amino-terminal portion of the first BPAR.

4. The nucleic acid molecule of claim 1, wherein the second polynucleotide encoding a carboxy-terminal portion of the cognate BPAR of the RBD comprises a sequence encoding a BPAR at least 80% identical to a sequence selected from the group consisting of SEQ ID NOs: 88, 91, 93, 95, 97, 99, 101, 103, 105, 107, 109, 111, and 115.

5. The nucleic acid molecule of claim 1, further comprising a third polynucleotide encoding a cognate chaperone of the RBD.

6. The nucleic acid molecule of claim 5, wherein the cognate chaperone is selected from the group consisting of SEQ ID NOs: 89, 90, 113, 114, and 117.

7. An expression cassette comprising a nucleic acid molecule of claim 1.

8. The expression cassette of claim 7, wherein the expression of the R-type high molecular weight (hmw) bacteriocin is inducible or repressible.

9. The expression cassette of claim 8, wherein the expression is induced by a small molecule inducer or de-repressor.

10. The expression cassette of claim 9 wherein the small molecule inducer or de-repressor is a reactive oxygen species (ROS) or a generator of an ROS.

11. The expression cassette of claim 10 wherein the ROS is a peroxide that is non-toxic to humans or other animals.

12. The expression cassette of claim 11, wherein the peroxide is hydrogen peroxide.

13. An R-type hmw bacteriocin encoded by claim 1.

14. The R-type hmw bacteriocin of claim 13, wherein the bacteriocin can be administered orally to animals and be excreted in feces in a form still exhibiting bactericidal activity.

15. The R-type hmw bacteriocin of claim 13, wherein the bacteriocin retains some bactericidal activity after incubation at a pH between 2.5 and 10 for 30 minutes at 25° C.

16. The R-type hmw bacteriocin of claim 13, wherein the bacteriocin retains some bactericidal activity after incubation for 30 minutes at 45° C.

17. A method of producing an R-type hmw bacteriocin, comprising exposing a producer cell comprising a nucleic acid molecule according to claim 1, operably linked to an inducible promoter, to an inducing agent in a concentration effective to induce expression of the R-type hmw bacteriocin, thereby producing the R-type hmw bacteriocin.

18. The method of claim 17, wherein the nucleic acid molecule encoding the R-type hmw bacteriocin is heterologous to the genome of the producer cell, and wherein the nucleic acid molecule is contained within the producer cell's chromosome or is contained in an extrachromosomal expression vector within the producer cell.

19. The method of claim 17, wherein the producer cell is a non-pathogenic and not an obligate anaerobic bacterium.

20. The method of claim 19, wherein the non-pathogenic and not obligate anaerobic bacterium is a species from a genus of bacteria selected from the group consisting of *Bacillus, Lactobacillus, Lactococcus*, and *Listeria*.

21. The method of claim 20, wherein the species is *Bacillus subtilis*.

22. The method of claim 21, wherein the *B. subtilis* does not lyse when induced to produce the R-type hmw bacteriocin.

23. A method of killing a *Clostridium difficile*, comprising contacting the pathogenic *C. difficile* with an effective amount of the R-type hmw bacteriocin of claim 13, whereby the R-type hmw bacteriocin binds and kills the pathogenic *C. difficile*.

24. The method of claim 23, wherein the *Clostridium difficile* is in an animal and a bactericidal amount of the R-type hmw bacteriocin is administered to the animal.

25. The method of claim 24, wherein the animal is a mammal.

26. The method of claim 25, wherein the mammal is a human.

27. A method of treating an infection of *Clostridium difficile* in an animal comprising, administering to an animal in need thereof an amount of the producer cell comprising a nucleic acid molecule according to claim 1, to produce a bactericidal amount of the bacteriocin, thereby treating the infection.

28. A composition comprising the R-type hmw bacteriocin of claim 13 and a pharmaceutically acceptable carrier.

29. The nucleic acid molecule of claim 1, wherein the RBD is from a bacteriophage that infects a second strain of *C. difficile*.

* * * * *

SEQUENCE LISTING

```
<160> NUMBER OF SEQ ID NOS: 163

<210> SEQ ID NO 1
<211> LENGTH: 22825
<212> TYPE: DNA
<213> ORGANISM: Clostridium difficile

<400> SEQUENCE: 1
ggccgcaata cccactacac cttcgtcatc tttaaattta agagttttta ctattgaata      60
ataaaggtat attccagtaa aaataatctt taaatacaag aaaaataaac tctttgggta     120
tattaaaaag ctaaaaagtg taaatataaa agcaagtaga gtacttatcc tgtaaaagaa     180
atctatttgt gtaatgtctt tatattttat cataaacacc gaatataaaa tgatgaaaat     240
aattgcgacg attgcatata tggtaaataa catattttca agagtaccat ttgaaattac     300
tatccactta taccacataa ttggccaaaa taatagtgct aagaacttaa aataattatc     360
aaacaacttt tctttataca ttcatcaaac aacctttctt aacaaaagca tatatttgtt     420
tttagaattt taaataatat gatatcatta ttatatatta atattgaatt tatagaaacc     480
aaaatttgtt aaaataaata tatagatttt actgttaagc cagttaaaat tactactatt     540
tttattatga aattggatca aatatgtaga aatacggcaa attagttaat attaaatatt     600
tattatttcc aagttgtaaa gactgttttt ttaatgataa aaattctaat ctttttttgaa    660 agaaagtaat atccacatta agtatgtctg ccatttcata aacgcaagtg atgccagaat     720
taattatgtt tattatatct tcttcagtaa ttaagaactc acaagcccat tttaaggctt     780
tattttcgca cttatctata ataattttg tataataatc gttataagag gatacatagt      840
atccaaggct agtgaaatga tgtccaagtt cttcagctaa gatggatgtc aattttttttg    900 agttttgttt taaattactg agtaatgata taattttaat accatgtttg tttatatata     960
gcccttctaa atcacctgca atataagtgg tataatgaat tattatctct tcttgagaag    1020
ctaattcaaa aagcttatcc aaattattca taaaaatccc cctaaaatag aatgtatgtt    1080
tgcctttaaa ttatattaaa agagcagaaa aatagactgc tcatcatatg gtttattttt    1140
ttttatattt atttagtaaa aattctatat aatcattaag ttgttcttgt gcttcttcag    1200
gtaactcttc atgtggattt tttctatgtg cagctactgt atcaatattt tccttaacta    1260
aggttcttcc aagaaggtaa tcaactgata cattaaatac atcagccaat ttgtttaaaa    1320
tgtgttcatc aggaaatctg tttttctgttt catagtaccc taagactctt tgggaaacgc    1380
ctactttttc tccaagttct ctttgagtca atccaaattc ctttctaagt tctcttaatc    1440
```

```
ttttggcaaa cattataaca ccaccttatg tatagattat aacaaattgt tctaaaaaat    1500
aaaactaata aaatataaaa gaatattttt tctaaaatct attgataaag aacaaatgat    1560
tctatataat ctaagtgtgg aagaacaaaa tattcttaat ggtaatggag gtataaaaca    1620
atgtttaaaa ataacttgaa atattataga aaatgcaaag gtatgacaca aattcaactt    1680
gccagaaagg ctggaattac aaatgactat atatctcaaa tagaaagagg tataaaaaat    1740
cctggtcttc ttatggctaa gaagatttct agtattttag aacaaaatat agaagaagtt    1800 tttttatac agttatagaa caatatgttc ttgaaagttg tgagattagt aaaaaactgt    1860
gcactaaaga gattattgta aatttgaagc taataataag tatataaaaa aggagaagta    1920
ctatggaaaa caaaaaagat atattattta agaaacaga tgaaagatta cataattata    1980
agtatttgga tataaagata agaatatta atttggacat aaaagatgt gagaatgaat    2040 actctggatg tggagcaatg gtatatacag aaaagactag taacacatat aacataagtt    2100
cttctgtgga aaatgaggtg ttaaaaagag aggaaagatt aagaaaatta aaaatggaaa    2160
aagaagatat agaaatagaa aaagagaaga tagaaaatgc tctaacatgt ctaaatgata    2220
tagaaatgga attttttaat ctttttttata atagtaagac aaaaaacaat atgacatata    2280
tttctatgaa actacactta gatagaacat cttgctacaa tttaaagaaa aaaatgatat    2340
ttaaattgag tgagatatta taaaaaatat gacaacttta caacacttta tatacactat    2400
tgcaacacta ggcaataaaa tatgtgagat aatgttattg tgaaagaaat ccatattgaa    2460
ggaggtgata aattgaaaag aataatatta cctaaaaata tagaagatat ttgacaggaa    2520
taaatgagat gtatatttaa aaatgactta tatcatttat agtaagatta tcagattaag    2580
caagaatatt tagtgatagt gtggtgatta tttgcttaaa tacaaggaaa tattagaaac    2640
aattattgag attctcaaaa aaaactttac tgaaagtatt tttattgatg atgaaagtgt    2700
gcaaggctct gaagggtctt gttttttgt aagtatacta tcagttattt gtacacctat    2760
aatgttaaat acgaataata aagatattgt tatctctata aaatacttac caaaaccaca    2820
gtcaaagagt attagaatgt atgaaatttc agatgaatta aataagttat tcaacagaaa    2880
tataaaggta acagacagaa aattaaatat aacaaagcta gaacaaagta ttaaaaaaga    2940
agagtcaatt tatgtattga actttacaat tacactaaat tatctggata gtgtatatga    3000
agaagatgta gtatatgaaa atatggaaga aatcaattta aatttaggag agtgatagta    3060
tggctatagg attaccaagt atcaacatat catttaagga gctagctaca actgttaaag    3120
aacgttcagc tagaggaata attgcaatgg tgcttaaaga tgctaaggca ctaggtctta    3180
atgaaataca tgaaaaagag gatataccag ttgatttatc tgctgaaaat aaagagtata    3240
taaatttagc tttgatggga aatgttaaca ctccaaataa attattagtt tatgtaatag    3300
aaggagaagc agatattcaa actgcattag attttttaga gactaaggaa tttaattatc    3360
tatgtatgcc aaaagcagta gaagctgata agactgctat aaaaaattgg ataattaaac    3420
ttagagatat agataaggtt aaggttaaag ctgtattagg aaaagttgta ggaaatcatg    3480
aagggataat taattttact acagaagatg tgttagttgg agaaaagaaa tacagtgttg    3540
atgagtttac aagtagggtg gctggactta tagcaggaac acctttaagt caatcagtaa    3600
cttatactaa gcttagtgat gtagttgata tacctaagat gacgaaagtt gatgcagaat    3660
caagggttaa taaggagag cttatactta ttaaggaagc aggggctata agaattgcaa    3720
gaggagtaaa ttctttaact gagttaacag aagaaaagg agaaatgttc cagaaaataa    3780
aaatagttga cactttagat attatacata gtgacataag aaaggtgata atagatgact    3840
```

```
atataggaaa ggttactaac agttatgaca acaaatgttt attgatagta gctataaaaa    3900
gttatttaga agaattagaa aagtcagcac ttatagaatc tgattctact gttgaaatag    3960
attttgaagc acaaaaatcg tatttaaaat caaaggagt agatttatct tatatgacat     4020
tacaagaaat aaaagaagct aacacaggtt ctaaagtatt tttaaaagca aaaataaaag    4080
tacttgatgc tatggaagat atagatttat caatagaaat ataggaggat tattaatatg    4140
gcaaatatgg aagctagaaa tgtaatgagt ggtacttggg agaactttg gcttgatgga    4200 aacaaagtag cagaagtaaa gaagtttcaa gcaagatgg aatttacaaa agaggatatt    4260
ataatagcag gtcaaatggg tactgataca agtatatgg gatataaagg aaaaggttca    4320
ataactctat accatgttag ttcaagaatg cacaagttaa ttggagaaaa gataaagaga    4380
ggttctgaac ctagatttgt tgctatatct aaattaaatg acccagattc ttatggagca    4440
gaaagaatag cagtaaaaaa tatagcattt gatgatttaa ctttagctga ttgggaggtt    4500
ggagtaaaag gagagataga agcacctttc acatttactg agtatgattt tcttgatata    4560 atttagttttt atatttggtt ttatactgat atttagtaga tatatactta ataaatttag    4620
gtagttaata agtaaaaaag ttagttgatt gaatttgatt gataaaggag caaataataa    4680
tgaatgaaaa tggattatca aaaaatataa acatagtaga tttacttttta aatgcagata    4740 cagaaaactt agaagacca agtactatag ttgaacttaa gagattatca actatatttg    4800
ggcaggaatt taaagtaatg tgtagagctt taacaataag taaagatgaa gagatacaaa    4860
atacttgtct taaaattgat gaaaatatga aaacggatat agacttaccg gagatgcaga    4920
tgcttacaat tatagaaggt gtttgtgatt tggatggaaa gcttttattt aaaaataagg    4980
aactaatgga taaattaag gctccaacac caaagaatt ggcaagaaaa ctattattac     5040
caggtgaaat taccaaccta tatagaatac ttcaagatgt tatgggttat ggtaaaaatg    5100
cagtgataga agaggtaaaa aactaatagg gacggatacc aagactacaa taatgtacta    5160
ttattggaag aaaaaaggta taagaccgtc cctttttat gcaatggata aaggcgaatt     5220
aaagcttatt gaagcttttt tcgccttaga aattgaggaa gaagttgaaa aatgaaaca     5280 tggatatgga gtgtgtcctt tgacaggagg tggtatgtaa tgggaaatgt gagagaagaa    5340
ggtataaata tgtatcttac agataattac acaccaaaaa tgaaccaaat tatatcagta    5400
actgataatt ttaggagagc aactgtggct gtttcacttt ccactaatgt aatggctagt    5460
agcataaaaa attctattgg aagtgcaagt agtagagtaa acagtttaaa ttcctcgtta    5520
agaaaagttc aaactactgc tagtagtgta agttcaacta tggcaaaatt aagttctagc    5580
ataaatgctg tttcaggagt tattggaagt ttaaatggaa gtattatgag actagcaata    5640
actatagcta tgattattga ttatttaat aagttgattc aaaagaaaaa tgagtttaat    5700
tcaaatatta tgattatatt aatatttaaa gctaaaagtg atgaagtaga aaaaactaaa    5760
aataaattac ttgaaatttt aaaaagatt ggtggcaaga tttggaatat cgtaataaaa    5820
gcaaaagata tgactaagag agtgataagt agtatcttgg gaaaattaaa acgagtagag    5880
aaacgtcctt atcaaggaag tattaatctt aaagatatgg taagtagtgc tatggctaga    5940
attttgccta agttaatgtt gttttaaaaat acttttttgga gtggtgtaat agctataaaa    6000
gatatggcaa gtagcattat aagtaaagta tttcccaaat tgagattgtt tgcaggtaag    6060
gtatggagtg gtgcaatagc tgtaaaggat atggcaagtg gaatacttgg ttcgataaaa    6120
gggaagatat ctgatttgac aaatggtgct actataggtg tcgctgtgaa aaagggtgtt    6180
```

```
gacttacttg gtcaggaaca aaatcagaaa gttgttctag aaagtgtaat gaaaagaaat    6240
actggaaaaa ctagccaaaa agatgttgat aagtattatg acagtttagt aaatatggca    6300
aatgatacgc cttttgaccc tgaagatgtt gttgcaatgg gaactaaagc taaaatgatt    6360
agtaatatta ctggtggcaa aaaagaaaaa gatataactc aagctatggt agatgttaga    6420
gctttaaata tgaatacaag tagtgaacaa gatgtatcag cagctttctt aagtgcagca    6480
aaaggaaata tggaatctct taatactctg gtaggagaaa attataaaac ttttgatgaa    6540
gcattggaag cataagtgt aaagcagatg gggttagcta agaaatgag taatacaata     6600 ccaggtataa tatcaggagc tcaaacaagc attaacaatg gtttgaagag tattgttaaa    6660
ccttttgatg atattttagg tcaaggacta agaaaaataa aaacttttat agaaagtgga    6720
ttagggaatt tagctggctt atctgaaaaa atggctggta aaataggcaa tgtaatgaat    6780
ggtaagataa ttattggcaa caaatatgac cagatgcaat ctagaagtgt aaaaaatgga    6840
aaagagtttt ctgattctac tcaatatcga atttctaatg aggctgaaaa gcgtaaaatg    6900
atggttgaaa ataagcaaga acgttttgaa aatcatgcag caacaatgat agggaatgca    6960
ccaaaagcaa ttgttaacgc aggaagtaca ctattacaaa atattgattt tacagcatta    7020
atagattcac tacttccagt agtaaactta gtaaataatt tactagatag tataaacaat    7080
aaatcaccaa ttgcacaagg attaataagt atatttggta caatagtaac tacagcattc    7140
caactaatcg gacctgtagt tgaagctgtt agtcctatta tcacaagaat ttttactttt    7200
ttaggtgaat atgcacctca aataaacaat tttatagaga cactgggtgt tatttggaaa    7260
actgtatggg agaccttagg acctctgttg gaaactggat ggaaaattat agagccaata    7320
ttgggagctt tttttaacat attagataaa gtatgtaaaa tagttaaaga tatatgcaaa    7380
tggtggcaaa ctatgattaa taagataaaa aatggaagca tcacaggaac agttttaaat    7440
ctagtggaaa agagtaaaaa aaattacaaa gataatccat atgctggaac aaaggctggt    7500
gattctggta aagcttattc aagtaagaaa ggtaataatg catttggatt gaactatgtt    7560
ccttataatg actatcaaac cagactccat gaaggtgaaa tggttttaac taaacaagaa    7620
gcaaatcaat atagaagcag aaaaaatggt ggaaatataa acatagctaa gttagctgat    7680
acaatagtga ttagagaaga agctgatata gaaaagataa catcaaaatt agttgcaagt    7740
atccaattgg cacagttagg gggtgtctta taatggaaat gtggcttaga caagcagaag    7800
atagatttag atttccagta tttccatctt cctttagtat taatggaaaa gctgctgtaa    7860
actcttctag tatactcaaa ataggtgaag tagcaacttt tggtggtgta gctcttaaaa    7920
gcatttcaat atcaagtttt tttccaaata aagactacac tttctgtgac tatacaggtt    7980
ttccatcacc atatgattgt gtaaataaga tagaaaaatg gatgaaggaa ggttttatat    8040
taagatttac aattacggaa acaaatataa atatggaagt cataattgaa gggtttagtt    8100
atgaagaaag agatgggact cgagatgtat attttacatt agatttaaaa gagtataaaa    8160
gaataaagat accaaaagta actccaaaac aataactatt atagataata agttgtaagt    8220
aactgctgat agaattaaat gaaaaggcag gtgattttt attattaaga tttgggtaca    8280
cataaaaaac ggaagtatat atgacataac tgacatagta gacaaggtat catggtcagg    8340
tgattataaa tctccatcaa ggacactaga gttttcaata atacaatcat catttgatgt    8400
aaatttccaa caaatcgata taccaatagc tagtacagtc tgtttctatg tagatgagaa    8460
agaactcttt agaggaatga taattaatag gtctaaagat tcaagcagta atgaaattag    8520
ttttgtatct aaagatatgg gatttttact tacacaaagt gaagtgtcat acaattttaa    8580
```

```
agataagtta gttgaagaca tagcaaagca agtatttgct gaaaataggc tttcagttgg   8640
aacaatagca aagaccaatg tcaagtatac aaagatgttt ataggagtaa atggttatga   8700
cacaataatg agtgcatata cagaggcaag taaaaagaca agaaaaagt atatgataga    8760 ggctaatttta gataagttta atgttattga aaaaggaact gttacattaa gtgttatgtt   8820
tgaagaggga tttaatatta taaataccac cttttcggag agcatggaaa atgtaaaaaa   8880
taaagtaata gtggtagacc agtatggaag caagattagc gaaaaaatag ataatgaaat   8940
ttttaaggaa gtaaatgtaa taatgcaaaa agtaattcag caacaagaaa atcaagatgt   9000
agatattgat agcgagttta atgggataga aaaaagctgt tctcttaaag gttatggaga   9060
tgtaagttgt ataactggta gaggagtaaa agttaaagat tcttatacaa agcttgtagg   9120
actattttat atagatacag acaaacatac ttggcaaaat ggagaatatc aaattgagct   9180
tgaacttaat tttcaaaatc ttatggatga aaagtcagca ggacaggatg aacctaagga   9240
agaaagtaat ttaggggggag aagattatgc aggaggaaaa gagtttacag cagaatttac   9300
agcttactgt cctagaaaag aagaaggtgg agatacagat tgtagaaaga aaaaacttga   9360
cccatctaaa aaacttgcgc tgctcctatg gttggtaaat atgagcaaac ttattataca   9420
aaagagtttt taaataaaca tcctttattg aactatggag atgaaataca ggtaattaca   9480
ggagtttctg gtcgtgatgg agtctataaa gtaaatgacg taggacctgc aataactata   9540
gaaaaaaatg gaacatacca tatagatatt ttatttggaa atgttgaaga agctagtaaa   9600
tttggaagaa gaaaaggaaa aattattatt ggtggttatt ctggtaatgt atctgataaa   9660
gctaaaatag taatatcaga ggcaaaaaaa catctaggta aaccttataa atggggtgga   9720
aatggaccaa gtagttttga ctgttctggt ttaatggtct actgttttaa aaaagttaat   9780
gttagtttgc caagaacgtc aaatcaacaa tctaaaaaag gcaagaaagt agaacaaaaa   9840
aatcttcaag caggagattt agtatttttt cataatccag tcagccatgt tggattatat   9900
ataggtaatg gagaattttt acatgctcca caaaaaggtg atgtagttaa aataagtaag   9960
ttaagtagta gaaagagattt taatacagct aggagagtat tataaaagga tggtgatata  10020
atggctaatc aataaatga atttatagga ataataagag aagaaggaaa gtatcataat  10080
caaccttctt ttttattgga aaattaaaag taaattacca gatttaaaaa tagagacaaa  10140
taacatcata ttagaaaaag aagatatttt gatagatagt tggatgattg atagacagct  10200
agaaacattt gacacagaaa caaatcaaga acaccagcat gaagtaaaaa atccttttat  10260
agataacttt gaatctgggg atatggtaat aatgtttaga ataggcgaaa aatttgctgt  10320
tgtaagtaag ttggtgagct tataatgagt acaatatttc cttttatagg tgtcccagag  10380
gattatatct tacctaaaac agaagaattg ccaatctttc gtgaagtggc atgggatttt  10440
gaaaaagatg aacctatttt agaaaaaggt gactttaaaa taattgaaaa aaaaagaagc  10500
cttaaaagtt tggatataca agtgtataaa gacaaataga tatgaacatg agatatactc  10560
tttagaatat gggacagagc tttcagaact aataggacaa aaatatacaa aaggtcttac  10620
agaaagtgaa gctagtagat tcataaaaga ggcccttcta ataaatccat atatattaga  10680
agtaaacgta aaaagtgcta actttaacag agacgtattg agtgcaaatg taaaagtatc  10740
cactatctat ggggaggtgg aaataaatgt atagtgacca gacatatgaa gtaataaaaa  10800
atagaactct tgaaaatatt aatcttgata tttataaagg agaaggttct tttctaaaca  10860
acatggtatc tggaaataat ctagaacttt cgaagatata tctagaactt tcaaagatac  10920
```

```
ataaaatggc ttttatacaa gacacatata accagtttct tgataaaaga gtcaatgaat   10980
ttggtgtata tagaaagtta ggtacagagt caaatggaga agttgaattt attggagaga   11040
aaggaactgt aataaataat ggcacaataa tatcatatag agatttacta tttgtagtaa   11100
taaaagatgt aactattggt agtgaagaag gtgacaatag cccagttcaa gctctggaag   11160
ttggtaagaa atataattta cctacaaatt gtgaatttaa actagttgat aatatatctg   11220
gagtaacaaa gattactaac acaagaagtt ttgaaggtgg tacagatata gagacagatg   11280
aagaactaaa agaaagattt tataaaatcc aaagaaatca agctacaagt ggaaataaag   11340
ctcactatga agaatgggct ttggaagtag atggagtcta taatgttaag gtttatccaa   11400
gatgggatgg tccaggaaca gttaaggtct tgatatttgg ggaaaataat caagctgttg   11460
atacagaaac gattgaaagg tgtcagcaac atatagatga agagaagcct attggaccaa   11520
ctataacagt tgtgacacca ttaccaatag aaataagtat aagtgcagta atgaaactag   11580
aagatggata tacattagac aatgtaaaag aatctttcct agaaagtata aatacatact   11640
ttagagatat tagaggagag ataatctata caaaagtcat gggaatactt ataaatacta   11700
ctggtgtaca cgatttaagt aatctactta taaatggaag tacagataat ataactatta   11760
atgaagataa aatacctagt gtaacaactg ttaattttag tgaggtggaa aatcaatgaa   11820
gctaattgat aaactaccat catttgatag aaattacatt gtagaggaga tacaaggtgc   11880
atacgataca gaattaaata ttcttaaaga agatattgat gataccttta accaattatt   11940
tgttgataca gcgacatggg gattagatat gtgggaagac atactctgca ttgaaaaaaa   12000
agaacttgat tttgacacaa gacgtagcaa tataaaagct aaaatgagaa gcagaggtac   12060
tagtactatt gaagttataa aaagtatatg tgaggcatat acaaaatcag aaacagatat   12120
aaaagtttat agtgatgaat ttacattcgt attgagtttt atagcaaata actgtgacta   12180
taaaactctt ttagattgta gcgagatgat tgaaagagta aaacctgctc acttattaca   12240
ctatttagaa ccaataatac tagataaaag tatggtctat tgtggtggag gtatggtatg   12300
tagtgaagag gtaaaagttc atccatactt tgaaccaatt ataaaatgta gtgctgttgt   12360
aaactgtgga gctggaatgt taagtagaga agaaataaag gtttatcctt taagcattaa   12420
atgcattgaa aataattgta agattaatat agctattgca aatgatacag gcgtagaaaa   12480
tgtagtagtt tatcctaaat cggaggtggt ataattggaa gaaaaatttt atataatatt   12540
aaccaaaatt ggtagagaaa aaatagcaaa tgcaactgca ctaggagagc ttgttggatt   12600
aaccaagttt caagttggag atagtaatgg agaatattat gagccaacag aggaacaaac   12660
tgctttaaag aatgtagttt gggaaggaaa tataaattct ctaagaattg atgaaaaaaa   12720
tcctaattgg atagttatag agactatttt accaggaaca gttggtggat ttatgataag   12780
agaagctgct gttctggata tgagaataaa tataatagct atwggtaagt atccagagac   12840
gtataagcca cgtgctgaag atggcagtat taaagatttg gttgtaaaaa tgattttaca   12900
attgtccaat acttcaaatg ttacattaga agtagacccg acgttggttt ttgtaactca   12960
aaaggatatt caagatttag atgataagtt tgataaaaat ataaagaaa taaaagtaaa   13020 aattggagat acagatatat taactacaga ttctaaagat ttatcaggag ctataaatga   13080
ggtagttaaa aaaatagaaa atatatcttt tgatgatgtt ataagtggtc aaatacaaac   13140
tgatatatca gtattaaaaa atagctataa caaattatct gaaaaagtgc tagatatatt   13200
aatataccta gaattagagt cagaagtaac tgtgatgag gctggttatt ggtatgatac   13260
attagcaaat ggaaataaca tagtagctat agaagggctt aagttagatt taaatagaaa   13320
```

```
atgtataaca ggtgaaattg gtaatgtgat ttttagagat gtagtattac catttagtgc  13380
aaatagagtt agatatatac atgatatgga taataacttt gttgagacaa aatctagtaa  13440
cacttattta aaagaacaaa aagatataac tctaagtaaa tattcatatg aaataagata  13500
aataaaggag gtagtactaa taatgaagca aaataaactt ttacagcgtg gtgcttattt  13560
taatgataag aacatattga ttgatgattt tgataaaaga tataatgatt atgattttgt  13620 agaattttt actggtataa gtaatagtac ctttggttta aaatcagatg gtaatttata  13680
tgcttgtggc gataatacag gttttcaact aggacttgga aaagattcgt cagagagaag  13740
gatgtttagt aaagtaaaaa ttgataatgt aaaatatgta tcttgtggtt caaaacacag  13800
tgtagcagta actaaagatg gatttgcata tggagcagga acaagtaatg taggtcaatt  13860
aggtgtaatt gagtctacag tatattatga atttactaag ctaccaatag atgatgtaaa  13920
aactgttgca tgtggttatg actttacatt tgtgcttaaa aatgatggaa cattatattc  13980
agcaggttta aactcaagtg gtcaacttgg actaggtgat actaacaata gagctacttt  14040
tactaaagta aatatagata gtgtgaaaga tgtagtgact tataatcaat ctgtatttat  14100
cataaaaatg gatgggacag cacatgcatg tggattaaat tcaaatgggc agttgggaat  14160
taatagtact ttaaataaaa gtgtatttaa taaaatagaa ggtatggata atgtaaaaca  14220
gatagcgtgt ggtagtagtc atacaattct tattaagaat gatggaacta tgtatactac  14280
aggctataat ggagttggtc agcttggtac aggaaataat aataattcaa ttgtatttac  14340
tctttctagt ataaataatg ttaagtatgc ttcttgtgga aataatcata ctatgatatt  14400
aaaatacgat aatacactgt ttagtacagg acaaaacaat tatggtcaac tagccaatgc  14460
caataaagat gtagcatcaa gaaatacttt tgctaaggtt aatgtagaaa atataaaaga  14520
tattaaatgt ggttctcaat ttaatttttt aataaatggt tcaaaagaga tatttgtatc  14580
tggctgtaat ttagcaggtc aacttggttc atttttcat acaacttttc tgtatgagtt  14640
ttcaaatgtg caatcttcaa atttagataa ttattcaggt ttattggtta atgatgatta  14700
tttatatgtt acaaaggaca atagtgaatt tttaaatgta aagttaagtg ataattttca  14760
agattataag aagatagagt taacagatag caatatgttt attgttatga atgatggtac  14820
attgtatgct tgtggtttaa ataattatgg acagttagga ttgggagata ctgttaacag  14880
gtcagttatg actaaggtgg atatagataa tgttttggat ataaaaggaa acggaaactc  14940
aacttttgtg cttaagaata atggaacatt atattcatgt ggtttaaata gtaatggaca  15000
attgggttta agagatgaag ttaatagaaa tatatttaca aaaatagaaa tagaatgt   15060 aaaggattt tgtgtaggaa gcaattatgt catagcttta aatcactcaa aagaagtata  15120
tggatgggga aataatcctt ataataatat agaaaaaact tctaattatc catataagca  15180
gggaataagt aatattgaaa agatagcagc atatgattat tctgtatata tgataaacag  15240
tgaagggaaa ctatatgttt ctggatacaa ttataattat caattaggta aaggaaataa  15300
tagtaaccaa agcaaagcat tagtatctca atgtagaaca aattcaacat cttctacatc  15360
aaatggactt agaacgttac ctaaaataac taatgttttt ccttttatg atggttgtgc  15420 aataattgac gaaggaggtt atgttttattt aacaggatat catggatatt taagaacatt  15480
aaatagcagt ccaagtatat ctgattattc aagatatgga actttattg aggctacaaa  15540 ttcaaatcat aatacttatt ttatacaaga gactgatttt agtggaattg aaaaagtaat  15600
agggatgtca aataatatat tatttttta gaaaggaagt tcatatatta ctggatatcc  15660
```

```
aaaaacattt ggctcaacca ttactggaca tagaagttat actagtatta attctgagag    15720
ttctaattta ggaagtaatt tttaatatat tcatagtaat tccaagttat atggaaaagg    15780
gattgctaat agtgggcaat ttgggaattc aacaaatata gatggcacaa gtaactatga    15840
tacaggatta aaagacataa aagatataat tgtaaaagga aatactgtag tagtagtaga    15900
taaaaataac aatatatatg taacaggaat gaatcagaat aacaaacttg ggatagggga    15960
atataacaac gaaccagtaa aaaaattcac aaatataact gaacaatcaa actcattat    16020 atttatggat gatataaaag aaattacaac atcaagaaat acaatgttta tagtaaaaaa    16080
tgatggaaca gcctatgcca caggaaataa tagttctgga caattaggat taggtgacac    16140
aataaataga aataagttca ctcagataaa ccttgataat ataaagaaaa tatcaacaag    16200
tatagatggt aacacaacat ttgcaattag aaatgatgga acactatact ccacaggatt    16260
aaataccaaa ggacaactgg gattaggtga tatagtaaat agaaatacat ttaccaaagt    16320
aaacatccaa aatgtaagag atgttgtttt agggactact cactcgcatg caatcaaaga    16380
tgataacaca ttatattcat gtggagaaaa cactcatggg caactgggct taggaagcga    16440
aagcaaccat ccagacgtat tgacatttac tgtaaacaat ataactaatg taagagatgt    16500
gtactgctca gatacaacaa catttattgt aaaggacaca aacattgcat attgttgtgg    16560
atacaataat aattcacaac taggtatggg aaatactact gaccagtata gttttataaa    16620
gtgtatggaa aatgtaaaag aagttatacc aaatgaaata aatacctata taataacaat    16680
ctataatact gcatatagta caggtttaaa tactgattat tgcttaggtc taaatagtaa    16740
tagcaatcaa agttcatttt ctgaaattcc aatttcaaat gtagtaaaag tagctccaaa    16800
cagaaataat gcagtacttt tacttacaag tgaaggggat gtatatactg caggcaaatg    16860
tagtaatggt tcaggtacag gaagtgagac tccagagaag attaaaaaaa tagcatcaaa    16920
ggcaaaggat attggaatga attatagatg tggacattat gtaagtgata atggagacct    16980
atatggtaca ggttttaata taatggaca attaggtgtt ggtgatgtaa caaaagaga    17040 tacatttata aaaccaata caagagtaaa gaaaatactt cctttagaat atgcaaatat    17100
agcaataaaa gatactaatg atatatatat ttgtggatta ataactatg gacaattagg    17160 tgttggaaat agatacgata gtagaaataa tgataataga atatttaatt ataagcatat    17220
gaattttgta atgggtgatt tgacatctat taaaaacaga cataacttta tacttctaaa    17280
caataagata gtgataccta ccacaaaaga catagattat ggtttagtat taggaaattt    17340
atacaaagga gacctttata ctgagcttcc atatgaagat ataaaagaag tatctatttc    17400
taagactcat attattatat tacttaatga tggaacaatg tatggatgtg gtacaaacta    17460
ccatggagaa ttattgcaag acttgtctat aaatcaagtg gatgaatttg tgcagattaa    17520
tgtatcagat gtaaagcatg tttcatgtgg agataacttt acttatttta taaaatctga    17580
tgatagtctt tggtctattg gtaaaaattc cgaatatcaa ttaggtatag gtcacaataa    17640
tccagttact gaattacaaa gaattacaac tatatctagc tgtaaagaag tacattgtgg    17700
taaaaactat acattagtag taactacagg taatgaatta tttgtacaag gatataatga    17760
taagggagct ttaggattag gaagcgatag tgaaaatact ataattaagt tctttacaaa    17820
agcactaaca gacataagag aaataaaatc ttatggaagt gaccatatat tagtacttaa    17880
aaatgataat tcagtatggg ttactggaaa aaataggggat gtatataaaa ttgaacaacc    17940
agtagaattt ttaaaagaat ttactatagt acctatttct gaagatgtaa atacagtaaa    18000
ggatgtactt gcaacagaca atacattata tattatatca gaagtaggaa cgacaaatgc    18060
```

```
tgctatagaa attactgaaa aatcaatttc atcaattaag ataaaaatac aagaccctaa   18120
taaagatata agtagaatag aaatgcttat aaatggtgaa agtgtaaaat ctgtaagtga   18180
tttaactact gaaaaaatat cctttgaagt accaccagat aaaattaaaa taggagagaa   18240
taagatacta tttagagctt attgtaaagg tgatgattta tatgcatctt tatttatttt   18300
taaagagagt actggaaatt ctataattaa agattcttat gttatgatag gtaatagaat   18360
gtacaaggta gttaatacaa catctaatga acaagatatt acaattacac tagatagagg   18420
acttgaagaa gatttaaatc ttggagaccc tatatatcaa ttaataaata aaactaaagt   18480
tcaagtaaaa ataaataaat ctgacttatt caaagacatg aaactagttg aaatcaaaaa   18540
atcagactca agttatcaag aaatctatga attagaagaa gccaacataa aaagtgctca   18600
gcctaaaatc atagtagaaa aaggagataa atggacagct ataaaacgtc catctatgat   18660
ttttagatat gatgctgaaa acaacgagcc acaagcttaa aatggaggtg taaaaattgt   18720
ttaaattcga taaaaataaa atagaacaaa tcaaacaagg tagaaaagta gaaatgcagt   18780
ataaagacat ttcagacata agtataggtc aagcaaagca agatgatgat ataacaaata   18840
attttatagc aaatgcagaa atatatgaga tgttgttaag tcaaagttct gtcaatgaag   18900
caagtaatat aagcactttt agtgtaagaa aatctggagg tgagagtgga atggtagaag   18960
tatatgtagc tttaatttta agaggcagaa aaacaaataga agaagtacca gcagtaatta   19020
gagagcaagt tagaattaga tgtaaagaat tagaaatacc agttgaatag taaatttaga   19080
ataactatgt attagttatt tttttatgt aaagtacaag gtcttaactt taataagtaa   19140
gccttgtact tatttttgt tatattagaa attgtatata tatttattat ttattcaatc   19200
tataaattaa acctacaatt taagtacag aagattaaat tgataatcct gaaaatataa   19260
tattgcatga tgtaagaata taacaaaaat taaagctata agtataaaaa atttagacaa   19320
taggaggcta taatggataa attaataacc gaattgagta gtctgggggc aataggtata   19380
ctatgtgctc tattatttaa aaatactatg caggagaaaa aagaagatag agacatgtat   19440
aaaaaaactg tagaaaattt tatagaatta tctacacaac aacaagaaat aaacaaaaat   19500
atacttgttc aaatgggaat aatgaaaaca gatgtagagg aaattaagga agatgttact   19560
gatataaaag gtatgttaca aaacggtgta taacatgaaa gtagcagtag caccagatta   19620
tatattatta ggaaaagata aagtagtatt gtagatagtg ccctatttta ttgagaagga   19680
ttttatattt taaatatta attaaaaaaa gtaataaaaa taatatataa aaataacata   19740
taaaaattca aaaaggagtt aagcttaaat ttgattagaa aaaatcaatt ttaagacaac   19800 tcctttttt tattaaatta ttgtctatta accaaaatag ctattttagc atctggatta   19860
taacttatct gaaccatttg attttttcta acatgttcaa ggtcttcacc accataagct   19920
atttgtaact taactggtaa cttaccttgt tttataatag caacgtactc ttttttacct   19980
ttttctctaa actaatcaaa ttgccaacat aaggtttaaa gttctgatac ttttactag    20040 aatttcttat gtagaagaaa gcaccaacag caataactaa atttatgcca agtgtaaccc   20100
aagaattgat tttaagcata gctccagcga ttattatcac gaacattaaa acgataggta   20160 atatagctt cttaagaagc aatttaccca ttatttcatt agccttttc tcagggccac   20220 tcatagtttt tgatctagca aatgattgcg cgaatttgtc tcttaagccc attttatcct   20280
cctaatttta ataaatattt agttataata acgagatatt acttgaaact aaaaatttac   20340
tacatttata ttatgtttga cttttgtata aataattaca ttcaagtaaa gcaaaatata   20400
```

```
ctaattattt tatcataaaa ttataaaaaa gaaaataaat gaaataaaaa tattagaaca    20460
aagaaatgat gtaaaatcgt atcaaaagca acataaaaat tatttatcta ttttctcatc    20520 tttattttg ttatactcaa ttttcctaa atccttctct ttttcatatt catgaagttt      20580
taattcaatc ataccttcta ttttggcttt atcataatca tttaactttc taaagttgtt    20640
taaaagcttt atttcattag agtttatgct attaagtgga tagtttgagg aggaatcgca    20700
aattaaatct gatttatgtg atagattatc tccatttaat agccagtcta ctgaaacatt    20760
aaatatctca gctatagatt ttaatatttc ataatttggt tttctaatgt ttctctcaaa    20820
tttacttaag ttgtcacagc ctaacatttc ttctagttca tattgtttaa ggttttttgc    20880
ttttctcaaa taaacaattc tttctcctaa agtatccata aacactctcc attcaattaa    20940
tgtcaaaaag acttttttaag atgtaaatag tttcaaatta aaggtcaaaa tgacataaaa    21000
accattgact taaggtcaaa atgactttat aattaactta atgatacgaa tttacatcct    21060
aattttagca caaagtaatc aaaaaatctt atttagtatt aaataaattt atatacttaa    21120
tatgtgtaca tattaaaaat atatactaaa tagaggggggt gcgtaagcta aagtaatata    21180
aaagtaaata taaatcactt agaaaggaag ttgataaatg gatgctcgaa aaaaatggat    21240
accttttttg ggagtgcaag tcaagcaaag acttattgaa ttaaatatga ctcaaaggga    21300
attagcgaag aaaataggtg ttaatgaaaa ctatttgtca gctatttta atggaagaag    21360 aacaggtaaa aaatataaat catcaattta tcaattactt aatatagaat attcagaaga    21420
tgattaataa atagtatata aagtaggtga atattcttgt gtgcaaattg gattcagatg    21480
gggttataga gtgttgtaga gcaattgatg atttttattac agcacttagt aatataaaaa    21540
gcttaaatat ggaaagatta aatactttaa ctaaatattc tagtacatgt tcaatccttc    21600
ttaaagaggg gaattatgaa ggatgtacaa ttgtgtatag aaagatgttg gaagaattaa    21660
aaacatgagt aatgcatttc ttaggaatat aaattataca tagaaatgta ttatattttt    21720
caaagtactt aaactaaaat atggataaga taatctaaat attataaatg tgcttgaaat    21780
tagactatac ttgttttaaa ataatccaat atccatattt tagtaatata ctacaaaaaa    21840
agaaggttaa tagatgatgt aaaatcgtat caaattatgt atgtttaaac cattttatct    21900
tcattattat tagaggaatg cttttttaag tctttatatt cagatatctt aagttcaagt    21960
attccttcta ttttatttt atcacgttcg tttagttgtc tgtatagatt taatatcatc    22020
atttcatcat tagtaacatg taagtaatct tctttatctt cttttacact actattgaca    22080
tttaccttct ctttaccata gagaagccag tcagtcgtaa cattaaaata atcagctatt    22140
gacattagta tatcacaatt aggttttcta tctcctgttt catacttgcc taagttttca    22200
aattttaaaa tatccataag tttgcgctga gtaagttttt tggagtttct caaataagca    22260 attcttttc ctaaagtatc cacaaaatac actcctttct ttttatgagt aatgtctaaa    22320
tgacatttga aattaaaaat atataaattt ataatataaa actactaaat taaagtctaa    22380
atgacatttt gcttaaatta atatgctcat aaatatgattt taacatatta tagttgaaaa    22440
tatatggttt attttgattt gtatatataa caatagattt aattgttata aaaatgtaaa    22500
ggggtgtatg aatagattgt ataaatttat ttcgataaac taagattgct ttttgattgt    22560
ctgtaaaaga gaaaagatt aagataaaaa tagtattata ttgtaattta tattaatcaa    22620
ttacaaagat tttatgaatt tattcttag ggtaaaatat ttaagaataa gataaattta    22680
caatataata ctataacact ctttatctta gttttattt cttatagaa caataatatt    22740 ataaatgcta gtagatttac acagaatact gttatataca tctgtttgaa tcctgagttt    22800
```
agagtagatt gtagtgtgga tccgg                                    22825

<210> SEQ ID NO 2
<211> LENGTH: 65
<212> TYPE: PRT
<213> ORGANISM: Clostridium difficile

<400> SEQUENCE: 2

Met Phe Lys Asn Asn Leu Lys Tyr Tyr Arg Lys Cys Lys Gly Met Thr
1               5                   10                  15

Gln Ile Gln Leu Ala Arg Lys Ala Gly Ile Thr Asn Asp Tyr Ile Ser
            20                  25                  30

Gln Ile Glu Arg Gly Ile Lys Asn Pro Gly Leu Leu Met Ala Lys Lys
        35                  40                  45

Ile Ser Ser Ile Leu Glu Gln Asn Ile Glu Glu Val Phe Phe Ile Gln
    50                  55                  60

Leu
65

<210> SEQ ID NO 3
<211> LENGTH: 146
<212> TYPE: PRT
<213> ORGANISM: Clostridium difficile

<400> SEQUENCE: 3

Met Glu Asn Lys Lys Asp Ile Leu Phe Lys Glu Thr Asp Glu Arg Leu
1               5                   10                  15

His Asn Tyr Lys Tyr Leu Asp Ile Lys Ile Lys Asn Ile Asn Leu Asp
            20                  25                  30

Ile Lys Arg Cys Glu Asn Glu Tyr Ser Gly Cys Gly Ala Met Val Tyr
        35                  40                  45

Thr Glu Lys Thr Ser Asn Thr Tyr Asn Ile Ser Ser Ser Val Glu Asn
    50                  55                  60

Glu Val Leu Lys Arg Glu Glu Arg Leu Arg Lys Leu Lys Met Glu Lys
65                  70                  75                  80

Glu Asp Ile Glu Ile Glu Lys Glu Lys Ile Glu Asn Ala Leu Thr Cys
                85                  90                  95

Leu Asn Asp Ile Glu Met Glu Phe Phe Asn Leu Phe Tyr Asn Ser Lys
            100                 105                 110

Thr Lys Asn Asn Met Thr Tyr Ile Ser Met Lys Leu His Leu Asp Arg
        115                 120                 125

Thr Ser Cys Tyr Asn Leu Lys Lys Met Ile Phe Lys Leu Ser Glu
    130                 135                 140

Ile Leu
145

<210> SEQ ID NO 4
<211> LENGTH: 130
<212> TYPE: PRT
<213> ORGANISM: Clostridium difficile

<400> SEQUENCE: 4

Asn Phe Thr Glu Ser Ile Phe Ile Asp Asp Glu Ser Val Gln Gly Ser
1               5                   10                  15

Glu Gly Ser Cys Phe Phe Val Ser Ile Leu Ser Val Ile Cys Thr Pro
            20                  25                  30

Ile Met Leu Asn Thr Asn Asn Lys Asp Ile Val Ile Ser Ile Lys Tyr

```
                35                  40                  45
Leu Pro Lys Pro Gln Ser Lys Ser Ile Arg Met Tyr Glu Ile Ser Asp
 50                  55                  60

Glu Leu Asn Lys Leu Phe Asn Arg Asn Ile Lys Val Thr Asp Arg Lys
 65                  70                  75                  80

Leu Asn Ile Thr Lys Leu Glu Gln Ser Ile Lys Lys Glu Glu Ser Ile
                 85                  90                  95

Tyr Val Leu Asn Phe Thr Ile Thr Leu Asn Tyr Leu Asp Ser Val Tyr
                100                 105                 110

Glu Glu Asp Val Val Tyr Glu Asn Met Glu Glu Ile Asn Leu Asn Leu
                115                 120                 125

Gly Glu
130

<210> SEQ ID NO 5
<211> LENGTH: 354
<212> TYPE: PRT
<213> ORGANISM: Clostridium difficile

<400> SEQUENCE: 5

Met Ala Ile Gly Leu Pro Ser Ile Asn Ile Ser Phe Lys Glu Leu Ala
 1               5                  10                  15

Thr Thr Val Lys Glu Arg Ser Ala Arg Gly Ile Ile Ala Met Val Leu
                 20                  25                  30

Lys Asp Ala Lys Ala Leu Gly Leu Asn Glu Ile His Glu Lys Glu Asp
                 35                  40                  45

Ile Pro Val Asp Leu Ser Ala Glu Asn Lys Glu Tyr Ile Asn Leu Ala
 50                  55                  60

Leu Met Gly Asn Val Asn Thr Pro Asn Lys Leu Leu Val Tyr Val Ile
 65                  70                  75                  80

Glu Gly Glu Ala Asp Ile Gln Thr Ala Leu Asp Phe Leu Glu Thr Lys
                 85                  90                  95

Glu Phe Asn Tyr Leu Cys Met Pro Lys Ala Val Glu Ala Asp Lys Thr
                100                 105                 110

Ala Ile Lys Asn Trp Ile Ile Lys Leu Arg Asp Ile Asp Lys Val Lys
                115                 120                 125

Val Lys Ala Val Leu Gly Lys Val Val Gly Asn His Glu Gly Ile Ile
130                 135                 140

Asn Phe Thr Thr Glu Asp Val Leu Val Gly Glu Lys Lys Tyr Ser Val
145                 150                 155                 160

Asp Glu Phe Thr Ser Arg Val Ala Gly Leu Ile Ala Gly Thr Pro Leu
                165                 170                 175

Ser Gln Ser Val Thr Tyr Thr Lys Leu Ser Asp Val Val Asp Ile Pro
                180                 185                 190

Lys Met Thr Lys Val Asp Ala Glu Ser Arg Val Asn Lys Gly Glu Leu
                195                 200                 205

Ile Leu Ile Lys Glu Ala Gly Ala Ile Arg Ile Ala Arg Gly Val Asn
                210                 215                 220

Ser Leu Thr Glu Leu Thr Glu Glu Lys Gly Glu Met Phe Gln Lys Ile
225                 230                 235                 240

Lys Ile Val Asp Thr Leu Asp Ile Ile His Ser Asp Ile Arg Lys Val
                245                 250                 255

Ile Ile Asp Asp Tyr Ile Gly Lys Val Thr Asn Ser Tyr Asp Asn Lys
                260                 265                 270
```

```
Cys Leu Leu Ile Val Ala Ile Lys Ser Tyr Leu Glu Glu Leu Glu Lys
                275                 280                 285

Ser Ala Leu Ile Glu Ser Asp Ser Thr Val Glu Ile Asp Phe Glu Ala
        290                 295                 300

Gln Lys Ser Tyr Leu Lys Ser Lys Gly Val Asp Leu Ser Tyr Met Thr
305                 310                 315                 320

Leu Gln Glu Ile Lys Glu Ala Asn Thr Gly Ser Lys Val Phe Leu Lys
                325                 330                 335

Ala Lys Ile Lys Val Leu Asp Ala Met Glu Asp Ile Asp Leu Ser Ile
                340                 345                 350

Glu Ile

<210> SEQ ID NO 6
<211> LENGTH: 142
<212> TYPE: PRT
<213> ORGANISM: Clostridium difficile

<400> SEQUENCE: 6

Met Ala Asn Met Glu Ala Arg Asn Val Met Ser Gly Thr Trp Gly Glu
1               5                   10                  15

Leu Trp Leu Asp Gly Asn Lys Val Ala Glu Val Lys Lys Phe Gln Ala
                20                  25                  30

Lys Met Glu Phe Thr Lys Glu Asp Ile Ile Ala Gly Gln Met Gly
                35                  40                  45

Thr Asp Thr Lys Tyr Met Gly Tyr Lys Gly Lys Gly Ser Ile Thr Leu
50                  55                  60

Tyr His Val Ser Ser Arg Met His Lys Leu Gly Glu Lys Ile Lys
65                  70                  75                  80

Arg Gly Ser Glu Pro Arg Phe Val Ala Ile Ser Lys Leu Asn Asp Pro
                85                  90                  95

Asp Ser Tyr Gly Ala Glu Arg Ile Ala Val Lys Asn Ile Ala Phe Asp
                100                 105                 110

Asp Leu Thr Leu Ala Asp Trp Glu Val Gly Val Lys Gly Glu Ile Glu
                115                 120                 125

Ala Pro Phe Thr Phe Thr Glu Tyr Asp Phe Leu Asp Ile Ile
                130                 135                 140

<210> SEQ ID NO 7
<211> LENGTH: 148
<212> TYPE: PRT
<213> ORGANISM: Clostridium difficile

<400> SEQUENCE: 7

Met Asn Glu Asn Gly Leu Ser Lys Asn Ile Asn Ile Val Asp Leu Leu
1               5                   10                  15

Leu Asn Ala Asp Thr Glu Asn Leu Glu Arg Pro Ser Thr Ile Val Glu
                20                  25                  30

Leu Lys Arg Leu Ser Thr Ile Phe Gly Gln Phe Lys Val Met Cys
                35                  40                  45

Arg Ala Leu Thr Ile Ser Lys Asp Glu Glu Ile Gln Asn Thr Cys Leu
50                  55                  60

Lys Ile Asp Glu Asn Met Lys Thr Asp Ile Leu Pro Glu Met Gln
65                  70                  75                  80

Met Leu Thr Ile Ile Glu Gly Val Cys Asp Leu Asp Gly Lys Leu Leu
                85                  90                  95

Phe Lys Asn Lys Glu Leu Met Asp Lys Phe Lys Ala Pro Thr Pro Lys
```

```
            100                 105                 110
Glu Leu Ala Arg Lys Leu Leu Pro Gly Glu Ile Thr Asn Leu Tyr
            115                 120                 125

Arg Ile Leu Gln Asp Val Met Gly Tyr Gly Lys Asn Ala Val Ile Glu
            130                 135                 140

Glu Val Lys Asn
145

<210> SEQ ID NO 8
<211> LENGTH: 55
<212> TYPE: PRT
<213> ORGANISM: Clostridium difficile

<400> SEQUENCE: 8

Met Tyr Tyr Tyr Trp Lys Lys Gly Ile Arg Pro Ser Leu Phe Tyr
1               5                   10                  15

Ala Met Asp Lys Gly Glu Leu Lys Leu Ile Glu Ala Phe Phe Ala Leu
            20                  25                  30

Glu Ile Glu Glu Val Glu Lys Met Lys His Gly Tyr Gly Val Cys
        35                  40                  45

Pro Leu Thr Gly Gly Gly Met
        50                  55

<210> SEQ ID NO 9
<211> LENGTH: 817
<212> TYPE: PRT
<213> ORGANISM: Clostridium difficile

<400> SEQUENCE: 9

Met Gly Asn Val Arg Glu Glu Gly Ile Asn Met Tyr Leu Thr Asp Asn
1               5                   10                  15

Tyr Thr Pro Lys Met Asn Gln Ile Ile Ser Val Thr Asp Asn Phe Arg
            20                  25                  30

Arg Ala Thr Val Ala Val Ser Leu Ser Thr Asn Val Met Ala Ser Ser
        35                  40                  45

Ile Lys Asn Ser Ile Gly Ser Ala Ser Ser Arg Val Asn Ser Leu Asn
    50                  55                  60

Ser Ser Leu Arg Lys Val Gln Thr Thr Ala Ser Ser Val Ser Ser Thr
65                  70                  75                  80

Met Ala Lys Leu Ser Ser Ser Ile Asn Ala Val Ser Gly Val Ile Gly
                85                  90                  95

Ser Leu Asn Gly Ser Ile Met Arg Leu Ala Ile Thr Ile Ala Met Ile
            100                 105                 110

Ile Asp Tyr Phe Asn Lys Leu Ile Gln Lys Lys Asn Glu Phe Asn Ser
            115                 120                 125

Asn Ile Met Ile Ile Leu Ile Phe Lys Ala Lys Ser Asp Glu Val Glu
        130                 135                 140

Lys Thr Lys Asn Lys Leu Leu Gly Asn Leu Lys Lys Ile Gly Gly Lys
145                 150                 155                 160

Ile Trp Asn Ile Val Ile Lys Ala Lys Asp Met Thr Lys Arg Val Ile
                165                 170                 175

Ser Ser Ile Leu Gly Lys Leu Lys Arg Val Glu Lys Arg Pro Tyr Gln
            180                 185                 190

Gly Ser Ile Asn Leu Lys Asp Met Val Ser Ser Ala Met Ala Arg Ile
            195                 200                 205

Leu Pro Lys Leu Met Leu Phe Lys Asn Thr Phe Trp Ser Gly Val Ile
```

```
                    210                 215                 220
Ala Ile Lys Asp Met Ala Ser Ile Ile Ser Lys Val Phe Pro Lys
225                 230                 235                 240

Leu Arg Leu Phe Ala Gly Lys Val Trp Ser Gly Ala Ile Ala Val Lys
                    245                 250                 255

Asp Met Ala Ser Gly Ile Leu Gly Ser Ile Lys Gly Lys Ile Ser Asp
                260                 265                 270

Leu Thr Asn Gly Ala Thr Ile Gly Val Ala Val Lys Lys Gly Val Asp
                275                 280                 285

Leu Leu Gly Gln Glu Gln Asn Gln Lys Val Val Leu Glu Ser Val Met
            290                 295                 300

Lys Arg Asn Thr Gly Lys Thr Ser Gln Lys Asp Val Asp Lys Tyr Tyr
305                 310                 315                 320

Asp Ser Leu Val Asn Met Ala Asn Asp Thr Pro Phe Asp Pro Glu Asp
                325                 330                 335

Val Val Ala Met Gly Thr Lys Ala Lys Met Ile Ser Asn Ile Thr Gly
                340                 345                 350

Gly Lys Lys Glu Lys Asp Ile Thr Gln Ala Met Val Asp Val Arg Ala
            355                 360                 365

Leu Asn Met Asn Thr Ser Ser Glu Gln Asp Val Ser Ala Ala Phe Leu
370                 375                 380

Ser Ala Ala Lys Gly Asn Met Glu Ser Leu Asn Thr Leu Val Gly Glu
385                 390                 395                 400

Asn Tyr Lys Thr Phe Asp Glu Ala Leu Glu Gly Ile Ser Val Lys Gln
                405                 410                 415

Met Gly Leu Ala Lys Glu Met Ser Asn Thr Ile Pro Gly Ile Ile Ser
                420                 425                 430

Gly Ala Gln Thr Ser Ile Asn Asn Gly Leu Lys Ser Ile Val Lys Pro
            435                 440                 445

Phe Asp Asp Ile Leu Gly Gln Gly Leu Lys Lys Ile Lys Thr Phe Ile
450                 455                 460

Glu Ser Gly Leu Gly Asn Leu Ala Gly Leu Ser Glu Lys Met Ala Gly
465                 470                 475                 480

Lys Ile Gly Asn Val Met Asn Gly Lys Ile Ile Gly Asn Lys Tyr
                485                 490                 495

Asp Gln Met Gln Ser Arg Ser Val Lys Asn Gly Lys Glu Phe Ser Asp
                500                 505                 510

Ser Thr Gln Tyr Arg Ile Ser Asn Glu Ala Glu Lys Arg Lys Met Met
            515                 520                 525

Val Glu Asn Lys Gln Glu Arg Phe Glu Asn His Ala Ala Thr Met Ile
530                 535                 540

Gly Asn Ala Pro Lys Ala Ile Val Asn Ala Gly Ser Thr Leu Leu Gln
545                 550                 555                 560

Asn Ile Asp Phe Thr Ala Leu Ile Asp Ser Leu Leu Pro Val Val Asn
                565                 570                 575

Leu Val Asn Asn Leu Leu Asp Ser Ile Asn Asn Lys Ser Pro Ile Ala
            580                 585                 590

Gln Gly Leu Ile Ser Ile Phe Gly Thr Ile Val Thr Thr Ala Phe Gln
            595                 600                 605

Leu Ile Gly Pro Val Val Glu Ala Val Ser Pro Ile Ile Thr Arg Ile
            610                 615                 620

Phe Thr Phe Leu Gly Glu Tyr Ala Pro Gln Ile Asn Asn Phe Ile Glu
625                 630                 635                 640
```

```
Thr Leu Gly Val Ile Trp Lys Thr Val Trp Glu Thr Leu Gly Pro Leu
                645                 650                 655

Leu Glu Thr Gly Trp Lys Ile Ile Glu Pro Ile Leu Gly Ala Phe Phe
            660                 665                 670

Asn Ile Leu Asp Lys Val Cys Lys Ile Val Lys Asp Ile Cys Lys Trp
        675                 680                 685

Trp Gln Thr Met Ile Asn Lys Ile Lys Asn Gly Ser Ile Thr Gly Thr
    690                 695                 700

Val Leu Asn Leu Val Glu Lys Ser Lys Lys Asn Tyr Lys Asp Asn Pro
705                 710                 715                 720

Tyr Ala Gly Thr Lys Ala Gly Asp Ser Gly Lys Ala Tyr Ser Ser Lys
                725                 730                 735

Lys Gly Asn Asn Ala Phe Gly Leu Asn Tyr Val Pro Tyr Asn Asp Tyr
            740                 745                 750

Gln Thr Arg Leu His Glu Gly Glu Met Val Leu Thr Lys Gln Glu Ala
        755                 760                 765

Asn Gln Tyr Arg Ser Arg Lys Asn Gly Gly Asn Ile Asn Ile Ala Lys
    770                 775                 780

Leu Ala Asp Thr Ile Val Ile Arg Glu Glu Ala Asp Ile Glu Lys Ile
785                 790                 795                 800

Thr Ser Lys Leu Val Ala Ser Ile Gln Leu Ala Gln Leu Gly Gly Val
                805                 810                 815

Leu

<210> SEQ ID NO 10
<211> LENGTH: 140
<212> TYPE: PRT
<213> ORGANISM: Clostridium difficile

<400> SEQUENCE: 10

Met Glu Met Trp Leu Arg Gln Ala Glu Asp Arg Phe Arg Phe Pro Val
1               5                   10                  15

Phe Pro Ser Ser Phe Ser Ile Asn Gly Lys Ala Ala Val Asn Ser Ser
            20                  25                  30

Ser Ile Leu Lys Ile Gly Glu Val Ala Thr Phe Gly Gly Val Ala Leu
        35                  40                  45

Lys Ser Ile Ser Ile Ser Ser Phe Phe Pro Asn Lys Asp Tyr Thr Phe
    50                  55                  60

Cys Asp Tyr Thr Gly Phe Pro Ser Pro Tyr Asp Cys Val Asn Lys Ile
65                  70                  75                  80

Glu Lys Trp Met Lys Glu Gly Phe Ile Leu Arg Phe Thr Ile Thr Glu
                85                  90                  95

Thr Asn Ile Asn Met Glu Val Ile Ile Glu Gly Phe Ser Tyr Glu Glu
            100                 105                 110

Arg Asp Gly Thr Arg Asp Val Tyr Phe Thr Leu Asp Leu Lys Glu Tyr
        115                 120                 125

Lys Arg Ile Lys Ile Pro Lys Val Thr Pro Lys Gln
    130                 135                 140

<210> SEQ ID NO 11
<211> LENGTH: 509
<212> TYPE: PRT
<213> ORGANISM: Clostridium difficile

<400> SEQUENCE: 11
```

```
Met Ile Ile Asn Arg Ser Lys Asp Ser Ser Asn Glu Ile Ser Phe
1               5                   10                  15

Val Ser Lys Asp Met Gly Phe Leu Leu Thr Gln Ser Val Ser Tyr
            20                  25                  30

Asn Phe Lys Asp Lys Leu Val Glu Asp Ile Ala Lys Gln Val Phe Ala
        35                  40                  45

Glu Asn Arg Leu Ser Val Gly Thr Ile Ala Lys Thr Asn Val Lys Tyr
50                  55                  60

Thr Lys Met Phe Ile Gly Val Asn Gly Tyr Asp Thr Ile Met Ser Ala
65                  70                  75                  80

Tyr Thr Glu Ala Ser Lys Lys Thr Lys Lys Tyr Met Ile Glu Ala
                85                  90                  95

Asn Leu Asp Lys Phe Asn Val Ile Glu Lys Gly Thr Val Thr Leu Ser
            100                 105                 110

Val Met Phe Glu Glu Gly Phe Asn Ile Ile Asn Thr Thr Phe Ser Glu
        115                 120                 125

Ser Met Glu Asn Val Lys Asn Lys Val Ile Val Asp Gln Tyr Gly
    130                 135                 140

Ser Lys Ile Ser Glu Lys Ile Asp Asn Glu Ile Phe Lys Glu Val Asn
145                 150                 155                 160

Val Ile Met Gln Lys Val Ile Gln Gln Glu Asn Gln Asp Val Asp
            165                 170                 175

Ile Asp Ser Glu Phe Asn Gly Ile Glu Lys Ser Cys Ser Leu Lys Gly
        180                 185                 190

Tyr Gly Asp Val Ser Cys Ile Thr Gly Arg Gly Val Lys Val Lys Asp
            195                 200                 205

Ser Tyr Thr Lys Leu Val Gly Leu Phe Tyr Ile Asp Thr Asp Lys His
    210                 215                 220

Thr Trp Gln Asn Gly Glu Tyr Gln Ile Glu Leu Glu Leu Asn Phe Gln
225                 230                 235                 240

Asn Leu Met Asp Glu Lys Ser Ala Gly Gln Asp Glu Pro Lys Glu Glu
            245                 250                 255

Ser Asn Leu Gly Gly Glu Asp Tyr Ala Gly Gly Lys Glu Phe Thr Ala
        260                 265                 270

Glu Phe Thr Ala Tyr Cys Pro Arg Lys Glu Glu Gly Gly Asp Thr Asp
            275                 280                 285

Cys Arg Lys Lys Lys Leu Asp Pro Ser Lys Lys Thr Cys Ala Ala Pro
    290                 295                 300

Met Val Gly Lys Tyr Glu Gln Thr Tyr Tyr Thr Lys Glu Phe Leu Asn
305                 310                 315                 320

Lys His Pro Leu Leu Asn Tyr Gly Asp Glu Ile Gln Val Ile Thr Gly
            325                 330                 335

Val Ser Gly Arg Asp Gly Val Tyr Lys Val Asn Asp Val Gly Pro Ala
        340                 345                 350

Ile Thr Ile Glu Lys Asn Gly Thr Tyr His Ile Asp Ile Leu Phe Gly
            355                 360                 365

Asn Val Glu Glu Ala Ser Lys Phe Gly Arg Arg Lys Gly Lys Ile Ile
    370                 375                 380

Ile Gly Gly Tyr Ser Gly Asn Val Ser Asp Lys Ala Lys Ile Val Ile
385                 390                 395                 400

Ser Glu Ala Lys Lys His Leu Gly Lys Pro Tyr Lys Trp Gly Gly Asn
            405                 410                 415

Gly Pro Ser Ser Phe Asp Cys Ser Gly Leu Met Val Tyr Cys Phe Lys
```

```
                420                 425                 430
Lys Val Asn Val Ser Leu Pro Arg Thr Ser Asn Gln Gln Ser Lys Lys
            435                 440                 445

Gly Lys Lys Val Glu Gln Lys Asn Leu Gln Ala Gly Asp Leu Val Phe
        450                 455                 460

Phe His Asn Pro Val Ser His Val Gly Leu Tyr Ile Gly Asn Gly Glu
465                 470                 475                 480

Phe Leu His Ala Pro Gln Lys Gly Asp Val Val Lys Ile Ser Lys Leu
                485                 490                 495

Ser Ser Arg Arg Asp Phe Asn Thr Ala Arg Arg Val Leu
            500                 505

<210> SEQ ID NO 12
<211> LENGTH: 108
<212> TYPE: PRT
<213> ORGANISM: Clostridium difficile

<400> SEQUENCE: 12

Met Ala Asn Pro Ile Asn Glu Phe Ile Gly Ile Ile Arg Glu Glu Gly
1               5                   10                  15

Lys Tyr His Asn Gln Pro Ser Phe Phe Ile Gly Lys Ile Lys Ser Lys
            20                  25                  30

Leu Pro Asp Leu Lys Ile Glu Thr Asn Asn Ile Ile Leu Glu Lys Glu
        35                  40                  45

Asp Ile Leu Ile Asp Ser Trp Met Ile Asp Arg Gln Leu Glu Thr Phe
    50                  55                  60

Asp Thr Glu Thr Asn Gln Glu His Gln His Glu Val Lys Asn Pro Phe
65                  70                  75                  80

Ile Asp Asn Phe Glu Ser Gly Asp Met Val Ile Met Phe Arg Ile Gly
                85                  90                  95

Glu Lys Phe Ala Val Val Ser Lys Leu Val Ser Leu
            100                 105

<210> SEQ ID NO 13
<211> LENGTH: 142
<212> TYPE: PRT
<213> ORGANISM: Clostridium difficile

<400> SEQUENCE: 13

Met Ser Thr Ile Phe Pro Phe Ile Gly Val Pro Glu Asp Tyr Ile Leu
1               5                   10                  15

Pro Lys Thr Glu Glu Leu Pro Ile Phe Arg Glu Val Ala Trp Asp Phe
            20                  25                  30

Glu Lys Asp Glu Pro Ile Leu Glu Lys Gly Asp Phe Lys Ile Ile Glu
        35                  40                  45

Lys Lys Glu Ala Leu Lys Val Trp Ile Tyr Lys Cys Ile Lys Thr Asn
    50                  55                  60

Arg Tyr Glu His Glu Ile Tyr Ser Leu Gly Tyr Gly Thr Glu Leu Ser
65                  70                  75                  80

Glu Leu Ile Gly Gln Lys Tyr Thr Lys Gly Leu Thr Glu Ser Glu Ala
            85                  90                  95

Ser Arg Phe Ile Lys Glu Ala Leu Leu Ile Asn Pro Tyr Ile Leu Glu
        100                 105                 110

Val Asn Val Lys Ser Ala Asn Phe Asn Arg Asp Val Leu Ser Ala Asn
    115                 120                 125

Val Lys Val Ser Thr Ile Tyr Gly Glu Val Glu Ile Asn Val
```

<210> SEQ ID NO 14
<211> LENGTH: 350
<212> TYPE: PRT
<213> ORGANISM: Clostridium difficile

<400> SEQUENCE: 14

```
Met Tyr Ser Asp Gln Thr Tyr Glu Val Ile Lys Asn Arg Thr Leu Glu
1               5                   10                  15
Asn Ile Asn Leu Asp Ile Tyr Lys Gly Glu Gly Ser Phe Leu Asn Asn
                20                  25                  30
Met Val Ser Gly Asn Asn Leu Glu Leu Ser Lys Ile Tyr Leu Glu Leu
            35                  40                  45
Ser Lys Ile His Lys Met Ala Phe Ile Gln Asp Thr Tyr Asn Gln Phe
50                  55                  60
Leu Asp Lys Arg Val Asn Glu Phe Gly Val Tyr Arg Lys Leu Gly Thr
65                  70                  75                  80
Glu Ser Asn Gly Glu Val Glu Phe Ile Gly Glu Lys Gly Thr Val Ile
                85                  90                  95
Asn Asn Gly Thr Ile Ile Ser Tyr Arg Asp Leu Leu Phe Val Val Ile
                100                 105                 110
Lys Asp Val Thr Ile Gly Ser Glu Glu Gly Asp Asn Ser Pro Val Gln
            115                 120                 125
Ala Leu Glu Val Gly Lys Lys Tyr Asn Leu Pro Thr Asn Cys Glu Phe
        130                 135                 140
Lys Leu Val Asp Asn Ile Ser Gly Val Thr Lys Ile Thr Asn Thr Arg
145                 150                 155                 160
Ser Phe Glu Gly Gly Thr Asp Ile Glu Thr Asp Glu Glu Leu Lys Glu
                165                 170                 175
Arg Phe Tyr Lys Ile Gln Arg Asn Gln Ala Thr Ser Gly Asn Lys Ala
                180                 185                 190
His Tyr Glu Glu Trp Ala Leu Glu Val Asp Gly Val Tyr Asn Val Lys
            195                 200                 205
Val Tyr Pro Arg Trp Asp Gly Pro Gly Thr Val Lys Val Leu Ile Phe
        210                 215                 220
Gly Glu Asn Asn Gln Ala Val Asp Thr Glu Thr Ile Glu Arg Cys Gln
225                 230                 235                 240
Gln His Ile Asp Glu Glu Lys Pro Ile Gly Pro Thr Ile Thr Val Val
                245                 250                 255
Thr Pro Leu Pro Ile Glu Ile Ser Ile Ser Ala Val Met Lys Leu Glu
                260                 265                 270
Asp Gly Tyr Thr Leu Asp Asn Val Lys Glu Ser Phe Leu Glu Ser Ile
            275                 280                 285
Asn Thr Tyr Phe Arg Asp Ile Arg Gly Glu Ile Ile Tyr Thr Lys Val
        290                 295                 300
Met Gly Ile Leu Ile Asn Thr Thr Gly Val His Asp Leu Ser Asn Leu
305                 310                 315                 320
Leu Ile Asn Gly Ser Thr Asp Asn Ile Thr Ile Asn Glu Asp Lys Ile
                325                 330                 335
Pro Ser Val Thr Thr Val Asn Phe Ser Glu Val Glu Asn Gln
                340                 345                 350
```

<210> SEQ ID NO 15
<211> LENGTH: 232

<212> TYPE: PRT
<213> ORGANISM: Clostridium difficile

<400> SEQUENCE: 15

```
Met Lys Leu Ile Asp Lys Leu Pro Ser Phe Asp Arg Asn Tyr Ile Val
1               5                   10                  15

Glu Glu Ile Gln Gly Ala Tyr Asp Thr Glu Leu Asn Ile Leu Lys Glu
            20                  25                  30

Asp Ile Asp Asp Thr Phe Asn Gln Leu Phe Val Asp Thr Ala Thr Trp
        35                  40                  45

Gly Leu Asp Met Trp Glu Asp Ile Leu Cys Ile Glu Lys Lys Glu Leu
    50                  55                  60

Asp Phe Asp Thr Arg Arg Ser Asn Ile Lys Ala Lys Met Arg Ser Arg
65                  70                  75                  80

Gly Thr Ser Thr Ile Glu Val Ile Lys Ser Ile Cys Glu Ala Tyr Thr
                85                  90                  95

Lys Ser Glu Thr Asp Ile Lys Val Tyr Ser Asp Glu Phe Thr Phe Val
            100                 105                 110

Leu Ser Phe Ile Ala Asn Asn Cys Asp Tyr Lys Thr Leu Leu Asp Cys
        115                 120                 125

Ser Glu Met Ile Glu Arg Val Lys Pro Ala His Leu Leu His Tyr Leu
    130                 135                 140

Glu Pro Ile Ile Leu Asp Lys Ser Met Val Tyr Cys Gly Gly Gly Met
145                 150                 155                 160

Val Cys Ser Glu Glu Val Lys Val His Pro Tyr Phe Glu Pro Ile Ile
                165                 170                 175

Lys Cys Ser Ala Val Val Asn Cys Gly Ala Gly Met Leu Ser Arg Glu
            180                 185                 190

Glu Ile Lys Val Tyr Pro Leu Ser Ile Lys Cys Ile Glu Asn Asn Cys
        195                 200                 205

Lys Ile Asn Ile Ala Ile Ala Asn Asp Thr Gly Val Glu Asn Val Val
    210                 215                 220

Val Tyr Pro Lys Ser Glu Val Val
225                 230
```

<210> SEQ ID NO 16
<211> LENGTH: 328
<212> TYPE: PRT
<213> ORGANISM: Clostridium difficile

<400> SEQUENCE: 16

```
Met Glu Glu Lys Phe Tyr Ile Ile Leu Thr Lys Ile Gly Arg Glu Lys
1               5                   10                  15

Ile Ala Asn Ala Thr Ala Leu Gly Glu Leu Val Gly Leu Thr Lys Phe
            20                  25                  30

Gln Val Gly Asp Ser Asn Gly Glu Tyr Tyr Glu Pro Thr Glu Glu Gln
        35                  40                  45

Thr Ala Leu Lys Asn Val Val Trp Glu Gly Asn Ile Asn Ser Leu Arg
    50                  55                  60

Ile Asp Glu Lys Asn Pro Asn Trp Ile Val Ile Glu Thr Ile Leu Pro
65                  70                  75                  80

Gly Thr Val Gly Gly Phe Met Ile Arg Glu Ala Ala Val Leu Asp Asn
                85                  90                  95

Glu Asn Asn Ile Ile Ala Ile Gly Lys Tyr Pro Glu Thr Tyr Lys Pro
            100                 105                 110
```

```
Arg Ala Glu Asp Gly Ser Ile Lys Asp Leu Val Val Lys Met Ile Leu
            115                 120                 125
Gln Leu Ser Asn Thr Ser Asn Val Thr Leu Glu Val Asp Pro Thr Leu
    130                 135                 140
Val Phe Val Thr Gln Lys Asp Ile Gln Asp Leu Asp Asp Lys Phe Asp
145                 150                 155                 160
Lys Asn Ile Lys Glu Ile Lys Val Lys Ile Gly Asp Thr Asp Ile Leu
                165                 170                 175
Thr Thr Asp Ser Lys Asp Leu Ser Gly Ala Ile Asn Glu Val Val Lys
            180                 185                 190
Lys Ile Glu Asn Ile Ser Phe Asp Asp Val Ile Ser Gly Gln Ile Gln
        195                 200                 205
Thr Asp Ile Ser Val Leu Lys Asn Ser Tyr Asn Lys Leu Ser Glu Lys
    210                 215                 220
Val Leu Asp Ile Leu Ile Tyr Leu Glu Leu Glu Ser Glu Val Thr Val
225                 230                 235                 240
Asp Glu Ala Gly Tyr Trp Tyr Asp Thr Leu Ala Asn Gly Asn Asn Ile
                245                 250                 255
Val Ala Ile Glu Gly Leu Lys Leu Asp Leu Asn Arg Lys Cys Ile Thr
            260                 265                 270
Gly Glu Ile Gly Asn Val Ile Phe Arg Asp Val Val Leu Pro Phe Ser
        275                 280                 285
Ala Asn Arg Val Arg Tyr Ile His Asp Met Asp Asn Asn Phe Val Glu
    290                 295                 300
Thr Lys Ser Ser Asn Thr Tyr Leu Lys Glu Gln Lys Asp Ile Thr Leu
305                 310                 315                 320
Ser Lys Tyr Ser Tyr Glu Ile Arg
                325

<210> SEQ ID NO 17
<211> LENGTH: 1725
<212> TYPE: PRT
<213> ORGANISM: Clostridium difficile

<400> SEQUENCE: 17

Met Lys Gln Asn Lys Leu Leu Gln Arg Gly Ala Tyr Phe Asn Asp Lys
1               5                   10                  15
Asn Ile Leu Ile Asp Asp Phe Asp Lys Arg Tyr Asn Asp Tyr Asp Phe
            20                  25                  30
Val Glu Phe Phe Thr Gly Ile Ser Asn Ser Thr Phe Gly Leu Lys Ser
        35                  40                  45
Asp Gly Asn Leu Tyr Ala Cys Gly Asp Asn Thr Gly Phe Gln Leu Gly
    50                  55                  60
Leu Gly Lys Asp Ser Ser Glu Arg Arg Met Phe Ser Lys Val Lys Ile
65                  70                  75                  80
Asp Asn Val Lys Tyr Val Ser Cys Gly Ser Lys His Ser Val Ala Val
                85                  90                  95
Thr Lys Asp Gly Phe Ala Tyr Gly Ala Gly Thr Ser Asn Val Gly Gln
            100                 105                 110
Leu Gly Val Ile Glu Ser Thr Val Tyr Tyr Glu Phe Thr Lys Leu Pro
        115                 120                 125
Ile Asp Asp Val Lys Thr Val Ala Cys Gly Tyr Asp Phe Thr Phe Val
    130                 135                 140
Leu Lys Asn Asp Gly Thr Leu Tyr Ser Ala Gly Leu Asn Ser Ser Gly
145                 150                 155                 160
```

```
Gln Leu Gly Leu Gly Asp Thr Asn Asn Arg Ala Thr Phe Thr Lys Val
                165                 170                 175

Asn Ile Asp Ser Val Lys Asp Val Val Thr Tyr Asn Gln Ser Val Phe
            180                 185                 190

Ile Ile Lys Met Asp Gly Thr Ala His Ala Cys Gly Leu Asn Ser Asn
        195                 200                 205

Gly Gln Leu Gly Ile Asn Ser Thr Leu Asn Lys Ser Val Phe Asn Lys
    210                 215                 220

Ile Glu Gly Met Asp Asn Val Lys Gln Ile Ala Cys Gly Ser Ser His
225                 230                 235                 240

Thr Ile Leu Ile Lys Asn Asp Gly Thr Met Tyr Thr Thr Gly Tyr Asn
                245                 250                 255

Gly Val Gly Gln Leu Gly Thr Gly Asn Asn Asn Ser Ile Val Phe
            260                 265                 270

Thr Leu Ser Ser Ile Asn Asn Val Lys Tyr Ala Ser Cys Gly Asn Asn
        275                 280                 285

His Thr Met Ile Leu Lys Tyr Asp Asn Thr Leu Phe Ser Thr Gly Gln
    290                 295                 300

Asn Asn Tyr Gly Gln Leu Ala Asn Ala Asn Lys Asp Val Ala Ser Arg
305                 310                 315                 320

Asn Thr Phe Ala Lys Val Asn Val Glu Asn Ile Lys Asp Ile Lys Cys
                325                 330                 335

Gly Ser Gln Phe Asn Phe Leu Ile Asn Gly Ser Lys Glu Ile Phe Val
            340                 345                 350

Ser Gly Cys Asn Leu Ala Gly Gln Leu Gly Ser Phe Phe His Thr Thr
        355                 360                 365

Phe Leu Tyr Glu Phe Ser Asn Val Gln Ser Ser Asn Leu Asp Asn Tyr
    370                 375                 380

Ser Gly Leu Leu Val Asn Asp Asp Tyr Leu Tyr Val Thr Lys Asp Asn
385                 390                 395                 400

Ser Glu Phe Leu Asn Val Lys Leu Ser Asp Asn Phe Gln Asp Tyr Lys
                405                 410                 415

Lys Ile Glu Leu Thr Asp Ser Asn Met Phe Ile Val Met Asn Asp Gly
            420                 425                 430

Thr Leu Tyr Ala Cys Gly Leu Asn Asn Tyr Gly Gln Leu Gly Leu Gly
        435                 440                 445

Asp Thr Val Asn Arg Ser Val Met Thr Lys Val Asp Ile Asp Asn Val
450                 455                 460

Leu Asp Ile Lys Gly Asn Gly Asn Ser Thr Phe Val Leu Lys Asn Asn
465                 470                 475                 480

Gly Thr Leu Tyr Ser Cys Gly Leu Asn Ser Asn Gly Gln Leu Gly Leu
                485                 490                 495

Arg Asp Glu Val Asn Arg Asn Ile Phe Thr Lys Ile Glu Ile Glu Asn
            500                 505                 510

Val Lys Asp Phe Cys Val Gly Ser Asn Tyr Val Ile Ala Leu Asn His
        515                 520                 525

Ser Lys Glu Val Tyr Gly Trp Gly Asn Asn Pro Tyr Asn Asn Ile Glu
    530                 535                 540

Lys Thr Ser Asn Tyr Pro Tyr Lys Gln Gly Ile Ser Asn Ile Glu Lys
545                 550                 555                 560

Ile Ala Ala Tyr Asp Tyr Ser Val Tyr Met Ile Asn Ser Glu Gly Lys
                565                 570                 575
```

-continued

```
Leu Tyr Val Ser Gly Tyr Asn Tyr Asn Tyr Gln Leu Gly Lys Gly Asn
            580                 585                 590

Asn Ser Asn Gln Ser Lys Ala Leu Val Ser Gln Cys Arg Thr Asn Ser
        595                 600                 605

Thr Ser Ser Thr Ser Asn Gly Leu Arg Thr Leu Pro Lys Ile Thr Asn
    610                 615                 620

Val Phe Pro Phe Tyr Asp Gly Cys Ala Ile Ile Asp Glu Gly Gly Tyr
625                 630                 635                 640

Val Tyr Leu Thr Gly Tyr His Gly Tyr Leu Arg Thr Leu Asn Ser Ser
                645                 650                 655

Pro Ser Ile Ser Asp Tyr Ser Arg Tyr Gly Thr Phe Ile Glu Ala Thr
            660                 665                 670

Asn Ser Asn His Asn Thr Tyr Phe Ile Gln Glu Thr Asp Phe Ser Gly
        675                 680                 685

Ile Glu Lys Val Ile Gly Met Ser Asn Asn Ile Leu Phe Phe Lys Lys
    690                 695                 700

Gly Ser Ser Tyr Ile Thr Gly Tyr Pro Lys Thr Phe Gly Ser Thr Ile
705                 710                 715                 720

Thr Gly His Arg Ser Tyr Thr Ser Ile Asn Ser Glu Ser Ser Asn Leu
                725                 730                 735

Gly Ser Asn Phe Ile Ile Tyr His Ser Asn Ser Lys Leu Tyr Gly Lys
            740                 745                 750

Gly Ile Ala Asn Ser Gly Gln Phe Gly Asn Ser Thr Asn Ile Asp Gly
        755                 760                 765

Thr Ser Asn Tyr Asp Thr Gly Leu Lys Asp Ile Lys Asp Ile Ile Val
    770                 775                 780

Lys Gly Asn Thr Val Val Val Asp Lys Asn Asn Ile Tyr Val
785                 790                 795                 800

Thr Gly Met Asn Gln Asn Asn Lys Leu Gly Ile Gly Glu Tyr Asn Asn
                805                 810                 815

Glu Pro Val Lys Lys Phe Thr Asn Ile Thr Glu Gln Ser Asn Ser Phe
            820                 825                 830

Ile Phe Met Asp Asp Ile Lys Glu Ile Thr Thr Ser Arg Asn Thr Met
        835                 840                 845

Phe Ile Val Lys Asn Asp Gly Thr Ala Tyr Ala Thr Gly Asn Asn Ser
    850                 855                 860

Ser Gly Gln Leu Gly Leu Gly Asp Thr Ile Asn Arg Asn Lys Phe Thr
865                 870                 875                 880

Gln Ile Asn Leu Asp Asn Ile Lys Lys Ile Ser Thr Ser Ile Asp Gly
                885                 890                 895

Asn Thr Thr Phe Ala Ile Arg Asn Asp Gly Thr Leu Tyr Ser Thr Gly
            900                 905                 910

Leu Asn Thr Lys Gly Gln Leu Gly Leu Gly Asp Ile Val Asn Arg Asn
        915                 920                 925

Thr Phe Thr Lys Val Asn Ile Gln Asn Val Arg Asp Val Val Leu Gly
    930                 935                 940

Thr Thr His Ser His Ala Ile Lys Asp Asp Asn Thr Leu Tyr Ser Cys
945                 950                 955                 960

Gly Glu Asn Thr His Gly Gln Leu Gly Leu Gly Ser Glu Ser Asn His
                965                 970                 975

Pro Asp Val Leu Thr Phe Thr Val Asn Asn Ile Thr Asn Val Arg Asp
            980                 985                 990

Val Tyr Cys Ser Asp Thr Thr Thr  Phe Ile Val Lys Asp  Thr Asn Ile
```

-continued

```
                995                 1000                1005
Ala Tyr Cys Cys Gly Tyr Asn Asn Asn Ser Gln Leu Gly Met Gly
            1010                1015                1020

Asn Thr Thr Asp Gln Tyr Ser Phe Ile Lys Cys Met Glu Asn Val
            1025                1030                1035

Lys Glu Val Ile Pro Asn Glu Ile Asn Thr Tyr Ile Ile Thr Ile
            1040                1045                1050

Tyr Asn Thr Ala Tyr Ser Thr Gly Leu Asn Thr Asp Tyr Cys Leu
            1055                1060                1065

Gly Leu Asn Ser Asn Ser Asn Gln Ser Ser Phe Ser Glu Ile Pro
            1070                1075                1080

Ile Ser Asn Val Val Lys Val Ala Pro Asn Arg Asn Asn Ala Val
            1085                1090                1095

Leu Leu Leu Thr Ser Glu Gly Asp Val Tyr Thr Ala Gly Lys Cys
            1100                1105                1110

Ser Asn Gly Ser Gly Thr Gly Ser Glu Thr Pro Glu Lys Ile Lys
            1115                1120                1125

Lys Ile Ala Ser Lys Ala Lys Asp Ile Gly Met Asn Tyr Arg Cys
            1130                1135                1140

Gly His Tyr Val Ser Asp Asn Gly Asp Leu Tyr Gly Thr Gly Phe
            1145                1150                1155

Asn Asn Asn Gly Gln Leu Gly Val Gly Asp Val Thr Lys Arg Asp
            1160                1165                1170

Thr Phe Ile Lys Thr Asn Thr Arg Val Lys Lys Ile Leu Pro Leu
            1175                1180                1185

Glu Tyr Ala Asn Ile Ala Ile Lys Asp Thr Asn Asp Ile Tyr Ile
            1190                1195                1200

Cys Gly Leu Asn Asn Tyr Gly Gln Leu Gly Val Gly Asn Arg Tyr
            1205                1210                1215

Asp Ser Arg Asn Asn Asp Asn Arg Ile Phe Asn Tyr Lys His Met
            1220                1225                1230

Asn Phe Val Met Gly Asp Leu Thr Ser Ile Lys Asn Arg His Asn
            1235                1240                1245

Phe Ile Leu Leu Asn Asn Lys Ile Val Ile Pro Thr Thr Lys Asp
            1250                1255                1260

Ile Asp Tyr Gly Leu Val Leu Gly Asn Leu Tyr Lys Gly Asp Leu
            1265                1270                1275

Tyr Thr Glu Leu Pro Tyr Glu Asp Ile Lys Glu Val Ser Ile Ser
            1280                1285                1290

Lys Thr His Ile Ile Ile Leu Leu Asn Asp Gly Thr Met Tyr Gly
            1295                1300                1305

Cys Gly Thr Asn Tyr His Gly Glu Leu Leu Gln Asp Leu Ser Ile
            1310                1315                1320

Asn Gln Val Asp Glu Phe Val Gln Ile Asn Val Ser Asp Val Lys
            1325                1330                1335

His Val Ser Cys Gly Asp Asn Phe Thr Tyr Phe Ile Lys Ser Asp
            1340                1345                1350

Asp Ser Leu Trp Ser Ile Gly Lys Asn Ser Glu Tyr Gln Leu Gly
            1355                1360                1365

Ile Gly His Asn Asn Pro Val Thr Glu Leu Gln Arg Ile Thr Thr
            1370                1375                1380

Ile Ser Ser Cys Lys Glu Val His Cys Gly Lys Asn Tyr Thr Leu
            1385                1390                1395
```

```
Val Val Thr Thr Gly Asn Glu Leu Phe Val Gln Gly Tyr Asn Asp
    1400                1405                1410

Lys Gly Ala Leu Gly Leu Gly Ser Asp Ser Glu Asn Thr Ile Ile
    1415                1420                1425

Lys Phe Phe Thr Lys Ala Leu Thr Asp Ile Arg Glu Ile Lys Ser
    1430                1435                1440

Tyr Gly Ser Asp His Ile Leu Val Leu Lys Asn Asp Asn Ser Val
    1445                1450                1455

Trp Val Thr Gly Lys Asn Arg Asp Val Tyr Lys Ile Glu Gln Pro
    1460                1465                1470

Val Glu Phe Leu Lys Glu Phe Thr Ile Val Pro Ile Ser Glu Asp
    1475                1480                1485

Val Asn Thr Val Lys Asp Val Leu Ala Thr Asp Asn Thr Leu Tyr
    1490                1495                1500

Ile Ile Ser Glu Val Gly Thr Thr Asn Ala Ala Ile Glu Ile Thr
    1505                1510                1515

Glu Lys Ser Ile Ser Ser Ile Lys Ile Lys Ile Gln Asp Pro Asn
    1520                1525                1530

Lys Asp Ile Ser Arg Ile Glu Met Leu Ile Asn Gly Glu Ser Val
    1535                1540                1545

Lys Ser Val Ser Asp Leu Thr Thr Glu Lys Ile Ser Phe Glu Val
    1550                1555                1560

Pro Pro Asp Lys Ile Lys Ile Gly Glu Asn Lys Ile Leu Phe Arg
    1565                1570                1575

Ala Tyr Cys Lys Gly Asp Asp Leu Tyr Ala Ser Leu Phe Ile Phe
    1580                1585                1590

Lys Glu Ser Thr Gly Asn Ser Ile Ile Lys Asp Ser Tyr Val Met
    1595                1600                1605

Ile Gly Asn Arg Met Tyr Lys Val Val Asn Thr Thr Ser Asn Glu
    1610                1615                1620

Gln Asp Ile Thr Ile Thr Leu Asp Arg Gly Leu Glu Glu Asp Leu
    1625                1630                1635

Asn Leu Gly Asp Pro Ile Tyr Gln Leu Ile Asn Lys Thr Lys Val
    1640                1645                1650

Gln Val Lys Ile Asn Lys Ser Asp Leu Phe Lys Asp Met Lys Leu
    1655                1660                1665

Val Glu Ile Lys Lys Ser Asp Ser Ser Tyr Gln Glu Ile Tyr Glu
    1670                1675                1680

Leu Glu Glu Ala Asn Ile Lys Ser Ala Gln Pro Lys Ile Ile Val
    1685                1690                1695

Glu Lys Gly Asp Lys Trp Thr Ala Ile Lys Arg Pro Ser Met Ile
    1700                1705                1710

Phe Arg Tyr Asp Ala Glu Asn Asn Glu Pro Gln Ala
    1715                1720                1725

<210> SEQ ID NO 18
<211> LENGTH: 98
<212> TYPE: PRT
<213> ORGANISM: Clostridium difficile

<400> SEQUENCE: 18

Met Gln Tyr Lys Asp Ile Ser Asp Ile Ser Ile Gly Gln Ala Lys Gln
1               5                   10                  15

Asp Asp Asp Ile Thr Asn Asn Phe Ile Ala Asn Ala Glu Ile Tyr Glu
```

```
                    20                  25                  30
Met Leu Leu Ser Gln Ser Ser Val Asn Glu Ala Ser Asn Ile Ser Thr
                35                  40                  45

Phe Ser Val Arg Lys Ser Gly Gly Glu Ser Gly Met Val Glu Val Tyr
            50                  55                  60

Val Ala Leu Ile Leu Arg Gly Arg Lys Thr Ile Glu Glu Val Pro Ala
65                  70                  75                  80

Val Ile Arg Glu Gln Val Arg Ile Arg Cys Lys Glu Leu Glu Ile Pro
                85                  90                  95

Val Glu

<210> SEQ ID NO 19
<211> LENGTH: 86
<212> TYPE: PRT
<213> ORGANISM: Clostridium difficile

<400> SEQUENCE: 19

Met Asp Lys Leu Ile Thr Glu Leu Ser Ser Leu Gly Ala Ile Gly Ile
1               5                   10                  15

Leu Cys Ala Leu Leu Phe Lys Asn Thr Met Gln Glu Lys Lys Glu Asp
                20                  25                  30

Arg Asp Met Tyr Lys Lys Thr Val Glu Asn Phe Ile Glu Leu Ser Thr
            35                  40                  45

Gln Gln Gln Glu Ile Asn Lys Asn Ile Leu Val Gln Met Gly Ile Met
        50                  55                  60

Lys Thr Asp Val Glu Glu Ile Lys Glu Asp Val Thr Asp Ile Lys Gly
65                  70                  75                  80

Met Leu Gln Asn Gly Val
                85

<210> SEQ ID NO 20
<211> LENGTH: 151
<212> TYPE: PRT
<213> ORGANISM: Clostridium difficile

<400> SEQUENCE: 20

Met Gly Leu Arg Asp Lys Phe Ala Gln Ser Phe Ala Arg Ser Lys Thr
1               5                   10                  15

Met Ser Gly Pro Glu Lys Lys Ala Asn Glu Ile Met Gly Lys Leu Leu
                20                  25                  30

Leu Lys Lys Ala Ile Leu Pro Ile Val Leu Met Phe Val Ile Ile
            35                  40                  45

Ala Gly Ala Met Leu Lys Ile Asn Ser Trp Val Thr Leu Gly Ile Asn
        50                  55                  60

Leu Val Ile Ala Val Gly Ala Phe Phe Tyr Ile Arg Asn Ser Ser Lys
65                  70                  75                  80

Lys Tyr Gln Asn Phe Lys Pro Tyr Val Gly Asn Leu Ile Ser Leu Glu
                85                  90                  95

Lys Lys Gly Lys Lys Glu Tyr Val Ala Ile Ile Lys Gln Gly Lys Leu
            100                 105                 110

Pro Val Lys Leu Gln Ile Ala Tyr Gly Gly Glu Asp Leu Glu His Val
        115                 120                 125

Lys Lys Asn Gln Met Val Gln Ile Ser Tyr Asn Pro Asp Ala Lys Ile
    130                 135                 140

Ala Ile Leu Val Asn Arg Gln
145                 150
```

<210> SEQ ID NO 21
<211> LENGTH: 139
<212> TYPE: PRT
<213> ORGANISM: Clostridium difficile

<400> SEQUENCE: 21

Met Asp Thr Leu Gly Glu Arg Ile Val Tyr Leu Arg Lys Ala Lys Asn
1               5                   10                  15

Leu Lys Gln Tyr Glu Leu Glu Glu Met Leu Gly Cys Asp Asn Leu Ser
            20                  25                  30

Lys Phe Glu Arg Asn Ile Arg Lys Pro Asn Tyr Glu Ile Leu Lys Ser
        35                  40                  45

Ile Ala Glu Ile Phe Asn Val Ser Val Asp Trp Leu Leu Asn Gly Asp
    50                  55                  60

Asn Leu Ser His Lys Ser Asp Leu Ile Cys Asp Ser Ser Ser Asn Tyr
65                  70                  75                  80

Pro Leu Asn Ser Ile Asn Ser Asn Glu Ile Lys Leu Leu Asn Asn Phe
                85                  90                  95

Arg Lys Leu Asn Asp Tyr Asp Lys Ala Lys Ile Glu Gly Met Ile Glu
            100                 105                 110

Leu Lys Leu His Glu Tyr Glu Lys Glu Lys Asp Leu Gly Lys Ile Glu
        115                 120                 125

Tyr Asn Lys Asn Lys Asp Glu Lys Ile Asp Lys
    130                 135

<210> SEQ ID NO 22
<211> LENGTH: 69
<212> TYPE: PRT
<213> ORGANISM: Clostridium difficile

<400> SEQUENCE: 22

Met Asp Ala Arg Lys Lys Trp Ile Pro Phe Leu Gly Val Gln Val Lys
1               5                   10                  15

Gln Arg Leu Ile Glu Leu Asn Met Thr Gln Arg Glu Leu Ala Lys Lys
            20                  25                  30

Ile Gly Val Asn Glu Asn Tyr Leu Ser Ala Ile Leu Asn Gly Arg Arg
        35                  40                  45

Thr Gly Lys Lys Tyr Lys Ser Ser Ile Tyr Gln Leu Leu Asn Ile Glu
    50                  55                  60

Tyr Ser Glu Asp Asp
65

<210> SEQ ID NO 23
<211> LENGTH: 132
<212> TYPE: PRT
<213> ORGANISM: Clostridium difficile

<400> SEQUENCE: 23

Val Asp Thr Leu Gly Lys Arg Ile Ala Tyr Leu Arg Asn Ser Lys Lys
1               5                   10                  15

Leu Thr Gln Arg Lys Leu Met Asp Ile Leu Lys Phe Glu Asn Leu Gly
            20                  25                  30

Lys Tyr Glu Thr Gly Asp Arg Lys Pro Asn Cys Asp Ile Leu Met Ser
        35                  40                  45

Ile Ala Asp Tyr Phe Asn Val Thr Thr Asp Trp Leu Leu Tyr Gly Lys
    50                  55                  60

```
Glu Lys Val Asn Val Asn Ser Ser Val Lys Glu Asp Lys Glu Asp Tyr
 65                  70                  75                  80

Leu His Val Thr Asn Asp Glu Met Met Ile Leu Asn Leu Tyr Arg Gln
                 85                  90                  95

Leu Asn Glu Arg Asp Lys Ile Lys Ile Glu Gly Ile Leu Glu Leu Lys
            100                 105                 110

Ile Ser Glu Tyr Lys Asp Leu Lys Lys His Ser Ser Asn Asn Asn Glu
        115                 120                 125

Asp Lys Met Val
    130

<210> SEQ ID NO 24
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
tttcttgaag accatcgaag caccaccacc accaccactg                          40

<210> SEQ ID NO 25
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25 tttttttgaag acaatcgaag ggcttcgccc tgtcgctcga c                        41
```

Note: above SEQ 25 line reproduced from image as "tttttttgaag acaatcgaag ggcttcgccc tgtcgctcga c"

```
<210> SEQ ID NO 26
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
ttccttgaag acctaatttg gggcaatccc gcaaggag                            38

<210> SEQ ID NO 27
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27 cccccttgaag acccaatttc gtatggcaat gaaagacgg                          39

<210> SEQ ID NO 28
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
aattgcggcc gcagctcgct agcggtacct cgaggatatc ttcgaagaag acacatccg    59
```

-continued

<210> SEQ ID NO 29
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
aattccggga tgcatgcctc taggatccgg cgcgcc 36

<210> SEQ ID NO 30
<211> LENGTH: 55
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
agctggcgcg ccggatccta gaggcatgca tcccggaatt cggatgtgtc ttctt 55

<210> SEQ ID NO 31
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
cgaagatatc ctcgaggtac cgctagcgag ctgcggccgc 40

<210> SEQ ID NO 32
<211> LENGTH: 8119
<212> TYPE: DNA
<213> ORGANISM: Clostridium difficile

<400> SEQUENCE: 32
ggccgcaata cccactacac cttcgtcatc tttaaattta agagttttta ctattgaata 60
ataaaggtat attccagtaa aaataatctt taaatacaag aaaaataaac tctttgggta 120
tattaaaaag ctaaaaagtg taaatataaa agcaagtaga gtacttatcc tgtaaaagaa 180
atctatttgt gtaatgtctt tatattttat cataaacacc gaatataaaa tgatgaaaat 240
aattgcgacg attgcatata tggtaaataa catattttca agagtaccat ttgaaattac 300
tatccactta taccacataa ttggccaaaa taatagtgct aagaacttaa aataattatc 360
aaacaacttt tctttataca ttcatcaaac aacctttctt aacaaaagca tatatttgtt 420
tttagaattt taaataatat gatatcatta ttatatatta atattgaatt tatagaaacc 480
aaaatttgtt aaaataaata tatagatttt actgttaagc cagttaaaat tactactatt 540
tttattatga aattggatca aatatgtaga aatacggcaa attagttaat attaaatatt 600
tattatttcc aagttgtaaa gactgttttt ttaatgataa aaattctaat cttttttgaa 660
agaaagtaat atccacatta agtatgtctg ccatttcata aacgcaagtg atgccagaat 720
taattatgtt tattatatct tcttcagtaa ttaagaactc acaagcccat tttaaggctt 780
tattttcgca cttatctata ataatttttg tataataatc gttataagag gatacatagt 840
atccaaggct agtgaaatga tgtccaagtt cttcagctaa gatggatgtc aatttttttg 900
agttttgttt taaattactg agtaatgata taattttaat accatgtttg tttatatata 960

```
gcccttctaa atcacctgca atataagtgg tataatgaat tattatctct tcttgagaag    1020
ctaattcaaa aagcttatcc aaattattca taaaaatccc cctaaaatag aatgtatgtt    1080
tgcctttaaa ttatattaaa agagcagaaa aatagactgc tcatcatatg gtttattttt    1140
ttttatattt atttagtaaa aattctatat aatcattaag ttgttcttgt gcttcttcag    1200
gtaactcttc atgtggattt tttctatgtg cagctactgt atcaatattt tccttaacta    1260
aggttcttcc aagaaggtaa tcaactgata cattaaatac atcagccaat ttgtttaaaa    1320
tgtgttcatc aggaaatctg ttttctgttt catagtaccc taagactctt tgggaaacgc    1380 ctacttttc tccaagttct ctttgagtca atccaaattc ctttctaagt tctcttaatc    1440
ttttggcaaa cattataaca ccaccttatg tatagattat aacaaattgt tctaaaaaat    1500
aaaactaata aaatataaaa gaatattttt tctaaaatct attgataaag aacaaatgat    1560
tctatataat ctaagtgtgg aagaacaaaa tattcttaat ggtaatggag gtataaaaca    1620
atgtttaaaa ataacttgaa atattataga aaatgcaaag gtatgacaca aattcaactt    1680
gccagaaagg ctggaattac aaatgactat atatctcaaa tagaagagg tataaaaaat     1740 cctggtcttc ttatggctaa gaagatttct agtattttag aacaaatat agaagaagtt     1800 tttttatac agttatagaa caatatgttc ttgaaagttg tgagattagt aaaaaactgt     1860
gcactaaaga gattattgta aatttgaagc taataataag tatataaaaa aggagaagta    1920
ctatggaaaa caaaaaagat atattattta agaaacaga tgaaagatta cataattata     1980
agtatttgga tataaagata aagaatatta atttggacat aaaaagatgt gagaatgaat    2040
actctggatg tggagcaatg gtatatacag aaaagactag taacacatat aacataagtt    2100
cttctgtgga aaatgaggtg ttaaaaagag aggaaagatt aagaaaatta aaatggaaa     2160 aagaagatat agaaatagaa aaagagaaga tagaaaatgc tctaacatgt ctaaatgata    2220
tagaaatgga atttttttaat cttttttata atagtaagac aaaaaacaat atgacatata    2280
tttctatgaa actacactta gatagaacat cttgctacaa tttaaagaaa aaaatgatat    2340
ttaaattgag tgagatatta taaaaaatat gacaacttta caacacttta tatacactat    2400
tgcaacacta ggcaataaaa tatgtgagat aatgttattg tgaaagaaat ccatattgaa    2460
ggaggtgata aattgaaaag aataatatta cctaaaaata tagaagatat ttgacaggaa    2520
taaatgagat gtatatttaa aaatgactta tatcatttat agtaagatta tcagattaag    2580
caagaatatt tagtgatagt gtggtgatta tttgcttaaa tacaaggaaa tattagaaac    2640
aattattgag attctcaaaa aaaactttac tgaaagtatt tttattgatg atgaaagtgt    2700
gcaaggctct gaagggtctt gttttttttgt aagtatacta tcagttattt gtacacctat   2760
aatgttaaat acgaataata aagatattgt tatctctata aaatacttac caaaccaca    2820 gtcaaagagt attagaatgt atgaaatttc agatgaatta aataagttat tcaacagaaa    2880
tataaaggta acagacagaa aattaaatat aacaaagcta gaacaaagta ttaaaaaaga    2940
agagtcaatt tatgtattga actttacaat tacactaaat tatctggata gtgtatatga    3000
agaagatgta gtatatgaaa atatggaaga aatcaattta aatttaggag agtgatagta    3060
tggctatagg attaccaagt atcaacatat catttaagga gctagctaca actgttaaag    3120
aacgttcagc tagaggaata attgcaatgg tgcttaaaga tgctaaggca ctaggtctta    3180
atgaaataca tgaaaagag gatataccag ttgatttatc tgctgaaaat aaagagtata     3240
taaatttagc tttgatggga aatgttaaca ctccaaataa attattagtt tatgtaatag    3300
```

```
aaggagaagc agatattcaa actgcattag atttttaga gactaaggaa tttaattatc    3360
tatgtatgcc aaaagcagta gaagctgata agactgctat aaaaaattgg ataattaaac    3420
ttagagatat agataaggtt aaggttaaag ctgtattagg aaaagttgta ggaaatcatg    3480
aagggataat taattttact acagaagatg tgttagttgg agaaaagaaa tacagtgttg    3540
atgagtttac aagtagggtg gctggactta tagcaggaac cctttaagt caatcagtaa     3600
cttatactaa gcttagtgat gtagttgata tacctaagat gacgaaagtt gatgcagaat    3660
caagggttaa taaggagag cttatactta ttaaggaagc aggggctata agaattgcaa     3720
gaggagtaaa ttctttaact gagttaacag aagaaaaagg agaaatgttc cagaaaataa    3780
aaatagttga cactttagat attatacata gtgacataag aaaggtgata atagatgact    3840
atataggaaa ggttactaac agttatgaca acaaatgttt attgatagta gctataaaaa    3900
gttatttaga agaattagaa aagtcagcac ttatagaatc tgattctact gttgaaatag    3960
attttgaagc acaaaaatcg tatttaaaat caaaaggagt agatttatct tatatgacat    4020
tacaagaaat aaaagaagct aacacaggtt ctaaagtatt tttaaaagca aaaataaaag    4080
tacttgatgc tatggaagat atagatttat caatagaaat ataggaggat tattaatatg    4140
gcaaatatgg aagctagaaa tgtaatgagt ggtacttggg gagaactttg gcttgatgga    4200
aacaaagtag cagaagtaaa gaagtttcaa gcaaagatgg aatttacaaa gaggatatt     4260
ataatagcag gtcaaatggg tactgataca agtatatgg gatataaagg aaaaggttca     4320
ataactctat accatgttag ttcaagaatg cacaagttaa ttggagaaaa gataaagaga    4380
ggttctgaac ctagatttgt tgctatatct aaattaaatg acccagattc ttatggagca    4440
gaaagaatag cagtaaaaaa tatagcattt gatgatttaa ctttagctga ttgggaggtt    4500
ggagtaaaag gagagataga agcaccttc acatttactg agtatgattt tcttgatata     4560
atttagttt atatttggtt ttatactgat atttagtaga tatatactta ataaatttag     4620
gtagttaata agtaaaaaag ttagttgatt gaatttgatt gataaaggag caaataataa    4680
tgaatgaaaa tggattatca aaaaatataa acatagtaga tttactttta aatgcagata    4740
cagaaaactt agaagaccca agtactatag ttgaacttaa gagattatca actatatttg    4800
ggcaggaatt taaagtaatg tgtagagctt taacaataag taaagatgaa gagatacaaa    4860
atacttgtct taaaattgat gaaaatatga aaacggatat agacttaccg gagatgcaga    4920
tgcttacaat tatagaaggt gtttgtgatt tggatggaaa gctttatttt aaaaataagg    4980
aactaatgga taaatttaag gctccaacac caaaagaatt ggcaagaaaa ctattattac    5040
caggtgaaat taccaaccta tatagaatac ttcaagatgt tatgggttat ggtaaaaatg    5100
cagtgataga agaggtaaaa aactaatagg gacggatacc aagactacaa taatgtacta    5160
ttattggaag aaaaaaggta taagaccgtc ccttttttat gcaatggata aaggcgaatt    5220
aaagcttatt gaagcttttt tcgccttaga aattgaggaa gaagttgaaa aaatgaaaca    5280
tggatatgga gtgtgtcctt tgacaggagg tggtatgtaa tgggaaatgt gagagaagaa    5340
ggtataaaata tgtatcttac agataattac acaccaaaaa tgaaccaaat tatatcagta    5400
actgataatt ttaggagagc aactgtggct gtttcacttt ccactaatgt aatggctagt    5460
agcataaaaa attctattgg aagtgcaagt agtagagtaa acagtttaaa ttcctcgtta    5520
agaaaagttc aaactactgc tagtagtgta agttcaacta tggcaaaatt aagttctagc    5580
ataaatgctg tttcaggagt tattggaagt ttaaatggaa gtattatgag actagcaata    5640
actatagcta tgattattga ttattttaat aagttgattc aaaagaaaaa tgagtttaat    5700
```

```
tcaaatatta tgattatatt aatatttaaa gctaaaagtg atgaagtaga aaaaactaaa    5760
aataaattac ttggaaattt aaaaaagatt ggtggcaaga tttggaatat cgtaataaaa    5820
gcaaaagata tgactaagag agtgataagt agtatcttgg gaaaattaaa acgagtagag    5880
aaacgtcctt atcaaggaag tattaatctt aaagatatgg taagtagtgc tatggctaga    5940
attttgccta agttaatgtt gtttaaaaat acttttggga gtggtgtaat agctataaaa    6000
gatatggcaa gtagcattat aagtaaagta tttcccaaat tgagattgtt tgcaggtaag    6060
gtatggagtg gtgcaatagc tgtaaaggat atggcaagtg gaatacttgg ttcgataaaa    6120
gggaagatat ctgatttgac aaatggtgct actataggtg tcgctgtgaa aaagggtgtt    6180
gacttacttg gtcaggaaca aaatcagaaa gttgttctag aaagtgtaat gaaaagaaat    6240
actggaaaaa ctagccaaaa agatgttgat aagtattatg acagtttagt aaatatggca    6300
aatgatacgc cttttgaccc tgaagatgtt gttgcaatgg gaactaaagc taaaatgatt    6360
agtaatatta ctggtggcaa aaaagaaaaa gatataactc aagctatggt agatgttaga    6420
gctttaaata tgaatacaag tagtgaacaa gatgtatcag cagcttttctt aagtgcagca    6480 aaaggaaata tggaatctct taatactctg gtaggagaaa attataaaac ttttgatgaa    6540
gcattggaag gcataagtgt aaagcagatg gggttagcta agaaatgag taatacaata    6600 ccaggtataa tatcaggagc tcaaacaagc attaacaatg gtttgaagag tattgttaaa    6660
ccttttgatg atatttttagg tcaaggacta agaaaataa aaactttttat agaaagtgga    6720 ttagggaatt tagctggctt atctgaaaaa atggctggta aaataggcaa tgtaatgaat    6780
ggtaagataa ttattggcaa caaatatgac cagatgcaat ctagaagtgt aaaaaatgga    6840
aaagagtttt ctgattctac tcaatatcga atttctaatg aggctgaaaa gcgtaaaatg    6900
atggttgaaa ataagcaaga acgttttgaa aatcatgcag caacaatgat agggaatgca    6960
ccaaaagcaa ttgttaacgc aggaagtaca ctattacaaa atattgattt tacagcatta    7020
atagattcac tacttccagt agtaaactta gtaaataatt tactagatag tataaacaat    7080
aaatcaccaa ttgcacaagg attaataagt atatttggta caatagtaac tacagcattc    7140
caactaatcg gacctgtagt tgaagctgtt agtcctatta tcacaagaat tttttacttttt    7200 ttaggtgaat atgcacctca aataaacaat tttatagaga cactgggtgt tatttggaaa    7260
actgtatggg agaccttagg acctctgttg gaaactggat ggaaaattat agagccaata    7320
ttgggagctt tttttaacat attagataaa gtatgtaaaa tagttaaaga tatatgcaaa    7380
tggtggcaaa ctatgattaa taagataaaa aatggaagca tcacaggaac agttttaaat    7440
ctagtggaaa agagtaaaaa aaattacaaa gataatccat atgctggaac aaaggctggt    7500
gattctggta aagcttattc aagtaagaaa ggtaataatg catttggatt gaactatgtt    7560
ccttataatg actatcaaac cagactccat gaaggtgaaa tggttttaac taaacaagaa    7620
gcaaatcaat atagaagcag aaaaaatggt ggaaatataa acatagctaa gttagctgat    7680
acaatagtga ttagagaaga agctgatata gaaaagataa catcaaaatt agttgcaagt    7740
atccaattgg cacagttagg gggtgtctta taatggaaat gtggcttaga caagcagaag    7800
atagatttag atttccagta tttccatctt cctttagtat taatgaaaaa gctgctgtaa    7860
actcttctag tatactcaaa ataggtgaag tagcaacttt tggtggtgta gctcttaaaa    7920
gcatttcaat atcaagtttt tttccaaata aagactacac tttctgtgac tatacaggtt    7980
ttccatcacc atatgattgt gtaaataaga tagaaaaatg gatgaaggaa ggttttatat    8040
```

```
taagatttac aattacggaa acaaatataa atatggaagt cataattgaa gggtttagtt    8100
atgaagaaag agatgggac                                                 8119

<210> SEQ ID NO 33
<211> LENGTH: 7686
<212> TYPE: DNA
<213> ORGANISM: Clostridium difficile

<400> SEQUENCE: 33
tcgagatgta tattttacat tagatttaaa agagtataaa agaataaaga taccaaaagt      60
aactccaaaa caataactat tatagataat aagttgtaag taactgctga tagaattaaa     120
tgaaaaggca ggtgattttt tattattaag atttgggtac acataaaaaa cggaagtata     180
tatgacataa ctgacatagt agacaaggta tcatggtcag gtgattataa atctccatca     240
aggacactag agttttcaat aatacaatca tcatttgatg taaatttcca acaaatcgat     300
ataccaatag ctagtacagt ctgtttctat gtagatgaga agaactctt tagaggaatg      360 ataattaata ggtctaaaga ttcaagcagt aatgaaatta gttttgtatc taagatatg      420 ggatttttac ttacacaaag tgaagtgtca tacaatttta aagataagtt agttgaagac     480
atagcaaagc aagtatttgc tgaaaatagg ctttcagttg gaacaatagc aaagaccaat     540
gtcaagtata caaagatgtt tataggagta atggttatg acacaataat gagtgcatat      600
acagaggcaa gtaaaagac aaagaaaaag tatatgatag aggctaattt agataagttt      660
aatgttattg aaaaggaac tgttacatta agtgttatgt ttgaagaggg atttaatatt     720
ataaatacca cctttttcgga gagcatggaa atgtaaaaaa ataagtaat agtggtagac     780 cagtatggaa gcaagattag cgaaaaaata gataatgaaa ttttaagga gtaaatgta      840 ataatgcaaa aagtaattca gcaacaagaa atcaagatg tagatattga tagcgagttt     900
aatgggatag aaaaaagctg ttctcttaaa ggttatggag atgtaagttg tataactggt     960
agaggagtaa aagttaaaga ttcttataca agcttgtag gactatttta tatagataca    1020
gacaaacata cttggcaaaa tggagaatat caaattgagc ttgaacttaa ttttcaaaat    1080
cttatggatg aaaagtcagc aggacaggat gaacctaagg aagaaagtaa tttaggggga    1140
gaagattatg caggaggaaa agagtttaca gcagaattta cagcttactg tcctagaaaa    1200
gaagaaggtg gagatacaga ttgtagaaag aaaaaaacttg acccatctaa aaaacttgcg    1260
ctgctcctat ggttggtaaa tatgagcaaa cttattatac aaaagagttt ttaaataaac    1320
atcctttatt gaactatgga gatgaaatac aggtaattac aggagtttct ggtcgtgatg    1380
gagtctataa agtaaatgac gtaggacctg caataactat agaaaaaaat ggaacatacc    1440
atatagatat tttatttgga aatgttgaag aagctagtaa atttggaaga agaaaaggaa    1500
aaattattat tggtggttat tctggtaatg tatctgataa agctaaaata gtaatatcag    1560
aggcaaaaaa acatctaggt aaaccttata atggggtgg aaatggacca agtagttttg    1620
actgttctgg tttaatggtc tactgtttta aaaaagttaa tgttagtttg ccaagaacgt    1680
caaatcaaca atctaaaaaa ggcaagaaag tagaacaaaa aaatcttcaa gcaggagatt    1740 tagtatttt tcataatcca gtcagccatg ttggattata tataggtaat ggagaatttt    1800
tacatgctcc acaaaaaggt gatgtagtta aaataagtaa gttaagtagt agaagagatt    1860
ttaatacagc taggagagta ttataaaagg atggtgatat aatggctaat ccaataaatg    1920
aatttatagg aataataaga gaagaaggaa agtatcataa tcaaccttct ttttattgg     1980 aaaattaaaa gtaaattacc agatttaaaa atagagacaa ataacatcat attagaaaaa    2040
```

```
gaagatattt tgatagatag ttggatgatt gatagacagc tagaaacatt tgacacagaa    2100
acaaatcaag aacaccagca tgaagtaaaa aatccttta tagataactt tgaatctggg     2160
gatatggtaa taatgtttag aataggcgaa aaatttgctg ttgtaagtaa gttggtgagc    2220
ttataatgag tacaatattt ccttttatag gtgtcccaga ggattatatc ttacctaaaa    2280
cagaagaatt gccaatcttt cgtgaagtgg catgggattt tgaaaagat gaacctattt     2340 tagaaaaagg tgactttaaa ataattgaaa aaaaagaag ccttaaaagt ttggatatac     2400
aagtgtataa agacaaatag atatgaacat gagatatact ctttagaata tgggacagag    2460 cttcagaac taataggaca aaatataca aaggtctta cagaaagtga agctagtaga       2520
ttcataaaag aggcccttct aataaatcca tatatattag aagtaaacgt aaaaagtgct    2580
aactttaaca gagacgtatt gagtgcaaat gtaaaagtat ccactatcta tggggaggtg    2640
gaaataaatg tatagtgacc agacatatga agtaataaaa aatagaactc ttgaaaatat    2700
taatcttgat atttataaag gagaaggttc ttttctaaac aacatggtat ctggaaataa    2760
tctagaactt tcgaagatat atctagaact ttcaaagata cataaaatgg cttttataca    2820
agacacatat aaccagtttc ttgataaaag agtcaatgaa tttggtgtat atagaaagtt    2880
aggtacagag tcaaatggag aagttgaatt tattggagag aaaggaactg taataaataa    2940
tggcacaata atatcatata gagatttact atttgtagta ataaaagatg taactattgg    3000
tagtgaagaa ggtgacaata gcccagttca agctctggaa gttggtaaga aatataattt    3060
acctacaaat tgtgaatttta aactagttga taatatatct ggagtaacaa agattactaa    3120
cacaagaagt tttgaaggtg gtacagatat agagacagat gaagaactaa aagaaagatt    3180
ttataaaatc caaagaaatc aagctacaag tggaaataaa gctcactatg aagaatgggc    3240
tttggaagta gatggagtct ataatgttaa ggtttatcca agatgggatg gtccaggaac    3300
agttaaggtc ttgatatttg gggaaaataa tcaagctgtt gatacagaaa cgattgaaag    3360
gtgtcagcaa catatagatg aagagaagcc tattggacca actataacag ttgtgacacc    3420
attaccaata gaaataagta taagtgcagt aatgaaacta gaagatggat atacattaga    3480
caatgtaaaa gaatctttcc tagaaagtat aaatacatac tttagagata ttagaggaga    3540
gataatctat acaaaagtca tgggaatact tataaatact actggtgtac acgatttaag    3600
taatctactt ataatggaa gtacagataa tataactatt aatgaagata aaatacctag    3660
tgtaacaact gttaatttta gtgaggtgga aaatcaatga agctaattga taaactacca    3720
tcatttgata gaaattacat tgtagaggag atacaaggtg catcgatac agaattaaat     3780 attcttaaag aagatattga tgatacccttt aaccaattat tgttgatac agcgacatgg    3840 ggattagata tgtgggaaga catactctgc attgaaaaaa aagaacttga ttttgacaca    3900
agacgtagca atataaaagc taaaatgaga agcagaggta ctagtactat tgaagttata    3960 aaagtatat gtgaggcata tacaaaatca gaaacagata taaagtttta tagtgatgaa    4020
tttacattcg tattgagttt tatagcaaat aactgtgact ataaaactct tttagattgt    4080
agcgagatga ttgaaagagt aaaacctgct cacttattac actatttaga accaataata    4140
ctagataaaa gtatggtcta ttgtggtgga ggtatggtat gtagtgaaga ggtaaaagtt    4200
catccatact ttgaaccaat tataaaatgt agtgctgttg taaactgtgg agctggaatg    4260
ttaagtagag aagaaataaa ggtttatcct ttaagcatta aatgcattga aaataattgt    4320
aagattaata tagctattgc aaatgataca ggcgtagaaa atgtagtagt ttatcctaaa    4380
```

```
tcggaggtgg tataattgga agaaaaattt tatataatat taaccaaaat tggtagagaa    4440
aaaatagcaa atgcaactgc actaggagag cttgttggat taaccaagtt tcaagttgga    4500
gatagtaatg gagaatatta tgagccaaca gaggaacaaa ctgctttaaa gaatgtagtt    4560
tgggaaggaa atataaattc tctaagaatt gatgaaaaaa atcctaattg gatagttata    4620
gagactattt taccaggaac agttggtgga tttatgataa gagaagctgc tgttctggat    4680
aatgagaata atataaatagc tatwggtaag tatccagaga cgtataagcc acgtgctgaa    4740
gatggcagta ttaaagattt ggttgtaaaa atgattttac aattgtccaa tacttcaaat    4800
gttacattag aagtagaccc gacgttggtt tttgtaactc aaaaggatat tcaagattta    4860
gatgataagt ttgataaaaa tataaaagaa ataaaagtaa aaattggaga tacagatata    4920
ttaactacag attctaaaga tttatcagga gctataaatg aggtagttaa aaaaatagaa    4980
aatatatctt ttgatgatgt tataagtggt caaatacaaa ctgatatatc agtattaaaa    5040
aatagctata acaaattatc tgaaaaagtg ctagatatat aatataccct agaattagag    5100
tcagaagtaa ctgtagatga ggctggttat tggtatgata cattagcaaa tggaaataac    5160
atagtagcta taagggct taagttagat ttaaatagaa aatgtataac aggtgaaatt    5220
ggtaatgtga tttttagaga tgtagtatta ccatttagtg caaatagagt tagatatata    5280
catgatatgg ataataactt tgttgagaca aaatctagta acacttattt aaaagaacaa    5340
aaagatataa ctctaagtaa atattcatat gaaataagt aaataaagga ggtagtacta    5400
ataatgaagc aaaataaact tttacagcgt ggtgcttatt ttaatgataa gaacatattg    5460
attgatgatt ttgataaaag atataatgat tatgattttg tagaatttt tactggtata    5520 agtaatagta cctttggttt aaaatcagat ggtaatttat atgcttgtgg cgataataca    5580
ggttttcaac taggacttgg aaaagattcg tcagagagaa ggatgtttag taaagtaaaa    5640
attgataatg taaatatgt atcttgtggt tcaaaacaca gtgtagcagt aactaaagat    5700
ggatttgcat atggagcagg aacaagtaat gtaggtcaat taggtgtaat tgagtctaca    5760
gtatattatg aatttactaa gctaccaata gatgatgtaa aaactgttgc atgtggttat    5820
gactttacat ttgtgcttaa aaatgatgga acattatatt cagcaggttt aaactcaagt    5880
ggtcaacttg gactaggtga tactaacaat agagctactt ttactaaagt aaatatagat    5940
agtgtgaaag atgtagtgac ttataatcaa tctgtattta tcataaaaat ggatgggaca    6000
gcacatgcat gtggattaaa ttcaaatggg cagttgggaa ttaatagtac tttaaataaa    6060 agtgtatttta ataaaataga aggtatggat aatgtaaaac agatagcgtg tggtagtagt    6120
catacaattc ttattaagaa tgatggaact atgtatacta caggctataa tggagttggt    6180
cagcttggta caggaaataa taataattca attgtattta ctctttctag tataaataat    6240
gttaagtatg cttcttgtgg aaataatcat actatgatat taaaatacga taatacactg    6300
tttagtacag gacaaaacaa ttatggtcaa ctagccaatg ccaataaaga tgtagcatca    6360
agaaatactt ttgctaaggt taatgtagaa aatataaaag atattaaatg tggttctcaa    6420
tttaattttt taataaatgg ttcaaaagag atatttgtat ctggctgtaa tttagcaggt    6480
caacttggtt cattttttca tacaactttt ctgtatgagt tttcaaatgt gcaatcttca    6540
aatttagata attattcagg tttattggtt aatgatgatt atttatatgt tacaaaggac    6600
aatagtgaat ttttaaatgt aaagttaagt gataattttc aagattataa gaagatagag    6660
ttaacagata gcaatatgtt tattgttatg aatgatggta cattgtatgc ttgtggttta    6720
aataattatg gacagttagg attgggagat actgttaaca ggtcagttat gactaaggtg    6780
```
gatatagata atgttttgga tataaaagga aacggaaact caacttttgt gcttaagaat 6840
aatggaacat tatattcatg tggtttaaat agtaatggac aattgggttt aagagatgaa 6900
gttaatagaa atatatttac aaaaatagaa atagagaatg taaaggattt ttgtgtagga 6960
agcaattatg tcatagcttt aaatcactca aaagaagtat atggatgggg aaataatcct 7020
tataataata tagaaaaaac ttctaattat ccatataagc agggaataag taatattgaa 7080
aagatagcag catatgatta ttctgtatat atgataaaca gtgaagggaa actatatgtt 7140
tctggataca attataatta tcaattaggt aaaggaaata atagtaacca aagcaaagca 7200
ttagtatctc aatgtagaac aaattcaaca tcttctacat caaatggact tagaacgtta 7260
cctaaaataa ctaatgtttt tcctttttat gatggttgtg caataattga cgaaggaggt 7320
tatgtttatt taacaggata tcatggatat ttaagaacat taaatagcag tccaagtata 7380
tctgattatt caagatatgg aacttttatt gaggctacaa attcaaatca taatacttat 7440
tttatacaag agactgattt tagtggaatt gaaaaagtaa tagggatgtc aaataatata 7500
ttatttttta agaaaggaag ttcatatatt actggatatc caaaaacatt tggctcaacc 7560
attactggac atagaagtta tactagtatt aattctgaga gttctaattt aggaagtaat 7620
tttataatat atcatagtaa ttccaagtta tatggaaaag ggattgctaa tagtgggcaa 7680
tttggg 7686

<210> SEQ ID NO 34
<211> LENGTH: 7020
<212> TYPE: DNA
<213> ORGANISM: Clostridium difficile

<400> SEQUENCE: 34
aattcaacaa atatagatgg cacaagtaac tatgatacag gattaaaaga cataaaagat 60
ataattgtaa aaggaaatac tgtagtagta gtagataaaa ataacaatat atatgtaaca 120
ggaatgaatc agaataacaa acttgggata ggggaatata acaacgaacc agtaaaaaaa 180
ttcacaaata taactgaaca atcaaactca tttatattta tggatgatat aaaagaaatt 240
acaacatcaa gaaatacaat gtttatagta aaaaatgatg gaacagccta tgccacagga 300
aataatagtt ctggacaatt aggattaggt gacacaataa atagaaataa gttcactcag 360
ataaaccttg ataatataaa gaaaatatca acaagtatag atggtaacac aacatttgca 420
attagaaatg atggaacact atactccaca ggattaaata ccaaaggaca actgggatta 480
ggtgatatag taaatagaaa tacatttacc aaagtaaaca tccaaaatgt aagagatgtt 540
gttttaggga ctactcactc gcatgcaatc aaagatgata acacattata ttcatgtgga 600
gaaaacactc atgggcaact gggcttagga agcgaaagca accatccaga cgtattgaca 660
tttactgtaa acaatataac taatgtaaga gatgtgtact gctcagatac aacaacattt 720
attgtaaagg acacaaacat tgcatattgt tgtggataca ataataattc acaactaggt 780
atgggaaata ctactgacca gtatagtttt ataaagtgta tggaaaatgt aaaagaagtt 840
ataccaaatg aaataaatac ctatataata acaatctata atactgcata tagtacaggt 900
ttaaatactg attattgctt aggtctaaat agtaatagca atcaaagttc attttctgaa 960
attccaattt caaatgtagt aaaagtagct ccaaacagaa ataatgcagt acttttactt 1020
acaagtgaag ggatgtata tactgcaggc aaatgtagta atggttcagg tacaggaagt 1080
gagactccag agaagattaa aaaaatagca tcaaaggcaa aggatattgg aatgaattat 1140

```
agatgtggac attatgtaag tgataatgga gacctatatg gtacaggttt taataataat    1200
ggacaattag gtgttggtga tgtaacaaaa agagatacat ttataaaaac caatacaaga    1260
gtaaagaaaa tacttccttt agaatatgca aatatagcaa taaagatac taatgatata     1320 tatatttgtg gattaaataa ctatggacaa ttaggtgttg gaaatagata cgatagtaga    1380
aataatgata atagaatatt taattataag catatgaatt ttgtaatggg tgatttgaca    1440
tctattaaaa acagacataa ctttatactt ctaaacaata agatagtgat acctaccaca    1500
aaagacatag attatggttt agtattagga aatttataca aaggagacct ttatactgag    1560
cttccatatg aagatataaa agaagtatct atttctaaga ctcatattat tatattactt    1620
aatgatggaa caatgtatgg atgtggtaca aactaccatg gagaattatt gcaagacttg    1680
tctataaatc aagtggatga atttgtgcag attaatgtat cagatgtaaa gcatgtttca    1740
tgtggagata actttactta ttttataaaa tctgatgata gtctttggtc tattggtaaa    1800
aattccgaat atcaattagg tataggtcac aataatccag ttactgaatt acaaagaatt    1860
acaactatat ctagctgtaa agaagtacat tgtggtaaaa actatacatt agtagtaact    1920
acaggtaatg aattatttgt acaaggatat aatgataagg gagctttagg attaggaagc    1980
gatagtgaaa atactataat taagttcttt acaaaagcac taacagacat aagagaaata    2040
aaatcttatg gaagtgacca tatattagta cttaaaaatg ataattcagt atgggttact    2100
ggaaaaaata gggatgtata taaaattgaa caaccagtaa attttttaaa agaatttact    2160
atagtaccta tttctgaaga tgtaaataca gtaaggatg tacttgcaac agacaataca    2220
ttatatatta tatcagaagt aggaacgaca aatgctgcta tagaaattac tgaaaaatca    2280
atttcatcaa ttaagataaa aatacaagac cctaataaag atataagtag aatagaaatg    2340 cttataaaatg gtgaaagtgt aaaatctgta agtgatttaa ctactgaaaa aatatccttt    2400
gaagtaccac cagataaaat taaaatagga gagaataaga tactatttag agcttattgt    2460
aaaggtgatg atttatatgc atctttattt attttttaaag agagtactgg aaattctata    2520
attaaagatt cttatgttat gataggtaat agaatgtaca aggtagttaa tacaacatct    2580
aatgaacaag atattacaat tacactagat agaggacttg aagaagattt aaatcttgga    2640
gaccctatat atcaattaat aaataaaact aaagttcaag taaaaataaa taaatctgac    2700
ttattcaaag acatgaaact agttgaaatc aaaaaatcag actcaagtta tcaagaaatc    2760
tatgaattag aagaagccaa cataaaaagt gctcagccta aaatcatagt agaaaaagga    2820
gataaatgga cagctataaa acgtccatct atgatttta gatatgatgc tgaaaacaac    2880
gagccacaag cttaaaatgg aggtgtaaaa attgttaaa ttcgataaaa ataaaataga    2940
acaaatcaaa caaggtagaa aagtagaaat gcagtataaa gacatttcag acataagtat    3000
aggtcaagca aagcaagatg atgatataac aaataatttt atagcaaatg cagaaatata    3060
tgagatgttg ttaagtcaaa gttctgtcaa tgaagcaagt aatataagca cttttagtgt    3120
aagaaaatct ggaggtgaga gtggaatggt agaagtatat gtagctttaa ttttaagagg    3180
cagaaaaaca atagaagaag taccagcagt aattagagag caagttagaa ttagatgtaa    3240
agaattagaa ataccagttg aatagtaaat ttagaataac tatgtattag ttattttttt    3300
tatgtaaagt acaaggtctt aactttaata agtaagcctt gtacttattt tttgttatat    3360
tagaaattgt atatatattt attatttatt caatctataa attaaaccta caatttaaag    3420
tacagaagat taaattgata atcctgaaaa tataatattg catgatgtaa gaatataaca    3480
aaaattaaag ctataagtat aaaaaattta gacaatagga ggctataatg gataaattaa    3540
```

```
taaccgaatt gagtagtctg ggggcaatag gtatactatg tgctctatta tttaaaaata    3600
ctatgcagga gaaaaagaa gatagagaca tgtataaaaa aactgtagaa aattttatag    3660
aattatctac acaacaacaa gaaataaaca aaaatatact tgttcaaatg ggaataatga   3720
aaacagatgt agaggaaatt aaggaagatg ttactgatat aaaaggtatg ttacaaaacg   3780
gtgtataaca tgaaagtagc agtagcacca gattatatat tattaggaaa agataaagta   3840
gtattgtaga tagtgcccta ttttattgag aaggatttta tattttaaaa tattaattaa   3900
aaaaagtaat aaaaataata tataaaaata acatataaaa attcaaaaag gagttaagct   3960
taaatttgat tagaaaaaat caattttaag acaactcctt tttttatta aattattgtc    4020 tattaaccaa aatagctatt ttagcatctg gattataact tatctgaacc atttgatttt   4080
tcttaacatg ttcaaggtct tcaccaccat aagctatttg taacttaact ggtaacttac    4140
cttgttttat aatagcaacg tactcttttt tacctttttc tctaaactaa tcaaattgcc   4200
aacataaggt ttaaagttct gatacttttt actagaattt cttatgtaga agaaagcacc    4260
aacagcaata actaaattta tgccaagtgt aacccaagaa ttgattttaa gcatagctcc   4320
agcgattatt atcacgaaca ttaaaacgat aggtaatata gctttcttaa gaagcaattt   4380
acccattatt tcattagcct ttttctcagg gccactcata gttttgatc tagcaaatga    4440 ttgcgcgaat ttgtctctta agcccatttt atcctcctaa ttttaataaa tatttagtta   4500
taataacgag atattacttg aaactaaaaa tttactacat ttatattatg tttgactttt   4560
gtataaataa ttcattcaa gtaaagcaaa atatactaat tattttatca taaaattata    4620
aaaaagaaaa taaatgaaat aaaaatatta gaacaaagaa atgatgtaaa atcgtatcaa   4680
aagcaacata aaaattattt atctattttc tcatctttat ttttgttata ctcaattttt    4740
cctaaatcct tctcttttc atattcatga agttttaatt caatcatacc ttctattttg   4800
gctttatcat aatcatttaa ctttctaaag ttgtttaaaa gctttatttc attagagttt   4860
atgctattaa gtggatagtt tgaggaggaa tcgcaaatta aatctgattt atgtgataga   4920
ttatctccat ttaatagcca gtctactgaa acattaaata tctcagctat agattttaat   4980
atttcataat ttggttttct aatgtttctc tcaaatttac ttaagttgtc acagcctaac   5040
atttcttcta gttcatattg tttaaggttt tttgcttttc tcaaataaac aattctttct   5100
cctaaagtat ccataaacac tctccattca attaatgtca aaaagacttt ttaagatgta    5160
aatagtttca aattaaaggt caaaatgaca taaaaaccat tgacttaagg tcaaaatgac   5220
tttataatta acttaatgat acgaatttac atcctaattt tagcacaaag taatcaaaaa   5280
atcttattta gtattaaata aatttatata cttaatatgt gtacatatta aaaatatata   5340
ctaaatagag ggggtgcgta agctaaagta atataaaagt aaatataaat cacttagaaa   5400
ggaagttgat aaatggatgc tcgaaaaaaa tggatacctt ttttgggagt gcaagtcaag   5460
caaagactta ttgaattaaa tatgactcaa agggaattag cgaagaaaat aggtgttaat    5520
gaaaactatt tgtcagctat tttaaatgga agaagaacag gtaaaaaata taaatcatca    5580
atttatcaat tacttaatat agaatattca gaagatgatt aataaatagt atataaagta   5640
ggtgaatatt cttgtgtgca aattggattc agatggggtt atagagtgtt gtagagcaat   5700
tgatgatttt attacagcac ttagtaatat aaaaagctta aatatggaaa gattaaatac    5760
tttaactaaa tattctagta catgttcaat ccttcttaaa gagggaatt atgaaggatg    5820 tacaattgtg tatagaaaga tgttggaaga attaaaaaca tgagtaatgc atttcttagg   5880
```

-continued

```
aatataaatt atacatagaa atgtattata tttttcaaag tacttaaact aaaatatgga    5940
taagataatc taaatattat aaatgtgctt gaaattagac tatacttgtt tttaaataat    6000
ccaatatcca tattttagta atatactaca aaaaagaag gttaatagat gatgtaaaat     6060
cgtatcaaat tatgtatgtt taaccattt tatcttcatt attattagag gaatgctttt     6120
ttaagtcttt atattcagat atcttaagtt caagtattcc ttctattttt attttatcac    6180
gttcgtttag ttgtctgtat agatttaata tcatcatttc atcattagta acatgtaagt    6240
aatcttcttt atcttctttt acactactat tgacatttac cttctcttta ccatagagaa    6300
gccagtcagt cgtaacatta aaataatcag ctattgacat tagtatatca caattaggtt    6360
ttctatctcc tgtttcatac ttgcctaagt tttcaaattt taaaatatcc ataagtttgc    6420
gctgagtaag ttttttggag tttctcaaat aagcaattct ttttcctaaa gtatccacaa    6480
aatacactcc tttcttttta tgagtaatgt ctaaatgaca tttgaaatta aaaatatata    6540
aatttataat ataaaactac taattaaag tctaaatgac attttgctta aattaatatg     6600
ctcataatat gattttaaca tattatagtt gaaaatatat ggtttatttt gatttgtata    6660
tataacaata gattaattg ttataaaaat gtaaaggggt gtatgaatag attgtataaa     6720
tttatttcga taaactaaga ttgcttttg attgtctgta aaagagaaaa agattaagat     6780
aaaaatagta ttatattgta atttatatta atcaattaca aagatttat gaatttattc     6840 tttagggtaa aatatttaag aataagataa atttacaata taatactata acactctttt    6900
atctagtttt attttctttta tagaacaata atattataaa tgctagtaga tttacacaga   6960
atactgttat atacatctgt ttgaatcctg agtttagagt agattgtagt gtggatccgg    7020
```

<210> SEQ ID NO 35
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35 tttttttgcgg ccgcaatacc cactacacct tcgtc                              35

<210> SEQ ID NO 36
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
tatacatctc gagtcccatc tctttc                                         26

<210> SEQ ID NO 37
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
gaagaaagag atgggactcg agatg                                          25

<210> SEQ ID NO 38

```
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
cttgtgccat ctatatttgt tg                                              22

<210> SEQ ID NO 39
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
ggaaaaggga ttgctaatag tg                                              22

<210> SEQ ID NO 40
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
tcccccggat ccacactaca atctactcta aactcagg                             38

<210> SEQ ID NO 41
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
ggcgcgccac tagtaccggt gccatggcgg ccgc                                 34

<210> SEQ ID NO 42
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
agctgcggcc gccatggcac cggtactagt ggcgcgccca tg                        42

<210> SEQ ID NO 43
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
ttccttggtc tcacgcgaac aaaattctcc agtcttc                              37

<210> SEQ ID NO 44
<211> LENGTH: 37
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
ttccttggtc tcaggccgtc gcgactaaga aaatgcc                              37

<210> SEQ ID NO 45
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
gtgagcggat aacaattccc                                                20

<210> SEQ ID NO 46
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
agattgtagt gtggatccgg                                                20

<210> SEQ ID NO 47
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
tccttcggcg cgcctcaaat ttaagcttaa ctcc                                34

<210> SEQ ID NO 48
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
tttagggact actcactcgc                                                20

<210> SEQ ID NO 49
<211> LENGTH: 1773
<212> TYPE: PRT
<213> ORGANISM: Clostridium difficile

<400> SEQUENCE: 49

Met Lys Arg Thr Lys Leu Leu Gln Arg Gly Asn Phe Phe Gly Asp Lys
1               5                   10                  15

Asn Met Val Val Asp Glu Phe Asp Glu Gly Tyr Asp Asn Tyr Asp Phe
                20                  25                  30

Ile Asn Phe Phe Thr Gly Cys Cys Asn Tyr Thr Phe Gly Leu Lys Asn
            35                  40                  45
```

-continued

```
Asn Asn Ile Leu Tyr Gly Cys Gly Asp Asn Ser Asn Phe Gln Leu Gly
 50                  55                  60

Leu Gly Glu Asp Asn Thr Thr Arg Lys Leu Phe Thr Lys Ile Pro Asn
 65                  70                  75                  80

Ile Ser Thr Asn Ile Lys Lys Val Ala Cys Gly Glu Ser His Ala Val
                 85                  90                  95

Ile Leu Thr Ser Asp Gly Glu Leu Leu Val Ala Gly Ile Asn Thr Asp
                100                 105                 110

Gly Gln Met Gly Leu Gly Leu Glu Lys Val Gly Lys Thr Val Ser Thr
                115                 120                 125

Phe Glu Lys Val Pro Glu Ile Lys Gly Val Lys Asp Ile Ala Cys Gly
130                 135                 140

Leu Gln Ser Thr Tyr Leu Leu Tyr Asn Asp Gly Thr Leu Tyr Val Ala
145                 150                 155                 160

Gly Asn Asn Leu Tyr Gly Gln Leu Gly Leu Gly Thr Asn Gly Ala Ser
                165                 170                 175

Ala Asn Val Asn Thr Phe Thr Lys Val Asp Val Asp Asn Val Lys Ala
                180                 185                 190

Val Phe Ser Tyr Asn Lys Ser Ala Phe Ile Ile Lys Asn Asp Asn Lys
                195                 200                 205

Cys Tyr Ser Thr Gly Phe Asn Gln Gly Gln Leu Gly Leu Gly Asp
210                 215                 220

Lys Asn Asn Arg Asp Leu Phe Ser Leu Val Ser Ile Asn Asp Val Lys
225                 230                 235                 240

Thr Ile Ala Cys Gly Ser Glu His Thr Val Leu Met Thr Tyr Asn Asn
                245                 250                 255

Asp Ile Tyr Gly Cys Gly Lys Glu Lys Cys Phe Gly Asn Ala Leu Gln
                260                 265                 270

Ser Ser Leu Phe Thr Lys Ile Glu Glu Val Asn Ile Lys Thr Ile Ala
                275                 280                 285

Cys Gly His Gly Asn Thr Met Leu Ile Asp Asn Lys Gly Thr Leu Lys
                290                 295                 300

Val Ala Gly Asn Asn Asp Ile Tyr Gln Leu Gly Ile Ala Asn Tyr Ser
305                 310                 315                 320

Glu Asn Ile Asp Asn Ser Phe Ile Asp Leu Lys Asn Ile Val Ala Lys
                325                 330                 335

Asn Ile Phe Ile Gly Leu Ser His Ser Ile Leu Ile Asp Ser Asn Asn
                340                 345                 350

Asp Ser Tyr Cys Thr Gly Asp Asn Thr Tyr Gly Gln Leu Gly Ser Phe
                355                 360                 365

Phe Asp Asp Met His Ile Val Glu Phe Lys Lys Met Asp Ser Glu Lys
                370                 375                 380

Tyr Ser Tyr Ser Asn Tyr Ile Asn Leu Ile Lys Ser Glu Asp Lys Leu
385                 390                 395                 400

Thr Leu Leu Lys Glu Glu Met Glu Ile Lys Asp Ile Glu Leu Pro Leu
                405                 410                 415

Asp Ile His Ser Val Arg Asp Val Val Phe Ser Pro Tyr Cys Thr Leu
                420                 425                 430

Val Ile Leu Gly Asn Gly Asp Val Tyr Gly Leu Gly Asn Asn Arg Tyr
                435                 440                 445

Lys Gly Met Gly Ser Asp Leu Pro Ser Gln Leu Asn Glu Leu Thr Lys
                450                 455                 460

Leu Ser Ile Ser Asn Val Lys Ser Ile Val Ala Ser Lys Asn Ile Ser
```

```
            465                 470                 475                 480

Gly Gly Ile Phe Tyr Ile Lys Asn Asp Asp Thr Cys Tyr Tyr Ser Gly
                        485                 490                 495

Pro Asn Ser Asn Ser Ile Ala Gly Val Leu Pro Ser Asn Ser Asp Val
                        500                 505                 510

Phe Lys Lys Ile Ser Ile Asp Asn Val Lys Val Val Ile Asn Thr
                        515                 520                 525

Asp Leu Ser Asn Trp Phe Ser Leu Ile Val Thr Asn Asn Lys Gln Ile
                    530                 535                 540

Tyr Thr Ser Gly Lys Ser Ser Tyr Val Asn Gly Leu Ser Asn Ala
        545                 550                 555                 560

Leu Ile Ser Gln Tyr Thr Glu Ile Ser Leu Ser Asn Val Thr Asp Ala
                            565                 570                 575

Tyr Ser Ser Tyr Asn Ala Thr Phe Ile Val Val Asp Glu Lys Lys Val
                        580                 585                 590

Tyr Ala Thr Gly Ile Asn Thr Asn Tyr Leu Leu Gly Phe Ser Thr Ser
                    595                 600                 605

Asp Gly Ser Asn Val Asn Leu Gly Leu Leu Ser Asp Trp Tyr Tyr Ile
                610                 615                 620

Asn Ile Ser Gly Ser Ser Tyr Ser Arg Val Ser Cys Thr Asn Asn Ile
        625                 630                 635                 640

Thr Lys Ile Asn Asn Ile Ile Ile Tyr Glu Tyr Val Thr Val Phe Cys
                        645                 650                 655

Thr Asn Ile Gly Ser Phe Leu Thr Gly Tyr His Gly Thr Ser Trp Thr
                        660                 665                 670

Lys Pro Thr Asp Ser Ser Tyr Arg Val Gln Tyr Gln Gly Ile Ser Tyr
                    675                 680                 685

Ala Gly Tyr Leu Asp Ser Tyr Ile Tyr Asn Tyr Pro Thr Arg Cys
                690                 695                 700

Thr Gln Ser Ser Ser Thr Thr Phe Ala Tyr Leu Tyr Asn Gly Glu
        705                 710                 715                 720

Ser Ser Ser Asn Leu Lys Asn Val Asn Pro Asp Asn Leu Leu Ile Ser
                        725                 730                 735

Gly Gly Ser Ser Tyr Ile His Gln Tyr Gly Arg Asn Tyr Leu Asn Asn
                        740                 745                 750

Gln Ser Ser Asn Ile Ala Ala Ser Asn Ile Asn Ser Gly Pro Ile
                    755                 760                 765

Thr Ser Asp Lys Ala Ile Phe Leu Tyr Lys Ala Leu Leu Tyr Leu Ser
        770                 775                 780

Ser Asn Thr Leu Tyr Gly Phe Gly Asn Ile Ser Glu Ser Ala Lys Glu
        785                 790                 795                 800

Leu Asp Val Ser Asp Thr Gln Asp Gly Tyr Asn Ala Thr Asn Tyr Lys
                        805                 810                 815

Lys Val Met Lys Asn Ile Lys Asn Ile Phe Ile Pro Pro Tyr Asp Leu
                        820                 825                 830

Ser Arg Asp Lys Thr Arg Phe Ala Ile Leu Thr Asp Lys Ser Leu Phe
                    835                 840                 845

Ile Cys Gly Tyr Asn Ser Lys Gly Thr His Gly Ile Ser Val Asn Ser
                    850                 855                 860

Ser Leu Asn Leu Asn Asn Lys Ile Asn Tyr Asn Lys Lys Asn Ser Ser
        865                 870                 875                 880

Ser Glu Ile Ser Ser Asn Ile Gln Glu Ile Tyr Ser His Ser Lys Ser
                        885                 890                 895
```

-continued

Thr Tyr Leu Leu Thr Asn Asn Asn Met Leu Tyr Ser Val Gly Leu Asn
             900                 905                 910
Asp Val Gly Gln Leu Gly Val Gly Asp Glu Ile Asn Arg Lys Val Phe
             915                 920                 925
Thr Lys Ile Asn Ile Asp Asn Ile Lys Ser Ile Asn Val Asn Arg Phe
             930                 935                 940
Thr Asp Asn Ser Lys His Ala Phe Ala Ile Lys Asn Asp Asn Thr Cys
945                 950                 955                 960
Tyr Ala Val Gly Leu Asn Asn Ser Gly Gln Leu Gly Ile Gly Asp Asn
                 965                 970                 975
Val Asn Arg Asn Ile Phe Thr Lys Ile Asn Val Glu Asn Val Lys Tyr
             980                 985                 990
Val Ala Val Tyr Gly Asn Thr Ser Leu Leu Leu Thr Asn Asp Gly Leu
             995                1000                1005
Leu Tyr Gly Ala Gly Asn Asn Gly Lys Gly Gln Leu Gly Leu Gly
        1010                1015            1020
Asp Thr Thr Ser Arg Asn Ile Phe Thr Arg Ile Pro Ile Asn Gly
        1025                1030            1035
Val Arg Asp Val Tyr Leu Cys Asn Asp Val Ser Ile Ile Val Lys
        1040                1045            1050
Asn Asp Asn Thr Cys Tyr Val Cys Gly Leu Val Asn Gly Tyr Phe
        1055                1060            1065
Gly Phe Thr Glu Gly Ser Ile Ser Thr Phe Thr Lys Ile Asn Ile
        1070                1075            1080
Glu Asn Val Lys Ser Val Val Thr Ala Gly Ser Glu Ala Thr Phe
        1085                1090            1095
Phe Ile Thr Asn Asp Asn Met Ile Tyr Thr Thr Gly Lys Lys Glu
        1100                1105            1110
Arg Val Phe Phe Ser Thr Glu Thr Asn Asp Ile Lys Gly Ile Arg
        1115                1120            1125
Val Ile Asn Asn Ile Ile Asn Ala Lys Lys Ile Val Val Asn Gly
        1130                1135            1140
Tyr Thr Ser Ala Ile Leu Thr Asn Asp Asn Lys Leu Phe Val Gly
        1145                1150            1155
Gly Leu Ser Gly Tyr Gly Ser Ile Ala Asn Asn Asn Thr Asn
        1160                1165            1170
Ser Val Glu Asp Val Lys Asp Val Phe Val Thr Ala Asn Asn Thr
        1175                1180            1185
Leu Tyr Ile Asp Asn Asn Asn Leu Ile Ser Ser Gly Arg Asp
        1190                1195            1200
Thr Tyr Gly Ile Ser Asp Glu Ser Tyr Arg Asp Met Ser Val Pro
        1205                1210            1215
Tyr Tyr Lys Val Ser Ile Lys Lys Asp Val Asp Thr Val Phe Ser
        1220                1225            1230
Ser Tyr Asn Thr Ile Phe Ile Lys Asp Ile Tyr Gly Lys Phe Tyr
        1235                1240            1245
Ser Ser Thr Arg Asp Asn Arg Tyr Asn His Leu Gly Ile His His
        1250                1255            1260
Arg Tyr Asp Asn Asp Lys Asn Glu Ala Leu Glu Gly Ser Leu His
        1265                1270            1275
Ser Tyr Phe Lys Thr Asp Asn Thr Ser Asp Lys Ile Val Phe Asn
        1280                1285            1290

```
Lys Lys Asn Glu Lys Leu Val Met Phe Asn Asp Lys Tyr Ile Lys
1295                1300                1305

Thr Asn Asn Lys Tyr Ile Asn Tyr Lys Asn Ile Phe Lys Asp Asn
1310                1315                1320

Phe Lys Tyr Thr Ser Ile Ile Leu Pro Phe Glu Val Ser Asp Ile
1325                1330                1335

Asp Ile Ser Lys Thr His Ser Leu Ala Val Ala Lys Asp Gly Lys
1340                1345                1350

Leu Tyr Gly Ile Gly Ser Asn Ser Tyr Lys Glu Ile Asn Gln Thr
1355                1360                1365

Leu Glu Asp Ile Glu Leu Leu Thr Leu Thr Glu Val Asn Ile Ser
1370                1375                1380

Asp Val Lys Lys Val Ala Cys Gly Asp Asn Tyr Ser Tyr Ile Ile
1385                1390                1395

Lys Thr Asp Asn Thr Leu Trp Ser Tyr Gly Lys Asn Thr Glu Tyr
1400                1405                1410

Gln Leu Gly Val Gly His Asn Asn Asp Val Arg Glu Leu Gln Lys
1415                1420                1425

Val Thr Gly Leu Pro Ser Val Lys Asp Ile Ser Ile Tyr Asn Ser
1430                1435                1440

Met Thr Leu Val Leu Thr Asn Glu Gly Glu Leu Tyr Ala Gln Gly
1445                1450                1455

Tyr Asn Thr Asn Gly Leu Phe Gly Leu Gly Glu Ser Glu Lys Asp
1460                1465                1470

Lys Ile Ile Arg Thr Phe Thr Lys Val Leu Thr Asn Val Lys Glu
1475                1480                1485

Ile Lys Ser His Asn Asp Asp His Ile Leu Val Ile Lys Asn Asp
1490                1495                1500

Asn Ser Leu Trp Ile Thr Gly Lys Asn Lys Ser Met Tyr Lys Ile
1505                1510                1515

Ser Ile Ser Ile Thr Asp Leu Tyr Glu Phe Thr Lys Ile Pro Ile
1520                1525                1530

Pro Glu His Leu Asn Asp Ile Leu Asp Ile Glu Leu Ser Asp Asp
1535                1540                1545

Thr Ile Tyr Met Ile Thr Lys Val Asp Thr Ser Lys Ala Ser Ile
1550                1555                1560

Glu Ile Val Glu Lys Ser Ile Ser Gln Val Arg Val Val Val Gln
1565                1570                1575

Asp Pro Asn Asn Val Ile Glu Lys Leu Glu Met Phe Ile Asn Asp
1580                1585                1590

Glu Leu Ile Ser Thr Lys Thr Asn Leu Glu Ile Asn Ser Ile Ile
1595                1600                1605

Phe Glu Ile Pro Gln Asn Lys Ile Val Leu Gly Glu Asn Lys Ile
1610                1615                1620

Leu Ile Lys Ala Ser Ser Pro Thr Gly Asp Leu Tyr Ser Ser Met
1625                1630                1635

Phe Ile Phe Lys Ser Glu Thr Gly Leu Lys Val Lys Lys Asp Ser
1640                1645                1650

Ile Leu Met Ile Asn Asn Lys Val Tyr Ser Ile Ile Asn Ile Thr
1655                1660                1665

Glu Asn Asn Thr Asp Leu Ile Val Thr Leu Asn Glu Gly Leu Lys
1670                1675                1680

Asp Asp Met Met Glu Asn Asn Pro Ile Tyr Gln Leu Ile Asn Lys
```

```
    1685                1690                1695

Thr Lys  Val Gln Val Lys Ile  Asn Lys Ser Asp Leu  Phe Lys Asp
    1700                1705                1710

Met Lys  Leu Val Glu Ile Lys  Lys Ser Asp Ser Ser  Tyr Gln Glu
    1715                1720                1725

Ile Tyr  Glu Leu Glu Glu Ala  Asn Ile Lys Ser Ala  Gln Pro Lys
    1730                1735                1740

Ile Ile  Val Glu Lys Gly Asp  Lys Trp Thr Ala Ile  Lys Arg Pro
    1745                1750                1755

Ser Met  Ile Phe Arg Tyr Asp  Ala Glu Asn Asn Glu  Pro Gln Ala
    1760                1765                1770

<210> SEQ ID NO 50
<211> LENGTH: 1743
<212> TYPE: PRT
<213> ORGANISM: Clostridium difficile

<400> SEQUENCE: 50

Met Lys Gln Asn Lys Leu Leu Gln Arg Gly Ala Tyr Phe Asn Asp Lys
1               5                   10                  15

Asn Ile Leu Ile Asp Asp Phe Asp Lys Arg Tyr Asn Asp Tyr Asp Phe
            20                  25                  30

Val Glu Phe Phe Thr Gly Ile Ser Asn Ser Thr Phe Gly Leu Lys Ser
        35                  40                  45

Asp Gly Asn Leu Tyr Ala Cys Gly Asp Asn Thr Gly Phe Gln Leu Gly
    50                  55                  60

Leu Gly Lys Asp Ser Ser Glu Arg Arg Met Phe Ser Lys Val Lys Ile
65                  70                  75                  80

Asp Asn Val Lys Tyr Val Ser Cys Gly Ser Lys His Ser Val Ala Val
                85                  90                  95

Thr Lys Asp Gly Phe Ala Tyr Gly Ala Gly Thr Ser Asn Val Gly Gln
            100                 105                 110

Leu Gly Val Ile Glu Ser Thr Val Tyr Tyr Glu Phe Thr Lys Leu Pro
        115                 120                 125

Ile Asp Asp Val Lys Thr Val Ala Cys Gly Tyr Asp Phe Thr Phe Val
    130                 135                 140

Leu Lys Asn Asp Gly Thr Leu Tyr Ser Ala Gly Leu Asn Ser Ser Gly
145                 150                 155                 160

Gln Leu Gly Leu Gly Asp Thr Asn Asn Arg Val Thr Phe Thr Lys Val
                165                 170                 175

Asn Ile Asp Ser Val Lys Asp Val Val Thr Tyr Asn Gln Ser Val Phe
            180                 185                 190

Ile Ile Lys Met Asp Gly Thr Ala His Ala Cys Gly Leu Asn Ser Asn
        195                 200                 205

Gly Gln Leu Gly Ile Asn Ser Thr Leu Asn Lys Ser Val Phe Asn Lys
    210                 215                 220

Ile Glu Gly Met Asp Asn Val Lys Gln Ile Ala Cys Gly Ser Ser His
225                 230                 235                 240

Thr Ile Leu Ile Lys Asn Asp Gly Thr Met Tyr Thr Thr Gly Ser Asn
                245                 250                 255

Gly Tyr Gly Gln Leu Gly Thr Gly Asn Asn Asn Ser Ile Val Phe
            260                 265                 270

Thr Leu Ser Ser Ile Asn Asn Val Lys Tyr Ala Ser Cys Gly Asn Asn
        275                 280                 285
```

His Thr Met Ile Leu Lys Tyr Asp Asn Thr Leu Phe Ser Thr Gly Gln
290                 295                 300

Asn Asn Tyr Gly Gln Leu Ala Asn Ala Asn Lys Asp Val Ala Ser Arg
305                 310                 315                 320

Asn Thr Phe Val Lys Val Asn Val Glu Asn Ile Lys Asp Ile Lys Cys
                325                 330                 335

Gly Ser Gln Phe Asn Phe Leu Ile Asn Gly Ser Lys Glu Ile Phe Val
                340                 345                 350

Ser Gly Cys Asn Leu Ala Gly Gln Leu Gly Ser Phe His Thr Thr
            355                 360                 365

Phe Leu Tyr Glu Phe Ser Lys Val Gln Ser Ser Asn Leu Asp Asn Tyr
370                 375                 380

Ser Gly Leu Leu Val Asn Asp Asp Tyr Leu Tyr Val Thr Lys Asp Asn
385                 390                 395                 400

Ser Glu Phe Leu Asn Val Lys Leu Ser Asp Asn Phe Gln Asp Tyr Lys
                405                 410                 415

Lys Ile Glu Leu Thr Asp Asn Asn Met Phe Ile Val Met Asn Asp Gly
                420                 425                 430

Thr Leu Tyr Ala Cys Gly Leu Asn Asn Tyr Gly Gln Leu Gly Leu Gly
            435                 440                 445

Asp Thr Val Asn Arg Ser Val Met Thr Lys Val Asp Ile Asp Asn Val
450                 455                 460

Leu Asp Ile Lys Gly Asn Gly Asn Ser Thr Phe Val Leu Lys Asn Asn
465                 470                 475                 480

Gly Thr Leu Tyr Ser Cys Gly Tyr Asn Ser Ser Gly Ile Leu Gly Leu
                485                 490                 495

Lys Asp Asn Thr Asn Arg Asn Ile Phe Thr Lys Ile Glu Ile Glu Asn
                500                 505                 510

Ile Lys Glu Phe Cys Val Glu Ser Asn Tyr Ile Val Ala Leu Asn His
            515                 520                 525

Ser Lys Glu Leu Tyr Gly Trp Gly Asn Gln Ser Tyr Ile Val Tyr Gly
530                 535                 540

Asp Asn Arg Asn Tyr Pro Tyr Lys Asp Thr Arg Val Ser Asn Val Glu
545                 550                 555                 560

Lys Ile Ala Thr Trp Ser Asp Thr Leu Tyr Ile Leu Asp Ser Thr Gly
                565                 570                 575

Ala Thr Lys Thr Ile Gly Tyr Ser Tyr Asn Gly Ser Gly Gly Tyr Pro
                580                 585                 590

Ala Pro Ser Ser Ser Thr Tyr Arg Glu Gly Tyr Ile Asn Lys
            595                 600                 605

Asn Thr Ser Tyr Arg Thr Leu Glu Phe Tyr Asn Thr Ser Lys Thr Lys
610                 615                 620

Leu Val Asn Leu Phe Ala Phe Tyr Asn Gly Cys Val Phe Val Asp Glu
625                 630                 635                 640

Asn Gly Leu Ala Tyr Cys Ile Gly Glu Asn Asn Ile Asn Phe Arg Gly
                645                 650                 655

Gly Ser Thr Thr Asn Glu Asn Asn Ser Leu Arg Phe Ile Asn Asn Ser
                660                 665                 670

Gly Val Tyr Tyr Thr Asn Thr Asp Gly Thr Asp Tyr Thr Cys Tyr Gln
            675                 680                 685

Trp Thr Tyr Lys Leu Ile Arg Cys Ser Ile Phe Asp Ser Pro Gln Asn
690                 695                 700

Ile Ile Gly Asn Ser Lys Asn Ile Leu Tyr Leu Ser Lys Asn Asn Ser

-continued

```
705                 710                 715                 720
Thr Phe Lys Cys Thr Gly Asn Cys Ile Thr Tyr Gly Ile Asn Ser Gln
                725                 730                 735
Asn Trp Tyr Ser Tyr Phe Ser Asp Ser Ser Asn Gly Ala Ile Ala Leu
                740                 745                 750
Gly Asn Glu Phe Ile Leu Lys Asn Tyr Ser Gly Glu Cys Leu Leu Lys
                755                 760                 765
Gly Tyr Gly Lys Ala Thr Asn Gly Glu Phe Gly Asn Ser Thr Asn Ile
                770                 775                 780
Ser Ser Ile Ser Asn Tyr Asp Thr Gly Leu Lys Asp Ile Lys Asp Ile
785                 790                 795                 800
Ile Val Lys Asn Asn Thr Val Val Val Asp Lys Asn Asn Asn Ile
                805                 810                 815
Tyr Val Thr Gly Ala Asn Gln Phe Asn Lys Leu Gly Ile Gly Glu Tyr
                820                 825                 830
Asn Asn Gln Pro Ile Arg Lys Phe Thr Asn Ile Thr Glu Gln Ser Asn
                835                 840                 845
Ser Phe Ile Phe Met Asp Asp Ile Lys Glu Ile Thr Thr Ser Arg Asn
850                 855                 860
Thr Met Phe Ile Val Lys Asn Asp Gly Thr Ala Tyr Ala Thr Gly Asn
865                 870                 875                 880
Asn Ser Ser Gly Gln Leu Gly Leu Gly Asp Thr Ile Asn Arg Asn Lys
                885                 890                 895
Phe Thr Gln Ile Asn Leu Asp Asn Ile Lys Lys Ile Ser Thr Ser Ile
                900                 905                 910
Asp Gly Asn Thr Thr Phe Ala Ile Arg Asn Asp Gly Thr Leu Tyr Ser
                915                 920                 925
Thr Gly Leu Asn Thr Lys Gly Gln Leu Gly Leu Gly Asp Ile Val Asn
                930                 935                 940
Arg Asn Thr Phe Thr Lys Val Asn Ile Gln Asn Val Arg Asp Val Val
945                 950                 955                 960
Leu Gly Thr Thr His Ser His Ala Ile Lys Asp Asp Asn Thr Leu Tyr
                965                 970                 975
Ser Cys Gly Glu Asn Thr His Gly Gln Leu Gly Leu Gly Ser Glu Ser
                980                 985                 990
Asn His Pro Asp Val Leu Thr Phe Thr Val Asn Asn Ile Thr Asn Val
                995                 1000                1005
Arg Asp Val Tyr Cys Ser Asp Thr Thr Thr Phe Ile Val Lys Asp
     1010                1015                1020
Thr Asn Ile Ala Tyr Cys Cys Gly Tyr Asn Asn Ser Gln Leu
     1025                1030                1035
Gly Met Gly Asn Thr Thr Asp Gln Tyr Ser Phe Ile Lys Cys Met
     1040                1045                1050
Glu Asn Val Lys Glu Val Ile Pro Asn Glu Ile Asn Thr Tyr Ile
     1055                1060                1065
Ile Thr Ile Tyr Asn Thr Ala Tyr Ser Thr Gly Leu Asn Thr Asp
     1070                1075                1080
Tyr Cys Leu Gly Leu Asn Ser Asn Ser Asn Gln Ser Ser Phe Ser
     1085                1090                1095
Glu Ile Pro Ile Ser Asn Val Lys Val Ala Pro Asn Arg Asn
     1100                1105                1110
Asn Ala Val Leu Leu Leu Thr Ser Glu Gly Asp Val Tyr Thr Ala
     1115                1120                1125
```

-continued

```
Gly Lys Cys Ser Asn Gly Ser Gly Thr Gly Ser Glu Thr Pro Glu
    1130                1135                1140

Lys Ile Lys Lys Ile Ala Ser Lys Ala Lys Asp Ile Gly Met Asn
    1145                1150                1155

Tyr Arg Cys Gly His Tyr Val Ser Asp Asn Gly Asp Leu Tyr Gly
    1160                1165                1170

Thr Gly Phe Asn Asp Cys Gly Gln Leu Gly Val Gly Asn Val Thr
    1175                1180                1185

Lys Arg Asp Thr Phe Ile Lys Thr Asn Thr Arg Val Lys Lys Ile
    1190                1195                1200

Leu Pro Leu Glu Tyr Ala Asn Ile Ala Ile Lys Asp Thr Asn Asp
    1205                1210                1215

Ile Tyr Ile Cys Gly Leu Asn Asn Tyr Gly Gln Leu Gly Val Gly
    1220                1225                1230

Asn Arg Tyr Asp Ser Arg Asn Asn Asp Asn Arg Ile Phe Asn Tyr
    1235                1240                1245

Lys His Met Asn Phe Val Met Gly Asp Leu Thr Ser Ile Lys Asn
    1250                1255                1260

Arg His Asn Phe Ile Leu Leu Asn Asn Lys Ile Val Ile Pro Thr
    1265                1270                1275

Thr Lys Asp Ile Asp Tyr Gly Leu Val Leu Gly Asn Leu Tyr Lys
    1280                1285                1290

Gly Asp Leu Tyr Thr Glu Leu Pro Tyr Glu Asp Ile Lys Glu Val
    1295                1300                1305

Ser Ile Ser Lys Thr His Ile Ile Ile Leu Leu Asn Asp Gly Thr
    1310                1315                1320

Met Tyr Gly Cys Gly Thr Asn Tyr His Gly Glu Leu Leu Gln Asp
    1325                1330                1335

Leu Ser Ile Asn Gln Val Asp Glu Phe Val Gln Ile Asn Val Ser
    1340                1345                1350

Asp Val Lys His Val Ser Cys Gly Asp Asn Phe Thr Tyr Phe Ile
    1355                1360                1365

Lys Ser Asp Asp Ser Leu Trp Ser Ile Gly Lys Asn Ser Glu Tyr
    1370                1375                1380

Gln Leu Gly Ile Gly His Asn Asn Pro Val Thr Glu Leu Gln Arg
    1385                1390                1395

Ile Thr Thr Ile Ser Ser Cys Lys Glu Val His Cys Gly Lys Asn
    1400                1405                1410

Tyr Thr Leu Val Val Thr Thr Ser Asn Glu Leu Phe Val Gln Gly
    1415                1420                1425

Tyr Asn Asp Lys Gly Ala Leu Gly Leu Gly Ser Asp Ser Glu Asn
    1430                1435                1440

Thr Ile Ile Lys Phe Phe Thr Lys Ala Leu Thr Asp Ile Arg Glu
    1445                1450                1455

Ile Lys Ser Tyr Gly Ser Asp His Ile Leu Val Leu Lys Asn Asp
    1460                1465                1470

Asn Ser Val Trp Val Thr Gly Lys Asn Arg Asp Val Tyr Lys Ile
    1475                1480                1485

Glu Gln Pro Val Glu Phe Leu Lys Glu Phe Thr Ile Val Pro Ile
    1490                1495                1500

Ser Glu Asp Val Asn Thr Val Lys Asp Val Leu Ala Thr Asp Asn
    1505                1510                1515
```

```
Thr Leu Tyr Ile Ile Ser Glu Val Gly Thr Asn Ala Ala Ile
    1520                1525                1530

Glu Ile Thr Glu Lys Ser Ile Ser Ser Ile Lys Ile Lys Ile Gln
    1535                1540                1545

Asp Pro Asn Lys Asp Ile Ser Arg Ile Glu Met Leu Ile Asn Gly
    1550                1555                1560

Glu Ser Val Lys Ser Val Ser Asp Leu Ile Thr Glu Lys Ile Ser
    1565                1570                1575

Phe Glu Val Pro Pro Asp Lys Ile Lys Ile Gly Glu Asn Lys Ile
    1580                1585                1590

Leu Phe Arg Ala Tyr Cys Lys Gly Asp Asp Leu Tyr Ala Ser Leu
    1595                1600                1605

Phe Ile Phe Lys Glu Ser Thr Gly Asn Ser Ile Ile Lys Asp Ser
    1610                1615                1620

Tyr Val Met Ile Gly Asn Arg Met Tyr Lys Val Val Asn Thr Thr
    1625                1630                1635

Ser Asn Glu Gln Asp Ile Thr Ile Thr Leu Asp Arg Gly Leu Glu
    1640                1645                1650

Glu Asp Leu Asn Leu Gly Asp Pro Ile Tyr Gln Leu Ile Asn Lys
    1655                1660                1665

Thr Lys Val Gln Val Lys Ile Asn Lys Ser Asp Leu Phe Lys Asp
    1670                1675                1680

Met Lys Leu Val Glu Ile Lys Lys Ser Asp Ser Ser Tyr Gln Glu
    1685                1690                1695

Ile Tyr Glu Leu Glu Glu Ala Asn Ile Lys Ser Ala Gln Pro Lys
    1700                1705                1710

Ile Ile Val Glu Lys Gly Asp Lys Trp Thr Ala Ile Lys Arg Pro
    1715                1720                1725

Ser Met Ile Phe Arg Tyr Asp Ala Glu Asn Asn Glu Pro Gln Ala
    1730                1735                1740

<210> SEQ ID NO 51
<211> LENGTH: 1773
<212> TYPE: PRT
<213> ORGANISM: Clostridium difficile

<400> SEQUENCE: 51

Met Lys Arg Thr Lys Leu Leu Gln Arg Gly Asn Phe Phe Gly Asp Lys
1               5                   10                  15

Asn Met Val Val Asp Glu Phe Asp Glu Gly Tyr Asp Asn Tyr Asp Phe
                20                  25                  30

Ile Asn Phe Phe Thr Gly Cys Cys Asn Tyr Thr Phe Gly Leu Lys Asn
            35                  40                  45

Asn Asn Ile Leu Tyr Gly Cys Gly Asp Asn Ser Asn Phe Gln Leu Gly
        50                  55                  60

Leu Gly Glu Asp Asn Thr Thr Arg Lys Leu Phe Thr Lys Ile Pro Asn
65                  70                  75                  80

Ile Ser Thr Asn Ile Lys Lys Val Ala Cys Gly Glu Ser His Ala Val
                85                  90                  95

Ile Leu Thr Ser Asp Gly Glu Leu Leu Val Ala Gly Ile Asn Thr Asp
            100                 105                 110

Gly Gln Met Gly Leu Gly Leu Glu Lys Val Gly Lys Thr Val Ser Thr
        115                 120                 125

Phe Glu Lys Val Pro Glu Ile Lys Gly Val Lys Asp Ile Ala Cys Gly
    130                 135                 140
```

-continued

```
Leu Gln Ser Thr Tyr Leu Leu Tyr Asn Asp Gly Thr Leu Tyr Val Ala
145                 150                 155                 160

Gly Asn Asn Leu Tyr Gly Gln Leu Gly Leu Gly Thr Asn Gly Ala Ser
                165                 170                 175

Ala Asn Val Asn Thr Phe Thr Lys Val Asp Val Asp Asn Val Lys Ala
            180                 185                 190

Val Phe Ser Tyr Asn Lys Ser Ala Phe Ile Ile Lys Asn Asp Asn Lys
        195                 200                 205

Cys Tyr Ser Thr Gly Phe Asn Asn Gln Gly Gln Leu Gly Leu Gly Asp
    210                 215                 220

Lys Asn Asn Arg Asp Leu Phe Ser Leu Val Ser Ile Asn Asp Val Lys
225                 230                 235                 240

Thr Ile Ala Cys Gly Ser Glu His Thr Val Leu Met Thr Tyr Asn Asn
                245                 250                 255

Asp Ile Tyr Gly Cys Gly Lys Glu Lys Cys Phe Gly Asn Ala Leu Gln
                260                 265                 270

Ser Ser Leu Phe Thr Lys Ile Glu Glu Val Asn Ile Lys Thr Ile Ala
            275                 280                 285

Cys Gly His Gly Asn Thr Met Leu Ile Asp Asn Lys Gly Thr Leu Lys
        290                 295                 300

Val Ala Gly Asn Asn Asp Ile Tyr Gln Leu Gly Ile Ala Asn Tyr Ser
305                 310                 315                 320

Glu Asn Ile Asp Asn Ser Phe Ile Asp Leu Lys Asn Ile Val Ala Lys
                325                 330                 335

Asn Ile Phe Ile Gly Leu Ser His Ser Ile Leu Ile Asp Ser Asn Asn
                340                 345                 350

Asp Ser Tyr Cys Thr Gly Asp Asn Thr Tyr Gly Gln Leu Gly Ser Phe
            355                 360                 365

Phe Asp Asp Met His Ile Val Glu Phe Lys Lys Met Asp Ser Glu Lys
        370                 375                 380

Tyr Ser Tyr Ser Asn Tyr Ile Asn Leu Ile Lys Ser Glu Asp Lys Leu
385                 390                 395                 400

Thr Leu Leu Lys Glu Glu Met Glu Ile Lys Asp Ile Glu Leu Pro Leu
                405                 410                 415

Asp Ile His Ser Val Arg Asp Val Val Phe Ser Pro Tyr Cys Thr Leu
            420                 425                 430

Val Ile Leu Gly Asn Gly Asp Val Tyr Gly Leu Gly Asn Asn Arg Tyr
        435                 440                 445

Lys Gly Met Gly Ser Asp Leu Pro Ser Gln Leu Asn Glu Leu Thr Lys
    450                 455                 460

Leu Ser Ile Ser Asn Val Lys Ser Ile Val Ala Ser Lys Asn Ile Ser
465                 470                 475                 480

Gly Gly Ile Phe Tyr Ile Lys Asn Asp Asp Thr Cys Tyr Tyr Ser Gly
                485                 490                 495

Pro Asn Ser Asn Ser Ile Ala Gly Val Leu Pro Ser Asn Ser Asp Val
            500                 505                 510

Phe Lys Lys Ile Ser Ile Asp Asn Val Lys Lys Val Val Ile Asn Thr
        515                 520                 525

Asp Leu Ser Asn Trp Phe Ser Leu Ile Val Thr Asn Asn Lys Gln Ile
    530                 535                 540

Tyr Thr Ser Gly Lys Ser Ser Ser Tyr Val Asn Gly Leu Ser Asn Ala
545                 550                 555                 560
```

```
Leu Ile Ser Gln Tyr Thr Glu Ile Ser Leu Ser Asn Val Thr Asp Ala
                565                 570                 575

Tyr Ser Ser Tyr Asn Ala Thr Phe Ile Val Val Asp Glu Lys Lys Val
            580                 585                 590

Tyr Ala Thr Gly Ile Asn Thr Asn Tyr Leu Leu Gly Phe Ser Thr Ser
        595                 600                 605

Asp Gly Ser Asn Val Asn Leu Gly Leu Leu Ser Asp Trp Tyr Tyr Ile
    610                 615                 620

Asn Ile Ser Gly Ser Ser Tyr Ser Arg Val Ser Cys Thr Asn Asn Ile
625                 630                 635                 640

Thr Lys Ile Asn Asn Ile Ile Tyr Glu Tyr Val Thr Val Phe Cys
                645                 650                 655

Thr Asn Ile Gly Ser Phe Leu Thr Gly Tyr His Gly Thr Ser Trp Thr
                660                 665                 670

Lys Pro Thr Asp Ser Ser Tyr Arg Val Gln Tyr Gln Gly Ile Ser Tyr
            675                 680                 685

Ala Gly Tyr Leu Asp Ser Tyr Ile Tyr Asn Tyr Pro Thr Arg Cys
        690                 695                 700

Thr Gln Ser Ser Ser Thr Thr Phe Ala Tyr Leu Tyr Asn Gly Glu
705                 710                 715                 720

Ser Ser Ser Asn Leu Lys Asn Val Asn Pro Asp Asn Leu Leu Ile Ser
                725                 730                 735

Gly Gly Ser Ser Tyr Ile His Gln Tyr Gly Arg Asn Tyr Leu Asn Asn
            740                 745                 750

Gln Ser Ser Asn Asn Ile Ala Ala Ser Asn Ile Asn Ser Gly Pro Ile
        755                 760                 765

Thr Ser Asp Lys Ala Ile Phe Leu Tyr Lys Ala Leu Leu Tyr Leu Ser
770                 775                 780

Ser Asn Thr Leu Tyr Gly Phe Gly Asn Ile Ser Glu Ser Ala Lys Glu
785                 790                 795                 800

Leu Asp Val Ser Asp Thr Gln Asp Gly Tyr Asn Ala Thr Asn Tyr Lys
                805                 810                 815

Lys Val Met Lys Asn Ile Lys Asn Ile Phe Ile Pro Pro Tyr Asp Leu
            820                 825                 830

Ser Arg Asp Lys Thr Arg Phe Ala Ile Leu Thr Asp Lys Ser Leu Phe
    835                 840                 845

Ile Cys Gly Tyr Asn Ser Lys Gly Thr His Gly Ile Ser Val Asn Ser
    850                 855                 860

Ser Leu Asn Leu Asn Asn Lys Ile Asn Tyr His Lys Lys Asn Ser Ser
865                 870                 875                 880

Ser Glu Ile Ser Ser Asn Ile Gln Glu Ile Tyr Ser His Ser Lys Ser
                885                 890                 895

Thr Tyr Leu Leu Thr Asn Asn Asn Met Leu Tyr Ser Val Gly Leu Asn
            900                 905                 910

Asp Val Gly Gln Leu Gly Val Gly Asp Glu Ile Asn Arg Lys Val Phe
        915                 920                 925

Thr Lys Ile Asn Ile Asp Asn Ile Lys Ser Ile Asn Val Asn Arg Phe
    930                 935                 940

Thr Asp Asn Ser Lys His Ala Phe Ala Ile Lys Asn Asp Asn Thr Cys
945                 950                 955                 960

Tyr Ala Val Gly Leu Asn Ser Gly Gln Leu Gly Ile Gly Asp Asn
                965                 970                 975

Val Asn Arg Asn Ile Phe Thr Lys Ile Asn Val Glu Asn Val Lys Tyr
```

-continued

```
                980             985              990
Val Ala Val Tyr Gly Asn Thr Ser  Leu Leu Leu Thr Asn  Asp Gly Leu
           995              1000             1005
Leu Tyr Gly Ala Gly Asn Asn  Gly Lys Gly Gln Leu  Gly Leu Gly
      1010              1015              1020
Asp Thr Thr Ser Arg Asn Ile  Phe Thr Arg Ile Pro  Ile Asn Gly
      1025              1030              1035
Val Arg Asp Val Tyr Leu Cys  Asn Asp Val Ser Ile  Ile Val Lys
      1040              1045              1050
Asn Asp Asn Thr Cys Tyr Val  Cys Gly Leu Val Asn  Gly Tyr Phe
      1055              1060              1065
Gly Phe Thr Glu Gly Ser Ile  Ser Thr Phe Thr Lys  Ile Asn Ile
      1070              1075              1080
Glu Asn Val Lys Ser Val Val  Thr Ala Gly Ser Glu  Ala Thr Phe
      1085              1090              1095
Phe Ile Thr Asn Asp Asn Met  Ile Tyr Thr Thr Gly  Lys Lys Glu
      1100              1105              1110
Arg Val Phe Phe Ser Thr Glu  Thr Asn Asp Ile Lys  Gly Ile Arg
      1115              1120              1125
Val Ile Asn Asn Ile Ile Asn  Ala Lys Lys Ile Val  Val Asn Gly
      1130              1135              1140
Tyr Thr Ser Ala Ile Leu Thr  Asn Asp Asn Lys Leu  Phe Val Gly
      1145              1150              1155
Gly Leu Ser Gly Tyr Gly Ser  Ile Ala Asn Asn Asn  Asn Thr Asn
      1160              1165              1170
Ser Val Glu Asp Val Lys Asp  Val Phe Val Thr Ala  Asn Asn Thr
      1175              1180              1185
Leu Tyr Ile Asp Asn Asn Asn  Asn Leu Ile Ser Ser  Gly Arg Asp
      1190              1195              1200
Thr Tyr Gly Ile Ser Asp Glu  Ser Tyr Arg Asp Met  Ser Val Pro
      1205              1210              1215
Tyr Tyr Lys Val Ser Ile Lys  Lys Asp Val Asp Thr  Val Phe Ser
      1220              1225              1230
Ser Tyr Asn Thr Ile Phe Ile  Lys Asp Ile Tyr Gly  Lys Phe Tyr
      1235              1240              1245
Ser Ser Thr Arg Asp Asn Arg  Tyr Asn His Leu Gly  Ile His His
      1250              1255              1260
Arg Tyr Asp Asn Asp Lys Asn  Glu Ala Leu Glu Gly  Ser Leu His
      1265              1270              1275
Ser Tyr Phe Lys Thr Asp Asn  Thr Ser Asp Lys Ile  Val Phe Asn
      1280              1285              1290
Lys Lys Asn Glu Lys Leu Val  Met Phe Asn Asp Lys  Tyr Ile Lys
      1295              1300              1305
Thr Asn Asn Lys Tyr Ile Asn  Tyr Lys Asn Ile Phe  Lys Asp Asn
      1310              1315              1320
Phe Lys Tyr Thr Ser Ile Ile  Leu Pro Phe Glu Val  Ser Asp Ile
      1325              1330              1335
Asp Ile Ser Lys Thr His Ser  Leu Ala Val Ala Lys  Asp Gly Lys
      1340              1345              1350
Leu Tyr Gly Ile Gly Ser Asn  Ser Tyr Lys Glu Ile  Asn Gln Thr
      1355              1360              1365
Leu Glu Asp Ile Glu Leu Leu  Thr Leu Thr Glu Val  Asn Ile Ser
      1370              1375              1380
```

-continued

```
Asp Val Lys Lys Val Ala Cys Gly Asp Asn Tyr Ser Tyr Ile Ile
    1385            1390                1395

Lys Thr Asp Asn Thr Leu Trp Ser Tyr Gly Lys Asn Thr Glu Tyr
    1400            1405                1410

Gln Leu Gly Val Gly His Asn Asn Asp Val Arg Glu Leu Gln Lys
    1415            1420                1425

Val Thr Gly Leu Pro Ser Val Lys Asp Ile Ser Ile Tyr Asn Ser
    1430            1435                1440

Met Thr Leu Val Leu Thr Asn Glu Gly Glu Leu Tyr Ala Gln Gly
    1445            1450                1455

Tyr Asn Thr Asn Gly Leu Phe Gly Leu Gly Glu Ser Glu Lys Asp
    1460            1465                1470

Lys Ile Ile Arg Thr Phe Thr Lys Val Leu Thr Asn Val Lys Glu
    1475            1480                1485

Ile Lys Ser His Asn Asp Asp His Ile Leu Val Ile Lys Asn Asp
    1490            1495                1500

Asn Ser Leu Trp Ile Thr Gly Lys Asn Lys Ser Met Tyr Lys Ile
    1505            1510                1515

Ser Ile Ser Ile Thr Asp Leu Tyr Glu Phe Thr Lys Ile Pro Ile
    1520            1525                1530

Pro Glu His Leu Asn Asp Ile Leu Asp Ile Glu Leu Ser Asp Asp
    1535            1540                1545

Thr Ile Tyr Met Ile Thr Lys Val Asp Thr Ser Lys Ala Ser Ile
    1550            1555                1560

Glu Ile Val Glu Lys Ser Ile Ser Gln Val Arg Val Val Val Gln
    1565            1570                1575

Asp Pro Asn Asn Val Ile Glu Lys Leu Glu Met Phe Ile Asn Asp
    1580            1585                1590

Glu Leu Ile Ser Thr Lys Thr Asn Leu Glu Ile Asn Ser Ile Ile
    1595            1600                1605

Phe Glu Ile Pro Gln Asn Lys Ile Val Leu Gly Glu Asn Lys Ile
    1610            1615                1620

Leu Ile Lys Ala Ser Ser Pro Thr Gly Asp Leu Tyr Ser Ser Met
    1625            1630                1635

Phe Ile Phe Lys Ser Glu Thr Gly Leu Lys Val Lys Lys Asp Ser
    1640            1645                1650

Ile Leu Met Ile Asn Asn Lys Val Tyr Ser Ile Ile Asn Ile Thr
    1655            1660                1665

Glu Asn Asn Thr Asp Leu Ile Val Thr Leu Asn Glu Gly Leu Lys
    1670            1675                1680

Asp Asp Met Met Glu Asn Asn Pro Ile Tyr Gln Leu Ile Asn Lys
    1685            1690                1695

Thr Lys Val Gln Val Lys Ile Asn Lys Ser Asp Leu Phe Lys Asp
    1700            1705                1710

Met Lys Leu Val Glu Ile Lys Lys Ser Asp Ser Ser Tyr Gln Glu
    1715            1720                1725

Ile Tyr Glu Leu Glu Glu Ala Asn Ile Lys Ser Ala Gln Pro Lys
    1730            1735                1740

Ile Ile Val Glu Lys Gly Asp Lys Trp Thr Ala Ile Lys Arg Pro
    1745            1750                1755

Ser Met Ile Phe Arg Tyr Asp Ala Glu Asn Asn Glu Pro Gln Ala
    1760            1765                1770
```

<210> SEQ ID NO 52
<211> LENGTH: 1725
<212> TYPE: PRT
<213> ORGANISM: Clostridium difficile

<400> SEQUENCE: 52

```
Met Lys Gln Asn Lys Leu Leu Gln Arg Gly Ala Tyr Phe Asn Asp Lys
1               5                   10                  15

Asn Ile Leu Ile Asp Asp Phe Asp Lys Arg Tyr Asn Asp Tyr Asp Phe
            20                  25                  30

Val Glu Phe Phe Thr Gly Ile Ser Asn Ser Thr Phe Gly Leu Lys Ser
        35                  40                  45

Asp Gly Asn Leu Tyr Ala Cys Gly Asp Asn Thr Gly Phe Pro Leu Gly
    50                  55                  60

Leu Gly Lys Asp Ser Ser Glu Arg Arg Met Phe Ser Lys Val Lys Ile
65                  70                  75                  80

Asp Asn Val Lys Tyr Val Ser Cys Gly Ser Lys His Ser Val Ala Val
                85                  90                  95

Thr Lys Asp Gly Phe Ala Tyr Gly Ala Gly Thr Ser Asn Val Gly Gln
            100                 105                 110

Leu Gly Val Ile Glu Ser Thr Val Tyr Tyr Glu Phe Thr Lys Leu Pro
        115                 120                 125

Ile Asp Asp Val Lys Thr Val Ala Cys Gly Tyr Asp Phe Thr Phe Val
    130                 135                 140

Leu Lys Asn Asp Gly Thr Leu Tyr Ser Ala Gly Leu Asn Ser Ser Gly
145                 150                 155                 160

Gln Leu Gly Leu Gly Asp Thr Asn Asn Arg Ala Thr Phe Thr Lys Val
                165                 170                 175

Asn Ile Asp Ser Val Lys Asp Val Val Thr Tyr Asn Gln Ser Val Phe
            180                 185                 190

Ile Ile Lys Met Asp Gly Thr Ala His Ala Cys Gly Leu Asn Ser Asn
        195                 200                 205

Gly Gln Leu Gly Ile Asn Ser Thr Leu Asn Lys Ser Val Phe Asn Lys
    210                 215                 220

Ile Glu Gly Met Asp Asn Val Lys Gln Ile Ala Cys Gly Ser Ser His
225                 230                 235                 240

Thr Ile Leu Ile Lys Asn Asp Gly Thr Met Tyr Thr Thr Gly Tyr Asn
                245                 250                 255

Gly Val Gly Gln Leu Gly Thr Gly Asn Asn Asn Ser Ile Val Phe
            260                 265                 270

Thr Leu Ser Ser Ile Asn Asn Val Lys Tyr Ala Ser Cys Gly Asn Asn
        275                 280                 285

His Thr Met Ile Leu Lys Tyr Asp Asn Thr Leu Phe Ser Thr Gly Gln
    290                 295                 300

Asn Asn Tyr Gly Gln Leu Ala Asn Ala Asn Lys Asp Val Ala Ser Arg
305                 310                 315                 320

Asn Thr Phe Ala Lys Val Asn Val Glu Asn Ile Lys Asp Ile Lys Cys
                325                 330                 335

Gly Ser Gln Phe Asn Phe Leu Ile Asn Gly Ser Lys Glu Ile Phe Val
            340                 345                 350

Ser Gly Cys Asn Leu Ala Gly Gln Leu Gly Ser Phe His Thr Thr
        355                 360                 365

Phe Leu Tyr Glu Phe Ser Asn Val Gln Ser Ser Asn Leu Asp Asn Tyr
    370                 375                 380
```

```
Ser Gly Leu Leu Val Asn Asp Asp Tyr Leu Tyr Val Thr Lys Asp Asn
385                 390                 395                 400

Ser Glu Phe Leu Asn Val Lys Leu Ser Asp Asn Phe Gln Asp Tyr Lys
            405                 410                 415

Lys Ile Glu Leu Thr Asp Ser Asn Met Phe Ile Val Met Asn Asp Gly
        420                 425                 430

Thr Leu Tyr Ala Cys Gly Leu Asn Asn Tyr Gly Gln Leu Gly Leu Gly
    435                 440                 445

Asp Thr Val Asn Arg Ser Val Met Thr Lys Val Asp Ile Asp Asn Val
450                 455                 460

Leu Asp Ile Lys Gly Asn Gly Asn Ser Thr Phe Val Leu Lys Asn Asn
465                 470                 475                 480

Gly Thr Leu Tyr Ser Cys Gly Leu Asn Ser Asn Gly Gln Leu Gly Leu
            485                 490                 495

Arg Asp Glu Val Asn Arg Asn Ile Phe Thr Lys Ile Glu Ile Glu Asn
        500                 505                 510

Val Lys Asp Phe Cys Val Gly Ser Asn Tyr Val Ile Ala Leu Asn His
    515                 520                 525

Ser Lys Glu Val Tyr Gly Trp Gly Asn Asn Pro Tyr Asn Asn Ile Glu
530                 535                 540

Lys Thr Ser Asn Tyr Pro Tyr Lys Gln Gly Ile Ser Asn Ile Glu Lys
545                 550                 555                 560

Ile Ala Ala Tyr Asp Tyr Ser Val Tyr Met Ile Asn Ser Glu Gly Lys
            565                 570                 575

Leu Tyr Val Ser Gly Tyr Asn Tyr Asn Tyr Gln Leu Lys Gly Lys Asn
        580                 585                 590

Asn Ser Asn Gln Ser Lys Ala Leu Val Ser Gln Cys Arg Thr Asn Ser
    595                 600                 605

Thr Ser Ser Thr Ser Asn Gly Leu Arg Thr Leu Pro Lys Ile Thr Asn
610                 615                 620

Val Phe Pro Phe Tyr Asp Gly Cys Ala Ile Ile Asp Glu Gly Gly Tyr
625                 630                 635                 640

Val Tyr Leu Thr Gly Tyr His Gly Tyr Leu Arg Thr Leu Asn Ser Ser
            645                 650                 655

Pro Ser Ile Ser Asp Tyr Ser Arg Tyr Gly Thr Phe Ile Glu Ala Thr
        660                 665                 670

Asn Ser Asn His Asn Thr Tyr Phe Ile Gln Glu Thr Asp Phe Ser Gly
    675                 680                 685

Ile Glu Lys Val Ile Gly Met Ser Asn Asn Ile Leu Phe Phe Lys Lys
690                 695                 700

Gly Ser Ser Tyr Ile Thr Gly Tyr Pro Lys Thr Phe Gly Ser Thr Ile
705                 710                 715                 720

Thr Gly His Arg Ser Tyr Thr Ser Ile Asn Ser Glu Ser Ser Asn Leu
            725                 730                 735

Gly Ser Asn Phe Ile Ile Tyr His Ser Asn Ser Lys Leu Tyr Gly Lys
        740                 745                 750

Gly Ile Ala Asn Ser Gly Gln Phe Gly Asn Ser Thr Asn Ile Asp Gly
    755                 760                 765

Thr Ser Asn Tyr Asp Thr Gly Leu Lys Asp Ile Lys Asp Ile Ile Val
770                 775                 780

Lys Gly Asn Thr Val Val Val Asp Lys Asn Asn Asn Ile Tyr Val
785                 790                 795                 800
```

```
Thr Gly Met Asn Gln Asn Asn Lys Leu Gly Ile Gly Glu Tyr Asn Asn
            805                 810                 815

Glu Pro Val Lys Lys Phe Thr Asn Ile Thr Glu Gln Ser Asn Ser Phe
        820                 825                 830

Ile Phe Met Asp Asp Ile Lys Glu Ile Thr Thr Ser Arg Asn Thr Met
        835                 840                 845

Phe Ile Val Lys Asn Asp Gly Thr Ala Tyr Ala Thr Gly Asn Asn Ser
    850                 855                 860

Ser Gly Gln Leu Gly Leu Gly Asp Thr Ile Arg Asn Lys Phe Thr
865                 870                 875                 880

Gln Ile Asn Leu Asp Asn Ile Lys Lys Ile Ser Thr Ser Ile Asp Gly
            885                 890                 895

Asn Thr Thr Phe Ala Ile Arg Asn Asp Gly Thr Leu Tyr Ser Thr Gly
            900                 905                 910

Leu Asn Thr Lys Gly Gln Leu Gly Leu Gly Asp Ile Val Asn Arg Asn
            915                 920                 925

Thr Phe Thr Lys Val Asn Ile Gln Asn Val Arg Asp Val Val Leu Gly
            930                 935                 940

Thr Thr His Ser His Ala Ile Lys Asp Asp Asn Thr Leu Tyr Ser Cys
945                 950                 955                 960

Gly Glu Asn Thr His Gly Gln Leu Gly Leu Gly Ser Glu Ser Asn His
            965                 970                 975

Pro Asp Val Leu Thr Phe Thr Val Asn Asn Ile Thr Asn Val Arg Asp
            980                 985                 990

Val Tyr Cys Ser Asp Thr Thr Thr Phe Ile Val Lys Asp Thr Asn Ile
            995                1000                1005

Ala Tyr Cys Cys Gly Tyr Asn Asn Asn Ser Gln Leu Gly Met Gly
        1010                1015                1020

Asn Thr Thr Asp Gln Tyr Ser Phe Ile Lys Cys Met Glu Asn Val
        1025                1030                1035

Lys Glu Val Ile Pro Asn Glu Ile Asn Thr Tyr Ile Ile Thr Ile
        1040                1045                1050

Tyr Asn Thr Ala Tyr Ser Thr Gly Leu Asn Thr Asp Tyr Cys Leu
        1055                1060                1065

Gly Leu Asn Ser Asn Ser Asn Gln Ser Ser Phe Ser Glu Ile Pro
        1070                1075                1080

Ile Ser Asn Val Val Lys Val Ala Pro Asn Arg Asn Asn Ala Val
        1085                1090                1095

Leu Leu Leu Thr Ser Glu Gly Asp Val Tyr Thr Ala Gly Lys Cys
        1100                1105                1110

Ser Asn Gly Ser Gly Thr Gly Ser Glu Thr Pro Glu Lys Ile Lys
        1115                1120                1125

Lys Ile Ala Ser Lys Ala Lys Asp Ile Gly Met Asn Tyr Arg Cys
        1130                1135                1140

Gly His Tyr Val Ser Asp Asn Gly Asp Leu Tyr Gly Thr Gly Phe
        1145                1150                1155

Asn Asn Asn Gly Gln Leu Gly Val Gly Asp Val Thr Lys Arg Asp
        1160                1165                1170

Thr Phe Ile Lys Thr Asn Thr Arg Val Lys Lys Ile Leu Pro Leu
        1175                1180                1185

Glu Tyr Ala Asn Ile Ala Ile Lys Asp Thr Asn Asp Ile Tyr Ile
        1190                1195                1200

Cys Gly Leu Asn Asn Tyr Gly Gln Leu Gly Val Gly Asn Arg Tyr
```

-continued

```
           1205                1210                1215
Asp Ser Arg Asn Asn Asp Asn Arg Ile Phe Asn Tyr Lys His Met
       1220                1225                1230
Asn Phe Val Met Gly Asp Leu Thr Ser Ile Lys Asn Arg His Asn
       1235                1240                1245
Phe Ile Leu Leu Asn Asn Lys Ile Val Ile Pro Thr Thr Lys Asp
       1250                1255                1260
Ile Asp Tyr Gly Leu Val Leu Gly Asn Leu Tyr Lys Gly Asp Leu
       1265                1270                1275
Tyr Thr Glu Leu Pro Tyr Glu Asp Ile Lys Val Ser Ile Ser
       1280                1285                1290
Lys Thr His Ile Ile Ile Leu Leu Asn Asp Gly Thr Met Tyr Gly
       1295                1300                1305
Cys Gly Thr Asn Tyr His Gly Glu Leu Leu Gln Asp Leu Ser Ile
       1310                1315                1320
Asn Gln Val Asp Glu Phe Val Gln Ile Asn Val Ser Asp Val Lys
       1325                1330                1335
His Val Ser Cys Gly Asp Asn Phe Thr Tyr Phe Ile Lys Ser Asp
       1340                1345                1350
Asp Ser Leu Trp Ser Ile Gly Lys Asn Ser Glu Tyr Gln Leu Gly
       1355                1360                1365
Ile Gly His Asn Asn Pro Val Thr Glu Leu Gln Arg Ile Thr Thr
       1370                1375                1380
Ile Ser Ser Cys Lys Glu Val His Cys Gly Lys Asn Tyr Thr Leu
       1385                1390                1395
Val Val Thr Thr Gly Asn Glu Leu Phe Val Gln Gly Tyr Asn Asp
       1400                1405                1410
Lys Gly Ala Leu Gly Leu Gly Ser Asp Ser Glu Asn Thr Ile Ile
       1415                1420                1425
Lys Phe Phe Thr Lys Ala Leu Thr Asp Ile Arg Glu Ile Lys Ser
       1430                1435                1440
Tyr Gly Ser Asp His Ile Leu Val Leu Lys Asn Asp Asn Ser Val
       1445                1450                1455
Trp Val Thr Gly Lys Asn Arg Asp Val Tyr Lys Ile Glu Gln Pro
       1460                1465                1470
Val Glu Phe Leu Lys Glu Phe Thr Ile Val Pro Ile Ser Glu Asp
       1475                1480                1485
Val Asn Thr Val Lys Asp Val Leu Ala Thr Asp Asn Thr Leu Tyr
       1490                1495                1500
Ile Ile Ser Glu Val Gly Thr Thr Asn Ala Ala Ile Glu Ile Thr
       1505                1510                1515
Glu Lys Ser Ile Ser Ser Ile Lys Ile Lys Ile Gln Asp Pro Asn
       1520                1525                1530
Lys Asp Ile Ser Arg Ile Glu Met Leu Ile Asn Gly Glu Ser Val
       1535                1540                1545
Lys Ser Val Ser Asp Leu Thr Thr Glu Lys Ile Ser Phe Glu Val
       1550                1555                1560
Pro Pro Asp Lys Ile Lys Ile Gly Glu Asn Lys Ile Leu Phe Arg
       1565                1570                1575
Ala Tyr Cys Lys Gly Asp Asp Leu Tyr Ala Ser Leu Phe Ile Phe
       1580                1585                1590
Lys Glu Ser Thr Gly Asn Ser Ile Ile Lys Asp Ser Tyr Val Met
       1595                1600                1605
```

Ile Gly Asn Arg Met Tyr Lys Val Val Asn Thr Thr Ser Asn Glu
    1610                1615                1620

Gln Asp Ile Thr Ile Thr Leu Asp Arg Gly Leu Glu Glu Asp Leu
    1625                1630                1635

Asn Leu Gly Asp Pro Ile Tyr Gln Leu Ile Asn Lys Thr Lys Val
    1640                1645                1650

Gln Val Lys Ile Asn Lys Ser Asp Leu Phe Lys Asp Met Lys Leu
    1655                1660                1665

Val Glu Ile Lys Lys Ser Asp Ser Ser Tyr Gln Glu Ile Tyr Glu
    1670                1675                1680

Leu Glu Glu Ala Asn Ile Lys Ser Ala Gln Pro Lys Ile Ile Val
    1685                1690                1695

Glu Lys Gly Asp Lys Trp Thr Ala Ile Lys Arg Pro Ser Met Ile
    1700                1705                1710

Phe Arg Tyr Asp Ala Glu Asn Asn Glu Pro Gln Ala
    1715                1720                1725

<210> SEQ ID NO 53
<211> LENGTH: 1743
<212> TYPE: PRT
<213> ORGANISM: Clostridium difficile

<400> SEQUENCE: 53

Met Lys Gln Asn Lys Leu Leu Gln Arg Gly Ala Tyr Phe Asn Asp Lys
1               5                   10                  15

Asn Ile Leu Ile Asp Asp Phe Asp Lys Arg Tyr Asn Asp Tyr Asp Phe
            20                  25                  30

Val Glu Phe Phe Thr Gly Ile Ser Asn Ser Thr Phe Gly Leu Lys Ser
        35                  40                  45

Asp Gly Asn Leu Tyr Ala Cys Gly Asn Asn Thr Gly Phe Pro Leu Gly
    50                  55                  60

Leu Gly Lys Asp Ser Ser Glu Arg Arg Met Phe Ser Lys Val Lys Ile
65                  70                  75                  80

Asp Asn Val Lys Tyr Val Ser Cys Gly Ser Lys His Ser Val Ala Val
                85                  90                  95

Thr Lys Asp Gly Phe Ala Tyr Gly Ala Gly Thr Ser Asn Val Gly Gln
            100                 105                 110

Leu Gly Val Ile Glu Ser Thr Val Tyr Tyr Glu Phe Thr Lys Leu Pro
        115                 120                 125

Ile Asp Asp Val Lys Thr Val Ala Cys Gly Tyr Asp Phe Thr Phe Val
    130                 135                 140

Leu Lys Asn Asp Gly Thr Leu Tyr Ser Ala Gly Leu Asn Ser Ser Gly
145                 150                 155                 160

Gln Leu Gly Leu Gly Asp Thr Asn Asn Arg Ala Thr Phe Thr Lys Val
                165                 170                 175

Asn Ile Asp Ser Val Lys Asp Val Thr Tyr Asn Gln Ser Val Phe
            180                 185                 190

Ile Ile Lys Met Asp Gly Thr Ala His Ala Cys Gly Leu Asn Ser Asn
        195                 200                 205

Gly Gln Leu Gly Ile Asn Ser Thr Leu Asn Lys Ser Val Phe Asn Lys
    210                 215                 220

Ile Glu Gly Met Asp Asn Val Lys Gln Ile Ala Cys Gly Ser Ser His
225                 230                 235                 240

Thr Ile Leu Ile Lys Asn Asp Gly Thr Met Tyr Thr Thr Gly Tyr Asn

```
            245                 250                 255
Gly Val Gly Gln Leu Gly Thr Gly Asn Asn Asn Ser Ile Val Phe
            260                 265                 270

Thr Leu Ser Ser Ile Asn Asn Val Lys Tyr Ala Ser Cys Gly Asn Asn
            275                 280                 285

His Thr Met Ile Leu Lys Tyr Asp Asn Thr Leu Phe Ser Thr Gly Gln
            290                 295                 300

Asn Thr Tyr Gly Gln Leu Ala Asn Ala Asn Lys Asp Val Ala Ser Arg
305                     310                 315                 320

Asn Thr Phe Ala Lys Val Asn Val Glu Asn Ile Lys Asp Ile Lys Cys
                325                 330                 335

Gly Ser Gln Phe Asn Phe Leu Ile Asn Gly Ser Lys Glu Ile Phe Val
                340                 345                 350

Ser Gly Cys Asn Leu Ala Gly Gln Leu Gly Ser Phe Phe His Thr Thr
                355                 360                 365

Phe Leu Tyr Glu Phe Ser Lys Val Gln Ser Ser Asn Leu Asp Asn Tyr
            370                 375                 380

Ser Gly Leu Leu Val Asn Asp Asp Tyr Leu Tyr Val Thr Lys Asp Asn
385                 390                 395                 400

Ser Glu Phe Leu Asn Val Lys Leu Ser Asp Asn Phe Gln Asp Tyr Lys
                405                 410                 415

Lys Ile Glu Leu Thr Asp Asn Asn Met Phe Ile Val Met Asn Asp Gly
                420                 425                 430

Thr Leu Tyr Ala Cys Gly Leu Asn Asn Tyr Gly Gln Leu Gly Leu Gly
                435                 440                 445

Asp Thr Val Asn Arg Ser Val Met Thr Lys Val Asp Ile Asp Asn Val
450                 455                 460

Leu Asp Ile Lys Gly Asn Gly Asn Ser Thr Phe Val Leu Lys Asn Asn
465                 470                 475                 480

Gly Thr Leu Tyr Ser Cys Gly Tyr Asn Ser Ser Gly Ile Leu Gly Leu
                485                 490                 495

Lys Asp Asn Thr Asn Arg Asn Ile Phe Thr Lys Ile Glu Ile Glu Asn
                500                 505                 510

Val Lys Ala Phe Cys Val Glu Ser Asn Tyr Ile Val Val Leu Asn His
                515                 520                 525

Ser Lys Glu Leu Tyr Gly Trp Gly Asn Glu Ser Tyr Ile Val Tyr Gly
                530                 535                 540

Asn Ser Arg Asn Tyr Pro Tyr Lys Asp Thr Arg Val Ser Asn Val Glu
545                 550                 555                 560

Lys Ile Ala Thr Trp Ser Asp Thr Leu Tyr Ile Leu Asp Ser Thr Gly
                565                 570                 575

Ala Thr Lys Thr Ile Gly Tyr Ser Tyr Asn Gly Ser Gly Gly Tyr Pro
                580                 585                 590

Ala Pro Ser Ser Ser Thr Tyr Arg Asp Gly Gly Tyr Ile Asn Lys
                595                 600                 605

Asn Thr Ser Tyr Arg Thr Leu Glu Phe Tyr Asn Thr Ser Lys Thr Lys
                610                 615                 620

Leu Val Asn Leu Phe Ala Phe Tyr Asn Gly Cys Val Phe Val Asp Glu
625                 630                 635                 640

Asn Gly Leu Ala Tyr Cys Ile Gly Glu Asn Asn Ile Asn Phe Arg Gly
                645                 650                 655

Asn Ser Thr Thr Asn Glu Asn Asn Ser Leu Arg Phe Ile Asn Asn Ser
                660                 665                 670
```

```
Gly Val Tyr Tyr Thr Asn Thr Asp Gly Thr Asp Tyr Thr Cys Tyr Gln
        675                 680                 685

Trp Thr Tyr Lys Leu Ile Arg Cys Ser Ile Phe Asp Ser Pro Gln Asn
690             695                 700

Ile Ile Gly Asn Ser Lys Asn Ile Leu Tyr Leu Ser Lys Asn Asn Ser
705             710                 715                 720

Thr Phe Lys Cys Thr Gly Asn Cys Ile Thr Tyr Gly Ile Asn Ser Gln
                725                 730                 735

Asn Trp Tyr Ser Tyr Phe Ser Asp Ser Ser Asn Gly Ala Ile Ala Leu
                740                 745                 750

Gly Asn Glu Phe Ile Leu Lys Asn Tyr Ser Gly Glu Cys Leu Leu Lys
                755                 760                 765

Gly Tyr Gly Lys Ala Thr Asn Gly Glu Phe Gly Asn Ser Thr Asn Ile
        770                 775                 780

Ser Ser Ile Ser Asn Tyr Asp Thr Gly Leu Lys Asp Ile Lys Asp Ile
785             790                 795                 800

Ile Val Lys Asn Asn Thr Val Val Val Asp Lys Asn Asn Asn Ile
                805                 810                 815

Tyr Val Thr Gly Ala Asn Gln Phe Asn Lys Leu Gly Ile Gly Glu Tyr
        820                 825                 830

Asn Asn Gln Pro Ile Lys Lys Phe Thr Asn Ile Thr Glu Gln Ser Asn
        835                 840                 845

Ser Phe Ile Phe Met Asp Asp Ile Lys Glu Ile Thr Thr Ser Arg Asn
850             855                 860

Thr Met Phe Ile Val Lys Asn Asp Gly Thr Ala Tyr Ala Thr Gly Asn
865                 870                 875                 880

Asn Ser Ser Gly Gln Leu Gly Leu Gly Asp Thr Ile Asn Arg Asn Lys
                885                 890                 895

Phe Thr Gln Ile Asn Leu Asp Asn Ile Lys Lys Ile Ser Thr Ser Ile
                900                 905                 910

Asp Gly Asn Thr Thr Phe Ala Ile Arg Asn Asp Gly Thr Leu Tyr Ser
        915                 920                 925

Thr Gly Leu Asn Thr Lys Gly Gln Leu Gly Leu Gly Asp Ile Val Asn
        930                 935                 940

Arg Asn Thr Phe Thr Lys Val Asn Ile Gln Asn Val Arg Asp Val Val
945                 950                 955                 960

Leu Gly Thr Thr His Ser His Ala Ile Lys Asp Asn Thr Leu Tyr
                965                 970                 975

Ser Cys Gly Glu Asn Thr His Gly Gln Leu Gly Leu Gly Ser Glu Ser
                980                 985                 990

Asn His Pro Asp Val Leu Thr Phe Thr Val Asn Asn Ile Thr Asn Val
        995                 1000                1005

Arg Asp Val Tyr Cys Ser Asp Thr Thr Thr Phe Ile Val Lys Asp
    1010                1015                1020

Thr Asn Ile Ala Tyr Cys Cys Gly Tyr Asn Asn Asn Ser Gln Leu
    1025                1030                1035

Gly Met Gly Asn Thr Thr Asp Gln Tyr Ser Phe Ile Lys Cys Met
    1040                1045                1050

Glu Asn Val Lys Glu Val Ile Pro Asn Glu Ile Asn Thr Tyr Ile
    1055                1060                1065

Ile Thr Ile Tyr Asn Thr Ala Tyr Ser Thr Gly Leu Asn Thr Asp
    1070                1075                1080
```

```
Tyr Cys Leu Gly Leu Asn Ser Asn Ser Asn Gln Ser Ser Phe Ser
    1085             1090             1095

Glu Ile Pro Ile Ser Asn Val Val Lys Val Ala Pro Asn Arg Asn
    1100             1105             1110

Asn Ala Val Leu Leu Leu Thr Ser Glu Gly Asp Val Tyr Thr Ala
    1115             1120             1125

Gly Lys Cys Ser Asn Gly Ser Gly Thr Gly Ser Glu Thr Pro Glu
    1130             1135             1140

Lys Ile Lys Lys Ile Ala Ser Lys Ala Lys Asp Ile Gly Met Asn
    1145             1150             1155

Tyr Arg Cys Gly His Tyr Val Ser Asp Asn Gly Asp Leu Tyr Gly
    1160             1165             1170

Thr Gly Phe Asn Asp Cys Gly Gln Leu Gly Val Gly Asp Val Thr
    1175             1180             1185

Lys Arg Asp Thr Phe Ile Lys Thr Asn Thr Arg Val Lys Lys Ile
    1190             1195             1200

Leu Pro Leu Glu Tyr Ala Asn Ile Ala Ile Lys Asp Thr Asn Asp
    1205             1210             1215

Ile Tyr Ile Cys Gly Leu Asn Asn Tyr Gly Gln Leu Gly Val Gly
    1220             1225             1230

Asn Arg Tyr Asp Ser Arg Asn Asn Asp Asn Arg Ile Phe Asn Tyr
    1235             1240             1245

Lys His Met Asn Phe Val Met Gly Asp Leu Thr Ser Ile Lys Asn
    1250             1255             1260

Arg His Asn Phe Ile Leu Leu Asn Asn Lys Ile Val Ile Pro Thr
    1265             1270             1275

Thr Lys Asp Ile Asp Tyr Gly Leu Val Leu Gly Asn Leu Tyr Lys
    1280             1285             1290

Gly Asp Leu Tyr Thr Glu Leu Pro Tyr Glu Asp Ile Lys Glu Val
    1295             1300             1305

Ser Ile Ser Lys Thr His Ile Ile Ile Leu Leu Asn Asp Gly Thr
    1310             1315             1320

Met Tyr Gly Cys Gly Thr Asn Tyr His Gly Glu Leu Leu Gln Asp
    1325             1330             1335

Leu Ser Ile Asn Gln Val Asp Glu Phe Val Gln Ile Asn Val Ser
    1340             1345             1350

Asp Val Lys His Val Ser Cys Gly Asp Asn Phe Thr Tyr Phe Ile
    1355             1360             1365

Lys Ser Asp Asp Ser Leu Trp Ser Ile Gly Lys Asn Ser Glu Tyr
    1370             1375             1380

Gln Leu Gly Ile Gly His Asn Asn Pro Val Thr Glu Leu Gln Arg
    1385             1390             1395

Ile Thr Thr Ile Ser Ser Cys Lys Glu Val His Cys Gly Lys Asn
    1400             1405             1410

Tyr Thr Leu Val Val Thr Thr Gly Asn Glu Leu Phe Val Gln Gly
    1415             1420             1425

Tyr Asn Asp Lys Gly Ala Leu Gly Leu Gly Ser Asp Ser Glu Asn
    1430             1435             1440

Thr Ile Ile Lys Phe Phe Thr Lys Ala Leu Thr Asp Ile Arg Glu
    1445             1450             1455

Ile Lys Ser Tyr Gly Ser Asp His Ile Leu Val Leu Lys Asn Asp
    1460             1465             1470

Asn Ser Val Trp Val Thr Gly Lys Asn Arg Asp Val Tyr Lys Ile
```

```
                1475                1480                1485

Glu Gln Pro Val Glu Phe Leu Lys Glu Phe Thr Ile Ile Pro Ile
    1490                1495                1500

Ser Glu Asp Val Asn Thr Val Lys Asp Val Leu Ala Thr Asp Asn
    1505                1510                1515

Thr Leu Tyr Ile Ile Ser Glu Val Gly Thr Thr Asn Ala Ala Ile
    1520                1525                1530

Glu Ile Thr Glu Lys Ser Ile Ser Ser Ile Lys Ile Lys Ile Gln
    1535                1540                1545

Asp Pro Asn Lys Asp Ile Ser Arg Ile Glu Met Leu Ile Asn Gly
    1550                1555                1560

Glu Ser Val Lys Ser Val Ser Asp Leu Ile Thr Glu Lys Ile Ser
    1565                1570                1575

Phe Glu Val Pro Pro Asp Lys Ile Lys Ile Gly Glu Asn Lys Ile
    1580                1585                1590

Leu Phe Arg Ala Tyr Cys Lys Gly Asp Asp Leu Tyr Ala Ser Leu
    1595                1600                1605

Phe Ile Phe Lys Glu Ser Thr Gly Asn Ser Ile Ile Lys Asp Ser
    1610                1615                1620

Tyr Val Met Ile Gly Asn Arg Met Tyr Lys Val Val Asn Thr Thr
    1625                1630                1635

Ser Asn Glu Gln Asp Ile Thr Ile Thr Leu Asp Arg Gly Leu Glu
    1640                1645                1650

Glu Asp Leu Asn Leu Gly Asp Pro Ile Tyr Gln Leu Ile Asn Lys
    1655                1660                1665

Thr Lys Val Gln Val Lys Ile Asn Lys Ser Asp Leu Phe Lys Asp
    1670                1675                1680

Met Lys Leu Val Glu Ile Lys Lys Ser Asp Ser Ser Tyr Gln Glu
    1685                1690                1695

Ile Tyr Glu Leu Glu Glu Ala Asn Ile Lys Ser Ala Gln Pro Lys
    1700                1705                1710

Ile Ile Val Glu Lys Gly Asp Lys Trp Thr Ala Ile Lys Arg Pro
    1715                1720                1725

Ser Met Ile Phe Arg Tyr Asp Ala Glu Asn Asn Glu Pro Gln Ala
    1730                1735                1740

<210> SEQ ID NO 54
<211> LENGTH: 341
<212> TYPE: PRT
<213> ORGANISM: Clostridium difficile

<400> SEQUENCE: 54

Met Ala Ile Asp Lys Ser Tyr Tyr Thr Ile Thr Asp Val Gly Lys
1               5                   10                  15

Ala Lys Ile Ala Asn Ala Ser Val Thr Gly Asn Lys Val Gly Phe Val
                20                  25                  30

Lys Ile Gln Leu Gly Asp Gly Gly Ser Glu Tyr Thr Pro Thr Glu
                35                  40                  45

Ser Gln Thr Ala Leu Lys Asn Val Val Trp Glu Gly Asn Ile Gly Asn
    50                  55                  60

Thr Thr Thr Asp Glu Thr Ala Pro Asn Cys Ile Ile Leu Glu Ser Leu
65                  70                  75                  80

Ile Pro Ser Ser Val Gly Gly Phe Met Ile Arg Glu Ile Gly Tyr Leu
                85                  90                  95
```

```
Asp Asp Glu Asn Asn Leu Ile Ala Ile Ser Lys Tyr Lys Glu Cys Tyr
                100                 105                 110

Lys Pro Ser Ile Glu Gln Gly Ala Val Val Asp Met Lys Val Lys Thr
            115                 120                 125

Val Leu Ile Val Ser Asn Val Asn Asn Ile Glu Leu Lys Ile Asp Pro
        130                 135                 140

Thr Ile Ile Phe Ala Thr Leu Lys Asp Ile Gln Asp Leu Glu Thr Lys
145                 150                 155                 160

Ile Gly Thr Val Asn Thr Lys Ile Asp Thr Thr Lys Thr Glu Leu Thr
                165                 170                 175

Ser Asn Ile Glu Thr Thr Lys Thr Glu Leu Asn Thr Arg Ile Asp Thr
            180                 185                 190

Glu Asn Glu Lys Gln Asn Ile Lys Ile Asp Gln Leu Ile Ala Gly Gly
        195                 200                 205

Ser Asn Val Ala Ser Thr Gln Ile Ile Thr Ile Asp Asp Trp Val Glu
210                 215                 220

Asp Ala Glu Asn Gly Phe Lys Ala Thr Val Thr His Ser Leu Leu Thr
225                 230                 235                 240

Gln Arg Ile Val Val Asn Ile Ile Asp Ala Thr Thr Lys Glu Asn Val
                245                 250                 255

Val Thr Asn Phe Lys Ile Ile Asp Asp Asn Ser Ile Glu Ile Arg Ser
            260                 265                 270

Glu Val Lys Val Glu Leu Asn Val Tyr Val Ile Asn Gly Asn Ala Glu
        275                 280                 285

Thr His Phe Ile Asn Ala Thr Val Asp Asp Asn Arg Val Ser Glu Met
290                 295                 300

Thr Thr Tyr Ser Ser Lys Lys Ile Glu Asp Arg Leu Val Asn Ile Glu
305                 310                 315                 320

Glu Lys Val Asn Gly Gly Leu Ser Asn Ile Ala Thr Ser Val Asn Glu
                325                 330                 335

Leu Ile Thr Tyr Cys
                340

<210> SEQ ID NO 55
<211> LENGTH: 132
<212> TYPE: PRT
<213> ORGANISM: Clostridium difficile

<400> SEQUENCE: 55

Met Ala Glu Gln Gln Tyr Phe Thr Leu Val Thr Asp Ile Gly Lys Ala
1               5                   10                  15

Ala Ile Ala Asn Ala Ser Val Thr Gly Glu Lys Val Asp Phe Ala Lys
            20                  25                  30

Ile Lys Val Gly Asp Gly Gly Ser Ser Tyr Thr Pro Asn Glu Ser
            35                  40                  45

Gln Thr Ala Leu Lys Asn Val Val Trp Glu Ser Thr Leu Glu His Ala
        50                  55                  60

Gln Val Asp Lys Asp Asn Pro Asn Trp Val Val Ile Gln Lys Phe Ile
65                  70                  75                  80

Pro Gly Asp Val Gly Gly Phe Glu Ile Arg Glu Val Gly Leu Phe Asp
                85                  90                  95

Ser Lys Asp Gln Leu Leu Ala Val Ser Ser Tyr Pro Thr Thr Tyr Lys
            100                 105                 110

Pro Glu Ser Arg Phe Gly Asp Cys Lys Arg Thr Ile Asn Lys Ser Asn
        115                 120                 125
```

```
Ile Ser Cys Ile
        130

<210> SEQ ID NO 56
<211> LENGTH: 205
<212> TYPE: PRT
<213> ORGANISM: Clostridium difficile

<400> SEQUENCE: 56

Met Pro Asn Glu Leu Asn Phe Asn Asn Glu Ile Glu Glu Tyr Leu Ile
1               5                   10                  15

Thr Thr Pro Ala His Ala Asn Glu Phe Asn Asn Arg Gln Gln Lys Leu
            20                  25                  30

Leu Asp Asn Asp Lys Tyr Leu Asn Asn Lys Ile Asp Thr Thr Lys Thr
        35                  40                  45

Glu Leu Asn Thr Arg Ile Asp Thr Glu Asn Glu Lys Gln Asn Ile Lys
    50                  55                  60

Ile Asp Gln Leu Ile Ala Gly Gly Ser Asn Val Ala Tyr Thr Gln Arg
65                  70                  75                  80

Val Ala Ile Asp Asp Trp Val Glu Asp Ala Glu Asn Gly Phe Lys Ala
                85                  90                  95

Thr Val Thr His Ser Leu Leu Thr Gln Arg Ile Val Val Asn Ile Ile
            100                 105                 110

Asp Ala Thr Thr Lys Glu Asn Val Val Thr Asn Phe Lys Ile Ile Asp
        115                 120                 125

Asp Asn Ser Ile Glu Ile Arg Ser Glu Thr Arg Ser Glu Leu Asn Val
    130                 135                 140

Tyr Val Ile Asn Gly Asn Ala Glu Thr His Phe Ile Asn Ala Thr Val
145                 150                 155                 160

Asp Asp Asn Arg Val Ser Glu Met Thr Thr Tyr Ser Ser Lys Lys Ile
                165                 170                 175

Glu Asp Arg Leu Val Asn Ile Glu Glu Lys Val Asn Gly Gly Leu Ser
            180                 185                 190

Asn Ile Ala Thr Ser Val Asn Glu Leu Ile Thr Tyr Cys
        195                 200                 205

<210> SEQ ID NO 57
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 57
ggccgcctcg aggg                                                      14

<210> SEQ ID NO 58
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 58
cgcgccctcg aggc                                                      14

<210> SEQ ID NO 59
```

```
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
tgaagtacca tggtatccag                                                 20

<210> SEQ ID NO 60
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
actggatacc atggtacttc                                                 20

<210> SEQ ID NO 61
<211> LENGTH: 19897
<212> TYPE: DNA
<213> ORGANISM: Clostridium difficile

<400> SEQUENCE: 61
gcaataccca ctacaccttc gtcatcttta aatttaagag ttttttactat tgaataataa     60 aggtatattc cagtaaaaat aatctttaaa tacaagaaaa ataaactctt tgggtatatt    120
aaaaagctaa aaagtgtaaa tataaaagca agtagagtac ttatcctgta aagaaaatct    180
atttgtgtaa tgtctttata ttttatcata acaccgaat ataaaatgat gaaaacaatt     240
gcgacgattg catatatggt aaataacata ttttcaagag taccatttga aattactatc    300
cacttatacc acataattgg ccaaaataat agtgctaaga acttaaaata attatcaaac    360 aactttctt tatacattca tcaaacaacc tttcttaaca aaagcatata tttgttttta     420
gaattttaaa taatatgata tcattattat atattaatat tgaatttata gaaaccaaaa    480
tttgttaaaa taaatatata gattttactg ttaagccagt taaaattact actattttta    540
ttatgaaatt ggatcaaata tgtagaaata cggcaaatta gttaatatta aatatttatt    600
atttccaagt tgtaaagact gttttttttaa tgatagaaat tctaatcttt tttgaaagaa    660
agtaatatcc acattaagta tgtctgccat tcataaacg caagtgatgc cagagttaat     720
tatgtttatt atatcttctt cagtaattaa gaactcacaa gcccatttta aggctttatt    780
ttcgcactta tctataataa ttttttgtata ataatcgtta taagaggata catagtatcc    840
aaggctagtg aaatgatgtc caagttcttc agctaagatg gatgtcaatt ttttttgagtt    900 ttgttttaaa ttactgagta atgatataat tttaatacca tgtttgttta tatatagtcc    960
ttctaaatca cctgcaatat aagtggtata atgaattatt atctcttctt gagaagctaa   1020
ttcaaaaagc ttatccaaat tattcataaa aatcccccta aaatagaatg tatgtttgcc   1080
tttaaattat attaaaagag cagaaaaata gactgctcat catatggttt atttttttt    1140 atatttattt agtaaaaatt ctatataatc attaagttgt tcttgtgctt cttcaggtaa   1200
ctcttcatgt ggattttttc tatgtgcagc tactgtatca atatttcct taactaaggt    1260 tcttccaaga aggtaatcaa ctgatacatt aaatacatca gccaatttat ttaaaatgtg   1320
ttcatcagga aatctgtttt ctgtttcata gtacccctaag actctttggg aaacgcctac  1380 ttttctcca gttctctttt gagtcaatcc aaattccttt ctaagttctc ttaatctttt    1440
```

```
ggcaaacatt ataacaccac cttatgtata gattataaca aattgttcta aaaaataaaa    1500
ctaataaaat ataaaagaat attttttct aaaatctatt gataaagaac aaataattct     1560
atataatcta agtgaggaag aacaaaatat tcttaatagt aatggaggta taaaacaatg    1620
tttaaaaata acttgaaata ttatagaaaa tgcaaaggta tgacacaaat tcaacttgcc    1680
agaaaggctg gaattacaaa tgattatata tctcaaatag aaagaggtat aaaaaatcct    1740
ggacttctta tggctaagaa gatttctagt attttagaac aaaatataga agaagttttt    1800
tttatacagt tatagaacaa tatgttcttg aaagttgtga gattagtaaa aaactgtgca    1860
ctaaagagat tattgtaaat ttgaagctaa taataagtat ataaaaaagg ggaagtacta    1920
tggaaaacaa aaaagatata ttatttaaag aaacagataa aagattacat aattataagt    1980
atttggatat aaagataaag aatattaact tggacataaa aagatgtgag aatgaatact    2040
ctggatgtgg agcaatggta tatacagaaaa agactagtaa cacatataac ataagctctt   2100
ctgtggaaaa tgaggtgtta aaaagagagg aaagattaag aaaattaaaa atggaaaaag    2160
aagatataga aatagaaaaa gagaagatag aaaatgctct aacgtgtcta aatgatatag    2220
aaatggaatt ttttaatctt ttttataata gtaagacaaa aaacaatatg acatatattt    2280
ctatgaaact acacttagat agaacatctt gctacaattt aaagaaaaag atgatattta    2340
aattgagtga gatattataa aaaataggac aattttacaa cactttatat acaccattgc    2400
aacaataggc aataaaatat gtgagataat gttattgtga agaaatcca tattgaagga    2460 ggtgatagat tgaaaagaat aatattacct aaaaatatag aagatacttg acaggaataa    2520
atgagatata tatttaaaaa tgacttatat catttatagt aagattatca gattaagcaa    2580
gaatatttag tgatagtgtg gtgattattt gcttaaatac aaggaaatat tagaaacaat    2640
tattgagatt ctcaaaaaaa actttactga agtattttt attgatgatg aaagtgtgca    2700
aggctctgaa gggtcttgtt tttttgtaag tatactatca gttatttgta cacctgtaat    2760
gttaaatacg aataacaaag atattgttat ctctataaaa tacttaccaa aaccacagtc    2820
aaagagtatt agaatgtatg aaatttcaga tgaattaaat aagctattta acagaaatat    2880
aaaggtaaca gacagaaaat taaatataac aaagctagaa caaagtatta aaaaagaaga    2940
gtcaatttat gtattgaact ttacatttac actaaactat ctggatagtg tatatgaaga    3000
agatgtagta tatgaaaata tgaaagaaat caattttaaat ttaggagagt gatagtatgg    3060
ctataggatt accaagtatc aacatatcat ttaaggagct agctacaact gttaaagaac    3120
gttcagctag aggaataatt gcaatggtac ttaaagatgc taaggcacta ggtcttaatg    3180
aaatacatga aaagaggat ataccagttg atttatctgc tgaaaataaa gaatatataa     3240
atttagcttt gatgggaaat gttaacactc caaataaatt attagtttat gtaatagaag    3300
gagaagcaga tattcaaact gcattagatt ttttagagac taaggaattt aattatctat    3360
gtatgccaaa agcagtagaa gctgataaga ctgctataaa aaattggata attaaactta    3420
gagatataga taaggttaag gttaaagctg tattaggaaa agttgtagga aatcatgaag    3480
ggataattaa ttttactaca gaagatgtgt tagttggaga aaagaaatac agtgttgatg    3540
agtttacaag caggggtggct ggacttatag caggtacacc tttaagtcaa tcagtaactt   3600
atactaaact tagtgatgta gtcgatatac ctaagatgac gaaagttgat gcagaatcaa    3660
gggttaataa aggagagctt atacttatta aagaagcagg agctataaga attgctagag    3720
gagtaaattc tttaactgaa ttaacagcag aaaaaggaga aatgttccag aaaataaaaa    3780
```

```
tagttgacac tttagatatt atacatagtg acataagaaa ggtgataata gatgactata    3840
taggaaaggt tactaacagt tatgacaaca aatgtttatt gatagtagct ataaaaagtt    3900
atttagaaga attagaaaaa tcagcactta tagaatctga ttctactgtt gaaatagatt    3960
ttgaagcaca aaaatcgtat ttaaaatcaa aaggagtaga tttatcttat atgacattac    4020
aagaaataaa agaagctaac acaggttcta aagtattttt aaaagcaaaa ataaaagtac    4080
ttgatgctat ggaagatata gatttatcaa tagaaatata ggaggattat taatatggca    4140
aatatggaag ctagaaatgt aatgagtggt acttggggag aactttggct tgatggaaac    4200
aaagtagcag aagtaaagaa atttcaagca aagatggaat ttacaaaaga agatattata    4260
atagcaggtc aaatgggtac tgatacaaag tatatgggat ataaaggaaa aggctcaata    4320
actctatacc acgttagttc aagaatgcac aagttaattg gagaaaagat aaagagaggt    4380
tctgaaccta gatttgttgc tatatcaaaa ttaaatgacc cagattctta tggagcagaa    4440
agaatagcag taaaaaatat agcatttgat gatttaactt tagctgattg ggaggttgga    4500
gtaaaaggag agatagaagc tccttttcaca tttactgagt atgattttct tgatataatt    4560
tagttttata tttagtttta tactgatatt tagtaagtat atacttaata aattcagata    4620
gttaataagt aaaaaagtta gttgattgaa tttgattgat aaaggagcaa ataataatga    4680
gtgaaaatgg attatcaaaa aatataaaca tagtagattt acttttaaat tcagatacag    4740
aaaacttaga aagaccaagt actatagttg aacttaagag attatcaact atatttgggc    4800
aggaatttaa agtaatgtgt agagctttaa caataagtaa agatgaagaa atacaaaata    4860
cttgtcttaa aattgatgaa aatatgaaaa cggatataga cttaccggag atgcagatgc    4920
ttacaattat agaaggtgtt tgtgatttgg atggaaagct tttatttaaa aataaggagc    4980
taatggataa atttaaggct ccaacaccaa aagaattagc aagaaaatta ttattaccag    5040
gtgaaattac caacttatat agaatacttc aagatgttat gggttatggt aaaaatgcag    5100
tgatagaaga ggtaaaaaac taataggggac ggataccagg actacaataa tgtactatta    5160
ttggaagaaa aaaggtataa gaccgtccct ttttatgca atggataaag gcgaattaaa    5220
gcttattgaa gcttttttcg ccttagaaat tgaggaagaa gttgaaaaaa tgaaacatgg    5280
atatggagtg tgtcctttga caggaggtgg tatgtaatgg gaaatgtgag agaagaaggt    5340
ataaatatgt accttacaga taattacaca ccaaaaatga atcaaattat atcagtaact    5400
gataatttta ggagagcaac tgtggctgtt tcactttcca ctaatgtaat ggctagtagc    5460
ataaaaaatt ctattggaag tgcaagtaat agagtaaaca gtttaaattc ctcgttaaga    5520
aaagttcaaa ctactgctag tagtgtaagt tcaactatga caaaattaag ttctagcata    5580
aatgctgttt caggagttat tggaagttta aatggaagta ttatgagact agcaataact    5640
atagctatga ttattgatta ttttaataag ttgattcaaa agaaaaatga gtttaattca    5700
aatattatga ttatattaat atttaaagct aaaagtgatg aagtagaaaa aactaaaaat    5760
aaattacttg gaaatttaaa aaagattggt ggcaagattt ggaatatcgt aataaaagca    5820
aaagatatga ctaagagagt gataagtagt atcttgggaa aattaaaaca agtagagaaa    5880
cgtccttatc aaggaagtat taatcttaaa gatatggtga gtagtgctat gggtagaatt    5940
ttgcctaagt taatgttgtt taaaaatact ttttggagtg gtgtaatagc tataaaagat    6000
atggcaagtg gcattataag taagtatttt cccaaattga gattatttgc aggtaaggta    6060
tggagtggtc aatagctgt aaaggatatg gcaagtggaa tacttggttc gataaaaggg    6120
aagatatctg atttgacaaa tggtgctact ataggtgtcg ctgtgaaaaa gggtgttgat    6180
```

```
ttacttggtc aggaacaaaa tcagaaagtt gttctagaaa gtgtaatgaa aagaaatact   6240
ggaaaagtta atcaaataga tgttgatgat tattatggca gtttagtaag aatggcaaat   6300
gatacgcctt ttgaccctga agatgttgtt gcaatgggaa ctaaagctaa atgattagt    6360 aatattactg gtggcaaaaa agaaaaagat ataactcaag ctatggtaga tgttagagct   6420
ttaaatatga atacaagtag tgaacaagat gtatcagcag ctttcttaag tgcagcaaaa   6480
ggaaacatgg aatctcttaa tactctggta ggagaaaatt ataaaacttt tgatgaagca   6540
ttggaaggca taagtgtaaa gcagatgggg ttagctaaag aaatgagtaa tacaatacca   6600
ggtataatat caggagctca aacaagcatt aacaatggct tgaagagtat tgttaaacct   6660
tttgatgata ttttaggtca aggactaaag aaaataaaaa cttttataga aagtggatta   6720
ggcaatttag ctggcttatc tgaaaaaatg gctggtaaaa taggcaatgt aatgaatggt   6780
aagataatta ttggcaacaa atatgaccag atgcaatcta gaagtgtaaa aaatggaaaa   6840
gagttttctg attctactca atatcgaatt tctaatgagg ctgaaaagcg taaaatgatg   6900
gttgaaaata agcaagaacg ttttgaaaat catgcagcaa caatgatagg gaatgcacca   6960
aaagcaattg ttaacgcagg aagtacacta ttacaaaata tcgattttac agcattaata   7020
gattcattac ttccagtagt aaacttagta aataatttac tagatagtat aaacaataaa   7080
tcaccaattg cacaaggatt aataagtata tttggtacaa tagtaactac agcattccaa   7140
ctaatcggac ctgtagttga agctgttagt cctattatca caagaatttt tactttttta   7200
ggtgaatatg cacctcaaat aaacaatttt atagagacac tgggtgttat ttggaaaact   7260
gtatgggaga ccttaggacc tctgttggaa actggatgga aaattataga gccaatattg   7320
ggagcttttt ttaacatatt agataaagta tgtaaaatag ttaaagatat atgtaaatgg   7380
tggcaaacta tgattaataa gataaaaaat ggaagcatca caggaacagt tttaaatcta   7440
gtggaaaaga gtaaaaaaaa ttacaaagat aatccatatg ctggaacaaa ggctggtgat   7500
tctggtaaag cttattcagg taagaaaggt aataatgcat ttggattgaa ctatgttcct   7560
tataatgact atcaaaccag actccatgaa ggtgaaatgg ttttaactaa acaagaagca   7620
aatcaatata gaagcagaaa aaatggtgga aatataaaca tagctaagtt agctgataca   7680
atagtgatta gagaagaagc tgatatagaa aagataacat caaaattagt tgcaagtatc   7740
caattggcac agttaggggg tgtcttataa tggaaatgtg gcttagacaa gctgaagata   7800
gatttagatt tccagtattt ccatcttcct ttagtattaa tggaaaagct gctgtaaact   7860
cttctagtat actcaaaata ggtgaaatag caacttttgg tggtgtagct cttaaaagca   7920
tttcaatatc aagttttttt ccaaataaag actatacttt ctgtgactat acaggttttc   7980
catcaccata tgattgtgta aataagatag aaaatggat gaaggaaggt tttatattaa   8040
gatttacaat tacggaaaca aatataaata tggaagtcat aattgaaggg tttagttatg   8100
aagaaagaga tgggactcga gatgtatatt ttacattaga tttaaagag tataaaagaa   8160 taaagatacc aaaagtaact ccaaaacaat aactattata gataataagt tataaataac   8220
tgctgataga attaaatgaa aaggcaggtg atttttttatt attaagatttt gggtacacat   8280 aaaaaacgga agtatatatg acataactga catagtagaa aaggtatcat ggtcaggtga   8340
ttataaatct ccatcaagga cactagagtt ttcaataata caatcatcat ttgatgtaaa   8400
tttccaacaa atcgatatac caatagctag tacagtctgt ttctatgtag atgagaaaga   8460
actctttaga ggaatgataa ttaataggtc taaagattca agcagtaatg aaattagttt   8520
```

```
tgtatctaaa gatatgggat ttttacttac acaaagtgaa gtgtcataca atttttaaaga    8580
taagttagtt gaagacatag caaagcaagt atttgctgaa aataggcttt cagttggaat    8640
aatagcaaag accaatgtca agtatacaaa gatgtttata ggagtaaatg gttatgacac    8700
aataatgagt gcatatacag aagcaagtaa aaagacaaag aaaaagtata tgatagaggc    8760
caatttagat aagtttaatg ttattgaaaa aggaactgtt acattaagtg ttatgtttga    8820
agagggattt aatattataa ataccaccct ttcggagagc atggaaaatg taaaaaataa    8880
agtaatagtg gtagaccagt atggaagcaa gattagcgaa aaaatagata atgaaatttt    8940
taaggaagta aatgtaataa tgcaaaaagt aattcagcaa caagaaaatc aagatgtaga    9000
tattgatagc gagtttaatg ggatagaaaa aagctgttct cttaaaggtt atggagatgt    9060
aagttgtata actggtagag gagtaaaagt taaagattct tatacaaagc ttgtaggact    9120
atttttatata gatacagaca aacatacttg gcaaaatgga gaatatcaaa ttgagcttga    9180
acttaatttt caaaatctta tggatgaaaa gtcagcagga caggatgaac ctaaggaaga    9240
aagtaattta gggggagaag attatgcagg aggaaaaagg tttacagcag aatttacagc    9300
ttactgtcct agaaaagaag aaggtggaga tacagattgt agaaagaaaa aacttgaccc    9360
atctaaaaaa acttgcgctg ctcctatggt tggtaaatat gagcaaactt attatacaaa    9420
agagttttta aataaacatc ctttattaaa ctatggagat gaaatacagg taattcagg    9480
agtttctggt cgtgatggag tctataaagt aaatgacgta ggacctgcaa taactataga    9540
aaagaatgga acataccata tagatatttt atttggaaat gttgaagaag ctagtaaatt    9600
tggaagaaga aaaggaaaaa ttattattgg tggttattct ggtaatgtat ctgataaagc    9660
taaaatagta atatcagaag caaaaaaaca tctaggtaaa ccttataaat ggggtggaaa    9720
tggaccaagt agttttgact gttctggttt aatggtctat tgttttaaaa aagttaatgt    9780
tagtttgcca agaacgtcaa atcaacaatc taaaaaaggc aagaaagtag aacaaaaaaa    9840
tcttcaagca ggagatttag tatttttca taatccagtc agccatgttg gattatatat    9900
aggtaatgga gaatttttac atgctccaca aaaaggtgat gtagttaaaa taagtaagtt    9960
aagtagtaga agagatttta acacagctag gagagtatta taaaaggatg gtgatataat   10020
ggctaatcca ataaatgaat ttataggaat aataagagaa gaaggaaagt atcataatca   10080
accttctttt tttattggaa aaattaaaag taaattacca gatttaaaaa tagagacaaa   10140
taacatcata ttagaaaaag aagatatttt gatagatagt tggatgattg atagacagct   10200
agaaacattt gacacagaaa caaatcaaga acaccagcat gaagtaaaaa atccttttat   10260
agataacttt gaatctgggg atatggtaat aatgtttaga ataggcgaaa aatttgctgt   10320
tgtaagtaag ttggtgagct tataatgagt acaatatttc cttttatagg tgtcccagag   10380
gattatatct tacctaaaac agaagaattg ccaatctttc gtgaagtggc atgggatttt   10440
gaaaaagatg aacctatttt agaaaaaggt gactttaaaa taattgaaaa aaaagaagcc   10500
ttaaaagttt ggatatacaa gtgtataaag acaaatagat atgaacatga gatatactct   10560
ttagaatatg ggacagagct ttcagaacta ataggacaaa aatatacaaa aggtcttaca   10620
gaaagtgaag ctagtagatt cataaaagag gcccttctaa taaatccata tatattagaa   10680
gtaaacgtaa aaagtgctaa ctttaacaga gacatattga gtgcaaatgt aaaagtatcc   10740
actatctatg gggaggtgga aataaatgta tagtgaccag acatatgaag taataaaaaa   10800
tagaactctt gaaaatatta atcttgatat ttataaagga gaaggttctt ttctaaacaa   10860
catggtatct ggaaataatc tagaactttc gaagatatat ctagaacttt caaagatgca   10920
```

```
taaaatggct tttatacaag acacatataa ccagtttctt gataaaagag tcaatgaatt   10980
tggtgtatat agaaagttag gtacagagtc aaatggagaa gttgaattta ttggagagaa   11040
aggtactgta ataaataatg gcacaataat atcatataga gatttactat ttgtagtaat   11100
aaaagatgta actattggta gtgaagaagg tgacaatagc ccagttcaag ctctggaagt   11160
tggtaagaaa tataatttac ctacaaattg tgaatttaaa ctagttgata atatatctgg   11220
agtaacaaag attactaaca caagaagttt gaaggtggt acagatatag agacagatga    11280
agaactaaaa gaaagatttt ataaaatcca agaaatcaa gctacaagtg gaaataaagc    11340
tcactatgaa gaatgggctt tggaagtaga tggagtctat aatgttaagg tttatccaag   11400
atgggatggt ccgggaacag ttaaggtctt gatatttggg aaaaataatc aagctgttga   11460
tacagaaaca attgaaaggt gtcagcaaca tatagatgaa gagaagccta ttggaccaac   11520
tataacagtt gtgacaccat taccaataga aataagtata agtgcagtaa tgaaactaga   11580
agatggatat acattagaca atgtaaaaga atctttccta gaaagtataa atacatactt   11640
tagagatatt agaggagaga taatctatac aaaagtaatg ggaatactta taaatactac   11700
tggtgtacac gatttaagta acctacttat aaatggaagt acagataata taactattaa   11760
tgaagataaa atacctagtg taacaactgt taatttagt gaggtggaaa atcaatgaag    11820
ctaattgata aactaccatc atttgataga aattacattg tagaggagat acaaggtgca   11880
tacgatacag aattaaatat tcttaaagaa gatattgatg atacctttaa ccaattattt   11940
gttgacactg caacatgggg attagatatg tgggaagaca tactctgcat tgaaaaaaaa   12000
gaacttgatt ttgacacaag acgtagcaat ataaaagcta aatgagaag cagaggtact    12060 agtactattg aagttataaa aagtatatgt gaggcatata caaaatcaga aacagatata   12120
aaagtttata gtgatgaatt tacattcgta ttgagtttta tagcaaataa ctgtgactat   12180
aaaactcttt tagattgtag cgatatgatt gaaagagtaa aacctgctca cttattacac   12240
tatttagaac caataatact agataaaagt atggtctatt gtggtggagg tatggtatgt   12300
agtgaagagg taaaagttca tccatacttt gaaccaatta taaatgtag tgctgttgta    12360 aactgtggag ctggaatgat aagtagagaa gaaataaagg tttatccttt aagcattaaa   12420
tgcattgaaa ataattgtaa gattaatata gctattgcaa atgatacagg tgtagaaaat   12480
gtagtagttt atcctaaatc ggaggtggta taattggaag aaaaatttta tataatatta   12540
accaaaattg gtagagaaaa aatagcaaat gcaactgcac taggagagct tgttggatta   12600
accaagtttc aagttggaga tagtaatgga gaatattatg agccaacaga ggaacaaact   12660
gctttaaaga atgtagtttg ggaaggaaat ataaattctc taagaattga tgaaaaaaat   12720
cctaattgga tagttatagaga gactatttta ccaggaacag ttggtggatt tatgataaga   12780
gaagctgctg ttctggataa tgagaataat ataatagcta taggtaagta tccagagacg   12840
tataagccac gtgctgaaga tggcagtatt aaagatttgg ttgtaaaaat gattttacaa   12900
ttgtccaata cttcaaatgt tacattagaa gtagacccga cgttggtttt tgtaactcaa   12960
aaggatattc aagatttaga tgataagttt gataaaaata taaagaaat aaaagtaaaa    13020 attggcgaag aactcttatc tacagaagct aaaaacttat caggagctat aaatgaggta   13080
gtagaaaaaa ttaaaaatat atctattgat gatgtaatag gaggtcaaat acaaactgaa   13140
ctatctgtat taaaaaatag ttacaataaa ttatctgaaa aagtattaga tatcttaata   13200
tacttagaat tagagtcaga aatagatgta gatgaagctg gatattggta tgatacctta   13260
```

```
actaatgcta aaaacataat agctatagaa ggccttaagt tagatttaaa tagaaagtgt   13320
ataactggag aacttggtag tgttacattt aagaatgtgg tgctaccatt taatgcaaat   13380
agagttagat atatacatga aatggataat aactttgttg aaacaaaatc taatagggca   13440
tattcaattg gtcagacaga tataacttta aataaatatt cgtatgaaat aagataatta   13500
ggaggttttt ataatgaaaa gaactaaact acttcaaaga ggtaatttct ttggcgataa   13560
aaatatggta gttgatgaat tgatgaagg gtatgataat tatgacttta ttaatttttt   13620
tactggatgt tgtaactata catttggtct aaaaaataat aatatcttgt atggatgtgg   13680
agataatagt aactttcaac ttggattggg agaagacaa acaacaagaa aattatttac    13740
gaaaatacca aatatatcta ccaatattaa aaaagttgca tgtggagaat ctcatgcagt   13800
tatacttact tcagatggag aattacttgt cgcaggtata aatacagatg gtcaaatggg   13860
attgggatta gaaaaagtag ggaaaacagt ttctacattt gagaaggttc cagaaataaa   13920
aggcgtaaag gatattgcat gtggacttca atcaacatat cttttataca atgatggaac   13980
tttatatgtt gctggaaata atttgtatgg tcaattaggt ctaggaacta atggagcatc   14040
tgcaaatgta aatacattta caaaagtaga tgttgacaat gtaaaggctg tattttcata   14100
taataaatca gcttttataa taagaatga caataaatgc tattctactg gttttaataa    14160
tcaaggtcaa ctaggtttag gagataagaa taatagagat ttatttagtt tagtttctat   14220
taatgatgtt aagactatag cttgtggttc tgaacacact gtgttaatga cgtataataa   14280
tgatatatat ggttgtggaa aggaaaaatg ttttggaaat gcacttcaat catcactatt   14340
tactaagata gaagaagtaa atataaaaac tattgcatgt ggtcatggta acactatgct   14400
tatagataac aaaggtactt taaaggttgc tggaaataat gatatatatc agttaggtat   14460
agcaaattac tctgagaata tagataattc atttatagat ttaaaaaata ttgtagctaa   14520
gaatattttc attggtttat cacatagcat actaattgat tcaaataatg attcatattg   14580
tacaggagat aatacttatg gacaattagg ttcgtttttt gatgatatgc acattgtaga   14640
atttaagaaa atggatagtg aaaaatatag ttatagtaat tatataaatt taattaaatc   14700
tgaggataaa ttaactttat taaaagaaga aatggaaata aaggatattg aacttccact   14760
agatatacat tctgtaagag atgtcgtttt tagtccttat tgtactctgg ttattttagg   14820
gaatggagat gtatatggtc taggaaataa tagatacaaa ggaatgggtt ctgacttacc   14880
aagtcaatta aatgagttga caaaattaag tatctctaat gtaaagtcta tagtagcatc   14940
aaaaaatatt tctggaggaa tattctacat taaaaatgat gatacttgtt attattctgg   15000
accaaatagt aactcaatag caggtgttct tccttctaat tcagatgtat ttaagaaaat   15060
atctatagat aatgtaaaaa aagttgttat aaatactgat ttatcaaact ggttttcatt   15120
aattgtaact aataataagc aaatatacac ttctggaaag agttcaagtt atgttaatgg   15180
acttagtaat gcattaataa gtcaatatac tgagattagc cttagtaatg taactgatgc   15240
ttatagttca tataatgcaa catttattgt agttgatgaa aaaaaggtat atgcaactgg   15300
tataaataca aattacctgt taggttttag tacttctgat ggatctaatg taaatctagg   15360
tttattaagt gattggtatt atataaatat atcagggtca agttatagta gagtttcatg   15420
cacgaataat attactaaaa ttaataatat tatcatatat gagtatgtaa ctgtatttg    15480
tacaaacatt ggatcttttc taactggata ccatggtact tcatggacaa aaccaactga   15540
ttcaagctat agagttcaat atcagggaat ttcatatgca ggatatcttg attcttatat   15600
atataattat tatcctacaa gatgtacaca atcatcatct tctacaactt tgcttatttt   15660
```

```
atataatggg gaatcgtcaa gtaatttaaa aaatgtcaat ccagataatt tacttatttc   15720
tggaggttca tcttatatac atcaatatgg aaggaattat cttaacaatc aatcatctaa   15780
taatattgca gcatctaata taaattcagg tcctattacc tctgataaag ccatattttt   15840
atataaagct ctattgtatt tatcttctaa cacgctatat ggttttggga atatatctga   15900
aagtgcaaaa gaactagatg tttcagatac acaagatgga tataatgcca ctaattataa   15960
aaaggtaatg aaaaatataa aaaatatatt tatacctcct tatgatttaa gtagagataa   16020
aactagattt gcaatattaa ctgataagag cttatttata tgtggatata actctaaggg   16080
tacgcatggt atatcagtta atagtagttt aaatttaaat aataagataa attacaataa   16140
aaagaatagc agtagtgaaa tatcttctaa tatacaagaa atatatagcc attcaaagtc   16200
tacatattta ttaactaata ataatatgct ttacagtgtt ggtttaaatg atgtaggtca   16260
attaggagtg ggagatgaga taaatagaaa ggtatttact aaaataaata ttgataatat   16320
aaaatctata aatgtaaata gattactga caatagtaaa catgcatttg cgataaaaaa   16380
tgataatacc tgttatgctg ttggtttaaa taattctggt cagttaggaa taggagataa   16440
tgtaaataga aatatatttta ctaaaataaa tgttgaaaat gtaaaatatg tagctgtata   16500
tggaaacaca tctctattat taactaatga tggtcttttta tatggagcag gtaataatgg   16560
aaaaggacag ttaggattgg gtgatactac aagtaggaat atatttacac gtataccctat   16620 aaatggtgtt agagatgtat atctatgtaa tgatgtatca atcattgtta aaaatgataa   16680
tacatgctat gtatgtggac ttgtaaatgg ctattttggg tttactgaag gaagtataag   16740
tacatttaca aaaataaata ttgagaatgt aaaatctgtt gtgacagcag gaagtgaagc   16800 tacattttt ataacaaatg acaatatgat ttatactaca gggaaaaaag agagggtatt   16860
cttttcaaca gagactaatg atataaaggg gatacgagta attaataata ttataaatgc   16920
aaaaaaaata gtagttaatg gatatacttc agccatttta acaaatgaca ataaactatt   16980
tgttggaggt cttagtggat atggaagtat agcaaataat aataatacaa atagtgtgga   17040
agatgttaaa gatgttttttg taacagctaa taatacactt tatatagata ataataacaa   17100
tttgatatca tcaggtagag atacttatgg tatatctgat gaatcttata gggatatgtc   17160
agttccatat tataaagtat ctataaagaa agatgttgat actgtatttt ctagttacaa   17220
tactatattt attaaagata tatatggaaa attttattct tcaacaagag ataatagata   17280
taatcattta ggtattcacc atagatatga taatgataaa aatgaagctc ttgaaggttc   17340
cctacattca tatttaaaaa cagataacac atcagataaa atagttttta ataagaaaaa   17400
tgaaaagcta gtaatgttta atgataagta tataaaaaca aataataagt atataaatta   17460
taaaaacata tttaaagata attttaagta tacttcaata atattgccat ttgaggtatc   17520
tgatattgat atatcaaaaa cacattcatt ggctgttgct aaggatggca agttatatgg   17580
aataggaagt aattcatata agaaattaa tcaaaccctt gaagatatag aattattaac   17640
tcttactgaa gtaaatatat cagatgtcaa aaaagttgct tgtggagata actactccta   17700
tattattaag acagataata ctctatggtc atatggaaag aatactgagt accaattggg   17760
agttggccac aataatgatg taagagagtt acaaaaggtt actggattac cttctgttaa   17820
agatataagt atatataact caatgacact tgttttaact aatgagggag agttgtacgc   17880
tcaagggtac aatacaaatg gattatttgg actaggagaa agtgaaaaag ataagataat   17940
aagaactttt actaaagtat taactaatgt taaagaaatt aagtcacata atgatgacca   18000
```

```
catactagta attaaaaatg ataatagtct atggataact ggtaaaaata aatctatgta    18060
taaaatatct atatcaatta ctgatttata tgaatttact aaaataccaa ttcctgaaca    18120
tctaaatgat attttagata tagagctttc agatgataca atatacatga taacaaaagt    18180
agatacaagt aaagcatcta tagaaatagt tgaaaaatca atatctcaag tgagagttgt    18240
agtacaagac cctaataatg ttatagaaaa acttgaaatg tttataaatg atgaattaat    18300
atctactaag actaatttgg aaataaatag cattatattt gagataccac aaaataaaat    18360
agtattagga gaaataaaga tactgattaa agccagtagt cctacaggcg atttatattc    18420
aagtatgttt atatttaaat cagaaacagg gcttaaagta aaaaaggatt ctatttttaat   18480 gataaacaat aaagtatatt caatcataaa cattactgaa ataacactg acttaatagt    18540 aacattaaat gagggattaa aggatgatat gatggaaaac aatcctatat atcaattaat    18600
aaataaaact aaagttcaag taaaaataaa taaatctgac ttattcaaag acatgaaact    18660
agttgaaatc aaaaaatcag actcaagtta ccaagaaatc tatgaattag aagaagccaa    18720
cataaaaagt gctcagccta aaatcatagt agaaaaagga gataaatgga cagctataaa    18780
acgtccatct atgattttta gatatgatgc tgaaaacaac gagccacaag cttaaaatgg    18840
aggtgtgaaa attgtttaaa ttcgataaaa ataaatata acaaatcaaa caaggtagaa    18900
aagtagaaat gcagtataaa gacatttcag ataagtat aggtcaagta aagcaagatg     18960 atgataaca aataatttt atagcaatg tagaaatata tgagatgttg ttaaatcaaa      19020
gttctgtcaa tgaagcaagt aatataagca ctttagtgt aagaaaatct ggaggtgaga    19080
gtggaatggt agaagtatat gtagctttaa ttttaagagg caaaaaaaca atagaagaag    19140
taccagcagt aattagagag caagttagaa ttagatgtaa agaattagaa ataccagttg    19200
aatagtaaat ttagaataac tatgtattag ttatttttt tatgtaaagt acaaggtctt    19260
aactttaata agtaagcctt gtacttattt tttgttacat tagaacttgt atatatattt    19320
attatttatt caatctataa attacaccta caatttaaag tacagaagat taaattgata    19380
atcctgaaaa tataatattg catgatgtaa gaatacaaca aaaattaaag ctataagtat    19440
aaaaaattta gacaatagga ggctataatg gataaattaa taaccgaatt gagtagtcta    19500
ggggcaatag gtatactatg tgctctatta tttaaaaata ctatgcagga gaaaaagaa    19560 gatagagaca tgtataaaaa aactgtgaaa aattttatag aattatctac acaacaacaa    19620
gaaataaaca aaaatatact tgttcaaatg ggtataatga aaacagatgt agaggaaatt    19680
aaggaagatt ttactgatat aaaaggtatg ttacaaaatg gtgtataaca tgaaagagta    19740
gcaccagatt atatattgtt aggaaaagat aaagtagtat tgtagatagt tcactatttt    19800
attgagaagg atttaatatt taaaatatta attaaaaaa gtaataaaaa taacatataa    19860
aaattaaaaa aggagttaag cttaaatttg aggcgcg                            19897
```

<210> SEQ ID NO 62
<211> LENGTH: 168
<212> TYPE: PRT
<213> ORGANISM: Clostridium difficile

<400> SEQUENCE: 62

Met Asn Asn Leu Asp Lys Leu Phe Glu Leu Ala Ser Gln Glu Glu Ile
1               5                   10                  15

Ile Ile His Tyr Thr Thr Tyr Ile Ala Gly Asp Leu Glu Gly Leu Tyr
            20                  25                  30

Ile Asn Lys His Gly Ile Lys Ile Ile Ser Leu Leu Ser Asn Leu Lys

```
                    35                  40                  45
Gln Asn Ser Lys Lys Leu Thr Ser Ile Leu Ala Glu Glu Leu Gly His
 50                  55                  60

His Phe Thr Ser Leu Gly Tyr Tyr Val Ser Ser Tyr Asn Asp Tyr Tyr
 65                  70                  75                  80

Thr Lys Ile Ile Ile Asp Lys Cys Glu Asn Lys Ala Leu Lys Trp Ala
                 85                  90                  95

Cys Glu Phe Leu Ile Thr Glu Glu Asp Ile Asn Ile Ile Asn Ser
            100                 105                 110

Gly Ile Thr Cys Val Tyr Glu Met Ala Asp Ile Leu Asn Val Asp Ile
            115                 120                 125

Thr Phe Phe Gln Lys Arg Leu Glu Phe Leu Ser Leu Lys Lys Gln Ser
        130                 135                 140

Leu Gln Leu Gly Asn Asn Lys Tyr Leu Ile Leu Thr Asn Leu Pro Tyr
145                 150                 155                 160

Phe Tyr Ile Phe Asp Pro Ile Ser
                165
```

<210> SEQ ID NO 63
<211> LENGTH: 106
<212> TYPE: PRT
<213> ORGANISM: Clostridium difficile

<400> SEQUENCE: 63

```
Met Phe Ala Lys Arg Leu Arg Glu Leu Arg Lys Glu Phe Gly Leu Thr
  1               5                  10                  15

Gln Arg Glu Leu Gly Glu Lys Val Gly Val Ser Gln Arg Val Leu Gly
                 20                  25                  30

Tyr Tyr Glu Thr Glu Asn Arg Phe Pro Asp Glu His Ile Leu Asn Lys
             35                  40                  45

Leu Ala Asp Val Phe Asn Val Ser Val Asp Tyr Leu Leu Gly Arg Thr
 50                  55                  60

Leu Val Lys Glu Asn Ile Asp Thr Val Ala Ala His Arg Lys Asn Pro
 65                  70                  75                  80

His Glu Glu Leu Pro Glu Glu Ala Gln Glu Gln Leu Asn Asp Tyr Ile
                 85                  90                  95

Glu Phe Leu Leu Asn Lys Tyr Lys Lys Lys
            100                 105
```

<210> SEQ ID NO 64
<211> LENGTH: 65
<212> TYPE: PRT
<213> ORGANISM: Clostridium difficile

<400> SEQUENCE: 64

```
Met Phe Lys Asn Asn Leu Lys Tyr Tyr Arg Lys Cys Lys Gly Met Thr
  1               5                  10                  15

Gln Ile Gln Leu Ala Arg Lys Ala Gly Ile Thr Asn Asp Tyr Ile Ser
                 20                  25                  30

Gln Ile Glu Arg Gly Ile Lys Asn Pro Gly Leu Leu Met Ala Lys Lys
             35                  40                  45

Ile Ser Ser Ile Leu Glu Gln Asn Ile Glu Glu Val Phe Phe Ile Gln
 50                  55                  60

Leu
 65
```

<210> SEQ ID NO 65
<211> LENGTH: 146
<212> TYPE: PRT
<213> ORGANISM: Clostridium difficile

<400> SEQUENCE: 65

Met Glu Asn Lys Lys Asp Ile Leu Phe Lys Glu Thr Asp Lys Arg Leu
1               5                   10                  15

His Asn Tyr Lys Tyr Leu Asp Ile Lys Ile Lys Asn Ile Asn Leu Asp
            20                  25                  30

Ile Lys Arg Cys Glu Asn Glu Tyr Ser Gly Cys Gly Ala Met Val Tyr
        35                  40                  45

Thr Glu Lys Thr Ser Asn Thr Tyr Asn Ile Ser Ser Val Glu Asn
    50                  55                  60

Glu Val Leu Lys Arg Glu Arg Leu Arg Lys Leu Lys Met Glu Lys
65                  70                  75                  80

Glu Asp Ile Glu Ile Glu Lys Glu Lys Ile Glu Asn Ala Leu Thr Cys
                85                  90                  95

Leu Asn Asp Ile Glu Met Glu Phe Phe Asn Leu Phe Tyr Asn Ser Lys
            100                 105                 110

Thr Lys Asn Asn Met Thr Tyr Ile Ser Met Lys Leu His Leu Asp Arg
        115                 120                 125

Thr Ser Cys Tyr Asn Leu Lys Lys Lys Met Ile Phe Lys Leu Ser Glu
    130                 135                 140

Ile Leu
145

<210> SEQ ID NO 66
<211> LENGTH: 147
<212> TYPE: PRT
<213> ORGANISM: Clostridium difficile

<400> SEQUENCE: 66

Leu Leu Lys Tyr Lys Glu Ile Leu Glu Thr Ile Glu Ile Leu Lys
1               5                   10                  15

Lys Asn Phe Thr Glu Ser Ile Phe Ile Asp Asp Glu Ser Val Gln Gly
            20                  25                  30

Ser Glu Gly Ser Cys Phe Phe Val Ser Ile Leu Ser Val Ile Cys Thr
        35                  40                  45

Pro Val Met Leu Asn Thr Asn Asn Lys Asp Ile Val Ile Ser Ile Lys
    50                  55                  60

Tyr Leu Pro Lys Pro Gln Ser Lys Ser Ile Arg Met Tyr Glu Ile Ser
65                  70                  75                  80

Asp Glu Leu Asn Lys Leu Phe Asn Arg Asn Ile Lys Val Thr Asp Arg
                85                  90                  95

Lys Leu Asn Ile Thr Lys Leu Glu Gln Ser Ile Lys Lys Glu Ser
            100                 105                 110

Ile Tyr Val Leu Asn Phe Thr Phe Thr Leu Asn Tyr Leu Asp Ser Val
        115                 120                 125

Tyr Glu Glu Asp Val Val Tyr Glu Asn Met Lys Glu Ile Asn Leu Asn
    130                 135                 140

Leu Gly Glu
145

<210> SEQ ID NO 67
<211> LENGTH: 354
<212> TYPE: PRT

<213> ORGANISM: Clostridium difficile

<400> SEQUENCE: 67

Met Ala Ile Gly Leu Pro Ser Ile Asn Ile Ser Phe Lys Glu Leu Ala
1               5                   10                  15

Thr Thr Val Lys Glu Arg Ser Ala Arg Gly Ile Ile Ala Met Val Leu
            20                  25                  30

Lys Asp Ala Lys Ala Leu Gly Leu Asn Glu Ile His Glu Lys Glu Asp
        35                  40                  45

Ile Pro Val Asp Leu Ser Ala Glu Asn Lys Glu Tyr Ile Asn Leu Ala
    50                  55                  60

Leu Met Gly Asn Val Asn Thr Pro Asn Lys Leu Val Tyr Val Ile
65                  70                  75                  80

Glu Gly Glu Ala Asp Ile Gln Thr Ala Leu Asp Phe Leu Glu Thr Lys
                85                  90                  95

Glu Phe Asn Tyr Leu Cys Met Pro Lys Ala Val Glu Ala Asp Lys Thr
            100                 105                 110

Ala Ile Lys Asn Trp Ile Ile Lys Leu Arg Asp Ile Asp Lys Val Lys
        115                 120                 125

Val Lys Ala Val Leu Gly Lys Val Val Gly Asn His Glu Gly Ile Ile
130                 135                 140

Asn Phe Thr Thr Glu Asp Val Leu Val Gly Lys Lys Tyr Ser Val
145                 150                 155                 160

Asp Glu Phe Thr Ser Arg Val Ala Gly Leu Ile Ala Gly Thr Pro Leu
                165                 170                 175

Ser Gln Ser Val Thr Tyr Thr Lys Leu Ser Asp Val Val Asp Ile Pro
            180                 185                 190

Lys Met Thr Lys Val Asp Ala Glu Ser Arg Val Asn Lys Gly Glu Leu
        195                 200                 205

Ile Leu Ile Lys Glu Ala Gly Ala Ile Arg Ile Ala Arg Gly Val Asn
    210                 215                 220

Ser Leu Thr Glu Leu Thr Ala Glu Lys Gly Glu Met Phe Gln Lys Ile
225                 230                 235                 240

Lys Ile Val Asp Thr Leu Asp Ile Ile His Ser Asp Ile Arg Lys Val
                245                 250                 255

Ile Ile Asp Asp Tyr Ile Gly Lys Val Thr Asn Ser Tyr Asp Asn Lys
            260                 265                 270

Cys Leu Leu Ile Val Ala Ile Lys Ser Tyr Leu Glu Glu Leu Glu Lys
        275                 280                 285

Ser Ala Leu Ile Glu Ser Asp Ser Thr Val Glu Ile Asp Phe Glu Ala
    290                 295                 300

Gln Lys Ser Tyr Leu Lys Ser Leu Gly Val Asp Leu Ser Tyr Met Thr
305                 310                 315                 320

Leu Gln Glu Ile Lys Glu Ala Asn Thr Gly Ser Lys Val Phe Leu Lys
                325                 330                 335

Ala Lys Ile Lys Val Leu Asp Ala Met Glu Asp Ile Asp Leu Ser Ile
            340                 345                 350

Glu Ile

<210> SEQ ID NO 68
<211> LENGTH: 142
<212> TYPE: PRT
<213> ORGANISM: Clostridium difficile

<400> SEQUENCE: 68

```
Met Ala Asn Met Glu Ala Arg Asn Val Met Ser Gly Thr Trp Gly Glu
1               5                  10                 15

Leu Trp Leu Asp Gly Asn Lys Val Ala Glu Val Lys Lys Phe Gln Ala
            20                 25                 30

Lys Met Glu Phe Thr Lys Glu Asp Ile Ile Ile Ala Gly Gln Met Gly
        35                 40                 45

Thr Asp Thr Lys Tyr Met Gly Tyr Lys Gly Gly Ser Ile Thr Leu
    50                 55                 60

Tyr His Val Ser Ser Arg Met His Lys Leu Ile Gly Glu Lys Ile Lys
65                  70                 75                 80

Arg Gly Ser Glu Pro Arg Phe Val Ala Ile Ser Lys Leu Asn Asp Pro
                85                 90                 95

Asp Ser Tyr Gly Ala Glu Arg Ile Ala Val Lys Asn Ile Ala Phe Asp
            100                105                110

Asp Leu Thr Leu Ala Asp Trp Glu Val Gly Val Lys Gly Glu Ile Glu
            115                120                125

Ala Pro Phe Thr Phe Thr Glu Tyr Asp Phe Leu Asp Ile Ile
            130                135                140
```

<210> SEQ ID NO 69
<211> LENGTH: 148
<212> TYPE: PRT
<213> ORGANISM: Clostridium difficile

<400> SEQUENCE: 69

```
Met Ser Glu Asn Gly Leu Ser Lys Asn Ile Asn Ile Val Asp Leu Leu
1               5                  10                 15

Leu Asn Ser Asp Thr Glu Asn Leu Glu Arg Pro Ser Thr Ile Val Glu
            20                 25                 30

Leu Lys Arg Leu Ser Thr Ile Phe Gly Gln Glu Phe Lys Val Met Cys
        35                 40                 45

Arg Ala Leu Thr Ile Ser Lys Asp Glu Ile Gln Asn Thr Cys Leu
    50                 55                 60

Lys Ile Asp Glu Asn Met Lys Thr Asp Ile Asp Leu Pro Glu Met Gln
65                  70                 75                 80

Met Leu Thr Ile Ile Glu Gly Val Cys Asp Leu Asp Gly Lys Leu Leu
                85                 90                 95

Phe Lys Asn Lys Glu Leu Met Asp Lys Phe Lys Ala Pro Thr Pro Lys
            100                105                110

Glu Leu Ala Arg Lys Leu Leu Leu Pro Gly Ile Thr Asn Leu Tyr
            115                120                125

Arg Ile Leu Gln Asp Val Met Gly Tyr Gly Lys Asn Ala Val Ile Glu
    130                135                140

Glu Val Lys Asn
145
```

<210> SEQ ID NO 70
<211> LENGTH: 55
<212> TYPE: PRT
<213> ORGANISM: Clostridium difficile

<400> SEQUENCE: 70

```
Met Tyr Tyr Tyr Trp Lys Lys Lys Gly Ile Arg Pro Ser Leu Phe Tyr
1               5                  10                 15

Ala Met Asp Lys Gly Glu Leu Lys Leu Ile Glu Ala Phe Phe Ala Leu
            20                 25                 30
```

```
Glu Ile Glu Glu Glu Val Glu Lys Met Lys His Gly Tyr Gly Val Cys
            35                  40                  45

Pro Leu Thr Gly Gly Met
 50                  55

<210> SEQ ID NO 71
<211> LENGTH: 817
<212> TYPE: PRT
<213> ORGANISM: Clostridium difficile

<400> SEQUENCE: 71

Met Gly Asn Val Arg Glu Gly Ile Asn Met Tyr Leu Thr Asp Asn
 1               5                  10                  15

Tyr Thr Pro Lys Met Asn Gln Ile Ile Ser Val Thr Asp Asn Phe Arg
                20                  25                  30

Arg Ala Thr Val Ala Val Ser Leu Ser Thr Asn Val Met Ala Ser Ser
            35                  40                  45

Ile Lys Asn Ser Ile Gly Ser Ala Ser Asn Arg Val Asn Ser Leu Asn
        50                  55                  60

Ser Ser Leu Arg Lys Val Gln Thr Thr Ala Ser Ser Val Ser Ser Thr
 65                  70                  75                  80

Met Thr Lys Leu Ser Ser Ser Ile Asn Ala Val Ser Gly Val Ile Gly
                85                  90                  95

Ser Leu Asn Gly Ser Ile Met Arg Leu Ala Ile Thr Ile Ala Met Ile
                100                 105                 110

Ile Asp Tyr Phe Asn Lys Leu Ile Gln Lys Lys Asn Glu Phe Asn Ser
            115                 120                 125

Asn Ile Met Ile Ile Leu Ile Phe Lys Ala Lys Ser Asp Glu Val Glu
        130                 135                 140

Lys Thr Lys Asn Lys Leu Leu Gly Asn Leu Lys Lys Ile Gly Gly Lys
145                 150                 155                 160

Ile Trp Asn Ile Val Ile Lys Ala Lys Asp Met Thr Lys Arg Val Ile
                165                 170                 175

Ser Ser Ile Leu Gly Lys Leu Lys Gln Val Glu Lys Arg Pro Tyr Gln
                180                 185                 190

Gly Ser Ile Asn Leu Lys Asp Met Val Ser Ser Ala Met Gly Arg Ile
            195                 200                 205

Leu Pro Lys Leu Met Leu Phe Lys Asn Thr Phe Trp Ser Gly Val Ile
        210                 215                 220

Ala Ile Lys Asp Met Ala Ser Gly Ile Ile Ser Lys Val Phe Pro Lys
225                 230                 235                 240

Leu Arg Leu Phe Ala Gly Lys Val Trp Ser Gly Ala Ile Ala Val Lys
                245                 250                 255

Asp Met Ala Ser Gly Ile Leu Gly Ser Ile Lys Gly Lys Ile Ser Asp
                260                 265                 270

Leu Thr Asn Gly Ala Thr Ile Gly Val Ala Val Lys Lys Gly Val Asp
            275                 280                 285

Leu Leu Gly Gln Glu Gln Asn Gln Lys Val Val Leu Glu Ser Val Met
        290                 295                 300

Lys Arg Asn Thr Gly Lys Val Asn Gln Ile Asp Val Asp Asp Tyr Tyr
305                 310                 315                 320

Gly Ser Leu Val Arg Met Ala Asn Asp Thr Pro Phe Asp Pro Glu Asp
                325                 330                 335

Val Val Ala Met Gly Thr Lys Ala Lys Met Ile Ser Asn Ile Thr Gly
```

```
                340                 345                 350
Gly Lys Lys Glu Lys Asp Ile Thr Gln Ala Met Val Asp Val Arg Ala
            355                 360                 365

Leu Asn Met Asn Thr Ser Ser Glu Gln Asp Val Ser Ala Ala Phe Leu
        370                 375                 380

Ser Ala Ala Lys Gly Asn Met Glu Ser Leu Asn Thr Leu Val Gly Glu
385                 390                 395                 400

Asn Tyr Lys Thr Phe Asp Glu Ala Leu Glu Gly Ile Ser Val Lys Gln
                405                 410                 415

Met Gly Leu Ala Lys Glu Met Ser Asn Thr Ile Pro Gly Ile Ile Ser
            420                 425                 430

Gly Ala Gln Thr Ser Ile Asn Asn Gly Leu Lys Ser Ile Val Lys Pro
        435                 440                 445

Phe Asp Asp Ile Leu Gly Gln Gly Leu Lys Lys Ile Lys Thr Phe Ile
    450                 455                 460

Glu Ser Gly Leu Gly Asn Leu Ala Gly Leu Ser Glu Lys Met Ala Gly
465                 470                 475                 480

Lys Ile Gly Asn Val Met Asn Gly Lys Ile Ile Gly Asn Lys Tyr
                485                 490                 495

Asp Gln Met Gln Ser Arg Ser Val Lys Asn Gly Lys Glu Phe Ser Asp
            500                 505                 510

Ser Thr Gln Tyr Arg Ile Ser Asn Glu Ala Glu Lys Arg Lys Met Met
        515                 520                 525

Val Glu Asn Lys Gln Glu Arg Phe Glu Asn His Ala Ala Thr Met Ile
    530                 535                 540

Gly Asn Ala Pro Lys Ala Ile Val Asn Ala Gly Ser Thr Leu Leu Gln
545                 550                 555                 560

Asn Ile Asp Phe Thr Ala Leu Ile Asp Ser Leu Leu Pro Val Val Asn
                565                 570                 575

Leu Val Asn Asn Leu Leu Asp Ser Ile Asn Asn Lys Ser Pro Ile Ala
            580                 585                 590

Gln Gly Leu Ile Ser Ile Phe Gly Thr Ile Val Thr Thr Ala Phe Gln
        595                 600                 605

Leu Ile Gly Pro Val Val Glu Ala Val Ser Pro Ile Ile Thr Arg Ile
    610                 615                 620

Phe Thr Phe Leu Gly Glu Tyr Ala Pro Gln Ile Asn Asn Phe Ile Glu
625                 630                 635                 640

Thr Leu Gly Val Ile Trp Lys Thr Val Trp Glu Thr Leu Gly Pro Leu
                645                 650                 655

Leu Glu Thr Gly Trp Lys Ile Ile Glu Pro Ile Leu Gly Ala Phe Phe
            660                 665                 670

Asn Ile Leu Asp Lys Val Cys Lys Ile Val Lys Asp Ile Cys Lys Trp
        675                 680                 685

Trp Gln Thr Met Ile Asn Lys Ile Lys Asn Gly Ser Ile Thr Gly Thr
    690                 695                 700

Val Leu Asn Leu Val Glu Lys Ser Lys Asn Tyr Lys Asp Asn Pro
705                 710                 715                 720

Tyr Ala Gly Thr Lys Ala Gly Asp Ser Gly Lys Ala Tyr Ser Gly Lys
                725                 730                 735

Lys Gly Asn Asn Ala Phe Gly Leu Asn Tyr Val Pro Tyr Asn Asp Tyr
            740                 745                 750

Gln Thr Arg Leu His Glu Gly Glu Met Val Leu Thr Lys Gln Glu Ala
        755                 760                 765
```

```
Asn Gln Tyr Arg Ser Arg Lys Asn Gly Gly Asn Ile Asn Ile Ala Lys
            770                 775                 780
Leu Ala Asp Thr Ile Val Ile Arg Glu Glu Ala Asp Ile Glu Lys Ile
785                 790                 795                 800
Thr Ser Lys Leu Val Ala Ser Ile Gln Leu Ala Gln Leu Gly Gly Val
                805                 810                 815
Leu

<210> SEQ ID NO 72
<211> LENGTH: 140
<212> TYPE: PRT
<213> ORGANISM: Clostridium difficile

<400> SEQUENCE: 72

Met Glu Met Trp Leu Arg Gln Ala Glu Asp Arg Phe Arg Phe Pro Val
1               5                   10                  15
Phe Pro Ser Ser Phe Ser Ile Asn Gly Lys Ala Ala Val Asn Ser Ser
                20                  25                  30
Ser Ile Leu Lys Ile Gly Glu Ile Ala Thr Phe Gly Gly Val Ala Leu
            35                  40                  45
Lys Ser Ile Ser Ile Ser Ser Phe Phe Pro Asn Lys Asp Tyr Thr Phe
50                  55                  60
Cys Asp Tyr Thr Gly Phe Pro Ser Pro Tyr Asp Cys Val Asn Lys Ile
65                  70                  75                  80
Glu Lys Trp Met Lys Glu Gly Phe Ile Leu Arg Phe Thr Ile Thr Glu
                85                  90                  95
Thr Asn Ile Asn Met Glu Val Ile Ile Glu Gly Phe Ser Tyr Glu Glu
                100                 105                 110
Arg Asp Gly Thr Arg Asp Val Tyr Phe Thr Leu Asp Leu Lys Glu Tyr
            115                 120                 125
Lys Arg Ile Lys Ile Pro Lys Val Thr Pro Lys Gln
            130                 135                 140

<210> SEQ ID NO 73
<211> LENGTH: 509
<212> TYPE: PRT
<213> ORGANISM: Clostridium difficile

<400> SEQUENCE: 73

Met Ile Ile Asn Arg Ser Lys Asp Ser Ser Asn Glu Ile Ser Phe
1               5                   10                  15
Val Ser Lys Asp Met Gly Phe Leu Leu Thr Gln Ser Glu Val Ser Tyr
                20                  25                  30
Asn Phe Lys Asp Lys Leu Val Glu Asp Ile Ala Lys Gln Val Phe Ala
            35                  40                  45
Glu Asn Arg Leu Ser Val Gly Ile Ile Ala Lys Thr Asn Val Lys Tyr
50                  55                  60
Thr Lys Met Phe Ile Gly Val Asn Gly Tyr Asp Thr Ile Met Ser Ala
65                  70                  75                  80
Tyr Thr Glu Ala Ser Lys Lys Thr Lys Lys Tyr Met Ile Glu Ala
                85                  90                  95
Asn Leu Asp Lys Phe Asn Val Ile Glu Lys Gly Thr Val Thr Leu Ser
                100                 105                 110
Val Met Phe Glu Glu Gly Phe Asn Ile Ile Asn Thr Thr Phe Ser Glu
            115                 120                 125
```

```
Ser Met Glu Asn Val Lys Asn Lys Val Ile Val Asp Gln Tyr Gly
    130                 135                 140
Ser Lys Ile Ser Glu Lys Ile Asp Asn Glu Ile Phe Lys Glu Val Asn
145                 150                 155                 160
Val Ile Met Gln Lys Val Ile Gln Gln Glu Asn Gln Asp Val Asp
                165                 170                 175
Ile Asp Ser Glu Phe Asn Gly Ile Glu Lys Ser Cys Ser Leu Lys Gly
            180                 185                 190
Tyr Gly Asp Val Ser Cys Ile Thr Gly Arg Gly Val Lys Val Lys Asp
            195                 200                 205
Ser Tyr Thr Lys Leu Val Gly Leu Phe Tyr Ile Asp Thr Asp Lys His
    210                 215                 220
Thr Trp Gln Asn Gly Glu Tyr Gln Ile Glu Leu Glu Leu Asn Phe Gln
225                 230                 235                 240
Asn Leu Met Asp Glu Lys Ser Ala Gly Gln Asp Pro Lys Glu Glu
                245                 250                 255
Ser Asn Leu Gly Gly Glu Asp Tyr Ala Gly Lys Glu Phe Thr Ala
                260                 265                 270
Glu Phe Thr Ala Tyr Cys Pro Arg Lys Glu Gly Gly Asp Thr Asp
                275                 280                 285
Cys Arg Lys Lys Lys Leu Asp Pro Ser Lys Lys Thr Cys Ala Ala Pro
290                 295                 300
Met Val Gly Lys Tyr Glu Gln Thr Tyr Tyr Thr Lys Glu Phe Leu Asn
305                 310                 315                 320
Lys His Pro Leu Leu Asn Tyr Gly Asp Glu Ile Gln Val Ile Thr Gly
                325                 330                 335
Val Ser Gly Arg Asp Gly Val Tyr Lys Val Asn Asp Val Gly Pro Ala
                340                 345                 350
Ile Thr Ile Glu Lys Asn Gly Thr Tyr His Ile Asp Ile Leu Phe Gly
            355                 360                 365
Asn Val Glu Glu Ala Ser Lys Phe Gly Arg Arg Lys Gly Lys Ile Ile
            370                 375                 380
Ile Gly Gly Tyr Ser Gly Asn Val Ser Asp Lys Ala Lys Ile Val Ile
385                 390                 395                 400
Ser Glu Ala Lys Lys His Leu Gly Lys Pro Tyr Lys Trp Gly Gly Asn
                405                 410                 415
Gly Pro Ser Ser Phe Asp Cys Ser Gly Leu Met Val Tyr Cys Phe Lys
            420                 425                 430
Lys Val Asn Val Ser Leu Pro Arg Thr Ser Asn Gln Gln Ser Lys Lys
            435                 440                 445
Gly Lys Lys Val Glu Gln Lys Asn Leu Gln Ala Gly Asp Leu Val Phe
450                 455                 460
Phe His Asn Pro Val Ser His Val Gly Leu Tyr Ile Gly Asn Gly Glu
465                 470                 475                 480
Phe Leu His Ala Pro Gln Lys Gly Asp Val Val Lys Ile Ser Lys Leu
                485                 490                 495
Ser Ser Arg Arg Asp Phe Asn Thr Ala Arg Arg Val Leu
                500                 505
```

<210> SEQ ID NO 74
<211> LENGTH: 108
<212> TYPE: PRT
<213> ORGANISM: Clostridium difficile

<400> SEQUENCE: 74

```
Met Ala Asn Pro Ile Asn Glu Phe Ile Gly Ile Ile Arg Glu Glu Gly
1               5                   10                  15

Lys Tyr His Asn Gln Pro Ser Phe Phe Ile Gly Lys Ile Lys Ser Lys
            20                  25                  30

Leu Pro Asp Leu Lys Ile Glu Thr Asn Asn Ile Ile Leu Glu Lys Glu
        35                  40                  45

Asp Ile Leu Ile Asp Ser Trp Met Ile Asp Arg Gln Leu Glu Thr Phe
50                  55                  60

Asp Thr Glu Thr Asn Gln Glu His Gln His Glu Val Lys Asn Pro Phe
65                  70                  75                  80

Ile Asp Asn Phe Glu Ser Gly Asp Met Val Ile Met Phe Arg Ile Gly
            85                  90                  95

Glu Lys Phe Ala Val Val Ser Lys Leu Val Ser Leu
            100                 105
```

<210> SEQ ID NO 75
<211> LENGTH: 142
<212> TYPE: PRT
<213> ORGANISM: Clostridium difficile

<400> SEQUENCE: 75

```
Met Ser Thr Ile Phe Pro Phe Ile Gly Val Pro Glu Asp Tyr Ile Leu
1               5                   10                  15

Pro Lys Thr Glu Glu Leu Pro Ile Phe Arg Glu Val Ala Trp Asp Phe
            20                  25                  30

Glu Lys Asp Glu Pro Ile Leu Glu Lys Gly Asp Phe Lys Ile Ile Glu
        35                  40                  45

Lys Lys Glu Ala Leu Lys Val Trp Ile Tyr Lys Cys Ile Lys Thr Asn
50                  55                  60

Arg Tyr Glu His Glu Ile Tyr Ser Leu Glu Tyr Gly Thr Glu Leu Ser
65                  70                  75                  80

Glu Leu Ile Gly Gln Lys Tyr Thr Lys Gly Leu Thr Glu Ser Glu Ala
            85                  90                  95

Ser Arg Phe Ile Lys Glu Ala Leu Leu Ile Asn Pro Tyr Ile Leu Glu
            100                 105                 110

Val Asn Val Lys Ser Ala Asn Phe Asn Arg Asp Ile Leu Ser Ala Asn
        115                 120                 125

Val Lys Val Ser Thr Ile Tyr Gly Glu Val Glu Ile Asn Val
    130                 135                 140
```

<210> SEQ ID NO 76
<211> LENGTH: 350
<212> TYPE: PRT
<213> ORGANISM: Clostridium difficile

<400> SEQUENCE: 76

```
Met Tyr Ser Asp Gln Thr Tyr Glu Val Ile Lys Asn Arg Thr Leu Glu
1               5                   10                  15

Asn Ile Asn Leu Asp Ile Tyr Lys Gly Glu Gly Ser Phe Leu Asn Asn
            20                  25                  30

Met Val Ser Gly Asn Asn Leu Glu Leu Ser Lys Ile Tyr Leu Glu Leu
        35                  40                  45

Ser Lys Met His Lys Met Ala Phe Ile Gln Asp Thr Tyr Asn Gln Phe
50                  55                  60

Leu Asp Lys Arg Val Asn Glu Phe Gly Val Tyr Arg Lys Leu Gly Thr
65                  70                  75                  80
```

```
Glu Ser Asn Gly Glu Val Glu Phe Ile Gly Glu Lys Gly Thr Val Ile
                85                  90                  95

Asn Asn Gly Thr Ile Ile Ser Tyr Arg Asp Leu Leu Phe Val Val Ile
            100                 105                 110

Lys Asp Val Thr Ile Gly Ser Glu Gly Asp Asn Ser Pro Val Gln
            115                 120                 125

Ala Leu Glu Val Gly Lys Lys Tyr Asn Leu Pro Thr Asn Cys Glu Phe
    130                 135                 140

Lys Leu Val Asp Asn Ile Ser Gly Val Thr Lys Ile Thr Asn Thr Arg
145                 150                 155                 160

Ser Phe Glu Gly Gly Thr Asp Ile Glu Thr Asp Glu Glu Leu Lys Glu
                165                 170                 175

Arg Phe Tyr Lys Ile Gln Arg Asn Gln Ala Thr Ser Gly Asn Lys Ala
            180                 185                 190

His Tyr Glu Glu Trp Ala Leu Glu Val Asp Gly Val Tyr Asn Val Lys
            195                 200                 205

Val Tyr Pro Arg Trp Asp Gly Pro Gly Thr Val Lys Val Leu Ile Phe
    210                 215                 220

Gly Lys Asn Asn Gln Ala Val Asp Thr Glu Thr Ile Glu Arg Cys Gln
225                 230                 235                 240

Gln His Ile Asp Glu Glu Lys Pro Ile Gly Pro Thr Ile Thr Val Val
                245                 250                 255

Thr Pro Leu Pro Ile Glu Ile Ser Ile Ser Ala Val Met Lys Leu Glu
            260                 265                 270

Asp Gly Tyr Thr Leu Asp Asn Val Lys Glu Ser Phe Leu Glu Ser Ile
            275                 280                 285

Asn Thr Tyr Phe Arg Asp Ile Arg Gly Glu Ile Ile Tyr Thr Lys Val
    290                 295                 300

Met Gly Ile Leu Ile Asn Thr Thr Gly Val His Asp Leu Ser Asn Leu
305                 310                 315                 320

Leu Ile Asn Gly Ser Thr Asp Asn Ile Thr Ile Asn Glu Asp Lys Ile
                325                 330                 335

Pro Ser Val Thr Thr Val Asn Phe Ser Glu Val Glu Asn Gln
            340                 345                 350

<210> SEQ ID NO 77
<211> LENGTH: 232
<212> TYPE: PRT
<213> ORGANISM: Clostridium difficile

<400> SEQUENCE: 77

Met Lys Leu Ile Asp Lys Leu Pro Ser Phe Asp Arg Asn Tyr Ile Val
1               5                   10                  15

Glu Glu Ile Gln Gly Ala Tyr Asp Thr Glu Leu Asn Ile Leu Lys Glu
                20                  25                  30

Asp Ile Asp Asp Thr Phe Asn Gln Leu Phe Val Asp Thr Ala Thr Trp
            35                  40                  45

Gly Leu Asp Met Trp Glu Asp Ile Leu Cys Ile Glu Lys Lys Glu Leu
    50                  55                  60

Asp Phe Asp Thr Arg Arg Ser Asn Ile Lys Ala Lys Met Arg Ser Arg
65                  70                  75                  80

Gly Thr Ser Thr Ile Glu Val Ile Lys Ser Ile Cys Glu Ala Tyr Thr
                85                  90                  95

Lys Ser Glu Thr Asp Ile Lys Val Tyr Ser Asp Glu Phe Thr Phe Val
```

```
            100                 105                 110
Leu Ser Phe Ile Ala Asn Asn Cys Asp Tyr Lys Thr Leu Leu Asp Cys
        115                 120                 125

Ser Asp Met Ile Glu Arg Val Lys Pro Ala His Leu Leu His Tyr Leu
130                 135                 140

Glu Pro Ile Ile Leu Asp Lys Ser Met Val Tyr Cys Gly Gly Gly Met
145                 150                 155                 160

Val Cys Ser Glu Glu Val Lys Val His Pro Tyr Phe Glu Pro Ile Ile
                165                 170                 175

Lys Cys Ser Ala Val Val Asn Cys Gly Ala Gly Met Ile Ser Arg Glu
            180                 185                 190

Glu Ile Lys Val Tyr Pro Leu Ser Ile Lys Cys Ile Glu Asn Asn Cys
        195                 200                 205

Lys Ile Asn Ile Ala Ile Ala Asn Asp Thr Gly Val Glu Asn Val Val
210                 215                 220

Val Tyr Pro Lys Ser Glu Val Val
225                 230

<210> SEQ ID NO 78
<211> LENGTH: 327
<212> TYPE: PRT
<213> ORGANISM: Clostridium difficile

<400> SEQUENCE: 78

Leu Glu Glu Lys Phe Tyr Ile Ile Leu Thr Lys Ile Gly Arg Glu Lys
1               5                   10                  15

Ile Ala Asn Ala Thr Ala Leu Gly Glu Leu Val Gly Leu Thr Lys Phe
            20                  25                  30

Gln Val Gly Asp Ser Asn Gly Glu Tyr Tyr Glu Pro Thr Glu Glu Gln
        35                  40                  45

Thr Ala Leu Lys Asn Val Val Trp Glu Gly Asn Ile Asn Ser Leu Arg
    50                  55                  60

Ile Asp Glu Lys Asn Pro Asn Trp Ile Val Ile Glu Thr Ile Leu Pro
65                  70                  75                  80

Gly Thr Val Gly Gly Phe Met Ile Arg Glu Ala Ala Val Leu Asp Asn
                85                  90                  95

Glu Asn Asn Ile Ile Ala Ile Gly Lys Tyr Pro Glu Thr Tyr Lys Pro
            100                 105                 110

Arg Ala Glu Asp Gly Ser Ile Lys Asp Leu Val Val Lys Met Ile Leu
        115                 120                 125

Gln Leu Ser Asn Thr Ser Asn Val Thr Leu Glu Val Asp Pro Thr Leu
    130                 135                 140

Val Phe Val Thr Gln Lys Asp Ile Gln Asp Leu Asp Asp Lys Phe Asp
145                 150                 155                 160

Lys Asn Ile Lys Glu Ile Lys Val Lys Ile Gly Glu Glu Leu Leu Ser
                165                 170                 175

Thr Glu Ala Lys Asn Leu Ser Gly Ala Ile Asn Glu Val Val Glu Lys
            180                 185                 190

Ile Lys Asn Ile Ser Ile Asp Asp Val Ile Gly Gly Gln Ile Gln Thr
        195                 200                 205

Glu Leu Ser Val Leu Lys Asn Ser Tyr Asn Lys Leu Ser Glu Lys Val
    210                 215                 220

Leu Asp Ile Leu Ile Tyr Leu Glu Leu Glu Ser Glu Ile Asp Val Asp
225                 230                 235                 240
```

```
Glu Ala Gly Tyr Trp Tyr Asp Thr Leu Thr Asn Ala Lys Asn Ile Ile
                245                 250                 255

Ala Ile Glu Gly Leu Lys Leu Asp Leu Asn Arg Lys Cys Ile Thr Gly
            260                 265                 270

Glu Leu Gly Ser Val Thr Phe Lys Asn Val Val Leu Pro Phe Asn Ala
        275                 280                 285

Asn Arg Val Arg Tyr Ile His Glu Met Asp Asn Asn Phe Val Glu Thr
    290                 295                 300

Lys Ser Asn Arg Ala Tyr Ser Ile Gly Gln Thr Asp Ile Thr Leu Asn
305                 310                 315                 320

Lys Tyr Ser Tyr Glu Ile Arg
                325

<210> SEQ ID NO 79
<211> LENGTH: 98
<212> TYPE: PRT
<213> ORGANISM: Clostridium difficile

<400> SEQUENCE: 79

Met Gln Tyr Lys Asp Ile Ser Asp Ile Ser Ile Gly Gln Val Lys Gln
1               5                   10                  15

Asp Asp Asp Ile Thr Asn Asn Phe Ile Ala Asn Val Glu Ile Tyr Glu
                20                  25                  30

Met Leu Leu Asn Gln Ser Ser Val Asn Glu Ala Ser Asn Ile Ser Thr
            35                  40                  45

Phe Ser Val Arg Lys Ser Gly Gly Glu Ser Gly Met Val Glu Val Tyr
        50                  55                  60

Val Ala Leu Ile Leu Arg Gly Lys Lys Thr Ile Glu Glu Val Pro Ala
65                  70                  75                  80

Val Ile Arg Glu Gln Val Arg Ile Arg Cys Lys Glu Leu Glu Ile Pro
                85                  90                  95

Val Glu

<210> SEQ ID NO 80
<211> LENGTH: 86
<212> TYPE: PRT
<213> ORGANISM: Clostridium difficile

<400> SEQUENCE: 80

Met Asp Lys Leu Ile Thr Glu Leu Ser Ser Leu Gly Ala Ile Gly Ile
1               5                   10                  15

Leu Cys Ala Leu Leu Phe Lys Asn Thr Met Gln Glu Lys Lys Glu Asp
                20                  25                  30

Arg Asp Met Tyr Lys Lys Thr Val Glu Asn Phe Ile Glu Leu Ser Thr
            35                  40                  45

Gln Gln Gln Glu Ile Asn Lys Asn Ile Leu Val Gln Met Gly Ile Met
        50                  55                  60

Lys Thr Asp Val Glu Glu Ile Lys Glu Asp Val Thr Asp Ile Lys Gly
65                  70                  75                  80

Met Leu Gln Asn Gly Val
                85

<210> SEQ ID NO 81
<211> LENGTH: 1802
<212> TYPE: PRT
<213> ORGANISM: Clostridium difficile

<400> SEQUENCE: 81
```

```
Met Lys Gln Asn Lys Leu Leu Gln Arg Gly Ala Tyr Phe Asn Asp Lys
1               5                   10                  15

Asn Ile Leu Ile Asp Asp Phe Asp Lys Arg Tyr Asn Asp Tyr Asp Phe
            20                  25                  30

Val Glu Phe Phe Thr Gly Ile Ser Asn Ser Thr Phe Gly Leu Lys Ser
        35                  40                  45

Asp Gly Asn Leu Tyr Ala Cys Gly Asp Asn Thr Gly Met Lys Gln Asn
    50                  55                  60

Lys Leu Leu Gln Arg Gly Ala Tyr Phe Asn Asp Lys Asn Ile Leu Ile
65                  70                  75                  80

Asp Asp Phe Asp Lys Arg Tyr Asn Asp Tyr Asp Phe Val Glu Phe Phe
                85                  90                  95

Thr Gly Ile Ser Asn Ser Thr Phe Gly Leu Lys Ser Asp Gly Asn Leu
            100                 105                 110

Tyr Ala Cys Gly Asp Asn Thr Gly Phe Gln Leu Gly Leu Gly Lys Asp
        115                 120                 125

Ser Ser Glu Arg Arg Met Phe Ser Lys Val Lys Ile Asp Asn Val Lys
    130                 135                 140

Tyr Val Ser Cys Gly Ser Lys His Ser Val Ala Val Thr Lys Asp Gly
145                 150                 155                 160

Phe Ala Tyr Gly Ala Gly Thr Ser Asn Val Gly Gln Leu Gly Val Ile
                165                 170                 175

Glu Ser Thr Val Tyr Tyr Glu Phe Thr Lys Leu Pro Ile Asp Asp Val
            180                 185                 190

Lys Thr Val Ala Cys Gly Tyr Asp Phe Thr Phe Val Leu Lys Asn Asp
        195                 200                 205

Gly Thr Leu Tyr Ser Ala Gly Leu Asn Ser Ser Gly Gln Leu Gly Leu
    210                 215                 220

Gly Asp Thr Asn Asn Arg Val Thr Phe Thr Lys Val Asn Ile Asp Ser
225                 230                 235                 240

Val Lys Asp Val Val Thr Tyr Asn Gln Ser Val Phe Ile Ile Lys Met
                245                 250                 255

Asp Gly Thr Ala His Ala Cys Gly Leu Asn Ser Asn Gly Gln Leu Gly
            260                 265                 270

Ile Asn Ser Thr Leu Asn Lys Ser Val Phe Asn Lys Ile Glu Gly Met
        275                 280                 285

Asp Asn Val Lys Gln Ile Ala Cys Gly Ser Ser His Thr Ile Leu Ile
    290                 295                 300

Lys Asn Asp Gly Thr Met Tyr Thr Thr Gly Ser Asn Gly Tyr Gly Gln
305                 310                 315                 320

Leu Gly Thr Gly Asn Asn Asn Ser Ile Val Phe Thr Leu Ser Ser
                325                 330                 335

Ile Asn Asn Val Lys Tyr Ala Ser Cys Gly Asn Asn His Thr Met Ile
            340                 345                 350

Leu Lys Tyr Asp Asn Thr Leu Phe Ser Thr Gly Gln Asn Asn Tyr Gly
        355                 360                 365

Gln Leu Ala Asn Ala Asn Lys Asp Val Ala Ser Arg Asn Thr Phe Val
    370                 375                 380

Lys Val Asn Val Glu Asn Ile Lys Asp Ile Lys Cys Gly Ser Gln Phe
385                 390                 395                 400

Asn Phe Leu Ile Asn Gly Ser Lys Glu Ile Phe Val Ser Gly Cys Asn
                405                 410                 415
```

-continued

```
Leu Ala Gly Gln Leu Gly Ser Phe Phe His Thr Thr Phe Leu Tyr Glu
            420                 425                 430

Phe Ser Lys Val Gln Ser Ser Asn Leu Asp Asn Tyr Ser Gly Leu Leu
        435                 440                 445

Val Asn Asp Asp Tyr Leu Tyr Val Thr Lys Asp Asn Ser Glu Phe Leu
    450                 455                 460

Asn Val Lys Leu Ser Asp Asn Phe Gln Asp Tyr Lys Lys Ile Glu Leu
465                 470                 475                 480

Thr Asp Asn Asn Met Phe Ile Val Met Asn Asp Gly Thr Leu Tyr Ala
                485                 490                 495

Cys Gly Leu Asn Asn Tyr Gly Gln Leu Gly Leu Gly Asp Thr Val Asn
            500                 505                 510

Arg Ser Val Met Thr Lys Val Asp Ile Asp Asn Val Leu Asp Ile Lys
        515                 520                 525

Gly Asn Gly Asn Ser Thr Phe Val Leu Lys Asn Asn Gly Thr Leu Tyr
    530                 535                 540

Ser Cys Gly Tyr Asn Ser Ser Gly Ile Leu Gly Leu Lys Asp Asn Thr
545                 550                 555                 560

Asn Arg Asn Ile Phe Thr Lys Ile Glu Ile Glu Asn Ile Lys Glu Phe
                565                 570                 575

Cys Val Glu Ser Asn Tyr Ile Val Ala Leu Asn His Ser Lys Glu Leu
            580                 585                 590

Tyr Gly Trp Gly Asn Gln Ser Tyr Ile Val Tyr Gly Asp Asn Arg Asn
        595                 600                 605

Tyr Pro Tyr Lys Asp Thr Arg Val Ser Asn Val Glu Lys Ile Ala Thr
    610                 615                 620

Trp Ser Asp Thr Leu Tyr Ile Leu Asp Ser Thr Gly Ala Thr Lys Thr
625                 630                 635                 640

Ile Gly Tyr Ser Tyr Asn Gly Ser Gly Gly Tyr Pro Ala Pro Ser Ser
                645                 650                 655

Ser Ser Thr Tyr Arg Glu Gly Gly Tyr Ile Asn Lys Asn Thr Ser Tyr
            660                 665                 670

Arg Thr Leu Glu Phe Tyr Asn Thr Ser Lys Thr Lys Leu Val Asn Leu
        675                 680                 685

Phe Ala Phe Tyr Asn Gly Cys Val Phe Val Asp Glu Asn Gly Leu Ala
    690                 695                 700

Tyr Cys Ile Gly Glu Asn Asn Ile Asn Phe Arg Gly Gly Ser Thr Thr
705                 710                 715                 720

Asn Glu Asn Asn Ser Leu Arg Phe Ile Asn Asn Ser Gly Val Tyr Tyr
                725                 730                 735

Thr Asn Thr Asp Gly Thr Asp Tyr Thr Cys Tyr Gln Trp Thr Tyr Lys
            740                 745                 750

Leu Ile Arg Cys Ser Ile Phe Asp Ser Pro Gln Asn Ile Ile Gly Asn
        755                 760                 765

Ser Lys Asn Ile Leu Tyr Leu Ser Lys Asn Asn Ser Thr Phe Lys Cys
    770                 775                 780

Thr Gly Asn Cys Ile Thr Tyr Gly Ile Asn Ser Gln Asn Trp Tyr Ser
785                 790                 795                 800

Tyr Phe Ser Asp Ser Ser Asn Gly Ala Ile Ala Leu Gly Asn Glu Phe
                805                 810                 815

Ile Leu Lys Asn Tyr Ser Gly Glu Cys Leu Leu Lys Gly Tyr Gly Lys
            820                 825                 830

Ala Thr Asn Gly Glu Phe Gly Asn Ser Thr Asn Ile Ser Ser Ile Ser
```

```
                835                 840                 845
Asn Tyr Asp Thr Gly Leu Lys Asp Ile Lys Asp Ile Val Lys Asn
        850                 855                 860
Asn Thr Val Val Val Asp Lys Asn Asn Ile Tyr Val Thr Gly
865                 870                 875                 880
Ala Asn Gln Phe Asn Lys Leu Gly Ile Gly Glu Tyr Asn Asn Gln Pro
                885                 890                 895
Ile Arg Lys Phe Thr Asn Ile Thr Glu Gln Ser Asn Ser Phe Ile Phe
                900                 905                 910
Met Asp Asp Ile Lys Glu Ile Thr Thr Ser Arg Asn Thr Met Phe Ile
                915                 920                 925
Val Lys Asn Asp Gly Thr Ala Tyr Ala Thr Gly Asn Asn Ser Ser Gly
            930                 935                 940
Gln Leu Gly Leu Gly Asp Thr Ile Asn Arg Asn Lys Phe Thr Gln Ile
945                 950                 955                 960
Asn Leu Asp Asn Ile Lys Lys Ile Ser Thr Ser Ile Asp Gly Asn Thr
                965                 970                 975
Thr Phe Ala Ile Arg Asn Asp Gly Thr Leu Tyr Ser Thr Gly Leu Asn
                980                 985                 990
Thr Lys Gly Gln Leu Gly Leu Gly Asp Ile Val Asn Arg Asn Thr Phe
            995                1000                1005
Thr Lys Val Asn Ile Gln Asn Val Arg Asp Val Val Leu Gly Thr
        1010                1015                1020
Thr His Ser His Ala Ile Lys Asp Asp Asn Thr Leu Tyr Ser Cys
        1025                1030                1035
Gly Glu Asn Thr His Gly Gln Leu Gly Leu Gly Ser Glu Ser Asn
        1040                1045                1050
His Pro Asp Val Leu Thr Phe Thr Val Asn Asn Ile Thr Asn Val
        1055                1060                1065
Arg Asp Val Tyr Cys Ser Asp Thr Thr Thr Phe Ile Val Lys Asp
        1070                1075                1080
Thr Asn Ile Ala Tyr Cys Cys Gly Tyr Asn Asn Asn Ser Gln Leu
        1085                1090                1095
Gly Met Gly Asn Thr Thr Asp Gln Tyr Ser Phe Ile Lys Cys Met
        1100                1105                1110
Glu Asn Val Lys Glu Val Ile Pro Asn Glu Ile Asn Thr Tyr Ile
        1115                1120                1125
Ile Thr Ile Tyr Asn Thr Ala Tyr Ser Thr Gly Leu Asn Thr Asp
        1130                1135                1140
Tyr Cys Leu Gly Leu Asn Ser Asn Ser Asn Gln Ser Ser Phe Ser
        1145                1150                1155
Glu Ile Pro Ile Ser Asn Val Val Lys Val Ala Pro Asn Arg Asn
        1160                1165                1170
Asn Ala Val Leu Leu Leu Thr Ser Glu Gly Asp Val Tyr Thr Ala
        1175                1180                1185
Gly Lys Cys Ser Asn Gly Ser Gly Thr Gly Ser Glu Thr Pro Glu
        1190                1195                1200
Lys Ile Lys Lys Ile Ala Ser Lys Ala Lys Asp Ile Gly Met Asn
        1205                1210                1215
Tyr Arg Cys Gly His Tyr Val Ser Asp Asn Gly Asp Leu Tyr Gly
        1220                1225                1230
Thr Gly Phe Asn Asp Cys Gly Gln Leu Gly Val Gly Asn Val Thr
        1235                1240                1245
```

-continued

```
Lys Arg Asp Thr Phe Ile Lys Thr Asn Thr Arg Val Lys Lys Ile
    1250                1255                1260

Leu Pro Leu Glu Tyr Ala Asn Ile Ala Ile Lys Asp Thr Asn Asp
    1265                1270                1275

Ile Tyr Ile Cys Gly Leu Asn Asn Tyr Gly Gln Leu Gly Val Gly
    1280                1285                1290

Asn Arg Tyr Asp Ser Arg Asn Asn Asp Asn Arg Ile Phe Asn Tyr
    1295                1300                1305

Lys His Met Asn Phe Val Met Gly Asp Leu Thr Ser Ile Lys Asn
    1310                1315                1320

Arg His Asn Phe Ile Leu Leu Asn Asn Lys Ile Val Ile Pro Thr
    1325                1330                1335

Thr Lys Asp Ile Asp Tyr Gly Leu Val Leu Gly Asn Leu Tyr Lys
    1340                1345                1350

Gly Asp Leu Tyr Thr Glu Leu Pro Tyr Glu Asp Ile Lys Glu Val
    1355                1360                1365

Ser Ile Ser Lys Thr His Ile Ile Ile Leu Leu Asn Asp Gly Thr
    1370                1375                1380

Met Tyr Gly Cys Gly Thr Asn Tyr His Gly Glu Leu Leu Gln Asp
    1385                1390                1395

Leu Ser Ile Asn Gln Val Asp Glu Phe Val Gln Ile Asn Val Ser
    1400                1405                1410

Asp Val Lys His Val Ser Cys Gly Asp Asn Phe Thr Tyr Phe Ile
    1415                1420                1425

Lys Ser Asp Asp Ser Leu Trp Ser Ile Gly Lys Asn Ser Glu Tyr
    1430                1435                1440

Gln Leu Gly Ile Gly His Asn Asn Pro Val Thr Glu Leu Gln Arg
    1445                1450                1455

Ile Thr Thr Ile Ser Ser Cys Lys Glu Val His Cys Gly Lys Asn
    1460                1465                1470

Tyr Thr Leu Val Val Thr Thr Ser Asn Glu Leu Phe Val Gln Gly
    1475                1480                1485

Tyr Asn Asp Lys Gly Ala Leu Gly Leu Gly Ser Asp Ser Glu Asn
    1490                1495                1500

Thr Ile Ile Lys Phe Phe Thr Lys Ala Leu Thr Asp Ile Arg Glu
    1505                1510                1515

Ile Lys Ser Tyr Gly Ser Asp His Ile Leu Val Leu Lys Asn Asp
    1520                1525                1530

Asn Ser Val Trp Val Thr Gly Lys Asn Arg Asp Val Tyr Lys Ile
    1535                1540                1545

Glu Gln Pro Val Glu Phe Leu Lys Glu Phe Thr Ile Val Pro Ile
    1550                1555                1560

Ser Glu Asp Val Asn Thr Val Lys Asp Val Leu Ala Thr Asp Asn
    1565                1570                1575

Thr Leu Tyr Ile Ile Ser Glu Val Gly Thr Thr Asn Ala Ala Ile
    1580                1585                1590

Glu Ile Thr Glu Lys Ser Ile Ser Ser Ile Lys Ile Lys Ile Gln
    1595                1600                1605

Asp Pro Asn Lys Asp Ile Ser Arg Ile Glu Met Leu Ile Asn Gly
    1610                1615                1620

Glu Ser Val Lys Ser Val Ser Asp Leu Ile Thr Glu Lys Ile Ser
    1625                1630                1635
```

-continued

```
Phe Glu Val Pro Pro Asp Lys Ile Lys Ile Gly Glu Asn Lys Ile
    1640                1645                1650

Leu Phe Arg Ala Tyr Cys Lys Gly Asp Asp Leu Tyr Ala Ser Leu
    1655                1660                1665

Phe Ile Phe Lys Glu Ser Thr Gly Asn Ser Ile Ile Lys Asp Ser
    1670                1675                1680

Tyr Val Met Ile Gly Asn Arg Met Tyr Lys Val Val Asn Thr Thr
    1685                1690                1695

Ser Asn Glu Gln Asp Ile Thr Ile Thr Leu Asp Arg Gly Leu Glu
    1700                1705                1710

Glu Asp Leu Asn Leu Gly Asp Pro Ile Tyr Gln Leu Ile Asn Lys
    1715                1720                1725

Thr Lys Val Gln Val Lys Ile Asn Lys Ser Asp Leu Phe Lys Asp
    1730                1735                1740

Met Lys Leu Val Glu Ile Lys Lys Ser Asp Ser Tyr Gln Glu
    1745                1750                1755

Ile Tyr Glu Leu Glu Glu Ala Asn Ile Lys Ser Ala Gln Pro Lys
    1760                1765                1770

Ile Ile Val Glu Lys Gly Asp Lys Trp Thr Ala Ile Lys Arg Pro
    1775                1780                1785

Ser Met Ile Phe Arg Tyr Asp Ala Glu Asn Asn Glu Pro Gln
    1790                1795                1800

<210> SEQ ID NO 82
<211> LENGTH: 1742
<212> TYPE: PRT
<213> ORGANISM: Clostridium difficile

<400> SEQUENCE: 82

Met Lys Gln Asn Lys Leu Leu Gln Arg Gly Ala Tyr Phe Asn Asp Lys
1               5                   10                  15

Asn Ile Leu Ile Asp Asp Phe Asp Lys Arg Tyr Asn Asp Tyr Asp Phe
            20                  25                  30

Val Glu Phe Phe Thr Gly Ile Ser Asn Ser Thr Phe Gly Leu Lys Ser
        35                  40                  45

Asp Gly Asn Leu Tyr Ala Cys Gly Asn Asn Thr Gly Phe Pro Leu Gly
    50                  55                  60

Leu Gly Lys Asp Ser Ser Glu Arg Arg Met Phe Ser Val Lys Ile
65                  70                  75                  80

Asp Asn Val Lys Tyr Val Ser Cys Gly Ser Lys His Ser Val Ala Val
                85                  90                  95

Thr Lys Asp Gly Phe Ala Tyr Gly Ala Gly Thr Ser Asn Val Gly Gln
            100                 105                 110

Leu Gly Val Ile Glu Ser Thr Val Tyr Tyr Glu Phe Thr Lys Leu Pro
        115                 120                 125

Ile Asp Asp Val Lys Thr Val Ala Cys Gly Tyr Asp Phe Thr Phe Val
    130                 135                 140

Leu Lys Asn Asp Gly Thr Leu Tyr Ser Ala Gly Leu Asn Ser Ser Gly
145                 150                 155                 160

Gln Leu Gly Leu Gly Asp Thr Asn Asn Arg Ala Thr Phe Thr Lys Val
                165                 170                 175

Asn Ile Asp Ser Val Lys Asp Val Val Thr Tyr Asn Gln Ser Val Phe
            180                 185                 190

Ile Ile Lys Met Asp Gly Thr Ala His Ala Cys Gly Leu Asn Ser Asn
        195                 200                 205
```

```
Gly Gln Leu Gly Ile Asn Ser Thr Leu Asn Lys Ser Val Phe Asn Lys
    210                 215                 220
Ile Glu Gly Met Asp Asn Val Lys Gln Ile Ala Cys Gly Ser Ser His
225                 230                 235                 240
Thr Ile Leu Ile Lys Asn Asp Gly Thr Met Tyr Thr Thr Gly Tyr Asn
                245                 250                 255
Gly Val Gly Gln Leu Gly Thr Gly Asn Asn Asn Ser Ile Val Phe
                260                 265                 270
Thr Leu Ser Ser Ile Asn Asn Val Lys Tyr Ala Ser Cys Gly Asn Asn
            275                 280                 285
His Thr Met Ile Leu Lys Tyr Asp Asn Thr Leu Phe Ser Thr Gly Gln
    290                 295                 300
Asn Thr Tyr Gly Gln Leu Ala Asn Ala Asn Lys Asp Val Ala Ser Arg
305                 310                 315                 320
Asn Thr Phe Ala Lys Val Asn Val Glu Asn Ile Lys Asp Ile Lys Cys
                325                 330                 335
Gly Ser Gln Phe Asn Phe Leu Ile Asn Gly Ser Lys Glu Ile Phe Val
                340                 345                 350
Ser Gly Cys Asn Leu Ala Gly Gln Leu Gly Ser Phe Phe His Thr Thr
            355                 360                 365
Phe Leu Tyr Glu Phe Ser Lys Val Gln Ser Ser Asn Leu Asp Asn Tyr
    370                 375                 380
Ser Gly Leu Leu Val Asn Asp Asp Tyr Leu Tyr Val Thr Lys Asp Asn
385                 390                 395                 400
Ser Glu Phe Leu Asn Val Lys Leu Ser Asp Asn Phe Gln Asp Tyr Lys
                405                 410                 415
Lys Ile Glu Leu Thr Asp Asn Asn Met Phe Ile Val Met Asn Asp Gly
                420                 425                 430
Thr Leu Tyr Ala Cys Gly Leu Asn Asn Tyr Gly Gln Leu Gly Leu Gly
            435                 440                 445
Asp Thr Val Asn Arg Ser Val Met Thr Lys Val Asp Ile Asp Asn Val
    450                 455                 460
Leu Asp Ile Lys Gly Asn Gly Asn Ser Thr Phe Val Leu Lys Asn Asn
465                 470                 475                 480
Gly Thr Leu Tyr Ser Cys Gly Tyr Asn Ser Ser Gly Ile Leu Gly Leu
                485                 490                 495
Lys Asp Asn Thr Asn Arg Asn Ile Phe Thr Lys Ile Glu Ile Glu Asn
                500                 505                 510
Val Lys Ala Phe Cys Val Glu Ser Asn Tyr Ile Val Val Leu Asn His
            515                 520                 525
Ser Lys Glu Leu Tyr Gly Trp Gly Asn Glu Ser Tyr Ile Val Tyr Gly
    530                 535                 540
Asn Ser Arg Asn Tyr Pro Tyr Lys Asp Thr Arg Val Ser Asn Val Glu
545                 550                 555                 560
Lys Ile Ala Thr Trp Ser Asp Thr Leu Tyr Ile Leu Asp Ser Thr Gly
                565                 570                 575
Ala Thr Lys Thr Ile Gly Tyr Ser Tyr Asn Gly Ser Gly Gly Tyr Pro
            580                 585                 590
Ala Pro Ser Ser Ser Thr Tyr Arg Asp Gly Gly Tyr Ile Asn Lys
    595                 600                 605
Asn Thr Ser Tyr Arg Thr Leu Glu Phe Tyr Asn Thr Ser Lys Thr Lys
    610                 615                 620
```

```
Leu Val Asn Leu Phe Ala Phe Tyr Asn Gly Cys Val Phe Val Asp Glu
625                 630                 635                 640

Asn Gly Leu Ala Tyr Cys Ile Gly Glu Asn Asn Ile Asn Phe Arg Gly
            645                 650                 655

Asn Ser Thr Thr Asn Glu Asn Asn Ser Leu Arg Phe Ile Asn Asn Ser
                660                 665                 670

Gly Val Tyr Tyr Thr Asn Thr Asp Gly Thr Asp Tyr Thr Cys Tyr Gln
        675                 680                 685

Trp Thr Tyr Lys Leu Ile Arg Cys Ser Ile Phe Asp Ser Pro Gln Asn
    690                 695                 700

Ile Ile Gly Asn Ser Lys Asn Ile Leu Tyr Leu Ser Lys Asn Asn Ser
705                 710                 715                 720

Thr Phe Lys Cys Thr Gly Asn Cys Ile Thr Tyr Gly Ile Asn Ser Gln
                725                 730                 735

Asn Trp Tyr Ser Tyr Phe Ser Asp Ser Ser Asn Gly Ala Ile Ala Leu
            740                 745                 750

Gly Asn Glu Phe Ile Leu Lys Asn Tyr Ser Gly Glu Cys Leu Leu Lys
                755                 760                 765

Gly Tyr Gly Lys Ala Thr Asn Gly Glu Phe Gly Asn Ser Thr Asn Ile
770                 775                 780

Ser Ser Ile Ser Asn Tyr Asp Thr Gly Leu Lys Asp Ile Lys Asp Ile
785                 790                 795                 800

Ile Val Lys Asn Asn Thr Val Val Val Asp Lys Asn Asn Ile
                805                 810                 815

Tyr Val Thr Gly Ala Asn Gln Phe Asn Lys Leu Gly Ile Gly Glu Tyr
        820                 825                 830

Asn Asn Gln Pro Ile Lys Lys Phe Thr Asn Ile Thr Glu Gln Ser Asn
            835                 840                 845

Ser Phe Ile Phe Met Asp Asp Ile Lys Glu Ile Thr Thr Ser Arg Asn
    850                 855                 860

Thr Met Phe Ile Val Lys Asn Asp Gly Thr Ala Tyr Ala Thr Gly Asn
865                 870                 875                 880

Asn Ser Ser Gly Gln Leu Gly Leu Gly Asp Thr Ile Asn Arg Asn Lys
            885                 890                 895

Phe Thr Gln Ile Asn Leu Asp Asn Ile Lys Lys Ile Ser Thr Ser Ile
                900                 905                 910

Asp Gly Asn Thr Thr Phe Ala Ile Arg Asn Asp Gly Thr Leu Tyr Ser
        915                 920                 925

Thr Gly Leu Asn Thr Lys Gly Gln Leu Gly Leu Gly Asp Ile Val Asn
    930                 935                 940

Arg Asn Thr Phe Thr Lys Val Asn Ile Gln Asn Val Arg Asp Val Val
945                 950                 955                 960

Leu Gly Thr Thr His Ser His Ala Ile Lys Asp Asp Asn Thr Leu Tyr
                965                 970                 975

Ser Cys Gly Glu Asn Thr His Gly Gln Leu Gly Leu Gly Ser Glu Ser
            980                 985                 990

Asn His Pro Asp Val Leu Thr Phe Thr Val Asn Asn Ile Thr Asn Val
        995                 1000                1005

Arg Asp Val Tyr Cys Ser Asp Thr Thr Thr Phe Ile Val Lys Asp
    1010                1015                1020

Thr Asn Ile Ala Tyr Cys Cys Gly Tyr Asn Asn Asn Ser Gln Leu
    1025                1030                1035

Gly Met Gly Asn Thr Thr Asp Gln Tyr Ser Phe Ile Lys Cys Met
```

-continued

```
            1040                1045                1050
Glu Asn Val Lys Glu Val Ile Pro Asn Glu Ile Asn Thr Tyr Ile
    1055                1060                1065
Ile Thr Ile Tyr Asn Thr Ala Tyr Ser Thr Gly Leu Asn Thr Asp
    1070                1075                1080
Tyr Cys Leu Gly Leu Asn Ser Asn Ser Asn Gln Ser Ser Phe Ser
    1085                1090                1095
Glu Ile Pro Ile Ser Asn Val Val Lys Val Ala Pro Asn Arg Asn
    1100                1105                1110
Asn Ala Val Leu Leu Leu Thr Ser Glu Gly Asp Val Tyr Thr Ala
    1115                1120                1125
Gly Lys Cys Ser Asn Gly Ser Gly Thr Gly Ser Glu Thr Pro Glu
    1130                1135                1140
Lys Ile Lys Lys Ile Ala Ser Lys Ala Lys Asp Ile Gly Met Asn
    1145                1150                1155
Tyr Arg Cys Gly His Tyr Val Ser Asp Asn Gly Asp Leu Tyr Gly
    1160                1165                1170
Thr Gly Phe Asn Asp Cys Gly Gln Leu Gly Val Gly Asp Val Thr
    1175                1180                1185
Lys Arg Asp Thr Phe Ile Lys Thr Asn Thr Arg Val Lys Lys Ile
    1190                1195                1200
Leu Pro Leu Glu Tyr Ala Asn Ile Ala Ile Lys Asp Thr Asn Asp
    1205                1210                1215
Ile Tyr Ile Cys Gly Leu Asn Asn Tyr Gly Gln Leu Gly Val Gly
    1220                1225                1230
Asn Arg Tyr Asp Ser Arg Asn Asn Asp Asn Arg Ile Phe Asn Tyr
    1235                1240                1245
Lys His Met Asn Phe Val Met Gly Asp Leu Thr Ser Ile Lys Asn
    1250                1255                1260
Arg His Asn Phe Ile Leu Leu Asn Asn Lys Ile Val Ile Pro Thr
    1265                1270                1275
Thr Lys Asp Ile Asp Tyr Gly Leu Val Leu Gly Asn Leu Tyr Lys
    1280                1285                1290
Gly Asp Leu Tyr Thr Glu Leu Pro Tyr Glu Asp Ile Lys Glu Val
    1295                1300                1305
Ser Ile Ser Lys Thr His Ile Ile Leu Leu Asn Asp Gly Thr
    1310                1315                1320
Met Tyr Gly Cys Gly Thr Asn Tyr His Gly Glu Leu Leu Gln Asp
    1325                1330                1335
Leu Ser Ile Asn Gln Val Asp Glu Phe Val Gln Ile Asn Val Ser
    1340                1345                1350
Asp Val Lys His Val Ser Cys Gly Asp Asn Phe Thr Tyr Phe Ile
    1355                1360                1365
Lys Ser Asp Asp Ser Leu Trp Ser Ile Gly Lys Asn Ser Glu Tyr
    1370                1375                1380
Gln Leu Gly Ile Gly His Asn Asn Pro Val Thr Glu Leu Gln Arg
    1385                1390                1395
Ile Thr Thr Ile Ser Ser Cys Lys Glu Val His Cys Gly Lys Asn
    1400                1405                1410
Tyr Thr Leu Val Val Thr Thr Gly Asn Glu Leu Phe Val Gln Gly
    1415                1420                1425
Tyr Asn Asp Lys Gly Ala Leu Gly Leu Gly Ser Asp Ser Glu Asn
    1430                1435                1440
```

```
Thr Ile Ile Lys Phe Phe Thr Lys Ala Leu Thr Asp Ile Arg Glu
    1445                1450                1455

Ile Lys Ser Tyr Gly Ser Asp His Ile Leu Val Leu Lys Asn Asp
    1460                1465                1470

Asn Ser Val Trp Val Thr Gly Lys Asn Arg Asp Val Tyr Lys Ile
    1475                1480                1485

Glu Gln Pro Val Glu Phe Leu Lys Glu Phe Thr Ile Ile Pro Ile
    1490                1495                1500

Ser Glu Asp Val Asn Thr Val Lys Asp Val Leu Ala Thr Asp Asn
    1505                1510                1515

Thr Leu Tyr Ile Ile Ser Glu Val Gly Thr Thr Asn Ala Ala Ile
    1520                1525                1530

Glu Ile Thr Glu Lys Ser Ile Ser Ser Ile Lys Ile Lys Ile Gln
    1535                1540                1545

Asp Pro Asn Lys Asp Ile Ser Arg Ile Glu Met Leu Ile Asn Gly
    1550                1555                1560

Glu Ser Val Lys Ser Val Ser Asp Leu Ile Thr Glu Lys Ile Ser
    1565                1570                1575

Phe Glu Val Pro Pro Asp Lys Ile Lys Ile Gly Glu Asn Lys Ile
    1580                1585                1590

Leu Phe Arg Ala Tyr Cys Lys Gly Asp Asp Leu Tyr Ala Ser Leu
    1595                1600                1605

Phe Ile Phe Lys Glu Ser Thr Gly Asn Ser Ile Ile Lys Asp Ser
    1610                1615                1620

Tyr Val Met Ile Gly Asn Arg Met Tyr Lys Val Val Asn Thr Thr
    1625                1630                1635

Ser Asn Glu Gln Asp Ile Thr Ile Thr Leu Asp Arg Gly Leu Glu
    1640                1645                1650

Glu Asp Leu Asn Leu Gly Asp Pro Ile Tyr Gln Leu Ile Asn Lys
    1655                1660                1665

Thr Lys Val Gln Val Lys Ile Asn Lys Ser Asp Leu Phe Lys Asp
    1670                1675                1680

Met Lys Leu Val Glu Ile Lys Lys Ser Asp Ser Ser Tyr Gln Glu
    1685                1690                1695

Ile Tyr Glu Leu Glu Glu Ala Asn Ile Lys Ser Ala Gln Pro Lys
    1700                1705                1710

Ile Ile Val Glu Lys Gly Asp Lys Trp Thr Ala Ile Lys Arg Pro
    1715                1720                1725

Ser Met Ile Phe Arg Tyr Asp Ala Glu Asn Asn Glu Pro Gln
    1730                1735                1740

<210> SEQ ID NO 83
<211> LENGTH: 1724
<212> TYPE: PRT
<213> ORGANISM: Clostridium difficile

<400> SEQUENCE: 83

Met Lys Gln Asn Lys Leu Leu Gln Arg Gly Ala Tyr Phe Asn Asp Lys
1               5                   10                  15

Asn Ile Leu Ile Asp Asp Phe Asp Lys Arg Tyr Asn Asp Tyr Asp Phe
                20                  25                  30

Val Glu Phe Phe Thr Gly Ile Ser Asn Ser Thr Phe Gly Leu Lys Ser
        35                  40                  45

Asp Gly Asn Leu Tyr Ala Cys Gly Asp Asn Thr Gly Phe Gln Leu Gly
```

```
              50                  55                  60
Leu Gly Lys Asp Ser Ser Glu Arg Arg Met Phe Ser Lys Val Lys Ile
 65                  70                  75                  80

Asp Asn Val Lys Tyr Val Ser Cys Gly Ser Lys His Ser Val Ala Val
                 85                  90                  95

Thr Lys Asp Gly Phe Ala Tyr Gly Ala Gly Thr Ser Asn Val Gly Gln
            100                 105                 110

Leu Gly Val Ile Glu Ser Thr Val Tyr Tyr Glu Phe Thr Lys Leu Pro
            115                 120                 125

Ile Asp Asp Val Lys Thr Val Ala Cys Gly Tyr Asp Phe Thr Phe Val
130                 135                 140

Leu Lys Asn Asp Gly Thr Leu Tyr Ser Ala Gly Leu Asn Ser Ser Gly
145                 150                 155                 160

Gln Leu Gly Leu Gly Asp Thr Asn Asn Arg Ala Thr Phe Thr Lys Val
            165                 170                 175

Asn Ile Asp Ser Val Lys Asp Val Val Thr Tyr Asn Gln Ser Val Phe
            180                 185                 190

Ile Ile Lys Met Asp Gly Thr Ala His Ala Cys Gly Leu Asn Ser Asn
            195                 200                 205

Gly Gln Leu Gly Ile Asn Ser Thr Leu Asn Lys Ser Val Phe Asn Lys
210                 215                 220

Ile Glu Gly Met Asp Asn Val Lys Gln Ile Ala Cys Gly Ser Ser His
225                 230                 235                 240

Thr Ile Leu Ile Lys Asn Asp Gly Thr Met Tyr Thr Thr Gly Tyr Asn
            245                 250                 255

Gly Val Gly Gln Leu Gly Thr Gly Asn Asn Asn Ser Ile Val Phe
            260                 265                 270

Thr Leu Ser Ser Ile Asn Asn Val Lys Tyr Ala Ser Cys Gly Asn Asn
            275                 280                 285

His Thr Met Ile Leu Lys Tyr Asp Asn Thr Leu Phe Ser Thr Gly Gln
            290                 295                 300

Asn Asn Tyr Gly Gln Leu Ala Asn Ala Asn Lys Asp Val Ala Ser Arg
305                 310                 315                 320

Asn Thr Phe Ala Lys Val Asn Val Glu Asn Ile Lys Asp Ile Lys Cys
            325                 330                 335

Gly Ser Gln Phe Asn Phe Leu Ile Asn Gly Ser Lys Glu Ile Phe Val
            340                 345                 350

Ser Gly Cys Asn Leu Ala Gly Gln Leu Gly Ser Phe Phe His Thr Thr
            355                 360                 365

Phe Leu Tyr Glu Phe Ser Asn Val Gln Ser Ser Asn Leu Asp Asn Tyr
            370                 375                 380

Ser Gly Leu Leu Val Asn Asp Asp Tyr Leu Tyr Val Thr Lys Asp Asn
385                 390                 395                 400

Ser Glu Phe Leu Asn Val Lys Leu Ser Asp Asn Phe Gln Asp Tyr Lys
            405                 410                 415

Lys Ile Glu Leu Thr Asp Ser Asn Met Phe Ile Val Met Asn Asp Gly
            420                 425                 430

Thr Leu Tyr Ala Cys Gly Leu Asn Asn Tyr Gly Gln Leu Gly Leu Gly
            435                 440                 445

Asp Thr Val Asn Arg Ser Val Met Thr Lys Val Asp Ile Asp Asn Val
            450                 455                 460

Leu Asp Ile Lys Gly Asn Gly Asn Ser Thr Phe Val Leu Lys Asn Asn
465                 470                 475                 480
```

```
Gly Thr Leu Tyr Ser Cys Gly Leu Asn Ser Asn Gly Gln Leu Gly Leu
                485                 490                 495

Arg Asp Glu Val Asn Arg Asn Ile Phe Thr Lys Ile Glu Ile Glu Asn
            500                 505                 510

Val Lys Asp Phe Cys Val Gly Ser Asn Tyr Val Ile Ala Leu Asn His
        515                 520                 525

Ser Lys Glu Val Tyr Gly Trp Gly Asn Pro Tyr Asn Asn Ile Glu
    530                 535                 540

Lys Thr Ser Asn Tyr Pro Tyr Lys Gln Gly Ile Ser Asn Ile Glu Lys
545                 550                 555                 560

Ile Ala Ala Tyr Asp Tyr Ser Val Tyr Met Ile Asn Ser Glu Gly Lys
                565                 570                 575

Leu Tyr Val Ser Gly Tyr Asn Tyr Asn Tyr Gln Leu Gly Lys Gly Asn
            580                 585                 590

Asn Ser Asn Gln Ser Lys Ala Leu Val Ser Gln Cys Arg Thr Asn Ser
        595                 600                 605

Thr Ser Ser Thr Ser Asn Gly Leu Arg Thr Leu Pro Lys Ile Thr Asn
    610                 615                 620

Val Phe Pro Phe Tyr Asp Gly Cys Ala Ile Ile Asp Glu Gly Gly Tyr
625                 630                 635                 640

Val Tyr Leu Thr Gly Tyr His Gly Tyr Leu Arg Thr Leu Asn Ser Ser
                645                 650                 655

Pro Ser Ile Ser Asp Tyr Ser Arg Tyr Gly Thr Phe Ile Glu Ala Thr
            660                 665                 670

Asn Ser Asn His Asn Thr Tyr Phe Ile Gln Glu Thr Asp Phe Ser Gly
        675                 680                 685

Ile Glu Lys Val Ile Gly Met Ser Asn Asn Ile Leu Phe Phe Lys Lys
    690                 695                 700

Gly Ser Ser Tyr Ile Thr Gly Tyr Pro Lys Thr Phe Gly Ser Thr Ile
705                 710                 715                 720

Thr Gly His Arg Ser Tyr Thr Ser Ile Asn Ser Glu Ser Ser Asn Leu
                725                 730                 735

Gly Ser Asn Phe Ile Ile Tyr His Ser Asn Ser Lys Leu Tyr Gly Lys
            740                 745                 750

Gly Ile Ala Asn Ser Gly Gln Phe Gly Asn Ser Thr Asn Ile Asp Gly
        755                 760                 765

Thr Ser Asn Tyr Asp Thr Gly Leu Lys Asp Ile Lys Asp Ile Val
    770                 775                 780

Lys Gly Asn Thr Val Val Val Asp Lys Asn Asn Ile Tyr Val
785                 790                 795                 800

Thr Gly Met Asn Gln Asn Asn Lys Leu Gly Ile Gly Glu Tyr Asn Asn
                805                 810                 815

Glu Pro Val Lys Lys Phe Thr Asn Ile Thr Glu Gln Ser Asn Ser Phe
            820                 825                 830

Ile Phe Met Asp Asp Ile Lys Glu Ile Thr Ser Arg Asn Thr Met
        835                 840                 845

Phe Ile Val Lys Asn Asp Gly Thr Ala Tyr Ala Thr Gly Asn Asn Ser
    850                 855                 860

Ser Gly Gln Leu Gly Leu Gly Asp Thr Ile Asn Arg Asn Lys Phe Thr
865                 870                 875                 880

Gln Ile Asn Leu Asp Asn Ile Lys Lys Ile Ser Thr Ser Ile Asp Gly
                885                 890                 895
```

-continued

Asn Thr Thr Phe Ala Ile Arg Asn Asp Gly Thr Leu Tyr Ser Thr Gly
            900                 905                 910

Leu Asn Thr Lys Gly Gln Leu Gly Leu Gly Asp Ile Val Asn Arg Asn
        915                 920                 925

Thr Phe Thr Lys Val Asn Ile Gln Asn Val Arg Asp Val Val Leu Gly
    930                 935                 940

Thr Thr His Ser His Ala Ile Lys Asp Asp Asn Thr Leu Tyr Ser Cys
945                 950                 955                 960

Gly Glu Asn Thr His Gly Gln Leu Gly Leu Gly Ser Glu Ser Asn His
                965                 970                 975

Pro Asp Val Leu Thr Phe Thr Val Asn Asn Ile Thr Asn Val Arg Asp
            980                 985                 990

Val Tyr Cys Ser Asp Thr Thr Thr Phe Ile Val Lys Asp Thr Asn Ile
        995                 1000                1005

Ala Tyr Cys Cys Gly Tyr Asn Asn Asn Ser Gln Leu Gly Met Gly
    1010                1015                1020

Asn Thr Thr Asp Gln Tyr Ser Phe Ile Lys Cys Met Glu Asn Val
    1025                1030                1035

Lys Glu Val Ile Pro Asn Glu Ile Asn Thr Tyr Ile Ile Thr Ile
    1040                1045                1050

Tyr Asn Thr Ala Tyr Ser Thr Gly Leu Asn Thr Asp Tyr Cys Leu
    1055                1060                1065

Gly Leu Asn Ser Asn Ser Asn Gln Ser Ser Phe Ser Glu Ile Pro
    1070                1075                1080

Ile Ser Asn Val Val Lys Val Ala Pro Asn Arg Asn Asn Ala Val
    1085                1090                1095

Leu Leu Leu Thr Ser Glu Gly Asp Val Tyr Thr Ala Gly Lys Cys
    1100                1105                1110

Ser Asn Gly Ser Gly Thr Gly Ser Glu Thr Pro Glu Lys Ile Lys
    1115                1120                1125

Lys Ile Ala Ser Lys Ala Lys Asp Ile Gly Met Asn Tyr Arg Cys
    1130                1135                1140

Gly His Tyr Val Ser Asp Asn Gly Asp Leu Tyr Gly Thr Gly Phe
    1145                1150                1155

Asn Asn Asn Gly Gln Leu Gly Val Gly Asp Val Thr Lys Arg Asp
    1160                1165                1170

Thr Phe Ile Lys Thr Asn Thr Arg Val Lys Lys Ile Leu Pro Leu
    1175                1180                1185

Glu Tyr Ala Asn Ile Ala Ile Lys Asp Thr Asn Asp Ile Tyr Ile
    1190                1195                1200

Cys Gly Leu Asn Asn Tyr Gly Gln Leu Gly Val Gly Asn Arg Tyr
    1205                1210                1215

Asp Ser Arg Asn Asn Asp Asn Arg Ile Phe Asn Tyr Lys His Met
    1220                1225                1230

Asn Phe Val Met Gly Asp Leu Thr Ser Ile Lys Asn Arg His Asn
    1235                1240                1245

Phe Ile Leu Leu Asn Asn Lys Ile Val Ile Pro Thr Thr Lys Asp
    1250                1255                1260

Ile Asp Tyr Gly Leu Val Leu Gly Asn Leu Tyr Lys Gly Asp Leu
    1265                1270                1275

Tyr Thr Glu Leu Pro Tyr Glu Asp Ile Lys Glu Val Ser Ile Ser
    1280                1285                1290

Lys Thr His Ile Ile Ile Leu Leu Asn Asp Gly Thr Met Tyr Gly

-continued

```
          1295                1300                1305
Cys Gly Thr Asn Tyr His Gly Glu Leu Leu Gln Asp Leu Ser Ile
         1310                1315                1320
Asn Gln Val Asp Glu Phe Val Gln Ile Asn Val Ser Asp Val Lys
         1325                1330                1335
His Val Ser Cys Gly Asp Asn Phe Thr Tyr Phe Ile Lys Ser Asp
         1340                1345                1350
Asp Ser Leu Trp Ser Ile Gly Lys Asn Ser Glu Tyr Gln Leu Gly
         1355                1360                1365
Ile Gly His Asn Asn Pro Val Thr Glu Leu Gln Arg Ile Thr Thr
         1370                1375                1380
Ile Ser Ser Cys Lys Glu Val His Cys Gly Lys Asn Tyr Thr Leu
         1385                1390                1395
Val Val Thr Thr Gly Asn Glu Leu Phe Val Gln Gly Tyr Asn Asp
         1400                1405                1410
Lys Gly Ala Leu Gly Leu Gly Ser Asp Ser Glu Asn Thr Ile Ile
         1415                1420                1425
Lys Phe Phe Thr Lys Ala Leu Thr Asp Ile Arg Glu Ile Lys Ser
         1430                1435                1440
Tyr Gly Ser Asp His Ile Leu Val Leu Lys Asn Asp Asn Ser Val
         1445                1450                1455
Trp Val Thr Gly Lys Asn Arg Asp Val Tyr Lys Ile Glu Gln Pro
         1460                1465                1470
Val Glu Phe Leu Lys Glu Phe Thr Ile Val Pro Ile Ser Glu Asp
         1475                1480                1485
Val Asn Thr Val Lys Asp Val Leu Ala Thr Asp Asn Thr Leu Tyr
         1490                1495                1500
Ile Ile Ser Glu Val Gly Thr Thr Asn Ala Ala Ile Glu Ile Thr
         1505                1510                1515
Glu Lys Ser Ile Ser Ser Ile Lys Ile Lys Ile Gln Asp Pro Asn
         1520                1525                1530
Lys Asp Ile Ser Arg Ile Glu Met Leu Ile Asn Gly Glu Ser Val
         1535                1540                1545
Lys Ser Val Ser Asp Leu Thr Thr Glu Lys Ile Ser Phe Glu Val
         1550                1555                1560
Pro Pro Asp Lys Ile Lys Ile Gly Glu Asn Lys Ile Leu Phe Arg
         1565                1570                1575
Ala Tyr Cys Lys Gly Asp Asp Leu Tyr Ala Ser Leu Phe Ile Phe
         1580                1585                1590
Lys Glu Ser Thr Gly Asn Ser Ile Ile Lys Asp Ser Tyr Val Met
         1595                1600                1605
Ile Gly Asn Arg Met Tyr Lys Val Val Asn Thr Thr Ser Asn Glu
         1610                1615                1620
Gln Asp Ile Thr Ile Thr Leu Asp Arg Gly Leu Glu Glu Asp Leu
         1625                1630                1635
Asn Leu Gly Asp Pro Ile Tyr Gln Leu Ile Asn Lys Thr Lys Val
         1640                1645                1650
Gln Val Lys Ile Asn Lys Ser Asp Leu Phe Lys Asp Met Lys Leu
         1655                1660                1665
Val Glu Ile Lys Lys Ser Asp Ser Ser Tyr Gln Glu Ile Tyr Glu
         1670                1675                1680
Leu Glu Glu Ala Asn Ile Lys Ser Ala Gln Pro Lys Ile Ile Val
         1685                1690                1695
```

Glu Lys Gly Asp Lys Trp Thr Ala Ile Lys Arg Pro Ser Met Ile
   1700            1705             1710

Phe Arg Tyr Asp Ala Glu Asn  Asn Glu Pro Gln
   1715            1720

<210> SEQ ID NO 84
<211> LENGTH: 1724
<212> TYPE: PRT
<213> ORGANISM: Clostridium difficile

<400> SEQUENCE: 84

Met Lys Gln Asn Lys Leu Leu Gln Arg Gly Ala Tyr Phe Asn Asp Lys
1                5                   10                  15

Asn Ile Leu Ile Asp Asp Phe Asp Lys Arg Tyr Asn Asp Tyr Asp Phe
                20                  25                  30

Val Glu Phe Phe Thr Gly Ile Ser Asn Ser Thr Phe Gly Leu Lys Ser
            35                  40                  45

Asp Gly Asn Leu Tyr Ala Cys Gly Asp Asn Thr Gly Phe Pro Leu Gly
        50                  55                  60

Leu Gly Lys Asp Ser Ser Glu Arg Arg Met Phe Ser Lys Val Lys Ile
65                  70                  75                  80

Asp Asn Val Lys Tyr Val Ser Cys Gly Ser Lys His Ser Val Ala Val
                85                  90                  95

Thr Lys Asp Gly Phe Ala Tyr Gly Ala Gly Thr Ser Asn Val Gly Gln
            100                 105                 110

Leu Gly Val Ile Glu Ser Thr Val Tyr Tyr Glu Phe Thr Lys Leu Pro
        115                 120                 125

Ile Asp Asp Val Lys Thr Val Ala Cys Gly Tyr Asp Phe Thr Phe Val
130                 135                 140

Leu Lys Asn Asp Gly Thr Leu Tyr Ser Ala Gly Leu Asn Ser Ser Gly
145                 150                 155                 160

Gln Leu Gly Leu Gly Asp Thr Asn Asn Arg Ala Thr Phe Thr Lys Val
                165                 170                 175

Asn Ile Asp Ser Val Lys Asp Val Val Thr Tyr Asn Gln Ser Val Phe
            180                 185                 190

Ile Ile Lys Met Asp Gly Thr Ala His Ala Cys Gly Leu Asn Ser Asn
        195                 200                 205

Gly Gln Leu Gly Ile Asn Ser Thr Leu Asn Lys Ser Val Phe Asn Lys
    210                 215                 220

Ile Glu Gly Met Asp Asn Val Lys Gln Ile Ala Cys Gly Ser Ser His
225                 230                 235                 240

Thr Ile Leu Ile Lys Asn Asp Gly Thr Met Tyr Thr Thr Gly Tyr Asn
                245                 250                 255

Gly Val Gly Gln Leu Gly Thr Gly Asn Asn Asn Ser Ile Val Phe
            260                 265                 270

Thr Leu Ser Ser Ile Asn Asn Val Lys Tyr Ala Ser Cys Gly Asn Asn
        275                 280                 285

His Thr Met Ile Leu Lys Tyr Asp Asn Thr Leu Phe Ser Thr Gly Gln
    290                 295                 300

Asn Asn Tyr Gly Gln Leu Ala Asn Ala Asn Asp Val Ala Ser Arg
305                 310                 315                 320

Asn Thr Phe Ala Lys Val Asn Val Glu Asn Ile Lys Asp Ile Lys Cys
                325                 330                 335

Gly Ser Gln Phe Asn Phe Leu Ile Asn Gly Ser Lys Glu Ile Phe Val

```
              340             345             350
Ser Gly Cys Asn Leu Ala Gly Gln Leu Gly Ser Phe Phe His Thr Thr
            355             360             365

Phe Leu Tyr Glu Phe Ser Asn Val Gln Ser Ser Asn Leu Asp Asn Tyr
370             375             380

Ser Gly Leu Leu Val Asn Asp Asp Tyr Leu Tyr Val Thr Lys Asp Asn
385             390             395             400

Ser Glu Phe Leu Asn Val Lys Leu Ser Asp Asn Phe Gln Asp Tyr Lys
            405             410             415

Lys Ile Glu Leu Thr Asp Ser Asn Met Phe Ile Val Met Asn Asp Gly
            420             425             430

Thr Leu Tyr Ala Cys Gly Leu Asn Asn Tyr Gly Gln Leu Gly Leu Gly
            435             440             445

Asp Thr Val Asn Arg Ser Val Met Thr Lys Val Asp Ile Asp Asn Val
450             455             460

Leu Asp Ile Lys Gly Asn Gly Asn Ser Thr Phe Val Leu Lys Asn Asn
465             470             475             480

Gly Thr Leu Tyr Ser Cys Gly Leu Asn Ser Asn Gly Gln Leu Gly Leu
            485             490             495

Arg Asp Glu Val Asn Arg Asn Ile Phe Thr Lys Ile Glu Ile Glu Asn
            500             505             510

Val Lys Asp Phe Cys Val Gly Ser Asn Tyr Val Ile Ala Leu Asn His
            515             520             525

Ser Lys Glu Val Tyr Gly Trp Gly Asn Pro Tyr Asn Asn Ile Glu
            530             535             540

Lys Thr Ser Asn Tyr Pro Tyr Lys Gln Gly Ile Ser Asn Ile Glu Lys
545             550             555             560

Ile Ala Ala Tyr Asp Tyr Ser Val Tyr Met Ile Asn Ser Glu Gly Lys
            565             570             575

Leu Tyr Val Ser Gly Tyr Asn Tyr Asn Tyr Gln Leu Gly Lys Gly Asn
            580             585             590

Asn Ser Asn Gln Ser Lys Ala Leu Val Ser Gln Cys Arg Thr Asn Ser
            595             600             605

Thr Ser Ser Thr Ser Asn Gly Leu Arg Thr Leu Pro Lys Ile Thr Asn
            610             615             620

Val Phe Pro Phe Tyr Asp Gly Cys Ala Ile Ile Asp Glu Gly Gly Tyr
625             630             635             640

Val Tyr Leu Thr Gly Tyr His Gly Tyr Leu Arg Thr Leu Asn Ser Ser
            645             650             655

Pro Ser Ile Ser Asp Tyr Ser Arg Tyr Gly Thr Phe Ile Glu Ala Thr
            660             665             670

Asn Ser Asn His Asn Thr Tyr Phe Ile Gln Glu Thr Asp Phe Ser Gly
            675             680             685

Ile Glu Lys Val Ile Gly Met Ser Asn Asn Ile Leu Phe Phe Lys Lys
            690             695             700

Gly Ser Ser Tyr Ile Thr Gly Tyr Pro Lys Thr Phe Gly Ser Thr Ile
705             710             715             720

Thr Gly His Arg Ser Tyr Thr Ser Ile Asn Ser Glu Ser Ser Asn Leu
            725             730             735

Gly Ser Asn Phe Ile Ile Tyr His Ser Asn Ser Lys Leu Tyr Gly Lys
            740             745             750

Gly Ile Ala Asn Ser Gly Gln Phe Gly Asn Ser Thr Asn Ile Asp Gly
            755             760             765
```

-continued

```
Thr Ser Asn Tyr Asp Thr Gly Leu Lys Asp Ile Lys Asp Ile Ile Val
        770             775             780

Lys Gly Asn Thr Val Val Val Asp Lys Asn Asn Ile Tyr Val
785             790             795             800

Thr Gly Met Asn Gln Asn Asn Lys Leu Gly Ile Gly Glu Tyr Asn Asn
                805             810             815

Glu Pro Val Lys Lys Phe Thr Asn Ile Thr Glu Gln Ser Asn Ser Phe
            820             825             830

Ile Phe Met Asp Asp Ile Lys Glu Ile Thr Thr Ser Arg Asn Thr Met
        835             840             845

Phe Ile Val Lys Asn Asp Gly Thr Ala Tyr Ala Thr Gly Asn Asn Ser
    850             855             860

Ser Gly Gln Leu Gly Leu Gly Asp Thr Ile Asn Arg Asn Lys Phe Thr
865             870             875             880

Gln Ile Asn Leu Asp Asn Ile Lys Lys Ile Ser Thr Ser Ile Asp Gly
                885             890             895

Asn Thr Thr Phe Ala Ile Arg Asn Asp Gly Thr Leu Tyr Ser Thr Gly
                900             905             910

Leu Asn Thr Lys Gly Gln Leu Gly Leu Gly Asp Ile Val Asn Arg Asn
            915             920             925

Thr Phe Thr Lys Val Asn Ile Gln Asn Val Arg Asp Val Val Leu Gly
    930             935             940

Thr Thr His Ser His Ala Ile Lys Asp Asp Asn Thr Leu Tyr Ser Cys
945             950             955             960

Gly Glu Asn Thr His Gly Gln Leu Gly Leu Gly Ser Glu Ser Asn His
                965             970             975

Pro Asp Val Leu Thr Phe Thr Val Asn Asn Ile Thr Asn Val Arg Asp
            980             985             990

Val Tyr Cys Ser Asp Thr Thr Thr Phe Ile Val Lys Asp Thr Asn Ile
            995             1000            1005

Ala Tyr Cys Cys Gly Tyr Asn Asn Asn Ser Gln Leu Gly Met Gly
        1010            1015            1020

Asn Thr Thr Asp Gln Tyr Ser Phe Ile Lys Cys Met Glu Asn Val
        1025            1030            1035

Lys Glu Val Ile Pro Asn Glu Ile Asn Thr Tyr Ile Ile Thr Ile
        1040            1045            1050

Tyr Asn Thr Ala Tyr Ser Thr Gly Leu Asn Thr Asp Tyr Cys Leu
        1055            1060            1065

Gly Leu Asn Ser Asn Ser Asn Gln Ser Ser Phe Ser Glu Ile Pro
        1070            1075            1080

Ile Ser Asn Val Val Lys Val Ala Pro Asn Arg Asn Asn Ala Val
        1085            1090            1095

Leu Leu Leu Thr Ser Glu Gly Asp Val Tyr Thr Ala Gly Lys Cys
        1100            1105            1110

Ser Asn Gly Ser Gly Thr Gly Ser Glu Thr Pro Glu Lys Ile Lys
        1115            1120            1125

Lys Ile Ala Ser Lys Ala Lys Asp Ile Gly Met Asn Tyr Arg Cys
        1130            1135            1140

Gly His Tyr Val Ser Asp Asn Gly Asp Leu Tyr Gly Thr Gly Phe
        1145            1150            1155

Asn Asn Asn Gly Gln Leu Gly Val Gly Asp Val Thr Lys Arg Asp
        1160            1165            1170
```

-continued

```
Thr Phe Ile Lys Thr Asn Thr Arg Val Lys Lys Ile Leu Pro Leu
1175                1180                1185

Glu Tyr Ala Asn Ile Ala Ile Lys Asp Thr Asn Asp Ile Tyr Ile
1190                1195                1200

Cys Gly Leu Asn Asn Tyr Gly Gln Leu Gly Val Gly Asn Arg Tyr
1205                1210                1215

Asp Ser Arg Asn Asn Asp Asn Arg Ile Phe Asn Tyr Lys His Met
1220                1225                1230

Asn Phe Val Met Gly Asp Leu Thr Ser Ile Lys Asn Arg His Asn
1235                1240                1245

Phe Ile Leu Leu Asn Asn Lys Ile Val Ile Pro Thr Thr Lys Asp
1250                1255                1260

Ile Asp Tyr Gly Leu Val Leu Gly Asn Leu Tyr Lys Gly Asp Leu
1265                1270                1275

Tyr Thr Glu Leu Pro Tyr Glu Asp Ile Lys Glu Val Ser Ile Ser
1280                1285                1290

Lys Thr His Ile Ile Ile Leu Leu Asn Asp Gly Thr Met Tyr Gly
1295                1300                1305

Cys Gly Thr Asn Tyr His Gly Glu Leu Leu Gln Asp Leu Ser Ile
1310                1315                1320

Asn Gln Val Asp Glu Phe Val Gln Ile Asn Val Ser Asp Val Lys
1325                1330                1335

His Val Ser Cys Gly Asp Asn Phe Thr Tyr Phe Ile Lys Ser Asp
1340                1345                1350

Asp Ser Leu Trp Ser Ile Gly Lys Asn Ser Glu Tyr Gln Leu Gly
1355                1360                1365

Ile Gly His Asn Asn Pro Val Thr Glu Leu Gln Arg Ile Thr Thr
1370                1375                1380

Ile Ser Ser Cys Lys Glu Val His Cys Gly Lys Asn Tyr Thr Leu
1385                1390                1395

Val Val Thr Thr Gly Asn Glu Leu Phe Val Gln Gly Tyr Asn Asp
1400                1405                1410

Lys Gly Ala Leu Gly Leu Gly Ser Asp Ser Glu Asn Thr Ile Ile
1415                1420                1425

Lys Phe Phe Thr Lys Ala Leu Thr Asp Ile Arg Glu Ile Lys Ser
1430                1435                1440

Tyr Gly Ser Asp His Ile Leu Val Leu Lys Asn Asp Asn Ser Val
1445                1450                1455

Trp Val Thr Gly Lys Asn Arg Asp Val Tyr Lys Ile Glu Gln Pro
1460                1465                1470

Val Glu Phe Leu Lys Glu Phe Thr Ile Val Pro Ile Ser Glu Asp
1475                1480                1485

Val Asn Thr Val Lys Asp Val Leu Ala Thr Asp Asn Thr Leu Tyr
1490                1495                1500

Ile Ile Ser Glu Val Gly Thr Thr Asn Ala Ala Ile Glu Ile Thr
1505                1510                1515

Glu Lys Ser Ile Ser Ser Ile Lys Ile Lys Ile Gln Asp Pro Asn
1520                1525                1530

Lys Asp Ile Ser Arg Ile Glu Met Leu Ile Asn Gly Glu Ser Val
1535                1540                1545

Lys Ser Val Ser Asp Leu Thr Thr Glu Lys Ile Ser Phe Glu Val
1550                1555                1560

Pro Pro Asp Lys Ile Lys Ile Gly Glu Asn Lys Ile Leu Phe Arg
```

```
                   1565                1570                1575

Ala Tyr Cys Lys Gly Asp Asp Leu Tyr Ala Ser Leu Phe Ile Phe
            1580                1585                1590

Lys Glu Ser Thr Gly Asn Ser Ile Ile Lys Asp Ser Tyr Val Met
        1595                1600                1605

Ile Gly Asn Arg Met Tyr Lys Val Val Asn Thr Thr Ser Asn Glu
    1610                1615                1620

Gln Asp Ile Thr Ile Thr Leu Asp Arg Gly Leu Glu Glu Asp Leu
1625                1630                1635

Asn Leu Gly Asp Pro Ile Tyr Gln Leu Ile Asn Lys Thr Lys Val
    1640                1645                1650

Gln Val Lys Ile Asn Lys Ser Asp Leu Phe Lys Asp Met Lys Leu
        1655                1660                1665

Val Glu Ile Lys Lys Ser Asp Ser Ser Tyr Gln Glu Ile Tyr Glu
            1670                1675                1680

Leu Glu Glu Ala Asn Ile Lys Ser Ala Gln Pro Lys Ile Ile Val
                1685                1690                1695

Glu Lys Gly Asp Lys Trp Thr Ala Ile Lys Arg Pro Ser Met Ile
                    1700                1705                1710

Phe Arg Tyr Asp Ala Glu Asn Asn Glu Pro Gln
                        1715                1720

<210> SEQ ID NO 85
<211> LENGTH: 1772
<212> TYPE: PRT
<213> ORGANISM: Clostridium difficile

<400> SEQUENCE: 85

Met Lys Arg Thr Lys Leu Leu Gln Arg Gly Asn Phe Phe Gly Asp Lys
1               5                   10                  15

Asn Met Val Val Asp Glu Phe Asp Glu Gly Tyr Asp Asn Tyr Asp Phe
                20                  25                  30

Ile Asn Phe Phe Thr Gly Cys Cys Asn Tyr Thr Phe Gly Leu Lys Asn
            35                  40                  45

Asn Asn Ile Leu Tyr Gly Cys Gly Asp Asn Ser Asn Phe Gln Leu Gly
        50                  55                  60

Leu Gly Glu Asp Asn Thr Thr Arg Lys Leu Phe Thr Lys Ile Pro Asn
65                  70                  75                  80

Ile Ser Thr Asn Ile Lys Lys Val Ala Cys Gly Glu Ser His Ala Val
                85                  90                  95

Ile Leu Thr Ser Asp Gly Glu Leu Leu Val Ala Gly Ile Asn Thr Asp
            100                 105                 110

Gly Gln Met Gly Leu Gly Leu Glu Lys Val Gly Lys Thr Val Ser Thr
        115                 120                 125

Phe Glu Lys Val Pro Glu Ile Lys Gly Val Lys Asp Ile Ala Cys Gly
    130                 135                 140

Leu Gln Ser Thr Tyr Leu Leu Tyr Asn Asp Gly Thr Leu Tyr Val Ala
145                 150                 155                 160

Gly Asn Asn Leu Tyr Gly Gln Leu Gly Leu Gly Thr Asn Gly Ala Ser
                165                 170                 175

Ala Asn Val Asn Thr Phe Thr Lys Val Asp Val Asp Asn Val Lys Ala
            180                 185                 190

Val Phe Ser Tyr Asn Lys Ser Ala Phe Ile Ile Lys Asn Asp Asn Lys
        195                 200                 205
```

```
Cys Tyr Ser Thr Gly Phe Asn Asn Gln Gly Gln Leu Gly Leu Gly Asp
    210                 215                 220

Lys Asn Asn Arg Asp Leu Phe Ser Leu Val Ser Ile Asn Asp Val Lys
225                 230                 235                 240

Thr Ile Ala Cys Gly Ser Glu His Thr Val Leu Met Thr Tyr Asn Asn
                245                 250                 255

Asp Ile Tyr Gly Cys Gly Lys Glu Lys Cys Phe Gly Asn Ala Leu Gln
                260                 265                 270

Ser Ser Leu Phe Thr Lys Ile Glu Glu Val Asn Ile Lys Thr Ile Ala
            275                 280                 285

Cys Gly His Gly Asn Thr Met Leu Ile Asp Asn Lys Gly Thr Leu Lys
        290                 295                 300

Val Ala Gly Asn Asn Asp Ile Tyr Gln Leu Gly Ile Ala Asn Tyr Ser
305                 310                 315                 320

Glu Asn Ile Asp Asn Ser Phe Ile Asp Leu Lys Asn Ile Val Ala Lys
                325                 330                 335

Asn Ile Phe Ile Gly Leu Ser His Ser Ile Leu Ile Asp Ser Asn Asn
            340                 345                 350

Asp Ser Tyr Cys Thr Gly Asp Asn Thr Tyr Gly Gln Leu Gly Ser Phe
        355                 360                 365

Phe Asp Asp Met His Ile Val Glu Phe Lys Lys Met Asp Ser Glu Lys
    370                 375                 380

Tyr Ser Tyr Ser Asn Tyr Ile Asn Leu Ile Lys Ser Glu Asp Lys Leu
385                 390                 395                 400

Thr Leu Leu Lys Glu Glu Met Glu Ile Lys Asp Ile Glu Leu Pro Leu
                405                 410                 415

Asp Ile His Ser Val Arg Asp Val Val Phe Ser Pro Tyr Cys Thr Leu
            420                 425                 430

Val Ile Leu Gly Asn Gly Asp Val Tyr Gly Leu Gly Asn Asn Arg Tyr
        435                 440                 445

Lys Gly Met Gly Ser Asp Leu Pro Ser Gln Leu Asn Glu Leu Thr Lys
    450                 455                 460

Leu Ser Ile Ser Asn Val Lys Ser Ile Val Ala Ser Lys Asn Ile Ser
465                 470                 475                 480

Gly Gly Ile Phe Tyr Ile Lys Asn Asp Asp Thr Cys Tyr Tyr Ser Gly
                485                 490                 495

Pro Asn Ser Asn Ser Ile Ala Gly Val Leu Pro Ser Asn Ser Asp Val
            500                 505                 510

Phe Lys Lys Ile Ser Ile Asp Asn Val Lys Lys Val Val Ile Asn Thr
        515                 520                 525

Asp Leu Ser Asn Trp Phe Ser Leu Ile Val Thr Asn Asn Lys Gln Ile
    530                 535                 540

Tyr Thr Ser Gly Lys Ser Ser Tyr Val Asn Gly Leu Ser Asn Ala
545                 550                 555                 560

Leu Ile Ser Gln Tyr Thr Glu Ile Ser Leu Ser Asn Val Thr Asp Ala
                565                 570                 575

Tyr Ser Ser Tyr Asn Ala Thr Phe Ile Val Val Asp Glu Lys Lys Val
            580                 585                 590

Tyr Ala Thr Gly Ile Asn Thr Asn Tyr Leu Leu Gly Phe Ser Thr Ser
        595                 600                 605

Asp Gly Ser Asn Val Asn Leu Gly Leu Leu Ser Asp Trp Tyr Tyr Ile
    610                 615                 620

Asn Ile Ser Gly Ser Ser Tyr Ser Arg Val Ser Cys Thr Asn Asn Ile
```

```
                625                 630                 635                 640
        Thr Lys Ile Asn Asn Ile Ile Ile Tyr Glu Tyr Val Thr Val Phe Cys
                        645                 650                 655
        Thr Asn Ile Gly Ser Phe Leu Thr Gly Tyr His Gly Thr Ser Trp Thr
                        660                 665                 670
        Lys Pro Thr Asp Ser Ser Tyr Arg Val Gln Tyr Gln Gly Ile Ser Tyr
                        675                 680                 685
        Ala Gly Tyr Leu Asp Ser Tyr Ile Tyr Asn Tyr Pro Thr Arg Cys
                        690                 695                 700
        Thr Gln Ser Ser Ser Ser Thr Thr Phe Ala Tyr Leu Tyr Asn Gly Glu
        705                 710                 715                 720
        Ser Ser Ser Asn Leu Lys Asn Val Asn Pro Asp Asn Leu Leu Ile Ser
                        725                 730                 735
        Gly Gly Ser Ser Tyr Ile His Gln Tyr Gly Arg Asn Tyr Leu Asn Asn
                        740                 745                 750
        Gln Ser Ser Asn Ile Ala Ala Ser Asn Ile Asn Ser Gly Pro Ile
                        755                 760                 765
        Thr Ser Asp Lys Ala Ile Phe Leu Tyr Lys Ala Leu Leu Tyr Leu Ser
        770                 775                 780
        Ser Asn Thr Leu Tyr Gly Phe Gly Asn Ile Ser Glu Ser Ala Lys Glu
        785                 790                 795                 800
        Leu Asp Val Ser Asp Thr Gln Asp Gly Tyr Asn Ala Thr Asn Tyr Lys
                        805                 810                 815
        Lys Val Met Lys Asn Ile Lys Asn Ile Phe Ile Pro Pro Tyr Asp Leu
                        820                 825                 830
        Ser Arg Asp Lys Thr Arg Phe Ala Ile Leu Thr Asp Lys Ser Leu Phe
                        835                 840                 845
        Ile Cys Gly Tyr Asn Ser Lys Gly Thr His Gly Ile Ser Val Asn Ser
                        850                 855                 860
        Ser Leu Asn Leu Asn Asn Lys Ile Asn Tyr Asn Lys Lys Asn Ser Ser
        865                 870                 875                 880
        Ser Glu Ile Ser Ser Asn Ile Gln Glu Ile Tyr Ser His Ser Lys Ser
                        885                 890                 895
        Thr Tyr Leu Leu Thr Asn Asn Asn Met Leu Tyr Ser Val Gly Leu Asn
                        900                 905                 910
        Asp Val Gly Gln Leu Gly Val Gly Asp Glu Ile Asn Arg Lys Val Phe
                        915                 920                 925
        Thr Lys Ile Asn Ile Asp Asn Ile Lys Ser Ile Asn Val Asn Arg Phe
                        930                 935                 940
        Thr Asp Asn Ser Lys His Ala Phe Ala Ile Lys Asn Asp Asn Thr Cys
        945                 950                 955                 960
        Tyr Ala Val Gly Leu Asn Ser Gly Gln Leu Gly Ile Gly Asp Asn
                        965                 970                 975
        Val Asn Arg Asn Ile Phe Thr Lys Ile Asn Val Glu Asn Val Lys Tyr
                        980                 985                 990
        Val Ala Val Tyr Gly Asn Thr Ser Leu Leu Leu Thr Asn Asp Gly Leu
                        995                 1000                1005
        Leu Tyr Gly Ala Gly Asn Asn Gly Lys Gly Gln Leu Gly Leu Gly
                        1010                1015                1020
        Asp Thr Thr Ser Arg Asn Ile Phe Thr Arg Ile Pro Ile Asn Gly
                        1025                1030                1035
        Val Arg Asp Val Tyr Leu Cys Asn Asp Val Ser Ile Ile Val Lys
                        1040                1045                1050
```

```
Asn Asp Asn Thr Cys Tyr Val Cys Gly Leu Val Asn Gly Tyr Phe
    1055            1060            1065

Gly Phe Thr Glu Gly Ser Ile Ser Thr Phe Thr Lys Ile Asn Ile
    1070            1075            1080

Glu Asn Val Lys Ser Val Val Thr Ala Gly Ser Glu Ala Thr Phe
    1085            1090            1095

Phe Ile Thr Asn Asp Asn Met Ile Tyr Thr Thr Gly Lys Lys Glu
    1100            1105            1110

Arg Val Phe Phe Ser Thr Glu Thr Asn Asp Ile Lys Gly Ile Arg
    1115            1120            1125

Val Ile Asn Asn Ile Ile Asn Ala Lys Lys Ile Val Val Asn Gly
    1130            1135            1140

Tyr Thr Ser Ala Ile Leu Thr Asn Asp Asn Lys Leu Phe Val Gly
    1145            1150            1155

Gly Leu Ser Gly Tyr Gly Ser Ile Ala Asn Asn Asn Thr Asn
    1160            1165            1170

Ser Val Glu Asp Val Lys Asp Val Phe Val Thr Ala Asn Asn Thr
    1175            1180            1185

Leu Tyr Ile Asp Asn Asn Asn Asn Leu Ile Ser Ser Gly Arg Asp
    1190            1195            1200

Thr Tyr Gly Ile Ser Asp Glu Ser Tyr Arg Asp Met Ser Val Pro
    1205            1210            1215

Tyr Tyr Lys Val Ser Ile Lys Lys Asp Val Asp Thr Val Phe Ser
    1220            1225            1230

Ser Tyr Asn Thr Ile Phe Ile Lys Asp Ile Tyr Gly Lys Phe Tyr
    1235            1240            1245

Ser Ser Thr Arg Asp Asn Arg Tyr Asn His Leu Gly Ile His His
    1250            1255            1260

Arg Tyr Asp Asn Asp Lys Asn Glu Ala Leu Glu Gly Ser Leu His
    1265            1270            1275

Ser Tyr Phe Lys Thr Asp Asn Thr Ser Asp Lys Ile Val Phe Asn
    1280            1285            1290

Lys Lys Asn Glu Lys Leu Val Met Phe Asn Asp Lys Tyr Ile Lys
    1295            1300            1305

Thr Asn Asn Lys Tyr Ile Asn Tyr Lys Asn Ile Phe Lys Asp Asn
    1310            1315            1320

Phe Lys Tyr Thr Ser Ile Ile Leu Pro Phe Glu Val Ser Asp Ile
    1325            1330            1335

Asp Ile Ser Lys Thr His Ser Leu Ala Val Ala Lys Asp Gly Lys
    1340            1345            1350

Leu Tyr Gly Ile Gly Ser Asn Ser Tyr Lys Glu Ile Asn Gln Thr
    1355            1360            1365

Leu Glu Asp Ile Glu Leu Leu Thr Leu Thr Glu Val Asn Ile Ser
    1370            1375            1380

Asp Val Lys Lys Val Ala Cys Gly Asp Asn Tyr Ser Tyr Ile Ile
    1385            1390            1395

Lys Thr Asp Asn Thr Leu Trp Ser Tyr Gly Lys Asn Thr Glu Tyr
    1400            1405            1410

Gln Leu Gly Val Gly His Asn Asn Asp Val Arg Glu Leu Gln Lys
    1415            1420            1425

Val Thr Gly Leu Pro Ser Val Lys Asp Ile Ser Ile Tyr Asn Ser
    1430            1435            1440
```

```
Met Thr Leu Val Leu Thr Asn Glu Gly Glu Leu Tyr Ala Gln Gly
    1445                1450                1455

Tyr Asn Thr Asn Gly Leu Phe Gly Leu Gly Glu Ser Glu Lys Asp
    1460                1465                1470

Lys Ile Ile Arg Thr Phe Thr Lys Val Leu Thr Asn Val Lys Glu
    1475                1480                1485

Ile Lys Ser His Asn Asp Asp His Ile Leu Val Ile Lys Asn Asp
    1490                1495                1500

Asn Ser Leu Trp Ile Thr Gly Lys Asn Lys Ser Met Tyr Lys Ile
    1505                1510                1515

Ser Ile Ser Ile Thr Asp Leu Tyr Glu Phe Thr Lys Ile Pro Ile
    1520                1525                1530

Pro Glu His Leu Asn Asp Ile Leu Asp Ile Glu Leu Ser Asp Asp
    1535                1540                1545

Thr Ile Tyr Met Ile Thr Lys Val Asp Thr Ser Lys Ala Ser Ile
    1550                1555                1560

Glu Ile Val Glu Lys Ser Ile Ser Gln Val Arg Val Val Val Gln
    1565                1570                1575

Asp Pro Asn Asn Val Ile Glu Lys Leu Glu Met Phe Ile Asn Asp
    1580                1585                1590

Glu Leu Ile Ser Thr Lys Thr Asn Leu Glu Ile Asn Ser Ile Ile
    1595                1600                1605

Phe Glu Ile Pro Gln Asn Lys Ile Val Leu Gly Glu Asn Lys Ile
    1610                1615                1620

Leu Ile Lys Ala Ser Ser Pro Thr Gly Asp Leu Tyr Ser Ser Met
    1625                1630                1635

Phe Ile Phe Lys Ser Glu Thr Gly Leu Lys Val Lys Lys Asp Ser
    1640                1645                1650

Ile Leu Met Ile Asn Asn Lys Val Tyr Ser Ile Ile Asn Ile Thr
    1655                1660                1665

Glu Asn Asn Thr Asp Leu Ile Val Thr Leu Asn Glu Gly Leu Lys
    1670                1675                1680

Asp Asp Met Met Glu Asn Asn Pro Ile Tyr Gln Leu Ile Asn Lys
    1685                1690                1695

Thr Lys Val Gln Val Lys Ile Asn Lys Ser Asp Leu Phe Lys Asp
    1700                1705                1710

Met Lys Leu Val Glu Ile Lys Lys Ser Asp Ser Ser Tyr Gln Glu
    1715                1720                1725

Ile Tyr Glu Leu Glu Glu Ala Asn Ile Lys Ser Ala Gln Pro Lys
    1730                1735                1740

Ile Ile Val Glu Lys Gly Asp Lys Trp Thr Ala Ile Lys Arg Pro
    1745                1750                1755

Ser Met Ile Phe Arg Tyr Asp Ala Glu Asn Asn Glu Pro Gln
    1760                1765                1770

<210> SEQ ID NO 86
<211> LENGTH: 1772
<212> TYPE: PRT
<213> ORGANISM: Clostridium difficile

<400> SEQUENCE: 86

Met Lys Arg Thr Lys Leu Leu Gln Arg Gly Asn Phe Phe Gly Asp Lys
1               5                   10                  15

Asn Met Val Val Asp Glu Phe Asp Glu Gly Tyr Asp Asn Tyr Asp Phe
                20                  25                  30
```

```
Ile Asn Phe Phe Thr Gly Cys Cys Asn Tyr Thr Phe Gly Leu Lys Asn
         35                  40                  45

Asn Asn Ile Leu Tyr Gly Cys Gly Asp Asn Ser Asn Phe Gln Leu Gly
 50                  55                  60

Leu Gly Glu Asp Asn Thr Thr Arg Lys Leu Phe Thr Lys Ile Pro Asn
 65                  70                  75                  80

Ile Ser Thr Asn Ile Lys Lys Val Ala Cys Gly Glu Ser His Ala Val
                 85                  90                  95

Ile Leu Thr Ser Asp Gly Glu Leu Leu Val Ala Gly Ile Asn Thr Asp
                100                 105                 110

Gly Gln Met Gly Leu Gly Leu Glu Lys Val Gly Lys Thr Val Ser Thr
             115                 120                 125

Phe Glu Lys Val Pro Glu Ile Lys Gly Val Lys Asp Ile Ala Cys Gly
         130                 135                 140

Leu Gln Ser Thr Tyr Leu Leu Tyr Asn Asp Gly Thr Leu Tyr Val Ala
145                 150                 155                 160

Gly Asn Asn Leu Tyr Gly Gln Leu Gly Leu Gly Thr Asn Gly Ala Ser
                165                 170                 175

Ala Asn Val Asn Thr Phe Thr Lys Val Asp Val Asp Asn Val Lys Ala
             180                 185                 190

Val Phe Ser Tyr Asn Lys Ser Ala Phe Ile Ile Lys Asn Asp Asn Lys
         195                 200                 205

Cys Tyr Ser Thr Gly Phe Asn Asn Gln Gly Gln Leu Gly Leu Gly Asp
     210                 215                 220

Lys Asn Asn Arg Asp Leu Phe Ser Leu Val Ser Ile Asn Asp Val Lys
225                 230                 235                 240

Thr Ile Ala Cys Gly Ser Glu His Thr Val Leu Met Thr Tyr Asn Asn
                245                 250                 255

Asp Ile Tyr Gly Cys Gly Lys Glu Lys Cys Phe Gly Asn Ala Leu Gln
             260                 265                 270

Ser Ser Leu Phe Thr Lys Ile Glu Glu Val Asn Ile Lys Thr Ile Ala
         275                 280                 285

Cys Gly His Gly Asn Thr Met Leu Ile Asp Asn Lys Gly Thr Leu Lys
     290                 295                 300

Val Ala Gly Asn Asn Asp Ile Tyr Gln Leu Gly Ile Ala Asn Tyr Ser
305                 310                 315                 320

Glu Asn Ile Asp Asn Ser Phe Ile Asp Leu Lys Asn Ile Val Ala Lys
             325                 330                 335

Asn Ile Phe Ile Gly Leu Ser His Ser Ile Leu Ile Asp Ser Asn Asn
         340                 345                 350

Asp Ser Tyr Cys Thr Gly Asp Asn Thr Tyr Gly Gln Leu Gly Ser Phe
     355                 360                 365

Phe Asp Asp Met His Ile Val Glu Phe Lys Lys Met Asp Ser Glu Lys
     370                 375                 380

Tyr Ser Tyr Ser Asn Tyr Ile Asn Leu Ile Lys Ser Glu Asp Lys Leu
385                 390                 395                 400

Thr Leu Leu Lys Glu Glu Met Glu Ile Lys Asp Ile Glu Leu Pro Leu
             405                 410                 415

Asp Ile His Ser Val Arg Asp Val Val Phe Ser Pro Tyr Cys Thr Leu
         420                 425                 430

Val Ile Leu Gly Asn Gly Asp Val Tyr Gly Leu Gly Asn Asn Arg Tyr
     435                 440                 445
```

```
Lys Gly Met Gly Ser Asp Leu Pro Ser Gln Leu Asn Glu Leu Thr Lys
    450                 455                 460
Leu Ser Ile Ser Asn Val Lys Ser Ile Val Ala Ser Lys Asn Ile Ser
465                 470                 475                 480
Gly Gly Ile Phe Tyr Ile Lys Asn Asp Asp Thr Cys Tyr Tyr Ser Gly
                485                 490                 495
Pro Asn Ser Asn Ser Ile Ala Gly Val Leu Pro Ser Asn Ser Asp Val
            500                 505                 510
Phe Lys Lys Ile Ser Ile Asp Asn Val Lys Val Val Ile Asn Thr
        515                 520                 525
Asp Leu Ser Asn Trp Phe Ser Leu Ile Val Thr Asn Asn Lys Gln Ile
    530                 535                 540
Tyr Thr Ser Gly Lys Ser Ser Tyr Val Asn Gly Leu Ser Asn Ala
545                 550                 555                 560
Leu Ile Ser Gln Tyr Thr Glu Ile Ser Leu Ser Asn Val Thr Asp Ala
                565                 570                 575
Tyr Ser Ser Tyr Asn Ala Thr Phe Ile Val Val Asp Glu Lys Lys Val
            580                 585                 590
Tyr Ala Thr Gly Ile Asn Thr Asn Tyr Leu Leu Gly Phe Ser Thr Ser
        595                 600                 605
Asp Gly Ser Asn Val Asn Leu Gly Leu Leu Ser Asp Trp Tyr Tyr Ile
    610                 615                 620
Asn Ile Ser Gly Ser Ser Tyr Ser Arg Val Ser Cys Thr Asn Asn Ile
625                 630                 635                 640
Thr Lys Ile Asn Asn Ile Ile Tyr Glu Tyr Val Thr Val Phe Cys
                645                 650                 655
Thr Asn Ile Gly Ser Phe Leu Thr Gly Tyr His Gly Thr Ser Trp Thr
            660                 665                 670
Lys Pro Thr Asp Ser Ser Tyr Arg Val Gln Tyr Gln Gly Ile Ser Tyr
        675                 680                 685
Ala Gly Tyr Leu Asp Ser Tyr Ile Tyr Asn Tyr Pro Thr Arg Cys
    690                 695                 700
Thr Gln Ser Ser Ser Ser Thr Thr Phe Ala Tyr Leu Tyr Asn Gly Glu
705                 710                 715                 720
Ser Ser Ser Asn Leu Lys Asn Val Asn Pro Asp Asn Leu Leu Ile Ser
                725                 730                 735
Gly Gly Ser Ser Tyr Ile His Gln Tyr Gly Arg Asn Tyr Leu Asn Asn
            740                 745                 750
Gln Ser Ser Asn Asn Ile Ala Ala Ser Asn Ile Asn Ser Gly Pro Ile
        755                 760                 765
Thr Ser Asp Lys Ala Ile Phe Leu Tyr Lys Ala Leu Leu Tyr Leu Ser
    770                 775                 780
Ser Asn Thr Leu Tyr Gly Phe Gly Asn Ile Ser Glu Ser Ala Lys Glu
785                 790                 795                 800
Leu Asp Val Ser Asp Thr Gln Asp Gly Tyr Asn Ala Thr Asn Tyr Lys
                805                 810                 815
Lys Val Met Lys Asn Ile Lys Asn Ile Phe Ile Pro Pro Tyr Asp Leu
            820                 825                 830
Ser Arg Asp Lys Thr Arg Phe Ala Ile Leu Thr Asp Lys Ser Leu Phe
        835                 840                 845
Ile Cys Gly Tyr Asn Ser Lys Gly Thr His Gly Ile Ser Val Asn Ser
    850                 855                 860
Ser Leu Asn Leu Asn Asn Lys Ile Asn Tyr His Lys Lys Asn Ser Ser
```

```
                  865               870               875               880
        Ser Glu Ile Ser Ser Asn Ile Gln Glu Ile Tyr Ser His Ser Lys Ser
                          885               890               895
        Thr Tyr Leu Leu Thr Asn Asn Asn Met Leu Tyr Ser Val Gly Leu Asn
                          900               905               910
        Asp Val Gly Gln Leu Gly Val Gly Asp Glu Ile Asn Arg Lys Val Phe
                          915               920               925
        Thr Lys Ile Asn Ile Asp Asn Ile Lys Ser Ile Asn Val Asn Arg Phe
            930               935               940
        Thr Asp Asn Ser Lys His Ala Phe Ala Ile Lys Asn Asp Asn Thr Cys
        945               950               955               960
        Tyr Ala Val Gly Leu Asn Asn Ser Gly Gln Leu Gly Ile Gly Asp Asn
                          965               970               975
        Val Asn Arg Asn Ile Phe Thr Lys Ile Asn Val Glu Asn Val Lys Tyr
                          980               985               990
        Val Ala Val Tyr Gly Asn Thr Ser Leu Leu Leu Thr Asn Asp Gly Leu
                          995              1000              1005
        Leu Tyr Gly Ala Gly Asn Asn Gly Lys Gly Gln Leu Gly Leu Gly
            1010              1015              1020
        Asp Thr Thr Ser Arg Asn Ile Phe Thr Arg Ile Pro Ile Asn Gly
            1025              1030              1035
        Val Arg Asp Val Tyr Leu Cys Asn Asp Val Ser Ile Ile Val Lys
            1040              1045              1050
        Asn Asp Asn Thr Cys Tyr Val Cys Gly Leu Val Asn Gly Tyr Phe
            1055              1060              1065
        Gly Phe Thr Glu Gly Ser Ile Ser Thr Phe Thr Lys Ile Asn Ile
            1070              1075              1080
        Glu Asn Val Lys Ser Val Val Thr Ala Gly Ser Glu Ala Thr Phe
            1085              1090              1095
        Phe Ile Thr Asn Asp Asn Met Ile Tyr Thr Thr Gly Lys Lys Glu
            1100              1105              1110
        Arg Val Phe Phe Ser Thr Glu Thr Asn Asp Ile Lys Gly Ile Arg
            1115              1120              1125
        Val Ile Asn Asn Ile Ile Asn Ala Lys Lys Ile Val Val Asn Gly
            1130              1135              1140
        Tyr Thr Ser Ala Ile Leu Thr Asn Asp Asn Lys Leu Phe Val Gly
            1145              1150              1155
        Gly Leu Ser Gly Tyr Gly Ser Ile Ala Asn Asn Asn Asn Thr Asn
            1160              1165              1170
        Ser Val Glu Asp Val Lys Asp Val Phe Val Thr Ala Asn Asn Thr
            1175              1180              1185
        Leu Tyr Ile Asp Asn Asn Asn Leu Ile Ser Ser Gly Arg Asp
            1190              1195              1200
        Thr Tyr Gly Ile Ser Asp Glu Ser Tyr Arg Asp Met Ser Val Pro
            1205              1210              1215
        Tyr Tyr Lys Val Ser Ile Lys Lys Asp Val Asp Thr Val Phe Ser
            1220              1225              1230
        Ser Tyr Asn Thr Ile Phe Ile Lys Asp Ile Tyr Gly Lys Phe Tyr
            1235              1240              1245
        Ser Ser Thr Arg Asp Asn Arg Tyr Asn His Leu Gly Ile His His
            1250              1255              1260
        Arg Tyr Asp Asn Asp Lys Asn Glu Ala Leu Glu Gly Ser Leu His
            1265              1270              1275
```

```
Ser Tyr Phe Lys Thr Asp Asn Thr Ser Asp Lys Ile Val Phe Asn
    1280                1285                1290
Lys Lys Asn Glu Lys Leu Val Met Phe Asn Asp Lys Tyr Ile Lys
    1295                1300                1305
Thr Asn Asn Lys Tyr Ile Asn Tyr Lys Asn Ile Phe Lys Asp Asn
    1310                1315                1320
Phe Lys Tyr Thr Ser Ile Ile Leu Pro Phe Glu Val Ser Asp Ile
    1325                1330                1335
Asp Ile Ser Lys Thr His Ser Leu Ala Val Ala Lys Asp Gly Lys
    1340                1345                1350
Leu Tyr Gly Ile Gly Ser Asn Ser Tyr Lys Glu Ile Asn Gln Thr
    1355                1360                1365
Leu Glu Asp Ile Glu Leu Leu Thr Leu Thr Glu Val Asn Ile Ser
    1370                1375                1380
Asp Val Lys Lys Val Ala Cys Gly Asp Asn Tyr Ser Tyr Ile Ile
    1385                1390                1395
Lys Thr Asp Asn Thr Leu Trp Ser Tyr Gly Lys Asn Thr Glu Tyr
    1400                1405                1410
Gln Leu Gly Val Gly His Asn Asn Asp Val Arg Glu Leu Gln Lys
    1415                1420                1425
Val Thr Gly Leu Pro Ser Val Lys Asp Ile Ser Ile Tyr Asn Ser
    1430                1435                1440
Met Thr Leu Val Leu Thr Asn Glu Gly Glu Leu Tyr Ala Gln Gly
    1445                1450                1455
Tyr Asn Thr Asn Gly Leu Phe Gly Leu Gly Glu Ser Glu Lys Asp
    1460                1465                1470
Lys Ile Ile Arg Thr Phe Thr Lys Val Leu Thr Asn Val Lys Glu
    1475                1480                1485
Ile Lys Ser His Asn Asp Asp His Ile Leu Val Ile Lys Asn Asp
    1490                1495                1500
Asn Ser Leu Trp Ile Thr Gly Lys Asn Lys Ser Met Tyr Lys Ile
    1505                1510                1515
Ser Ile Ser Ile Thr Asp Leu Tyr Glu Phe Thr Lys Ile Pro Ile
    1520                1525                1530
Pro Glu His Leu Asn Asp Ile Leu Asp Ile Glu Leu Ser Asp Asp
    1535                1540                1545
Thr Ile Tyr Met Ile Thr Lys Val Asp Thr Ser Lys Ala Ser Ile
    1550                1555                1560
Glu Ile Val Glu Lys Ser Ile Ser Gln Val Arg Val Val Val Gln
    1565                1570                1575
Asp Pro Asn Asn Val Ile Glu Lys Leu Glu Met Phe Ile Asn Asp
    1580                1585                1590
Glu Leu Ile Ser Thr Lys Thr Asn Leu Glu Ile Asn Ser Ile Ile
    1595                1600                1605
Phe Glu Ile Pro Gln Asn Lys Ile Val Leu Gly Glu Asn Lys Ile
    1610                1615                1620
Leu Ile Lys Ala Ser Ser Pro Thr Gly Asp Leu Tyr Ser Ser Met
    1625                1630                1635
Phe Ile Phe Lys Ser Glu Thr Gly Leu Lys Val Lys Lys Asp Ser
    1640                1645                1650
Ile Leu Met Ile Asn Asn Lys Val Tyr Ser Ile Ile Asn Ile Thr
    1655                1660                1665
```

-continued

```
Glu Asn Asn Thr Asp Leu Ile Val Thr Leu Asn Glu Gly Leu Lys
    1670                1675                1680

Asp Asp Met Met Glu Asn Asn Pro Ile Tyr Gln Leu Ile Asn Lys
    1685                1690                1695

Thr Lys Val Gln Val Lys Ile Asn Lys Ser Asp Leu Phe Lys Asp
    1700                1705                1710

Met Lys Leu Val Glu Ile Lys Lys Ser Asp Ser Tyr Gln Glu
    1715                1720                1725

Ile Tyr Glu Leu Glu Glu Ala Asn Ile Lys Ser Ala Gln Pro Lys
    1730                1735                1740

Ile Ile Val Glu Lys Gly Asp Lys Trp Thr Ala Ile Lys Arg Pro
    1745                1750                1755

Ser Met Ile Phe Arg Tyr Asp Ala Glu Asn Asn Glu Pro Gln
    1760                1765                1770

<210> SEQ ID NO 87
<211> LENGTH: 1743
<212> TYPE: PRT
<213> ORGANISM: Clostridium difficile

<400> SEQUENCE: 87

Met Lys Gln Asn Lys Leu Leu Gln Arg Gly Ala Tyr Phe Asn Asp Lys
1               5                   10                  15

Asn Ile Leu Ile Asp Asp Phe Asp Lys Arg Tyr Asn Asp Tyr Asp Phe
            20                  25                  30

Val Glu Phe Phe Thr Gly Ile Ser Asn Ser Thr Phe Gly Leu Lys Ser
        35                  40                  45

Asp Gly Asn Leu Tyr Ala Cys Gly Asp Asn Thr Gly Phe Gln Leu Gly
    50                  55                  60

Leu Gly Lys Asp Ser Ser Glu Arg Arg Met Phe Ser Val Lys Ile
65                  70                  75                  80

Asp Asn Val Lys Tyr Val Ser Cys Gly Ser Lys His Ser Val Ala Val
                85                  90                  95

Thr Lys Asp Gly Phe Ala Tyr Gly Ala Gly Thr Ser Asn Val Gly Gln
            100                 105                 110

Leu Gly Val Ile Glu Ser Thr Val Tyr Tyr Glu Phe Thr Lys Leu Pro
        115                 120                 125

Ile Asp Asp Val Lys Thr Val Ala Cys Gly Tyr Asp Phe Thr Phe Val
    130                 135                 140

Leu Lys Asn Asp Gly Thr Leu Tyr Ser Ala Gly Leu Asn Ser Ser Gly
145                 150                 155                 160

Gln Leu Gly Leu Gly Asp Thr Asn Asn Arg Ala Thr Phe Thr Lys Val
                165                 170                 175

Asn Ile Asp Ser Val Lys Asp Val Thr Tyr Asn Gln Ser Val Phe
            180                 185                 190

Ile Ile Lys Met Asp Gly Thr Ala His Ala Cys Gly Leu Asn Ser Asn
        195                 200                 205

Gly Gln Leu Gly Ile Asn Ser Thr Leu Asn Lys Ser Val Phe Asn Lys
    210                 215                 220

Ile Glu Gly Met Asp Asn Val Lys Gln Ile Ala Cys Gly Ser Ser His
225                 230                 235                 240

Thr Ile Leu Ile Lys Asn Asp Gly Thr Met Tyr Thr Thr Gly Tyr Asn
                245                 250                 255

Gly Val Gly Gln Leu Gly Thr Gly Asn Asn Asn Asn Ser Ile Val Phe
            260                 265                 270
```

```
Thr Leu Ser Ser Ile Asn Asn Val Lys Tyr Ala Ser Cys Gly Asn Asn
                275                 280                 285

His Thr Met Ile Leu Lys Tyr Asp Asn Thr Leu Phe Ser Thr Gly Gln
290                 295                 300

Asn Asn Tyr Gly Gln Leu Ala Asn Ala Asn Lys Asp Val Ala Ser Arg
305                 310                 315                 320

Asn Thr Phe Ala Lys Val Asn Val Glu Asn Ile Lys Asp Ile Lys Cys
                325                 330                 335

Gly Ser Gln Phe Asn Phe Leu Ile Asn Gly Ser Lys Glu Ile Phe Val
                340                 345                 350

Ser Gly Cys Asn Leu Ala Gly Gln Leu Gly Ser Phe Phe His Thr Thr
                355                 360                 365

Phe Leu Tyr Glu Phe Ser Lys Val Gln Ser Ser Asn Leu Asp Asn Tyr
                370                 375                 380

Ser Gly Leu Leu Val Asn Asp Asp Tyr Leu Tyr Val Thr Lys Asp Asn
385                 390                 395                 400

Ser Glu Phe Leu Asn Val Lys Leu Ser Asp Asn Phe Gln Asp Tyr Lys
                405                 410                 415

Lys Ile Glu Leu Thr Asp Asn Asn Met Phe Ile Val Met Asn Asp Gly
                420                 425                 430

Ser Leu Tyr Ala Cys Gly Leu Asn Asn Ala Gly Gln Leu Gly Leu Gly
                435                 440                 445

Asp Thr Val Asn Arg Ser Val Met Thr Lys Val Asp Ile Asp Asn Val
450                 455                 460

Leu Asp Ile Lys Gly Asn Gly Ser Ser Thr Phe Val Leu Lys Asn Asn
465                 470                 475                 480

Gly Thr Leu Tyr Ser Cys Gly Leu Asn Ser Ser Gly Ile Leu Gly Leu
                485                 490                 495

Lys Asp Asn Thr Asn Arg Asn Ile Phe Thr Lys Ile Glu Ile Glu Asn
                500                 505                 510

Ile Lys Glu Phe Cys Val Glu Ser Asn Tyr Ile Val Ala Leu Asn His
                515                 520                 525

Ser Lys Glu Leu Tyr Gly Trp Gly Asn Gln Ser Tyr Ile Val Tyr Gly
                530                 535                 540

Asp Asn Arg Asn Tyr Pro Tyr Lys Asp Thr Arg Val Ser Asn Val Glu
545                 550                 555                 560

Lys Ile Ala Thr Trp Ser Asp Thr Leu Tyr Ile Leu Asp Ser Thr Gly
                565                 570                 575

Ala Ala Lys Thr Ile Gly Tyr Ser Tyr Asn Gly Ser Gly Gly Tyr Pro
                580                 585                 590

Ala Pro Ser Thr Ser Ser Tyr Gln Ser Lys Gly Tyr Asn Ala Trp
                595                 600                 605

Asn Thr Ser Tyr Arg Thr Leu Glu Phe Tyr Asn Thr Ala Gln Thr Lys
610                 615                 620

Leu Ile Asn Leu Phe Ala Phe Tyr Arg Gly Cys Met Phe Phe Asp Glu
625                 630                 635                 640

Ser Asp Arg Ala Tyr Cys Ile Gly Glu Asn Asn Met Lys Phe Thr Ser
                645                 650                 655

Ser Ser Gln Ile Thr Pro Glu Ser Glu Leu Arg Phe Ser Ser Asn Ser
                660                 665                 670

Gly Ile Tyr His Thr Asn Ser Asp Gly Gly Val Tyr Thr Cys Tyr Gln
                675                 680                 685
```

```
Trp Thr Tyr Lys Leu Ile Arg Cys Ser Val Phe Asp Ser Ser Lys Ser
    690             695                 700

Val Val Gly Asn Ser Lys Asn Ile Leu Ser Leu Leu Lys Asn Asn Ser
705                 710                 715                 720

Thr Phe Arg Cys Thr Gly Ser Cys Leu Thr Tyr Gly Gln Thr Asn Gln
                725                 730                 735

Asn Trp Ser Ser Tyr Leu Ser Asp Asn Cys Asn Gly Ala Val Ser Leu
            740                 745                 750

Gly Asn Glu Phe Ile Leu Lys Asn Tyr Ser Gly Glu Ser Val Leu Lys
                755                 760                 765

Gly Tyr Gly Lys Ser Asn Asn Gly Glu Phe Gly Ser Ser Thr Ser Ile
770                 775                 780

Ser Asn Ala Ser Asn Tyr Asp Thr Gly Leu Lys Asp Ile Lys Asp Ile
785                 790                 795                 800

Ile Val Lys Asn Asn Thr Val Val Val Asp Lys Asn Asn Asn Ile
                805                 810                 815

Tyr Val Thr Gly Thr Asn Gln Phe Asn Lys Leu Gly Ile Gly Glu Tyr
                820                 825                 830

Asn Asn Gln Pro Ile Lys Lys Phe Thr Asn Ile Thr Glu Gln Ser Asn
            835                 840                 845

Ser Phe Ile Phe Met Asp Asp Ile Lys Glu Ile Thr Thr Ser Arg Asn
850                 855                 860

Thr Met Phe Ile Val Lys Asn Asp Gly Thr Ala Tyr Ala Thr Gly Asn
865                 870                 875                 880

Asn Ser Ser Gly Gln Leu Gly Leu Gly Asp Thr Ile Asn Arg Asn Lys
                885                 890                 895

Phe Thr Gln Ile Asn Ile Asp Asn Ile Lys Lys Ile Ser Thr Ser Ile
                900                 905                 910

Asp Gly Asn Thr Thr Phe Ala Ile Arg Asn Asp Gly Thr Leu Tyr Ser
        915                 920                 925

Thr Gly Leu Asn Thr Lys Gly Gln Leu Gly Leu Gly Asp Ile Val Asn
    930                 935                 940

Arg Asn Thr Phe Thr Lys Val Asn Ile Gln Asn Val Arg Asp Val Val
945                 950                 955                 960

Leu Gly Thr Thr His Ser His Ala Ile Lys Asp Asp Asn Thr Leu Tyr
                965                 970                 975

Ser Cys Gly Glu Asn Thr His Gly Gln Leu Gly Leu Gly Ser Glu Ser
            980                 985                 990

Asn His Pro Asp Val Leu Thr Phe Thr Val Asn Asn Ile Thr Asn Val
        995                 1000                1005

Arg Asp Val Tyr Cys Ser Asp Thr Thr Thr Phe Ile Val Lys Asp
    1010                1015                1020

Thr Asn Ile Ala Tyr Cys Cys Gly Tyr Asn Asn Asn Ser Gln Leu
    1025                1030                1035

Gly Met Gly Asn Thr Thr Asp Gln Tyr Ser Phe Ile Lys Cys Met
    1040                1045                1050

Glu Asn Val Lys Glu Val Ile Pro Asn Glu Ile Asn Thr Tyr Ile
    1055                1060                1065

Ile Thr Ile Tyr Asn Thr Ala Tyr Ser Thr Gly Leu Asn Thr Asp
    1070                1075                1080

Tyr Cys Leu Gly Leu Asn Ser Asn Ser Asn Gln Ser Ser Phe Ser
    1085                1090                1095

Glu Ile Pro Ile Ser Asn Val Val Lys Val Ala Pro Asn Arg Asn
```

```
                1100               1105                1110

Asn Ala Val Leu Leu Leu Thr Ser Glu Gly Asp Val Tyr Thr Ala
            1115                1120                1125

Gly Lys Cys Ser Asn Gly Ser Gly Thr Gly Ser Glu Thr Pro Glu
            1130                1135                1140

Lys Ile Lys Lys Ile Ala Ser Lys Ala Lys Asp Ile Gly Met Asn
            1145                1150                1155

Tyr Arg Cys Gly His Tyr Val Ser Asp Asn Gly Asp Leu Tyr Gly
            1160                1165                1170

Thr Gly Phe Asn Asn Gly Gln Leu Gly Val Gly Asp Val Thr
            1175                1180                1185

Lys Arg Asp Thr Phe Ile Lys Thr Asn Thr Arg Val Lys Lys Ile
            1190                1195                1200

Leu Pro Leu Glu Tyr Ala Asn Ile Ala Ile Lys Asp Thr Asn Asp
            1205                1210                1215

Ile Tyr Ile Cys Gly Leu Asn Asn Tyr Gly Gln Leu Gly Val Gly
            1220                1225                1230

Asn Arg Tyr Asp Ser Arg Asn Asn Asp Asn Arg Ile Phe Asn Tyr
            1235                1240                1245

Lys His Met Asn Phe Val Met Gly Asp Leu Thr Ser Ile Lys Asn
            1250                1255                1260

Arg His Asn Phe Ile Leu Leu Asn Asn Lys Ile Val Ile Pro Thr
            1265                1270                1275

Thr Lys Asp Ile Asp Tyr Gly Leu Val Leu Gly Asn Leu Tyr Lys
            1280                1285                1290

Gly Asp Leu Tyr Thr Glu Leu Pro Tyr Glu Asp Ile Lys Glu Val
            1295                1300                1305

Ser Ile Ser Lys Thr His Ile Ile Ile Leu Leu Asn Asp Gly Thr
            1310                1315                1320

Met Tyr Gly Cys Gly Thr Asn Tyr His Gly Glu Leu Leu Gln Asp
            1325                1330                1335

Leu Ser Ile Asn Gln Val Asp Glu Phe Val Gln Ile Asn Val Ser
            1340                1345                1350

Asp Val Lys His Val Ser Cys Gly Asp Asn Phe Thr Tyr Phe Ile
            1355                1360                1365

Lys Ser Asp Asp Ser Leu Trp Ser Ile Gly Lys Asn Ser Glu Tyr
            1370                1375                1380

Gln Leu Gly Ile Gly His Asn Asn Pro Val Thr Glu Leu Gln Arg
            1385                1390                1395

Ile Thr Thr Ile Ser Ser Cys Lys Glu Val His Cys Gly Lys Asn
            1400                1405                1410

Tyr Thr Leu Val Val Thr Thr Gly Asn Glu Leu Phe Val Gln Gly
            1415                1420                1425

Tyr Asn Asp Lys Gly Ala Leu Gly Leu Gly Ser Asp Ser Glu Asn
            1430                1435                1440

Thr Ile Ile Lys Phe Phe Thr Lys Ala Leu Thr Asp Ile Arg Glu
            1445                1450                1455

Ile Lys Ser Tyr Gly Ser Asp His Ile Leu Val Leu Lys Asn Asp
            1460                1465                1470

Asn Ser Val Trp Val Thr Gly Lys Asn Arg Asp Val Tyr Lys Ile
            1475                1480                1485

Glu Gln Pro Val Glu Phe Leu Lys Glu Phe Thr Ile Ile Pro Ile
            1490                1495                1500
```

-continued

Ser Glu Asp Val Asn Thr Val Lys Asp Val Leu Ala Thr Asp Asn
1505                1510                1515

Thr Leu Tyr Ile Ile Ser Glu Val Gly Thr Thr Asn Ala Ala Ile
1520                1525                1530

Glu Ile Thr Glu Lys Ser Ile Ser Ser Ile Lys Ile Lys Ile Gln
1535                1540                1545

Asp Pro Asn Lys Asp Ile Ser Arg Ile Glu Met Leu Ile Asn Gly
1550                1555                1560

Glu Ser Val Lys Ser Val Ser Asp Leu Ile Thr Glu Lys Ile Ser
1565                1570                1575

Phe Glu Val Pro Pro Asp Lys Ile Lys Ile Gly Glu Asn Lys Ile
1580                1585                1590

Leu Phe Arg Ala Tyr Cys Lys Gly Asp Asp Leu Tyr Ala Ser Leu
1595                1600                1605

Phe Ile Phe Lys Glu Ser Thr Gly Asn Ser Ile Ile Lys Asp Ser
1610                1615                1620

Tyr Val Met Ile Gly Asn Arg Met Tyr Lys Val Val Asn Thr Thr
1625                1630                1635

Ser Asn Glu Gln Asp Ile Thr Ile Thr Leu Asp Arg Gly Leu Glu
1640                1645                1650

Glu Asp Leu Asn Leu Gly Asp Pro Ile Tyr Gln Leu Ile Asn Lys
1655                1660                1665

Thr Lys Val Gln Val Lys Ile Asn Lys Ser Asp Leu Phe Lys Asp
1670                1675                1680

Met Lys Leu Val Glu Ile Lys Lys Ser Asp Ser Ser Tyr Gln Glu
1685                1690                1695

Ile Tyr Glu Leu Glu Glu Ala Asn Ile Lys Ser Ala Gln Pro Lys
1700                1705                1710

Ile Ile Val Glu Lys Gly Asp Lys Trp Thr Ala Ile Lys Arg Pro
1715                1720                1725

Ser Met Ile Phe Arg Tyr Asp Ala Glu Asn Asn Glu Pro Gln Ala
1730                1735                1740

<210> SEQ ID NO 88
<211> LENGTH: 327
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 88

Leu Glu Glu Lys Phe Tyr Ile Ile Leu Thr Lys Ile Gly Arg Glu Lys
1               5                   10                  15

Ile Ala Asn Ala Thr Ala Leu Gly Glu Leu Val Gly Leu Thr Lys Phe
                20                  25                  30

Gln Val Gly Asp Ser Asn Gly Thr Tyr Glu Pro Thr Glu Glu Gln
        35                  40                  45

Thr Ala Leu Lys Asn Val Val Trp Glu Gly Asn Ile Asn Ser Leu Arg
    50                  55                  60

Ile Asp Glu Lys Asn Pro Asn Trp Ile Val Glu Thr Ile Leu Pro
65                  70                  75                  80

Gly Thr Val Gly Gly Phe Met Ile Arg Glu Ala Ala Val Leu Asp Asn
                85                  90                  95

Glu Asn Asn Ile Ile Ala Ile Gly Lys Tyr Pro Glu Thr Tyr Lys Pro

```
                100             105             110
Arg Ala Glu Asp Gly Ser Ile Lys Asp Leu Val Val Lys Met Ile Leu
            115                 120                 125
Gln Leu Ser Asn Thr Ser Asn Val Thr Leu Glu Val Asp Pro Thr Leu
            130                 135                 140
Val Phe Val Thr Gln Lys Asp Ile Gln Asp Leu Asp Asp Lys Phe Asp
145                 150                 155                 160
Lys Asn Ile Lys Glu Ile Lys Val Asn Ile Gly Asp Val Asn Ile Leu
                165                 170                 175
Thr Thr Tyr Ser Lys Asp Leu Ser Gly Ala Ile Asn Glu Val Val Lys
                180                 185                 190
Lys Ile Glu Asn Ile Ser Phe Asp Asp Val Ile Ser Gly Gln Ile Gln
                195                 200                 205
Thr Asp Ile Ser Val Leu Lys Asn Ser Tyr Asn Lys Leu Ser Glu Lys
                210                 215                 220
Val Leu Asp Ile Leu Ile Tyr Leu Glu Leu Glu Ser Glu Val Thr Val
225                 230                 235                 240
Asp Glu Ala Gly Tyr Trp Tyr Asp Thr Leu Ala Asn Gly Asn Asn Ile
                245                 250                 255
Val Ala Ile Glu Gly Leu Lys Leu Asp Leu Asn Arg Lys Cys Ile Thr
                260                 265                 270
Gly Glu Ile Gly Asn Val Ile Phe Arg Asp Val Val Leu Pro Phe Ser
                275                 280                 285
Ala Asn Arg Val Arg Tyr Ile His Asp Met Asp Asn Asn Phe Val Glu
                290                 295                 300
Thr Lys Ser Ser Asn Thr Tyr Leu Lys Glu Gln Lys Asp Ile Thr Leu
305                 310                 315                 320
Asn Lys Tyr Ser Tyr Glu Ile
                325

<210> SEQ ID NO 89
<211> LENGTH: 117
<212> TYPE: PRT
<213> ORGANISM: Clostridium difficile

<400> SEQUENCE: 89

Leu Phe Lys Phe Asp Lys Asn Lys Ile Glu Gln Ile Lys Gln Gly Arg
1               5                   10                  15
Lys Val Glu Met Gln Tyr Lys Asp Ile Ser Asp Ile Ser Ile Gly Gln
                20                  25                  30
Val Lys Gln Asp Asp Asp Ile Thr Asn Asn Phe Ile Ala Asn Ala Glu
            35                  40                  45
Ile Tyr Glu Met Leu Leu Ser Gln Ser Ser Val Asn Glu Ala Ser Asn
        50                  55                  60
Ile Ser Thr Phe Ser Val Arg Lys Ser Gly Gly Glu Ser Gly Met Val
65                  70                  75                  80
Glu Val Tyr Val Ala Leu Ile Leu Arg Gly Lys Lys Thr Ile Glu Glu
                85                  90                  95
Val Pro Ala Val Ile Arg Glu Gln Val Arg Ile Arg Cys Lys Glu Leu
                100                 105                 110
Glu Ile Pro Val Glu
            115

<210> SEQ ID NO 90
<211> LENGTH: 86
```

<212> TYPE: PRT
<213> ORGANISM: Clostridium difficile

<400> SEQUENCE: 90

Met Asp Lys Leu Ile Thr Glu Leu Ser Ser Leu Gly Ala Ile Gly Ile
1               5                   10                  15

Leu Cys Ala Leu Leu Phe Lys Asn Thr Met Gln Glu Lys Lys Glu Asp
            20                  25                  30

Arg Asp Met Tyr Lys Lys Thr Val Glu Asn Phe Ile Glu Leu Ser Thr
        35                  40                  45

Gln Gln Gln Glu Ile Asn Lys Asn Ile Leu Val Gln Met Gly Ile Met
    50                  55                  60

Lys Thr Asp Val Glu Glu Ile Lys Glu Asp Val Thr Asp Ile Lys Gly
65                  70                  75                  80

Met Leu Gln Asn Gly Val
                85

<210> SEQ ID NO 91
<211> LENGTH: 327
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 91

Leu Glu Glu Lys Phe Tyr Ile Ile Leu Thr Lys Ile Gly Arg Glu Lys
1               5                   10                  15

Ile Ala Asn Ala Thr Ala Leu Gly Glu Leu Val Gly Leu Thr Lys Phe
            20                  25                  30

Gln Val Gly Asp Ser Asn Gly Glu Tyr Tyr Glu Pro Thr Glu Glu Gln
        35                  40                  45

Thr Ala Leu Lys Asn Val Val Trp Glu Gly Asn Ile Asn Ser Leu Arg
    50                  55                  60

Ile Asp Glu Lys Asn Pro Asn Trp Ile Val Ile Glu Thr Ile Leu Pro
65                  70                  75                  80

Gly Thr Val Gly Gly Phe Met Ile Arg Glu Ala Ala Val Leu Asp Asn
                85                  90                  95

Glu Asn Asn Ile Ile Ala Ile Gly Lys Tyr Pro Glu Thr Tyr Lys Pro
            100                 105                 110

Arg Ala Glu Asp Gly Ser Ile Lys Asp Leu Val Val Lys Met Ile Leu
        115                 120                 125

Gln Leu Ser Asn Thr Ser Asn Val Thr Leu Glu Val Asp Pro Thr Leu
    130                 135                 140

Val Phe Val Thr Gln Lys Asp Ile Gln Asp Leu Glu Thr Lys Ile Gly
145                 150                 155                 160

Thr Val Asn Thr Lys Ile Asp Thr Thr Lys Thr Glu Leu Thr Ser Asn
                165                 170                 175

Ile Glu Thr Ala Lys Thr Glu Leu Asn Thr Lys Ile Asp Gln Leu Ile
            180                 185                 190

Ala Gly Gly Ser Asn Val Ala Tyr Thr Gln Arg Val Ala Ile Asp Asp
        195                 200                 205

Trp Val Glu Asp Ala Glu Ser Gly Phe Lys Ala Thr Val Thr His Ser
    210                 215                 220

Leu Leu Thr His Arg Ile Val Val Asn Ile Ile Asp Ala Thr Thr Lys
225                 230                 235                 240

-continued

```
Glu Asn Ile Val Pro Asn Phe Lys Ile Val Asp Asp Asn Ser Ile Glu
                245                 250                 255

Ile Arg Ser Glu Val Lys Val Glu Leu Asn Val Tyr Val Ile Asn Gly
            260                 265                 270

Asn Ala Glu Thr His Phe Ile Asn Ala Thr Val Asp Asp Asn Arg Val
        275                 280                 285

Ser Glu Met Thr Thr Tyr Ser Ser Lys Lys Ile Glu Asp Arg Leu Val
    290                 295                 300

Asn Ile Glu Glu Lys Val Asn Gly Gly Leu Ser Asn Ile Ala Thr Ser
305                 310                 315                 320

Val Asn Glu Leu Ile Thr Tyr
                325

<210> SEQ ID NO 92
<211> LENGTH: 570
<212> TYPE: PRT
<213> ORGANISM: Clostridium difficile

<400> SEQUENCE: 92

Met Gln Thr Glu Trp Asn Phe Asn Tyr Ala Asn Tyr Val Gln Asn Val
1               5                   10                  15

Ser Leu Pro Pro Gly Arg Tyr Lys Leu Glu Cys Trp Gly Ala Cys Gly
            20                  25                  30

Gly Ala Val Asp Thr Ser Asp Trp Thr Asp Cys Ala Lys Gly Gly Tyr
        35                  40                  45

Ser Lys Gly Glu Ile Val Phe Lys Lys Arg Thr Asn Leu Gln Ile Cys
    50                  55                  60

Val Gly Gln Ser Gly Tyr Glu Lys Val Ser Glu Gly Ser Ser Leu Thr
65                  70                  75                  80

Arg Ser Gly Phe Asn Gly Ala Gly Ala Ala Gly Lys Val Thr Thr Gly
                85                  90                  95

Ser Phe Ala Tyr Ser Lys Tyr Gly Gly Gly Ala Thr Asp Ile Arg Leu
            100                 105                 110

Tyr His Pro Ser Ala Thr Trp Gly Asn Thr Glu Ser Leu Leu Ser Arg
        115                 120                 125

Ile Leu Val Ala Gly Gly Gly Gly Gly Met Lys Asn Asn Phe Ala Ser
    130                 135                 140

Ala Arg Ser Ile Gly His Gly Gly Gly Tyr Val Gly Val Asn Gly Val
145                 150                 155                 160

Gly Arg Asp Arg Asp Phe Cys Gly Gly Gly Ser Gln Tyr Gln Gly Gly
                165                 170                 175

Thr Ser Tyr Asp Thr Glu Glu Tyr His Gly Ser Leu Gly Lys Gly Gly
            180                 185                 190

Tyr Gly Asn Ile Gly Ile Gly Gly Gly Gly Gly Trp Tyr Gly Gly Ala
        195                 200                 205

Gly Ser Tyr Ser Asn Glu Cys Gly Gly Gly Gly Ser Gly Tyr Ala Leu
    210                 215                 220

Asn Lys Asp Ser Tyr Lys Ala Pro Gly Tyr Ile Pro Thr Pro Glu Tyr
225                 230                 235                 240

Tyr Leu Glu Asn Ile Val Met Thr Thr Gly Gly Asn Thr Thr Lys Ala
                245                 250                 255

Asp Gly Tyr Ala Lys Ile Thr Leu Leu Gln Ala Leu Pro Phe Leu Thr
            260                 265                 270

Val Ser Ser Tyr Asn Ser Thr Gln Ala Thr Phe Lys Ala Asp His Thr
        275                 280                 285
```

```
Asp Pro Ala Leu Leu Thr Lys Ile Glu Trp Phe Ile Asp Asp Val Leu
            290                 295                 300

Lys Glu Thr Ile Thr Thr Asn Leu Thr Glu Glu Lys Thr Ile Asn Tyr
305                 310                 315                 320

Thr Leu Glu Asp Asn Ala Leu His Thr Leu Lys Ile Val Val Thr Asp
                325                 330                 335

Ser Asn Asn Ala Thr Ala Glu Lys Val Leu Ser Ile Ser Lys Asn Ile
            340                 345                 350

Met Pro Leu Pro Glu Asn Val Asn Leu Asn Asp Ile Ser Thr Lys Leu
            355                 360                 365

Val Glu Val Asn Ala Gly Phe Lys Val Gly Lys Thr Ser Ile Ile Asn
370                 375                 380

Thr Leu Ala Leu Lys Asn Ile Glu Ala Ser Leu Asn Asn Thr Leu Val
385                 390                 395                 400

Glu Leu Ser Glu Lys Ile Lys Thr Ser Phe Asp Ser Ser Asp Thr Ser
                405                 410                 415

Val Gln Asp Leu Gln Asn Gln Val Thr Gln Lys Asn Asn Thr Ile Thr
            420                 425                 430

Gln Leu Glu Thr Glu Leu Ser Lys Arg Lys Arg Phe Ile Thr Gly Thr
            435                 440                 445

Tyr Thr Phe Thr Lys Thr Asp Ala Glu Asn Phe Asn Leu Ser Ile Tyr
450                 455                 460

Asp Lys Glu Gly Thr Ser Lys Thr Leu Thr Ile Pro Val Asn Met Gly
465                 470                 475                 480

Phe Ser Pro Ser Leu Ile Val Leu Ser Gly Val Thr Phe Ser Thr Thr
                485                 490                 495

Ser Lys Ser Tyr Val Tyr Phe Asp Asn Val Cys Asn Ser Asn Phe Tyr
            500                 505                 510

Asn Phe Gly Tyr Asn Ser Asp Ser Thr His Ser Asn Pro Lys Ala Val
            515                 520                 525

Gly Ile Leu Asn Val Ser Asn Val Gly Tyr Ser Ser Leu Val Leu Thr
530                 535                 540

Leu Tyr Lys Leu Ser Met Ser Glu Ala Val Gly Ile Trp Ala Lys Glu
545                 550                 555                 560

Gly Ala Thr Leu Thr Tyr Lys Ile Tyr Ile
                565                 570

<210> SEQ ID NO 93
<211> LENGTH: 266
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 93

Leu Glu Glu Lys Phe Tyr Ile Ile Leu Thr Lys Ile Gly Arg Glu Lys
1               5                   10                  15

Ile Ala Asn Ala Thr Ala Leu Gly Glu Leu Val Gly Leu Thr Lys Phe
            20                  25                  30

Gln Val Gly Asp Ser Asn Gly Glu Tyr Tyr Glu Pro Thr Glu Glu Gln
        35                  40                  45

Thr Ala Leu Lys Asn Val Val Trp Glu Gly Asn Ile Asn Ser Leu Arg
50                  55                  60

Ile Asp Glu Lys Asn Pro Asn Trp Ile Val Ile Glu Thr Ile Leu Pro
```

```
                65                  70                  75                  80
Gly Thr Val Gly Gly Phe Met Ile Arg Glu Ala Ala Val Leu Asp Asn
                    85                  90                  95

Glu Asn Asn Ile Ile Ala Ile Gly Lys Tyr Pro Glu Thr Tyr Lys Pro
                100                 105                 110

Arg Ala Glu Asp Gly Ser Ile Lys Asp Leu Val Val Lys Met Ile Leu
                115                 120                 125

Gln Leu Ser Asn Thr Ser Asn Val Thr Leu Glu Val Asp Pro Thr Leu
        130                 135                 140

Val Phe Val Thr Gln Lys Asp Ile Gln Asp Leu Glu Thr Lys Ile Gly
145                 150                 155                 160

Thr Val Asn Ile Lys Ile Asp Thr Thr Lys Thr Glu Leu Thr Ser Asn
                165                 170                 175

Ile Glu Thr Thr Lys Thr Glu Leu Ile Gly Lys Ile Gly Asp Thr Thr
                180                 185                 190

Gln Leu Thr Thr Thr Asp Lys Thr Asn Ile Val Ser Ala Leu Asn Glu
        195                 200                 205

Val Lys Thr Ser Val Asp Ser Ile Glu Thr Thr Ala Asp Lys Thr Ser
210                 215                 220

Ile Lys Asp Thr Asp Asn Leu Phe Glu Ser Asp Asn Val Glu Gly Ala
225                 230                 235                 240

Leu Lys Glu Val Met Gln Glu Val Lys Gly Asn Arg Ser Ser Ile Ile
                245                 250                 255

Ser Ser Ile Asn Ser Asn Leu Ile Pro Met
                260                 265

<210> SEQ ID NO 94
<211> LENGTH: 497
<212> TYPE: PRT
<213> ORGANISM: Clostridium difficile

<400> SEQUENCE: 94

Met Ala Thr Tyr Asp Val Asp Arg Gly Val Lys Leu Arg Glu Gly Glu
1               5                   10                  15

His Thr Asp Glu Glu Ile Phe Leu Arg Ala Cys Ser Tyr Gln Thr Gly
                20                  25                  30

Gly Arg Thr Tyr Tyr Gly Thr Phe Glu Val Gly Asn Glu Ile Lys Val
            35                  40                  45

Phe Glu Leu Glu Thr Arg Leu Tyr Thr Ala Thr Thr Asn Val Arg
        50                  55                  60

Tyr Tyr Ser Thr Ser Gly Ser Glu Val Met Val Arg Asp Val Val Met
65                  70                  75                  80

Arg Gln Asn Val Thr Ala Met Phe Val Ala Lys Pro Thr Ile Asn Ile
                85                  90                  95

Lys Asp Asn Leu Gly Ile Ile Ser Asp Ala Cys Glu Ile Glu Tyr Thr
                100                 105                 110

Ile Ser Asp Gly Phe Pro Glu Leu Arg Tyr Asn Ile Val Tyr Lys Leu
            115                 120                 125

Asn Asn Asp Ile Ile Gly Gln Ile Val Asn Thr Val Asp Ser Lys Tyr
        130                 135                 140

Lys Ile Ser Leu Thr Asp Glu Tyr Leu Ser Lys Leu Ser His Asn Ser
145                 150                 155                 160

Thr Asn His Ile Val Ile Glu Phe Asn Asp Phe Asn Asn Arg Asn Met
                165                 170                 175
```

```
Leu Thr Lys Thr Val Ile Phe Thr Lys Gly Asn Thr Lys Pro Lys Leu
                180                 185                 190

Asn Ile Thr Ser Tyr Asn Ser Thr Thr Ile Phe Thr Ala Ile Asp
        195                 200                 205

Thr Asp Asn Asn Leu Ser Lys Ile Glu Trp Phe Ile Asp Asp Val Leu
210                 215                 220

Lys Glu Thr Ile Thr Thr Asp Leu Tyr Leu Glu Lys Ile Ile Asn Tyr
225                 230                 235                 240

Glu Leu Thr Asp Asn Ala Val His Thr Leu Lys Ile Val Ala Thr Asp
                245                 250                 255

Ala Glu Asn Ala Thr Val Glu Lys Val Leu Ser Ile Ser Lys Glu Ile
                260                 265                 270

Met Pro Phe Gln Ser Asp Ala Ser Leu Ser Asp Ile Ser Thr Lys Leu
                275                 280                 285

Ala Glu Ile Gly Glu Gly Phe Lys Asn Gly Lys Thr Ser Ile Ile Asn
                290                 295                 300

Thr Leu Ala Leu Lys Asn Ile Glu Ala Ser Leu Asn Asn Thr Leu Val
305                 310                 315                 320

Glu Leu Ser Glu Lys Ile Lys Thr Ser Phe Asp Ser Ser Asp Ala Ser
                325                 330                 335

Val Gln Asp Leu Met Asn Gln Leu Thr Gln Ala Asn Asn Thr Ile Ser
                340                 345                 350

Gln Leu Asp Ser Lys Tyr Lys Tyr Ala Ser Gly Thr Ala Asn Ala Arg
                355                 360                 365

Glu Asn Ser Ser Leu Ile Ala Cys Ile Tyr Asp Pro Asn Thr Ser His
                370                 375                 380

Thr Val Glu Glu Thr Ser Pro Tyr Trp Leu Asp Leu Asn Gly Ile Gly
385                 390                 395                 400

Phe Ile Pro Asp Ile Phe Phe Ala Glu Cys Glu Tyr Glu Pro Asn Ser
                405                 410                 415

Asp Ala Phe Tyr Lys Tyr Phe Val Phe Ala Ile Lys Asn Thr Phe Ser
                420                 425                 430

Ile Ser Asn Asn Thr Gly Phe Val Val Asn Ile Thr Phe Asn Lys Glu
                435                 440                 445

Tyr Gly Asp Arg Ser Phe Lys Leu Arg Gly Asp Leu Tyr Thr Leu Gly
                450                 455                 460

Lys Arg His Val Ser Met Asp Asn Thr Gly Val Arg Val Pro Ala Leu
465                 470                 475                 480

Asn Thr Leu Asn Asn Leu Arg Ala Tyr Lys Trp His Ala Ala Lys Phe
                485                 490                 495

Lys

<210> SEQ ID NO 95
<211> LENGTH: 332
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 95

Leu Glu Glu Lys Phe Tyr Ile Ile Leu Thr Lys Ile Gly Arg Glu Lys
1               5                   10                  15

Ile Ala Asn Ala Thr Ala Leu Gly Glu Leu Val Gly Leu Thr Lys Phe
                20                  25                  30
```

```
Gln Val Gly Asp Ser Asn Gly Glu Tyr Tyr Glu Pro Thr Glu Glu Gln
             35                  40                  45

Thr Ala Leu Lys Asn Val Val Trp Glu Gly Asn Ile Asn Ser Leu Arg
 50                  55                  60

Ile Asp Glu Lys Asn Pro Asn Trp Ile Val Glu Thr Ile Leu Pro
 65                  70                  75                  80

Gly Thr Val Gly Gly Phe Met Ile Arg Glu Ala Val Leu Asp Asn
                 85                  90                  95

Glu Asn Asn Ile Ile Ala Ile Gly Lys Tyr Pro Glu Thr Tyr Lys Pro
                100                 105                 110

Arg Ala Glu Asp Gly Ser Ile Lys Asp Leu Val Val Lys Met Ile Leu
            115                 120                 125

Gln Leu Ser Asn Thr Ser Asn Val Thr Leu Glu Val Asp Pro Thr Leu
130                 135                 140

Val Phe Val Thr Gln Lys Asp Ile Gln Glu Leu Asp Thr Lys Ile Asp
145                 150                 155                 160

Thr Thr Lys Thr Glu Leu Thr Ser Asn Ile Glu Thr Ala Lys Thr Glu
                165                 170                 175

Leu Asn Thr Arg Ile Asp Thr Glu Asn Glu Lys Gln Asn Ile Lys Ile
                180                 185                 190

Asp Gln Leu Val Ala Gly Gly Val Asn Val Ser His Thr His Ile Ile
            195                 200                 205

Glu Val Ala Asp Trp Ile Leu Asn Asn Glu Thr Asn Met Tyr Glu Val
210                 215                 220

Thr Ile Asn His Pro Leu Leu Thr Lys Arg Ile Leu Ile Ala Leu Tyr
225                 230                 235                 240

Asp Glu Ile Gly Glu Ala Leu Thr Pro Asn Ala Arg Ala Ile Asp Asp
                245                 250                 255

Asn Ser Ile Leu Val Arg Asn Glu Glu Asn Ile Lys Met Tyr Val Tyr
                260                 265                 270

Leu Ile Asn Gly Asn Ala Glu Thr His Phe Ile Asn Ala Thr Val Asp
            275                 280                 285

Asp Asn Arg Val Ser Glu Met Thr Thr Tyr Ser Ser Lys Lys Ile Glu
290                 295                 300

Asp Arg Leu Val Asn Ile Glu Glu Lys Leu Ser Gly Asn Leu Ser Asp
305                 310                 315                 320

Ile Ala Thr Ser Val Asn Glu Leu Ile Thr Tyr Cys
                325                 330

<210> SEQ ID NO 96
<211> LENGTH: 565
<212> TYPE: PRT
<213> ORGANISM: Clostridium difficile

<400> SEQUENCE: 96

Val Ala Thr Glu Trp Asn Phe Asp Phe Lys Ala Glu Ala Gln Pro Ile
 1                5                  10                  15

Thr Leu Lys Ala Gly Lys Tyr Lys Leu Glu Cys Trp Gly Ala His Gly
                 20                  25                  30

Lys Val Trp Gly Gly Asp Ser Gln Ser Ser Gly Gly Tyr Ser Tyr Gly
             35                  40                  45

Glu Leu Thr Leu Lys Lys Glu Thr Thr Leu Tyr Val Tyr Thr Gly Ala
 50                  55                  60

Thr Gly Ser Ser Asn Lys Tyr Glu Lys Phe Thr Phe Asn Gly Gly Gly
 65                  70                  75                  80
```

```
Leu Gly Val Asn Asn Gly Gly Gly Ala Thr Asp Ile Arg Leu Val
                85              90                  95

Asn Gly Asp Trp Asn Asn Glu Gln Gly Leu Leu Ser Arg Ile Ile Val
            100                 105                 110

Ala Gly Gly Gly Gly Ala Phe Ser Lys Thr Pro Ala Gly Lys Gly
        115                 120                 125

Gly Gly Phe Lys Gly Gly Asn Ser Thr Asn Asp Asp Asn Ser Ser Met
    130                 135                 140

Leu Ile Val Pro Gly Gly Thr Gln Tyr Asp Gly Arg Gly Tyr Cys
145                 150                 155                 160

Asp Glu Trp Asp Gly Val Phe Gly Cys Gly Gly Ser Ile Leu Gly
            165                 170                 175

Leu Glu Arg Gly Lys Tyr Pro Tyr Asn Ser Gly Gly Gly Trp Phe
        180                 185                 190

Gly Gly Ala Gly Ala Arg Asn Thr Ser Ser Gly Gly Gly Ser Gly
    195                 200                 205

Tyr Val Leu Thr Lys Asp Ser Tyr Lys Pro Val Gly Tyr Ile Pro Thr
    210                 215                 220

Ser Glu Tyr Trp Leu Glu Asn Val Gly Ser Ile Thr Gly Gly Asn Thr
225                 230                 235                 240

Ala Lys Val Asn Gly Tyr Ala Lys Ile Thr Leu Leu Gln Ala Leu Pro
            245                 250                 255

Ile Leu Thr Ile Ser Ser Tyr Asn Ser Thr Gln Ala Thr Phe Lys Ala
            260                 265                 270

Asp His Thr Asp Pro Thr Leu Leu Thr Lys Ile Glu Val Phe Ile Asp
            275                 280                 285

Asp Thr Leu Lys Glu Thr Ile Thr Thr Asp Leu Thr Leu Glu Lys Thr
    290                 295                 300

Ile Asn Tyr Thr Leu Glu Asp Asn Ala Leu His Thr Leu Lys Ile Val
305                 310                 315                 320

Val Thr Asp Ser Asn Asn Ala Thr Ala Glu Lys Val Leu Ser Ile Ser
            325                 330                 335

Lys Asn Ile Met Pro Leu Pro Glu Asn Val Asn Leu Gln Asp Ile Ser
            340                 345                 350

Thr Lys Leu Thr Glu Val Asn Ala Gly Phe Lys Ser Gly Lys Thr Ser
    355                 360                 365

Ile Ile Asn Thr Leu Ala Leu Lys Asn Ile Glu Ala Ser Leu Asn Asn
    370                 375                 380

Thr Leu Ile Glu Leu Ser Glu Lys Ile Lys Ile Ser Phe Asp Ser Ser
385                 390                 395                 400

Asp Ala Ser Val Gln Asp Leu Met Asn Gln Leu Thr Gln Ala Asn Asn
            405                 410                 415

Thr Ile Ser Gln Leu Asn Thr Lys Tyr Lys Val Ala Ser Gly Arg Thr
            420                 425                 430

Ser Thr Leu Thr Asp Thr Thr Ser Thr Ala Tyr Leu Tyr Val Asn Ser
        435                 440                 445

Gln Ser Asn Pro Asn Tyr Pro Ile Asn Pro Gly Gly Trp Val Asn Ile
    450                 455                 460

Lys Gly Leu Asn Phe Ile Pro Asn Ile Phe Phe Ala Glu Cys Glu Cys
465                 470                 475                 480

Thr Thr Asn Ser Pro Thr Gln Phe Pro Tyr Lys Tyr Leu Ile Phe Ala Thr
            485                 490                 495
```

```
Tyr Leu Ile Pro Ser Leu Ser Asp Lys Asp Phe Val Ile Thr Thr Ala
                500                 505                 510

Leu Arg Lys Thr Asn Ser Asp Thr Lys Phe Thr Ala Asp Ser Gln Val
            515                 520                 525

Tyr Ile Asn Asn Arg Gly Asn Thr Tyr Ile Asn Asn Gln Gly Val Tyr
        530                 535                 540

Val Pro Ala Tyr Arg Pro Ser Val Ser Tyr Thr Leu Tyr Asn Trp Tyr
545                 550                 555                 560

Ala Ile Lys Phe Val
                565

<210> SEQ ID NO 97
<211> LENGTH: 332
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 97

Leu Glu Glu Lys Phe Tyr Ile Ile Leu Thr Lys Ile Gly Arg Glu Lys
1               5                   10                  15

Ile Ala Asn Ala Thr Ala Leu Gly Glu Leu Val Gly Leu Thr Lys Phe
            20                  25                  30

Gln Val Gly Asp Ser Asn Gly Glu Tyr Tyr Glu Pro Thr Glu Glu Gln
        35                  40                  45

Thr Ala Leu Lys Asn Val Val Trp Glu Gly Asn Ile Asn Ser Leu Arg
    50                  55                  60

Ile Asp Glu Lys Asn Pro Asn Trp Ile Val Ile Glu Thr Ile Leu Pro
65                  70                  75                  80

Gly Thr Val Gly Gly Phe Met Ile Arg Glu Ala Ala Val Leu Asp Asn
                85                  90                  95

Glu Asn Asn Ile Ile Ala Ile Gly Lys Tyr Pro Glu Thr Tyr Lys Pro
            100                 105                 110

Arg Ala Glu Asp Gly Ser Ile Lys Asp Leu Val Val Lys Met Ile Leu
        115                 120                 125

Gln Leu Ser Asn Thr Ser Asn Val Thr Leu Glu Val Asp Pro Thr Leu
    130                 135                 140

Val Phe Val Thr Gln Lys Asp Ile Gln Asp Leu Asp Ser Lys Ile Asp
145                 150                 155                 160

Thr Thr Lys Thr Glu Leu Thr Ser Asn Ile Glu Thr Ala Lys Thr Glu
                165                 170                 175

Leu Asn Thr Arg Ile Asp Thr Glu Asn Glu Lys Gln Asn Ile Lys Ile
            180                 185                 190

Asp Gln Leu Ile Ala Gly Gly Ser Asn Val Ala Ser Thr Gln Thr Ile
        195                 200                 205

Thr Ile Asp Asp Trp Val Glu Asp Ala Glu Asn Gly Phe Lys Ala Thr
    210                 215                 220

Val Thr His Ser Leu Leu Thr Gln Arg Ile Val Val Asn Ile Ile Asp
225                 230                 235                 240

Ala Thr Thr Lys Glu Asn Val Val Thr Asn Phe Lys Ile Ile Asp Asp
                245                 250                 255

Asn Ser Ile Glu Ile Arg Ser Glu Thr Arg Ser Glu Leu Asn Val Tyr
            260                 265                 270

Val Ile Asn Gly Asn Ala Glu Thr Arg Phe Ile Asn Ala Thr Val Asp
        275                 280                 285
```

Asp Asn Arg Val Ser Glu Met Thr Thr Tyr Ser Ser Lys Lys Ile Glu
            290                 295                 300

Asp Arg Leu Val Asn Ile Glu Glu Lys Val Asn Gly Asn Leu Ser Asn
305                 310                 315                 320

Ile Ala Thr Ser Val Asn Glu Leu Ile Thr Tyr Cys
                325                 330

<210> SEQ ID NO 98
<211> LENGTH: 541
<212> TYPE: PRT
<213> ORGANISM: Clostridium difficile

<400> SEQUENCE:

```
            325                 330                 335
Lys Asn Ile Met Pro Leu Pro Glu Asn Val Asn Leu Gln Asp Ile Ser
            340                 345                 350

Ser Lys Leu Ile Glu Ile Asn Thr Gly Phe Lys Thr Gly Lys Thr Ser
            355                 360                 365

Ile Ile Asn Thr Leu Ala Leu Lys Asn Ile Glu Ala Ser Leu Asn Asn
            370                 375                 380

Thr Leu Val Glu Leu Ser Glu Lys Ile Lys Thr Ser Phe Asp Ser Ser
385                 390                 395                 400

Asp Ala Ser Val Gln Glu Leu Gln Asn Arg Ile Thr Glu Leu Thr Asn
            405                 410                 415

Gln Leu Ser Gln Arg Ile Lys Tyr Ala Thr Gly Thr Tyr Thr Ile Pro
            420                 425                 430

Asp Gly Thr Ser Ser Leu Val Val Pro Thr Asn Leu Thr Phe Val Pro
            435                 440                 445

Lys Thr Ile Ile Val Lys Ile Phe Ser Val Lys Asp Gly Ser Asn Pro
            450                 455                 460

Ser Lys Thr Leu Ser Ala Tyr Pro Cys Met Thr Gly Val Asn Gln Asn
465                 470                 475                 480

Leu Arg Tyr Asp Asn Gly Ser Tyr Thr Arg Val Ile Gly Asn Ala Ser
            485                 490                 495

Ile Arg Asp Val Thr Ala Asp Ser Phe Lys Ile Glu Leu Gly Lys Ser
            500                 505                 510

Asp Phe Asn Ala Gly Val Glu Phe Pro Phe Thr Phe Tyr Ser Lys Thr
            515                 520                 525

Phe Arg Trp Tyr Ala Leu Asp Ile Glu Phe Leu Asn Asn
            530                 535                 540

<210> SEQ ID NO 99
<211> LENGTH: 339
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 99

Leu Glu Glu Lys Phe Tyr Ile Ile Leu Thr Lys Ile Gly Arg Glu Lys
1               5                   10                  15

Ile Ala Asn Ala Thr Ala Leu Gly Glu Leu Val Gly Leu Thr Lys Phe
            20                  25                  30

Gln Val Gly Asp Ser Asn Gly Glu Tyr Tyr Glu Pro Thr Glu Glu Gln
            35                  40                  45

Thr Ala Leu Lys Asn Val Val Trp Glu Gly Asn Ile Asn Ser Leu Arg
            50                  55                  60

Ile Asp Glu Lys Asn Pro Asn Trp Ile Val Ile Glu Thr Ile Leu Pro
65                  70                  75                  80

Gly Thr Val Gly Gly Phe Met Ile Arg Glu Ala Ala Val Leu Asp Asn
            85                  90                  95

Glu Asn Asn Ile Ile Ala Ile Gly Lys Tyr Pro Glu Thr Tyr Lys Pro
            100                 105                 110

Arg Ala Glu Asp Gly Ser Ile Lys Asp Leu Val Val Lys Met Ile Leu
            115                 120                 125

Gln Leu Ser Asn Thr Ser Asn Val Thr Leu Glu Val Asp Pro Thr Leu
            130                 135                 140
```

```
Val Phe Val Thr Gln Lys Asp Ile Gln Asp Leu Asp Ala Lys Ile Ser
145                 150                 155                 160

Asn Val Asn Thr Lys Ile Asp Thr Thr Lys Thr Glu Leu Thr Ser Asn
                165                 170                 175

Ile Glu Thr Ala Lys Thr Glu Leu Asn Thr Arg Ile Asp Thr Glu Asn
            180                 185                 190

Glu Lys Gln Asn Ile Lys Ile Asp Gln Leu Ile Ala Gly Gly Ser Asn
        195                 200                 205

Val Ala Ser Thr Gln Thr Thr Ile Asp Asp Trp Ile Asp Asn Gln
    210                 215                 220

Glu Gly Gly Phe Lys Ala Thr Val Thr His Gly Leu Leu Thr Gln Arg
225                 230                 235                 240

Ile Thr Val Ser Ile Ile Asp Ala Thr Thr Lys Asp Asn Val Val Pro
                245                 250                 255

Asp Phe Thr Ile Ile Asp Asp Asn Ser Ile Glu Val Arg Ser Gly Val
            260                 265                 270

Lys Val Glu Leu Asn Val Tyr Val Ile Asn Gly Asn Ala Glu Thr His
        275                 280                 285

Phe Ile Asn Ala Thr Val Asp Asp Asn Arg Val Ser Glu Met Thr Thr
290                 295                 300

Tyr Ser Ser Lys Lys Ile His Glu Glu Ile Gly Lys Val Ala Glu Gln
305                 310                 315                 320

Leu Thr Gly Ile Asn Ser Asn Ile Ile Ser Thr Val Asn Asn Asp Ile
                325                 330                 335

Leu Pro Ile

<210> SEQ ID NO 100
<211> LENGTH: 508
<212> TYPE: PRT
<213> ORGANISM: Clostridium difficile

<400> SEQUENCE: 100

Met Ala Leu Ser Met Ser Tyr Phe Asn Leu Pro Asp Lys Arg Lys Tyr
1               5                   10                  15

Thr Lys Asn Leu Ala Phe Asn Pro Phe Ala Gly Gly Arg Gln Asn Phe
            20                  25                  30

Glu Trp Thr Gly Gly Asp His Gly Leu Asn Gly Glu Phe Lys Glu Thr
        35                  40                  45

Cys Leu Ser Cys Thr Tyr Asn Gly Ser Thr Leu Asn Trp Gly Ser Gly
    50                  55                  60

Asn Val Trp Val Leu Gly Glu Tyr Gly Gln Tyr Thr Phe Thr Tyr Asn
65                  70                  75                  80

Cys Glu Ser Met His Val Asp Thr Gln Gln Lys Phe Pro Tyr Thr Ser
                85                  90                  95

Asn Arg Ile Ile Thr Ile Lys Gly Arg Pro Val Ile Ser Gly Ser Asp
            100                 105                 110

Thr Ser Leu Gly Asn Lys Arg Lys Gly Phe Ser Val Asp Phe Thr Val
        115                 120                 125

Ser Asp Asp Thr Pro Asn Val Asn Leu Ile Val Arg Ala Tyr Leu Asp
130                 135                 140

Asp Lys Leu Ile Gln Asn Ile Thr Pro Val Val Gln Asn Ser Thr Leu
145                 150                 155                 160

Thr Ala Thr Val Thr Asp Ser Gln Leu Asn Ser Leu Ser Val Asp Gly
                165                 170                 175
```

Asn His Lys Leu Lys Ile Gln Leu Asn Asp Gly Tyr Asp Asn Phe Asp
            180                 185                 190

Arg Ile Phe Thr Phe Lys Lys Ile Glu Lys Gly Ile Asp Ile Ser Thr
            195                 200                 205

Ser Leu Val Thr Asp Ser Gln Ala Lys Phe Thr Val Thr Lys Ile Tyr
210                 215                 220

Ser Glu Leu Thr Lys Ile Glu Cys Tyr Leu Asp Glu Thr Leu Lys Glu
225                 230                 235                 240

Thr Phe Thr Thr Asp Leu Tyr Ser Glu Lys Thr Ile Asn Tyr Glu Leu
            245                 250                 255

Ile Asp Asn Ala Ile His Thr Leu Lys Ile Val Val Thr Asp Ala Glu
            260                 265                 270

Asn Val Val Glu Glu Lys Val Ile Ser Ile Ser Lys Asn Ile Met Pro
            275                 280                 285

Leu Gln Pro Asp Ala Thr Leu Gln Asp Ile Ser Thr Lys Leu Thr Glu
            290                 295                 300

Ile Gly Gln Gly Val Arg Asn Gly Lys Thr Ser Ile Ile Asn Thr Leu
305                 310                 315                 320

Ala Leu Lys Asn Ile Asp Ala Ser Leu Asn Asn Thr Leu Val Glu Leu
            325                 330                 335

Ser Glu Lys Ile Lys Gly Gly Phe Asp Ser Gly Asp Ala Ser Leu Gln
            340                 345                 350

Asp Leu Met Asn Gln Leu Thr Gln Ala Asn Asn Thr Ile Ser Gln Leu
            355                 360                 365

Asn Thr Lys Tyr Lys Val Ala Ser Gly Thr Val Thr Ser Phe Ala Asp
            370                 375                 380

Ser Thr Lys Ile Ala Tyr Pro Tyr Leu Thr Asp Asn Val Thr Lys Pro
385                 390                 395                 400

Gly Ser Trp Ile Lys Val Ser Asn Leu Gly Phe Lys Pro Asn Ile Phe
            405                 410                 415

Phe Ala Asp Phe Asp Tyr Tyr Asp Ala Glu Tyr Lys Asn Asn Tyr Lys
            420                 425                 430

Leu Phe Leu Phe Ala Cys Asn Gly Val Ala Thr Gln Arg Gly Val Asp
            435                 440                 445

Phe Ser Ser Val Thr Ser Phe Ile Arg Lys Ser Gly Asp Glu Tyr Phe
            450                 455                 460

His Ala Asn Gly Trp Leu Tyr Ser Asn Ser Glu Gly Asp Val Tyr Phe
465                 470                 475                 480

Asn Asn Thr Gly Val Gln Ile Pro Ala Tyr Asn Phe Asp Ser Thr Gln
            485                 490                 495

Lys His Thr Tyr Lys Trp Tyr Ala Ile Lys Phe Ile
            500                 505

<210> SEQ ID NO 101
<211> LENGTH: 256
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 101

Leu Glu Glu Lys Phe Tyr Ile Ile Leu Thr Lys Ile Gly Arg Glu Lys
1               5                   10                  15

Ile Ala Asn Ala Thr Ala Leu Gly Glu Leu Val Gly Leu Thr Lys Phe
            20                  25                  30

```
Gln Val Gly Asp Ser Asn Gly Glu Tyr Tyr Glu Pro Thr Glu Gln
                 35                  40                  45

Thr Ala Leu Lys Asn Val Val Trp Glu Gly Asn Ile Asn Ser Leu Arg
 50                  55                  60

Ile Asp Glu Lys Asn Pro Asn Trp Ile Val Glu Thr Ile Leu Pro
 65                  70                  75                  80

Gly Thr Val Gly Gly Phe Met Ile Arg Glu Ala Val Leu Asp Asn
                 85                  90                  95

Glu Asn Asn Ile Ile Ala Ile Gly Lys Tyr Pro Glu Thr Tyr Lys Pro
                100                 105                 110

Arg Ala Glu Asp Gly Ser Ile Lys Asp Leu Val Val Lys Met Ile Leu
                115                 120                 125

Gln Leu Ser Asn Thr Ser Asn Val Thr Leu Glu Val Asp Pro Thr Leu
                130                 135                 140

Val Phe Val Thr Gln Lys Asp Ile Gln Asp Leu Glu Thr Lys Ile Gly
145                 150                 155                 160

Thr Val Asn Thr Lys Ile Asp Thr Thr Lys Thr Glu Leu Asn Ser Lys
                165                 170                 175

Val Gly Asp Thr Thr Leu Leu Thr Thr Thr Asp Lys Thr Asn Ile Val
                180                 185                 190

Asn Ala Leu Asn Glu Val Lys Lys Thr Ser Val Asp Ser Ile Glu Thr
                195                 200                 205

Thr Ala Glu Lys Thr Ser Tyr Asn Asn Ala Thr Ser Lys Leu Asn Ala
                210                 215                 220

Thr Asn Val Gln Gly Ala Ile Asp Glu Ile Val Ala Glu Val Arg Gly
225                 230                 235                 240

Asn Arg Ser Ser Ile Ile Ser Ser Ile Asn Asp Asn Leu Ile Pro Met
                245                 250                 255

<210> SEQ ID NO 102
<211> LENGTH: 486
<212> TYPE: PRT
<213> ORGANISM: Clostridium difficile

<400> SEQUENCE: 102

Met Pro Pro Ala Glu Thr Phe Ile Cys Asn Arg Ile Val Lys Lys Arg
 1               5                  10                  15

Arg Gly Tyr Tyr Ser Glu Arg Asp Val Phe Leu Ser Pro Cys Pro Tyr
                 20                  25                  30

Val Tyr Gly Glu Gly Gly Met Tyr Glu Ser Thr Tyr Tyr Gly Glu Phe
                 35                  40                  45

Asp Leu Ser Asn Ser Lys Tyr Ile Thr Val Pro Thr Ser Thr Lys Tyr
 50                  55                  60

Glu Lys Thr Ala Thr Arg Val Tyr Phe Ile Ser Gly Gly Asn Met Ile
 65                  70                  75                  80

Thr Ser Ser Ser Gly Met Lys Gln Ala Ile Thr Leu Glu Leu Ile Pro
                 85                  90                  95

Asp Pro Asn Ile Ile Ile Asn Asp Asp Leu Gly Val Ile Ser Asp Ser
                100                 105                 110

Cys Asn Ile Asn Tyr Arg Ile Pro Asp Ser Asn Thr Ser Val Lys Phe
                115                 120                 125

Asp Val Thr Glu Lys Leu Asn Gly Val Val Ile Ser Lys Lys Asn Tyr
                130                 135                 140

Ala Leu Asp Gly Asn Tyr Thr Leu Asn Leu Thr Asp Glu His Leu Ser
```

```
                145                 150                 155                 160
Thr Leu Ser Phe Asn Ser Thr Asn Ile Thr Ile Glu Leu Ser Thr
                165                 170                 175
Tyr Gln Gly Gly Lys Phe Leu Glu Lys Thr Val Thr Phe Thr Lys Gly
                180                 185                 190
Asn Thr Lys Pro Lys Leu Asn Ile Thr Ser Tyr Asn Ser Thr Thr Ala
                195                 200                 205
Ile Phe Thr Ala Ile Asp Ile Asp Asn Leu Ser Lys Ile Glu Trp
                210                 215                 220
Phe Ile Asp Asp Val Leu Lys Glu Thr Ile Thr Thr Asp Leu Tyr Leu
225                             230                 235                 240
Glu Lys Thr Ile Asn Tyr Glu Leu Thr Asp Asn Ala Ile His Thr Leu
                        245                 250                 255
Lys Ile Val Ala Thr Asp Ala Glu Asn Ala Thr Val Glu Lys Val Leu
                260                 265                 270
Ser Ile Ser Lys Glu Ile Met Pro Leu Gln Glu Asp Ala Ser Leu Ser
                275                 280                 285
Asp Ile Ser Thr Lys Leu Ala Glu Ile Gly Glu Glu Phe Arg Asn Gly
                290                 295                 300
Lys Thr Ser Ile Ile Asn Thr Leu Ala Leu Lys Asn Ile Glu Ala Ser
305                             310                 315                 320
Leu Asn Asn Thr Leu Val Glu Leu Ser Glu Lys Ile Lys Thr Ser Phe
                        325                 330                 335
Asp Ser Ser Asp Ala Ser Val Gln Asp Leu Gln Asn Arg Ile Thr Glu
                340                 345                 350
Leu Asn Asn Gln Leu Ser Gln Arg Lys Lys Trp Ala Thr Gly Arg Tyr
                355                 360                 365
Thr Phe Thr Asp Leu Asp Ile Ser Asn Phe Thr Leu Asn Ser Glu Ser
                370                 375                 380
Ile Val Gln Thr Lys Ser Ile Ile Thr Asp Leu Ser Phe Thr Pro Ser
385                             390                 395                 400
Ile Ile Ile Ile Asp Ser Ile Gln Met Lys Ser Gly Thr Asp Arg Val
                        405                 410                 415
Tyr Phe Arg Ser Ile Thr Asn Leu Asp Ile Thr Ile Gly Ala Lys Tyr
                420                 425                 430
Thr Asn Ser Ser Leu Pro Val Gly Gly Ser Gly Tyr Ile Tyr Ile Gln
                435                 440                 445
Lys Pro Thr Pro Ser Asn Asn Phe Leu Leu Ile Leu Thr Arg Leu Asp
                450                 455                 460
Gly Gln Gly Arg Glu Ile Ser Phe Ser Pro Ile Val Gly Glu Thr Leu
465                             470                 475                 480
Thr Trp Tyr Ala Phe Glu
                485

<210> SEQ ID NO 103
<211> LENGTH: 258
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 103

Leu Glu Glu Lys Phe Tyr Ile Ile Leu Thr Lys Ile Gly Arg Glu Lys
1               5                   10                  15
```

Ile Ala Asn Ala Thr Ala Leu Gly Glu Leu Val Gly Leu Thr Lys Phe
20 25 30

Gln Val Gly Asp Ser Asn Gly Glu Tyr Tyr Glu Pro Thr Glu Glu Gln
35 40 45

Thr Ala Leu Lys Asn Val Val Trp Glu Gly Asn Ile Asn Ser Leu Arg
50 55 60

Ile Asp Glu Lys Asn Pro Asn Trp Ile Val Ile Glu Thr Ile Leu Pro
65 70 75 80

Gly Thr Val Gly Gly Phe Met Ile Arg Glu Ala Ala Val Leu Asp Asn
85 90 95

Glu Asn Asn Ile Ile Ala Ile Gly Lys Tyr Pro Glu Thr Tyr Lys Pro
100 105 110

Arg Ala Glu Asp Gly Ser Ile Lys Asp Leu Val Val Lys Met Ile Leu
115 120 125

Gln Leu Ser Asn Thr Ser Asn Val Thr Leu Glu Val Asp Pro Thr Leu
130 135 140

Val Phe Val Thr Gln Lys Asp Ile Gln Asp Leu Asp Thr Lys Ile Asp
145 150 155 160

Thr Thr Lys Ala Glu Leu Thr Ser Asn Ile Glu Thr Ala Lys Thr Glu
165 170 175

Leu Asn Asn Lys Ile Gly Asp Thr Thr Leu Leu Thr Thr Thr Asp Lys
180 185 190

Thr Asn Ile Val Ser Ala Ile Asn Glu Val Lys Thr Ser Val Asp Ser
195 200 205

Ile Glu Thr Thr Ala Glu Lys Thr Ser Tyr Asn Asn Ala Thr Ser Asn
210 215 220

Leu Asn Ala Thr Asn Val Gln Gly Ala Ile Asp Glu Val Val Arg Lys
225 230 235 240

Ile Glu Asn Phe Asn Glu Ile Asn Ile Asn Ile Gln Asn Asp Met Leu
245 250 255

Pro Ile

<210> SEQ ID NO 104
<211> LENGTH: 574
<212> TYPE: PRT
<213> ORGANISM: Clostridium difficile

<400> SEQUENCE: 104

Met Gln Thr Val Trp Asn Phe Asp Tyr Ala Asn Tyr Val Arg Ser Ile
1 5 10 15

Ser Leu Leu Pro Gly Arg Tyr Lys Leu Glu Cys Trp Gly Ala Cys Gly
20 25 30

Gly Gly Lys Gly Ala Ser Ser Phe Asn Glu Cys Ala Lys Gly Gly Tyr
35 40 45

Ala Lys Gly Glu Ile Ile Leu Lys Lys Arg Thr Asn Leu Ile Val Cys
50 55 60

Val Gly Gln Ser Gly Tyr Glu Lys Leu Ala Lys Asp Ser Asn Ile Thr
65 70 75 80

Arg Thr Gly Phe Asn Gly Gly Gly Arg Ala Gly Ser Thr Asn Ile Gly
85 90 95

Asp Tyr Ile Tyr Ala Gly Tyr Gly Gly Gly Ala Thr Asp Ile Arg Leu
100 105 110

Tyr Tyr Ser Ser Thr Thr Trp Asp Ser Ser Glu Gly Leu Leu Ser Arg
115 120 125

```
Ile Leu Val Ala Gly Gly Ala Gly Ala Ile Ser Gly Phe Ser Tyr Pro
    130                 135                 140

His Pro Ser Ile Gly His Gly Gly Glu Lys Gly Ser Asp Gly Val
145                 150                 155                 160

Ser Ala Asn Thr Asn Arg Phe Ser Gly Gly Ser Gln Tyr Gln Gly
                165                 170                 175

Gly Ser Asn Gln Glu Thr Ile Glu Tyr His Gly Ser Phe Gly Lys Gly
                180                 185                 190

Gly Ile Gly Tyr Tyr Ser Val Gly Gly Gly Gly Trp Tyr Gly Gly
                195                 200                 205

Gly Gly Thr Asn Ala Gly Asn Val Ala Gly Gly Ser Gly Tyr Ala
    210                 215                 220

Leu Thr Lys Asp Ser Tyr Lys Pro Pro Gly Tyr Ile Pro Thr Ser Glu
225                 230                 235                 240

Tyr Trp Leu Glu Asn Val Val Met Thr Thr Gly Gly Asn Thr Arg
                245                 250                 255

Ala Asp Gly Tyr Ala Lys Ile Thr Leu Leu Gln Ala Leu Pro Phe Leu
                260                 265                 270

Asn Ile Ser Ser Tyr Asn Ser Thr Gln Val Thr Phe Lys Ala Asp His
    275                 280                 285

Thr Asp Pro Thr Leu Leu Thr Lys Ile Glu Val Phe Ile Asp Asp Thr
    290                 295                 300

Leu Lys Glu Thr Ile Thr Thr Asp Leu Thr Thr Glu Lys Thr Ile Asn
305                 310                 315                 320

Tyr Thr Leu Glu Asp Asn Ala Leu His Thr Leu Lys Ile Val Val Thr
                325                 330                 335

Asp Ser Asn Asn Ala Thr Ala Glu Lys Val Leu Ser Ile Ser Lys Gly
                340                 345                 350

Ile Ala Pro Leu Pro Ala Gly Ser Thr Thr Asp Glu Val Thr Asn Lys
    355                 360                 365

Trp Ile Glu Ile Lys Asp Thr Phe Arg Ser Gly Lys Thr Ser Ile Ile
370                 375                 380

Asn Thr Leu Ala Leu Lys Asn Ile Glu Ala Ser Leu Asn Asn Thr Leu
385                 390                 395                 400

Val Glu Leu Ser Glu Lys Ile Lys Val Gly Phe Asp Ser Lys Asp Ala
                405                 410                 415

Ser Leu Gln Asp Leu Ile Lys Gln Leu Thr Gln Ala Asn Asn Thr Ile
                420                 425                 430

Ser Gln Leu Asn Thr Lys Tyr Lys Val Ala Ser Gly Thr Thr Thr Ala
                435                 440                 445

Leu Glu Ala Glu Gly Arg Gly Ser Leu Phe Glu Val Thr Tyr Ser Gly
    450                 455                 460

Gly Lys Ser Tyr Ala Tyr Asn Arg Trp Val Lys Val Thr Gly Leu Asn
465                 470                 475                 480

Phe Thr Pro Asn Ile Phe Ile Thr Phe Glu Asn His Lys Thr Ser Tyr
                485                 490                 495

Pro Tyr Phe Tyr Cys Asn Phe Thr Phe Ala Cys Gln Gly Val Phe Asp
                500                 505                 510

Lys Asp Phe Ala Val Val Thr Phe Tyr Ser Phe Arg Gly Gln Pro Gly
                515                 520                 525

Glu Thr Thr Tyr Asp Ala Thr Gly Asn Val Ile His Ile Asp Lys Gly
    530                 535                 540

Ala Pro Tyr Met Asn Glu Asn Gly Val Tyr Leu Pro Val Tyr Thr Gln
```

```
                545                 550                 555                 560
Glu Gly Tyr Leu Thr Arg Asn Trp Tyr Ala Ile Lys Phe Lys
                565                 570

<210> SEQ ID NO 105
<211> LENGTH: 265
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 105

Leu Glu Glu Lys Phe Tyr Ile Ile Leu Thr Lys Ile Gly Arg Glu Lys
1               5                   10                  15

Ile Ala Asn Ala Thr Ala Leu Gly Glu Leu Val Gly Leu Thr Lys Phe
            20                  25                  30

Gln Val Gly Asp Ser Asn Gly Glu Tyr Tyr Glu Pro Thr Glu Glu Gln
        35                  40                  45

Thr Ala Leu Lys Asn Val Val Trp Glu Gly Asn Ile Asn Ser Leu Arg
    50                  55                  60

Ile Asp Glu Lys Asn Pro Asn Trp Ile Val Ile Glu Thr Ile Leu Pro
65                  70                  75                  80

Gly Thr Val Gly Gly Phe Met Ile Arg Glu Ala Ala Val Leu Asp Asn
                85                  90                  95

Glu Asn Asn Ile Ile Ala Ile Gly Lys Tyr Pro Glu Thr Tyr Lys Pro
            100                 105                 110

Arg Ala Glu Asp Gly Ser Ile Lys Asp Leu Val Val Lys Met Ile Leu
        115                 120                 125

Gln Leu Ser Asn Thr Ser Asn Val Thr Leu Glu Val Asp Pro Thr Leu
    130                 135                 140

Val Phe Val Thr Gln Lys Asp Ile Gln Asp Leu Glu Thr Lys Ile Gly
145                 150                 155                 160

Thr Val Asn Thr Lys Ile Asp Thr Thr Lys Thr Glu Leu Thr Ser Asn
                165                 170                 175

Ile Glu Thr Ala Lys Thr Glu Leu Asn Asn Lys Ile Gly Asp Thr Thr
            180                 185                 190

Gln Leu Thr Thr Ile Asp Lys Thr Asn Ile Val Ser Ala Leu Asn Glu
        195                 200                 205

Val Lys Ala Ser Val Asp Ser Ile Glu Thr Thr Ala Glu Lys Thr Ser
    210                 215                 220

Tyr Asn Asn Ala Thr Ser Asn Leu Ile Ala Thr Asn Val Gln Gly Ala
225                 230                 235                 240

Ile Asp Glu Val Val Arg Lys Ile Glu Asn Phe Asn Glu Val Asn Ile
                245                 250                 255

Ser Ile Gln Asn Asp Met Leu Pro Ile
            260                 265

<210> SEQ ID NO 106
<211> LENGTH: 575
<212> TYPE: PRT
<213> ORGANISM: Clostridium difficile

<400> SEQUENCE: 106

Met Ala Ile Val Tyr Glu Phe Asn Tyr Thr Gly Ala Glu Gln Ser Val
1               5                   10                  15

Val Leu Pro Pro Gly Lys Tyr Lys Phe Glu Cys Phe Gly Ala Cys Gly
```

-continued

```
                 20                  25                  30
Gly Asn Tyr Tyr Asp Phe Val Gln Cys Ala Lys Gly Tyr Thr Ala
             35                  40                  45
Gly Ser Leu Ile Leu Lys Glu Asn Thr Thr Leu His Val Tyr Val Gly
 50                  55                  60
Gln Ser Gly Tyr Cys Lys Gly Val Asn Gly Ile Glu Thr Cys Arg Ser
 65                  70                  75                  80
Gly Phe Asn Gly Ala Gly Gly Ile Thr Thr Tyr Lys Ser Thr Ser Asp
                 85                  90                  95
Gly Tyr Tyr Ser Leu Ala Gly Gly Ala Thr Asp Ile Arg Leu Ile
                100                 105                 110
Gly Gly Asn Trp Asp Asn Leu Gln Ser Leu Leu Ser Arg Ile Ile Val
                115                 120                 125
Ala Gly Gly Gly Gly Gly Ser Gly Asn Ser His Asp Ser Ile Gly
                130                 135                 140
His Gly Gly Gly Thr Lys Gly Lys Asp Gly Ile Ser Ile Ala Asn Lys
145                 150                 155                 160
Tyr Phe Ala Gly Gly Gly Ser Gln Phe Gln Gly Gly Leu Thr Phe Asn
                165                 170                 175
Ser Leu Tyr Asn Gly Ser Phe Gly Val Ser Gly Ala Gly Asp Gly Ile
                180                 185                 190
Ser Gly Val Gly Gly Gly Gly Trp Tyr Cys Gly Ala Gly Ser Phe
                195                 200                 205
Tyr Ala Glu Phe Gly Gly Gly Ser Gly Tyr Ile Leu Thr Lys Asp
                210                 215                 220
Ser Tyr Lys Pro Ala Asn Tyr Ser Pro Ser Lys Tyr Tyr Phe Ser
225                 230                 235                 240
Asp Ile Asn Ser Val Val Gly Gly Asn Thr Thr Lys Gln Asp Gly Tyr
                245                 250                 255
Ala Lys Ile Thr Leu Leu Gln Ala Leu Pro Phe Leu Thr Ile Ser Ser
                260                 265                 270
Tyr Asn Ser Thr Thr Ala Thr Phe Lys Ala Asp His Thr Asp Pro Thr
                275                 280                 285
Leu Leu Thr Lys Ile Glu Tyr Phe Ile Asp Asp Val Leu Lys Glu Thr
                290                 295                 300
Ile Thr Thr Asp Leu Thr Leu Glu Lys Thr Ile Asn Tyr Thr Leu Glu
305                 310                 315                 320
Asp Asn Ala Leu His Thr Leu Lys Ile Val Val Thr Asp Ser Ala Asn
                325                 330                 335
Ala Thr Ala Glu Lys Val Val Ser Ile Ser Lys Gly Ile Ala Pro Leu
                340                 345                 350
Pro Ala Gly Ser Thr Thr Asp Glu Val Thr Ser Lys Trp Ile Glu Ile
                355                 360                 365
Lys Asp Ala Phe Lys Ser Gly Lys Thr Ser Ile Asn Thr Leu Ala
                370                 375                 380
Leu Lys Asn Ile Glu Ala Ser Leu Asn Asn Thr Leu Val Glu Leu Ser
385                 390                 395                 400
Glu Lys Ile Lys Thr Ser Phe Asp Ser Ser Asp Ala Ser Val Gln Asp
                405                 410                 415
Leu Met Asn Gln Leu Thr Gln Ala Asn Asn Thr Ile Ser Gln Leu Asn
                420                 425                 430
Thr Lys Tyr Lys Val Ala Ser Gly Arg Thr Ser Ala Leu Thr Asp Thr
                435                 440                 445
```

```
Ile Ser Thr Ala Tyr Leu Tyr Val Asn Ser Gln Ser Asn Pro Asn Tyr
    450                 455                 460

Pro Ile Asn Pro Gly Gly Trp Ile Asn Ile Glu Gly Leu Asn Phe Ile
465                 470                 475                 480

Pro Asn Ile Phe Phe Ala Glu Cys Glu Cys Thr Ala Asn Ser Pro Thr
                485                 490                 495

Gln Phe Tyr Lys Tyr Leu Val Phe Ala Thr Tyr Ser Ile Pro Ser Leu
                500                 505                 510

Ser Asp Lys Asp Phe Val Ile Thr Thr Ala Leu Arg Lys Thr Asn Ser
            515                 520                 525

Asp Thr Lys Phe Thr Ala Asp Ser Gln Val Tyr Ile Asn Asn Arg Gly
            530                 535                 540

Asn Thr Tyr Ile Asn Asn Gln Gly Val Tyr Val Pro Ala Tyr Arg Pro
545                 550                 555                 560

Ser Val Ser Tyr Thr Leu Tyr Asn Trp Tyr Ala Ile Lys Phe Ile
                565                 570                 575

<210> SEQ ID NO 107
<211> LENGTH: 259
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 107

Leu Glu Glu Lys Phe Tyr Ile Ile Leu Thr Lys Ile Gly Arg Glu Lys
1               5                   10                  15

Ile Ala Asn Ala Thr Ala Leu Gly Glu Leu Val Gly Leu Thr Lys Phe
            20                  25                  30

Gln Val Gly Asp Ser Asn Gly Glu Tyr Tyr Glu Pro Thr Glu Glu Gln
        35                  40                  45

Thr Ala Leu Lys Asn Val Val Trp Glu Gly Asn Ile Asn Ser Leu Arg
    50                  55                  60

Ile Asp Glu Lys Asn Pro Asn Trp Ile Val Ile Glu Thr Ile Leu Pro
65                  70                  75                  80

Gly Thr Val Gly Gly Phe Met Ile Arg Glu Ala Ala Val Leu Asp Asn
                85                  90                  95

Glu Asn Asn Ile Ile Ala Ile Gly Lys Tyr Pro Glu Thr Tyr Lys Pro
            100                 105                 110

Arg Ala Glu Asp Gly Ser Ile Lys Asp Leu Val Val Lys Met Ile Leu
        115                 120                 125

Gln Leu Ser Asn Thr Ser Asn Val Thr Leu Glu Val Asp Pro Thr Leu
    130                 135                 140

Val Phe Val Thr Gln Lys Asp Ile Gln Asp Leu Asp Ala Lys Ile Asp
145                 150                 155                 160

Thr Thr Lys Thr Glu Leu Thr Ser Asn Ile Glu Thr Thr Lys Thr Glu
                165                 170                 175

Leu Asn Thr Lys Ile Gly Asp Thr Thr Gln Leu Thr Thr Thr Asp Lys
            180                 185                 190

Thr Asn Ile Val Ser Ala Leu Asn Glu Val Lys Ser Ser Val Asp Ser
        195                 200                 205

Ile Glu Thr Thr Ala Glu Lys Thr Ser Ile Lys Asp Thr Asp Asn Leu
    210                 215                 220

Phe Ser Ser Asp Asn Val Glu Gly Ala Leu Lys Glu Val Met Gln Glu
```

```
                    225                 230                 235                 240
Val Lys Gly Asn Arg Ser Ser Ile Ile Ser Thr Val Asn Asn Leu
                245                 250                 255

Ile Pro Met

<210> SEQ ID NO 108
<211> LENGTH: 495
<212> TYPE: PRT
<213> ORGANISM: Clostridium difficile

<400> SEQUENCE: 108

Met Ser Thr Thr Val Leu Glu Arg Thr Val Lys Arg Arg Gly Tyr
1               5                   10                  15

Tyr Arg Met Thr Asp Ile His Ala Ser Arg Leu Thr Tyr Asn Asp Gly
                20                  25                  30

Ser Pro Tyr Tyr Thr Asp Phe Val Ala Tyr Thr Leu Asp Gln Tyr
                35                  40                  45

Glu Arg Val Ser Ile Ser Ala Thr Lys Lys Phe Val Ala Tyr Ser Thr
50                  55                  60

Arg Ala Cys Gln Ile Ile Asn Gly Arg Glu Val Asp Ile Ser Arg Asn
65                  70                  75                  80

Phe Thr Gln Glu Thr Thr Val Gln Phe Val Pro Asp Pro Thr Ile Phe
                85                  90                  95

Ile Ser Asn Asp Leu Gly Val Ile Gly Asn Ala Cys Ser Ile Asn Tyr
                100                 105                 110

Arg Ile Ser Asp Ser Asp Ser Ser Val Arg Phe Lys Ile Ile Glu Lys
                115                 120                 125

Ile Asn Gly Val Lys Ile Ala Glu Lys Asn Asn Val Val Asp Gly Asn
                130                 135                 140

Tyr Glu Leu Ile Ile Thr Asp Glu Leu Leu Ser Glu Leu Ala Phe Asn
145                 150                 155                 160

Ser Val Asn Asn Ile Thr Ile Glu Leu Asp Asn Gly Tyr Gly Gly Ile
                165                 170                 175

Phe Leu Asp Lys Thr Val Thr Phe Thr Lys Gly Asn Thr Lys Pro Lys
                180                 185                 190

Leu Asn Ile Thr Ser Tyr Asn Ser Thr Ser Ala Thr Phe Thr Ala Ile
                195                 200                 205

Asp Thr Asp Asn Asn Leu Ser Lys Ile Glu Trp Phe Ile Asp Asp Val
                210                 215                 220

Leu Lys Glu Thr Ile Thr Thr Asp Leu Thr Thr Glu Lys Thr Ile Asn
225                 230                 235                 240

Tyr Glu Leu Ala Asp Asn Ala Ile His Thr Leu Lys Ile Val Ala Thr
                245                 250                 255

Asp Ser Glu Asn Ala Thr Ala Glu Lys Val Leu Ser Ile Ser Lys Glu
                260                 265                 270

Ile Met Pro Leu Gln Ser Asp Ala Ser Leu Ser Asp Ile Ser Thr Lys
                275                 280                 285

Leu Ile Glu Ile Gly Glu Gly Phe Arg Asn Gly Lys Thr Ser Ile Ile
                290                 295                 300

Asn Thr Leu Ala Leu Lys Asn Ile Glu Ala Ser Leu Asn Asn Thr Leu
305                 310                 315                 320

Val Glu Leu Ser Glu Lys Ile Lys Gln Ser Phe Asp Ser Gly Asp Ala
                325                 330                 335

Ser Leu Gln Asp Leu Met Asn Gln Leu Thr Gln Ala Asn Asn Thr Ile
```

```
                340                 345                 350
Ser Gln Leu Asn Ser Lys Tyr Lys Val Ala Ser Gly Thr Val Thr Ser
            355                 360                 365

Phe Ala Asp Ser Ala Lys Ile Ala Tyr Pro Tyr Leu Thr Asp Arg Thr
        370                 375                 380

Phe Lys Pro Gly Thr Trp Val Lys Ile Ser Asn Leu Asp Phe Lys Pro
385                 390                 395                 400

Asn Ile Phe Phe Ala Asp Phe Asp Tyr Tyr Asp Thr Glu Tyr Lys Asn
                405                 410                 415

Asn Tyr Lys Leu Phe Leu Phe Ala Cys Arg Gly Val Ala Thr Gln Arg
            420                 425                 430

Gly Val Asp Phe Ser Ser Val Thr Ala Phe Ile Arg Lys Asn Ser Asp
        435                 440                 445

Glu Asn Phe His Ala Asn Gly Trp Leu Tyr Asn Ser Glu Gly Asp
                450                 455                 460

Val Tyr Phe Asn Asn Thr Gly Val Gln Ile Pro Ala Tyr Asn Phe Asp
465                 470                 475                 480

Ser Thr Gln Arg His Ile Tyr Lys Trp Tyr Ala Ile Lys Phe Ile
                485                 490                 495

<210> SEQ ID NO 109
<211> LENGTH: 259
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 109

Leu Glu Glu Lys Phe Tyr Ile Ile Leu Thr Lys Ile Gly Arg Glu Lys
1               5                   10                  15

Ile Ala Asn Ala Thr Ala Leu Gly Glu Leu Val Gly Leu Thr Lys Phe
            20                  25                  30

Gln Val Gly Asp Ser Asn Gly Glu Tyr Tyr Glu Pro Thr Glu Glu Gln
        35                  40                  45

Thr Ala Leu Lys Asn Val Val Trp Glu Gly Asn Ile Asn Ser Leu Arg
    50                  55                  60

Ile Asp Glu Lys Asn Pro Asn Trp Ile Val Ile Glu Thr Ile Leu Pro
65                  70                  75                  80

Gly Thr Val Gly Gly Phe Met Ile Arg Glu Ala Ala Val Leu Asp Asn
                85                  90                  95

Glu Asn Asn Ile Ile Ala Ile Gly Lys Tyr Pro Glu Thr Tyr Lys Pro
            100                 105                 110

Arg Ala Glu Asp Gly Ser Ile Lys Asp Leu Val Val Lys Met Ile Leu
        115                 120                 125

Gln Leu Ser Asn Thr Ser Asn Val Thr Leu Glu Val Asp Pro Thr Leu
    130                 135                 140

Val Phe Val Thr Gln Lys Asp Ile Gln Asp Leu Asp Ala Lys Ile Asp
145                 150                 155                 160

Thr Thr Lys Thr Glu Leu Thr Ser Asn Ile Glu Thr Lys Thr Glu
                165                 170                 175

Leu Asn Thr Lys Ile Gly Asp Thr Thr Gln Leu Thr Thr Asp Lys
            180                 185                 190

Thr Asn Ile Val Ser Ala Leu Asn Glu Val Lys Ser Ser Val Asp Ser
        195                 200                 205
```

Ile Glu Thr Thr Ala Glu Lys Thr Ser Ile Lys Asp Thr Asp Asn Leu
210                 215                 220

Phe Ser Ser Gly Asn Val Glu Gly Ala Leu Lys Glu Val Met Gln Glu
225                 230                 235                 240

Val Lys Gly Asn Arg Ser Ser Ile Ile Ser Thr Val Asn Asn Asn Leu
                245                 250                 255

Ile Pro Met

<210> SEQ ID NO 110
<211> LENGTH: 495
<212> TYPE: PRT
<213> ORGANISM: Clostridium difficile

<400> SEQUENCE: 110

Met Ser Thr Thr Val Leu Glu Arg Thr Val Lys Arg Arg Gly Tyr
1               5                   10                  15

Tyr Arg Met Thr Asp Ile His Ala Ser Arg Leu Thr Tyr Asn Asp Gly
                20                  25                  30

Ser Pro Tyr Tyr Thr Asp Phe Val Ala Tyr Tyr Thr Leu Asp Gln Tyr
                35                  40                  45

Glu Arg Val Ser Ile Ser Ala Thr Lys Lys Phe Val Ala Tyr Ser Thr
50                  55                  60

Arg Ala Cys Gln Ile Ile Asn Gly Arg Glu Val Asp Ile Ser Arg Asn
65                  70                  75                  80

Phe Thr Gln Glu Thr Thr Val Gln Phe Val Pro Asp Pro Thr Ile Phe
                85                  90                  95

Ile Ser Asn Asp Leu Gly Val Ile Gly Asn Ala Cys Ser Ile Asn Tyr
                100                 105                 110

Arg Ile Ser Asp Ser Asp Ser Ser Val Arg Phe Lys Ile Ile Glu Lys
                115                 120                 125

Ile Asn Gly Val Lys Ile Ala Glu Lys Asn Asn Val Val Asp Gly Asn
130                 135                 140

Tyr Glu Leu Ile Ile Thr Asp Glu Leu Leu Ser Glu Leu Ala Phe Asn
145                 150                 155                 160

Ser Val Asn Asn Ile Thr Ile Glu Leu Asp Asn Gly Tyr Gly Gly Ile
                165                 170                 175

Phe Leu Asp Lys Thr Val Thr Phe Thr Lys Gly Asn Thr Lys Pro Lys
                180                 185                 190

Leu Asn Ile Thr Ser Tyr Asn Ser Thr Ser Ala Thr Phe Thr Ala Ile
                195                 200                 205

Asp Thr Asp Asn Asn Leu Ser Lys Ile Glu Trp Phe Ile Asp Asp Val
                210                 215                 220

Leu Lys Glu Thr Ile Thr Thr Asp Leu Thr Thr Glu Lys Thr Ile Asn
225                 230                 235                 240

Tyr Glu Leu Ala Asp Asn Ala Ile His Thr Leu Lys Ile Val Ala Thr
                245                 250                 255

Asp Ser Glu Asn Ala Thr Ala Glu Lys Val Leu Ser Ile Ser Lys Glu
                260                 265                 270

Ile Met Pro Leu Gln Ser Asp Ala Ser Leu Ser Asp Ile Ser Thr Lys
                275                 280                 285

Leu Ile Glu Ile Gly Glu Gly Phe Arg Asn Gly Lys Thr Ser Ile Ile
                290                 295                 300

Asn Thr Leu Ala Leu Lys Asn Ile Glu Ala Ser Leu Asn Asn Thr Leu
305                 310                 315                 320

```
Val Glu Leu Ser Glu Lys Ile Lys Gln Ser Phe Asp Ser Gly Asp Ala
                325                 330                 335

Ser Leu Gln Asp Leu Met Asn Gln Leu Thr Gln Ala Asn Asn Thr Ile
            340                 345                 350

Ser Gln Leu Asn Ser Lys Tyr Lys Val Ala Ser Gly Thr Val Thr Ser
        355                 360                 365

Phe Ala Asp Ser Ala Lys Ile Ala Tyr Pro Tyr Leu Thr Asp Arg Thr
370                 375                 380

Phe Lys Pro Gly Thr Trp Val Lys Ile Ser Asn Leu Asp Phe Lys Pro
385                 390                 395                 400

Asn Ile Phe Phe Ala Asp Phe Asp Tyr Tyr Asp Thr Glu Tyr Lys Asn
                405                 410                 415

Asn Tyr Lys Leu Phe Leu Phe Ala Cys Arg Gly Val Ala Thr Gln Arg
            420                 425                 430

Gly Val Asp Phe Ser Ser Val Thr Ala Phe Ile Lys Lys Asn Ser Asp
        435                 440                 445

Glu Asn Phe His Ala Asn Gly Trp Leu Tyr Asn Ser Glu Gly Asp
    450                 455                 460

Val Tyr Phe Asn Asn Thr Gly Val Gln Ile Pro Ala Tyr Asn Phe Asp
465                 470                 475                 480

Ser Thr Gln Arg His Ile Tyr Lys Trp Tyr Ala Ile Lys Phe Ile
                485                 490                 495

<210> SEQ ID NO 111
<211> LENGTH: 265
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 111

Leu Glu Glu Lys Phe Tyr Ile Ile Leu Thr Lys Ile Gly Arg Glu Lys
1               5                   10                  15

Ile Ala Asn Ala Thr Ala Leu Gly Glu Leu Val Gly Leu Thr Lys Phe
            20                  25                  30

Gln Val Gly Asp Ser Asn Gly Glu Tyr Tyr Glu Pro Thr Glu Glu Gln
        35                  40                  45

Thr Ala Leu Lys Asn Val Val Trp Glu Gly Asn Ile Asn Ser Leu Arg
    50                  55                  60

Ile Asp Glu Lys Asn Pro Asn Trp Ile Val Ile Glu Thr Ile Leu Pro
65                  70                  75                  80

Gly Thr Val Gly Gly Phe Met Ile Arg Glu Ala Ala Val Leu Asp Asn
                85                  90                  95

Glu Asn Asn Ile Ile Ala Ile Gly Lys Tyr Pro Glu Thr Tyr Lys Pro
            100                 105                 110

Arg Ala Glu Asp Gly Ser Ile Lys Asp Leu Val Val Lys Met Ile Leu
        115                 120                 125

Gln Leu Ser Asn Thr Ser Asn Val Thr Leu Glu Val Asp Pro Thr Leu
    130                 135                 140

Val Phe Val Thr Gln Lys Asp Ile Gln Glu Leu Thr Lys Ile Gly
145                 150                 155                 160

Thr Ile Asn Thr Lys Ile Asp Thr Thr Lys Thr Glu Leu Thr Ser Asn
                165                 170                 175

Ile Glu Thr Ala Lys Thr Glu Leu Ser Asn Lys Ile Gly Asp Thr Thr
            180                 185                 190
```

```
Gln Leu Asn Thr Thr Asp Lys Thr Asn Ile Val Ser Ala Leu Asn Glu
            195                 200                 205

Val Lys Thr Ser Val Asp Ser Ile Glu Thr Thr Ala Glu Lys Thr Ser
        210                 215                 220

Tyr Asn Asn Ala Thr Ser Lys Leu Thr Ala Thr Thr Val Gln Gly Ala
225                 230                 235                 240

Ile Asp Glu Val Val Ala Lys Ile Glu Asn Phe Asn Glu Val Asn Ile
                245                 250                 255

Ser Ile Gln Asn Asp Met Leu Pro Ile
            260                 265

<210> SEQ ID NO 112
<211> LENGTH: 565
<212> TYPE: PRT
<213> ORGANISM: Clostridium difficile

<400> SEQUENCE: 112

Met Thr Thr Glu Trp Asn Phe Asn Tyr Ile Gly Thr Gly Lys Lys Val
1               5                   10                  15

Ile Leu Lys Pro Gly Lys Tyr Lys Leu Glu Cys Trp Gly Ala Ser Gly
            20                  25                  30

Gly Gly Arg Phe Asp Glu Trp Thr Glu Cys Ala Lys Gly Gly Tyr Ser
        35                  40                  45

Lys Gly Glu Leu Thr Leu Lys Lys Glu Thr Ile Leu Tyr Val Tyr Ala
    50                  55                  60

Gly Glu Ser Gly Tyr Lys Lys Phe Ser Asn Ile Ser Asp Trp Ala Gly
65                  70                  75                  80

Phe Asn Gly Gly Gly Arg Gly Pro Asn Glu Gly Val Asp Pro Lys Phe
                85                  90                  95

Thr Thr Cys Gly Gly Gly Ala Thr Asp Ile Arg Leu Ile Gly Gly Val
            100                 105                 110

Trp Asn Asp Glu Gln Gly Leu Leu Ser Arg Ile Ile Val Ala Gly Gly
        115                 120                 125

Gly Gly Ser Ile Gly Thr Ser Ser Phe Ser Ser Ile Gly Leu Gly Gly
    130                 135                 140

Gly Phe Ala Gly Gly Met Gly Val Gly Ala Gly Thr Cys Thr Gly
145                 150                 155                 160

Gly Thr Gln Tyr Glu Gly Gly Val Thr Val Asn Ser Asn Gly Asn Gly
                165                 170                 175

Ser Phe Gly Lys Gly Gly Ile Gly Asn Val Cys Ala Gly Gly Gly Gly
            180                 185                 190

Trp Tyr Gly Gly Ala Gly Ala Ser Ser Gly Val Gly Gly Gly Gly
        195                 200                 205

Ser Gly Tyr Val Leu Thr Lys Asp Ser Tyr Lys Pro Lys Gly Tyr Ile
    210                 215                 220

Pro Thr Ser Glu Tyr Trp Leu Glu Asn Val Asn Ser Ile Ala Gly Asp
225                 230                 235                 240

Asn Thr Ser Asn Ala His Gly Tyr Ala Lys Ile Thr Leu Leu Gln Ala
                245                 250                 255

Leu Pro Phe Leu Asn Ile Ser Ser Tyr Asn Ser Ser Thr Ala Thr Phe
            260                 265                 270

Lys Ala Asp His Thr Asp Pro Thr Leu Leu Thr Lys Ile Glu Tyr Phe
        275                 280                 285

Ile Asp Asp Val Leu Lys Glu Thr Ile Thr Thr Asp Leu Thr Leu Glu
```

```
                    290                 295                 300
Lys Thr Ile Asn Tyr Thr Leu Glu Asp Asn Ala Leu His Thr Leu Lys
305                 310                 315                 320

Ile Val Val Thr Asp Ser Ala Asn Ala Thr Val Glu Lys Val Val Ser
                    325                 330                 335

Val Ser Arg Gly Ile Ala Pro Leu Pro Ser Gly Ser Thr Thr Asp Glu
                340                 345                 350

Val Thr Asn Lys Trp Ile Glu Ile Lys Asp Ala Phe Lys Thr Gly Lys
                355                 360                 365

Thr Ser Ile Ile Asn Thr Leu Ala Leu Lys Asn Ile Glu Ala Asn Leu
            370                 375                 380

Asn Asn Thr Leu Val Glu Leu Ser Glu Lys Ile Lys Thr Ser Phe Asp
385                 390                 395                 400

Ser Ser Asp Ala Ser Val Gln Asp Leu Met Asn Gln Leu Thr Glu Lys
                    405                 410                 415

Asn Asn Ile Ile Ser Gln Leu Asn Ala Lys Tyr Lys Ile Ala His Gly
                420                 425                 430

Thr Thr Ser Ile Ile Gln Asn Ser Leu Trp Ser Ala Tyr Leu Tyr Asp
            435                 440                 445

Ser Asn His Asn Asn Tyr Glu Arg Gln Pro Lys Thr Trp Ile Gly
    450                 455                 460

Val Glu Gly Leu Asn Phe Val Pro Asn Leu Phe Phe Ala Glu Cys Glu
465                 470                 475                 480

Tyr Lys Asp Ser Ser Ser Val Tyr Tyr Lys His Phe Val Phe Gly Thr
                    485                 490                 495

Ser Gly Ile Pro Ser Ile Ser Gly Glu Thr Asp Phe Val Val Thr Ser
                500                 505                 510

Lys Phe Arg Lys Pro Tyr Gly Asn Gln Asn Tyr Ser Ala Phe Gly Gln
                515                 520                 525

Ala Tyr Lys Ser Asn Lys Gly Ser Ile Trp Ile Glu Asn Asn Thr Tyr
            530                 535                 540

Val Pro Ala Ile Ile Pro Glu Ile Asp Gly Val Leu Tyr Asn Trp Tyr
545                 550                 555                 560

Ala Ile Lys Phe Ile
                565

<210> SEQ ID NO 113
<211> LENGTH: 97
<212> TYPE: PRT
<213> ORGANISM: Clostridium difficile

<400> SEQUENCE: 113

Met Asn Val Pro Asn Arg Ile Ile Tyr Asp Gln Thr Gly Arg Thr Ile
1               5                   10                  15

Phe Glu Thr Gly Glu Ser Cys Gly Asp Val Leu Pro His Tyr Thr Ile
                20                  25                  30

Thr Glu Leu His Tyr Ile Asp Ile Glu Tyr Gly Ser Ile Asp Tyr Thr
            35                  40                  45

Arg Asn Arg Val Ile Gly Ile Asn Ile Glu Thr Lys Glu Pro Ile Leu
        50                  55                  60

Glu Glu Ile Pro Val Tyr Ile Thr Asp Glu Glu Lys Arg Ile Gln Glu
65                  70                  75                  80

Leu Glu Asn Gln Leu Leu Ile Ala Glu Asn Glu Lys Val Gly Gly Leu
                85                  90                  95
```

Leu

<210> SEQ ID NO 114
<211> LENGTH: 60
<212> TYPE: PRT
<213> ORGANISM: Clostridium difficile

<400> SEQUENCE: 114

Met Asn Ile Asn Asn Val Val Arg Ile Leu Ala Glu Arg Ile Leu
1               5                   10                  15

Ser Lys Gly Leu Asn Pro Leu Lys Asn Arg Glu Phe Gln Leu Asp Asp
            20                  25                  30

Val Thr Asn Thr Glu Tyr Arg Lys Ala Val Glu Asp Tyr Ile Ile Lys
            35                  40                  45

Asn Ser Gly Val Val Glu Gly Ala Glu Pro Thr Ile
    50                  55                  60

<210> SEQ ID NO 115
<211> LENGTH: 265
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 115

Leu Glu Glu Lys Phe Tyr Ile Ile Leu Thr Lys Ile Gly Arg Glu Lys
1               5                   10                  15

Ile Ala Asn Ala Thr Ala Leu Gly Glu Leu Val Gly Leu Thr Lys Phe
            20                  25                  30

Gln Val Gly Asp Ser Asn Gly Glu Tyr Tyr Glu Pro Thr Glu Glu Gln
            35                  40                  45

Thr Ala Leu Lys Asn Val Val Trp Glu Gly Asn Ile Asn Ser Leu Arg
    50                  55                  60

Ile Asp Glu Lys Asn Pro Asn Trp Ile Val Ile Glu Thr Ile Leu Pro
65                  70                  75                  80

Gly Thr Val Gly Gly Phe Met Ile Arg Glu Ala Ala Val Leu Asp Asn
                85                  90                  95

Glu Asn Asn Ile Ile Ala Ile Gly Lys Tyr Pro Glu Thr Tyr Lys Pro
            100                 105                 110

Arg Ala Glu Asp Gly Ser Ile Lys Asp Leu Val Val Lys Met Ile Leu
            115                 120                 125

Gln Leu Ser Asn Thr Ser Asn Val Thr Leu Glu Val Asp Pro Thr Leu
    130                 135                 140

Val Phe Val Thr Gln Lys Asp Ile Gln Asp Leu Glu Thr Lys Ile Gly
145                 150                 155                 160

Thr Val Asn Thr Lys Ile Asp Thr Thr Lys Thr Glu Leu Thr Ser Asn
                165                 170                 175

Ile Glu Thr Ala Lys Thr Glu Ile Asp Glu Lys Ile Gly Asp Thr Thr
            180                 185                 190

Gln Leu Thr Thr Thr Asp Lys Thr Asn Ile Val Gly Ala Leu Asn Glu
            195                 200                 205

Val Lys Thr Ser Val Asp Ser Ile Glu Thr Thr Ala Glu Lys Thr Ser
    210                 215                 220

Tyr Asn Asn Ala Thr Ser Asn Leu Ala Ala Thr Asn Val Gln Gly Ala
225                 230                 235                 240

Ile Asp Glu Val Val Arg Lys Ile Glu Lys Phe Asn Glu Val Asn Ile

-continued

```
                    245                 250                 255
Ser Ile Gln Asn Asp Met Leu Pro Ile
            260                 265

<210> SEQ ID NO 116
<211> LENGTH: 426
<212> TYPE: PRT
<213> ORGANISM: Clostridium difficile

<400> SEQUENCE: 116

Met Gln Ser Glu Trp Asn Phe Asp Tyr Thr Gly Ala Glu Gln Asn Val
1               5                   10                  15

Thr Leu Lys Pro Gly Lys Tyr Lys Leu Glu Cys Trp Gly Ala Cys Gly
            20                  25                  30

Gly Gly Trp Phe Ser Glu Trp Thr Lys Gly Ala Lys Gly Gly Tyr Ser
        35                  40                  45

Lys Ala Glu Leu Thr Leu Lys Lys Glu Thr Ile Leu Tyr Val Tyr Ala
50                  55                  60

Gly Glu Thr Gly Cys Gln Lys Phe Glu Asn Ser Ile Asn Asn Trp Thr
65                  70                  75                  80

Gly Phe Asn Gly Gly Arg Gly Thr Asn Ala Gly Ala Asp Pro Lys
                85                  90                  95

Phe Ile Leu Cys Gly Gly Ala Thr Asp Ile Arg Leu Ile Arg Gly
            100                 105                 110

Ser Trp Ser Asn Glu Gln Gly Leu Leu Ser Arg Ile Leu Val Ala Gly
        115                 120                 125

Gly Ala Gly Ala Ile Ser Ser Asp Tyr Gly Val Gly Asn Gly Gly
    130                 135                 140

Gly Met Glu Gly Ser Lys Gly Phe Asp Gly Ser Asn Ala Phe Val Thr
145                 150                 155                 160

Gly Gly Thr Gln Tyr Gln Gly Gly Ile Gly Leu Glu Asp Lys Tyr Asn
                165                 170                 175

Gly Ser Phe Gly Arg Ala Ser Ser Thr Gly Thr Gly Gln Gly Gly Gly
            180                 185                 190

Gly Gly Trp Phe Gly Gly Ala Gly Gly Leu Asn Tyr Asn Ala Ala Gly
        195                 200                 205

Gly Ser Gly Tyr Ala Leu Thr Lys Asp Ser Tyr Lys Pro Pro Gly Tyr
    210                 215                 220

Ile Pro Thr Ser Lys Tyr Tyr Leu Asp Asn Val Val Met Thr Thr Gly
225                 230                 235                 240

Gly Asn Thr Thr Lys Ala Asp Gly Tyr Ala Lys Ile Thr Leu Leu Gln
                245                 250                 255

Ala Leu Pro Phe Leu Thr Val Ser Ser Tyr Asn Ser Thr Thr Ala Thr
            260                 265                 270

Phe Lys Ala Asp His Thr Asp Pro Thr Leu Leu Thr Lys Ile Glu Trp
        275                 280                 285

Phe Ile Asp Glu Lys Leu Lys Glu Thr Ile Thr Ser Lys Leu Thr Ile
    290                 295                 300

Glu Lys Thr Ile Asn Tyr Thr Leu Glu Asp Asn Ala Leu His Thr Ile
305                 310                 315                 320

Lys Ile Val Val Thr Asp Ser Ser Asn Ala Thr Ala Glu Arg Ile Phe
                325                 330                 335

Thr Val Ser Lys Gly Ile Ala Pro Leu Pro Thr Gly Ser Ser Ser Glu
            340                 345                 350
```

```
Glu Val Thr Asn Lys Trp Arg Glu Ile Lys Asp Ser Phe Lys Thr Gly
            355                 360                 365

Lys Thr Ser Ile Ile Asn Thr Leu Ala Leu Lys Asn Ile Glu Ser Asn
        370                 375                 380

Leu Asn Asn Thr Leu Val Glu Leu Ser Glu Lys Ile Lys Gln Ser Phe
385                 390                 395                 400

Asp Ser Ser Asp Ala Ser Val Gln Glu Leu Glu Asn Gln Ile Leu Leu
                405                 410                 415

Asn Glu Asn Glu Lys Val Gly Gly Ile Leu
            420                 425

<210> SEQ ID NO 117
<211> LENGTH: 60
<212> TYPE: PRT
<213> ORGANISM: Clostridium difficile

<400> SEQUENCE: 117

Met Asn Ile Asn Asn Val Val Arg Ile Leu Ala Glu Arg Ile Leu
1               5                   10                  15

Asn Gly Gly Leu Asn Pro Leu Lys Asn Arg Glu Phe Gln Leu Asp Asp
            20                  25                  30

Val Thr Asn Ile Gly Tyr Arg Lys Ala Val Glu Asp Tyr Ile Ile Glu
        35                  40                  45

His Ser Gly Val Val Glu Gly Ala Glu Pro Thr Lys
    50                  55                  60

<210> SEQ ID NO 118
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 118
ttctaaacaa catggtatct gg                                          22

<210> SEQ ID NO 119
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 119
aacagtacct attttagttt ctaagtcttg aatatccttt tgagttacaa             50

<210> SEQ ID NO 120
<211> LENGTH: 55
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 120
ggtttttgta actcaaaagg atattcaaga cttagaaact aaaataggta ctgtt       55

<210> SEQ ID NO 121
<211> LENGTH: 59
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 121
cgaatttaaa caattttcac acctccattt taaatatata ttttgtaagt taatgtagc      59

<210> SEQ ID NO 122
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 122
gctacattaa cttacaaaat atatatttaa aatggaggtg tgaaaattgt                50

<210> SEQ ID NO 123
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 123
atttccttac gcgaaatacg                                                 20

<210> SEQ ID NO 124
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 124
aacagtacct attttagttt ctaagtcttg aatatccttt tgagttacaa                50

<210> SEQ ID NO 125
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 125
cgttggtttt tgtaactcaa aaggatattc aagacttaga aactaaaata ggtactgtta     60

<210> SEQ ID NO 126
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 126
tcgaatttaa acaattttca cacctccatt ttatttaaat tttgccgcat                50

<210> SEQ ID NO 127
<211> LENGTH: 50
<212> TYPE: DNA
<213> ORGANISM: Artificial Sequence
<220> FEATURE:
```

<223> OTHER INFORMATION: Description of Artificial Sequence: Synthetic
      oligonucleotide

<400> SEQUENCE: 127
tataaatggc atgcggcaaa atttaaataa aatggaggtg tgaaaattgt                50

<210> SEQ ID NO 128
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 128
tccttcggcg cgcctcaaat ttaagcttaa ctcc                                 34

<210> SEQ ID NO 129
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 129
agttgtatca attttagtgt ctaattcttg aatatccttt tgagttacaa                50

<210> SEQ ID NO 130
<211> LENGTH: 55
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 130
tggtttttgt aactcaaaag gatattcaag aattagacac taaaattgat acaac          55

<210> SEQ ID NO 131
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 131
tttaaacaat tttcacacct ccattttata caaattttat agcataccaa                50

<210> SEQ ID NO 132
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 132
tacaattggt atgctataaa atttgtataa aatggaggtg tgaaaattgt                50

<210> SEQ ID NO 133
<211> LENGTH: 50
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 133
agttgtatca attttagagt ctaggtcttg aatatccttt tgagttacaa    50

<210> SEQ ID NO 134
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 134
ttttgtaact caaaaggata ttcaagacct agactctaaa attgatacaa    50

<210> SEQ ID NO 135
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 135
atcgaattta aacaattttc acacctccat tttaattatt taaaaattct atatctaacg    60

<210> SEQ ID NO 136
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 136
gcgttagata tagaattttt aaataattaa aatggaggtg tgaaaattgt    50

<210> SEQ ID NO 137
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 137
tctggaaata atctagaact ttcgaagata tatctagaac tttcaaagat g    51

<210> SEQ ID NO 138
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 138
gcttatttta gcatctaaat cttgaatatc cttttgagtt aca    43

<210> SEQ ID NO 139
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 139
taactcaaaa ggatattcaa gatttagatg ctaaaataag ca                               42

<210> SEQ ID NO 140
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 140
aattttcaca cctccatttt aaataaattt aatagcatac catt                             44

<210> SEQ ID NO 141
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 141
ggtatgctat taaatttatt taaaatggag gtgtgaaaat tgt                              43

<210> SEQ ID NO 142
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 142
ggcgctcagg atccggcgcg cctcaaattt aagctt                                     36

<210> SEQ ID NO 143
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 143
gtacctattt tagtttctaa gtcttgaata tccttttgag ttaca                            45

<210> SEQ ID NO 144
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 144
aactcaaaag gatattcaag acttagaaac taaaataggt actg                             44

<210> SEQ ID NO 145
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 145
aattttcaca cctccatttt attcaaatgc ataccatg         38

<210> SEQ ID NO 146
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 146
tggtatgcat ttgaataaaa tggaggtgtg aaaattgt         38

<210> SEQ ID NO 147
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 147
tcaattttag tgtctaggtc ttgaatatcc ttttgagtta ca         42

<210> SEQ ID NO 148
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 148
taactcaaaa ggatattcaa gacctagaca ctaaaattga taca         44

<210> SEQ ID NO 149
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 149
aattttcaca cctccatttt atttaaattt tatagcatac cag         43

<210> SEQ ID NO 150
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 150
ggtatgctat aaaatttaaa taaaatggag gtgtgaaaat tgt         43

<210> SEQ ID NO 151
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 151
acctatttta gtttctaagt cttgaatatc cttttgagtt aca        43

<210> SEQ ID NO 152
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 152
attttcacac ctccatttta tatgaatttt atagcatacc aa        42

<210> SEQ ID NO 153
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 153
ggtatgctat aaaattcata taaaatggag gtgtgaaaat tgt        43

<210> SEQ ID NO 154
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 154
tatcaatttt agcgtctaaa tcttgaatat ccttttgagt taca        44

<210> SEQ ID NO 155
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 155
actcaaaagg atattcaaga tttagacgct aaaattgata c        41

<210> SEQ ID NO 156
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 156
attttcacac ctccatttta aataaattta atagcatacc at        42

<210> SEQ ID NO 157
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 157
ggtatgctat taaatttatt taaaatggag gtgtgaaaat tgt        43

<210> SEQ ID NO 158
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 158
cctattttag tttccaattc ttgaatatcc ttttgagtta ca        42

<210> SEQ ID NO 159
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 159
actcaaaagg atattcaaga attggaaact aaaataggta c        41

<210> SEQ ID NO 160
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 160
attttcacac ctccatttta aataaatttt atagcatacc aat        43

<210> SEQ ID NO 161
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 161
ggtatgctat aaaatttatt taaaatggag gtgtgaaaat tgt        43

<210> SEQ ID NO 162
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 162
ggcgctcagg atccggcgcg ccctatatag ttggttctgc tcc        43

<210> SEQ ID NO 163
<211> LENGTH: 44
<212> TYPE: DNA
<213> ORGANISM: Artificial Sequence -continued

```
<220> FEATURE:
<223> OTHER INFORMATION: Description of Artificial Sequence: Synthetic
      oligonucleotide

<400> SEQUENCE: 163
ggcgctcagg atccggcgcg cctccttta ctactccact atgc                          44
```